(12) United States Patent
Gradl et al.

(10) Patent No.: US 11,787,797 B2
(45) Date of Patent: *Oct. 17, 2023

(54) 4,5-ANNULATED 1,2,4-TRIAZOLONES

(71) Applicants: BAYER AKTIENGESELLSCHAFT, Leverkusen (DE); BAYER PHARMA AKTIENGESELLSCHAFT, Berlin (DE); THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US)

(72) Inventors: Stefan Nikolaus Gradl, Berlin (DE); Duy Nguyen, Berlin (DE); Knut Eis, Berlin (DE); Judith Günther, Berlin (DE); Timo Stellfeld, Berlin (DE); Andreas Janzer, Berlin (DE); Sven Christian, Berlin (DE); Thomas Mueller, Langenfeld (DE); Sherif El Sheikh, Mülheim/Ruhr (DE); Han Jie Zhou, Foster City, CA (US); Changjia Zhao, Beijing (CN); David B. Sykes, Cambridge, MA (US); Steven James Ferrara, Cambridge, MA (US); Kery Liu, Beijing (CN); Simon Anthony Herbert, Berlin (DE); Claudia Merz, Berlin (DE); Michael Niehues, Berlin (DE); Carl Friedrich Nising, Berlin (DE); Martina Schäfer, Berlin (DE); Katja Zimmermann, Düsseldorf (DE); Jörg Knäblein, Berlin (DE); Kai Thede, Berlin (DE); Thomas Faupel, Berlin (DE)

(73) Assignees: BAYER AKTIENGESELLSCHAFT, Leverkusen (DE); BAYER PHARMA AKTIENGESELLSCHAFT, Berlin (DE); THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 131 days.

This patent is subject to a terminal disclaimer.

(21) Appl. No.: 17/161,615

(22) Filed: Jan. 28, 2021

(65) Prior Publication Data
US 2021/0188846 A1 Jun. 24, 2021

Related U.S. Application Data

(60) Division of application No. 16/345,178, filed as application No. PCT/EP2017/077301 on Oct. 25, (Continued)

(51) Int. Cl.
C07D 471/04 (2006.01)
A61P 35/00 (2006.01)
(Continued)

(52) U.S. Cl.
CPC ............ *C07D 471/04* (2013.01); *A61P 35/00* (2018.01); *C07D 487/04* (2013.01);
(Continued)

(58) Field of Classification Search
CPC .. C07D 471/04; C07D 487/04; C07D 498/04; C07D 513/04; C07D 519/00;
(Continued)

(56) References Cited

U.S. PATENT DOCUMENTS

| 6,444,613 B1 | 9/2002 | Feurer et al. |
| 10,968,216 B2 | 4/2021 | Gradl et al. |

(Continued)

FOREIGN PATENT DOCUMENTS

| CN | 102574786 A | 7/2012 |
| CN | 103097353 A | 5/2013 |

(Continued)

OTHER PUBLICATIONS

Iwata et al., "High Catalytic Activity of Human Cytochrome P450 Co-expressed with Human NADPH-Cytochrome P450 Reductase in *Escherichia coli*," Biochemical Pharmacology, 1998, vol. 55, 1315-1325.

(Continued)

*Primary Examiner* — Daniel R Carcanague
(74) *Attorney, Agent, or Firm* — Melissa Hunter-Ensor; Scott Goncher; Greenberg Traurig, LLP

(57) ABSTRACT

The present invention provides triazolone compounds of general formula (I):

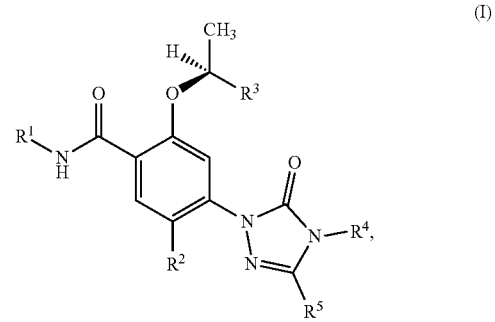

in which $R^1$, $R^2$, $R^3$, $R^4$ and $R^5$ are as defined herein, methods of preparing said compounds, intermediate compounds useful for preparing said compounds, pharmaceutical compositions and combinations comprising said compounds and the use of said compounds for manufacturing
(Continued)

pharmaceutical compositions for the treatment or prophylaxis of diseases, in particular of hyperproliferative disorders, as a sole agent or in combination with other active ingredients.

2 Claims, No Drawings

Specification includes a Sequence Listing.

Related U.S. Application Data 2017, now Pat. No. 10,968,216, which is a continuation-in-part of application No. PCT/CN2016/103642, filed on Oct. 27, 2016.

(51) Int. Cl.

| C07D 487/04 | (2006.01) |
|---|---|
| C07D 498/04 | (2006.01) |
| C07D 513/04 | (2006.01) |
| C07D 519/00 | (2006.01) |
| C12N 1/20 | (2006.01) |
| C12P 17/18 | (2006.01) |

(52) U.S. Cl.
CPC ......... *C07D 498/04* (2013.01); *C07D 513/04* (2013.01); *C07D 519/00* (2013.01); *C12N 1/20* (2013.01); *C12P 17/18* (2013.01); *C12P 17/182* (2013.01); *C12P 17/188* (2013.01)

(58) Field of Classification Search
CPC . A61P 35/00; C12N 1/20; C12P 17/18; C12P 17/182; C12P 17/188
See application file for complete search history.

(56) References Cited

U.S. PATENT DOCUMENTS

| 2011/0275603 | A1 | 11/2011 | Muthuppalaniappan et al. |
| 2012/0028959 | A1 | 2/2012 | Thunuguntla et al. |
| 2016/0251341 | A1 | 9/2016 | Short |
| 2019/0307728 | A1 | 10/2019 | Janzer et al. |
| 2020/0123129 | A1 | 4/2020 | Gradl et al. |

FOREIGN PATENT DOCUMENTS

| CN | 106543139 A | 3/2017 |
| EP | 3553052 A1 | 10/2019 |
| JP | 2015500308 A | 1/2015 |
| JP | 2015523353 A | 8/2015 |
| WO | 1998002422 A1 | 1/1998 |
| WO | 2003006425 A2 | 1/2003 |
| WO | 2010077686 A1 | 7/2010 |
| WO | 2013087579 A1 | 6/2013 |
| WO | 2013186692 A1 | 12/2013 |
| WO | 2014128669 A2 | 8/2014 |
| WO | 2019197239 A1 | 10/2019 |
| WO | 2019197269 A1 | 10/2019 |

OTHER PUBLICATIONS

Lau et al., "In Vitro Functional Characterisation of Cytochrome P450 (CYP) 2C19 Allelic Variants CYP2C19*23 and CYP2C19*24," Biochemical Genetics, 2017, vol. 55, pp. 48-62.

Office Action dated Aug. 9, 2022 in corresponding European Patent Application No. 17797091.0 (9 pages).

Baumann et al., "Dihydroorotate dehydrogenase inhibitor A771726 (leflunomide) induces apoptosis and diminishes proliferation of multiple myeloma cells," Molecular Cancer Therapeutics, Feb. 2009, vol. 8, No. 2, pp. 366-375.

Christian et al., "The novel dihydroorotate dehydrogenase (DHODH) inhibitor BAY 2402234 triggers differentiation and is effective in the treatment of myeloid malignancies," Leukemia, Apr. 2, 2019, vol. 33, pp. 2403-2415.

Ishige et al., "Whole organism biocatalysis," Current Opinion in Chemical Biology, Apr. 2005, vol. 9, Iss. 2, pp. 174-180.

Loffler et al., "Dihydroorotat-ubiquinone oxidoreductase links mitochondria in the biosynthesis of pyrimidine nucleotides," Molecular and Cellular Biochemistry, Sep. 1997, vol. 174, pp. 125-129.

Phillips et al., "Triazolopyrimidine-Based Dihydroorotate Dehydrogenase Inhibitors with Potent and Selective Activity against the Malaria Parasite *Plasmodium falciparum*," Journal of Medicinal Chemistry, Jan. 31, 2008, vol. 51, No. 12, pp. 3649-3653.

Sanz et al., "Management of acute promyelocytic leukemia: recommendations from an expert panel on behalf of the European LeukemiaNet," Blood, Feb. 26, 2009, vol. 113, No. 9, pp. 1875-1891.

Sykes et al., "Inhibition of Dihydroorotate Dehydrogenase Overcomes Differentiation Blockade in Acute Myeloid Leukemia," Cell, Sep. 22, 2016, vol. 167, Iss. 1, pp. 171-186, e15.

International Search Report and Written Opinion for corresponding International Patent Application No. PCT/EP2017/077301, dated May 4, 2018 (20 pages).

Office Action dated Jun. 26, 2023 in corresponding Japanese Patent Application No. 2022-103480 (4 pages).

English translation of the Office Action dated Jun. 26, 2023 in corresponding Japanese Patent Application No. 2022-103480 (6 pages).

SEQUENCE LISTING

<160> NUMBER OF SEQ ID NOS: 6

<210> SEQ ID NO 1
<211> LENGTH: 6129
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: pACYC_pelB_POR

<400> SEQUENCE: 1

```
ggccgcggca aagccgtttt tccataggct ccgcccccct gacaagcatc acgaaatctg      60
acgctcaaat cagtggtggc gaaacccgac aggactataa agataccagg cgtttccccc     120
tggcggctcc ctcgtgcgct ctcctgttcc tgcctttcgg tttaccggtg tcattccgct     180
gttatggccg cgtttgtctc attccacgcc tgacactcag ttccgggtag gcagttcgct     240
ccaagctgga ctgtatgcac gaaccccccg ttcagtccga ccgctgcgcc ttatccggta     300
actatcgtct tgagtccaac ccggaaagac atgcaaaagc accactggca gcagccactg     360
gtaattgatt tagaggagtt agtcttgaag tcatgcgccg gttaaggcta aactgaaagg     420
acaagttttg gtgactgcgc tcctccaagc cagttacctc ggttcaaaga gttggtagct     480
cagagaacct tcgaaaaacc gccctgcaag gcggtttttt cgttttcaga gcaagagatt     540
acgcgcagac caaaacgatc tcaagaagat catcttatta atcagataaa atatttctag     600
atttcagtgc aatttatctc ttcaaatgta gcacctgaag tcagcccat acgatataag      660 ttgtaattct catgttagtc atgccccgcg cccaccggaa ggagctgact gggttgaagg     720
ctctcaaggg catcggtcga gatcccggtg cctaatgagt gagctaactt acattaattg     780
cgttgcgctc actgcccgct ttccagtcgg gaaacctgtc gtgccagctg cattaatgaa     840
tcggccaacg cgcggggaga ggcggtttgc gtattgggcg ccagggtggt tttcttttc      900 accagtgaga cgggcaacag ctgattgccc ttcaccgcct ggccctgaga gagttgcagc     960
aagcggtcca cgctggtttg ccccagcagg cgaaaatcct gtttgatggt ggttaacggc    1020
gggatataac atgagctgtc ttcggtatcg tcgtatccca ctaccgagat gtccgcacca    1080
acgcgcagcc cggactcggt aatggcgcgc attgcgccca gcgccatctg atcgttggca    1140
accagcatcg cagtgggaac gatgccctca ttcagcattt gcatggtttg ttgaaaaccg    1200
gacatggcac tccagtcgcc ttcccgttcc gctatcggct gaatttgatt gcgagtgaga    1260
tatttatgcc agccagccag acgcagacgc gccgagacag aacttaatgg gcccgctaac    1320
agcgcgattt gctggtgacc caatgcgacc agatgctcca cgcccagtcg cgtaccgtct    1380
tcatgggaga aaataatact gttgatgggt gtctggtcag agacatcaag aaataacgcc    1440
```

-continued

```
ggaacattag tgcaggcagc ttccacagca atggcatcct ggtcatccag cggatagtta    1500
atgatcagcc cactgacgcg ttgcgcgaga agattgtgca ccgccgcttt acaggcttcg    1560
acgccgcttc gttctaccat cgacaccacc acgctggcac ccagttgatc ggcgcgagat    1620
ttaatcgccg cgacaatttg cgacggcgcg tgcagggcca gactggaggt ggcaacgcca    1680
atcagcaacg actgtttgcc cgccagttgt tgtgccacgc ggttgggaat gtaattcagc    1740
tccgccatcg ccgcttccac ttttcccgc gttttcgcag aaacgtggct ggcctggttc     1800
accacgcggg aaacggtctg ataagagaca ccggcatact ctgcgacatc gtataacgtt    1860 actgtttca cattcaccac cctgaattga ctctcttccg ggcgctatca tgccataccg     1920
cgaaaggttt tgcaccattc gatggtgtcc tggcacgaca ggtttcccga ctggaaagcg    1980
ggcagtgagc gcaacgcaat taatgtaagt tagctcactc attaggcacc ccaggcttta   2040
cactttatgc ttccggctcg tataatgtgt ggaattgtga gcggataaca atttcacaca   2100
ggaaacagga tcgatccatc gatgagctta ctccccatcc ccctgttgac aattaatcat   2160
cggctcgtat aatgtgtgga attgtgagcg ataacaatt tcacacagga aacaggatca     2220
gcttactccc catccccctg ttgacaatta atcatcggct cgtataatgt gtggaattgt   2280
gagcggataa caatttcaca caggaaacag gatccatcga tgcttaggag gtcatatgaa   2340
atacctgctg ccgaccgctg ctgctggtct gctgctcctc gctgcccagc cggcgatggc   2400
catggatatc ggaattaatt cggatccgat gggagactcc cacgtggaca ccagctccac   2460
cgtgtccgag gcggtggccg aagaagtatc tcttttcagc atgacggaca tgattctgtt   2520
ttcgctcatc gtgggtctcc taacctactg gttcctcttt agaaagaaaa agaagaagt    2580 ccccgagttc accaaaattc agacattgac ctcctctgtc agagagagca gctttgtgga   2640
aaagatgaag aaaacgggga ggaacatcat cgtgttctac ggctcccaga cggggactgc   2700
agaggagttt gccaaccgcc tgtccaagga cgcccaccgc tacggatgc gaggcatgtc    2760 agcggaccct gaggagtatg acctggccga cctgagcagc ctgccagaga tcgacaacgc   2820
cctggtggtt ttctgcatgg ccacctacgg tgagggagac cccaccgaca atgcccagga   2880
cttctacgac tggctgcagg agacagacgt ggatctctct ggggtcaagt tcgcggtgtt   2940
tggtcttggg aacaagacct acgagcactt caatgccatg ggcaagtacg tggacaagcg   3000
gctggagcag ctcggcgccc agcgcatctt tgagctgggg ttgggcgacg acgatgggaa   3060
cttggaggag gacttcatca cctggcgaga gcagttctgg ccggccgtgt gtgaacactt   3120
tgggggtgga gccactggcg aggagtccag cattcgccag tacgagcttg tggtccacac   3180
cgacatagat gcggccaagg tgtacatggg ggagatgggc cggctgaaga gctacgagaa   3240
ccagaagccc ccctttgatg ccaagaatcc gttcctggct gcagtcacca ccaaccggaa   3300
gctgaaccag ggaaccgagc gccacctcat gcacctggaa ttggacatct cggactccaa   3360
aatcaggtat gaatctgggg accacgtggc tgtgtaccca gccaacgact ctgctctcgt   3420
caaccagctg ggcaaaatcc tgggtgccga cctggacgtc gtcatgtccc tgaacaacct   3480
ggatgaggag tccaacaaga agcacccatt cccgtgccct acgtcctacc gcacggccct   3540
cacctactac ctggacatca ccaacccgcc gcgtaccaac gtgctgtacg agctggcgca   3600
gtacgcctcg gagccctcgg agcaggagct gctgcgcaag atggcctcct cctccggcga   3660
gggcaaggag ctgtacctga gctgggtggt ggaggcccgg aggcacatcc tggccatcct   3720
gcaggactgc ccgtccctgc ggcccccat cgaccacctg tgtgagctgc tgccgcgcct    3780
```

```
gcaggcccgc tactactcca tcgcctcatc ctccaaggtc caccccaact ctgtgcacat   3840
ctgtgcggtg gttgtggagt acgagaccaa ggccggccgc atcaacaagg cgtggccac    3900
caactggctg cgggccaagg agcctgccgg ggagaacggc ggccgtgcgc tggtgcccat   3960
gttcgtgcgc aagtcccagt tccgcctgcc cttcaaggcc accacgcctg tcatcatggt   4020
gggccccggc accggggtgg caccctttcat aggcttcatc caggagcggg cctggctgcg   4080
acagcagggc aaggaggtgg gggagacgct gctgtactac ggctgccgcc gctcagatga   4140
ggactacctg taccgggagg agctggcgca gttccacagg gacggtgcgc tcacccagct   4200
caacgtggcc ttctcccggg agcagtccca aggtctac gtccagcacc tgctaaagca    4260
agaccgagag cacctgtgga agttgatcga aggcggtgcc cacatctacg tctgtgggga   4320
tgcacggaac atggccaggg atgtgcagaa caccttctac gacatcgtgg ctgagctcgg   4380
ggccatggag cacgcgcagg cggtggacta catcaagaaa ctgatgacca agggccgcta   4440
ctccctggac gtgtggagct aggtcgacaa gcttgcggcc gcactcgagt ctggtaaaga   4500
aaccgctgct gcgaaatttg aacgccagca catggactcg tctactagcg cagcttaatt   4560
aacctaggct gctgccaccg ctgagcaata actagcataa ccccttgggg cctctaaacg   4620
ggtcttgagg ggttttttgc tgaaacctca ggcatttgag aagcacacgg tcacactgct   4680
tccggtagtc aataaaccgg taaaccagca atagacataa gcggctattt aacgaccctg   4740
ccctgaaccg acgaccgggt cgaatttgct ttcgaatttc tgccattcat ccgcttatta   4800
tcacttattc aggcgtagca accaggcgtt taagggcacc aataactgcc ttaaaaaaat   4860
tacgccccgc cctgccactc atcgcagtac tgttgtaatt cattaagcat ctgccgaca    4920
tggaagccat cacaaacggc atgatgaacc tgaatcgcca gcggcatcag caccttgtcg   4980
ccttgcgtat aatatttgcc catagtgaaa acgggggcga agaagttgtc catattggcc   5040
acgtttaaat caaaactggt gaaactcacc cagggattgg ctgagacgaa aaacatattc   5100
tcaataaacc ctttagggaa ataggccagg ttttcaccgt aacacgccac atcttgcgaa   5160
tatatgtgta gaaactgccg gaaatcgtcg tggtattcac tccagagcga tgaaaacgtt   5220
tcagtttgct catggaaaac ggtgtaacaa gggtgaacac tatcccatat caccagctca   5280
ccgtctttca ttgccatacg gaactccgga tgagcattca tcaggcgggc aagaatgtga   5340
ataaaggccg gataaaactt gtgcttattt tctttacgg tctttaaaaa ggccgtaata    5400
tccagctgaa cggtctggtt ataggtacat tgagcaactg actgaaatgc ctcaaaatgt   5460
tctttacgat gccattggga tatatcaacg gtggtatatc cagtgatttt tttctccatt   5520
ttagcttcct tagctcctga aaatctcgat aactcaaaaa atacgcccgg tagtgatctt   5580
atttcattat ggtgaaagtt ggaacctctt acgtgccgat caacgtctca ttttcgccaa   5640
aagttggccc agggcttccc ggtatcaaca gggacaccag gatttattta ttctgcgaag   5700
tgatcttccg tcacaggtat ttattcggcg caaagtgcgt cgggtgatgc tgccaactta   5760
ctgatttagt gtatgatggt gttttgaag tgctccagtg cttctgtttt ctatcagctg    5820
tccctcctgt tcagctactg acggggtggt gcgtaacggc aaaagcaccg ccggacatca   5880
gcgctagcgg agtgtatact ggcttactat gttggcactg atgagggtgt cagtgaagtg   5940
cttcatgtgg caggagaaaa aaggctgcac cggtgcgtca gcagaatatg tgatacagga   6000
tatattccgc ttcctcgctc actgactcgc tacgctcggt cgttcgactg cggcgagcgg   6060
aaatggctta cgaacggggc ggagatttcc tggaagatgc caggaagata cttaacaggg   6120
aagtgagag                                                          6129
```

<210> SEQ ID NO 2
<211> LENGTH: 6540
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pETDuet_delta3_CYP2C19

<400> SEQUENCE: 2

| | | | | | |
|---|---|---|---|---|---|
| ttgaagcatt | tatcagggtt | attgtctcat | gagcggatac | atatttgaat | gtatttagaa | 60 |
| aaataaacaa | ataggtcatg | accaaaatcc | cttaacgtga | gttttcgttc | cactgagcgt | 120 |
| cagaccccgt | agaaaagatc | aaaggatctt | cttgagatcc | ttttttttctg | cgcgtaatct | 180 |
| gctgcttgca | acaaaaaaaa | ccaccgctac | cagcggtggt | ttgtttgccg | gatcaagagc | 240 |
| taccaactct | ttttccgaag | gtaactggct | tcagcagagc | gcagatacca | aatactgtcc | 300 |
| ttctagtgta | gccgtagtta | ggccaccact | tcaagaactc | tgtagcaccg | cctacatacc | 360 |
| tcgctctgct | aatcctgtta | ccagtggctg | ctgccagtgg | cgataagtcg | tgtcttaccg | 420 |
| ggttggactc | aagacgatag | ttaccggata | aggcgcagcg | gtcgggctga | acggggggtt | 480 |
| cgtgcacaca | gcccagcttg | gagcgaacga | cctacaccga | actgagatac | ctacagcgtg | 540 |
| agctatgaga | aagcgccacg | cttcccgaag | ggagaaaggc | ggacaggtat | ccggtaagcg | 600 |
| gcagggtcgg | aacaggagag | cgcacgaggg | agcttccagg | gggaaacgcc | tggtatcttt | 660 |
| atagtcctgt | cgggtttcgc | cacctctgac | ttgagcgtcg | atttttgtga | tgctcgtcag | 720 |
| gggggcggag | cctatggaaa | aacgccagca | acgcggcctt | tttacggttc | ctggcctttt | 780 |
| gctggccttt | tgctcacatg | ttctttcctg | cgttatcccc | tgattctgtg | gataaccgta | 840 |
| ttaccgcctt | tgagtgagct | gataccgctc | gccgcagccg | aacgaccgag | cgcagcgagt | 900 |
| cagtgagcga | ggaagcggaa | gagcgcctga | tgcggtattt | tctccttacg | catctgtgcg | 960 |
| gtatttcaca | ccgcaatggt | gcactctcag | tacaatctgc | tctgatgccg | catagttaag | 1020 |
| ccagtataca | ctccgctatc | gctacgtgac | tgggtcatgg | ctgcgccccg | acacccgcca | 1080 |
| acacccgctg | acgcgccctg | acgggcttgt | ctgctcccgg | catccgctta | cagacaagct | 1140 |
| gtgaccgtct | ccgggagctg | catgtgtcag | aggttttcac | cgtcatcacc | gaaacgcgcg | 1200 |
| aggcagctgc | ggtaaagctc | atcagcgtgg | tcgtgaagcg | attcacagat | gtctgcctgt | 1260 |
| tcatccgcgt | ccagctcgtt | gagtttctcc | agaagcgtta | atgtctggct | tctgataaag | 1320 |
| cgggccatgt | taagggcggt | tttttcctgt | ttggtcactg | atgcctccgt | gtaaggggga | 1380 |
| tttctgttca | tgggggtaat | gataccgatg | aaacgagaga | ggatgctcac | gatacgggtt | 1440 |
| actgatgatg | aacatgcccg | gttactggaa | cgttgtgagg | gtaaacaact | ggcggtatgg | 1500 |
| atgcggcggg | accagagaaa | aatcactcag | ggtcaatgcc | agcgcttcgt | taatacagat | 1560 |
| gtaggtgttc | cacagggtag | ccagcagcat | cctgcgatgc | agatccggaa | cataatggtg | 1620 |
| cagggcgctg | acttccgcgt | ttccagactt | tacgaaacac | ggaaaccgaa | gaccattcat | 1680 |
| gttgttgctc | aggtcgcaga | cgttttgcag | cagcagtcgc | ttcacgttcg | ctcgcgtatc | 1740 |
| ggtgattcat | tctgctaacc | agtaaggcaa | ccccgccagc | ctagccgggt | cctcaacgac | 1800 |
| aggagcacga | tcatgctagt | catgccccgc | gcccaccgga | aggagctgac | tgggttgaag | 1860 |
| gctctcaagg | gcatcggtcg | agatcccggt | gcctaatgag | tgagctaact | tacattaatt | 1920 |
| gcgttgcgct | cactgcccgc | tttccagtcg | ggaaacctgt | cgtgccagct | gcattaatga | 1980 |

```
atcggccaac gcgcggggag aggcggtttg cgtattgggc gccagggtgg ttttctttt    2040
caccagtgag acgggcaaca gctgattgcc cttcaccgcc tggccctgag agagttgcag   2100
caagcggtcc acgctggttt gccccagcag gcgaaaatcc tgtttgatgg tggttaacgg   2160
cgggatataa catgagctgt cttcggtatc gtcgtatccc actaccgaga tgtccgcacc   2220
aacgcgcagc ccggactcgg taatggcgcg cattgcgccc agcgccatct gatcgttggc   2280
aaccagcatc gcagtgggaa cgatgccctc attcagcatt tgcatggttt gttgaaaacc   2340
ggacatggca ctccagtcgc cttcccgttc cgctatcggc tgaatttgat tgcgagtgag   2400
atatttatgc cagccagcca gacgcagacg cgccgagaca gaacttaatg ggcccgctaa   2460
cagcgcgatt tgctggtgac ccaatgcgac cagatgctcc acgcccagtc gcgtaccgtc   2520
ttcatgggag aaaataatac tgttgatggg tgtctggtca gagacatcaa gaaataacgc   2580
cggaacatta gtgcaggcag cttccacagc aatggcatcc tggtcatcca gcggatagtt   2640
aatgatcagc ccactgacgc gttgcgcgag aagattgtgc accgccgctt tacaggcttc   2700
gacgccgctt cgttctacca tcgacaccac cacgctggca cccagttgat cggcgcgaga   2760
tttaatcgcc gcgacaattt gcgacggcgc gtgcagggcc agactggagg tgcaacgcc   2820
aatcagcaac gactgtttgc ccgccagttg ttgtgccacg cggttgggaa tgtaattcag   2880
ctccgccatc gccgcttcca cttttttccg cgttttcgca gaaacgtggc tggcctggtt   2940
caccacgcgg gaaacggtct gataagagac accggcatac tctgcgacat cgtataacgt   3000
tactggtttc acattcacca ccctgaattg actctcttcc gggcgctatc atgccatacc   3060
gcgaaaggtt ttgcaccatt cgatggtgtc ctggcacgac aggtttcccg actggaaagc   3120
gggcagtgag cgcaacgcaa ttaatgtaag ttagctcact cattaggcac cccaggcttt   3180
acactttatg cttccggctc gtataatgtg tggaattgtg agcggataac aatttcacac   3240
aggaaacagg atcgatccat cgatgagctt actccccatc ccctgttga caattaatca   3300
tcggctcgta taatgtgtgg aattgtgagc ggataacaat ttcacacagg aaacaggatc   3360
agcttactcc ccatcccct gttgacaatt aatcatcggc tcgtataatg tgtgaattg   3420
tgagcggata acaatttcac acaggaaaca ggatccatcg atgcttagga ggtcatatgg   3480
ctcgacaatc ttctggacga ggaaaactcc ctcctggccc cactcctctc ccagtgattg   3540
gaaatatcct acagatagat attaaggatg tcagcaaatc cttaaccaat ctctcaaaaa   3600
tctatggccc tgtgttcact ctgtattttg gcctggaacg catggtggtg ctgcatggat   3660
atgaagtggt gaaggaagcc ctgattgatc ttggagagga gttttctgga agaggccatt   3720
tcccactggc tgaaagagct aacagaggat ttggaatcgt tttcagcaat ggaaagagat   3780
ggaaggagat ccggcgtttc tccctcatga cgctgcggaa ttttgggatg gggaagagga   3840
gcattgagga ccgtgttcaa gaggaagccc gctgccttgt ggaggagttg agaaaaacca   3900
aggcttcacc ctgtgatccc actttcatcc tgggctgtgc tccctgcaat gtgatctgct   3960
ccattatttt ccagaaacgt ttcgattata aagatcagca atttcttaac ttgatggaaa   4020
aattgaatga aaacatcagg attgtaagca ccccctggat ccagatatgc aataattttc   4080
ccactatcat tgattatttc ccgggaaccc ataacaaatt acttaaaaac cttgctttta   4140
tggaaagtga tattttggag aaagtaaaag aacaccaaga atcgatggac atcaacaacc   4200
ctcgggactt tattgattgc ttcctgatca aaatggagaa ggaaaagcaa aaccaacagt   4260
ctgaattcac tattgaaaac ttggtaatca ctgcagctga cttacttgga gctgggacag   4320
```

```
agacaacaag cacaaccctg agatatgctc tccttctcct gctgaagcac ccagaggtca    4380
cagctaaagt ccaggaagag attgaacgtg tcattggcag aaaccggagc ccctgcatgc    4440
aggacagggg ccacatgccc tacacagatg ctgtggtgca cgaggtccag agatacatcg    4500
acctcatccc caccagcctg ccccatgcag tgacctgtga cgttaaattc agaaactacc    4560
tcattcccaa gggcacaacc atattaactt ccctcacttc tgtgctacat gacaacaaag    4620
aatttcccaa cccagagatg tttgaccctc gtcactttct ggatgaaggt ggaaattttt a    4680
agaaaagtaa ctacttcatg cctttctcag caggaaaacg gatttgtgtg ggagagggcc    4740
tggcccgcat ggagctgttt ttattcctga ccttcatttt acagaacttt aacctgaaat    4800
ctctgattga cccaaaggac cttgacacaa ctcctgttgt caatggattt gcttctgtcc    4860
cgcccttcta tcagctgtgc ttcattcctg tctgactcga gtctggtaaa gaaaccgctg    4920
ctgcgaaatt tgaacgccag cacatggact cgtctactag cgcagcttaa ttaacctagg    4980
ctgctgccac cgctgagcaa taactagcat aaccccttgg ggcctctaaa cgggtcttga    5040
gggttttttt gctgaaagga ggaactatat ccggattggc gaatgggacg cgccctgtag    5100
cggcgcatta agcgcggcgg gtgtggtggt tacgcgcagc gtgaccgcta cacttgccag    5160
cgccctagcg cccgctcctt tcgctttctt cccttccttt ctcgccacgt tcgccggctt    5220
tccccgtcaa gctctaaatc gggggctccc tttagggttc cgatttagtg ctttacggca    5280
cctcgacccc aaaaaacttg attagggtga tggttcacgt agtgggccat cgccctgata    5340
gacggttttt cgccctttga cgttggagtc cacgttcttt aatagtggac tcttgttcca    5400
aactggaaca cactcaacc ctatctcggt ctattctttt gatttataag gattttgcc     5460
gatttcggcc tattggttaa aaaatgagct gatttaacaa aaatttaacg cgaattttaa    5520
caaaatatta cgtttacaa tttctggcgg cacgatggca tgagattatc aaaaaggatc    5580
ttcacctaga tccttttaaa ttaaaaatga agttttaaat caatctaaag tatatatgag    5640
taaacttggt ctgacagtta ccaatgctta atcagtgagg cacctatctc agcgatctgt    5700
ctatttcgtt catccatagt tgcctgactc cccgtcgtgt agataactac gatacgggag    5760
ggcttaccat ctggccccag tgctgcaatg ataccgcgag acccacgctc accggctcca    5820
gatttatcag caataaacca gccagccgga agggccgagc gcagaagtgg tcctgcaact    5880
ttatccgcct ccatccagtc tattaattgt tgccgggaag ctagagtaag tagttcgcca    5940
gttaatagtt tgcgcaacgt tgttgccatt gctacaggca tcgtggtgtc acgctcgtcg    6000
tttggtatgg cttcattcag ctccggttcc caacgatcaa ggcgagttac atgatccccc    6060
atgttgtgca aaaaagcggt tagctccttc ggtcctccga tcgttgtcag aagtaagttg    6120
gccgcagtgt tatcactcat ggttatggca gcactgcata attctcttac tgtcatgcca    6180
tccgtaagat gcttttctgt gactggtgag tactcaacca agtcattctg agaatagtgt    6240
atgcggcgac cgagttgctc ttgcccggcg tcaatacggg ataataccgc gccacatagc    6300
agaactttaa aagtgctcat cattggaaaa cgttcttcgg ggcgaaaact ctcaaggatc    6360
ttaccgctgt tgagatccag ttcgatgtaa cccactcgtg cacccaactg atcttcagca    6420
tcttttactt tcaccagcgt ttctgggtga gcaaaaacag gaaggcaaaa tgccgcaaaa    6480
aagggaataa gggcgacacg gaaatgttga atactcatac tcttcctttt tcaatcatga    6540
```

<210> SEQ ID NO 3
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
gaggatccga tgggagactc ccacgtg                                              27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagagtcgac ctagctccac acgtccag                                             28

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccatcgatca tatggctcga caatcttctg gacgaggaaa actccct                        47

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
attgagactc gagtcagaca ggaatgaagc aca                                       33
```

4,5-ANNULATED 1,2,4-TRIAZOLONES

CROSS REFERENCE TO RELATED APPLICATIONS

This application is a Divisional Application of U.S. application Ser. No. 16/345,178, filed Apr. 25, 2019, which is a U.S. national phase application, pursuant to 35 U.S.C. § 371, of PCT International Application Ser. No.: PCT/EP2017/077301, filed Oct. 25, 2017, designating the United States and published in English, which claims the benefit of and priority to PCT International Application Ser. No.: PCT/CN2016/103642, filed Oct. 27, 2016, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Jan. 28, 2021, is named 167741-016011US-DIV-20210128-SequenceListing.txt and is 18,348 bytes in size.

FIELD OF INVENTION

The present invention provides 4,5-a-annulated 1,2,4-triazolone compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative and/or inflammatory disorders, as a sole agent or in combination with other active ingredients.

BACKGROUND

The present invention provides 4,5-annulated 1,2,4-triazolone compounds of general formula (I) which inhibit Dihydroorotate Dehydrogenase (DHODH).

Acute myeloid leukemia (AML) is the most common acute leukemia in humans with a 5 year survival of only about 30%. AML is a malignancy of the myeloid line of blood cells. The incidence rates and chances of cure are highly age dependent. The chemotherapy standard of care for AML has not changed significantly over the last decades highlighting the need for novel therapies. A major hallmark of AML is differentiation arrest of the leukemic cells at early stages of cellular differentiation. The potential of leukemic differentiation therapy can be seen with the success of ATRA or arsenic trioxide inducing differentiation in acute promyelocytic leukemia (APL). Around 10% of AML belong to the APL subtype where leukemic cells are harbouring a chromosomal translocation resulting in fusions of oncoproteins involving the retinoic acid receptor. While treatment with ATRA or arsenic trioxide leads to a dramatic increase of patient survival, with overall survival rates of over 70%, unfortunately a comparable differentiation therapy for the non-APL AMLs is lacking (Management of acute promyelocytic leukemia: recommendations from an expert panel on behalf of the European LeukemiaNet, Sanz M. A. et al, Blood 2009, 113(9), 1875-1891). Therefore new therapies inducing differentiation of AML cells are of high interest and medical need.

Dihydroorotate Dehydroqenase (DHODH)

DHODH is located in the mitochondria and the enzyme responsible for the $4^{th}$ and rate limiting step in de novo pyrimidine synthesis converting dihydroorotate to orotate (Dihydroorotat-ubiquinone oxidoreductase links mitochondria in the biosynthesis of pyrimidine nucleotides, Löffler M. et al, Molecular and Cellular Biochemistry 1997, 174, 125-129).

As pyrimdine production is essential for DNA and RNA synthesis DHODH is highly important for cellular proliferation. The enzyme is considered an attractive drug target for cancer, immunological, parasitic and viral diseases and DHODH small molecule inhibitors like Leflunomide/Teriflunomide and Brequinar have been approved for clinical use in Rheumatoid Arthritis and Multiple Sclerosis. Additionally, preclinical studies indicate that DHODH inhibitors may be useful for the treatment of haematological cancer indications, for the treatment of solid tumors (e.g., neuroblastoma, melanoma, colon, breast and lung tumors), for the treatment of parasitic diseases (e.g., malaria), and for viral disease therapy.

U.S. Pat. No. 6,444,613 B1 relates to the field of defoliants, in particular thidiazuron-comprising mixtures, and their use in crops of cotton. These mixtures comprise among others 2,4,5-trisubstituted 1,2,4-triazolone compounds as herbicides, which inhibit the enzyme protoporphyrinogen-(IX) oxidase (PPO inhibitors).

WO199802422 describes substituted aromatic carbonyl compounds, among others 2,4,5-trisubstituted 1,2,4-triazolone compounds, as herbicides.

From CN106543139 some triazolone compounds are known as agrochemicals.

US 2016/0251341 A1 describes triazole compounds as serine protease inhibitors useful for the inhibition of thrombin and/or kallikrein.

WO 2013/186692 A1 describes triazolone compounds as mPGES-1 inhibitors, useful in the treatment of pain and/or inflammation from a variety of diseases or conditions, such as asthma, osteoarthritis, rheumatoid arthritis, acute or chronic pain and neurodegenerative diseases.

WO2010/077686 A1 describes sirtuin-modulating compounds, e.g. isoindolinone and related compounds, and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

DESCRIPTION OF THE INVENTION

It has now been found, and this partially constitutes the basis of the present invention, that the compounds of the present invention (e.g., 4,5-annulated 1,2,4-triazolone compounds of general formula (I)) have surprising and advantageous properties.

In particular, the compounds of the present invention have surprisingly been found to effectively inhibit DHODH and may therefore be used for the treatment or prophylaxis of disease including hyperproliferative and/or inflammatory disorders, such as cancer, for example.

In accordance with one aspect, the present invention provides compounds of general formula (I):

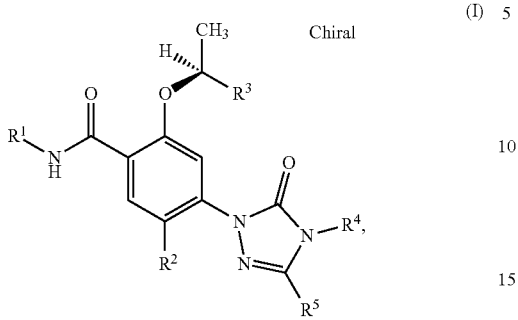

in which
R¹ represents a group selected from
  a $C_1$-$C_8$-alkyl group, which is optionally substituted with a group selected from $C_3$-$C_8$-cycloalkyl, phenyl and monocyclic or bicyclic heteroaryl,
    wherein said phenyl substituent is optionally substituted, one, two or three times with one or more substituents independently selected from a halogen atom, a $C_1$-$C_3$-alkyl group, a $C_1$-$C_4$-haloalkyl group, a $C_1$-$C_3$-alkoxy group and a hydroxy group,
  a $C_2$-$C_8$-haloalkyl group,
  a $C_3$-$C_8$-cycloalkyl group, which is optionally substituted, one or two times, each substituent independently selected from a halogen atom, a hydroxy group, a phenyl group and a —N(R⁷)(R⁸) group,
    wherein said phenyl substituent is optionally substituted, one, two or three times, each substituent independently selected from a halogen atom, a $C_1$-$C_3$-alkyl group, a $C_1$-$C_4$-haloalkyl group, a $C_1$-$C_3$-alkoxy group and a hydroxy group,
  a $C_2$-$C_6$-cyanoalkyl group,
  a $C_2$-$C_6$-hydroxyalkyl group,
  a ($C_2$-$C_6$-hydroxyalkyl)-O—($C_2$-$C_6$-alky)- group,
  a —($C_2$-$C_6$-alkyl)-N(R⁷)(R⁸) group,
  a —($C_1$-$C_6$-alkyl)-C(=O)N(R⁷)(R⁸) group,
  a 4- to 7-membered, optionally unsaturated, heterocyclic group, which is connected to the rest of the molecule via a carbon atom, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)₂($C_1$-$C_6$-alkyl) group and a oxo (=O) group,
    wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
  a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)OR⁶, —C(=O)N(R⁷)(R⁸), —N(R⁷)(R⁸), —($C_1$-$C_6$-alkyl)-N(R⁷)(R⁸), —($C_1$-$C_6$-alkyl)-C(=O)OR⁶, —($C_1$-$C_6$-alkyl)-C(=O)N(R⁷)(R⁸),), —SH, —S—($C_1$-$C_6$-alkyl), —S—($C_2$-$C_6$-alkenyl), —S(=O)₂N(R⁷)(R⁸), —S(=O)₂($C_1$-$C_6$-alkyl), —S(=O)₂—O—($C_2$-$C_6$-alkenyl), —S(=O)(=NR¹⁴)($C_1$-$C_3$-alkyl), —N(O)₂, —P(=O)($C_1$-$C_3$-alkyl)₂ and SF₅,
  or wherein two vicinal substituents of said phenyl groups may form together a 5- or 6-membered, optionally heterocyclic, aromatic or non-aromatic ring, having optionally 1-3 heteroatoms independently selected from —N=, —NH—, —N(R⁷)—, —O—, —S—, and optionally containing a C(=O) group, and wherein the so formed ring is optionally substituted one or two times, each substituent independently selected from a halogen atom or a group selected from
    $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)₂($C_1$-$C_6$-alkyl), —N(O)₂, and —N(R⁷)(R⁸)
  and
  a monocyclic or bicyclic heteroaryl group which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(=O)OR⁶, hydroxy, —SH, —S—($C_1$-$C_6$-alkyl), —S—($C_2$-$C_6$-alkenyl), —S(=O)₂($C_1$-$C_6$-alkyl), —N(O)₂, and —N(R⁷)(R⁸),
R² represents a hydrogen atom or a halogen atom,
R³ represents a group selected from
  a $C_1$-$C_6$-alkyl group,
  a $C_3$-$C_8$-cycloalkyl group,
  a $C_1$-$C_6$-haloalkyl group,
  a $C_1$-$C_6$-hydroxyalkyl group,
  a $C_2$-$C_6$-alkenyl group,
  a $C_2$-$C_6$-alkinyl group,
  a $C_4$-$C_8$-cycloalkenyl group,
  a ($C_1$-$C_6$-alkyl)-N(R⁷)R⁸ group,
  a —($C_1$-$C_6$-alkyl)-N(H)C(=O)R⁶ group,
  a —($C_1$-$C_6$-alkyl)-N(H)C(=O)OR¹⁵ group,
  a —($C_1$-$C_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and, wherein said 4- to 7-membered nitrogen containing heterocycloalkyl group is optionally substituted with a $C_1$-$C_3$-alkyl group,
  and
  a phenyl group,
    which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR⁶, hydroxy, —SH, —S—($C_1$-$C_6$-alkyl), —S—($C_2$-$C_6$-alkenyl), —S(=O)₂($C_1$-$C_6$-alkyl), —N(O)₂, and —N(R⁷)(R⁸), R⁴ and R⁵ jointly form a 5- to 6-membered, optionally unsaturated, heterocyclic ring A of partial formula (i)

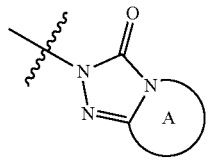

(i)

whereby ring A in addition to the two mandatory atoms, the nitrogen atom and the carbon atom bridging the two rings, bears additional 3 to 6 members selected from —O—, —S—, —S(=O)—, —S(=O)₂—, —S(=O)(=NR¹⁴)—, —N=, —N(R⁷)—, —C(=O)—, —CH=, —CR¹¹=, —C(R¹²)₂—, —C(H)(R¹³)—, R⁶ represents a hydrogen atom or a group selected from a $C_1$-$C_6$-alkyl group and a benzyl group, R⁷ and R³ represent, independently from each occurrence, a hydrogen atom or a group selected from
a $C_1$-$C_6$-alkyl group, a $C_2$-$C_6$-alkenyl group, a $C_2$-$C_6$-hydroxyalkyl group, a haloalkyl group, a aryl group, a ($C_1$-$C_6$-alkyl)-aryl group, and a —($C_2$-$C_6$-alkyl)-N(R⁹)(R¹⁰) group, or R⁷ and R⁸ together with the nitrogen to which they are attached represent a nitrogen containing 4- to 7-membered heterocycloalkyl group,
wherein said 4- to 7-membered nitrogen containing heterocycloalkyl group is optionally substituted with a group selected from
$C_1$-$C_6$-alkyl, —S—($C_1$-$C_6$-alkyl), —S—($C_2$-$C_6$-alkenyl), —S(=O)₂($C_1$-$C_3$-alkyl), —S(=O)₂—($C_2$-$C_6$-alkenyl), and —C(=O)OR⁶—, R⁹ and R¹⁰ represent, independently from each occurrence, a hydrogen atom or a $C_1$-$C_3$-alkyl group, or R⁹ and R¹⁰ together with the nitrogen to which they are attached represent a nitrogen containing 4- to 7-membered heterocycloalkyl group, R¹¹ represents, independently from each occurrence a hydrogen atom, a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR⁶—, hydroxy, —SH, —S—($C_1$-$C_6$-alkyl), —S—($C_2$-$C_6$-alkenyl), S(=O)₂($C_1$-$C_6$-alkyl), —S(=O)₂—($C_2$-$C_6$-alkenyl), —N(O)₂, and —N(R⁷)(R⁸)

R¹² represents, independently from each occurrence, a hydrogen atom, a halogen atom or a $C_1$-$C_3$-alkyl group, R¹³ represents a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR⁶—, hydroxy, —SH, —S—($C_1$-$C_6$-alkyl), —S—($C_2$-$C_6$-alkenyl), S(=O)₂($C_1$-$C_6$-alkyl), —S(=O)₂—($C_2$-$C_6$-alkenyl), —N(O)₂, and —N(R⁷)(R⁸), R¹⁴ represents a hydrogen atom or a group selected from a cyano group and a —C(=O)($C_1$-$C_3$-haloalkyl) group, R¹⁵ represents a group selected from
a $C_1$-$C_6$-alkyl group and a benzyl group, or a tautomer, an N-oxide, or a salt thereof, or a salt of a tautomer or an N-oxide of said compound.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_3$-alkoxy)-($C_1$-$C_6$-alkyl)-, it is possible for the position of a given part to be at any suitable position of said composite substituent, i.e. the $C_1$-$C_3$-alkoxy part can be attached to any carbon atom of the $C_1$-$C_6$-alkyl part of said ($C_1$-$C_3$-alkoxy)-($C_1$-$C_6$alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings: The term "halogen atom" means a fluorine, chlorine, bromine or iodine atom, particularly a fluorine, chlorine or bromine atom.

The term "$C_1$-$C_8$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl, 1,3-dimethylbutyl, heptyl or octyl group, or an isomer thereof. Particularly, said group has 1, 2, 3, 4, 5 or 6 carbon atoms ("$C_1$-$C_6$-alkyl"), e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-hydroxyalkyl" means a linear or branched, saturated, monovalent hydrocarbon group in which the term "$C_1$-$C_6$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methylpropyl, 2-hydroxy-2-methyl-propyl, 1-hydroxy-2-methyl-propyl group. Particularly, said group has 1, 2 or 3 carbon atoms ("$C_1$-$C_3$-hydroxyalkyl"), e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl or 1,3-dihydroxypropan-2-yl group.

The term "$C_1$-$C_6$-alkylsulfanyl" means a linear or branched, saturated, monovalent group of formula ($C_1$-$C_6$-alkyl)-S—, in which the term "$C_1$-$C_6$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "$C_2$-$C_8$-haloalkyl" means a linear or branched, saturated, monovalent hydrocarbon group in which the term "$C_2$-$C_8$-alkyl" is as defined supra, and in which one or more of the hydrogen atoms are replaced, identically or differently, with a halogen atom. Particularly, said halogen atom is a fluorine atom. Said $C_2$-$C_8$-haloalkyl group is, for example, 2-fluoroethyl, 2,2-difluoroethyl, 2,2,2-trifluoroethyl, pentafluoroethyl, 3,3,3-trifluoropropyl or 1,3-difluoropropan-2-yl. Particularly, said group has 2, 3, 4 5 or 6 carbon atoms ("$C_2$-$C_6$-haloalkyl").

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl. Particularly, said group has 1, 2, 3 or 4 carbon atoms ("$C_1$-$C_4$-haloalkyl"), more particularly 1, 2 or 3 carbon atoms ("$C_1$-$C_3$-haloalkyl"), e.g. fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof. Particularly, said group has 1, 2 or 3 carbon atoms ("$C_1$-$C_3$-alkoxy"), e.g. a methoxy, ethoxy, n-propoxy or isopropoxy group.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy. Particularly, said group has 1, 2 or 3 carbon atoms ("$C_1$-$C_3$-haloalkoxy"), e.g. a fluoromethoxy, difluoromethoxy, trifluoromethoxy, 2,2,2-trifluoroethoxy or pentafluoroethoxy group.

The term "$C_2$-$C_6$-alkenyl" means a linear or branched, monovalent hydrocarbon group, which contains one double bond, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, or 1-(1,1-dimethylethyl)ethenyl group. Particularly, said group is allyl.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group.

The term "$C_3$-$C_8$-cycloalkyl" means a saturated, monovalent, mono- or bicyclic hydrocarbon ring which contains 3, 4, 5, 6, 7 or 8 carbon atoms ("$C_1$-$C_3$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl. Particularly, said group contains 3, 4, 5 or 6 carbon atoms ("$C_3$-$C_6$-cycloalkyl"), e.g. a cyclopropyl, cyclobutyl, cyclopentyl or cyclohexyl group. Particularly, said group contains 4, 5, 6, 7 or 8 carbon atoms ("$C_4$-$C_8$-cycloalkyl"), e.g. a cyclobutyl, cyclopentyl, cyclohexyl, cycloheptyl or cyclooctyl group.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g. a cyclobutenyl, cyclopentenyl, cyclohexenyl, cycloheptenyl or cyclooctenyl group, or a bicyclic hydrocarbon ring, e.g. a bicyclo[2.2.1]hept-2-enyl or bicyclo[2.2.2]oct-2-enyl.

The term "$C_3$-$C_8$-cycloalkoxy" means a saturated, monovalent, mono- or bicyclic group of formula ($C_3$-$C_8$-cycloalkyl)-O—, which contains 3, 4, 5, 6, 7 or 8 carbon atoms, in which the term "$C_3$-$C_8$-cycloalkyl" is defined supra, e.g. a cyclopropyloxy, cyclobutyloxy, cyclopentyloxy, cyclohexyloxy, cycloheptyloxy or cyclooctyloxy group. Particularly, said group has 3, 4, 5 or 6 carbon atoms ("$C_3$-$C_8$-cycloalkoxy"), e.g. a cyclopropyloxy, cyclobutyloxy, cyclopentyloxy or cyclohexyloxy group.

The terms "4- to 7-membered heterocycloalkyl" and "4- to 6-membered heterocycloalkyl" mean a monocyclic, saturated heterocycle with 4, 5, 6 or 7 or, respectively, 4, 5 or 6 ring atoms in total, which contains one or two identical or different ring heteroatoms from the series N, O and S.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, dioxidotetrahydrothiopyranyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The terms "4- to 7-membered nitrogen containing heterocycloalkyl" and "4- to 6-membered nitrogen containing heterocycloalkyl" mean a monocyclic, saturated heterocycle with 4, 5, 6 or 7 or, respectively, 4, 5 or 6 ring atoms in total, containing one ring nitrogen atom and optionally one further ring heteroatom from the series: N, O, S. atom.

Said nitrogen containing heterocycloalkyl group, without being limited thereto, can be a 4-membered ring, such as azetidinyl for example; or a 5-membered ring, such as pyrrolidinyl, imidazolidinyl, pyrazolidinyl, 1,2-oxazolidinyl, 1,3-oxazolidinyl or 1,3-thiazolidinyl, for example; or a 6-membered ring, such as piperidinyl, morpholinyl, thiomorpholinyl, piperazinyl or 1,2-oxazinanyl, for example, or a 7-membered ring, such as azepanyl, 1,4-diazepanyl or 1,4-oxazepanyl, for example.

The term "5- to 7-membered heterocycloalkenyl" means a monocyclic, unsaturated, non-aromatic heterocycle with 5, 6 or 7 ring atoms in total, which contains one or two double bonds and one or two identical or different ring heteroatoms from the series: N, O, S.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "4-7-membered, optionally unsaturated, heterocyclic group" includes the terms "4- to 7-membered heterocycloalkyl" and "5- to 7-membered heterocycloalkenyl".

The term "aryl" includes aromatic ring systems being mono- or bicyclic, especially phenyl and naphthyl.

The term "phenyl groups of which two vicinal substituents may form together a 5- or 6-membered, optionally aromatic or non-aromatic ring, and optionally containing a C(=O) group" and specifically includes naphthalinyl, indanyl and tetralinyl.

The term "heteroaryl" means a monovalent, monocyclic or bicyclic aromatic ring having 5, 6, 8, 9 or 10 ring atoms (a "5- to 10-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms. Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_8$" encompasses $C_1$, $C_2$, $C_3$, $C_4$, $C_5$, $C_6$, $C_7$, $C_8$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_8$, $C_2$-$C_7$, $C_2$-$C_6$, $C_2$-$C_5$, $C_2$-$C_4$, $C_2$-$C_3$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$;

"$C_1$-$C_3$" encompasses $C_1$, $C_2$, $C_3$, $C_1$-$C_3$, $C_1$-$C_2$ and $C_2$-$C_3$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_5$, $C_3$-$C_4$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl] oxy, [(nonafluorobutyl)-sulfonyl]oxy, (phenylsulfonyl)oxy, [(4-methylphenyl)sulfonyl]oxy, [(4-bromophenyl)sulfonyl] oxy, [(4-nitrophenyl)sulfonyl]oxy, [(2-nitrophenyl)sulfonyl] oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl) sulfonyl]oxy.

The term "substituent" refers to a group "substituted" on, e.g. an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline It is possible for the compounds of general formula (I) to exist as isotopic variants. The invention therefore includes one or more isotopic variant(s) of the compounds of general formula (I), particularly deuterium-containing compounds of general formula (I).

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$ $^{15}N$, $^{18}O$, $^{32}P$, $^{33}P$, $^{33}S$, $^{34}S$ $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound' or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

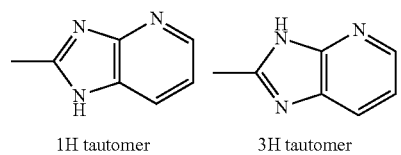

1H tautomer      3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also provides useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine,N-methylpiperidine,N-methyl-glucamine,N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

The present invention includes diastereomers, racemates, tautomers, N-oxides, hydrates, solvates, and salts of the compounds of the present invention, and mixtures of same.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF₃COOH", "x Na⁺", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with certain embodiments, the present invention provides compounds of general formula (I),

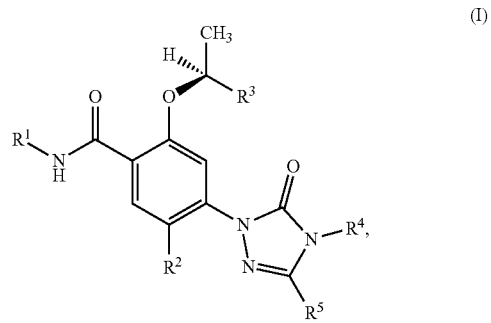

in which
R¹ represents a group selected from
   a $C_1$-$C_3$-alkyl group, which is optionally substituted with
     a group selected from $C_3$-$C_8$-cycloalkyl, phenyl and monocyclic or bicyclic heteroaryl, wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a $C_2$-$C_8$-haloalkyl group, a $C_3$-$C_8$-cycloalkyl group, which is optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-N($R^7$)($R^8$) group, a —($C_1$-$C_6$-alkyl)-C(=O)N($R^7$)($R^8$) group, a 4- to 7-membered, optionally unsaturated, heterocyclic group, which is connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$),), —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—O—($C_2$-$C_6$-alkenyl), —S(=O)(=N$R^{14}$)($C_1$-$C_3$-alkyl), —N(O)$_2$, —P(=O)($C_1$-$C_3$-alkyl)$_2$ and SF$_5$, or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)

and a monocyclic or bicyclic heteroaryl group, which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), $R^2$ represents a hydrogen atom or a halogen atom, $R^3$ represents a group selected from a $C_1$-$C_6$-alkyl group, a $C_3$-$C_8$-cycloalkyl group, a $C_1$-$C_6$-haloalkyl group, a $C_1$-$C_6$-hydroxyalkyl group, a $C_2$-$C_6$-alkenyl group, a $C_2$-$C_6$-alkinyl group a $C_4$-$C_8$-cycloalkenyl group, a ($C_1$-$C_6$-alkyl)-N($R^7$)$R^8$ group, a —($C_1$-$C_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and in which said 4- to 7-membered nitrogen containing heterocycloalkyl group is optionally substituted with a $C_1$-$C_3$-alkyl group, and a phenyl group, which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), $R^4$ and $R^5$ jointly form a 5- to 6-membered, optionally unsaturated, heterocyclic ring A of partial formula (i)

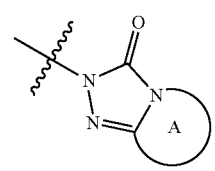

(i)

whereby ring A in addition to the two mandatory atoms, the nitrogen atom and the carbon atom bridging the two rings, bears additional 3 to 6 members selected from —O—, —S—, —S(=O)—, —S(=O)$_2$—, —N=, —N($R^7$)—, —C(=O)—, —CH=, —CR$^{11}$=, —C(R$^{12}$)$_2$—, —CHR$^{13}$—, R[6] represents a hydrogen atom or a group selected from
a $C_1$-$C_6$-alkyl group and a benzyl group, R[7] and R[8] represent, independently from each occurrence, a
hydrogen atom or a group selected from
a $C_1$-$C_6$-alkyl group, a $C_2$-$C_6$-alkenyl group, a $C_2$-$C_6$-hydroxyalkyl group, a haloalkyl group, an aryl group, a
($C_1$-$C_6$-alkyl)-aryl group, and a —($C_2$-$C_6$-alkyl)-N(R[9])(R[10]) group, or R[7] and R[8] together with the nitrogen to which they are
attached represent a nitrogen containing 4- to 7-membered heterocycloalkyl group,
wherein said 4- to 7-membered nitrogen containing heterocycloalkyl group is optionally substituted with a
group selected from
$C_1$-$C_6$-alkyl, —S—($C_1$-$C_6$-alkyl), —S—($C_2$-$C_6$-alkenyl), —S(=O)$_2$($C_1$-$C_3$-alkyl), —S(=O)$_2$—($C_2$-$C_6$-alkenyl), and —C(=O)OR[6]—, R[9] and R[10] represent, independently from each occurrence,
a hydrogen atom or a $C_1$-$C_3$-alkyl group,
or R[9] and R[10] together with the nitrogen to which they are
attached represent a nitrogen containing 4- to 7-membered heterocycloalkyl group, R[11] represents, independently from each occurrence a
hydrogen atom, a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR[6]—, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R[7])(R[8])

R[12] represents, independently from each occurrence, a
hydrogen atom, a halogen atom or
a $C_1$-$C_3$-alkyl group, R[13] represents a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR[6]—, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R[7])(R[8]), R[14] represents a hydrogen atom or a group selected from
a cyano group and a —C(=O)($C_1$-$C_3$-haloalkyl) group,
and tautomers, N-oxides, and salts thereof, or salts of
tautomers or N-oxides of said compounds.

In accordance with certain embodiments, the present
invention provides compounds of general formula (I),

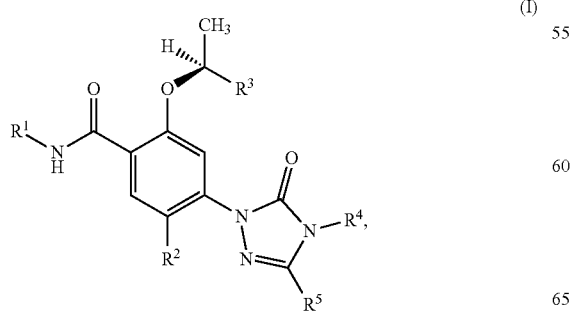

(I)

in which
R[1] represents a group selected from
a $C_1$-$C_3$-alkyl group, a $C_2$-$C_8$-haloalkyl group, a $C_3$-$C_8$-cycloalkyl group, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-N(R[7])(R[8]) group, a —($C_1$-$C_6$-alkyl)-C(=O)N(R[7])(R[8]) group, a 4- to
7-membered, optionally unsaturated, heterocyclic
group, a phenyl group, and a monocyclic or bicyclic
heteroaryl group,
wherein said $C_1$-$C_3$-alkyl group is optionally substituted with a group selected from
$C_3$-$C_8$-cycloalkyl, phenyl and monocyclic or bicyclic
heteroaryl, wherein said phenyl substituent is optionally substituted, one, two or three times, each substituent independently selected from a halogen atom
or a group selected from
$C_1$-$C_3$-alkyl, $C_1$-$C_4$-haloalkyl, $C_1$-$C_3$-alkoxy and
hydroxy, and
wherein said $C_3$-$C_8$-cycloalkyl group is optionally substituted, one or two times, each substituent independently selected from a halogen atom or a group
selected from
hydroxy, phenyl and —N(R[7])(R[8]),
wherein said phenyl substituent is optionally substituted, one, two or three times, each substituent
independently selected from a halogen atom or a
group selected from
$C_1$-$C_3$-alkyl, $C_1$-$C_4$-haloalkyl, $C_1$-$C_3$-alkoxy and
hydroxy,
and
wherein said 4-7-membered, optionally unsaturated,
heterocyclic group, which is connected to the rest of
the molecule via a carbon atom, and which is optionally substituted one or two times, each substituent
independently selected from a group selected from
$C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and
oxo (=O),
wherein said 5- to 6-membered heteroaryl substituent is optionally substituted, one, two or three
times, each substituent independently selected
from a halogen atom or a group selected from
$C_1$-$C_3$-alkyl, $C_1$-$C_4$-haloalkyl, $C_1$-$C_3$-alkoxy and
hydroxy,
and
wherein said phenyl group is optionally substituted,
one, two, three, four or five times, each substituent
independently selected from a halogen atom or a
group selected from
$C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)OR[6], —C(=O)N(R[7])(R[8]), —N(R[7])(R[8]), —($C_1$-$C_6$-alkyl)-N(R[7])(R[8]), —($C_1$-$C_6$-alkyl)-C(=O)OR[6], —($C_1$-$C_6$-alkyl)-C(=O)N(R[7])(R[8]),), —SH, —S—($C_1$-$C_6$-alkyl), —S—($C_2$-$C_6$-alkenyl), —S(=O)$_2$N(R[7])(R[8]), —S(=O)$_2$($C_1$-$C_6$-alkyl), —S(=O)$_2$—O—($C_2$-$C_6$-alkenyl), —S(=O)(=NR[14])($C_1$-$C_3$-alkyl), —N(O)$_2$, —P(=O)($C_1$-$C_3$-alkyl)$_2$ and SF$_5$,
or wherein two vicinal substituents of said phenyl
groups may form together a 5- or 6-membered,
optionally heterocyclic, aromatic or non-aromatic ring, having optionally 1-3 heteroatoms independently selected from —N═, —NH—, —N(R$^7$)—, —O—, —S—, and optionally containing a C(═O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$—C-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(O)$_2$, —N(O)$_2$, and —N(R$^7$)(R$^8$) and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(═O)OR$^6$, hydroxy, —SH, —S—($C_1$-$C_6$-alkyl), —S—($C_2$-$C_6$-alkenyl), —S(O)$_2$, —N(O)$_2$, and —N(R$^7$)(R$^8$), $R^2$ represents a hydrogen atom or a halogen atom,
$R^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkinyl group,
a $C_4$-$C_8$-cycloalkenyl group, a ($C_1$-$C_6$-alkyl)-N(R$^7$)R$^8$ group,
a —($C_1$-$C_6$-alkyl)-(4- to 7-membered nitrogen containing heterocycloalkyl) group and
a phenyl group,
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(═O)OR$^6$, hydroxy, —SH, —S—($C_1$-$C_6$-alkyl), —S—($C_2$-$C_6$-alkenyl), —S(O)$_2$, —N(O)$_2$, and —N(R$^7$)(R$^8$), $R^4$ and $R^5$ jointly form a 5- to 6-membered, optionally unsaturated, heterocyclic ring A of partial formula (i)

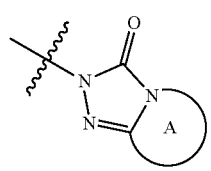

(i)

whereby ring A in addition to the two mandatory atoms, the nitrogen atom and the carbon atom bridging the two rings, bears additional 3 to 6 members selected from —O—, —S—, —S(═O)—, —S(═O)$_2$—, —N═, —N(R$^7$)—, —C(═O)—, —CH═, —CR$^{11}$═, —C(R$^{12}$)$_2$—, —CHR$^{13}$—, $R^6$ represents a hydrogen atom or a group selected from
a $C_1$-$C_6$-alkyl group and a benzyl group,
$R^7$ and $R^8$ represent, independently from each occurrence, a hydrogen atom or a group selected from
a $C_1$-$C_6$-alkyl group, a $C_2$-$C_6$-alkenyl group, a $C_2$-$C_6$-hydroxyalkyl group, a haloalkyl group, a aryl group, a ($C_1$-$C_6$-alkyl)-aryl group, and a —($C_2$-$C_6$-alkyl)-N(R$^9$)(R$^{10}$) group, or $R^7$ and $R^8$ together with the nitrogen to which they are attached represent a nitrogen containing 4- to 7-membered heterocycloalkyl group,
wherein said 4- to 7-membered nitrogen containing heterocycloalkyl group is optionally substituted with a group selected from
$C_1$-$C_6$-alkyl, —S—($C_1$-$C_6$-alkyl), —S—($C_2$-$C_6$-alkenyl), —S(═O)$_2$($C_1$-$C_3$-alkyl), —S(═O)$_2$—($C_2$-$C_6$-alkenyl), and —C(═O)OR$^6$—, $R^9$ and $R^{10}$ represent, independently from each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents, independently from each occurrence a hydrogen atom, a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(═O)OR$^6$—, hydroxy, —SH, —S—($C_1$-$C_6$-alkyl), —S—($C_2$-$C_6$-alkenyl), S(═O)$_2$($C_1$-$C_6$-alkyl), —S(═O)$_2$—($C_2$-$C_6$-alkenyl), —N(O)$_2$, and —N(R$^7$)(R$^8$)

$R^{12}$ represents, independently from each occurrence, a hydrogen atom, a halogen atom or a $C_1$-$C_3$-alkyl group, $R^{13}$ represents a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(═O)OR$^6$—, hydroxy, —SH, —S—($C_1$-$C_6$-alkyl), —S—($C_2$-$C_6$-alkenyl), S(═O)$_2$($C_1$-$C_6$-alkyl), —S(═O)$_2$—($C_2$-$C_6$-alkenyl), —N(O)$_2$, and —N(R$^7$)(R$^8$), $R^{14}$ represents a hydrogen atom or a group selected from
a cyano group and a —C(═O)($C_1$-$C_3$-haloalkyl) group,
and tautomers, N-oxides, or salts thereof, and salts of tautomers or N-oxides of said compound.

In accordance with certain embodiments, the present invention provides compounds of general formula (I), supra, in which:

$R^1$ represents a group selected from
a $C_1$-$C_3$-alkyl group, which is optionally substituted with a group selected from $C_3$-$C_8$-cycloalkyl, phenyl and monocyclic or bicyclic heteroaryl,
wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a $C_2$-$C_8$-haloalkyl group, a $C_3$-$C_8$-cycloalkyl group, which is optionally substituted, one or two times, each substituent independently selected from a halogen atom, a hydroxy group, a phenyl group and a —N($R^7$)($R^8$) group,
  wherein said phenyl substituent is optionally substituted, one, two or three times, each substituent independently selected from a halogen atom, a $C_1$-$C_3$-alkyl group, a $C_1$-$C_4$-haloalkyl group, a $C_1$-$C_3$-alkoxy group and a hydroxy group, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-N($R^7$)($R^8$) group, a —($C_1$-$C_6$-alkyl)-C(=O)N($R^7$)($R^8$) group, a 4- to 7-membered heterocycloalkyl group, which is connected to the rest of the molecule via a carbon atom of said 4- to 7-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group,
  wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a 5- to 7-membered heterocycloalkenyl group, which is connected to the rest of the molecule via a carbon atom of said 5- to 7-membered heterocycloalkenyl group and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group,
  wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N(R)($R^8$), —N(R)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{14}$)($C_1$-$C_3$-alkyl), —P(=O)($C_1$-$C_3$-alkyl)$_2$ and SF$_5$,
  or in which two substituents of said phenyl group, when they are attached to adjacent ring atoms, are optionally linked to one another in such a way that they jointly form a group selected from —CH$_2$—N(R)—CH$_2$—, —CH$_2$—O—CH$_2$—, —O—CH$_2$—C(=O)—NH— and —NH—C(=O)—NH—, an indanyl group, a tetralinyl group wherein said indanyl- or tetralinyl group is optionally substituted one or two times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N($R^7$)($R^8$) group, and a monocyclic or bicyclic heteroaryl group, which is optionally substituted one, two or three times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N($R^7$)($R^8$) group, $R^2$ represents a hydrogen atom or a chlorine atom or a fluorine atom, $R^3$ represents a group selected from a $C_1$-$C_6$-alkyl group, a $C_3$-$C_8$-cycloalkyl group, a $C_1$-$C_6$-haloalkyl group, a $C_1$-$C_6$-hydroxyalkyl group, a $C_2$-$C_6$-alkenyl group, a $C_2$-$C_6$-alkinyl group, a $C_4$-$C_8$-cycloalkenyl group, a ($C_1$-$C_6$-alkyl)-N($R^7$)$R^8$ group, a —($C_1$-$C_6$-alkyl)-N(H)C(=O)$R^6$ group, a —($C_1$-$C_6$-alkyl)-N(H)C(=O)O$R^{15}$ group, a —($C_1$-$C_6$-alkyl)-(4- to 7-membered nitrogen containing heterocycloalkyl) group wherein said 4- to 7-membered nitrogen containing heterocycloalkyl group is optionally substituted with a $C_1$-$C_3$-alkyl group, and
  wherein said 4- to 7-membered nitrogen containing heterocycloalkyl group is connected to the alkyl group via a carbon atom of the heterocycloalkyl group, and a phenyl group, which is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, $R^4$ and $R^5$ are linked to one another in such a way that they jointly form a group selected from

*—CH$_2$—X$^1$—X$^2$—#,

*—CH$_2$—X$^1$—X$^2$—X$^3$—#,

*—CH$_2$—X$^1$—X$^2$—X$^3$—X$^4$—#,

*—CH$_2$—X$^1$—X$^2$—X$^3$—X$^4$—X$^5$—#,

*—CH($R^{13}$)—X$^1$—X$^2$—X$^3$—#,

*—CH=CH—CH($R^{13}$)—X$^3$—#,

*—CH=C($R^{11}$)—C($R^{11}$)=C($R^{11}$)—#,

*—N=C($R^{11}$)—C($R^{11}$)=C($R^{11}$)—#,

*—CH=N—C($R^{11}$)=C($R^{11}$)—#,

*—CH=C($R^{11}$)—N=C($R^{11}$)—#, and

*—CH=C($R^{11}$)—C($R^{11}$)=N—#, in which groups "*" represents the point of attachment of $R^4$ to the rest of the molecule, and "#" represents the point of attachment of $R^5$ to the rest of the molecule, and one of $X^1$, $X^2$, $X^3$, $X^4$ and $X^5$ represents a group selected from C($R^{12}$)$_2$ and CH($R^{13}$), and the remaining of $X^1$, $X^2$, $X^3$, $X^4$ and $X^5$ each represent a CH$_2$ group, or one of $X^1$, $X^2$, $X^3$, $X^4$ and $X^5$ represents a group selected from —N($R^7$)—, —O—, —S—, —S(=O)—, —S(=O)(=N$R^{14}$)— and —S(=O)$_2$—, and one of $X^1$, $X^2$, $X^3$, $X^4$ and $X^5$ represents a group selected from $C(R^{12})_2$ and $CH(R^{13})$, and the remaining of $X^1$, $X^2$, $X^3$, $X^4$ and $X^5$ each represent a $CH_2$ group, $R^6$ represents a hydrogen atom or a group selected from a $C_1$-$C_6$-alkyl group and a benzyl group, $R^7$ and $R^8$ represent, independently from each occurrence, a hydrogen atom or a group selected from a $C_1$-$C_6$-alkyl group, a $C_2$-$C_6$-hydroxyalkyl group and a —($C_2$-$C_6$-alkyl)-$N(R^9)(R^{10})$ group, or $R^7$ and $R^8$ together with the nitrogen to which they are attached represent a nitrogen containing 4- to 7-membered heterocycloalkyl group, wherein said 4- to 7-membered nitrogen containing heterocycloalkyl group is optionally substituted with a group selected from $C_1$-$C_3$-alkyl, —$S(=O)_2(C_1$-$C_3$-alkyl) and —$C(=O)O(C_1$-$C_4$-alkyl), $R^9$ and $R^{10}$ represent, independently from each occurrence, a hydrogen atom or a $C_1$-$C_3$-alkyl group, or $R^9$ and $R^{10}$ together with the nitrogen to which they are attached represent a nitrogen containing 4- to 7-membered heterocycloalkyl group, $R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group, $R^{12}$ represents, independently from each occurrence, a hydrogen atom, a halogen atom or a $C_1$-$C_3$-alkyl group, $R^{13}$ represents a group selected from a hydroxy group, a —$C(=O)OR^6$ group and a —$C(=O)N(R^7)(R)$ group, $R^{14}$ represents a hydrogen atom or a group selected from a cyano group and a —$C(=O)(C_1$-$C_3$-haloalkyl) group, $R^{15}$ represents a group selected from a $C_1$-$C_6$-alkyl group and a benzyl group, or a tautomer, an N-oxide, or a salt thereof, or a salt of a tautomer or an N-oxide of said compound.

In accordance with certain embodiments, the present invention provides compounds of general formula (I), supra, in which:

$R^1$ represents a group selected from a $C_1$-$C_3$-alkyl group, a $C_2$-$C_8$-haloalkyl group, a $C_3$-$C_8$-cycloalkyl group, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-$N(R^7)(R^8)$ group, a —($C_1$-$C_6$-alkyl)-$C(=O)N(R^7)(R^8)$ group, a 4- to 7-membered heterocycloalkyl group, a 5- to 7-membered heterocycloalkenyl group, a phenyl group, an indanyl group, a tetralinyl group and a monocyclic or bicyclic heteroaryl group, wherein said $C_1$-$C_3$-alkyl group is optionally substituted with a group selected from $C_3$-$C_8$-cycloalkyl, phenyl and monocyclic or bicyclic heteroaryl, wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said $C_3$-$C_8$-cycloalkyl group is optionally substituted, one or two times, each substituent independently selected from a halogen atom or a group selected from hydroxy, phenyl and —$N(R^7)(R^8)$, wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and 5- to 7-membered heterocycloalkenyl group, which are connected to the rest of the molecule via a carbon atom of said 4- to 7-membered heterocycloalkyl group and of said 5- to 7-membered heterocycloalkenyl group, and which are optionally substituted one or two times, each substituent independently selected from a group selected from $C_1$-$C_3$-alkyl, 5- to 6-membered heteroaryl, —$C(=O)O(C_1$-$C_4$-alkyl), —$C(=O)(C_1$-$C_6$-alkyl), —$C(=O)(C_3$-$C_6$-cycloalkyl), —$S(=O)_2(C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said phenyl group is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —$C(=O)OR^6$, —$C(=O)N(R^7)(R^8)$, —$N(R^7)(R^8)$, —($C_1$-$C_6$-alkyl)-$N(R^7)(R^8)$, —($C_1$-$C_6$-alkyl)-$C(=O)OR^6$, —($C_1$-$C_6$-alkyl)-$C(=O)N(R^7)(R^8)$, —$S(=O)_2N(R^7)(R^8)$, —$S(=O)_2(C_1$-$C_3$-alkyl), —$S(=O)(=NR^{14})(C_1$-$C_3$-alkyl), —$P(=O)(C_1$-$C_3$-alkyl)_2$ and $SF_5$, or in which two substituents of said phenyl group, when they are attached to adjacent ring atoms, are optionally linked to one another in such a way that they jointly form a group selected from —$CH_2$—$N(R^7)$—$CH_2$—, —$CH_2$—O—$CH_2$—, —O—$CH_2$—$C(=O)$—NH— and —NH—C(=O)—NH—, wherein said indanyl- or tetralinyl group is optionally substituted one or two times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —$N(R^7)(R^8)$, and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), $R^2$ represents a hydrogen atom or a fluorine atom, $R^3$ represents a group selected from
- a $C_1$-$C_6$-alkyl group, a $C_3$-$C_8$-cycloalkyl group, a $C_1$-$C_6$-haloalkyl group,
- a $C_1$-$C_6$-hydroxyalkyl group, a $C_2$-$C_6$-alkenyl group, a $C_2$-$C_6$-alkinyl group,
- a $C_4$-$C_8$-cycloalkenyl group, a ($C_1$-$C_6$-alkyl)-N($R^7$)$R^8$ group,
- a —($C_1$-$C_6$-alkyl)-(4- to 7-membered nitrogen containing heterocycloalkyl) group and a phenyl group,
  wherein said 4- to 7-membered nitrogen containing heterocycloalkyl group is optionally substituted with a $C_1$-$C_3$-alkyl group,
  and
  wherein said 4- to 7-membered nitrogen containing heterocycloalkyl group is connected to the alkyl group via a carbon atom of the heterocycloalkyl group,
  and
  wherein said phenyl group is optionally substituted, one, two or three times, each substituent independently selected from a halogen atom or a group selected from
  $C_1$-$C_3$-alkyl, $C_1$-$C_4$-haloalkyl, $C_1$-$C_3$-alkoxy and hydroxy, $R^4$ and $R^5$ are linked to one another in such a way that they jointly form a group selected from
- *—$CH_2$—$X^1$—$X^2$—#,
- *—$CH_2$—$X^1$—$X^2$—$X^3$—#,
- *—$CH_2$—$X^1$—$X^2$—$X^3$—$X^4$—#,
- *—$CH_2$—$X^1$—$X^2$—$X^3$—$X^4$—$X^5$—#,
- *—CH=C($R^{11}$)—C($R^{11}$)=C($R^{11}$)—#,
- *—N=C($R^{11}$)—C($R^{11}$)=C($R^{11}$)—#,
- *—CH=N—C($R^{11}$)=C($R^{11}$)—#,
- *—CH=C($R^{11}$)—N=C($R^{11}$)—#,
and
- *—CH=C($R^{11}$)—C($R^{11}$)=N—#, in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
  $C(R^{12})_2$ and CH($R^{13}$),
  and the remaining of $X^1$, $X^2$, $X^3$, $X^4$ and $X^5$ each represent a $CH_2$ group,
  or
  one of $X^1$, $X^2$, $X^3$, $X^4$ and $X^5$ represents a group selected from
  —N($R^7$)—, —O—, —S—, —S(=O)— and —S(=O)$_2$—,
  and one of $X^1$, $X^2$, $X^3$, $X^4$ and $X^5$ represents a group selected from
  $C(R^{12})_2$ and CH($R^{13}$),
  and the remaining of $X^1$, $X^2$, $X^3$, $X^4$ and $X^5$ each represent a $CH_2$ group, $R^6$ represents a hydrogen atom or a group selected from
a $C_1$-$C_6$-alkyl group and a benzyl group, $R^7$ and $R^8$ represent, independently from each occurrence, a hydrogen atom or a group selected from
a $C_1$-$C_6$-alkyl group, a $C_2$-$C_6$-hydroxyalkyl group and a —($C_2$-$C_6$-alkyl)-N($R^9$)($R^{10}$) group, or $R^7$ and $R^8$ together with the nitrogen to which they are attached represent a nitrogen containing 4- to 7-membered heterocycloalkyl group,
  wherein said 4- to 7-membered nitrogen containing heterocycloalkyl group is optionally substituted with a group selected from
  $C_1$-$C_3$-alkyl, —S(=O)$_2$($C_1$-$C_3$-alkyl) and —C(=O)O($C_1$-$C_4$-alkyl), $R^9$ and $R^{10}$ represent, independently from each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents, independently from each occurrence a hydrogen atom, a halogen atom or a group selected from
a $C_1$-$C_3$-alkyl group, a $C_1$-$C_3$-haloalkyl group, a $C_1$-$C_3$-alkoxy group, a $C_1$-$C_3$-haloalkoxy group and a cyano group, $R^{12}$ represents, independently from each occurrence, a hydrogen atom, a halogen atom or
a $C_1$-$C_3$-alkyl group, $R^{13}$ represents a group selected from
a hydroxy group, a —C(=O)O$R^6$ group and a —C(=O)N($R^7$)($R^8$) group, $R^{14}$ represents a hydrogen atom or a group selected from
a cyano group and a —C(=O)($C_1$-$C_3$-haloalkyl) group,
or a tautomer, an N-oxide, or a salt thereof, and a salt of a tautomer or an N-oxide.

In accordance with certain embodiments, the present invention provides compounds of general formula (I), supra, in which:

$R^1$ represents a group selected from
a $C_1$-$C_6$-alkyl group, which is optionally substituted with a group selected from $C_3$-$C_6$-cycloalkyl, phenyl and monocyclic or bicyclic heteroaryl,
  wherein said phenyl substituent is optionally substituted, one, two or three times, each substituent independently selected from a halogen atom, a $C_1$-$C_3$-alkyl group, a $C_1$-$C_3$-haloalkyl group, a $C_1$-$C_3$-alkoxy group and a hydroxy group,
a $C_2$-$C_6$-haloalkyl group,
a $C_3$-$C_6$-cycloalkyl group, which is optionally substituted, one or two times, each substituent independently selected from a halogen atom, a hydroxy group, a phenyl group and a —N($R^7$)($R^8$) group,
  wherein said phenyl substituent is optionally substituted, one, two or three times, each substituent independently selected from a halogen atom, a $C_1$-$C_3$-alkyl group, a $C_1$-$C_3$-haloalkyl group, a $C_1$-$C_3$-alkoxy group and a hydroxy group,
a $C_2$-$C_6$-cyanoalkyl group,
a $C_2$-$C_6$-hydroxyalkyl group, a ($C_2$-$C_8$-hydroxyalkyl)-O—($C_2$-$C_6$-alky)- group,
a —($C_2$-$C_6$-alkyl)-N($R^7$)($R^8$) group,
a —($C_1$-$C_6$-alkyl)-C(=O)N($R^7$)($R^8$) group,
a 4- to 6-membered heterocycloalkyl group, which is connected to the rest of the molecule via a carbon atom of said 4- to 6-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and oxo (=O) group,
  wherein said 5- to 6-membered heteroaryl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, a 5- to 6-membered heterocycloalkenyl group, which is connected to the rest of the molecule via a carbon atom of said 5- to 6-membered heterocycloalkenyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and oxo (=O) group, and wherein said 5- to 6-membered heteroaryl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_3$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —($C_1$-$C_3$-alkyl)-C(=O)OR$^6$, —($C_1$-$C_3$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$, or in which two substituents of said phenyl group, when they are attached to adjacent ring atoms, are optionally linked to one another in such a way that they jointly form a group selected from
—CH$_2$—N(R$^7$)—CH$_2$—, —CH$_2$—O—CH$_2$—, —O—CH$_2$—C(=O)—NH— and —NH—C(=O)—NH—, an indanyl group, a tetralinyl group which are optionally substituted one or two times, each substituent independently selected from a halogen atom, a $C_1$-$C_3$-alkyl group, a $C_1$-$C_3$-haloalkyl group, a $C_3$-$C_6$-cycloalkyl group, a $C_1$-$C_3$-alkoxy group, a $C_1$-$C_3$-haloalkoxy group, a $C_3$-$C_6$-cycloalkoxy group, a cyano group, a hydroxy group and a —N(R$^7$)(R$^8$) group, and a monocyclic or bicyclic heteroaryl group,
which is optionally substituted one, two or three times, each substituent independently selected from a halogen atom, a $C_1$-$C_3$-alkyl group, a $C_1$-$C_3$-haloalkyl group, a $C_3$-$C_6$-cycloalkyl group, a $C_1$-$C_3$-alkoxy group, a $C_1$-$C_3$-haloalkoxy group, a $C_3$-$C_6$-cycloalkoxy group, a cyano group, a hydroxy group and a —N(R$^7$)(R$^8$) group, $R^2$ represents a hydrogen atom or a chlorine atom or a fluorine atom, $R^3$ represents a group selected from
a $C_1$-$C_6$-alkyl group, a $C_3$-$C_6$-cycloalkyl, a $C_1$-$C_6$-haloalkyl group,
a $C_1$-$C_6$-hydroxyalkyl group, a $C_2$-$C_6$-alkenyl, a $C_2$-$C_6$-alkinyl group,
a $C_4$-$C_6$-cycloalkenyl group, a ($C_1$-$C_6$-alkyl)-N(R$^7$)R$^8$ group,
a —($C_1$-$C_6$-alkyl)-N(H)C(=O)R$^6$ group, a —($C_1$-$C_6$-alkyl)-N(H)C(=O)OR$^{15}$ group,
a —($C_1$-$C_6$-alkyl)-(4- to 6-membered nitrogen containing heterocycloalkyl) group and a phenyl group,
wherein said 4- to 6-membered nitrogen containing heterocycloalkyl group is optionally substituted with a $C_1$-$C_3$-alkyl group,
and
wherein said 4- to 6-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy, $R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH(R$^{13}$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
or
one of X$^1$, X$^2$, X$^3$, X$^4$ and X$^5$ represents a group selected from
—N(R$^7$)—, —O—, —S—, —S(=O)—, —S(=O)(=NR$^{14}$)— and —S(=O)$_2$—,
and one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group, R$^6$ represents a hydrogen atom or a group selected from
a $C_1$-$C_4$-alkyl group and a benzyl group, R$^7$ and R$^8$ represent, independently from each occurrence, a hydrogen atom or a group selected from
a $C_1$-$C_3$-alkyl group, a $C_2$-$C_8$-hydroxyalkyl group and a —($C_2$-$C_8$-alkyl)-N(R$^9$)(R$^{10}$), or R$^7$ and R$^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from $C_1$-$C_3$-alkyl, —S(=O)$_2$($C_1$-$C_3$-alkyl) and —C(=O)O($C_1$-$C_4$-alkyl), R$^9$ and R$^{10}$ represent, independently from each occurrence, a hydrogen atom or a $C_1$-$C_3$-alkyl group,
or $R^9$ and $R^{10}$ together with the nitrogen to which they are attached represent a nitrogen containing 4- to 6-membered heterocycloalkyl group, $R^{11}$ represents, independently from each occurrence, a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group, $R^{12}$ represents, independently from each occurrence, a hydrogen atom, a halogen atom or a $C_1$-$C_3$-alkyl group, $R^{13}$ represents a group selected from
a hydroxy group, a —C(=O)OR$^6$ group and a —C(=O)N(R$^7$)(R$^8$) group, $R^{14}$ represents a hydrogen atom or a group selected from a cyano group and a —C(=O)($C_1$-$C_3$-haloalkyl) group, $R^{15}$ represents a group selected from
a $C_1$-$C_4$-alkyl group and a benzyl group, or a tautomer, an N-oxide, or a salt thereof, or a salt of a tautomer or an N-oxide of said compound.

In accordance with certain embodiments, the present invention provides compounds of general formula (I), supra, in which:

$R^1$ represents a group selected from
a $C_1$-$C_6$-alkyl group, a $C_2$-$C_6$-haloalkyl group, a $C_3$-$C_6$-cycloalkyl group, a $C_2$-$C_6$-cyanoalkyl group, a $C_2$-$C_6$-hydroxyalkyl group, a ($C_2$-$C_8$-hydroxyalkyl)-O—($C_2$-$C_6$-alky)- group, a —($C_2$-$C_6$-alkyl)-N(R$^7$)(R$^8$) group, a —($C_1$-$C_6$-alkyl)-C(=O)N(R$^7$)(R$^8$) group, a 4- to 6-membered heterocycloalkyl group, a 5-6-membered heterocycloalkenyl group, a phenyl group, an indanyl group, a tetralinyl group and a monocyclic or bicyclic heteroaryl group, wherein said $C_1$-$C_6$-alkyl group is optionally substituted with a group selected from
$C_3$-$C_6$-cycloalkyl, phenyl and monocyclic or bicyclic heteroaryl,
wherein said phenyl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said $C_3$-$C_6$-cycloalkyl group is optionally substituted, one or two times, each substituent independently selected from a halogen atom or a group selected from
hydroxy, phenyl and —N(R$^7$)(R$^8$),
wherein said phenyl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy, and
wherein said 4- to 6-membered heterocycloalkyl group and said 5- to 6-membered heterocycloalkenyl group, which are connected to the rest of the molecule via a carbon atom of said 4- to 6-membered heterocycloalkyl group and said heterocycloalkenyl group, are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy,
and
wherein said phenyl group is optionally substituted, one, two, three, four or five times, each substituent independently selected from a halogen atom or a group selected from
$C_1$-$C_3$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —($C_1$-$C_3$-alkyl)-C(=O)OR$^6$, —($C_1$-$C_3$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$),
or in which two substituents of said phenyl group, when they are attached to adjacent ring atoms, are optionally linked to one another in such a way that they jointly form a group selected from
—CH$_2$—N(R$^7$)—CH$_2$—, —CH$_2$—O—CH$_2$—, —O—CH$_2$—C(=O)—NH— and —NH—C(=O)—NH—, and
wherein said indanyl- or tetralinyl group is optionally substituted one or two times, each substituent independently selected from a halogen atom or a group selected from
$C_1$-$C_3$-alkyl, $C_1$-$C_3$-haloalkyl, $C_3$-$C_6$-cycloalkyl, $C_1$-$C_3$-alkoxy,
$C_1$-$C_3$-haloalkoxy, $C_3$-$C_6$-cycloalkoxy, cyano, hydroxy and —N(R$^7$)(R$^8$),
and
wherein said monocyclic or bicyclic heteroaryl group is optionally substituted one, two or three times, each substituent independently selected from a halogen atom or a group selected from
$C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$), $R^2$ represents a hydrogen atom or a fluorine atom,
$R^3$ represents a group selected from
a $C_1$-$C_6$-alkyl group, a $C_3$-$C_6$-cycloalkyl, a $C_1$-$C_6$-haloalkyl group,
a $C_1$-$C_6$-hydroxyalkyl group, a $C_2$-$C_6$-alkenyl, a $C_2$-$C_6$-alkinyl group,
a $C_4$-$C_6$-cycloalkenyl group, a ($C_1$-$C_6$-alkyl)-N(R$^7$)R$^8$ group,
a —($C_1$-$C_6$-alkyl)-(4- to 6-membered nitrogen containing heterocycloalkyl) group and a phenyl group,
wherein said 4- to 6-membered nitrogen containing heterocycloalkyl group is optionally substituted with a $C_1$-$C_3$-alkyl group,
and
wherein said 4- to 6-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, $R^4$ and $R^5$ are linked to one another in such a way that they jointly form a group selected from

*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—CH=C($R^{11}$)—C($R^{11}$)=C($R^{11}$)—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#, and

*—CH=C($R^{11}$)—C($R^{11}$)=N—#, in which groups "*" represents the point of attachment of $R^4$ to the rest of the molecule, and "#" represents the point of attachment of $R^5$ to the rest of the molecule, and in which groups one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a $CH_2$ group, or one of $X^1$, $X^2$, $X^3$, $X^4$ and $X^5$ represents a group selected from
—N($R^7$)—, —O—, —S—, —S(=O)— and —S(=O)$_2$—,
and one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a $CH_2$ group, $R^6$ represents a hydrogen atom or a group selected from a $C_1$-$C_4$-alkyl group and a benzyl group, $R^7$ and $R^8$ represent, independently from each occurrence, a hydrogen atom or a group selected from
a $C_1$-$C_3$-alkyl group, a $C_2$-$C_8$-hydroxyalkyl group and a —($C_2$-$C_8$-alkyl)-N($R^9$)($R^{10}$), or $R^7$ and $R^8$ together with the nitrogen to which they are attached represent a nitrogen containing 4- to 6-membered heterocycloalkyl group, wherein said 4- to 6-membered nitrogen containing heterocycloalkyl group is optionally substituted with a group selected from $C_1$-$C_3$-alkyl, —S(=O)$_2$($C_1$-$C_3$-alkyl) and —C(=O)O($C_1$-$C_4$-alkyl), $R^9$ and $R^{10}$ represent, independently from each occurrence, a hydrogen atom or a $C_1$-$C_3$-alkyl group, or $R^9$ and $R^{10}$ together with the nitrogen to which they are attached represent a nitrogen containing 4- to 6-membered heterocycloalkyl group, $R^{11}$ represents, independently from each occurrence, a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group, $R^{12}$ represents, independently from each occurrence, a hydrogen atom, a halogen atom or a $C_1$-$C_3$-alkyl group, $R^{13}$ represents a group selected from
a hydroxy group, a —C(=O)O$R^6$ group and a —C(=O)N($R^7$)(R) group, $R^{14}$ represents a hydrogen atom or a group selected from a cyano group and a —C(=O)($C_1$-$C_3$-haloalkyl) group, and tautomers, N-oxides, and salts thereof, and salts of tautomers or N-oxides.

In accordance with certain embodiments, the present invention provides compounds of general formula (I), supra, in which: $R^1$ represents a group selected from a $C_3$-$C_6$-cycloalkyl group, which is optionally substituted, one or two times, each substituent independently selected from a halogen atom, a phenyl group and -a N($R^7$)($R^8$) group, wherein said phenyl substituent is optionally substituted, one, two or three times, each substituent independently selected from a halogen atom, a $C_2$-$C_6$-hydroxyalkyl group, a —($C_2$-$C_6$-alkyl)-N($R^7$)($R^8$) group, a 4- to 6-membered heterocycloalkyl group, which is connected to the rest of the molecule via a carbon atom of said 4- to 6-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group, a phenyl group, which is optionally substituted, one, two, three or four times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a cyano group, a hydroxy group, a —C(=O)O$R^6$ group, a —C(=O)N($R^7$)($R^8$)group, a —N($R^7$)($R^8$) group, a —($C_1$-$C_3$-alkyl)-N($R^7$)($R^8$) group, a —S(=O)$_2$N($R^7$)($R^8$) group and a $SF_5$ group, or in which two substituents of said phenyl group, when they are attached to adjacent ring atoms, are optionally linked to one another in such a way that they jointly form a group selected from —$CH_2$—N($R^7$)—$CH_2$— and —O—$CH_2$—C(=O)—NH—, an indanyl group which is optionally substituted with a hydroxy group and a monocyclic or bicyclic heteroaryl group, which is optionally substituted one, two or three times, each substituent independently selected from a halogen atom, a $C_1$-$C_3$-alkyl group, a $C_1$-$C_3$-alkoxy group, a hydroxy group and a —N($R^7$)($R^8$) group, $R^2$ represents a hydrogen atom or a chlorine atom or a fluorine atom, $R^3$ represents a group selected from a $C_1$-$C_6$-alkyl group, a $C_3$-$C_6$-cycloalkyl group, a $C_1$-$C_6$-haloalkyl group, a $C_1$-$C_6$-hydroxyalkyl group, a $C_2$-$C_6$-alkenyl group, ($C_1$-$C_6$-alkyl)-N($R^7$)$R^8$ group, a —($C_1$-$C_6$-alkyl)-N(H)C(=O)O$R^{15}$ group and a phenyl group, $R^4$ and $R^5$ are linked to one another in such a way that they jointly form a group selected from

*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—CH($R^{13}$)—$X^1$—$X^2$—$X^3$—#,
*—CH=CH—CH($R^{13}$)—$X^3$—#,

*—CH=C(R$^{11}$)—C(R$^{11}$)=C(R$^{11}$)—#,

*—N=C(R$^{11}$)—C(R$^{11}$)=C(R$^{11}$)—#, and

*—CH=C(R$^{11}$)—N=C(R$^{11}$)—#, in which groups "*" represents the point of attachment of R$^4$ to the rest of the molecule, and "#" represents the point of attachment of R$^5$ to the rest of the molecule, and in which groups one of X$^1$, X$^2$, X$^3$ and X$^4$ represents a group selected from C(R$^{12}$)$_2$ and CH(R$^{13}$), and the remaining of X$^1$, X$^2$, X$^3$ and X$^4$ each represent a CH$_2$ group, or one of X$^1$, X$^2$, X$^3$ and X$^4$ represents a group selected from —N(R$^7$)—, —O—, —S— and —S(=O)(=NR$^{14}$)—, X$^1$, X$^2$, X$^3$ and X$^4$ represents a C(R$^{12}$)$_2$ group, and the remaining of X$^1$, X$^2$, X$^3$ and X$^4$ each represent a CH$_2$ group, R$^6$ represents a hydrogen atom or a group selected from a C$_1$-C$_4$-alkyl group and a benzyl group, R$^7$ and R$^8$ represent, independently from each occurrence, a hydrogen atom or a C$_1$-C$_3$-alkyl group, or R$^7$ and R$^8$ together with the nitrogen to which they are attached represent a nitrogen containing 4- to 6-membered heterocycloalkyl group, R$^{11}$ represents a hydrogen atom, R$^{12}$ represent, identically or differently, a hydrogen atom, a halogen atom or a C$_1$-C$_3$-alkyl group, R$^{13}$ represents a group selected from a hydroxy group and a —C(=O)OR$^6$ group, R$^{14}$ represents a hydrogen atom or a group selected from a cyano group and a —C(=O)CF$_3$ group, R$^{15}$ represents a C$_1$-C$_4$-alkyl group, or a tautomer, an N-oxide, or a salt thereof, or a salt of a tautomer or an N-oxide of said compound.

In accordance with certain embodiments, the present invention provides compounds of general formula (I), supra, in which:

R$^1$ represents a group selected from a C$_3$-C$_6$-cycloalkyl group, a C$_2$-C$_6$-hydroxyalkyl group, a —(C$_2$-C$_6$-alkyl)-N(R$^7$)(R$^8$) group, a 4- to 6-membered heterocycloalkyl group, a phenyl group, an indanyl group and a monocyclic or bicyclic heteroaryl group, wherein said C$_3$-C$_6$-cycloalkyl group is optionally substituted, one or two times, each substituent independently selected from a halogen atom or a group selected from phenyl and —N(R$^7$)(R$^8$), wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from C$_1$-C$_3$-alkyl, 5- to 6-membered heteroaryl, —C(=O)O(C$_1$-C$_4$-alkyl), —C(=O)(C$_1$-C$_3$-alkyl), —C(=O)(C$_3$-C$_6$-cycloalkyl), —S(=O)$_2$(C$_1$-C$_3$-alkyl) and oxo (=O), and wherein said phenyl group is optionally substituted, one, two, three or four times, each substituent independently selected from a halogen atom or a group selected from C$_1$-C$_3$-alkyl, C$_1$-C$_3$-haloalkyl, C$_1$-C$_3$-hydroxyalkyl, C$_1$-C$_3$-alkoxy, cyano, —C(=O)OR$^6$, —C(=O)N(R$^7$)(R$^8$), —N(R$^7$)(R$^8$), —(C$_1$-C$_3$-alkyl)-N(R$^7$)(R$^8$), —S(=O)$_2$N(R$^7$)(R$^8$) and SF$_5$, or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—, and wherein said indanyl group is optionally substituted with a hydroxy group, and wherein said monocyclic or bicyclic heteroaryl group is optionally substituted one, two or three times, each substituent independently selected from a halogen atom or a group selected from C$_1$-C$_3$-alkyl, C$_1$-C$_3$-alkoxy, hydroxy and —N(R$^7$)(R$^8$), R$^2$ represents a hydrogen atom or a fluorine atom, R$^3$ represents a group selected from a C$_1$-C$_6$-alkyl group, a C$_3$-C$_6$-cycloalkyl group, a C$_1$-C$_6$-haloalkyl group, a C$_1$-C$_6$-hydroxyalkyl group, a C$_2$-C$_6$-alkenyl group, (C$_1$-C$_6$-alkyl)-N(R$^7$)R$^8$ and a phenyl group, R$^4$ and R$^5$ are linked to one another in such a way that they jointly form a group selected from

*—CH$_2$—X$^1$—X$^2$—#,

*—CH$_2$—X$^1$—X$^2$—X$^3$—#,

*—CH$_2$—X$^1$—X$^2$—X$^3$—X$^4$—#,

*—CH=C(R$^{11}$)—C(R$^{11}$)=C(R$^{11}$)—#,

*—N=C(R$^{11}$)—C(R$^{11}$)=C(R$^{11}$)—#, and

*—CH=C(R$^{11}$)—N=C(R$^{11}$)—#, in which groups "*" represents the point of attachment of R$^4$ to the rest of the molecule, and "#" represents the point of attachment of R$^5$ to the rest of the molecule, and in which groups one of X$^1$, X$^2$, X$^3$ and X$^4$ represents a group selected from C(R$^{12}$)$_2$ and CH(R$^{13}$), and the remaining of X$^1$, X$^2$, X$^3$ and X$^4$ each represent a CH$_2$ group, or one of X$^1$, X$^2$, X$^3$ and X$^4$ represents a group selected from —N(R$^7$)—, —O— and —S—, X$^1$, X$^2$, X$^3$ and X$^4$ represents a C(R$^{12}$)$_2$ group, and the remaining of X$^1$, X$^2$, X$^3$ and X$^4$ each represent a CH$_2$ group, R$^6$ represents a hydrogen atom or a group selected from a C$_1$-C$_4$-alkyl group and a benzyl group, $R^7$ and $R^8$ represent, independently from each occurrence, a
hydrogen atom or
a $C_1$-$C_3$-alkyl group, or
$R^7$ and $R^8$ together with the nitrogen to which they are
attached represent a nitrogen containing 4- to 6-membered heterocycloalkyl group,
$R^{11}$ represent a hydrogen atom,
$R^{12}$ represent, identically or differently, a hydrogen atom, a
halogen atom or
a $C_1$-$C_3$-alkyl group,
$R^{13}$ represents a group selected from
a hydroxy group and a —C(=O)O$R^6$ group,
and tautomers, N-oxides, and salts thereof, and salts of tautomers or N-oxides.

In accordance with certain embodiments, the present invention provides compounds of general formula (I), supra, in which:
$R^1$ represents a group selected from
a $C_3$-$C_6$-cycloalkyl group, which is selected from cyclopropyl and cyclohexyl, and which is optionally substituted, one or two times, each substituent independently selected from a halogen atom, a phenyl group and a —N($R^7$)($R^8$) group,
wherein said phenyl substituent is optionally substituted, one, two or three times, each substituent independently selected from a halogen atom,
a $C_2$-$C_6$-hydroxyalkyl group,
a —($C_2$-$C_6$-alkyl)-N($R^7$)($R^8$) group,
a 4- to 6-membered heterocycloalkyl group, which is connected to the rest of the molecule via a carbon atom of said 4- to 6-membered heterocycloalkyl group, and which is selected from azetidinyl, oxetanyl, tetrahydro-2H-pyranyl, tetrahydro-2H-thiopyranyl and piperidinyl, and which is optionally substituted one or two times, each substituent independently selected from a $C_1$-$C_3$-alky group,
a 5- to 6-membered heteroaryl group, a —C(=O)O ($C_1$-$C_4$-alkyl) group,
a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group,
a phenyl group, which is optionally substituted, one, two or three times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a hydroxy group, a cyano group, a —C(=O)O$R^6$ group, a —C(=O)N ($R^7$)($R^8$) group, a —N($R^7$)($R^8$) group, a —($C_1$-$C_3$-alkyl)-N($R^7$)($R^8$) group, a —S(=O)$_2$N($R^7$)($R^8$) group and a SF$_5$ group,
or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—,
an indanyl group which is optionally substituted with a hydroxy group
and
a monocyclic or bicyclic heteroaryl group,
which is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, and
which is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), $R^2$ represents a hydrogen atom or a chlorine atom or a fluorine atom,
$R^3$ represents a group selected from
a $C_1$-$C_6$-alkyl group, a $C_3$-$C_6$-cycloalkyl group, a $C_1$-$C_6$-haloalkyl group,
a $C_1$-$C_6$-hydroxyalkyl group, a $C_2$-$C_6$-alkenyl group, a ($C_1$-$C_6$-alkyl)-N($R^7$)$R^8$ group,
a —($C_1$-$C_6$-alkyl)-N(H)C(=O)O$R^{15}$ and a phenyl group,
$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH($R^{13}$)—X$^1$—X$^2$—X$^3$—#,
*—CH=CH—CH($R^{13}$)—X$^3$—#,
*—CH=C($R^{11}$)—C($R^{11}$)=C($R^{11}$)—#,
*—N=C($R^{11}$)—C($R^{11}$)=C($R^{11}$)—#,
and
*—CH=C($R^{11}$)—N=C($R^{11}$)—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$ and X$^4$ represents a group selected from
C($R^{12}$)$_2$ and CH($R^{13}$),
and the remaining of X$^1$, X$^2$, X$^3$ and X$^4$ each represent a CH$_2$ group,
or
one of X$^1$, X$^2$, X$^3$ and X$^4$ represents a group selected from
—N($R^7$)—, —O—, —S— and —S(=O)(=NH)—,
and one of X$^1$, X$^2$, X$^3$ and X$^4$ represents a C($R^{12}$)$_2$ group,
and the remaining of X$^1$, X$^2$, X$^3$ and X$^4$ each represent a CH$_2$ group,
$R^6$ represents a hydrogen atom or a group selected from
a $C_1$-$C_4$-alkyl group and a benzyl group,
$R^7$ and $R^8$ represent, independently from each occurrence, a hydrogen atom or
a $C_1$-$C_3$-alkyl group, or
$R^7$ and $R^8$ together with the nitrogen to which they are attached represent a nitrogen containing 4- to 6-membered heterocycloalkyl group,
$R^{11}$ represents a hydrogen atom,
$R^{12}$ represent, identically or differently, a hydrogen atom, a halogen atom or
a $C_1$-$C_3$-alkyl group,
$R^{13}$ represents a group selected from
a hydroxy group and a —C(=O)O$R^6$ group,
$R^{15}$ represents a $C_1$-$C_4$-alkyl group,
or a tautomer, an N-oxide, or a salt thereof, or a salt of a tautomer or an N-oxide of said compound.

In accordance with certain embodiments, the present invention provides compounds of general formula (I), supra, in which:
$R^1$ represents a group selected from
a $C_3$-$C_6$-cycloalkyl group, a $C_2$-$C_6$-hydroxyalkyl group, a —($C_2$-$C_6$-alkyl)-N($R^7$)($R^8$) group,
a 4- to 6-membered heterocycloalkyl group, a phenyl group, an indanyl group and
a monocyclic or bicyclic heteroaryl group,
wherein said $C_3$-$C_6$-cycloalkyl group is selected from cyclopropyl and cyclohexyl, which $C_3$-$C_6$-cycloalkyl group is optionally substituted, one or two times, each substituent independently selected from a halogen atom or a group selected from phenyl and —N($R^7$)($R^8$),
wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is selected from azetidinyl, oxetanyl, tetrahydro-2H-pyranyl, tetrahydro-2H-thiopyranyl and piperidinyl, which 4- to 6-membered heterocycloalkyl group is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), and wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, and wherein said indanyl group is optionally substituted with a hydroxy group, and wherein said monocyclic or bicyclic heteroaryl group is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, which monocyclic or bicyclic heteroaryl group is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), $R^2$ represents a hydrogen atom or a fluorine atom, $R^3$ represents a group selected from a $C_1$-$C_6$-alkyl group, a $C_3$-$C_6$-cycloalkyl group, a $C_1$-$C_6$-haloalkyl group, a $C_1$-$C_6$-hydroxyalkyl group, a $C_2$-$C_6$-alkenyl group, a ($C_1$-$C_6$-alkyl)-N($R^7$)$R^8$ group and a phenyl group, $R^4$ and $R^5$ are linked to one another in such a way that they jointly form a group selected from

*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH=C($R^{11}$)—C($R^{11}$)=C($R^{11}$)—#,
*—N=C($R^{11}$)—C($R^{11}$)=C($R^{11}$)—#,
and
*—CH=C($R^{11}$)—N=C($R^{11}$)—#, in which groups "*" represents the point of attachment of $R^4$ to the rest of the molecule, and "#" represents the point of attachment of $R^5$ to the rest of the molecule, and in which groups one of $X^1$, $X^2$, $X^3$ and $X^4$ represents a group selected from C($R^{12}$)$_2$ and CH($R^{13}$), and the remaining of $X^1$, $X^2$, $X^3$ and $X^4$ each represent a CH$_2$ group, or one of $X^1$, $X^2$, $X^3$ and $X^4$ represents a group selected from —N($R^7$)—, —O— and —S—, and one of $X^1$, $X^2$, $X^3$ and $X^4$ represents a C($R^{12}$)$_2$ group, and the remaining of $X^1$, $X^2$, $X^3$ and $X^4$ each represent a CH$_2$ group, $R^6$ represents a hydrogen atom or a group selected from a $C_1$-$C_4$-alkyl group and a benzyl group, $R^7$ and $R^8$ represent, independently from each occurrence, a hydrogen atom or a $C_1$-$C_3$-alkyl group, or $R^7$ and $R^8$ together with the nitrogen to which they are attached represent a nitrogen containing 4- to 6-membered heterocycloalkyl group, $R^{11}$ represent a hydrogen atom, $R^{12}$ represent, identically or differently, a hydrogen atom, a halogen atom or a $C_1$-$C_3$-alkyl group, $R^{13}$ represents a group selected from a hydroxy group and a —C(=O)O$R^6$ group, and tautomers, N-oxides, and salts thereof, and salts of tautomers or N-oxides.

In accordance with certain embodiments, the present invention provides compounds of general formula (I), supra, in which:

$R^1$ represents a group selected from a $C_3$-$C_6$-cycloalkyl group, which is selected from a cyclopropyl group and a cyclohexyl group,
which $C_3$-$C_6$-cycloalkyl group is optionally substituted, one or two times, each substituent independently selected from a fluorine atom, a phenyl group and a dimethylamino group,
wherein said phenyl substituent is optionally substituted with a fluorine atom a 2-hydroxy-2-methylpropyl group, a 2-(dimethylamino)ethyl group, a 4- to 6-membered heterocycloalkyl group, which is selected from azetidin-3-yl, oxetan-3-yl, tetrahydro-2H-pyran-4-yl, tetrahydro-2H-thiopyran-4-yl and piperidin-4-yl, and which is optionally substituted one or two times, each substituent independently selected from a group selected from a methyl group, an ethyl group, a pyrazinyl group, a tert-butoxycarbonyl group, a acetyl group, a 1-cyclopropanecarbonyl group, a methylsulfonyl group and a oxo (=O) group, a phenyl group, which is optionally substituted, one, two or three times, each substituent independently selected from a fluorine atom, a chlorine atom, a methyl group, an ethyl group, a difluoromethyl group, a trifluoromethyl group, a hydroxymethyl group, a methoxy group, a hydroxy group, a cyano group, a —C(=O)OH group, a —C(=O)OCH$_3$ group, a —C(=O)OC(CH$_3$)$_3$ group, a —C(=O)NH$_2$ group, a —C(=O)N(CH$_3$)$_2$ group, an amino group, a methylamino group, an aminomethyl group, a —S(=O)$_2$NH$_2$ group and a SF$_5$ group, or in which two substituents of said phenyl group, when they are attached to adjacent ring atoms, are optionally linked to one another in such a way that they jointly form a group selected from —CH—CH$_2$—NH—CH$_2$— and —O—CH$_2$—C(=O)—NH—, a 2-hydroxyindan-1-yl group and a monocyclic or bicyclic heteroaryl group, which is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, and which is optionally substituted one, two or three times, each substituent independently selected from a fluorine atom, a chlorine atom, a methyl group, a methoxy group, a hydroxy group and a morpholin-4-yl group, R$^2$ represents a hydrogen atom or a chlorine atom or a fluorine atom, R$^3$ represents a group selected from propyl, cyclohexyl, trifluoromethyl, 1-hydroxyethyl, allyl, aminomethyl, (dimethylamino)methyl, (tert-butoxycarbonylamino)methyl, 2-(dimethylamino)ethyl, pyrrolidin-1-yl-methyl and phenyl, R$^4$ and R$^5$ are linked to one another in such a way that they jointly form a group selected from

*—(CH$_2$)$_2$—S—#,
*—(CH$_2$)$_4$—#,
*—CH$_2$—C(H)(C(=O)OH)—(CH$_2$)$_2$—#,
*—CH$_2$—CF$_2$—(CH$_2$)$_2$—#,
*—(CH$_2$)$_3$—C(H)(C(=O)OH)—#,
*—CH(OH)—(CH$_2$)$_3$—#,
*—CH$_2$—CH(OH)—(CH$_2$)$_2$—#,
*—(CH$_2$)$_2$—CH(OH)—CH$_2$—#,
*—(CH$_2$)$_3$—C(H)(OH)—#,
*—CH=CH—CH(OH)—CH$_2$—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#,
*—(CH$_2$)$_3$—S(=O)(=NH)—,#
*—(CH$_2$)$_5$—#,
*—(CH$_2$)$_3$O—CH$_2$—#,
*—(CH$_2$)$_2$—N(H)—(CH$_2$)$_2$—#
*—CH=CH—CH=CH—#,
*—N=CH—CH=CH—#,
and
*—CH=CH—N=CH—#, in which groups "*" represents the point of attachment of R$^4$ to the rest of the molecule, and "#" represents the point of attachment of R$^5$ to the rest of the molecule, or a tautomer, an N-oxide, or a salt thereof, or a salt of a tautomer or an N-oxide of said compound.

In accordance with certain embodiments, the present invention provides compounds of general formula (I), supra, in which:

R$^1$ represents a group selected from a C$_3$-C$_6$-cycloalkyl group, a 2-hydroxy-2-methylpropyl group, a 2-(dimethylamino)ethyl group, a 4- to 6-membered heterocycloalkyl group, a phenyl group, a 2-hydroxyindan-1-yl group and a monocyclic or bicyclic heteroaryl group, wherein said C$_3$-C$_6$-cycloalkyl group is selected from cyclopropyl and cyclohexyl, which C$_3$-C$_6$-cycloalkyl group is optionally substituted, one or two times, each substituent independently selected from a fluorine atom or a group selected from phenyl and dimethylamino, wherein said phenyl substituent is optionally substituted with a fluorine atom, and wherein said 4- to 6-membered heterocycloalkyl group is selected from azetidin-3-yl, oxetan-3-yl, tetrahydro-2H-pyran-4-yl, tetrahydro-2H-thiopyran-4-yl and piperidin-4-yl, which 4- to 6-membered heterocycloalkyl group is optionally substituted one or two times, each substituent independently selected from a group selected from methyl, ethyl, pyrazinyl, tert-butoxycarbonyl, acetyl, 1-cyclopropanecarbonyl, methylsulfonyl and oxo (=O), and wherein said phenyl group is optionally substituted, one, two or three times, each substituent independently selected from a fluorine atom or a chlorine atom or a group selected from methyl, ethyl, difluoromethyl, trifluoromethyl, hydroxymethyl, methoxy, cyano, —C(=O)OH, —C(=O)OCH$_3$, —C(=O)OC(CH$_3$)$_3$, —C(=O)NH$_2$, —C(=O)N(CH$_3$)$_2$, amino, methylamino, aminomethyl, —S(=O)$_2$NH$_2$ and SF$_5$, or in which two substituents of said phenyl group, when they are attached to adjacent ring atoms, are optionally linked to one another in such a way that they jointly form a group selected from —CH—CH$_2$—NH—CH$_2$— and —O—CH$_2$—C(=O)—NH—, and wherein said monocyclic or bicyclic heteroaryl group is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, which monocyclic or bicyclic heteroaryl group is optionally substituted one, two or three times, each substituent independently selected from a fluorine atom or a chlorine atom or a group selected from methyl, methoxy, hydroxy and morpholin-4-yl, R$^2$ represents a hydrogen atom or a fluorine atom, R$^3$ represents a group selected from propyl, cyclohexyl, trifluoromethyl, 1-hydroxyethyl, allyl, (dimethylamino)methyl, 2-(dimethylamino)ethyl, pyrrolidin-1-yl-methyl and phenyl, R$^4$ and R$^5$ are linked to one another in such a way that they jointly form a group selected from \*—$(CH_2)_2$—S—#,
\*—$(CH_2)_4$—#,
\*—$CH_2$—C(H)(C(=O)OH)—$(CH_2)_2$—#,
\*—$CH_2$—$CF_2$—$(CH_2)_2$—#,
\*—$(CH_2)_3$—C(H)(C(=O)OH)—#,
\*—$(CH_2)_3$—C(H)(OH)—#,
\*—$CH_2$—$C(CH_3)_2$—$CH_2$—O—#,
\*—$(CH_2)_2$—O—$CH_2$—#,
\*—$(CH_2)_3$—O—#,
\*—$(CH_2)_3$—$N(CH_3)$—#,
\*—$(CH_2)_3$—S—#
\*—$(CH_2)_5$—#,
\*—$(CH_2)_3$O—$CH_2$—#,
\*—$(CH_2)_2$—N(H)—$(CH_2)_2$—#
\*—CH=CH—CH=CH—#,
\*—N=CH—CH=CH—#,
and
\*—CH=CH—N=CH—#,
in which groups represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In accordance with further embodiments, the present invention provides the compounds of general formula (I), supra, which are exemplified in the experimental section.

In further embodiments, the present invention provides compounds of formula (I), supra, in which:
$R^1$ represents a group selected from
a $C_1$-$C_3$-alkyl group, which is optionally substituted with a group selected from $C_3$-$C_8$-cycloalkyl, phenyl and monocyclic or bicyclic heteroaryl,
wherein said phenyl substituent is optionally substituted, one, two or three times with one or more substituents independently selected from a halogen atom, a $C_1$-$C_3$-alkyl group, a $C_1$-$C_4$-haloalkyl group, a $C_1$-$C_3$-alkoxy group and a hydroxy group,
a $C_2$-$C_8$-haloalkyl group,
a $C_3$-$C_8$-cycloalkyl group, which is optionally substituted, one or two times, each substituent independently selected from a halogen atom, a hydroxy group, a phenyl group and a —$N(R^7)(R^8)$ group,
wherein said phenyl substituent is optionally substituted, one, two or three times, each substituent independently selected from a halogen atom, a $C_1$-$C_3$-alkyl group, a $C_1$-$C_4$-haloalkyl group, a $C_1$-$C_3$-alkoxy group and a hydroxy group,
a $C_2$-$C_6$-cyanoalkyl group,
a $C_2$-$C_6$-hydroxyalkyl group, a ($C_2$-$C_6$-hydroxyalkyl)-O—($C_2$-$C_6$-alky)- group,
a —($C_2$-$C_6$-alkyl)-$N(R^7)(R^8)$ group,
a —($C_1$-$C_6$-alkyl)-C(=O)$N(R^7)(R^8)$ group,
a 4- to 7-membered, optionally unsaturated, heterocyclic group, which is connected to the rest of the molecule via a carbon atom, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —$S(=O)_2$($C_1$-$C_6$-alkyl) group and a oxo (=O) group,
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)$OR^6$, —C(=O)$N(R^7)(R^8)$, —$N(R^7)(R^8)$, —($C_1$-$C_6$-alkyl)-$N(R^7)(R^8)$, —($C_1$-$C_6$-alkyl)-C(=O)$OR^6$, —($C_1$-$C_6$-alkyl)-C(=O)N$(R^7)(R^8)$,), —SH, —S—($C_1$-$C_6$-alkyl), —S—($C_2$-$C_6$-alkenyl), —$S(=O)_2N(R^7)(R^8)$, —$S(=O)_2$($C_1$-$C_6$-alkyl), —$S(=O)_2$—O—($C_2$-$C_6$-alkenyl), —S(=O)(=$NR^{14}$)($C_1$-$C_3$-alkyl), —$N(O)_2$, —P(=O)($C_1$-$C_3$-alkyl)$_2$ and $SF_5$,
or wherein two vicinal substituents of said phenyl groups may form together a 5- or 6-membered, optionally heterocyclic, aromatic or non-aromatic ring, having optionally 1-3 heteroatoms independently selected from —N=, —NH—, —$N(R^7)$—, —O—, —S—, and optionally containing a C(=O) group, and wherein the so formed ring is optionally substituted one or two times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_3$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —$S(=O)_2$($C_1$-$C_6$-alkyl), —$N(O)_2$, and —$N(R^7)(R^8)$
and
a monocyclic or bicyclic heteroaryl group which is optionally substituted one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(=O)$OR^6$, hydroxy, —SH, —S—($C_1$-$C_6$-alkyl), —S—($C_2$-$C_6$-alkenyl), —$S(=O)_2$($C_1$-$C_6$-alkyl), —$N(O)_2$, and —$N(R^7)(R^8)$, In further embodiments, the present invention provides compounds of formula (I), supra, in which:
$R^1$ represents a group selected from
a $C_1$-$C_3$-alkyl group, which is optionally substituted with a group selected from a $C_3$-$C_8$-cycloalkyl group, a phenyl group and a monocyclic- or bicyclic heteroaryl group,
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
a $C_2$-$C_8$-haloalkyl group,
a $C_3$-$C_8$-cycloalkyl group, which is optionally substituted, one or two times, each substituent independently selected from a halogen atom or a group selected from a hydroxy group, a phenyl group and a —$N(R^7)(R^8)$ group,
wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
a $C_2$-$C_6$-cyanoalkyl group,
a $C_2$-$C_6$-hydroxyalkyl group,
a ($C_2$-$C_6$-hydroxyalkyl)-O—($C_2$-$C_6$-alky)- group,
a —($C_2$-$C_6$-alkyl)-N($R^7$)($R^8$) group,
a —($C_1$-$C_6$-alkyl)-C(=O)N($R^7$)($R^8$) group,
a 4- to 7-membered, optionally unsaturated, heterocyclic group, which is connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O) O$R^6$, —($C_1$-$C_6$-alkyl)-C(=O)N($R^7$)($R^8$),), —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—O—($C_2$-$C_6$-alkenyl), —S(=O)(=N$R^{14}$) ($C_1$-$C_3$-alkyl), —N(O)$_2$, —P(=O)($C_1$-$C_3$-alkyl)$_2$ and SF$_5$,
or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)
and
a monocyclic or bicyclic heteroaryl group, which is optionally substituted one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$),
and tautomers, N-oxides, and salts thereof, or salts of tautomers or N-oxides of said compound.

In further embodiments, the present invention provides compounds of formula (I), supra, in which:
$R^1$ represents a group selected from
a $C_1$-$C_3$-alkyl group, a $C_2$-$C_8$-haloalkyl group, a $C_3$-$C_8$-cycloalkyl group, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-N($R^7$)($R^8$) group, a —($C_1$-$C_6$-alkyl)-C(=O)N($R^7$)($R^8$) group, a 4- to 7-membered, optionally unsaturated, heterocyclic group, a phenyl group, and a monocyclic or bicyclic heteroaryl group,
wherein said $C_1$-$C_3$-alkyl group is optionally substituted with a group selected from said
$C_3$-$C_8$-cycloalkyl, phenyl and monocyclic or bicyclic heteroaryl,
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said $C_3$-$C_8$-cycloalkyl group is optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4-7-membered, optionally unsaturated, heterocyclic group, which is connected to the rest of the molecule via a carbon atom, and which is optionally substituted one or two times, each substituent independently selected from a group selected from
$C_1$-$C_3$-alkyl, 5- to 6-membered heteroaryl, —C(=O) O($C_1$-$C_4$-alkyl), —C(=O)($C_1$-$C_6$-alkyl), —C(=O) ($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said phenyl group is optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N ($R^7$)($R^8$),), —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—O—($C_2$-$C_6$-alkenyl), —S(=O)(=N$R^{14}$)($C_1$-$C_3$-alkyl), —N(O)$_2$, —P(=O)($C_1$-$C_3$-alkyl)$_2$ and SF$_5$, or wherein two vicinal substituents of said phenyl groups may form together a 5- or 6-membered, optionally heterocyclic, aromatic or non-aromatic ring, having optionally 1-3 heteroatoms independently selected from —N═, —NH—, —N($R^7$)—, —O—, —S—, and optionally containing a C(═O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(O)$_2$, —N(O)$_2$, and —N($R^7$)($R^8$) and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(═O)O$R^6$, hydroxy, —SH, —S—($C_1$-$C_6$-alkyl), —S—($C_2$-$C_6$-alkenyl), —S(O)$_2$, —N(O)$_2$, and —N($R^7$)($R^8$), and tautomers, N-oxides, and salts thereof, and salts of tautomers or N-oxides.

In accordance with further embodiments, the present invention provides compounds of general formula (I), in which $R^1$ represents a phenyl group which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(═O)O$R^6$, —C(═O)N($R^7$)($R^8$), —N($R^7$)($R^8$), —($C_1$-$C_6$-alkyl)-N($R^7$)($R^8$), —($C_1$-$C_6$-alkyl)-C(═O)O$R^6$, —($C_1$-$C_6$-alkyl)-C(═O)N($R^7$)($R^8$), —S(═O)$_2$N($R^7$)($R^8$), —S(═O)$_2$($C_1$-$C_3$-alkyl), —S(═O)(═N$R^{11}$)($C_1$-$C_3$-alkyl), —P(═O)($C_1$-$C_3$-alkyl)$_2$ and SF$_5$, or in which two substituents of said phenyl groups, when they are attached to adjacent ring atoms, are optionally linked to one another in such a way that they jointly form a group selected from

*—CH$_2$—N($R^7$)—CH$_2$—, —CH$_2$—CH$_2$—, —O—CH$_2$—C(═O)—NH— and —NH—C(═O)—NH—, In accordance with further embodiments, the present invention provides compounds of general formula (I), in which $R^1$ represents a phenyl group, which is optionally substituted, one or two times, each substituent independently selected from a fluorine atom, a chlorine atom and a methyl group.

In accordance with further embodiments, the present invention provides compounds of general formula (I), in which $R^1$ represents a $C_4$-$C_8$-cycloalkyl group or a —($C_3$-$C_8$-cycloalkyl)-N($R^7$)($R^8$) group which are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy.

and tautomers, N-oxides, and salts thereof, and salts of tautomers or N-oxides.

In accordance with further embodiments, the present invention provides compounds of general formula (I), in which $R^1$ represents a 4- to 7-membered heterocycloalkyl group or a 5- to 7-membered heterocycloalkenyl group, wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(═O)O($C_1$-$C_4$-alkyl), —C(═O)($C_1$-$C_6$-alkyl), —C(═O)($C_3$-$C_6$-cycloalkyl), —S(═O)$_2$($C_1$-$C_6$-alkyl) and oxo (═O), and wherein said 4- to 7-membered heterocycloalkyl group and 5- to 7-membered heterocycloalkenyl group are connected to the rest of the molecule via a carbon atom of the said heterocycloalkyl- or heterocyclalkenyl group and tautomers, N-oxides, and salts thereof, and salts of tautomers or N-oxides.

In accordance with further embodiments, the present invention provides compounds of general formula (I), in which $R^1$ represents a indanyl group, a tetralinyl group and a monocyclic- or bicyclic heteroaryl group wherein said indanyl or tetralinyl group is optionally substituted one or two times, each substituent independently selected from a halogen atom or a group selected from $C_1$-$C_6$-alkyl, $C_1$-$C_6$-haloalkyl, $C_3$-$C_3$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_3$-$C_3$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$).

and tautomers, N-oxides, and salts thereof, and salts of tautomers or N-oxides.

In further embodiments, the present invention provides compounds of formula (I), supra, in which:

$R^1$ represents a group selected from a $C_1$-$C_3$-alkyl group, which is optionally substituted with a group selected from $C_3$-$C_8$-cycloalkyl, phenyl and monocyclic or bicyclic heteroaryl, wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a $C_2$-$C_8$-haloalkyl group, a $C_3$-$C_8$-cycloalkyl group, which is optionally substituted, one or two times, each substituent independently selected from a halogen atom, a hydroxy group, a phenyl group and a —N($R^7$)($R^8$) group, wherein said phenyl substituent is optionally substituted, one, two or three times, each substituent independently selected from a halogen atom, a $C_1$-$C_3$-alkyl group, a $C_1$-$C_4$-haloalkyl group, a $C_1$-$C_3$-alkoxy group and a hydroxy group, a $C_2$-$C_6$-cyanoalkyl group,
a $C_2$-$C_6$-hydroxyalkyl group,
a ($C_2$-$C_6$-hydroxyalkyl)-O—($C_2$-$C_6$-alky)- group,
a —($C_2$-$C_6$-alkyl)-N($R^7$)($R^8$) group,
a —($C_1$-$C_6$-alkyl)-C(=O)N($R^7$)($R^8$) group,
a 4- to 7-membered heterocycloalkyl group, which is connected to the rest of the molecule via a carbon atom of said 4- to 7-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group,
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
a 5- to 7-membered heterocycloalkenyl group, which is connected to the rest of the molecule via a carbon atom of said 5- to 7-membered heterocycloalkenyl group and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group,
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{14}$)($C_1$-$C_3$-alkyl), —P(=O)($C_1$-$C_3$-alkyl)$_2$ and $SF_5$,
or in which two substituents of said phenyl group, when they are attached to adjacent ring atoms, are optionally linked to one another in such a way that they jointly form a group selected from —CH$_2$—N(R)—CH$_2$—, —CH$_2$—O—CH$_2$—, —O—CH$_2$—C(=O)—NH— and —NH—C(=O)—NH—,
an indanyl group, a tetralinyl group wherein said indanyl- or tetralinyl group is optionally substituted one or two times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N($R^7$)($R^8$) group,
and
a monocyclic or bicyclic heteroaryl group, which is optionally substituted one, two or three times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N($R^7$)($R^8$) group, or tautomers, N-oxides, or salts thereof, or salts of tautomers or N-oxides of said compounds.

In further embodiments, the present invention provides compounds of formula (I), supra, in which:
$R^1$ represents a group selected from
a $C_1$-$C_3$-alkyl group, a $C_2$-$C_8$-haloalkyl group, a $C_3$-$C_8$-cycloalkyl group, a $C_2$-$C_6$-cyanoalkyl group, a $C_2$-$C_6$-hydroxyalkyl group, a ($C_2$-$C_6$-hydroxyalkyl)-O—($C_2$-$C_6$-alky)- group, a —($C_2$-$C_6$-alkyl)-N($R^7$)($R^8$) group, a —($C_1$-$C_6$-alkyl)-C(=O)N($R^7$)($R^8$) group, a 4- to 7-membered heterocycloalkyl group, a 5- to 7-membered heterocycloalkenyl group, a phenyl group, an indanyl group, a tetralinyl group and a monocyclic or bicyclic heteroaryl group,
wherein said $C_1$-$C_3$-alkyl group is optionally substituted with a group selected from
$C_3$-$C_8$-cycloalkyl, phenyl and monocyclic or bicyclic heteroaryl,
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said $C_3$-$C_8$-cycloalkyl group is optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and said 5- to 7-membered heterocycloalkenyl group, which are connected to the rest of the molecule via a carbon atom of said 4- to 7-membered heterocycloalkyl group
and
said 5- to 7-membered heterocycloalkenyl group, are optionally substituted one or two times, each substituent independently selected from a group selected from
$C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said phenyl group is optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R)(R$^8$), —N(R)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$, or in which two substituents of said phenyl group, when they are attached to adjacent ring atoms, are optionally linked to one another in such a way that they jointly form a group selected from —CH$_2$—N(R)—CH$_2$—, —CH$_2$—CH$_2$—, —O—CH$_2$—C(=O)—NH— and —NH—C(=O)—NH—, and wherein said indanyl- or tetralinyl group is optionally substituted one or two times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), and tautomers, N-oxides, and salts thereof, and salts of tautomers or N-oxides.

In further embodiments, the present invention provides compounds of formula (I), supra, in which:

$R^1$ represents a group selected from a $C_3$-$C_8$-cycloalkyl group, which is optionally substituted, one or two times, each substituent independently selected from a halogen atom, a hydroxy group, a phenyl group and a —N(R$^7$)(R$^8$) group,
wherein said phenyl substituent is optionally substituted, one, two or three times, each substituent independently selected from a halogen atom, a $C_1$-$C_3$-alkyl group, a $C_1$-$C_4$-haloalkyl group, a $C_1$-$C_3$-alkoxy group and a hydroxy group, a 4- to 7-membered heterocycloalkyl group, which is connected to the rest of the molecule via a carbon atom of said 4- to 7-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group,
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a 5- to 7-membered heterocycloalkenyl group, which is connected to the rest of the molecule via a carbon atom of said 5- to 7-membered heterocycloalkenyl group and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group, wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R)(R$^8$), —N(R)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$, or in which two substituents of said phenyl group, when they are attached to adjacent ring atoms, are optionally linked to one another in such a way that they jointly form a group selected from —CH$_2$—N(R)—CH$_2$—, —CH$_2$—O—CH$_2$—, —O—CH$_2$—C(=O)—NH— and —NH—C(=O)—NH—, an indanyl group, a tetralinyl group wherein said indanyl- or tetralinyl group is optionally substituted one or two times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N(R$^7$)(R$^8$) group, and a monocyclic or bicyclic heteroaryl group, which is optionally substituted one, two or three times, each substituent independently selected from a halogen atom, a $C_1$-$C_6$-alkyl group, a $C_1$-$C_6$-haloalkyl group, a $C_3$-$C_8$-cycloalkyl group, a $C_1$-$C_6$-alkoxy group, a $C_1$-$C_6$-haloalkoxy group, a $C_3$-$C_8$-cycloalkoxy group, a cyano group, a hydroxy group and a —N(R$^7$)(R$^8$) group, or tautomers, N-oxides, or salts thereof, or salts of tautomers or N-oxides of said compounds.

In further embodiments, the present invention provides compounds of formula (I), supra, in which:

$R^1$ represents a group selected from a $C_3$-$C_8$-cycloalkyl group, a 4- to 7-membered heterocycloalkyl group, a 5- to 7-membered heterocycloalkenyl group, a phenyl group, an indanyl group, a tetralinyl group and a monocyclic or bicyclic heteroaryl group,
wherein said $C_3$-$C_8$-cycloalkyl group is optionally substituted, one or two times, each substituent independently selected from a halogen atom or a group selected from hydroxy, phenyl and —N(R$^7$)(R$^8$),
wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and said 5- to 7-membered heterocycloalkenyl group, which are connected to the rest of the molecule via a carbon atom of said 4- to 7-membered heterocycloalkyl group
and
5- to 7-membered heterocycloalkenyl group, are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
  wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
and
wherein said phenyl group is optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R)(R$^8$), —N(R)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$,
or in which two substituents of said phenyl group, when they are attached to adjacent ring atoms, are optionally linked to one another in such a way that they jointly form a group selected from
—CH$_2$—N(R)—CH$_2$—, —CH$_2$—CH$_2$—, —O—CH$_2$—C(=O)—NH— and —NH—C(=O)—NH—, and
wherein said indanyl- or tetralinyl group is optionally substituted one or two times, each substituent independently selected from a halogen atom or a group selected from
$C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$),
and
wherein said monocyclic or bicyclic heteroaryl group is optionally substituted one or two or three times, each substituent independently selected from a halogen atom or a group selected from
$C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$),
and tautomers, N-oxides, and salts thereof, and salts of tautomers or N-oxides.

In further embodiments, the present invention provides compounds of formula (I), supra, in which:
R$^1$ represents a group selected from
a $C_1$-$C_6$-alkyl group, a $C_2$-$C_6$-haloalkyl group, a $C_3$-$C_6$-cycloalkyl group, a $C_2$-$C_6$-cyanoalkyl group, a $C_2$-$C_6$-hydroxyalkyl group, a ($C_2$-$C_8$-hydroxyalkyl)-O—($C_2$-$C_6$-alky)- group, a —($C_2$-$C_6$-alkyl)-N(R$^7$)(R$^8$) group, a —($C_1$-$C_6$-alkyl)-C(=O)N(R$^7$)(R$^8$) group, a 4- to 6-membered heterocycloalkyl group, a 5 to 6-membered heterocycloalkenyl group, a phenyl group, an indanyl group, a tetralinyl group and a monocyclic or bicyclic heteroaryl group,
  wherein said $C_1$-$C_6$-alkyl group is optionally substituted with a group selected from
$C_3$-$C_6$-cycloalkyl, phenyl and monocyclic or bicyclic heteroaryl,
    wherein said phenyl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said $C_3$-$C_6$-cycloalkyl group is optionally substituted, one or two times, each substituent independently selected from a halogen atom or a group selected from
hydroxy, phenyl and —N(R$^7$)(R$^8$),
    wherein said phenyl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said 4- to 6-membered heterocycloalkyl group and said heterocycloalkenyl group, which are connected to the rest of the molecule via a carbon atom of said 4- to 6-membered heterocycloalkyl group and said heterocycloalkenyl group, are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
  wherein said 5- to 6-membered heteroaryl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said phenyl group is optionally substituted, one, two, three, four or five times, each substituent independently selected from a halogen atom or a group selected from
$C_1$-$C_3$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)OR$^6$, —C(=O)N(R)(R$^3$), —N(R)(R$^3$), —($C_1$-$C_3$-alkyl)-N(R$^7$)(R$^8$), —($C_1$-$C_3$-alkyl)-C(=O)OR$^6$, —($C_1$-$C_3$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{14}$)($C_1$-$C_3$-alkyl), —P(=O)($C_1$-$C_3$-alkyl)$_2$ and SF$_5$,
or in which two substituents of said phenyl group, when they are attached to adjacent ring atoms, are optionally linked to one another in such a way that they jointly form a group selected from
—CH$_2$—N(R)—CH$_2$—, —CH$_2$—CH$_2$—, —O—CH$_2$—C(=O)—NH— and —NH—C(=O)—NH—,
and
wherein said indanyl- or tetralinyl group is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and wherein said monocyclic or bicyclic heteroaryl group is optionally substituted one, two or three times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, a 4- to 6-membered heterocycloalkyl group, a heterocycloalkenyl group, a phenyl group, an indanyl group, a tetralinyl group and a monocyclic or bicyclic heteroaryl group, wherein said $C_3$-$C_6$-cycloalkyl group is optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said 4- to 6-membered heterocycloalkyl group and said heterocycloalkenyl group, which are connected to the rest of the molecule via a carbon atom of said 4- to 6-membered heterocycloalkyl group and of said heterocycloalkenyl group, are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said phenyl group is optionally substituted, one, two, three, four or five times, each substituent independently selected from a halogen atom or a group selected from $C_1$-$C_3$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N(R)($R^3$), —N(R)($R^3$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{14}$)($C_1$-$C_3$-alkyl), —P(=O)($C_1$-$C_3$-alkyl)$_2$ and SF$_5$, or in which two substituents of said phenyl group, when they are attached to adjacent ring atoms, are optionally linked to one another in such a way that they jointly form a group selected from —CH$_2$—N(R)—CH$_2$—, —CH$_2$—O—CH$_2$—, —O—CH$_2$—C(=O)—NH— and —NH—C(=O)—NH—, and wherein said indanyl- or tetralinyl group is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and wherein said monocyclic or bicyclic heteroaryl group is optionally substituted one, two or three times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, which is optionally substituted, one or two times, each substituent independently selected from a halogen atom, a phenyl group and -a N($R^7$)($R^8$) group, wherein said phenyl substituent is optionally substituted, one, two or three times, each substituent independently selected from a halogen atom, a $C_2$-$C_6$-hydroxyalkyl group, a —($C_2$-$C_6$-alkyl)-N($R^7$)($R^8$) group, a 4- to 6-membered heterocycloalkyl group, which is connected to the rest of the molecule via a carbon atom of said 4- to 6-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group, a phenyl group, which is optionally substituted, one, two, three or four times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a cyano group, a hydroxy group, a —C(=O)O$R^6$ group, a —C(=O)N($R^7$)($R^8$)group, a —N($R^7$)($R^8$) group, a —($C_1$-$C_3$-alkyl)-N($R^7$)($R^8$) group, a —S(=O)$_2$N($R^7$)($R^8$) group and a SF$_5$ group, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, an indanyl group which is optionally substituted with a hydroxy group and a monocyclic or bicyclic heteroaryl group, which is optionally substituted one, two or three times, each substituent independently selected from a halogen atom, a $C_1$-$C_3$-alkyl group, a $C_1$-$C_3$-alkoxy group, a hydroxy group and a —N($R^7$)($R^8$) group, or tautomers, N-oxides, or salts thereof, or salts of tautomers or N-oxides of said compounds.

In further embodiments, the present invention provides compounds of formula (I), supra, in which:

$R^1$ represents a group selected from a $C_3$-$C_6$-cycloalkyl group, a $C_2$-$C_6$-hydroxyalkyl group, a —($C_2$-$C_6$-alkyl)-N($R^7$)($R^8$) group, a 4- to 6-membered heterocycloalkyl group, a phenyl group, an indanyl group and a monocyclic or bicyclic heteroaryl group, wherein said $C_3$-$C_6$-cycloalkyl group is optionally substituted, one or two times, each substituent independently selected from a halogen atom or a group selected from phenyl and —N($R^7$)($R^8$), wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), and wherein said phenyl group is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, and wherein said indanyl group is optionally substituted with a hydroxy group, and wherein said monocyclic or bicyclic heteroaryl group is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, which is optionally substituted, one or two times, each substituent independently selected from a halogen atom, a phenyl group and -a N($R^7$)($R^8$) group, wherein said phenyl substituent is optionally substituted, one, two or three times, each substituent independently selected from a halogen atom, a 4- to 6-membered heterocycloalkyl group, which is connected to the rest of the molecule via a carbon atom of said 4- to 6-membered heterocycloalkyl group, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group, a phenyl group, which is optionally substituted, one, two, three or four times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a cyano group, a hydroxy group, a —C(=O)O$R^6$ group, a —C(=O)N($R^7$)($R^8$) group, a —N($R^7$)($R^8$) group, a —($C_1$-$C_3$-alkyl)-N($R^7$)($R^8$) group, a —S(=O)$_2$N($R^7$)($R^8$) group and a SF$_5$ group, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, an indanyl group which is optionally substituted with a hydroxy group and a monocyclic or bicyclic heteroaryl group, which is optionally substituted one, two or three times, each substituent independently selected from a halogen atom, a $C_1$-$C_3$-alkyl group, a $C_1$-$C_3$-alkoxy group, a hydroxy group and a —N($R^7$)($R^8$) group, or tautomers, N-oxides, or salts thereof, or salts of tautomers or N-oxides of said compounds.

In further embodiments, the present invention provides compounds of formula (I), supra, in which:

$R^1$ represents a group selected from a $C_3$-$C_6$-cycloalkyl group, a 4- to 6-membered heterocycloalkyl group, a phenyl group, an indanyl group and a monocyclic or bicyclic heteroaryl group, wherein said $C_3$-$C_6$-cycloalkyl group is optionally substituted, one or two times, each substituent independently selected from a halogen atom or a group selected from phenyl and —N($R^7$)($R^8$), wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), and wherein said phenyl group is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$, or in which two substituents of said phenyl group, when they are attached to adjacent ring atoms, are optionally linked to one another in such a way that they jointly form a group selected from —$CH_2$—$N(R^7)$—$CH_2$— and —O—$CH_2$—C(=O)—NH—, and wherein said indanyl group is optionally substituted with a hydroxy group, and wherein said monocyclic or bicyclic heteroaryl group is optionally substituted one, two or three times, each substituent independently selected from a halogen atom or a group selected from $C_1$-$C_3$-alkyl, $C_1$-$C_3$-alkoxy, hydroxy and —$N(R^7)(R^8)$, and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, which is selected from cyclopropyl and cyclohexyl, and which is optionally substituted, one or two times, each substituent independently selected from a halogen atom, a phenyl group and a —$N(R^7)(R^8)$ group, wherein said phenyl substituent is optionally substituted, one, two or three times, each substituent independently selected from a halogen atom, a $C_2$-$C_6$-hydroxyalkyl group, a —($C_2$-$C_6$-alkyl)-$N(R^7)(R^8)$ group, a 4- to 6-membered heterocycloalkyl group, which is connected to the rest of the molecule via a carbon atom of said 4- to 6-membered heterocycloalkyl group, and which is selected from azetidinyl, oxetanyl, tetrahydro-2H-pyranyl, tetrahydro-2H-thiopyranyl and piperidinyl, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group, a phenyl group, which is optionally substituted, one, two or three times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a hydroxy group, a cyano group, a —C(=O)$OR^6$ group, a —C(=O)N($R^7$)($R^8$) group, a —$N(R^7)(R^8)$ group, a —($C_1$-$C_3$-alkyl)-$N(R^7)(R^8)$ group, a —S(=O)$_2$$N(R^7)(R^8)$ group and a $SF_5$ group, or in which two substituents of said phenyl group, when they are attached to adjacent ring atoms, are optionally linked to one another in such a way that they jointly form a group selected from —$CH_2$—$N(R^7)$—$CH_2$— and —O—$CH_2$—C(=O)—NH—, an indanyl group which is optionally substituted with a hydroxy group and a monocyclic or bicyclic heteroaryl group, which is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, and which is optionally substituted one, two or three times, each substituent independently selected from a halogen atom or a group selected from $C_1$-$C_3$-alkyl, $C_1$-$C_3$-alkoxy, hydroxy and —$N(R^7)(R^8)$, or tautomers, N-oxides, or salts thereof, or salts of tautomers or N-oxides of said compounds.

In further embodiments, the present invention provides compounds of formula (I), supra, in which:

$R^1$ represents a group selected from a $C_3$-$C_6$-cycloalkyl group, a $C_2$-$C_6$-hydroxyalkyl group, a —($C_2$-$C_6$-alkyl)-$N(R^7)(R^8)$ group, a 4- to 6-membered heterocycloalkyl group, a phenyl group, an indanyl group and a monocyclic or bicyclic heteroaryl group, wherein said $C_3$-$C_6$-cycloalkyl group is selected from cyclopropyl and cyclohexyl, which $C_3$-$C_6$-cycloalkyl group is optionally substituted, one or two times, each substituent independently selected from a halogen atom or a group selected from phenyl and —$N(R^7)(R^8)$, wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is selected from azetidinyl, oxetanyl, tetrahydro-2H-pyranyl, tetrahydro-2H-thiopyranyl and piperidinyl, which 4- to 6-membered heterocycloalkyl group is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), and wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)$OR^6$, —C(=O)N($R^7$)($R^8$), —$N(R^7)(R^8)$, —($C_1$-$C_3$-alkyl)-$N(R^7)(R^8)$, —S(=O)$_2$$N(R^7)(R^8)$ and $SF_5$, or in which two substituents of said phenyl group, when they are attached to adjacent ring atoms, are optionally linked to one another in such a way that they jointly form a group selected from —$CH_2$—$N(R^7)$—$CH_2$— and —O—$CH_2$—C(=O)—NH—, and wherein said indanyl group is optionally substituted with a hydroxy group, and wherein said monocyclic or bicyclic heteroaryl group is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, which monocyclic or bicyclic heteroaryl group is optionally substituted one, two or three times, each substituent independently selected from a halogen atom or a group selected from $C_1$-$C_3$-alkyl, $C_1$-$C_3$-alkoxy, hydroxy and —$N(R^7)(R^8)$, and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, which is selected from cyclopropyl and cyclohexyl, and which is optionally substituted, one or two times, each substituent independently selected from a halogen atom, a phenyl group and a —N($R^7$)($R^8$) group, wherein said phenyl substituent is optionally substituted, one, two or three times, each substituent independently selected from a halogen atom, a 4- to 6-membered heterocycloalkyl group, which is connected to the rest of the molecule via a carbon atom of said 4- to 6-membered heterocycloalkyl group, and which is selected from azetidinyl, oxetanyl, tetrahydro-2H-pyranyl, tetrahydro-2H-thiopyranyl and piperidinyl, and which is optionally substituted one or two times, each substituent independently selected from a $C_1$-$C_3$-alkyl group, a 5- to 6-membered heteroaryl group, a —C(=O)O($C_1$-$C_4$-alkyl) group, a —C(=O)($C_1$-$C_3$-alkyl) group, a —C(=O)($C_3$-$C_6$-cycloalkyl) group, a —S(=O)$_2$($C_1$-$C_3$-alkyl) group and a oxo (=O) group, a phenyl group, which is optionally substituted, one, two or three times, each substituent independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a hydroxy group, a cyano group, a —C(=O)O$R^6$ group, a —C(=O)N($R^7$)($R^8$) group, a —N($R^7$)($R^8$) group, a —($C_1$-$C_3$-alkyl)-N($R^7$)($R^8$) group, a —S(=O)$_2$N($R^7$)($R^8$) group and a SF$_5$ group, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, an indanyl group which is optionally substituted with a hydroxy group and a monocyclic or bicyclic heteroaryl group, which is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, and which is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), or tautomers, N-oxides, or salts thereof, or salts of tautomers or N-oxides of said compounds.

In further embodiments, the present invention provides compounds of formula (I), supra, in which:

$R^1$ represents a group selected from a $C_3$-$C_6$-cycloalkyl group, a 4- to 6-membered heterocycloalkyl group, a phenyl group, an indanyl group and a monocyclic or bicyclic heteroaryl group, wherein said $C_3$-$C_6$-cycloalkyl group is selected from cyclopropyl and cyclohexyl, which $C_3$-$C_6$-cycloalkyl group is optionally substituted, one or two times, each substituent independently selected from a halogen atom or a group selected from phenyl and —N($R^7$)($R^8$), wherein said phenyl substituent is optionally substituted, one, two or three times, each substituent independently selected from a halogen atom, and wherein said 4- to 6-membered heterocycloalkyl group, which is connected to the rest of the molecule via a carbon atom of said 4- to 6-membered heterocycloalkyl group, is selected from azetidinyl, oxetanyl, tetrahydro-2H-pyranyl, tetrahydro-2H-thiopyranyl and piperidinyl, which 4- to 6-membered heterocycloalkyl group is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), and wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$, or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—, and wherein said indanyl group is optionally substituted with a hydroxy group, and wherein said monocyclic or bicyclic heteroaryl group is selected from imidazolyl, 1,2-oxazolyl, pyrazolyl, pyridinyl, pyridazinyl, pyrazinyl, pyrimidinyl, indazolyl, 1,3-benzothiazolyl, pyrrolo[2,3-d]pyrimidinyl and quinolinyl, which monocyclic or bicyclic heteroaryl group is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_3$-$C_6$-cycloalkyl group, which is selected from a cyclopropyl group and a cyclohexyl group, which $C_3$-$C_6$-cycloalkyl group is optionally substituted, one or two times, each substituent independently selected from a fluorine atom, a phenyl group and a dimethylamino group, wherein said phenyl substituent is optionally substituted with a fluorine atom a 2-hydroxy-2-methylpropyl group, a 2-(dimethylamino)ethyl group, a 4- to 6-membered heterocycloalkyl group, which is selected from azetidin-3-yl, oxetan-3-yl, tetrahydro-2H-pyran-4-yl, tetrahydro-2H-thiopyran-4-yl and piperidin-4-yl, and which is optionally substituted one or two times, each substituent independently selected from a group selected from a methyl group, an ethyl group, a pyrazinyl group, a tert-butoxycarbonyl group, a acetyl group, a 1-cyclopropanecarbonyl group, amethylsulfonyl group and a oxo (=O) group, a phenyl group, which, is optionally substituted, one, two or three times, each substituent independently selected from a fluorine atom, a chlorine atom, a methyl group, an ethyl group, a difluoromethyl group, a trifluoromethyl group, a hydroxymethyl group, a methoxy group, a hydroxy group, a cyano group, a —C(=O)OH group, a —C(=O)OCH$_3$ group, a —C(=O)OC(CH$_3$)$_3$, group, a —C(=O)NH$_2$ group, a —C(=O)N(CH$_3$)$_2$ group, an amino group, a methylamino group, an aminomethyl group, a —S(=O)$_2$NH$_2$ group and a SF$_5$ group, or in which two substituents of said phenyl group, when they are attached to adjacent ring atoms, are optionally linked to one another in such a way that they jointly form a group selected from —CH—CH$_2$—NH—CH$_2$— and —O—CH$_2$—C(=O)—NH—, a 2-hydroxyindan-1-yl group and a monocyclic or bicyclic heteroaryl group, which is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, and which is optionally substituted one, two or three times, each substituent independently selected from a fluorine atom, a chlorine atom, a methyl group, a methoxy group, a hydroxy group and a morpholin-4-yl group, or tautomers, N-oxides, or salts thereof, or salts of tautomers or N-oxides of said compounds.

In further embodiments, the present invention provides compounds of formula (I), supra, in which:

R$^1$ represents a group selected from a C$_3$-C$_6$-cycloalkyl group, a 2-hydroxy-2-methylpropyl group, a 2-(dimethylamino)ethyl group, a 4- to 6-membered heterocycloalkyl group, a phenyl group, a 2-hydroxyindan-1-yl group and a monocyclic or bicyclic heteroaryl group, wherein said C$_3$-C$_6$-cycloalkyl group is selected from cyclopropyl and cyclohexyl, which C$_3$-C$_6$-cycloalkyl group is optionally substituted, one or two times, each substituent independently selected from a fluorine atom or a group selected from phenyl and dimethylamino, wherein said phenyl substituent is optionally substituted with a fluorine atom, and wherein said 4- to 6-membered heterocycloalkyl group is selected from azetidin-3-yl, oxetan-3-yl, tetrahydro-2H-pyran-4-yl, tetrahydro-2H-thiopyran-4-yl and piperidin-4-yl, which 4- to 6-membered heterocycloalkyl group is optionally substituted one or two times, each substituent independently selected from a group selected from methyl, ethyl, pyrazinyl, tert-butoxycarbonyl, acetyl, 1-cyclopropanecarbonyl, methylsulfonyl and oxo (=O), and wherein said phenyl group is optionally substituted, one, two or three times, each substituent independently selected from a fluorine atom or a chlorine atom or a group selected from methyl, ethyl, difluoromethyl, trifluoromethyl, hydroxymethyl, methoxy, cyano, —C(=O)OH, —C(=O)OCH$_3$, —C(=O)OC(CH$_3$)$_3$, —C(=O)NH$_2$, —C(=O)N(CH$_3$)$_2$, amino, methylamino, aminomethyl, —S(=O)$_2$NH$_2$ and SF$_5$, or in which two substituents of said phenyl group, when they are attached to adjacent ring atoms, are optionally linked to one another in such a way that they jointly form a group selected from —CH—CH$_2$—NH—CH$_2$— and —O—CH$_2$—C(=O)—NH—, and wherein said monocyclic or bicyclic heteroaryl group is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, which monocyclic or bicyclic heteroaryl group is optionally substituted one, two or three times, each substituent independently selected from a fluorine atom or a chlorine atom or a group selected from methyl, methoxy, hydroxy and morpholin-4-yl, and tautomers, N-oxides, and salts thereof, and salts of tautomers or N-oxides.

In further embodiments, the present invention provides compounds of formula (I), supra, in which:

R$^1$ represents a group selected from a C$_3$-C$_6$-cycloalkyl group, which is selected from a cyclopropyl group and a cyclohexyl group, which C$_3$-C$_6$-cycloalkyl group is optionally substituted, one or two times, each substituent independently selected from a fluorine atom, a phenyl group and a dimethylamino group, wherein said phenyl substituent is optionally substituted with a fluorine atom a 4- to 6-membered heterocycloalkyl group, which is selected from azetidin-3-yl, oxetan-3-yl, tetrahydro-2H-pyran-4-yl, tetrahydro-2H-thiopyran-4-yl and piperidin-4-yl, and which is optionally substituted one or two times, each substituent independently selected from a group selected from a methyl group, an ethyl group, a pyrazinyl group, a tert-butoxycarbonyl group, a acetyl group, a 1-cyclopropanecarbonyl group, a methylsulfonyl group and a oxo (=O) group, a phenyl group, which, is optionally substituted, one, two or three times, each substituent independently selected from a fluorine atom, a chlorine atom, a methyl group, an ethyl group, a difluoromethyl group, a trifluoromethyl group, a hydroxymethyl group, a methoxy group, a hydroxy group, a cyano group, a —C(=O)OH group, a —C(=O)OCH$_3$ group, a —C(=O)OC(CH$_3$)$_3$ group, a —C(=O)NH$_2$ group, a —C(=O)N(CH$_3$)$_2$ group, an amino group, a methylamino group, an aminomethyl group, a —S(=O)$_2$NH$_2$ group and a SF$_5$ group, or in which two substituents of said phenyl group, when they are attached to adjacent ring atoms, are optionally linked to one another in such a way that they jointly form a group selected from —CH=CH$_2$—NH—CH$_2$— and —O—CH$_2$—C(=O)—NH—, a 2-hydroxyindan-1-yl group and a monocyclic or bicyclic heteroaryl group, which is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, and which is optionally substituted one, two or three times, each substituent independently selected from a fluorine atom, a chlorine atom, a methyl group, a methoxy group, a hydroxy group and a morpholin-4-yl group, or tautomers, N-oxides, or salts thereof, or salts of tautomers or N-oxides of said compounds.

In further embodiments, the present invention provides compounds of formula (I), supra, in which:

R$^1$ represents a group selected from a C$_3$-C$_6$-cycloalkyl group, a 4- to 6-membered heterocycloalkyl group, a phenyl group, a 2-hydroxyindan-1-yl group and a monocyclic or bicyclic heteroaryl group, wherein said C$_3$-C$_6$-cycloalkyl group is selected from cyclopropyl and cyclohexyl, which C$_3$-C$_6$-cycloalkyl group is optionally substituted, one or two times, each substituent independently selected from a fluorine atom or a group selected from phenyl and dimethylamino, wherein said phenyl substituent is optionally substituted with a fluorine atom, and wherein said 4- to 6-membered heterocycloalkyl group is selected from azetidin-3-yl, oxetan-3-yl, tetrahydro-2H-pyran-4-yl, tetrahydro-2H-thiopyran-4-yl and piperidin-4-yl, which 4- to 6-membered heterocycloalkyl group is optionally substituted one or two times, each substituent independently selected from a group selected from methyl, ethyl, pyrazinyl, tert-butoxycarbonyl, acetyl, 1-cyclopropanecarbonyl, methylsulfonyl and oxo (=O), and wherein said phenyl group is optionally substituted, one, two or three times, each substituent independently selected from a fluorine atom or a chlorine atom or a group selected from methyl, ethyl, difluoromethyl, trifluoromethyl, hydroxymethyl, methoxy, cyano, —C(=O)OH, —C(=O)OCH$_3$, —C(=O)OC(CH$_3$)$_3$, —C(=O)NH$_2$, —C(=O)N(CH$_3$)$_2$, amino, methylamino, aminomethyl, —S(=O)$_2$NH$_2$ and SF$_5$, or in which two substituents of said phenyl group, when they are attached to adjacent ring atoms, are optionally linked to one another in such a way that they jointly form a group selected from —CH=CH$_2$—NH—CH$_2$— and —O—CH$_2$—C(=O)—NH—, and wherein said monocyclic or bicyclic heteroaryl group is selected from imidazol-4-yl, 1,2-oxazol-4-yl, 1,2-oxazol-5-yl, pyrazol-3-yl, pyrazol-4-yl, pyridin-2-yl, pyridin-3-yl, pyridin-4-yl, pyridazin-3-yl, pyrazinyl, pyrimidin-4-yl, pyrimidin-5-yl, indazol-5-yl, indazol-6-yl, indazol-7-yl, 1,3-benzothiazol-6-yl, pyrrolo[2,3-d]pyrimidin-4-yl, quinolin-5-yl, quinolin-6-yl, quinolin-7-yl and quinolin-8-yl, which monocyclic or bicyclic heteroaryl group is optionally substituted one, two or three times, each substituent independently selected from a fluorine atom or a chlorine atom or a group selected from methyl, methoxy, hydroxy and morpholin-4-yl, and tautomers, N-oxides, and salts thereof, and salts of tautomers or N-oxides.

In further embodiments, the present invention provides compounds of formula (I), supra, in which:

R$^2$ represents a hydrogen atom or a halogen atom, and tautomers, N-oxides, and salts thereof, and salts of tautomers or N-oxides.

In further embodiments, the present invention provides compounds of formula (I), supra, in which:

R$^2$ represents a hydrogen atom or a chlorine atom or a fluorine atom, or tautomers, N-oxides, or salts thereof, or salts of tautomers or N-oxides of said compound.

In further embodiments, the present invention provides compounds of formula (I), supra, in which:

R$^2$ represents a hydrogen atom or a fluorine atom, and tautomers, N-oxides, and salts thereof, and salts of tautomers or N-oxides.

In further embodiments, the present invention provides compounds of formula (I), supra, in which:

R$^2$ represents a fluorine atom, and tautomers, N-oxides, and salts thereof, and salts of tautomers or N-oxides.

In further embodiments, the present invention provides compounds of formula (I), supra, in which:

R$^2$ represents chlorine atom or a fluorine atom, and tautomers, N-oxides, and salts thereof, and salts of tautomers or N-oxides.

In further embodiments, the present invention provides compounds of formula (I), supra, in which:

R$^2$ represents chlorine atom, and tautomers, N-oxides, and salts thereof, and salts of tautomers or N-oxides.

In further embodiments, the present invention provides compounds of formula (I), supra, in which:

R$^2$ represents a hydrogen atom, and tautomers, N-oxides, and salts thereof, and salts of tautomers or N-oxides.

In further embodiments, the present invention provides compounds of formula (I), supra, in which:

R$^3$ represents a group selected from a C$_1$-C$_6$-alkyl group, a C$_3$-C$_8$-cycloalkyl group, a C$_1$-C$_6$-haloalkyl group, a C$_1$-C$_6$-hydroxyalkyl group, a $C_2$-$C_6$-alkenyl group,
a $C_2$-$C_6$-alkinyl group,
a $C_4$-$C_8$-cycloalkenyl group,
a ($C_1$-$C_6$-alkyl)-N($R^7$)$R^8$ group,
a —($C_1$-$C_6$-alkyl)-N(H)C(=O)$R^6$ group,
a —($C_1$-$C_6$-alkyl)-N(H)C(=O)O$R^{15}$ group,
a —($C_1$-$C_6$-alkyl)-(4- to 7-membered nitrogen containing heterocycloalkyl) group, which is connected to the alkyl group via a carbon atom of the heterocycloalkyl group and which is optionally substituted with a $C_1$-$C_3$-alkyl group,
and
a phenyl group,
  which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$—C-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), or tautomers, N-oxides, or salts thereof, or salts of tautomers or N-oxides of said compounds.

In further embodiments, the present invention provides compounds of formula (I), supra, in which:
$R^3$ represents a group selected from
  a $C_1$-$C_6$-alkyl group,
  a $C_3$-$C_8$-cycloalkyl group,
  a $C_1$-$C_6$-haloalkyl group,
  a $C_1$-$C_6$-hydroxyalkyl group,
  a $C_2$-$C_6$-alkenyl group,
  a $C_2$-$C_6$-alkinyl group,
  a $C_4$-$C_8$-cycloalkenyl group,
  a ($C_1$-$C_6$-alkyl)-N($R^7$)$R^8$ group,
  a —($C_1$-$C_6$-alkyl)-(4- to 7-membered nitrogen containing heterocycloalkyl) group
    wherein said 4- to 7-membered nitrogen containing heterocycloalkyl group is connected to the alkyl group via a carbon atom of the heterocycloalkyl group and wherein said 4- to 7-membered nitrogen containing heterocycloalkyl group is optionally substituted with a $C_1$-$C_3$-alkyl group, and
  a phenyl group,
    which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), or tautomers, N-oxides, or salts thereof, or salts of tautomers or N-oxides of said compounds.

In further embodiments, the present invention provides compounds of formula (I), supra, in which:
$R^3$ represents a group selected from
  a $C_1$-$C_6$-alkyl group, a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkinyl group,
  a $C_4$-$C_8$-cycloalkenyl group, a ($C_1$-$C_6$-alkyl)-N($R^7$)$R^8$ group,
  a —($C_1$-$C_6$-alkyl)-(4- to 7-membered nitrogen containing heterocycloalkyl) group and a phenyl group,
    wherein said 4- to 7-membered nitrogen containing heterocycloalkyl group is optionally substituted with a $C_1$-$C_3$-alkyl group,
    and
    wherein said 4- to 7-membered nitrogen containing heterocycloalkyl group is connected to the alkyl group via a carbon atom of the heterocycloalkyl group,
    and
    wherein said phenyl group is optionally substituted, one, two or three times, each substituent independently selected from a halogen atom or a group selected from
      $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$—C-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, hydroxy, —SH, —S—($C_1$-$C_6$-alkyl), —S—($C_2$-$C_6$-alkenyl), —S(O)$_2$, —N(O)$_2$, and —N($R^7$)($R^8$), and tautomers, N-oxides, and salts thereof, and salts of tautomers or N-oxides.

In further embodiments, the present invention provides compounds of formula (I), supra, in which:
$R^3$ represents a group selected from
  a $C_1$-$C_6$-alkyl group, a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkinyl group,
  a $C_4$-$C_8$-cycloalkenyl group, a ($C_1$-$C_6$-alkyl)-N($R^7$)$R^8$ group,
  a —($C_1$-$C_6$-alkyl)-N(H)C(=O)$R^6$ group, a —($C_1$-$C_6$-alkyl)-N(H)C(=O)O$R^{15}$ group,
  a —($C_1$-$C_6$-alkyl)-(4- to 7-membered nitrogen containing heterocycloalkyl) group and a phenyl group,
    wherein said 4- to 7-membered nitrogen containing heterocycloalkyl group is optionally substituted with a $C_1$-$C_3$-alkyl group,
    and
    wherein said 4- to 7-membered nitrogen containing heterocycloalkyl group is connected to the alkyl group via a carbon atom of the heterocycloalkyl group,
    and
    wherein said phenyl group is optionally substituted, one, two or three times, each substituent independently selected from a halogen atom or a group selected from
      $C_1$-$C_3$-alkyl, $C_1$-$C_4$-haloalkyl, $C_1$-$C_3$-alkoxy and hydroxy, and tautomers, N-oxides, and salts thereof, and salts of tautomers or N-oxides.

In further embodiments, the present invention provides compounds of formula (I), supra, in which:
$R^3$ represents a group selected from
  a $C_1$-$C_6$-alkyl group, a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkinyl group,
  a $C_4$-$C_8$-cycloalkenyl group, a ($C_1$-$C_6$-alkyl)-N($R^7$)$R^8$ group,
  a —($C_1$-$C_6$-alkyl)-(4- to 7-membered nitrogen containing heterocycloalkyl) group and a phenyl group, wherein said 4- to 7-membered nitrogen containing heterocycloalkyl group is optionally substituted with a $C_1$-$C_3$-alkyl group, and wherein said 4- to 7-membered nitrogen containing heterocycloalkyl group is connected to the alkyl group via a carbon atom of the heterocycloalkyl group, and wherein said phenyl group is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and tautomers, N-oxides, and salts thereof, and salts of tautomers or N-oxides.

In further embodiments, the present invention provides compounds of formula (I), supra, in which:

$R^3$ represents a group selected from a $C_1$-$C_6$-alkyl group, a $C_3$-$C_6$-cycloalkyl, a $C_1$-$C_6$-haloalkyl group, a $C_1$-$C_6$-hydroxyalkyl group, a $C_2$-$C_6$-alkenyl, a $C_2$-$C_6$-alkinyl group, a $C_4$-$C_6$-cycloalkenyl group, a $(C_1$-$C_6$-alkyl)-$N(R^7)R^8$ group, a —$(C_1$-$C_6$-alkyl)-N(H)C(=O)R^6$ group, a —$(C_1$-$C_6$-alkyl)-N(H)C(=O)OR^{15}$ group, a —$(C_1$-$C_6$-alkyl)-(4- to 6-membered nitrogen containing heterocycloalkyl) group wherein said 4- to 6-membered nitrogen containing heterocycloalkyl group is optionally substituted with a $C_1$-$C_3$-alkyl group, and wherein said 4- to 6-membered nitrogen containing heterocycloalkyl group is connected to the alkyl group via a carbon atom of the heterocycloalkyl group, and a phenyl group, which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, or tautomers, N-oxides, or salts thereof, or salts of tautomers or N-oxides of said compounds.

In further embodiments, the present invention provides compounds of formula (I), supra, in which:

$R^3$ represents a group selected from a $C_1$-$C_6$-alkyl group, a $C_3$-$C_6$-cycloalkyl, a $C_1$-$C_6$-haloalkyl group, a $C_1$-$C_6$-hydroxyalkyl group, a $C_2$-$C_6$-alkenyl, a $C_2$-$C_6$-alkinyl group, a $C_4$-$C_6$-cycloalkenyl group, a $(C_1$-$C_6$-alkyl)-$N(R^7)R^8$ group, a —$(C_1$-$C_6$-alkyl)-(4- to 6-membered nitrogen containing heterocycloalkyl) group and a phenyl group, wherein said 4- to 6-membered nitrogen containing heterocycloalkyl group is optionally substituted with a $C_1$-$C_3$-alkyl group, and wherein said 4- to 6-membered nitrogen containing heterocycloalkyl group is connected to the alkyl group via a carbon atom of the heterocycloalkyl group, and wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and tautomers, N-oxides, and salts thereof, and salts of tautomers or N-oxides.

In further embodiments, the present invention provides compounds of formula (I), supra, in which:

$R^3$ represents a group selected from a $C_1$-$C_6$-alkyl group, a $C_3$-$C_6$-cycloalkyl group, a $C_1$-$C_6$-haloalkyl group, a $C_1$-$C_6$-hydroxyalkyl group, a $C_2$-$C_6$-alkenyl group, $(C_1$-$C_6$-alkyl)-$N(R^7)R^8$ group, a —$(C_1$-$C_6$-alkyl)-N(H)C(=O)OR^{15}$ group and a phenyl group, or tautomers, N-oxides, or salts thereof, or salts of tautomers or N-oxides of said compounds.

In further embodiments, the present invention provides compounds of formula (I), supra, in which:

$R^3$ represents a group selected from a $C_1$-$C_6$-alkyl group, a $C_3$-$C_6$-cycloalkyl group, a $C_1$-$C_6$-haloalkyl group, a $C_1$-$C_6$-hydroxyalkyl group, a $C_2$-$C_6$-alkenyl group, $(C_1$-$C_6$-alkyl)-$N(R^7)R^8$ and a phenyl group, and tautomers, N-oxides, and salts thereof, and salts of tautomers or N-oxides.

In further embodiments, the present invention provides compounds of formula (I), supra, in which:

$R^3$ represents a group selected from propyl, cyclohexyl, trifluoromethyl, 1-hydroxyethyl, allyl, (dimethylamino)methyl, 2-(dimethylamino)ethyl, pyrrolidin-1-yl-methyl and phenyl, and tautomers, N-oxides, and salts thereof, and salts of tautomers or N-oxides.

In further embodiments, the present invention provides compounds of formula (I), supra, in which:

$R^3$ represents a group selected from propyl, cyclohexyl, trifluoromethyl, 1-hydroxyethyl, allyl, aminomethyl, (dimethylamino)methyl, (tert-butoxycarbonylamino)methyl, 2-(dimethylamino)ethyl, pyrrolidin-1-yl-methyl and phenyl, or tautomers, N-oxides, or salts thereof, or salts of tautomers or N-oxides of said compounds.

In further embodiments, the present invention provides compounds of formula (I), supra, in which $R^4$ and $R^5$ jointly form a 5- to 6-membered, optionally unsaturated, heterocyclic ring A of partial formula (i)

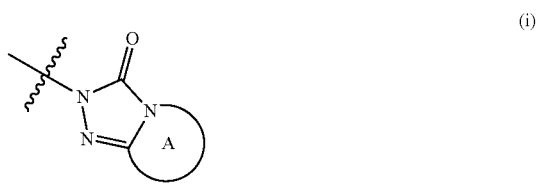

(i)

In which partial formula (i) includes but is not limited thereto e.g.

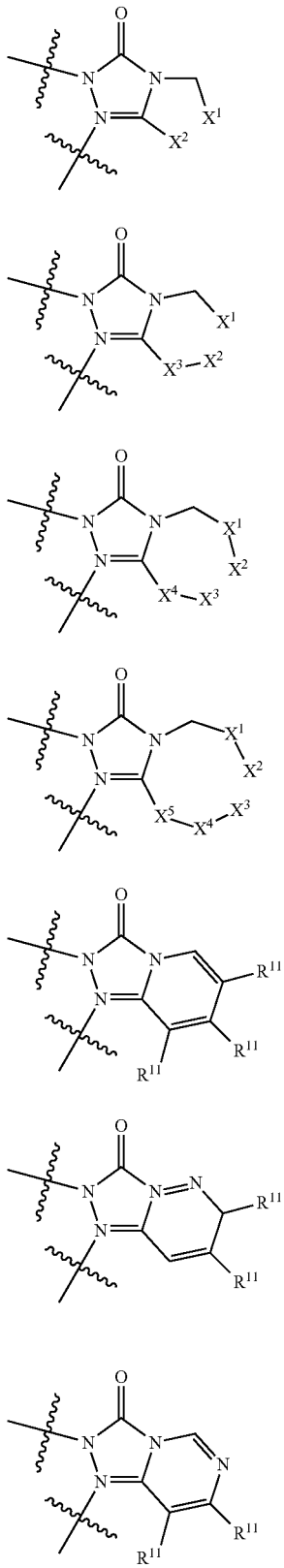

(ii)
(iii)
(iv)
(v)
(vi)
(vii)
(viii)

-continued

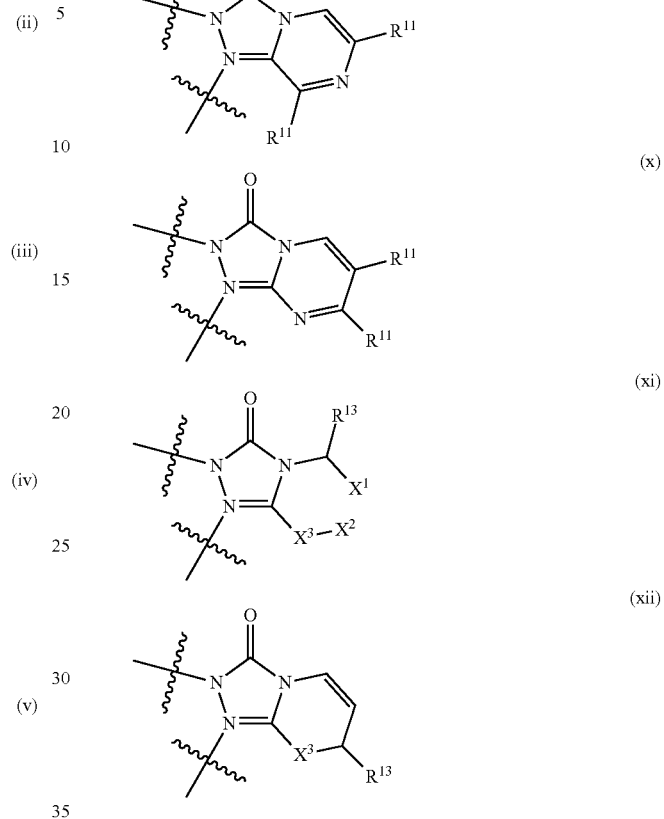

(ix)
(x)
(xi)
(xii)

in which $X^1$, $X^2$, $X^3$, $X^4$ and $X^5$ represents a group independently selected from —N(R$^7$)—, —O—, —S—, —S(=O)—, —S(=O)(=NR$^{14}$)— and —S(=O)$_2$— and
R$^{11}$ represents, independently from each occurrence a hydrogen atom, a halogen atom or a group selected from
C$_1$-C$_3$-alkyl, C$_1$-C$_3$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_3$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$—, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$)
more specifically a group selected from
a hydrogen atom, a halogen atom or a group selected from a C$_1$-C$_3$-alkyl group, a C$_1$-C$_3$-haloalkyl group, a C$_1$-C$_3$-alkoxy group, a C$_1$-C$_3$-haloalkoxy group and a cyano group, more specifically in which groups (ii) to (x)
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
or
one of X$^1$, X$^2$, X$^3$, X$^4$ and X$^5$ represents a group selected from —N(R$^7$)—, —O—, —S—, —S(=O)—, —S(=O)(=NR$^{14}$)— and —S(=O)$_2$—,
and one of X$^1$, X$^2$, X$^3$, X$^4$ and X$^5$ represents a group selected from C(R$^{12}$)$_2$ and CH(R$^{13}$), and the remaining of $X^1$, $X^2$, $X^3$, $X^4$ and $X^5$ each represent a $CH_2$ group, and $R^{11}$ represents independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group, even more specifically those ring systems as disclosed in the examples or tautomers, N-oxides, or salts thereof, or salts of tautomers or N-oxides of said compounds.

In further embodiments, the present invention provides compounds of formula (I), supra, in which $R^4$ and $R^5$ jointly form a 5- to 6-membered, optionally unsaturated, heterocyclic ring A of partial formula (i)

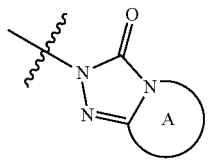
(i)

In which partial formula (i) includes but is not limited thereto e.g.

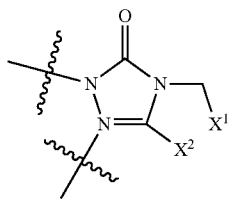
(ii)

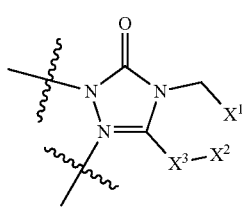
(iii)

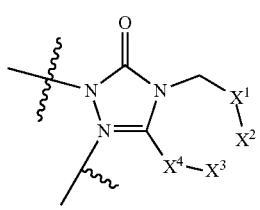
(iv)

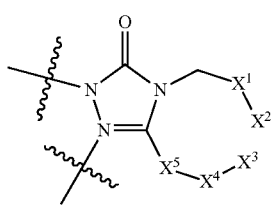
(v)

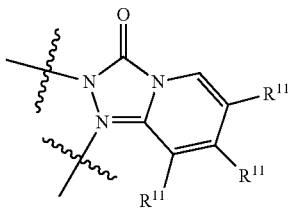
(vi)

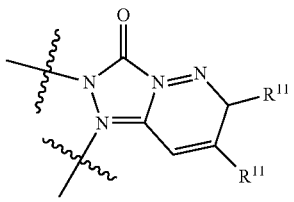
(vii)

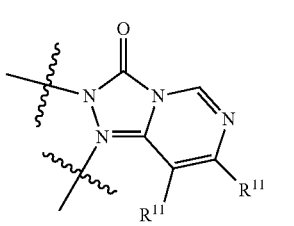
(viii)

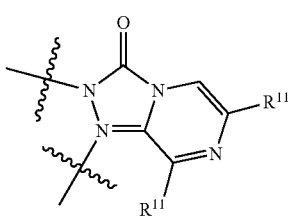
(ix)

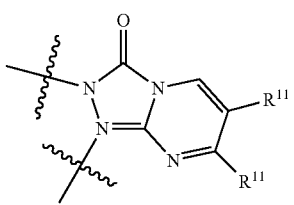
(x)

in which $X^1$, $X^2$, $X^3$, $X^4$ and $X^5$ represents a group independently selected from —N($R^7$)—, —O—, —S—, —S(=O)— and —S(=O)$_2$— and $R^{11}$ represents, independently from each occurrence a hydrogen atom, a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$—, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N($R^7$)($R^8$)

more specifically a group selected from a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group, more specifically in which groups (ii) to (x)

one of $X^1$, $X^2$, $X^3$, $X^4$ and $X^5$ represents a group selected from $C(R^{12})_2$ and $CH(R^{13})$,
and the remaining of $X^1$, $X^2$, $X^3$, $X^4$ and $X^5$ each represent a $CH_2$ group,
or
one of $X^1$, $X^2$, $X^3$, $X^4$ and $X^5$ represents a group selected from
—$N(R^7)$—, —O—, —S—, —S(=O)— and —S(=O)$_2$—,
and one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group, and
$R^{11}$ represents independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
even more specifically those ring systems as disclosed in the examples
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—$CH(R^{13})$—$X^1$—$X^2$—$X^3$—#,
*—CH=CH—$CH(R^{13})$—$X^3$—#,
*—CH=$C(R^{11})$—$C(R^{11})$=$C(R^{11})$—#,
*—N=$C(R^{11})$—$C(R^{11})$=$C(R^{11})$—#,
*—CH=N—$C(R^{11})$=$C(R^{11})$—#,
*—CH=$C(R^{11})$—N=$C(R^{11})$—#,
and
—CH=$C(R^{11})$—$C(R^{11})$=N—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or
one of $X^1$, $X^2$, $X^3$, $X^4$ and $X^5$ represents a group selected from
—$N(R^7)$—, —O—, —S—, —S(=O)—, —S(=O)(=$NR^{14}$)— and —S(=O)$_2$—,
and one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—CH=$C(R^{11})$—$C(R^{11})$=$C(R^{11})$—#,
*—N=$C(R^{11})$—$C(R^{11})$=$C(R^{11})$—#,
*—CH=N—$C(R^{11})$=$C(R^{11})$—#,
*—CH=$C(R^{11})$—N=$C(R^{11})$—#,
and
—CH=$C(R^{11})$—$C(R^{11})$=N—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or
one of $X^1$, $X^2$, $X^3$, $X^4$ and $X^5$ represents a group selected from
—$N(R^7)$—, —O—, —S—, —S(=O)— and —S(=O)$_2$—,
and one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—$CH(R^3)$—$X^1$—$X^2$—$X^3$—#,
*—CH=CH—$CH(R^{13})$—$X^3$—#,
*—CH=$C(R^{11})$—$C(R^{11})$=$C(R^{11})$—#,
*—N=$C(R^{11})$—$C(R^{11})$=$C(R^{11})$—#,
*—CH=N—$C(R^{11})$=$C(R^{11})$—#,
*—CH=$C(R^{11})$—N=$C(R^{11})$—#,
and
—CH=$C(R^{11})$—$C(R^{11})$=N—#, in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—$CH(R^{13})$—$X^1$—$X^2$—$X^3$—#,
*—CH=CH—$CH(R^{13})$—$X^3$—#,
*—CH=$C(R^{11})$—$C(R^{11})$=$C(R^{11})$—#,

*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
    in which groups "*" represents the point of attachment of R$^4$ to the rest of the molecule, and "#" represents the point of attachment of R$^5$ to the rest of the molecule,
    and in which groups
    one of X$^1$, X$^2$, X$^3$, X$^4$ and X$^5$ represents a group selected from
    —N(R$^7$)—, —O—, —S—, —S(=O)—, —S(=O)(=NR$^{14}$)— and —S(=O)$_2$—,
    and one of X$^1$, X$^2$, X$^3$, X$^4$ and X$^5$ represents a group selected from
    C(R$^{12}$)$_2$ and CH(R$^{13}$),
    and the remaining of X$^1$, X$^2$, X$^3$, X$^4$ and X$^5$ each represent a CH$_2$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
    in which groups "*" represents the point of attachment of R$^4$ to the rest of the molecule, and "#" represents the point of attachment of R$^5$ to the rest of the molecule,
    and in which groups
    one of X$^1$, X$^2$, X$^3$, X$^4$ and X$^5$ represents a group selected from
    C(R$^{12}$)$_2$ and CH(R$^{13}$),
    and the remaining of X$^1$, X$^2$, X$^3$, X$^4$ and X$^5$ each represent a CH$_2$ group,
and tautomers, N-oxides, and salts thereof, and salts of tautomers or N-oxides.

R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
    in which groups "*" represents the point of attachment of R$^4$ to the rest of the molecule, and "#" represents the point of attachment of R$^5$ to the rest of the molecule,
    and in which groups
    one of X$^1$, X$^2$, X$^3$, X$^4$ and X$^5$ represents a group selected from
    —N(R$^7$)—, —O—, —S—, —S(=O)— and —S(=O)$_2$—,
    and one of X$^1$, X$^2$, X$^3$, X$^4$ and X$^5$ represents a group selected from
    C(R$^{12}$)$_2$ and CH(R$^{13}$),
    and the remaining of X$^1$, X$^2$, X$^3$, X$^4$ and X$^5$ each represent a CH$_2$ group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
    in which groups "*" represents the point of attachment of R$^4$ to the rest of the molecule, and "#" represents the point of attachment of R$^5$ to the rest of the molecule,
    and in which groups
    one of X$^1$, X$^2$, X$^3$ and X$^4$ represents a group selected from
    C(R$^{12}$)$_2$ and CH(R$^{13}$),
    and the remaining of X$^1$, X$^2$, X$^3$ and X$^4$ each represent a CH$_2$ group,
    or
    one of X$^1$, X$^2$, X$^3$ and X$^4$ represents a group selected from
    —N(R$^7$)—, —O—, —S— and —S(=O)(=NR$^{14}$)—,
    X$^1$, X$^2$, X$^3$ and X$^4$ represents a C(R$^{12}$)$_2$ group,
    and the remaining of X$^1$, X$^2$, X$^3$ and X$^4$ each represent a CH$_2$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH=CH—CH(R$^{13}$)—X$^3$-+,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
    in which groups "*" represents the point of attachment of R$^4$ to the rest of the molecule, and "#" represents the point of attachment of R$^5$ to the rest of the molecule,
    and in which groups
    one of X$^1$, X$^2$, X$^3$ and X$^4$ represents a group selected from
    C(R$^{12}$)$_2$ and CH(R$^{13}$),
    and the remaining of X$^1$, X$^2$, X$^3$ and X$^4$ each represent a CH$_2$ group,
or tautomers, N-oxides, or salts thereof, or salts of tautomers or N-oxides of said compounds.

In further embodiments, the present invention provides compounds of formula (I), supra, in which:

$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH(R^{13})$—$X^1$—$X^2$—$X^3$—#,
*—$CH$=$CH$—$CH(R^{13})$—$X^3$—#,
*—$CH$=$C(R^{11})$—$C(R^{11})$=$C(R^{11})$—#,
*—$N$=$C(R^{11})$—$C(R^{11})$=$C(R^{11})$—#,
and
*—$CH$=$C(R^{11})$—$N$=$C(R^{11})$—#, in which groups "*" represents the point of attachment of $R^4$ to the rest of the molecule, and "#" represents the point of attachment of $R^5$ to the rest of the molecule,
and in which groups
one of $X^1$, $X^2$, $X^3$ and $X^4$ represents a group selected from
—$N(R^7)$—, —O—, —S— and —$S(=O)(=NR^{14})$—,
$X^1$, $X^2$, $X^3$ and $X^4$ represents a $C(R^{12})_2$ group,
and the remaining of $X^1$, $X^2$, $X^3$ and $X^4$ each represent a $CH_2$ group, or tautomers, N-oxides, or salts thereof, or salts of tautomers or N-oxides of said compounds.

In further embodiments, the present invention provides compounds of formula (I), supra, in which:

$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH$=$C(R^{11})$—$C(R^{11})$=$C(R^{11})$—#,
*—$N$=$C(R^{11})$—$C(R^{11})$=$C(R^{11})$—#,
and
*—$CH$=$C(R^{11})$—$N$=$C(R^{11})$—#, in which groups "*" represents the point of attachment of $R^4$ to the rest of the molecule, and "#" represents the point of attachment of $R^5$ to the rest of the molecule,
and in which groups
one of $X^1$, $X^2$, $X^3$ and $X^4$ represents a group selected from
$C(R^{12})_2$ and $CH(R^{13})$,
and the remaining of $X^1$, $X^2$, $X^3$ and $X^4$ each represent a $CH_2$ group,
or
one of $X^1$, $X^2$, $X^3$ and $X^4$ represents a group selected from
—$N(R^7)$—, —O— and —S—,
and one of $X^1$, $X^2$, $X^3$ and $X^4$ represents a $C(R^{12})_2$ group,
and the remaining of $X^1$, $X^2$, $X^3$ and $X^4$ each represent a $CH_2$ group,
and tautomers, N-oxides, and salts thereof, and salts of tautomers or N-oxides.

In further embodiments, the present invention provides compounds of formula (I), supra, in which:

$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH$=$C(R^{11})$—$C(R^{11})$=$C(R^{11})$—#,
*—$N$=$C(R^{11})$—$C(R^{11})$=$C(R^{11})$—#,
and
*—$CH$=$C(R^{11})$—$N$=$C(R^{11})$—#, in which groups "*" represents the point of attachment of $R^4$ to the rest of the molecule, and "#" represents the point of attachment of $R^5$ to the rest of the molecule,
and in which groups
one of $X^1$, $X^2$, $X^3$ and $X^4$ represents a group selected from
$C(R^{12})_2$ and $CH(R^{13})$,
and the remaining of $X^1$, $X^2$, $X^3$ and $X^4$ each represent a $CH_2$ group,
and tautomers, N-oxides, and salts thereof, and salts of tautomers or N-oxides.

In further embodiments, the present invention provides compounds of formula (I), supra, in which:

$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH$=$C(R^{11})$—$C(R^{11})$=$C(R^{11})$—#,
*—$N$=$C(R^{11})$—$C(R^{11})$=$C(R^{11})$—#,
and
*—$CH$=$C(R^{11})$—$N$=$C(R^{11})$—#, in which groups "*" represents the point of attachment of $R^4$ to the rest of the molecule, and "#" represents the point of attachment of $R^5$ to the rest of the molecule,
and in which groups
one of $X^1$, $X^2$, $X^3$ and $X^4$ represents a group selected from
—$N(R^7)$—, —O— and —S—,
and one of $X^1$, $X^2$, $X^3$ and $X^4$ represents a $C(R^{12})_2$ group,
and the remaining of $X^1$, $X^2$, $X^3$ and $X^4$ each represent a $CH_2$ group,
and tautomers, N-oxides, and salts thereof, and salts of tautomers or N-oxides.

In further embodiments, the present invention provides compounds of formula (I), supra, in which:

$R^4$ and $R^5$ are linked to one another in such a way that they jointly form a group selected from
*—$(CH_2)_2$—S—#,
*—$(CH_2)_4$—#,
*—$CH_2$—$C(H)(C(=O)OH)$—$(CH_2)_2$—#,
*—$CH_2$—$CF_2$—$(CH_2)_2$—#,
*—$(CH_2)_3$—$C(H)(C(=O)OH)$—#,
*—$CH(OH)$—$(CH_2)_3$—#,
*—$CH_2$—$CH(OH)$—$(CH_2)_2$—#,
*—$(CH_2)_2$—$CH(OH)$—$CH_2$—#,
*—$(CH_2)_3$—$C(H)(OH)$—#,
*—$CH$=$CH$—$CH(OH)$—$CH_2$—#,
*—$CH_2$—$C(CH_3)_2$—$CH_2$—O—#,
*—$(CH_2)_2$—O—$CH_2$—#,
*—$(CH_2)_3$—O—#,
*—$(CH_2)_3$—$N(CH_3)$—#,
*—$(CH_2)_3$—S—#,
*—$(CH_2)_3$—$S(=O)(=NH)$—,#
*—$(CH_2)_5$—#,
*—$(CH_2)_3O$—$CH_2$—#,

*—(CH$_2$)$_2$—N(H)—(CH$_2$)$_2$—#
*—CH═CH—CH═CH—#,
*—N═CH—CH═CH—#,
and
*—CH═CH—N═CH—#,
  in which groups "*" represents the point of attachment of R$^4$ to the rest of the molecule, and "#" represents the point of attachment of R$^5$ to the rest of the molecule,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—(CH$_2$)$_2$—S—#,
*—(CH$_2$)$_4$—#,
*—CH$_2$—C(H)(C(═O)OH)—(CH$_2$)$_2$—#,
*—CH$_2$—CF$_2$—(CH$_2$)$_2$—#,
*—(CH$_2$)$_3$—C(H)(C(═O)OH)—#,
*—(CH$_2$)$_3$—C(H)(OH)—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#
*—(CH$_2$)$_5$—#,
*—(CH$_2$)$_3$O—CH$_2$—#,
*—(CH$_2$)$_2$—N(H)—(CH$_2$)$_2$—#
*—CH═CH—CH═CH—#,
*—N═CH—CH═CH—#,
and
*—CH═CH—N═CH—#,
  in which groups represents the point of attachment of R$^4$ to the rest of the molecule, and "#" represents the point of attachment of R$^5$ to the rest of the molecule,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$ #,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH(R$^3$)—X$^1$—X$^2$—X$^3$—#,
*—CH═CH—CH(R$^{13}$)—X$^3$—,
and
*—CH═C(R$^{11}$)—C(R$^{11}$)═C(R$^{11}$)—#,
  in which groups "*" represents the point of attachment of R$^4$ to the rest of the molecule, and "#" represents the point of attachment of R$^5$ to the rest of the molecule,
  and in which groups
  one of X$^1$, X$^2$, X$^3$, X$^4$ and X$^5$ represents a group selected from
    C(R$^{12}$)$_2$ and CH(R$^{13}$),
  and the remaining of X$^1$, X$^2$, X$^3$, X$^4$ and X$^5$ each represent a CH$_2$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
and
*—CH═C(R$^{11}$)—C(R$^{11}$)═C(R$^{11}$)—#,
  in which groups "*" represents the point of attachment of R$^4$ to the rest of the molecule, and "#" represents the point of attachment of R$^5$ to the rest of the molecule,
  and in which groups
  one of X$^1$, X$^2$, X$^3$, X$^4$ and X$^5$ represents a group selected from
    C(R$^{12}$)$_2$ and CH(R$^{13}$),
  and the remaining of X$^1$, X$^2$, X$^3$, X$^4$ and X$^5$ each represent a CH$_2$ group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH═CH—CH(R$^{13}$)—X$^3$—
and
*—CH═C(R$^{11}$)—C(R$^{11}$)═C(R$^{11}$)—#,
  in which groups "*" represents the point of attachment of R$^4$ to the rest of the molecule, and "#" represents the point of attachment of R$^5$ to the rest of the molecule,
  and in which groups
  one of X$^1$, X$^2$, X$^3$ and X$^4$ represents a group selected from
    C(R$^{12}$)$_2$ and CH(R$^{13}$),
  and the remaining of X$^1$, X$^2$, X$^3$ and X$^4$ each represent a CH$_2$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
and
*—CH═C(R$^{11}$)—C(R$^{11}$)═C(R$^{11}$)—#,
  in which groups "*" represents the point of attachment of R$^4$ to the rest of the molecule, and "#" represents the point of attachment of R$^5$ to the rest of the molecule,
  and in which groups
  one of X$^1$, X$^2$, X$^3$ and X$^4$ represents a group selected from
    C(R$^{12}$)$_2$ and CH(R$^{13}$),
  and the remaining of X$^1$, X$^2$, X$^3$ and X$^4$ each represent a CH$_2$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—$(CH_2)_4$—#,
*—$CH_2$—$C(H)(C(=O)OH)$—$(CH_2)_2$—#,
*—$CH_2$—$CF_2$—$(CH_2)_2$—#,
*—$(CH_2)_3$—$C(H)(C(=O)OH)$—#,
*—$CH(OH)$—$(CH_2)_3$—#,
*—$CH_2$—$CH(OH)$—$(CH_2)_2$—#,
*—$(CH_2)_2$—$CH(OH)$—$CH_2$—#,
*—$(CH_2)_3$—$C(H)(OH)$—#,
*—$CH=CH$—$CH(OH)$—$CH_2$—#,
*—$(CH_2)_5$—#,
and
*—$CH=CH$—$CH=CH$—#,
in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
and
*—$CH(R^3)$—$X^1$—$X^2$—$X^3$—#,
in which groups represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
and
*—$CH_2$—$X^1$—$X^2$—$X^3$—$X^4$—$X^5$—#,
in which groups represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—$CH=CH$—$CH(R^{13})$—$X^3$—
and
*—$CH=C(R^{11})$—$C(R^{11})=C(R^{11})$—#,
in which groups "*" represents the point of attachment of $R^4$ to the rest of the molecule, and "#" represents the point of attachment of $R^5$ to the rest of the molecule,
and in which groups
$X^3$ represents a group selected from
$C(R^{12})_2$ and $CH(R^{13})$,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a
*—$CH=C(R^{11})$—$C(R^{11})=C(R^{11})$—#group,
in which group represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—$CH(R^3)$—$X^1$—$X^2$—$X^3$—#,
*—$CH=CH$—$CH(R^{13})$—$X^3$—
*—$N=C(R^{11})$—$C(R^{11})=C(R^{11})$—#,
*—$CH=N$—$C(R^{11})=C(R^{11})$—#,
*—$CH=C(R^{11})$—$N=C(R^{11})$—#,
and
*—$CH=C(R^{11})$—$C(R^{11})=N$—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
—$N(R^7)$—, —O—, —S—, —$S(=O)$—, —$S(=O)(=NR^{14})$— and —$S(=O)_2$—,
and one of $X^1$, $X^2$, $X^3$, $X^4$ and $X^5$ represents a group selected from
$C(R^{12})_2$ and $CH(R^{13})$,
and the remaining of $X^1$, $X^2$, $X^3$, $X^4$ and $X^5$ each represent a $CH_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,

*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
  —N($R^7$)—, —O—, —S—, —S(=O)— and —S(=O)$_2$—,
  and one of $X^1$, $X^2$, $X^3$, $X^4$ and $X^5$ represents a group selected from
  C($R^{12}$)$_2$ and CH($R^{13}$),
  and the remaining of $X^1$, $X^2$, $X^3$, $X^4$ and $X^5$ each represent a CH$_2$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
*—CH$_2$—$X^1$—$X^2$—$X^3$—$X^4$—$X^5$—#,
and
*—CH($R^3$)—$X^1$—$X^2$—$X^3$—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
  —N($R^7$)—, —O—, —S—, —S(=O)—, —S(=O)(=N$R^{14}$)— and —S(=O)$_2$—,
  and one of $X^1$, $X^2$, $X^3$, $X^4$ and $X^5$ represents a group selected from
  C($R^{12}$)$_2$ and CH($R^{13}$),
  and the remaining of $X^1$, $X^2$, $X^3$, $X^4$ and $X^5$ each represent a CH$_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
and
*—CH$_2$—$X^1$—$X^2$—$X^3$—$X^4$—$X^5$—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
  —N($R^7$)—, —O—, —S—, —S(=O)— and —S(=O)$_2$—,
  and one of $X^1$, $X^2$, $X^3$, $X^4$ and $X^5$ represents a group selected from
  C($R^{12}$)$_2$ and CH($R^{13}$),
  and the remaining of $X^1$, $X^2$, $X^3$, $X^4$ and $X^5$ each represent a CH$_2$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH=CH—CH($R^{13}$)—$X^3$—
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
  in which groups "*" represents the point of attachment of $R^4$ to the rest of the molecule, and "#" represents the point of attachment of $R^5$ to the rest of the molecule,
  and in which groups
  $X^3$ represents a group selected from
  —N($R^7$)—, —O—, —S—, —S(=O)—, —S(=O)(=N$R^{14}$)— and —S(=O)$_2$—,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from $R^4$ and $R^5$ are linked to one another in such a way that they jointly form a group selected from
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
  in which groups "*" represents the point of attachment of $R^4$ to the rest of the molecule, and "#" represents the point of attachment of $R^5$ to the rest of the molecule,
  and in which groups
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
*—CH($R^{13}$)—$X^1$—$X^2$—$X^3$—#,
*—CH=CH—CH($R^{13}$)—$X^3$—
and
*—CH=C($R^{11}$)—C($R^{11}$)=C($R^{11}$)—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$ and $X^4$ represents a group selected from
  C($R^{12}$)$_2$ and CH($R^{13}$),
  and the remaining of $X^1$, $X^2$, $X^3$ and $X^4$ each represent a CH$_2$ group, or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—(CH$_2$)$_4$—#,
*—CH$_2$—C(H)(C(=O)OH)—(CH$_2$)$_2$—#,
*—CH$_2$—CF$_2$—(CH$_2$)$_2$—#,
*—(CH$_2$)$_3$—C(H)(C(=O)OH)—#,
*—(CH$_2$)$_3$—C(H)(OH)—#,
*—(CH$_2$)$_5$—#,
and
*—CH=CH—CH=CH—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^3$)—X$^1$—X$^2$—X$^3$—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—(CH$_2$)$_4$—#,
*—CH$_2$—C(H)(C(=O)OH)—(CH$_2$)$_2$—#,
*—CH$_2$—CF$_2$—(CH$_2$)$_2$—#,
*—(CH$_2$)$_3$—C(H)(C(=O)OH)—#,
*—(CH$_2$)$_3$—C(H)(OH)—#,
and
*—(CH$_2$)$_5$—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—(CH$_2$)$_2$—S—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#,

*—(CH$_2$)$_3$—S(=O)(=NH)—,#
*—(CH$_2$)$_3$O—CH$_2$—#,
*—(CH$_2$)$_2$—N(H)—(CH$_2$)$_2$—#
*—N=CH—CH=CH—#,
and
*—CH=CH—N=CH—#,
in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—(CH$_2$)$_2$—S—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#
*—(CH$_2$)$_3$O—CH$_2$—#,
*—(CH$_2$)$_2$—N(H)—(CH$_2$)$_2$—#
*—N=CH—CH=CH—#,
and
*—CH=CH—N=CH—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—(CH$_2$)$_2$—S—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#,
*—(CH$_2$)$_3$—S(=O)(=NH)—,#
*—(CH$_2$)$_3$O—CH$_2$—#,
and
*—(CH$_2$)$_2$—N(H)—(CH$_2$)$_2$—#
in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—(CH$_2$)$_2$—S—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,

*—$(CH_2)_3$—S—#
*—$(CH_2)_3$O—$CH_2$—#,
and
*—$(CH_2)_2$—N(H)—$(CH_2)_2$—#
  in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—N=CH—CH=CH—#,
and
*—CH=CH—N=CH—#,
  in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—CH($R^3$)—$X^1$—$X^2$—$X^3$—#,
*—CH=CH—CH($R^{13}$)—$X^3$—,
*—CH=C($R^{11}$)—C($R^{11}$)=C($R^{11}$)—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
    $C(R^{12})_2$ and CH($R^{13}$),
    and the remaining of $X^1$, $X^2$, $X^3$, $X^4$ and $X^5$ each represent a $CH_2$ group,
  or
  one of $X^1$, $X^2$, $X^3$, $X^4$ and $X^5$ represents a group selected from
    —N($R^7$)—, —O—, —S—, —S(=O)—, —S(=O)(=NR$^{14}$)— and —S(=O)$_2$—,
    and one of $X^1$, $X^2$, $X^3$, $X^4$ and $X^5$ represents a group selected from
    $C(R^{12})_2$ and CH($R^{13}$),
    and the remaining of $X^1$, $X^2$, $X^3$, $X^4$ and $X^5$ each represent a $CH_2$ group,
and
$R^{11}$ represents, independently from each occurrence a hydrogen atom, a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$—, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R$^7$)(R$^8$)
and
$R^{12}$ represents, independently from each occurrence, a hydrogen atom, a halogen atom or a $C_1$-$C_3$-alkyl group,
and
$R^{13}$ represents a group selected from
  $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_3$-cycloalkoxy, aryl, —O-aryl, cyano, —C(=O)OR$^6$—, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R$^7$)(R$^8$),
and
$R^{14}$ represents a hydrogen atom or a group selected from
  a cyano group and a —C(=O)($C_1$-$C_3$-haloalkyl) group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$X^1$—$X^2$—#,
*—$CH_2$—$X^1$—$X^2$—$X^3$—#,
*—$CH_2$—$X^1$—$X^2$—$X^3$—$X^4$—#,
*—$CH_2$—$X^1$—$X^2$—$X^3$—$X^4$—$X^5$—#,
*—CH=C($R^{11}$)—C($R^{11}$)=C($R^{11}$)—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
  in which groups "*" represents the point of attachment of $R^4$ to the rest of the molecule, and "#" represents the point of attachment of $R^5$ to the rest of the molecule,
  and in which groups
  one of $X^1$, $X^2$, $X^3$, $X^4$ and $X^5$ represents a group selected from
    $C(R^{12})_2$ and CH($R^{13}$),
    and the remaining of $X^1$, $X^2$, $X^3$, $X^4$ and $X^5$ each represent a $CH_2$ group,
  or
  one of $X^1$, $X^2$, $X^3$, $X^4$ and $X^5$ represents a group selected from
    —N($R^7$)—, —O—, —S—, —S(=O)— and —S(=O)$_2$—,
    and one of $X^1$, $X^2$, $X^3$, $X^4$ and $X^5$ represents a group selected from
    $C(R^{12})_2$ and CH($R^{13}$),
    and the remaining of $X^1$, $X^2$, $X^3$, $X^4$ and $X^5$ each represent a $CH_2$ group,
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and
$R^{12}$ represents, independently from each occurrence, a hydrogen atom, a halogen atom or a $C_1$-$C_3$-alkyl group, and $R^{13}$ represents a group selected from
a hydroxy group, a —C(=O)OR$^6$ group and a —C(=O)N(R$^7$)(R$^8$) group,
and tautomers, N-oxides, and salts thereof, and salts of tautomers or N-oxides.

$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH(R$^3$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R)=C(R$^{11}$)—#,
*—CH=C(R$^{11}$)—N=C(R$^{11}$)—#,
and
*—CH=C(R)—C(R$^{11}$)=N—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and $R^{11}$ represents, independently from each occurrence a hydrogen atom, a halogen atom or a group selected from
C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$—, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$)
and $R^{12}$ represents, independently from each occurrence, a hydrogen atom, a halogen atom or
a C$_1$-C$_3$-alkyl group,
and $R^{13}$ represents a group selected from
C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$—, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$),
and $R^{14}$ represents a hydrogen atom or a group selected from
a cyano group and a —C(=O)(C$_1$-C$_3$-haloalkyl) group,
or tautomers, N-oxides, or salts thereof, or salts of tautomers or N-oxides of said compounds.

$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH(R$^{13}$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$, X$^4$ and X$^5$ represents a group selected from
—N(R$^7$)—, —O—, —S—, —S(=O)—, —S(=O)(=NR$^{14}$)— and —S(=O)$_2$—,
and one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and $R^{11}$ represents, independently from each occurrence a hydrogen atom, a halogen atom or a group selected from
C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$—, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$)
and $R^{12}$ represents, independently from each occurrence, a hydrogen atom, a halogen atom or
a C$_1$-C$_3$-alkyl group,
and $R^{13}$ represents a group selected from
C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_3$-cycloalkoxy, aryl, —O-aryl, cyano, —C(=O)OR$^6$—, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$),
and $R^{14}$ represents a hydrogen atom or a group selected from
a cyano group and a —C(=O)(C$_1$-C$_3$-haloalkyl) group,
or tautomers, N-oxides, or salts thereof, or salts of tautomers or N-oxides of said compounds.

In further embodiments, the present invention provides compounds of formula (I), supra, in which:

$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH=C(R$^{11}$)—C(R$^{11}$)=C(R$^{11}$)—#,
*—N=C(R$^{11}$)—C(R$^{11}$)=C(R$^{11}$)—#,

*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
R$^{11}$ represents, independently from each occurrence a hydrogen atom, a halogen atom or a group selected from a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
R$^{12}$ represents, independently from each occurrence, a hydrogen atom, a halogen atom or
a C$_1$-C$_3$-alkyl group,
and
R$^{13}$ represents a group selected from
a hydroxy group, a —C(=O)OR$^6$ group and a —C(=O)N(R$^7$)(R$^8$) group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH=C(R$^{11}$)—C(R$^{11}$)=C(R$^{11}$)—#,
*—N=C(R$^{11}$)—C(R$^{11}$)=C(R$^{11}$)—#,
*—CH=N—C(R$^{11}$)=C(R$^{11}$)—#,
*—CH=C(R$^{11}$)—N=C(R$^{11}$)—#,
and
*—CH=C(R$^{11}$)—C(R$^{11}$)=N—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$, X$^4$ and X$^5$ represents a group selected from
—N(R$^7$)—, —O—, —S—, —S(=O)— and —S(=O)$_2$—,
and one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
R$^{11}$ represents, independently from each occurrence a hydrogen atom, a halogen atom or a group selected from a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
R$^{12}$ represents, independently from each occurrence, a hydrogen atom, a halogen atom or
a C$_1$-C$_3$-alkyl group,
and
R$^{13}$ represents a group selected from
a hydroxy group, a —C(=O)OR$^6$ group and a —C(=O)N(R$^7$)(R) group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
or
one of X$^1$, X$^2$, X$^3$ and X$^4$ represents a group selected from
—N(R$^7$)—, —O—, —S— and —S(=O)(=NR$^{14}$)—,
X$^1$, X$^2$, X$^3$ and X$^4$ represents a C(R$^{12}$)$_2$ group,
and the remaining of X$^1$, X$^2$, X$^3$ and X$^4$ each represent a CH$_2$ group,
and
R$^{11}$ represents a hydrogen atom,
and
R$^{12}$ represent, identically or differently, a hydrogen atom, a halogen atom or
a C$_1$-C$_3$-alkyl group,
and
R$^{13}$ represents a group selected from
a hydroxy group and a —C(=O)OR$^6$ group,
and
R$^{14}$ represents a hydrogen atom or a group selected from
a cyano group and a —C(=O)CF$_3$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH=CH—CH(R$^{13}$)—X$^3$—#,

*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
and
R$^{11}$ represents a hydrogen atom,
and
R$^{12}$ represent, identically or differently, a hydrogen atom, a halogen atom or
a C$_1$-C$_3$-alkyl group,
and
R$^{13}$ represents a group selected from
a hydroxy group and a —C(=O)OR$^6$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH(R$^{13}$)—X$^1$—X$^2$—X$^3$—#,
*—CH=CH—CH(R$^{13}$)—X$^3$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
—N(R$^7$)—, —O—, —S— and —S(=O)(=NR$^{14}$)—,
X$^1$, X$^2$, X$^3$ and X$^4$ represents a C(R$^{12}$)$_2$ group,
and the remaining of X$^1$, X$^2$, X$^3$ and X$^4$ each represent a CH$_2$ group,
and
R$^{11}$ represents a hydrogen atom,
and
R$^{12}$ represent, identically or differently, a hydrogen atom, a halogen atom or
a C$_1$-C$_3$-alkyl group,
and
R$^{13}$ represents a group selected from
a hydroxy group and a —C(=O)OR$^6$ group,
and
R$^{14}$ represents a hydrogen atom or a group selected from
a cyano group and a —C(=O)CF$_3$ group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
or
one of X$^1$, X$^2$, X$^3$ and X$^4$ represents a group selected from
—N(R$^7$)—, —O— and —S—,
and one of X$^1$, X$^2$, X$^3$ and X$^4$ represents a C(R$^{12}$)$_2$ group,
and the remaining of X$^1$, X$^2$, X$^3$ and X$^4$ each represent a CH$_2$ group,
and
R$^{11}$ represents a hydrogen atom,
and
R$^{12}$ represents, independently from each occurrence, a hydrogen atom, a halogen atom or
a C$_1$-C$_3$-alkyl group,
and
R$^{13}$ represents a group selected from
a hydroxy group and a —C(=O)OR$^6$ group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
and
R$^{11}$ represents a hydrogen atom,
and
R$^{12}$ represents, independently from each occurrence, a hydrogen atom, a halogen atom or
a C$_1$-C$_3$-alkyl group, and
$R^{13}$ represents a group selected from
a hydroxy group and a —C(=O)OR$^6$ group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH=C(R$^{11}$)—C(R$^{11}$)=C(R$^{11}$)—#,
*—N=C(R$^{11}$)—C(R$^{11}$)=C(R$^{11}$)—#,
and
*—CH=C(R$^{11}$)—N=C(R$^{11}$)—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$ and X$^4$ represents a group selected from
—N(R$^7$)—, —O— and —S—,
and one of X$^1$, X$^2$, X$^3$ and X$^4$ represents a C(R$^{12}$)$_2$ group,
and the remaining of X$^1$, X$^2$, X$^3$ and X$^4$ each represent a CH$_2$ group,
and
$R^{11}$ represents a hydrogen atom,
and
$R^{12}$ represents, independently from each occurrence, a hydrogen atom, a halogen atom or
a C$_1$-C$_3$-alkyl group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—(CH$_2$)$_2$—S—#,
*—(CH$_2$)$_4$—#,
*—CH$_2$—C(H)(C(=O)OH)—(CH$_2$)$_2$—#,
*—CH$_2$—CF$_2$—(CH$_2$)$_2$—#,
*—(CH$_2$)$_3$—C(H)(C(=O)OH)—#,
*—(CH$_2$)$_3$—C(H)(OH)—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#
*—(CH$_2$)$_5$—#,
*—(CH$_2$)$_3$O—CH$_2$—#,
*—(CH$_2$)$_2$—N(H)—(CH$_2$)$_2$—#
*—CH=CH—CH=CH—#,
*—N=CH—CH=CH—#,
and
*—CH=CH—N=CH—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—X$^1$—X$^2$ #,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
*—CH(R$^3$)—X$^1$—X$^2$—X$^3$—#,
*—CH=CH—CH(R$^{13}$)—X$^3$—, and
*—CH=C(R$^{11}$)—C(R$^{11}$)=C(R$^{11}$)—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
$R^{11}$ represents, independently from each occurrence a hydrogen atom, a halogen atom or a group selected from
a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
$R^{12}$ represents, independently from each occurrence, a hydrogen atom, a halogen atom or
a C$_1$-C$_3$-alkyl group,
and
$R^{13}$ represents a group selected from
a hydroxy group, a —C(=O)OR$^6$ group and a —C(=O)N(R$^7$)(R$^8$) group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
*—CH$_2$—X$^1$—X$^2$—X$^3$—X$^4$—X$^5$—#,
and
*—CH=C(R$^{11}$)—C(R$^{11}$)=C(R$^{11}$)—#,
in which groups "*" represents the point of attachment of $R^4$ to the rest of the molecule, and "#" represents the point of attachment of $R^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
$R^{11}$ represents, independently from each occurrence a hydrogen atom, a halogen atom or a group selected from
a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
$R^{12}$ represents, independently from each occurrence, a hydrogen atom, a halogen atom or
a C$_1$-C$_3$-alkyl group,
and
$R^{13}$ represents a group selected from a hydroxy group, a —C(=O)OR$^6$ group and a —C(=O)N(R$^7$)(R$^8$) group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
\*—CH$_2$—X$^1$—X$^2$—#,
\*—CH$_2$—X$^1$—X$^2$—X$^3$—#,
\*—CH$_2$—X$^1$—X$^2$—X$^3$—X$^4$—#,
\*—CH(R$^3$)—X$^1$—X$^2$—X$^3$—#,
\*—CH=CH—CH(R$^13$)—X$^3$—
and
\*—CH=C(R$^{11}$)—C(R$^{11}$)=C(R$^{11}$)—#,
in which groups "\*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
and
R$^{11}$ represents, independently from each occurrence, a hydrogen atom, a halogen atom or a group selected from a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
R$^{12}$ represents, independently from each occurrence, a hydrogen atom, a halogen atom or
a C$_1$-C$_3$-alkyl group,
and
R$^{13}$ represents a group selected from
a hydroxy group, a —C(=O)OR$^6$ group and a —C(=O)N(R$^7$)(R$^8$) group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
\*—CH$_2$—X$^1$—X$^2$ #,
\*—CH$_2$—X$^1$—X$^2$—X$^3$—#,
\*—CH$_2$—X$^1$—X$^2$—X$^3$—X$^4$—#,
and
\*—CH=C(R$^{11}$)—C(R$^{11}$)=C(R$^{11}$)—#,
in which groups "\*" represents the point of attachment of R$^4$ to the rest of the molecule, and "#" represents the point of attachment of R$^5$ to the rest of the molecule,
and in which groups
one of X$^1$, X$^2$, X$^3$ and X$^4$ represents a group selected from
C(R$^{12}$)$_2$ and CH(R$^{13}$),
and the remaining of X$^1$, X$^2$, X$^3$ and X$^4$ each represent a CH$_2$ group,
and
R$^{11}$ represents a hydrogen atom,
and
R$^{12}$ represents, independently from each occurrence, a hydrogen atom, a halogen atom or a C$_1$-C$_3$-alkyl group,
and R$^{13}$ represents a group selected from
a hydroxy group and a —C(=O)OR$^6$ group,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
\*—CH$_2$—X$^1$—X$^2$—#,
\*—CH$_2$—X$^1$—X$^2$—X$^3$—#,
\*—CH$_2$—X$^1$—X$^2$—X$^3$—X$^4$—#,
\*—CH$_2$—X$^1$—X$^2$—X$^3$—X$^4$—X$^5$—#,
and
\*—CH(R$^{13}$)—X$^1$—X$^2$—X$^3$—#,
in which groups "\*" represents the point of attachment of R$^4$ to the rest of the molecule, and "#" represents the point of attachment of R$^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
R$^{11}$ represents, independently from each occurrence a hydrogen atom, a halogen atom or a group selected from a C$_1$-C$_3$-alkyl group, a C$_1$-C$_3$-haloalkyl group, a C$_1$-C$_3$-alkoxy group, a C$_1$-C$_3$-haloalkoxy group and a cyano group,
and
R$^{12}$ represents, independently from each occurrence, a hydrogen atom, a halogen atom or
a C$_1$-C$_3$-alkyl group,
and
R$^{13}$ represents a group selected from
a hydroxy group, a —C(=O)OR$^6$ group and a —C(=O)N(R$^7$)(R$^8$) group,
or tautomers, N-oxides, or salts thereof, or salts of tautomers or N-oxides of said compounds.

In further embodiments, the present invention provides compounds of formula (I), supra, in which:
R$^4$ and R$^5$ are linked to one another in such a way that they jointly form a group selected from
\*—CH$_2$—X$^1$—X$^2$—#,
\*—CH$_2$—X$^1$—X$^2$—X$^3$—#,
\*—CH$_2$—X$^1$—X$^2$—X$^3$—X$^4$—#,
and
\*—CH$_2$—X$^1$—X$^2$—X$^3$—X$^4$—X$^5$—#,
in which groups represents the point of attachment of R$^4$ to the rest of the molecule, and "#" represents the point of attachment of R$^5$ to the rest of the molecule,
and in which groups
one of X$^1$, X$^2$, X$^3$, X$^4$ and X$^5$ represents a group selected from
C(R$^{12}$)$_2$ and CH(R$^{13}$),
and the remaining of X$^1$, X$^2$, X$^3$, X$^4$ and X$^5$ each represent a CH$_2$ group,
and
R$^{12}$ represents, independently from each occurrence, a hydrogen atom, a halogen atom or
a C$_1$-C$_3$-alkyl group,
and
R$^{13}$ represents a group selected from
a hydroxy group, a —C(=O)OR$^6$ group and a —C(=O)N(R$^7$)(R$^8$) group, and tautomers, N-oxides, and salts thereof, and salts of tautomers or N-oxides.

In further embodiments, the present invention provides compounds of formula (I), supra, in which:

$R^4$ and $R^5$ are linked to one another in such a way that they jointly form a group selected from
*—CH=CH—CH($R^{13}$)—$X^3$—#,
and
*—CH=C($R^{11}$)—C($R^{11}$)=C($R^{11}$)—#,
in which groups "*" represents the point of attachment of $R^4$ to the rest of the molecule, and "#" represents the point of attachment of $R^5$ to the rest of the molecule,
and in which groups
$X^3$ represents a group selected from
C($R^{12}$)$_2$ and CH($R^{13}$),
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and
$R^{12}$ represents, independently from each occurrence, a hydrogen atom, a halogen atom or
a $C_1$-$C_3$-alkyl group,
and
$R^{13}$ represents a group selected from
a hydroxy group, a —C(=O)O$R^6$ group and a —C(=O)N($R^7$)($R^8$) group,
or tautomers, N-oxides, or salts thereof, or salts of tautomers or N-oxides of said compounds.

In further embodiments, the present invention provides compounds of formula (I), supra, in which:

$R^4$ and $R^5$ are linked to one another in such a way that they jointly form a
*—CH=C($R^{11}$)—C($R^{11}$)=C($R^{11}$)—#group,
in which group represents the point of attachment of $R^4$ to the rest of the molecule, and "#" represents the point of attachment of $R^5$ to the rest of the molecule,
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and tautomers, N-oxides, and salts thereof, and salts of tautomers or N-oxides.

In further embodiments, the present invention provides compounds of formula (I), supra, in which:

$R^4$ and Rare linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
*—CH$_2$—$X^1$—$X^2$—$X^3$—$X^4$—$X^5$—#,
*—CH($R^3$)—$X^1$—$X^2$—$X^3$—#,
*—CH=CH—CH($R^{13}$)—$X^3$—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
—N($R^7$)—, —O—, —S—, —S(=O)—, —S(=O)(=N$R^{14}$)— and —S(=O)$_2$—,
and one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a CH$_2$ group,
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and
$R^{12}$ represents, independently from each occurrence, a hydrogen atom, a halogen atom or
a $C_1$-$C_3$-alkyl group,
and
$R^{13}$ represents a group selected from
a hydroxy group, a —C(=O)O$R^6$ group and a —C(=O)N($R^7$)($R^8$) group,
and
$R^{14}$ represents a hydrogen atom or a group selected from
a cyano group and a —C(=O)($C_1$-$C_3$-haloalkyl) group,
or tautomers, N-oxides, or salts thereof, or salts of tautomers or N-oxides of said compounds.

In further embodiments, the present invention provides compounds of formula (I), supra, in which:

$R^4$ and $R^5$ are linked to one another in such a way that they jointly form a group selected from $R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
*—CH$_2$—$X^1$—$X^2$—$X^3$—$X^4$—$X^5$—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
—N($R^7$)—, —O—, —S—, —S(=O)— and —S(=O)$_2$—,
and one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a CH$_2$ group,
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and
$R^{12}$ represents, independently from each occurrence, a hydrogen atom, a halogen atom or a $C_1$-$C_3$-alkyl group,
and
$R^{13}$ represents a group selected from
a hydroxy group, a —C(=O)O$R^6$ group and a —C(=O)N($R^7$)($R^8$) group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
*—CH$_2$—$X^1$—$X^2$—$X^3$—$X^4$—$X^5$—#,
and
*—CH($R^{13}$)—$X^1$—$X^2$—$X^3$—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
—N($R^7$)—, —O—, —S—, —S(=O)—, —S(=O)(=N$R^{14}$)— and —S(=O)$_2$—,
and one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a CH$_2$ group,
and
$R^{12}$ represents, independently from each occurrence, a hydrogen atom, a halogen atom or
a $C_1$-$C_3$-alkyl group,
and
$R^{13}$ represents a group selected from
a hydroxy group, a —C(=O)O$R^6$ group and a —C(=O)N($R^7$)($R^8$) group,
and
$R^{14}$ represents a hydrogen atom or a group selected from
a cyano group and a —C(=O)(C$_1$-C$_3$-haloalkyl) group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—CH$_2$—$X^1$—$X^2$—#,
*—CH$_2$—$X^1$—$X^2$—$X^3$—#,
*—CH$_2$—$X^1$—$X^2$—$X^3$—$X^4$—#,
and
*—CH$_2$—$X^1$—$X^2$—$X^3$—$X^4$—$X^5$—#,
in which groups "*" represents the point of attachment of $R^4$ to the rest of the molecule, and "#" represents the point of attachment of $R^5$ to the rest of the molecule,
and in which groups
one of $X^1$, $X^2$, $X^3$, $X^4$ and $X^5$ represents a group selected from
—N($R^7$)—, —O—, —S—, —S(=O)— and —S(=O)$_2$—,
and one of $X^1$, $X^2$, $X^3$, $X^4$ and $X^5$ represents a group selected from
C($R^{12}$)$_2$ and CH($R^{13}$),
and the remaining of $X^1$, $X^2$, $X^3$, $X^4$ and $X^5$ each represent a CH$_2$ group,
and
$R^{12}$ represents, independently from each occurrence, a hydrogen atom, a halogen atom or
a $C_1$-$C_3$-alkyl group,
and
$R^{13}$ represents a group selected from
a hydroxy group, a —C(=O)O$R^6$ group and a —C(=O)N($R^7$)($R^8$) group,
and tautomers, N-oxides, and salts thereof, and salts of tautomers or N-oxides.

In further embodiments, the present invention provides compounds of formula (I), supra, in which:
$R^4$ and $R^5$ are linked to one another in such a way that they jointly form a group selected from
*—CH=CH—CH($R^{13}$)—$X^3$—#,
*—N=C($R^{11}$)—C($R^{11}$)=C($R^{11}$)—#,
*—CH=N—C($R^{11}$)=C($R^{11}$)—#,
*—CH=C($R^{11}$)—N=C($R^{11}$)—#,
and
*—CH=C($R^{11}$)—C($R^{11}$)=N—#,
in which groups "*" represents the point of attachment of $R^4$ to the rest of the molecule, and "#" represents the point of attachment of $R^5$ to the rest of the molecule,
and in which groups
$X^3$ represents a group selected from
—N($R^7$)—, —O—, —S—, —S(=O)—, —S(=O)(=N$R^{14}$)— and —S(=O)$_2$—,
and
$R^{11}$ represents, independently from each occurrence a hydrogen atom, a halogen atom or a group selected from
a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and
$R^{13}$ represents a group selected from
a hydroxy group, a —C(=O)O$R^6$ group and a —C(=O)N($R^7$)($R^8$) group,
and
$R^{14}$ represents a hydrogen atom or a group selected from
a cyano group and a —C(=O)(C$_1$-C$_3$-haloalkyl) group,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—(CH$_2$)$_2$—S—#,
*—CH$_2$—C(CH$_3$)$_2$—CH$_2$—O—#,
*—(CH$_2$)$_2$—O—CH$_2$—#,
*—(CH$_2$)$_3$—O—#,
*—(CH$_2$)$_3$—N(CH$_3$)—#,
*—(CH$_2$)$_3$—S—#,
*—(CH$_2$)$_3$—S(=O)(=NH)—,#
*—(CH$_2$)$_5$—#,
*—(CH$_2$)$_3$O—CH$_2$—#,
*—(CH$_2$)$_2$—N(H)—(CH$_2$)$_2$—#
*—N=CH—CH=CH—#,
and
*—CH=CH—N=CH—#,
in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$(CH_2)_4$—#,
*—$CH_2$—$C(H)(C(=O)OH)$—$(CH_2)_2$—#,
*—$CH_2$—$CF_2$—$(CH_2)_2$—#,
*—$(CH_2)_3$—$C(H)(C(=O)OH)$—#,
*—$CH(OH)$—$(CH_2)_3$—#,
*—$CH_2$—$CH(OH)$—$(CH_2)_2$—#,
*—$(CH_2)_2$—$CH(OH)$—$CH_2$—#,
*—$(CH_2)_3$—$C(H)(OH)$—#,
*—$CH=CH$—$CH(OH)$—$CH_2$—#,
*—$(CH_2)_5$—#, and
*—$CH=CH$—$CH=CH$—#,
   in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$CH_2$—$C(CH_3)_2$—$CH_2$—O—#,
*—$(CH_2)_2$—O—$CH_2$—#,
*—$(CH_2)_3$—O—#, and
*—$(CH_2)_3$O—$CH_2$—#,
   in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from
*—$(CH_2)_3$—$N(CH_3)$—#,
*—$(CH_2)_3$—$S(=O)(=NH)$—,#
*—$(CH_2)_2$—$N(H)$—$(CH_2)_2$—#
*—$N=CH$—$CH=CH$—#,
and
*—$CH=CH$—$N=CH$—#,
   in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In further embodiments, the present invention provides compounds of formula (I), supra, in which:
$R^4$ and $R^5$ are linked to one another in such a way that they jointly form a group selected from $R^4$ and $R^5$ are linked to one another in such a way that they jointly form a group selected from
*—$N=C(R^{11})$—$C(R^{11})=C(R^{11})$—#,
*—$CH=N$—$C(R^{11})=C(R^{11})$—#,
*—$CH=C(R^{11})$—$N=C(R^{11})$—#,
and
*—$CH=C(R^{11})$—$C(R^{11})=N$—#,
   in which groups "*" represents the point of attachment of $R^4$ to the rest of the molecule, and "#" represents the point of attachment of $R^5$ to the rest of the molecule,
   and in which groups
and
$R^{11}$ represents, independently from each occurrence a hydrogen atom, a halogen atom or a group selected from a $C_1$-$C_3$-alkyl group, a $C_1$-$C_3$-haloalkyl group, a $C_1$-$C_3$-alkoxy group, a $C_1$-$C_3$-haloalkoxy group and a cyano group,
and tautomers, N-oxides, and salts thereof, and salts of tautomers or N-oxides.

In further embodiments, the present invention provides compounds of formula (I), supra, in which:
$R^6$ represents a hydrogen atom or a group selected from a $C_1$-$C_6$-alkyl group and a benzyl group,
and tautomers, N-oxides, and salts thereof, and salts of tautomers or N-oxides.

In further embodiments, the present invention provides compounds of formula (I), supra, in which:
$R^6$ represents a hydrogen atom or a group selected from a $C_1$-$C_4$-alkyl group and a benzyl group,
and tautomers, N-oxides, and salts thereof, and salts of tautomers or N-oxides.

In further embodiments, the present invention provides compounds of formula (I), supra, in which:
$R^7$ and $R^8$ represent, independently from each occurrence, a hydrogen atom or a group selected from a $C_1$-$C_6$-alkyl group, a $C_2$-$C_6$-hydroxyalkyl group and a —$(C_2$-$C_6$-alkyl)-$N(R^9)(R^{10})$ group, or
$R^7$ and $R^8$ together with the nitrogen to which they are attached represent a nitrogen containing 4- to 7-membered heterocycloalkyl group,
   wherein said 4- to 7-membered nitrogen containing heterocycloalkyl group is optionally substituted with a group selected from $C_1$-$C_3$-alkyl, —$S(=O)_2(C_1$-$C_3$-alkyl) and —$C(=O)O(C_1$-$C_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently from each occurrence, a hydrogen atom or a group selected from
a $C_1$-$C_6$-alkyl group, a $C_2$-$C_6$-hydroxyalkyl group and a —$(C_2$-$C_6$-alkyl)-$N(R^9)(R^{10})$ group,
and tautomers, N-oxides, and salts thereof, and salts of tautomers or N-oxides.

In further embodiments, the present invention provides compounds of formula (I), supra, in which:
$R^7$ and $R^8$ together with the nitrogen to which they are attached represent a nitrogen containing 4- to 7-membered heterocycloalkyl group,
   wherein said 4- to 7-membered nitrogen containing heterocycloalkyl group is optionally substituted with a group selected from $C_1$-$C_3$-alkyl, —$S(=O)_2(C_1$-$C_3$-alkyl) and —$C(=O)O(C_1$-$C_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently from each occurrence, a hydrogen atom or a group selected from
a $C_1$-$C_3$-alkyl group, a $C_2$—C-hydroxyalkyl group and a —$(C_2$-$C_8$-alkyl)-$N(R^9)(R^{10})$, or
$R^7$ and $R^8$ together with the nitrogen to which they are attached represent a nitrogen containing 4- to 6-membered heterocycloalkyl group,
   wherein said 4- to 6-membered nitrogen containing heterocycloalkyl group is optionally substituted with a group selected from $C_1$-$C_3$-alkyl, —$S(=O)_2(C_1$-$C_3$-alkyl) and —$C(=O)O(C_1$-$C_4$-alkyl), and tautomers, N-oxides, and salts thereof, and salts of tautomers or N-oxides.

$R^7$ and $R^3$ represent, independently from each occurrence, a hydrogen atom or a group selected from
a $C_1$-$C_3$-alkyl group, a $C_2$-$C_3$-hydroxyalkyl group and a —($C_2$-$C_3$-alkyl)-N($R^9$)($R^{10}$), and tautomers, N-oxides, and salts thereof, and salts of tautomers or N-oxides.

$R^7$ and $R^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from $C_1$-$C_3$-alkyl, —S(=O)$_2$($C_1$-$C_3$-alkyl) and —C(=O)O($C_1$-$C_4$-alkyl), and tautomers, N-oxides, and salts thereof, and salts of tautomers or N-oxides.

In further embodiments, the present invention provides compounds of formula (I), supra, in which:
$R^7$ and $R^3$ represent, independently from each occurrence, a hydrogen atom or
a $C_1$-$C_3$-alkyl group, or $R^7$ and $R^8$ together with the nitrogen to which they are attached represent a nitrogen containing 4- to 6-membered heterocycloalkyl group, and tautomers, N-oxides, and salts thereof, and salts of tautomers or N-oxides.

In further embodiments, the present invention provides compounds of formula (I), supra, in which:
$R^7$ and $R^8$ represent, independently from each occurrence, a hydrogen atom or
a $C_1$-$C_3$-alkyl group, and tautomers, N-oxides, and salts thereof, and salts of tautomers or N-oxides.

In further embodiments, the present invention provides compounds of formula (I), supra, in which:
$R^7$ and $R^8$ together with the nitrogen to which they are attached represent a nitrogen containing 4- to 6-membered heterocycloalkyl group, and tautomers, N-oxides, and salts thereof, and salts of tautomers or N-oxides.

In further embodiments, the present invention provides compounds of formula (I), supra, in which:
$R^9$ and $R^{10}$ represent, independently from each occurrence, a hydrogen atom or a $C_1$-$C_3$-alkyl group, or $R^9$ and $R^{10}$ together with the nitrogen to which they are attached represent a nitrogen containing 4- to 7-membered heterocycloalkyl group, and tautomers, N-oxides, and salts thereof, and salts of tautomers or N-oxides.

In further embodiments, the present invention provides compounds of formula (I), supra, in which:
$R^9$ and $R^{10}$ represent, independently from each occurrence, a hydrogen atom or a $C_1$-$C_3$-alkyl group, and tautomers, N-oxides, and salts thereof, and salts of tautomers or N-oxides.

In further embodiments, the present invention provides compounds of formula (I), supra, in which:
$R^9$ and $R^{10}$ together with the nitrogen to which they are attached represent a nitrogen containing 4- to 7-membered heterocycloalkyl group, and tautomers, N-oxides, and salts thereof, and salts of tautomers or N-oxides.

In further embodiments, the present invention provides compounds of formula (I), supra, in which:
$R^9$ and $R^{10}$ represent, independently from each occurrence, a hydrogen atom or a $C_1$-$C_3$-alkyl group, or $R^9$ and $R^{10}$ together with the nitrogen to which they are attached represent a nitrogen containing 4- to 6-membered heterocycloalkyl group, and tautomers, N-oxides, and salts thereof, and salts of tautomers or N-oxides.

In further embodiments, the present invention provides compounds of formula (I), supra, in which:
$R^9$ and $R^{10}$ together with the nitrogen to which they are attached represent a nitrogen containing 4- to 6-membered heterocycloalkyl group, and tautomers, N-oxides, and salts thereof, and salts of tautomers or N-oxides.

In further embodiments, the present invention provides compounds of formula (I), supra, in which:
$R^{11}$ represents, independently from each occurrence a hydrogen atom, a halogen atom or a group selected from
a $C_1$-$C_3$-alkyl group, a $C_1$-$C_3$-haloalkyl group, a $C_1$-$C_3$-alkoxy group, a $C_1$-$C_3$-haloalkoxy group and a cyano group, and tautomers, N-oxides, and salts thereof, and salts of tautomers or N-oxides.

In further embodiments, the present invention provides compounds of formula (I), supra, in which:
$R^{11}$ represents a hydrogen atom,
and tautomers, N-oxides, and salts thereof, and salts of tautomers or N-oxides.

In further embodiments, the present invention provides compounds of formula (I), supra, in which:
$R^{12}$ represents, independently from each occurrence, a hydrogen atom, a halogen atom or
a $C_1$-$C_3$-alkyl group, and tautomers, N-oxides, and salts thereof, and salts of tautomers or N-oxides.

In further embodiments, the present invention provides compounds of formula (I), supra, in which:
$R^{13}$ represents a group selected from
a hydroxy group, a —C(=O)O$R^6$ group and a —C(=O)N($R^7$)($R^8$) group, and tautomers, N-oxides, and salts thereof, and salts of tautomers or N-oxides.

In further embodiments, the present invention provides compounds of formula (I), supra, in which:
$R^{13}$ represents a group selected from
a hydoxy group and a —C(=O)O$R^6$ group, and tautomers, N-oxides, and salts thereof, and salts of tautomers or N-oxides.

In further embodiments, the present invention provides compounds of formula (I), supra, in which:
$R^{14}$ represents a hydrogen atom or a group selected from
a cyano group and a —C(=O)($C_1$-$C_3$-haloalkyl) group, and tautomers, N-oxides, and salts thereof, and salts of tautomers or N-oxides.

In further embodiments, the present invention provides compounds of formula (I), supra, in which:
$R^{14}$ represents a hydrogen atom or a group selected from
a cyano group and a —C(=O)CF$_3$ group, or tautomers, N-oxides, or salts thereof, or salts of tautomers or N-oxides of said compounds.

In further embodiments, the present invention provides compounds of formula (I), supra, in which:
$R^{14}$ represents a hydrogen atom,
or tautomers, N-oxides, or salts thereof, or salts of tautomers or N-oxides of said compounds.

In further embodiments, the present invention provides compounds of formula (I), supra, in which:
$R^{14}$ represents a group selected from a cyano group and a —C(=O)CF$_3$ group,
or tautomers, N-oxides, or salts thereof, or salts of tautomers or N-oxides of said compounds.

In further embodiments, the present invention provides compounds of formula (I), supra, in which:
$R^{15}$ represents a group selected from a C$_1$-C$_6$-alkyl group and a benzyl group,
or tautomers, N-oxides, or salts thereof, or salts of tautomers or N-oxides of said compounds.

In further embodiments, the present invention provides compounds of formula (I), supra, in which:
$R^{15}$ represents a group selected from a C$_1$-C$_4$-alkyl group and a benzyl group,
or tautomers, N-oxides, or salts thereof, or salts of tautomers or N-oxides of said compounds.

In further embodiments, the present invention provides compounds of formula (I), supra, in which:
$R^{15}$ represents a C$_1$-C$_4$-alkyl group,
or tautomers, N-oxides, or salts thereof, or salts of tautomers or N-oxides of said compounds.

In further embodiments, the present invention provides compounds of formula (I), supra, in which:
$R^1$ represents a group selected from
  a C$_3$-C$_6$-cycloalkyl group, is optionally substituted, one or two times, each substituent independently selected from a halogen atom, a phenyl group and a —N(R$^7$)(R$^8$) group,
    wherein said phenyl substituent is optionally substituted, one, two or three times, each substituent independently selected from a halogen atom,
  a C$_2$-C$_6$-hydroxyalkyl group,
  a —(C$_2$-C$_6$-alkyl)-N(R$^7$)(R$^8$) group,
  a 4- to 6-membered heterocycloalkyl group, wherein said 4- to 6-membered heterocycloalkyl group is connected to the rest of the molecule via a carbon atom of said 4- to 6-membered heterocycloalkyl group, and said 4- to 6-membered heterocycloalkyl group is optionally substituted one or two times, each substituent independently selected from a group selected from C$_1$-C$_3$-alkyl, 5- to 6-membered heteroaryl, —C(=O)O(C$_1$-C$_4$-alkyl), —C(=O)(C$_1$-C$_3$-alkyl), —C(=O)(C$_3$-C$_6$-cycloalkyl), —S(=O)$_2$(C$_1$-C$_3$-alkyl) and oxo (=O),
  a phenyl group, which is optionally substituted, one, two, three or four times, each substituent independently selected from a halogen atom or a group selected from C$_1$-C$_3$-alkyl, C$_1$-C$_3$-haloalkyl, C$_1$-C$_3$-hydroxyalkyl, C$_1$-C$_3$-alkoxy, hydroxy, cyano, —C(=O)OR$^6$, —C(=O)N(R$^7$)(R$^8$), —N(R$^7$)(R$^8$), —(C$_1$-C$_3$-alkyl)-N(R$^7$)(R$^8$), —S(=O)$_2$N(R$^7$)(R$^8$) and SF$_5$,
    or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—,
  an indanyl group which is optionally substituted with a hydroxy group
  and
  a monocyclic or bicyclic heteroaryl group,
    which is optionally substituted one, two or three times, each substituent independently selected from a halogen atom or a group selected from C$_1$-C$_3$-alkyl, C$_1$-C$_3$-alkoxy, hydroxy and —N(R$^7$)(R$^8$), and
and
$R^2$ represents a hydrogen atom or a chlorine atom or a fluorine atom,
or tautomers, N-oxides, or salts thereof, or salts of tautomers or N-oxides of said compounds.

In further embodiments, the present invention provides compounds of formula (I), supra, in which:
$R^1$ represents a group selected from
  a C$_3$-C$_6$-cycloalkyl group, is optionally substituted, one or two times, each substituent independently selected from a halogen atom, a phenyl group and a —N(R$^7$)(R$^8$) group,
    wherein said phenyl substituent is optionally substituted, one, two or three times, each substituent independently selected from a halogen atom,
  a C$_2$-C$_6$-hydroxyalkyl group,
  a —(C$_2$-C$_6$-alkyl)-N(R$^7$)(R$^8$) group,
  a 4- to 6-membered heterocycloalkyl group, wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from C$_1$-C$_3$-alkyl, 5- to 6-membered heteroaryl, —C(=O)O(C$_1$-C$_4$-alkyl), —C(=O)(C$_1$-C$_3$-alkyl), —C(=O)(C$_3$-C$_6$-cycloalkyl), —S(=O)$_2$(C$_1$-C$_3$-alkyl) and oxo (=O),
  a phenyl group, which is optionally substituted, one, two, three or four times, each substituent independently selected from a halogen atom or a group selected from
    C$_1$-C$_3$-alkyl, C$_1$-C$_3$-haloalkyl, C$_1$-C$_3$-hydroxyalkyl, C$_1$-C$_3$-alkoxy, hydroxy, cyano, —C(=O)OR$^6$, —C(=O)N(R$^7$)(R$^8$), —N(R$^7$)(R$^8$), —(C$_1$-C$_3$-alkyl)-N(R$^7$)(R$^8$), —S(=O)$_2$N(R$^7$)(R$^8$) and SF$_5$,
    or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—,
  an indanyl group which is optionally substituted with a hydroxy group
  and
  a monocyclic or bicyclic heteroaryl group,
    which is optionally substituted one, two or three times, each substituent independently selected from a halogen atom or a group selected from C$_1$-C$_3$-alkyl, C$_1$-C$_3$-alkoxy, hydroxy and —N(R$^7$)(R$^8$), and
and
$R^2$ represents a hydrogen atom or a fluorine atom,
and tautomers, N-oxides, and salts thereof, and salts of tautomers or N-oxides.

In further embodiments, the present invention provides compounds of formula (I), supra, in which:
$R^1$ represents a group selected from
  a C$_3$-C$_6$-cycloalkyl group, is optionally substituted, one or two times, each substituent independently selected from a halogen atom or a group selected from a phenyl group and a —N(R$^7$)(R$^8$) group,
    wherein said phenyl substituent is optionally substituted, one, two or three times, each substituent independently selected from a halogen atom,
  a C$_2$-C$_6$-hydroxyalkyl group,
  a —(C$_2$-C$_6$-alkyl)-N(R$^7$)(R$^8$) group,
  a 4- to 6-membered heterocycloalkyl group, wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), a phenyl group, which is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —S(=O)$_2$N(R$^7$)(R$^8$) and SF$_5$, or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—, an indanyl group which is optionally substituted with a hydroxy group and a monocyclic or bicyclic heteroaryl group,
which is optionally substituted one, two or three times, each substituent independently selected from a halogen atom or a group selected from $C_1$-$C_3$-alkyl, $C_1$-$C_3$-alkoxy, hydroxy and —N(R$^7$)(R$^8$), and and R$^2$ represents a chlorine atom or a fluorine atom, or tautomers, N-oxides, or salts thereof, or salts of tautomers or N-oxides of said compounds.

In further embodiments, the present invention provides compounds of formula (I), supra, in which:

R$^1$ represents a group selected from a $C_3$-$C_6$-cycloalkyl group, a $C_2$-$C_6$-hydroxyalkyl group, a —($C_2$-$C_6$-alkyl)-N(R$^7$)(R$^8$) group, a 4- to 6-membered heterocycloalkyl group, a phenyl group, an indanyl group and a monocyclic or bicyclic heteroaryl group, wherein said $C_3$-$C_6$-cycloalkyl group is optionally substituted, one or two times, each substituent independently selected from a halogen atom or a group selected from
phenyl and —N(R$^7$)(R$^8$),
wherein said phenyl substituent is optionally substituted, one, two or three times, each substituent independently selected from a halogen atom,
and
wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
and
wherein said phenyl group is optionally substituted, one, two, three or four times, each substituent independently selected from a halogen atom or a group selected from
$C_1$-$C_3$-alkyl, $C_1$-$C_3$-haloalkyl, $C_1$-$C_3$-hydroxyalkyl, $C_1$-$C_3$-alkoxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —S(=O)$_2$N(R$^7$)(R$^8$) and SF$_5$, or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—, and wherein said indanyl group is optionally substituted with a hydroxy group, and wherein said monocyclic or bicyclic heteroaryl group is optionally substituted one, two or three times, each substituent independently selected from a halogen atom or a group selected from
$C_1$-$C_3$-alkyl, $C_1$-$C_3$-alkoxy, hydroxy and —N(R$^7$)(R$^8$),
and R$^2$ represents a hydrogen atom or a fluorine atom, and tautomers, N-oxides, and salts thereof, and salts of tautomers or N-oxides.

In further embodiments, the present invention provides compounds of formula (I), supra, in which:

R$^1$ represents a group selected from a $C_3$-$C_6$-cycloalkyl group, is optionally substituted, one or two times, each substituent independently selected from a halogen atom or a group selected from a phenyl group and a —N(R$^7$)(R$^8$) group,
wherein said phenyl substituent is optionally substituted, one, two or three times, each substituent independently selected from a halogen atom, a $C_2$-$C_6$-hydroxyalkyl group, a —($C_2$-$C_6$-alkyl)-N(R$^7$)(R$^8$) group, a 4- to 6-membered heterocycloalkyl group, wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_3$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), a phenyl group which is optionally substituted, one, two, three or four times, each substituent independently selected from a halogen atom or a group selected from
$C_1$-$C_3$-alkyl, $C_1$-$C_3$-haloalkyl, $C_1$-$C_3$-hydroxyalkyl, $C_1$-$C_3$-alkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —S(=O)$_2$N(R$^7$)(R$^8$) and SF$_5$, or in which two substituents of said phenyl group, when they are attached to adjacent ring atoms, are optionally linked to one another in such a way that they jointly form a group selected from —CH$_2$—N(R$^7$)—CH$_2$— and —O—CH$_2$—C(=O)—NH—, an indanyl group which is optionally substituted with a hydroxy group and a monocyclic or bicyclic heteroaryl group,
which is optionally substituted one, two or three times, each substituent independently selected from a halogen atom or a group selected from $C_1$-$C_3$-alkyl, $C_1$-$C_3$-alkoxy, hydroxy and —N(R$^7$)(R$^8$), and R$^2$ represents a fluorine atom, or tautomers, N-oxides, or salts thereof, or salts of tautomers or N-oxides of said compounds.

In further embodiments, the present invention provides compounds of formula (I), supra, in which:

In further embodiments, the present invention provides compounds of formula (I), supra, in which:

$R^1$ represents a group selected from
a $C_3$-$C_6$-cycloalkyl group, a $C_2$-$C_6$-hydroxyalkyl group, a —($C_2$-$C_6$-alkyl)-N($R^7$)($R^8$) group,
a 4- to 6-membered heterocycloalkyl group, a phenyl group, an indanyl group and a monocyclic or bicyclic heteroaryl group,
   wherein said $C_3$-$C_6$-cycloalkyl group is optionally substituted, one or two times, each substituent independently selected from a halogen atom or a group selected from
   phenyl and —N($R^7$)($R^8$),
      wherein said phenyl substituent is optionally substituted, one, two or three times, each substituent independently selected from a halogen atom,
   and
   wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
   and
   wherein said phenyl group is optionally substituted, one, two, three or four times, each substituent independently selected from a halogen atom or a group selected from
   $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$,
   or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—,
   and
   wherein said indanyl group is optionally substituted with a hydroxy group,
   and
   wherein said monocyclic or bicyclic heteroaryl group is optionally substituted one, two or three times, each substituent independently selected from a halogen atom or a group selected from
   $C_1$-$C_3$-alkyl, $C_1$-$C_3$-alkoxy, hydroxy and —N($R^7$)($R^8$), and $R^2$ represents a fluorine atom,
and tautomers, N-oxides, and salts thereof, and salts of tautomers or N-oxides.

In further embodiments, the present invention provides compounds of formula (I), supra, in which:

$R^1$ represents a group selected from
a $C_3$-$C_6$-cycloalkyl group, which is optionally substituted, one or two times, each substituent independently selected from a halogen atom or a group selected from a phenyl group and a —N($R^7$)($R^8$) group,
   wherein said phenyl substituent is optionally substituted, one or three times, each substituent independently selected from a halogen atom,
a $C_2$-$C_6$-hydroxyalkyl group,
a —($C_2$-$C_6$-alkyl)-N($R^7$)($R^8$) group, a 4- to 6-membered heterocycloalkyl group, wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
a phenyl group, which is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, hydroxy, cyano, C(=O)O$R^6$, —C(=O)N($R^7$)($R^8$), —N($R^7$)($R^8$), —($C_1$-$C_3$-alkyl)-N($R^7$)($R^8$), —S(=O)$_2$N($R^7$)($R^8$) and SF$_5$,
   or in which two substituents of said phenyl group, when they are attached to adjacent ring atoms, are optionally linked to one another in such a way that they jointly form a group selected from —CH$_2$—N($R^7$)—CH$_2$— and —O—CH$_2$—C(=O)—NH—,
an indanyl group which is optionally substituted with a hydroxy group
and
a monocyclic or bicyclic heteroaryl group,
   which is optionally substituted one, two or three times, each substituent independently selected from a halogen atom or a group selected from $C_1$-$C_3$-alkyl, $C_1$-$C_3$-alkoxy, hydroxy and —N($R^7$)($R^8$), and
and
$R^3$ represents a $C_1$-$C_6$-haloalkyl group,
or tautomers, N-oxides, or salts thereof, or salts of tautomers or N-oxides of said compounds.

In further embodiments, the present invention provides compounds of formula (I), supra, in which:

$R^1$ represents a group selected from
a $C_3$-$C_6$-cycloalkyl group, a $C_2$-$C_6$-hydroxyalkyl group, a —($C_2$-$C_6$-alkyl)-N($R^7$)($R^8$) group,
a 4- to 6-membered heterocycloalkyl group, a phenyl group, an indanyl group and a monocyclic or bicyclic heteroaryl group,
   wherein said $C_3$-$C_6$-cycloalkyl group is optionally substituted, one or two times, each substituent independently selected from a halogen atom or a group selected from
   phenyl and —N($R^7$)($R^8$),
      wherein said phenyl substituent is optionally substituted, one, two or three times, each substituent independently selected from a halogen atom,
   and
   wherein said 4- to 6-membered heterocycloalkyl group, which is connected to the rest of the molecule via a carbon atom of said 4- to 6-membered heterocycloalkyl group, is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
   and
   wherein said phenyl group is optionally substituted, one, two, three or four times, each substituent independently selected from a halogen atom or a group selected from
   $C_1$-$C_3$-alkyl, $C_1$-$C_3$-haloalkyl, $C_1$-$C_3$-hydroxyalkyl, $C_1$-$C_3$-alkoxy, cyano, —C(=O)O$R^6$, —C(=O)N $(R^7)(R^8)$, —$N(R^7)(R^8)$, —$(C_1-C_3$-alkyl$)$-$N(R^7)(R^8)$, —$S(=O)_2N(R^7)(R^8)$ and $SF_5$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and wherein said indanyl group is optionally substituted with a hydroxy group, and wherein said monocyclic or bicyclic heteroaryl group is optionally substituted one, two or three times, each substituent independently selected from a halogen atom or a group selected from $C_1-C_3$-alkyl, $C_1-C_3$-alkoxy, hydroxy and —$N(R^7)(R^8)$, and $R^3$ represents a $C_1-C_6$-haloalkyl group, and tautomers, N-oxides, and salts thereof, and salts of tautomers or N-oxides.

In further embodiments, the present invention provides compounds of formula (I), supra, in which:

$R^1$ represents a group selected from a phenyl group, which is optionally substituted, one, two, three or four times, each substituent independently selected from a halogen atom or a group selected from $C_1-C_6$-alkyl, $C_1-C_6$-haloalkyl, $C_2-C_6$-alkenyl, $C_2-C_6$-alkynyl, aryl, —$(C_1-C_6$-alkyl$)$-aryl, -aryl-$(C_1-C_6$-alkyl$)$, $C_3-C_8$-cycloalkyl, $C_1-C_6$-alkoxy, —$O(C_2-C_6$-alkenyl$)$, $C_1-C_6$-haloalkoxy, $C_3-C_8$-cycloalkoxy, aryl, —$O$-aryl, hydroxy, cyano, —$C(=O)OR^6$, hydroxy, —$SH$, —$S$—$(C_1-C_6$-alkyl$)$, —$S$—$(C_2-C_6$-alkenyl$)$, —$S(=O)_2(C_1-C_6$-alkyl$)$, —$N(O)_2$, and —$N(R^7)(R^8)$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and $R^3$ represents a $C_1-C_6$-haloalkyl group, or tautomers, N-oxides, or salts thereof, or salts of tautomers or N-oxides of said compounds.

In further embodiments, the present invention provides compounds of formula (I), supra, in which:

$R^1$ represents a group selected from a phenyl group, which is phenyl group is optionally substituted, one, two, three or four times, each substituent independently selected from a halogen atom or a group selected from $C_1-C_6$-alkyl, $C_1-C_6$-haloalkyl, $C_2-C_6$-alkenyl, $C_2-C_6$-alkynyl, aryl, —$(C_1-C_6$-alkyl$)$-aryl, -aryl-$(C_1-C_6$-alkyl$)$, $C_3-C_8$-cycloalkyl, $C_1-C_6$-alkoxy, —$O(C_2-C_6$-alkenyl$)$, $C_1-C_6$-haloalkoxy, $C_3-C_8$-cycloalkoxy, aryl, —$O$-aryl, cyano, —$C(=O)OR^6$, hydroxy, —$SH$, —$S$—$(C_1-C_6$-alkyl$)$, —$S$—$(C_2-C_6$-alkenyl$)$, —$S(=O)_2(C_1-C_6$-alkyl$)$, —$N(O)_2$, and —$N(R^7)(R^8)$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and $R^3$ represents a $C_1-C_6$-haloalkyl group, and tautomers, N-oxides, and salts thereof, and salts of tautomers or N-oxides.

In further embodiments, the present invention provides compounds of formula (I), supra, in which:

$R^1$ represents a group selected from a phenyl group, which is phenyl group is optionally substituted, one, two, three or four times, each substituent independently selected from a halogen atom or a group selected from $C_1-C_6$-alkyl, $C_1-C_6$-haloalkyl, $C_2-C_6$-alkenyl, $C_2-C_6$-alkynyl, aryl, —$(C_1-C_6$-alkyl$)$-aryl, -aryl-$(C_1-C_6$-alkyl$)$, $C_3-C_8$-cycloalkyl, $C_1-C_6$-alkoxy, —$O(C_2-C_6$-alkenyl$)$, $C_1-C_6$-haloalkoxy, $C_3-C_8$-cycloalkoxy, aryl, —$O$-aryl, cyano, —$C(=O)OR^6$, hydroxy, —$SH$, —$S$—$(C_1-C_6$-alkyl$)$, —$S$—$(C_2-C_6$-alkenyl$)$, —$S(O)_2$, —$N(O)_2$, and —$N(R^7)(R^8)$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and $R^3$ represents a $C_1-C_6$-haloalkyl group, and tautomers, N-oxides, and salts thereof, and salts of tautomers or N-oxides.

In further embodiments, the present invention provides compounds of formula (I), supra, in which:

$R^1$ represents a group selected from a phenyl group, which is optionally substituted, one, two, three or four times, each substituent independently selected from a halogen atom or a group selected from $C_1-C_3$-alkyl, $C_1-C_3$-haloalkyl, $C_1-C_3$-hydroxyalkyl, $C_1-C_3$-alkoxy, hydroxy, cyano, —$C(=O)OR^6$, —$C(=O)N(R^7)(R^8)$, —$N(R^7)(R^8)$, —$(C_1-C_3$-alkyl$)$-$N(R^7)(R^8)$, —$S(=O)_2N(R^7)(R^8)$ and $SF_5$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and $R^3$ represents a $C_1-C_6$-haloalkyl group, or tautomers, N-oxides, or salts thereof, or salts of tautomers or N-oxides.

In further embodiments, the present invention provides compounds of formula (I), supra, in which:

$R^1$ represents a group selected from a phenyl group, which is phenyl group is optionally substituted, one, two, three or four times, each substituent independently selected from a halogen atom or a group selected from $C_1-C_3$-alkyl, $C_1-C_3$-haloalkyl, $C_1-C_3$-hydroxyalkyl, $C_1-C_3$-alkoxy, cyano, —$C(=O)OR^6$, —$C(=O)N(R^7)(R^8)$, —$N(R^7)(R^8)$, —$(C_1-C_3$-alkyl$)$-$N(R^7)(R^8)$, —$S(=O)_2N(R^7)(R^8)$ and $SF_5$, or in which two substituents of said phenyl group, when they are attached to adjacent ring atoms, are optionally linked to one another in such a way that they jointly form a group selected from —$CH_2$—$N(R^7)$—$CH_2$— and —$O$—$CH_2$—$C(=O)$—$NH$—, and $R^3$ represents a $C_1-C_6$-haloalkyl group, and tautomers, N-oxides, and salts thereof, and salts of tautomers or N-oxides.

In further embodiments, the present invention provides compounds of formula (I), supra, in which:

R¹ represents a group selected from
a phenyl group, which is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, hydroxy, cyano, —C(=O)OR⁶, —C(=O)N(R⁷)(R⁸), —N(R⁷)(R⁸), —(C₁-C₃-alkyl)-N(R⁷)(R⁸), —S(=O)₂N(R⁷)(R⁸) and SF₅,
or in which two substituents of said phenyl group, when they are attached to adjacent ring atoms, are optionally linked to one another in such a way that they jointly form a group selected from
—CH₂—N(R⁷)—CH₂— and —O—CH₂—C(=O)—NH—,
and
R³ represents a CF₃ group,
or tautomers, N-oxides, or salts thereof, or salts of tautomers or N-oxides.

In further embodiments, the present invention provides compounds of formula (I), supra, in which:
R¹ represents a group selected from
a phenyl group,
which is phenyl group is optionally substituted, one, two, three or four times, each substituent independently selected from a halogen atom or a group selected from $C_1$-$C_3$-alkyl, $C_1$-$C_3$-haloalkyl, $C_1$-$C_3$-hydroxyalkyl, $C_1$-$C_3$-alkoxy, cyano, —C(=O)OR⁶, —C(=O)N(R⁷)(R⁸), —N(R⁷)(R⁸), —(C₁-C₃-alkyl)-N(R⁷)(R⁸), —S(=O)₂N(R⁷)(R⁸) and SF₅,
or in which two substituents of said phenyl group, when they are attached to adjacent ring atoms, are optionally linked to one another in such a way that they jointly form a group selected from
—CH₂—N(R⁷)—CH₂— and —O—CH₂—C(=O)—NH—,
and
R³ represents a CF₃ group,
and tautomers, N-oxides, and salts thereof, and salts of tautomers or N-oxides.

In accordance with further embodiments, the present invention provides compounds of general formula (I),

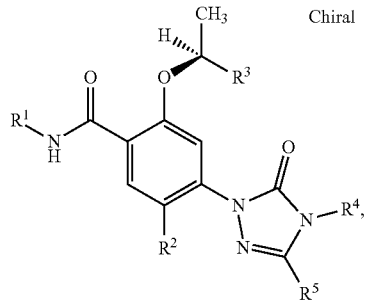

(I)

in which
R¹ represents a group selected from
a 4,4-difluorocyclohexyl group, a 1-(methylsulfonyl)piperidin-4-yl group, a phenyl group and a monocyclic or bicyclic heteroaryl group,
wherein said phenyl group is optionally substituted, one, two or three times, each substituent independently selected from a fluorine atom or a chlorine atom or a group selected from methyl, ethyl, difluoromethyl, trifluoromethyl, methoxy, hydroxy, cyano, —C(=O)OC(CH₃)₃, amino and —S(=O)₂NH₂,
and
wherein said monocyclic or bicyclic heteroaryl group is selected from 1,2-oxazol-4-yl, pyrazol-3-yl, pyridin-2-yl, pyridin-3-yl, pyridin-4-yl, pyridazin-3-yl, pyrimidin-4-yl, pyrimidin-5-yl and indazol-5-yl,
and which monocyclic or bicyclic heteroaryl group is optionally substituted one, two or three times, each substituent independently selected from a chlorine atom, a methyl group and a methoxy group,
R² represents a hydrogen atom or a chlorine atom or a fluorine atom,
R³ represents a group selected from
propyl, cyclohexyl, trifluoromethyl, (dimethylamino)methyl and phenyl,
R⁴ and R⁵ are linked to one another in such a way that they jointly form a group selected from
*—(CH₂)₄—#,
*—(CH₂)₃—C(H)(OH)—#,
*—(CH₂)₂—O—CH₂—#,
*—(CH₂)₅—#,
*—(CH₂)₃O—CH₂—#,
and
*—CH=CH—CH=CH—#,
in which groups "*" represents the point of attachment of R⁴ to the rest of the molecule, and "#" represents the point of attachment of R⁵ to the rest of the molecule,
or tautomers, N-oxides, or salts thereof, or salts of tautomers or N-oxides of said compounds.

In accordance with further embodiments, the present invention provides compounds of general formula (I),

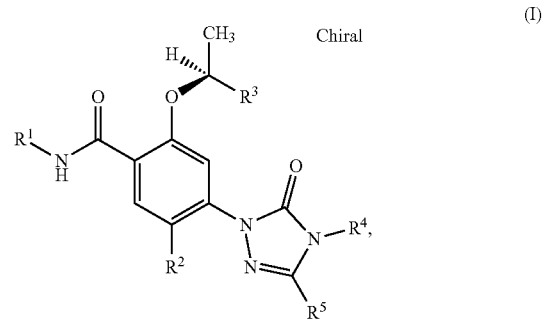

(I)

in which
R¹ represents a group selected from
a 4,4-difluorocyclohexyl group, a 1-(methylsulfonyl)piperidin-4-yl group, a phenyl group and a monocyclic or bicyclic heteroaryl group,
wherein said phenyl group is optionally substituted, one, two or three times, each substituent independently selected from a fluorine atom or a chlorine atom or a group selected from methyl, ethyl, difluoromethyl, trifluoromethyl, methoxy, cyano, —C(=O)OC(CH₃)₃, amino and —S(=O)₂NH₂,
and
wherein said monocyclic or bicyclic heteroaryl group is selected from 1,2-oxazol-4-yl, pyrazol-3-yl, pyridin-2-yl, pyridin-3-yl, pyridin-4-yl, pyridazin-3-yl, pyrimidin-4-yl, pyrimidin-5-yl and indazol-5-yl, which monocyclic or bicyclic heteroaryl group is optionally substituted one, two or three times, each substituent independently selected from a chlorine atom or a group selected from
methyl and methoxy,
$R^2$ represents a hydrogen atom or a fluorine atom,
$R^3$ represents a group selected from
propyl, cyclohexyl, trifluoromethyl, (dimethylamino)methyl and phenyl,
$R^4$ and $R^5$ are linked to one another in such a way that they jointly form a group selected from
*—$(CH_2)_4$—#
*—$(CH_2)_3$—C(H)(OH)—#,
*—$(CH_2)_2$—O—$CH_2$—#,
*—$(CH_2)_5$—#,
*—$(CH_2)_3$O—$CH_2$—#,
and
*—CH=CH—CH=CH—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In accordance with further embodiments, the present invention provides compounds of general formula (I),

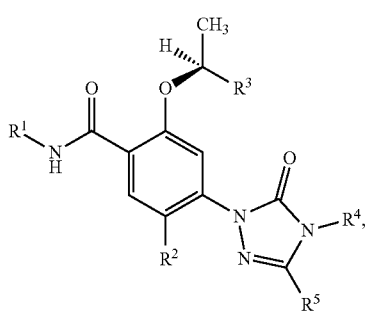

(I)

in which
$R^1$ represents a group selected from
a phenyl group and a monocyclic heteroaryl group,
wherein said phenyl group is optionally substituted, one, two or three times, each substituent independently selected from a fluorine atom, a chlorine atom a methyl group, an ethyl group, a difluoromethyl group, a trifluoromethyl group, a methoxy group, a hydroxy group and an amino group,
and
wherein said monocyclic heteroaryl group is selected from
pyridin-2-yl, pyridin-3-yl and pyridazin-3-yl,
which monocyclic heteroaryl group is optionally substituted one or two times, each substituent independently selected from a chlorine atom or a group selected from a methyl group and a methoxy group,
$R^2$ represents a fluorine atom,
$R^3$ represents a group selected from
propyl, cyclohexyl, trifluoromethyl and phenyl,
$R^4$ and $R^5$ are linked to one another in such a way that they jointly form a group selected from
*—$(CH_2)_4$—#,
*—$(CH_2)_2$—O—$CH_2$—#,
*—$(CH_2)_5$—#, and
*—$(CH_2)_3$O—$CH_2$—#,
in which groups "*" represents the point of attachment of $R^4$ to the rest of the molecule, and "#" represents the point of attachment of $R^5$ to the rest of the molecule,
or tautomers, N-oxides, or salts thereof, or salts of tautomers or N-oxides of said compounds.

In accordance with further embodiments, the present invention provides compounds of general formula (I),

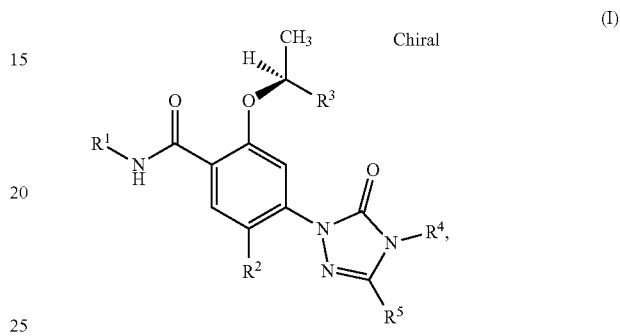

(I)

in which
$R^1$ represents a group selected from
a phenyl group and a monocyclic heteroaryl group,
wherein said phenyl group is optionally substituted, one, two or three times, each substituent independently selected from a fluorine atom or a chlorine atom or a group selected from
methyl, ethyl, difluoromethyl, trifluoromethyl, methoxy and amino,
and
wherein said monocyclic heteroaryl group is selected from
pyridin-2-yl, pyridin-3-yl and pyridazin-3-yl,
which monocyclic heteroaryl group is optionally substituted one or two times, each substituent independently selected from a chlorine atom or a group selected from
methyl and methoxy,
$R^2$ represents a fluorine atom,
$R^3$ represents a group selected from
propyl, cyclohexyl, trifluoromethyl and phenyl,
$R^4$ and $R^5$ are linked to one another in such a way that they jointly form a group selected from
*—$(CH_2)_4$—#,
*—$(CH_2)_2$—O—$CH_2$—#,
*—$(CH_2)_5$—#,
and
*—$(CH_2)_3$O—$CH_2$—#,
in which groups "*" represents the point of attachment of $R^4$ to the rest of the molecule, and "#" represents the point of attachment of $R^5$ to the rest of the molecule,
and tautomers, N-oxides, and salts thereof, and salts of tautomers or N-oxides.

In further embodiments, the present invention provides compounds of formula (I), supra, in which:
$R^1$ represents a group selected from
a 4,4-difluorocyclohexyl group, a 1-(methylsulfonyl)piperidin-4-yl group, a phenyl group and a monocyclic or bicyclic heteroaryl group, wherein said phenyl group is optionally substituted, one, two or three times, each substituent independently selected from a fluorine atom or a chlorine atom or a group selected from methyl, ethyl, difluoromethyl, trifluoromethyl, methoxy, hydroxy, cyano, —C(=O)OC(CH$_3$)$_3$, amino and —S(=O)$_2$NH$_2$,
and
wherein said monocyclic or bicyclic heteroaryl group is selected from 1,2-oxazol-4-yl, pyrazol-3-yl, pyridin-2-yl, pyridin-3-yl, pyridin-4-yl, pyridazin-3-yl, pyrimidin-4-yl, pyrimidin-5-yl and indazol-5-yl,
and which monocyclic or bicyclic heteroaryl group is optionally substituted one, two or three times, each substituent independently selected from a chlorine atom, a methyl group and a methoxy group, or tautomers, N-oxides, or salts thereof, or salts of tautomers or N-oxides of said compounds.

In further embodiments, the present invention provides compounds of formula (I), supra, in which:
R$^1$ represents a group selected from
a 4,4-difluorocyclohexyl group, a 1-(methylsulfonyl)piperidin-4-yl group, a phenyl group and a monocyclic or bicyclic heteroaryl group,
wherein said phenyl group is optionally substituted, one, two or three times, each substituent independently selected from a fluorine atom or a chlorine atom or a group selected from
methyl, ethyl, difluoromethyl, trifluoromethyl, methoxy, cyano, —C(=O)OC(CH$_3$)$_3$, amino and —S(=O)$_2$NH$_2$,
and
wherein said monocyclic or bicyclic heteroaryl group is selected from 1,2-oxazol-4-yl, pyrazol-3-yl, pyridin-2-yl, pyridin-3-yl, pyridin-4-yl, pyridazin-3-yl, pyrimidin-4-yl, pyrimidin-5-yl and indazol-5-yl,
which monocyclic or bicyclic heteroaryl group is optionally substituted one, two or three times, each substituent independently selected from a chlorine atom or a group selected from
methyl and methoxy, and tautomers, N-oxides, and salts thereof, and salts of tautomers or N-oxides.

In further embodiments, the present invention provides compounds of formula (I), supra, in which:
R$^3$ represents a group selected from
propyl, cyclohexyl, trifluoromethyl, (dimethylamino)methyl and phenyl,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—(CH$_2$)$_4$—#,
*—(CH$_2$)$_3$—C(H)(OH)—#,
*—(CH$_2$)$_2$—O—CH$_2$—#,
*—(CH$_2$)$_5$—#,
*—(CH$_2$)$_3$O—CH$_2$—#,
and
*—CH=CH—CH=CH—#,
in which groups "*" represents the point of attachment of R$^4$ to the rest of the molecule, and "#" represents the point of attachment of R$^5$ to the rest of the molecule,
and tautomers, N-oxides, and salts thereof, and salts of tautomers or N-oxides.

In further embodiments, the present invention provides compounds of formula (I), supra, in which:
R$^1$ represents a group selected from
a phenyl group and a monocyclic heteroaryl group,
wherein said phenyl group is optionally substituted, one, two or three times, each substituent independently selected from a fluorine atom or a chlorine atom or a group selected from
methyl, ethyl, difluoromethyl, trifluoromethyl, methoxy, hydroxy and amino,
and
wherein said monocyclic heteroaryl group is selected from
pyridin-2-yl, pyridin-3-yl and pyridazin-3-yl,
which monocyclic heteroaryl group is optionally substituted one or two times,
each substituent independently selected from a chlorine atom or a group
selected from
methyl and methoxy, or tautomers, N-oxides, or salts thereof, or salts of tautomers or N-oxides of said compounds.

In further embodiments, the present invention provides compounds of formula (I), supra, in which:
R$^1$ represents a group selected from
a phenyl group and a monocyclic heteroaryl group,
wherein said phenyl group is optionally substituted, one, two or three times, each substituent independently selected from a fluorine atom or a chlorine atom or a group selected from
methyl, ethyl, difluoromethyl, trifluoromethyl, methoxy and amino,
and
wherein said monocyclic heteroaryl group is selected from
pyridin-2-yl, pyridin-3-yl and pyridazin-3-yl,
which monocyclic heteroaryl group is optionally substituted one or two times, each substituent independently selected from a chlorine atom or a group selected from
methyl and methoxy, and tautomers, N-oxides, and salts thereof, and salts of tautomers or N-oxides.

In further embodiments, the present invention provides compounds of formula (I), supra, in which:
R$^3$ represents a group selected from
propyl, cyclohexyl, trifluoromethyl and phenyl,
and tautomers, N-oxides, and salts thereof, and salts of tautomers or N-oxides.

In further embodiments, the present invention provides compounds of formula (I), supra, in which:
R$^4$ and R$^5$ are linked to one another in such a way that they jointly form a group selected from
*—(CH$_2$)$_4$—#,
*—(CH$_2$)$_2$—O—CH$_2$—#,
*—(CH$_2$)$_5$—#,
and
*—(CH$_2$)$_3$O—CH$_2$—#,
in which groups "*" represents the point of attachment of R$^4$ to the rest of the molecule, and "#" represents the point of attachment of R$^5$ to the rest of the molecule,
and tautomers, N-oxides, and salts thereof, and salts of tautomers or N-oxides.

In further embodiments, the present invention provides compounds of formula (I), supra, which are selected from the group consisting of:

N-(2,6-difluorophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(2-fluorophenyl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-4-(3-oxo-5,6,7,8-tetrahydro[1,2,4]triazolo[4,3-a]pyridin-2(3H)-yl)-2-[(2S)-pentan-2-yl-oxy]-N-[3-(trifluoromethyl)phenyl]benzamide, N-(1-acetylpiperidin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, N-(3-chloropyridin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, N-(2-chloro-6-fluorophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(2-methylphenyl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(4-fluoro-2-methylphenyl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(5-fluoro-2-methylphenyl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(4-methylpyridin-3-yl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(2-methoxy-4-methylpyridin-3-yl)-4-(3-oxo-5,6,7,8-tetrahydro[1,2,4]triazolo[4,3-a]-pyridin-2(3H)-yl)-2-[(2S)-pentan-2-yloxy]benzamide, N-(3,5-dimethylpyrazin-2-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(5-methylpyrimidin-4-yl)-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(6-methoxy-4-methylpyridin-3-yl)-4-(3-oxo-5,6,7,8-tetrahydro[1,2,4]triazolo[4,3-a]-pyridin-2(3H)-yl)-2-[(2S)-pentan-2-yloxy]benzamide, 5-fluoro-N-[2-methyl-6-(trifluoromethyl)phenyl]-4-(3-oxo-5,6,7,8-tetrahydro[1,2,4]triazolo[4,3-a]pyridin-2(3H)-yl)-2-[(2S)-pentan-2-yloxy]benzamide, N-[2-(difluoromethyl)phenyl]-5-fluoro-4-(3-oxo-5,6,7,8-tetrahydro[1,2,4]triazolo[4,3-a]pyridin-2(3H)-yl)-2-[(2S)-pentan-2-yloxy]benzamide, N-(5-chloropyrimidin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, N-(3-chloropyridin-2-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-4-(3-oxo-5,6,7,8-tetrahydro[1,2,4]triazolo[4,3-a]pyridin-2(3H)-yl)-2-[(2S)-pentan-2-yloxy]-N-[1-(pyrazin-2-yl)piperidin-4-yl]benzamide, N-[1-(cyclopropylcarbonyl)piperidin-4-yl]-5-fluoro-4-(3-oxo-5,6,7,8-tetrahydro[1,2,4]triazolo-[4,3-a]pyridin-2(3H)-yl)-2-[(2S)-pentan-2-yloxy]benzamide, 5-fluoro-N-[1-(methylsulfonyl)piperidin-4-yl]-4-(3-oxo-5,6,7,8-tetrahydro[1,2,4]triazolo[4,3-a]-pyridin-2(3H)-yl)-2-[(2S)-pentan-2-yloxy]benzamide, 5-fluoro-N-(1-methyl-2-oxopiperidin-(4R,S)-4-yl)-4-(3-oxo-5,6,7,8-tetrahydro[1,2,4]triazolo[4,3-a]pyridin-2(3H)-yl)-2-[(2S)-pentan-2-yloxy]benzamide, mixture of diastereomers, 5-fluoro-N-(1-methylpiperidin-4-yl)-4-(3-oxo-5,6,7,8-tetrahydro[1,2,4]triazolo[4,3-a]pyridin-2(3H)-yl)-2-[(2S)-pentan-2-yloxy]benzamide, N-(2-aminophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-[2-(methylamino)phenyl]-4-(3-oxo-5,6,7,8-tetrahydro[1,2,4]triazolo[4,3-a]pyridin-2(3H)-yl)-2-[(2S)-pentan-2-yloxy]benzamide, N-(2-amino-6-methylphenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, N-(4-amino-2-methylphenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide, 5-fluoro-N-(2-fluoro-6-methylphenyl)-4-(3-oxo-5,6,7,8-tetrahydro[1,2,4]triazolo[4,3-a]pyridin-2(3H)-yl)-2-[(2S)-pentan-2-yloxy]benzamide, N-(2,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-[3-(trifluoromethyl)-phenyl]-2-{[(2S)-1,1,1-trifluoropropan-2-yl]oxy}benzamide, N-[2-chloro-4-(pentafluoro-lambda6-sulfanyl)phenyl]-5-fluoro-4-(3-oxo-5,6,7,8-tetrahydro-[1,2,4]triazolo[4,3-a]pyridin-2(3H)-yl)-2-{[(2S)-1,1,1-trifluoropropan-2-yl]oxy}benzamide, 5-fluoro-N-(oxetan-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-[2-(difluoromethyl)phenyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}-N-(1,3,5-trimethyl-1H-pyrazol-4-yl)benzamide, N-(2-chloro-3-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-4-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[2-methyl-3-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[2-methyl-4-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-3,5-difluorophenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(3,5-dimethyl-1,2-oxazol-4-yl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(4-methyl-1,2-oxazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(4-methyl-1H-imidazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(3-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-[2-(dimethylamino)ethyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(1-methylpiperidin-4-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-[4-(trifluoromethyl)-phenyl]-2-{[(2S)-1,1,1-trifluoropropan-2-yl]oxy}benzamide, N-cyclopropyl-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-cyano-4-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-cyano-5-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-6-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, tert-butyl 3-{[5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoyl]amino}azetidine-1-carboxylate, N-(azetidin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(6-methoxy-2-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-[1-(methylsulfonyl)piperidin-4-yl]-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(6-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(2-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(4,4-difluorocyclohexyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(1-ethylazetidin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-[4-(dimethylamino)cyclohexyl]-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(2-ethylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-6-methylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-4-fluoro-6-methylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chloro-4,6-difluorophenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(4-fluoro-2,6-dimethylphenyl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(2-chloro-4-methylpyridin-3-yl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(2,4-dimethylpyridin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}-N-(2,4,6-trimethylpyridin-3-yl)benzamide, N-(6-chloro-2,3-difluorophenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(2-methoxy-6-methylphenyl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(2-fluoro-6-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(2-fluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-phenyl-2-{[(2S)-1,1,1-trifluoropropan-2-yl]oxy}benzamide, 5-fluoro-N-(4-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(2,4,6-trifluoro-phenyl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-[2-(trifluoromethyl)-phenyl]-2-{[(2S)-1,1,1-trifluoropropan-2-yl]oxy}benzamide, 5-fluoro-N-(3-methylpyridin-2-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-chlorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2,6-dichlorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(5-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2-cyano-3-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(1-methyl-1H-pyrazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(tetrahydro-2H-pyran-4-yl)-2-{[(2S)-1,1,1-trifluoropropan-2-yl]oxy}benzamide, N-(2-chloro-5-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(4-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[2-methyl-5-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(3-methylpyridin-4-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[2-methyl-6-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(1,3-dimethyl-1H-pyrazol-4-yl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(1,4-dimethyl-1H-pyrazol-3-yl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(2-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(2-hydroxy-2-methylpropyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[2-(hydroxymethyl)-3-(trifluoromethyl)phenyl]-4-(3-oxo-5,6,7,8-tetrahydro[1,2,4]-triazolo[4,3-a]pyridin-2(3H)-yl)-2-{[(2S)-1,1,1-trifluoropropan-2-yl]oxy}benzamide, 5-fluoro-N-[3-(hydroxymethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(quinolin-8-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(quinolin-6-yl)-2-{[(2S)-1,1,1-trifluoropropan-2-yl]oxy}benzamide, 3-{[5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoyl]amino}-4-methylbenzoic acid, 5-fluoro-4-(3-oxo-5,6,7,8-tetrahydro[1,2,4]triazolo[4,3-a]pyridin-2(3H)-yl)-N-(quinolin-5-yl)-2-{[(2S)-1,1,1-trifluoropropan-2-yl]oxy}benzamide, 5-fluoro-N-(2-methylquinolin-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(quinolin-7-yl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(3-sulfamoyl-phenyl)-2-{[(2S)-1,1,1-trifluoropropan-2-yl]oxy}benzamide, 5-fluoro-4-(3-oxo-5,6,7,8-tetrahydro[1,2,4]triazolo[4,3-a]pyridin-2(3H)-yl)-N-(7H-pyrrolo[2,3-d]pyrimidin-4-yl)-2-{[(2S)-1,1,1-trifluoropropan-2-yl]oxy}benzamide, 5-fluoro-N-(2-methylquinolin-6-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(2-methyl-1,3-benzothiazol-6-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(6-methyl-1H-indazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(3-oxo-3,4-dihydro-2H-1,4-benzoxazin-7-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, N-(2,3-dimethoxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-(1H-indazol-7-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[1-(4-fluorophenyl)cyclopropyl]-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 5-fluoro-N-(4-fluoro-3-hydroxy-1H-indazol-6-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, 5-fluoro-N-[(1S,2S)-2-hydroxy-2,3-dihydro-1H-inden-1-yl]-4-(3-oxo-5,6,7,8-tetrahydro[1,2,4]-triazolo[4,3-a]pyridin-2(3H)-yl)-2-{[(2S)-1,1,1-trifluoropropan-2-yl]oxy}benzamide, N-(3-carbamoyl-2-methylphenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, 2-[(1S)-1-cyclohexylethoxy]-N-(1,1-dioxidotetrahydro-2H-thiopyran-4-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-N-(4,4-difluorocyclohexyl)-5-fluoro-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-[2-methoxy-5-(trifluoromethyl)phenyl]-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(6-methoxy-4-methylpyridin-3-yl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(6-methoxy-2-methylpyridin-3-yl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(2-methoxy-4-methylpyridin-3-yl)-4-(3-oxo-5,6,7,8-tetrahydro[1,2,4]triazolo[4,3-a]pyridin-2(3H)-yl)benzamide, 2-[(1S)-1-cyclohexylethoxy]-N-[3-(dimethylcarbamoyl)phenyl]-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-[1-(methylsulfonyl)piperidin-4-yl]-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(5-methoxy-4-methylpyridin-3-yl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-[6-(morpholin-4-yl)pyridazin-3-yl]-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(5-methoxypyrimidin-4-yl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(2-methoxypyrimidin-5-yl)-4-(3-oxo-5,6,7,8-tetrahydro[1,2,4]triazolo[4,3-a]pyridin-2(3H)-yl)benzamide, 2-[(1S)-1-cyclohexylethoxy]-N-(4,6-dimethoxypyrimidin-5-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-N-(3,5-dimethylpyrazin-2-yl)-5-fluoro-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(6-methoxypyrazin-2-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(3-methoxypyrazin-2-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(6-methoxypyridazin-3-yl)-4-(3-oxo-5,6,7,8-tetrahydro-[1,2,4]triazolo[4,3-a]pyridin-2(3H)-yl)benzamide, 2-[(1S)-1-cyclohexylethoxy]-N-(5,6-dimethylpyrimidin-4-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(4-methylpyrimidin-5-yl)-4-(3-oxo-5,6,7,8-tetrahydro-[1,2,4]triazolo[4,3-a]pyridin-2(3H)-yl)benzamide, 2-[(1S)-1-cyclohexylethoxy]-N-(2,4-dimethylpyrimidin-5-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(3-methylpyrazin-2-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(5-methylpyrimidin-4-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(4-methylpyridazin-3-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(5-fluoropyrimidin-4-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-[3-(morpholin-4-yl)pyrazin-2-yl]-4-(3-oxo-5,6,7,8-tetrahydro[1,2,4]triazolo[4,3-a]pyridin-2(3H)-yl)benzamide, 2-[(1S)-1-cyclohexylethoxy]-N-(4,6-dimethylpyrimidin-5-yl)-5-fluoro-4-(3-oxo-5,6,7,8-tetrahydro[1,2,4]triazolo[4,3-a]pyridin-2(3H)-yl)benzamide, N-(3-amino-2-methylphenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, N-[4-amino-2-(trifluoromethyl)phenyl]-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(2-methyl-4-sulfamoylphenyl)-4-(3-oxo-5,6,7,8-tetrahydro[1,2,4]triazolo[4,3-a]pyridin-2(3H)-yl)benzamide, N-[2-(aminomethyl)-6-methylphenyl]-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, methyl 2-({2-[(1R)-1-cyclohexylethoxy]-5-fluoro-4-(3-oxo-5,6,7,8-tetrahydro[1,2,4]triazolo[4,3-a]pyridin-2(3H)-yl)benzoyl}amino)-3-methylbenzoate, 2-[(1R)-1-cyclohexylethoxy]-N-(2,3-dihydro-1H-isoindol-4-yl)-5-fluoro-4-(3-oxo-5,6,7,8-tetrahydro[1,2,4]triazolo[4,3-a]pyridin-2(3H)-yl)benzamide, N-(5-amino-3-methylpyridin-2-yl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, 2-({2-[(1S)-1-cyclohexylethoxy]-5-fluoro-4-(3-oxo-5,6,7,8-tetrahydro[1,2,4]triazolo[4,3-a]-pyridin-2(3H)-yl)benzoyl}amino)-3-methylbenzoic acid, tert-butyl 4-({2-[(1S)-1-cyclohexylethoxy]-4-(3-oxo-5,6,7,8-tetrahydro[1,2,4]triazolo[4,3-a]-pyridin-2(3H)-yl)benzoyl}amino)-3-methylbenzoate, 2-[(1S)-1-cyclohexylethoxy]-5-fluoro-N-(2-fluorophenyl)-4-(3-oxo-5,6,7,8-tetrahydro-[1,2,4]-triazolo[4,3-a]pyridin-2(3H)-yl)benzamide, 2-[(1S)-1-cyclohexylethoxy]-5-fluoro-N-(2-fluorophenyl)-4-(3-oxo-5,6,7,8-tetrahydro[1,2,4]-triazolo[4,3-a]pyridin-2(3H)-yl)benzamide, 2-[(1S)-1-cyclohexylethoxy]-5-fluoro-4-(3-oxo-5,6,7,8-tetrahydro[1,2,4]triazolo[4,3-a]pyridin-2(3H)-yl)-N-[3-(trifluoromethyl)phenyl]benzamide, 2-[(1S)-1-cyclohexylethoxy]-N-(2,6-difluorophenyl)-5-fluoro-4-(3-oxo-5,6,7,8-tetrahydro[1,2,4]-triazolo[4,3-a]pyridin-2(3H)-yl)benzamide, 2-[(1S)-1-cyclohexylethoxy]-5-fluoro-N-(4-fluoro-2-methylphenyl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-4-(3-oxo-5,6,7,8-tetrahydro[1,2,4]triazolo[4,3-a]pyridin-2(3H)-yl)-N-(2,4,6-trifluorophenyl)benzamide, 2-[(1S)-1-cyclohexylethoxy]-5-fluoro-N-(3-fluoro-2-methylphenyl)-4-(3-oxo-5,6,7,8-tetrahydro-[1,2,4]triazolo[4,3-a]pyridin-2(3H)-yl)benzamide 2-[(1S)-1-cyclohexylethoxy]-5-fluoro-4-(3-oxo-5,6,7,8-tetrahydro[1,2,4]triazolo[4,3-a]pyridin-2(3H)-yl)-N-[2-(trifluoromethyl)phenyl]benzamide, 2-[(1S)-1-cyclohexylethoxy]-5-fluoro-N-(3-methylpyridin-2-yl)-4-(3-oxo-5,6,7,8-tetrahydro-[1,2,4]triazolo[4,3-a]pyridin-2(3H)-yl)benzamide, 2-[(1S)-1-cyclohexylethoxy]-N-(2,6-dichlorophenyl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(5-fluoro-2-methylphenyl)-4-(3-oxo-5,6,7,8-tetrahydro-[1,2,4]triazolo[4,3-a]pyridin-2(3H)-yl)benzamide, 2-[(1S)-1-cyclohexylethoxy]-N-(2,4-difluorophenyl)-5-fluoro-4-(3-oxo-5,6,7,8-tetrahydro[1,2,4]-triazolo[4,3-a]pyridin-2(3H)-yl)benzamide, 2-[(1S)-1-cyclohexylethoxy]-N-[2-(dimethylamino)ethyl]-5-fluoro-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-[2-fluoro-6-(trifluoromethyl)phenyl]-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-(1-methyl-1H-pyrazol-5-yl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-4-(3-oxo-5,6,7,8-tetrahydro[1,2,4]triazolo[4,3-a]pyridin-2(3H)-yl)-N-(tetrahydro-2H-pyran-4-yl)benzamide, N-(2-cyano-4-fluorophenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, N-(2-chloro-5-fluorophenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(4-methylpyridin-3-yl)-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-[2-methyl-5-(trifluoromethyl)phenyl]-4-(3-oxo-5,6,7,8-tetrahydro-[1,2,4]triazolo[4,3-a]pyridin-2(3H)-yl)benzamide 2-[(1S)-1-cyclohexylethoxy]-5-fluoro-N-(3-methylpyridin-4-yl)-4-(3-oxo-5,6,7,8-tetrahydro-[1,2,4]triazolo[4,3-a]pyridin-2(3H)-yl)benzamide N-(2-chloro-6-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide, 2-[(1S)-1-cyclohexylethoxy]-5-fluoro-N-[2-methyl-3-(trifluoromethyl)phenyl]-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-[2-methyl-4-(trifluoromethyl)phenyl]-4-(3-oxo-5,6,7,8-tetrahydro[1,2,4]triazolo[4,3-a]pyridin-2(3H)-yl)benzamide, N-(2-chloro-3-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide, 2-[(1S)-1-cyclohexylethoxy]-N-(1,3-dimethyl-1H-pyrazol-4-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(1-methylpiperidin-4-yl)-4-(3-oxo-5,6,7,8-tetrahydro-[1,2,4]triazolo[4,3-a]pyridin-2(3H)-yl)benzamide, 2-[(1S)-1-cyclohexylethoxy]-N-(1,4-dimethyl-1H-pyrazol-3-yl)-5-fluoro-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(2-hydroxy-2-methylpropyl)-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-[2-(hydroxymethyl)-3-(trifluoromethyl)phenyl]-4-(3-oxo-5,6,7,8-tetrahydro[1,2,4]triazolo[4,3-a]pyridin-2(3H)-yl)benzamide, 2-[(1S)-1-cyclohexylethoxy]-5-fluoro-N-(5-methyl-1,2-oxazol-4-yl)-4-(3-oxo-5,6,7,8-tetrahydro-[1,2,4]triazolo[4,3-a]pyridin-2(3H)-yl)benzamide, N-(2-chloro-4-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide, N-(2-chloro-6-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(6-methoxy-4-methylpyridin-3-yl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide, 5-fluoro-N-(4-methylpyridin-3-yl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2,6-difluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(2-fluoro-6-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide 5-fluoro-N-(2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2,6-dichlorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2-chloro-6-methylphenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2-chloro-4-fluoro-6-methylphenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide, N-(2-chloro-4,6-difluorophenyl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, 5-fluoro-N-(4-fluoro-2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(5-fluoro-2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-[2-methyl-6-(trifluoromethyl)phenyl]-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide, N-[2-(difluoromethyl)phenyl]-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2-chloro-3,6-difluorophenyl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, 5-fluoro-N-(3-fluoro-2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-4-(3-oxo-5,6-dihydro-3H-[1,2,4]triazolo[3,4-c][1,4]oxazin-2(8H)-yl)-N-(2,4,6-trifluoro-phenyl)-2-{[(2S)-1,1,1-trifluoropropan-2-yl]oxy}benzamide, N-(2,6-dichloro-4-fluorophenyl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, N-(4,5-difluoro-2-methylphenyl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, 5-fluoro-N-[2-methyl-4-(trifluoromethyl)phenyl]-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide, N-(2-chloro-5-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(4-fluoro-2,6-dimethylphenyl)-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, N-(2-chloro-4-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, N-(2-cyano-4-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(2-methoxy-4-methylpyridin-3-yl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide N-(4-chloro-2-methylpyridin-3-yl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, N-(2-chloro-4-methylpyridin-3-yl)-5-fluoro-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, N-(2-chloro-4,6-dimethylpyridin-3-yl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide, N-(2,4-dimethylpyridin-3-yl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(2-methoxy-6-methylphenyl)-4-(3-oxo-5,6-dihydro-3H-[1,2,4]triazolo[3,4-c][1,4]-oxazin-2(8H)-yl)-2-{[(2S)-1,1,1-trifluoropropan-2-yl]oxy}benzamide, N-(6-chloro-2,3-difluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide, 5-fluoro-N-(6-methoxy-4-methylpyridin-3-yl)-4-(3-oxo-5,6-dihydro-3H-[1,2,4]triazolo[3,4-c]-[1,4]oxazin-2(8H)-yl)-2-[(2S)-pentan-2-yloxy]benzamide, N-(2-chloro-6-fluorophenyl)-5-fluoro-4-(3-oxo-5,6-dihydro-3H-[1,2,4]triazolo[3,4-c][1,4]oxazin-2(8H)-yl)-2-[(2S)-pentan-2-yloxy]benzamide, 5-fluoro-N-(2-fluoro-6-methylphenyl)-4-(3-oxo[1,2,4]triazolo[4,3-a]pyridin-2(3H)-yl)-2-{[(2S)-1,1,1-trifluoropropan-2-yl]oxy}benzamide, 5-fluoro-N-(2-fluorophenyl)-4-(3-oxo[1,2,4]triazolo[4,3-a]pyridin-2(3H)-yl)-2-{[(2S)-1,1,1-trifluoropropan-2-yl]oxy}benzamide, N-(2,6-difluorophenyl)-5-fluoro-4-(3-oxo-5,6-dihydro-3H-[1,2,4]triazolo[3,4-c][1,4]oxazin-2(8H)-yl)-2-[(2S)-pentan-2-yloxy]benzamide, 5-fluoro-4-(3-oxo[1,2,4]triazolo[4,3-a]pyridin-2(3H)-yl)-2-[(2S)-pentan-2-yloxy]-N-[3-(trifluoro-methyl)phenyl]benzamide, 5-fluoro-N-(2-fluoro-6-methylphenyl)-4-(3-oxo[1,2,4]triazolo[4,3-a]pyridin-2(3H)-yl)-2-[(2S)-pentan-2-yloxy]benzamide, 5-fluoro-N-(2-fluorophenyl)-4-(3-oxo[1,2,4]triazolo[4,3-a]pyridin-2(3H)-yl)-2-[(2S)-pentan-2-yloxy]benzamide, 5-fluoro-N-(2-methylphenyl)-4-(3-oxo[1,2,4]triazolo[4,3-a]pyridin-2(3H)-yl)-2-[(2S)-pentan-2-yloxy]benzamide, N-(2,6-difluorophenyl)-5-fluoro-4-(3-oxo[1,2,4]triazolo[4,3-a]pyridin-2(3H)-yl)-2-[(2S)-pentan-2-yloxy]benzamide, 5-fluoro-N-(2-fluoro-6-methylphenyl)-4-(3-oxo[1,2,4]triazolo[4,3-a]pyridin-2(3H)-yl)-2-[(1S)-1-phenylethoxy]benzamide, N-(2,6-difluorophenyl)-5-fluoro-4-(3-oxo[1,2,4]triazolo[4,3-a]pyridin-2(3H)-yl)-2-[(1S)-1-phenylethoxy]benzamide, 5-fluoro-N-(2-fluorophenyl)-4-(3-oxo[1,2,4]triazolo[4,3-a]pyridin-2(3H)-yl)-2-[(1S)-1-phenylethoxy]benzamide, 5-fluoro-N-(2-methylphenyl)-4-(3-oxo-5,6,7,8-tetrahydro[1,2,4]triazolo[4,3-a]pyridin-2(3H)-yl)-2-[(1S)-1-phenylethoxy]benzamide, 5-fluoro-4-(3-oxo-5,6,7,8-tetrahydro[1,2,4]triazolo[4,3-a]pyridin-2(3H)-yl)-2-[(1S)-1-phenylethoxy]-N-[3-(trifluoromethyl)phenyl]benzamide, 5-fluoro-N-(2-methylphenyl)-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, 5-fluoro-N-(2-fluoro-6-methylphenyl)-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-(2-chloro-6-fluorophenyl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-[2-(difluoromethyl)phenyl]-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, 5-fluoro-N-(2-methoxy-4-methylpyridin-3-yl)-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, N-(2,6-dichlorophenyl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-(2-chloro-4-fluoro-6-methylphenyl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, N-(2-chloro-6-methylphenyl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-(2-chloro-4,6-difluorophenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide, 5-fluoro-N-[2-methyl-6-(trifluoromethyl)phenyl]-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, N-(2,6-dichloro-4-fluorophenyl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, 5-fluoro-N-(4-fluoro-2,6-dimethylphenyl)-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-(4-chloro-2-methylpyridin-3-yl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide, N-(2-chloro-4-methylpyridin-3-yl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide, N-(2-chloro-4,6-dimethylpyridin-3-yl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, N-(2,4-dimethylpyridin-3-yl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, 5-fluoro-N-(2-methoxy-6-methylphenyl)-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamide, N-(6-chloro-2,3-difluorophenyl)-5-fluoro-4-(3-oxo-6,7-dihydro-3H,5H-[1,2,4]triazolo[3,4-c][1,4]-oxazepin-2(9H)-yl)-2-{[(2S)-1,1,1-trifluoropropan-2-yl]oxy}benzamid,e N-(2,6-difluorophenyl)-5-fluoro-4-(3-oxo-6,7-dihydro-5H-[1,2,4]triazolo[3,4-b][1,3]oxazin-2(3H)-yl)-2-{[(2S)-1,1,1-trifluoropropan-2-yl]oxy}benzamide, N-(2,6-difluorophenyl)-5-fluoro-4-(8-methyl-3-oxo-5,6,7,8-tetrahydro[1,2,4]triazolo[4,3-a]-pyrimidin-2(3H)-yl)-2-{[(2S)-1,1,1-trifluoropropan-2-yl]oxy}benzamide, N-(2,6-difluorophenyl)-5-fluoro-4-(3-oxo-5,6-dihydro[1,3]thiazolo[2,3-c][1,2,4]triazol-2(3H)-yl)-2-{[(2S)-1,1,1-trifluoropropan-2-yl]oxy}benzamide, N-(2,6-difluorophenyl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide, N-(2,6-difluorophenyl)-5-fluoro-4-(3-oxo-6,7,8,9-tetrahydro-3H-[1,2,4]triazolo[4,3-a]azepin-2(5H)-yl)-2-{[(2S)-1,1,1-trifluoropropan-2-yl]oxy}benzamide, N-(2,6-difluorophenyl)-5-fluoro-4-(3-oxo[1,2,4]triazolo[4,3-a]pyrazin-2(3H)-yl)-2-{[(2S)-1,1,1-trifluoropropan-2-yl]oxy}benzamide, N-(2,6-difluorophenyl)-5-fluoro-4-(3-oxo-6,7-dihydro-5H-[1,2,4]triazolo[3,4-b][1,3]thiazin-2(3H)-yl)-2-{[(2S)-1,1,1-trifluoropropan-2-yl]oxy}benzamide, N-(2,6-difluorophenyl)-4-(6,6-dimethyl-3-oxo-6,7-dihydro-5H-[1,2,4]triazolo[3,4-b][1,3]oxazin-2(3H)-yl)-5-fluoro-2-{[(2S)-1,1,1-trifluoropropan-2-yl]oxy}benzamide, 4-(6,6-difluoro-3-oxo-5,6,7,8-tetrahydro[1,2,4]triazolo[4,3-a]pyridin-2(3H)-yl)-N-(2,6-difluoro-phenyl)-5-fluoro-2-{[(2S)-1,1,1-trifluoropropan-2-yl]oxy}benzamide, N-(2,6-difluorophenyl)-5-fluoro-4-(3-oxo[1,2,4]triazolo[4,3-b]pyridazin-2(3H)-yl)-2-{[(2S)-1,1,1-trifluoropropan-2-yl]oxy}benzamide, 2-(4-[(2,6-difluorophenyl)carbamoyl]-2-fluoro-5-{[(2S)-1,1,1-trifluoropropan-2-yl]oxy}phenyl)-3-oxo-2,3,5,6,7,8-hexahydro[1,2,4]triazolo[4,3-a]pyridine-8-(R,S)-carboxylic acid, mixture of diastereomers, 2-(4-[(2-chloro-6-fluorophenyl)carbamoyl]-2-fluoro-5-{[(2S)-1,1,1-trifluoropropan-2-yl]oxy}-phenyl)-3-oxo-2,3,5,6,7,8-hexahydro[1,2,4]triazolo[4,3-a]pyridine-8-(R,S)-carboxylic acid,
mixture of diastereomers,
2-(4-[(2-chloro-6-fluorophenyl)carbamoyl]-2-fluoro-5-{[(2S)-1,1,1-trifluoropropan-2-yl]oxy}-phenyl)-3-oxo-2,3,5,6,7,8-hexahydro[1,2,4]triazolo[4,3-a]pyridine-6-(R,S)-carboxylic acid,
mixture of diastereomers,
N-(2,6-difluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
N-(2,6-difluorophenyl)-5-fluoro-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide,
5-fluoro-N-(2-fluoro-6-methylphenyl)-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide,
5-fluoro-N-(2-fluorophenyl)-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide,
5-fluoro-N-(2-fluorophenyl)-4-(3-oxo-5,6,7,8-tetrahydro[1,2,4]triazolo[4,3-a]pyridin-2(3H)-yl)-2-[(1S)-1-phenylethoxy]benzamide,
N-(2,6-difluorophenyl)-5-fluoro-4-(3-oxo-5,6,7,8-tetrahydro[1,2,4]triazolo[4,3-a]pyridin-2(3H)-yl)-2-[(1S)-1-phenylethoxy]benzamide,
5-fluoro-N-(2-fluoro-6-methylphenyl)-4-(3-oxo-5,6,7,8-tetrahydro[1,2,4]triazolo[4,3-a]pyridin-2(3H)-yl)-2-[(1S)-1-phenylethoxy]benzamide,
5-fluoro-N-(2-fluoro-6-methylphenyl)-2-{[(2R,3R)-3-hydroxybutan-2-yl]oxy}-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(2-fluoro-6-methylphenyl)-4-(3-oxo-5,6,7,8-tetrahydro[1,2,4]triazolo[4,3-a]pyridin-2(3H)-yl)benzamide,
2-{[(2R)-1-(dimethylamino)propan-2-yl]oxy}-5-fluoro-N-(2-fluoro-6-methylphenyl)-4-(3-oxo-5,6,7,8-tetrahydro[1,2,4]triazolo[4,3-a]pyridin-2(3H)-yl)benzamide,
5-fluoro-N-(2-fluoro-6-methylphenyl)-4-(3-oxo-5,6,7,8-tetrahydro[1,2,4]triazolo[4,3-a]pyridin-2(3H)-yl)-2-{[(2S)-1-(pyrrolidin-1-yl)propan-2-yl]oxy}benzamide,
N-[2-(difluoromethyl)phenyl]-2-{[(2S)-1-(dimethylamino)propan-2-yl]oxy}-5-fluoro-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(4-fluoro-2-methylphenyl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(5-fluoro-2-methylphenyl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(4-methylpyridin-3-yl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-N-(3,5-dimethylpyrazin-2-yl)-5-fluoro-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(6-methoxy-4-methylpyridin-3-yl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(4-methylpyridazin-3-yl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(2-methoxy-4-methylpyridin-3-yl)-4-(3-oxo-5,6,7,8-tetrahydro[1,2,4]triazolo[4,3-a]pyridin-2(3H)-yl)benzamide,
2-{[(2S)-1-(dimethylamino)propan-2-yl]oxy}-5-fluoro-N-(2-methylphenyl)-4-(3-oxo-5,6,7,8-tetrahydro[1,2,4]triazolo[4,3-a]pyridin-2(3H)-yl)benzamide,
rac-2-{[4-(dimethylamino)butan-2-yl]oxy}-5-fluoro-N-(2-fluoro-6-methylphenyl)-4-(3-oxo-5,6-dihydro-3H-[1,2,4]triazolo[3,4-c][1,4]oxazin-2(8H)-yl)benzamide,
rac-5-fluoro-N-(2-fluoro-6-methylphenyl)-4-(3-oxo-5,6-dihydro-3H-[1,2,4]triazolo[3,4-c][1,4]-oxazin-2(8H)-yl)-2-{[1-(pyrrolidin-1-yl)propan-2-yl]oxy}benzamide,
N-(2,6-difluorophenyl)-5-fluoro-4-(3-oxo-6,7,8,9-tetrahydro-3H-[1,2,4]triazolo[4,3-d][1,4]-diazepin-2(5H)-yl)-2-{[(2S)-1,1,1-trifluoropropan-2-yl]oxy}benzamide, and
N-(2,6-difluorophenyl)-5-fluoro-4-[(8R,S)-8-hydroxy-3-oxo-5,6,7,8-tetrahydro[1,2,4]triazolo-[4,3-a]pyridin-2(3H)-yl]-2-{[(2S)-1,1,1-trifluoropropan-2-yl]oxy}benzamide, mixture of diastereomers,
and tautomers, N-oxides, and salts thereof, and salts of tautomers or N-oxides.

In further embodiments, the present invention provides compounds of formula (I), supra, which are selected from the group consisting of:
5-chloro-N-(2,6-difluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
5-chloro-N-(2-chloro-6-fluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
5-chloro-N-[1-(4-fluorophenyl)cyclopropyl]-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide,
5-chloro-N-[2-(difluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
5-chloro-N-(4-methylpyridazin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
5-chloro-N-(6-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide,
5-chloro-N-(2-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide,
5-chloro-N-(4-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide
5-chloro-N-(2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
N-(2,6-difluoro-4-hydroxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide,
N-(2,6-difluoro-3-hydroxyphenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide,
N-(2,6-difluorophenyl)-5-fluoro-4-(8-imino-3,8-dioxo-5,6,7,8-tetrahydro-8$\lambda^{6}$-[1,2,4]triazolo-[3,4-b][1,3]thiazin-2(3H)-yl)-2-{[(2S)-1,1,1-trifluoropropan-2-yl]oxy}benzamide,
N-(2,6-difluorophenyl)-5-fluoro-4-(7-hydroxy-3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(2,6-difluorophenyl)-5-fluoro-4-(6-hydroxy-3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide, N-(2,6-difluorophenyl)-5-fluoro-4-(6-hydroxy-3-oxo-5,6-dihydro[1,2,4]triazolo[4,3-a]pyridin-2(3H)-yl)-2-{[(2S)-1,1,1-trifluoropropan-2-yl]oxy}benzamide, N-(2,6-difluorophenyl)-5-fluoro-4-(8-hydroxy-3-oxo-5,6,7,8-tetrahydro[1,2,4]triazolo[4,3-a]pyridin-2(3H)-yl)-2-{[(2S)-1,1,1-trifluoropropan-2-yl]oxy}benzamide, rac-tert-butyl [2-{2-[(2-chloro-6-fluorophenyl)carbamoyl]-4-fluoro-5-(3-oxo-5,6,7,8-tetrahydro-[1,2,4]triazolo[4,3-a]pyridin-2(3H)-yl)phenoxy}propyl]carbamate, and rac-2-{[1-aminopropan-2-yl]oxy}-N-(2-chloro-6-fluorophenyl)-5-fluoro-4-(3-oxo-5,6,7,8-tetrahydro[1,2,4]triazolo[4,3-a]pyridin-2(3H)-yl)benzamide, salt with hydrochloric acid, and tautomers, N-oxides, and salts thereof, and salts of tautomers or N-oxides.

The present invention provides any sub-combination within any embodiment or aspect of the present invention of compounds of general formula (I), supra.

The present invention provides any sub-combination within any embodiment or aspect of the present invention of intermediate compounds of general formulae (IV), (VI), (VIII), (IX), (X), (XV), (XVIII), (XIX), (X) and (XXI).

The present invention provides the compounds of general formula (I) which are disclosed in the Example Section of this text, infra.

The compounds according to the invention of general formula (I) can be prepared according to the following schemes 1, 2, 3, 4 and 5. The schemes and procedures described below illustrate synthetic routes to the compounds of general formula (I) of the invention and are not intended to be limiting. It is clear to the person skilled in the art that the order of transformations as exemplified in schemes 1, 2, 3, 4 and 5 can be modified in various ways. The order of transformations exemplified in these schemes is therefore not intended to be limiting. In addition, interconversion of any of the substituents, $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Synthetic Routes

Five routes for the preparation of compounds of general formula (I) are described in schemes 1, 2, 3, 4 and 5.

Synthetic Route 1

Scheme 1: Route for the preparation of compounds of general formula (I) in which $R^1$, $R^2$, $R^3$, $R^4$ and $R^5$ have the meaning as given for general formula (I), supra.

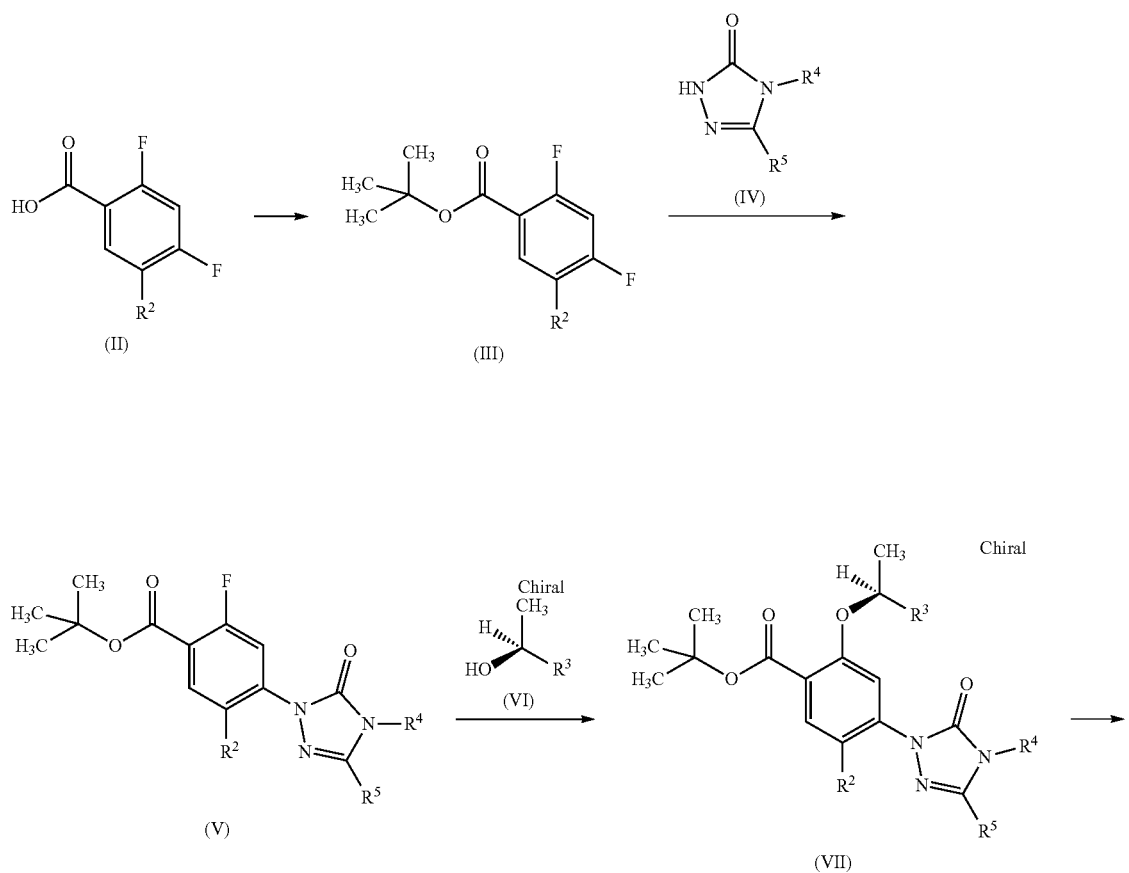

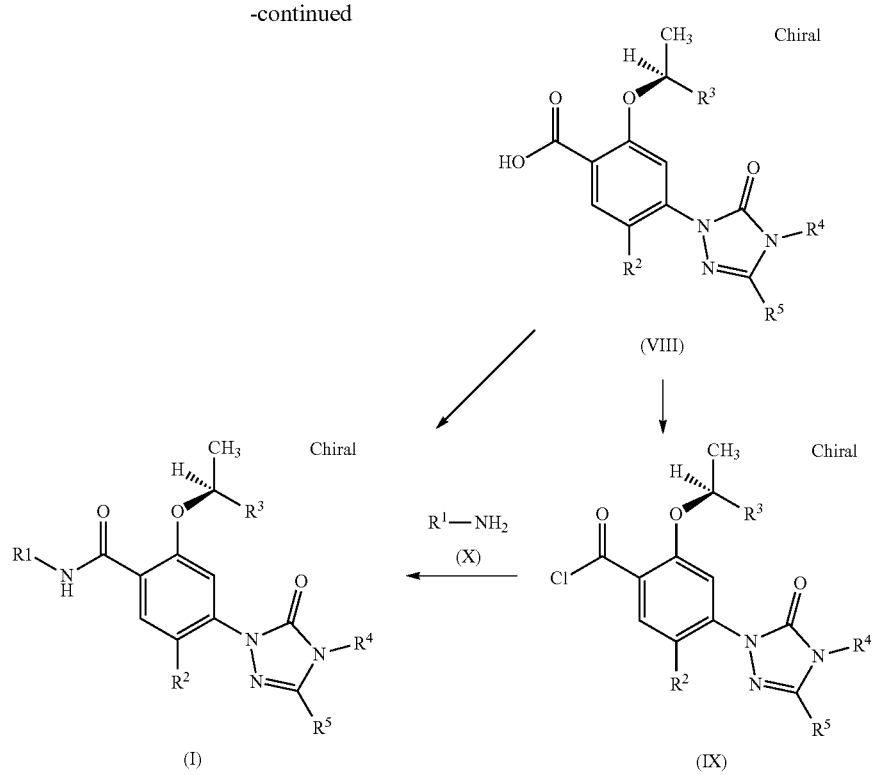

Compounds of general formulae (II), (IV), (VI) and (X) are either commercially available or can be prepared according to procedures available from the public domain, as understandable to the person skilled in the art. Specific examples are described in the Experimental Section.

(II)→(III):

tert-Butyl benzoates of general formula (III) can be prepared from benzoic acid derivatives of general formula (II) according to procedures available from the public domain, as understandable to the person skilled in the art.

In connection with the method of the invention, the use of di-tert-butyl-dicarbonate in tert-butanol was preferable.

Alternatively, the tert-butyl benzoates of general formula (III) can be prepared from benzoic acid derivatives of general formula (II) by in situ formation of the corresponding acid chlorides and subsequent reaction with tert-butanol.

In situ formation of acid chlorides from benzoic acids of general formular (II) can be accomplished, for example by using oxalyl chloride or thionyl chloride, both reagents used in the presence of catalytic amount of N,N-dimethylformamide.

(III)+(IV)→(V):

The formation of tert-butyl benzoates of general formula (V) can be accomplished by the reaction of triazolinones of general formula (IV) with tert-butyl benzoates of general formula (III) in the presence of a base. In connection with the method of the invention, the use of 1,8-diazabicyclo [5.4.0]undec-7-ene as organic base in acetonitrile at 80° C. was preferable.

(V)+(VI)→(VII)→(VIII):

The formation of benzoic acids of general formula (VIII) can be accomplished by reaction of tert-butyl benzoates of general formula (V) with alcohols of general formula (VI) in the presence of a base, and subsequent saponification of the resulting ester of general formula (VII).

Bases that can be employed for the reaction of tert-butyl benzoates of general formula (V) with alcohols of general formula (VI) are for example sodium hydride, sodium tert-butanolate, potassium tert-butanolate, or cesium carbonate. In connection with the method of the invention, potassium hexamethyldisilazide solution in tetrahydrofuran was preferably used as organic base.

Solvents that can be used for the reactions of tert-butyl benzoates of general formula (V) with alcohols of general formula (VI) are for example tetrahydrofuran, dimethyl sulfoxide and N,N-dimethylformamide. In connection with the method according to the invention tertahydrofuran was preferably used as solvent.

Reaction temperatures for the reactions of tert-butyl benzoates of general formula (V) with alcohols of general formula (VI) are for example ranging from room temperature to 130° C. Cooling of the reaction mixture is optionally necessary on adding the reactants or bases. In connection with the method of the invention, cooling the reaction to −10° C. prior addition of potassium hexamethyldisilazide solution in tetrahydrofuran and subsequent running the reaction at room temperature was preferable.

Suitable reaction times for the reaction of tert-butyl benzoates of general formula (V) with alcohols of general formula (VI) are ranging from 1h several days.

The reaction of tert-butyl benzoates of general formula (V) with alcohols of general formula (VI) can also result in transesterification, such as the tert-butoxide moiety of the tert-butyl benzoates of general formula (V) can be replaced by the alkoxide $R^3CH(CH_3)O$ moiety of the alcohols of general formula (VI). In order to obtain the benzoic acids of general formula (VIII), subsequent ester hydrolysis is required.

Ester hydrolysis can be achieved by various methods which are well known to the person skilled in the art, for example by treatment of the esters with lithium hydroxide, sodium hydroxide or potassium hydroxide, in solvents, such as, for example water, 1,4-dioxane, ethanol or tetrahydrofuran or mixtures thereof. The reactions can be carried out at temperatures ranging from room temperature to the boiling point of the respective solvent or solvent mixture.

In connection with the method of the invention, use of lithium hydroxide in water/dioxane was preferable.
(VIII)→(IX), (VIII)/((IX)+(X)→(I):

The compounds of general formula (I) can be prepared by the reaction of the benzoic acids of general formula (VIII) with amines of general formula (X) either by
- in situ formation of the corresponding acid chlorides of general formula (IX) and subsequent reaction with amines of general formula (X), or by
- amide coupling of the benzoic acids of general formula (VIII) with amines of general formula (X).

In situ formation of acid chlorides of general formula (IX) from benzoic acids of general formular (VIII) can be accomplished, for example by using oxalyl chloride or thionyl chloride, both reagents used in the presence of catalytic amount of N,N-dimethylformamide. In connection with the method according to the invention, oxalyl chloride is preferably used in the presence of N,N-dimethylformamide.

Suitable solvents for the in situ formation of acid chlorides of general formula (IX) from benzoic acids of general formula (VIII) include aprotic nonpolar solvents such as for example dichloromethane or toluene. In connection with the method according to the invention, dichloromethane is preferably used as solvent.

Suitable reaction temperatures for the in situ formation of acid chlorides of general formula (IX) from benzoic acids of general formula (VIII) mostly reflect the boiling point of the solvents used in the reaction. In connection with the method according to the invention, adding of oxalyl chloride was carried out at 0° C. and the reaction mixture was subsequently allowed to warm up to room temperature.

Subsequent reactions of the in situ formed acid chlorides of general formula (IX) with amines of general formula (X) can be carried out in the presence of an organic base. Suitable organic bases are for example triethylamine, pyridine or N-ethyl-N,N-diisopropylamine. In connection with the method according to the invention, triethylamine was preferably used as organic base.

Suitable solvents for the reaction of acid chlorides of general formula (IX) with amines of general formula (X) include aprotic polar solvents such as for example acetonitrile, N,N-dimethylformamide or aprotic nonpolar solvents such as dichloromethane. In connection with the method according to the invention dichoromethane was used as solvent.

Suitable coupling reagents for the reaction of benzoic acids of general formula (VIII) with amines of general formula (X) are for example O-(7-aza-1H-benzotriazol-1-yl)-N,N,N',N'-tetramethyluronium hexafluorophosphate (HATU), dicyclohexylcarbodiimide or a combination of 1H-benzotria-1-ol and 1-ethyl-3-[3-(diemthylaminopropyl] carbodiimide hydrochloride.

Suitable organic bases for the amide coupling of benzoic acids of general formula (VIII) with amines of general formula (X) are for example 4-(dimethylamino)pyridine, N-ethyl-N,N-diisopropylamine or triethylamine.

Suitable solvents for the for the amide coupling of benzoic acids of general formula (VIII) with amines of general formula (X) are for example N,N-dimethylformamide, dichoromethane or tetrahydrofuran.

For coupling of the amide bond, other methods which are well known to the person skilled in the art are also suitable, such as a condensation between amine and acid using propanephosphonic acid anhydride (T3P) as coupling reagent.

In connection with the invention, formation of the compounds according to the invention of general formula (I) were preferrably accomplished by in situ formation of acid chlorides of general formula (IX) from benzoic acids of general formula (VIII) and subsequent reaction with amines of general formula (X).

Synthetic Route 2

Scheme 2: Route for the preparation of compounds of general formula (I) in which $R^1$, $R^2$, $R^3$, $R^4$ and $R^5$ have the meaning as given for general formula (I), supra, and A represents a chlorine, bromine or iodine atom.

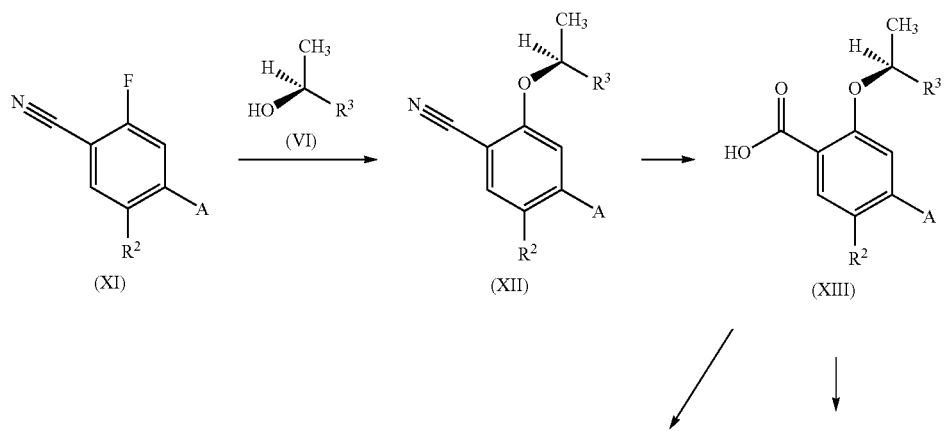

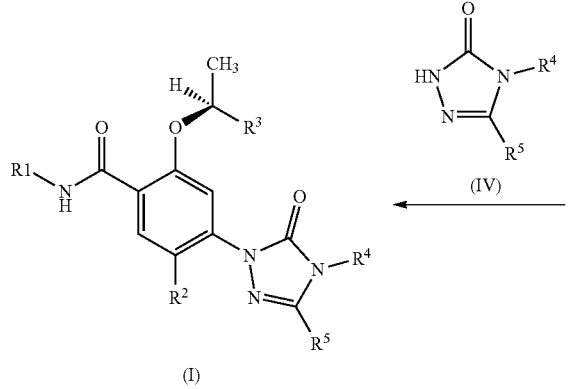
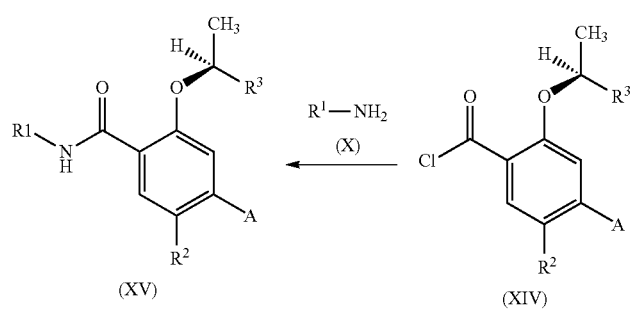

Compounds of general formulae (XI), (IV), (VI) and (X) are either commercially available or can be prepared according to procedures available from the public domain, as understandable to the person skilled in the art. Specific examples are described in the Experimental Section.

(XI)+(VI)→(XII):

Nitriles of general formula (XII) can be prepared from nitriles of general formula (XI) and with alcohols of general formula (VI) according to procedures available from the public domain, as understandable to the person skilled in the art.

In connection with the method of the invention, the use of sodium hydride in DMF was preferable.

Alternatively, for alcohols of sufficiently high acidity the use of potassium carbonate was preferable.

(XII)→(XIII):

The formation of benzoates of general formula (XIII) can be accomplished by hydrolysis of nitriles of general formula XII using strong acids or bases.

In connection with the method of the invention, the use of sodium hydroxide in ethanol at 90° C. was preferable.

(XIII)→(XIV)+(X)→(XV):

The compounds of general formula (XV) can be prepared by the reaction of the benzoic acids of general formula (XIII) with amines of general formula (X) either by in situ formation of the corresponding acid chlorides of general formula (XIV) and subsequent reaction with amines of general formula (X), or by amide coupling of the benzoic acids of general formula (XV) with amines of general formula (X).

In situ formation of acid chlorides of general formula (XIV) from benzoic acids of general formular (XIII) can be accomplished, for example by using oxalyl chloride or thionyl chloride, both reagents used in the presence of catalytic amount of N,N-dimethylformamide. In connection with the method according to the invention, oxalyl chloride is preferably used in the presence of N,N-dimethylformamide.

Suitable solvents for the in situ formation of acid chlorides of general formula (XIV) from benzoic acids of general formula (XIII) include aprotic nonpolar solvents such as for example dichloromethane or toluene. In connection with the method according to the invention, dichloromethane is preferably used as solvent.

Suitable reaction temperatures for the in situ formation of acid chlorides of general formula (XIV) from benzoic acids of general formula (XIII) mostly reflect the boiling point of the solvents used in the reaction. In connection with the method according to the invention, adding of oxalyl chloride was carried out at 0° C. and the reaction mixture was subsequently allowed to warm up to room temperature.

Subsequent reactions of the in situ formed acid chlorides of general formula (XIV) with amines of general formula (X) can be carried out in the presence of an organic base. Suitable organic bases are for example triethylamine, pyridine or N-ethyl-N,N-diisopropylamine. In connection with the method according to the invention, triethylamine was preferably used as organic base.

Suitable solvents for the reaction of acid chlorides of general formula (XIV) with amines of general formula (X) include aprotic polar solvents such as for example acetonitrile, N,N-dimethylformamide or aprotic nonpolar solvents such as dichloromethane. In connection with the method according to the invention dichoromethane was used as solvent.

Suitable coupling reagents for the reaction of benzoic acids of general formula (XIII) with amines of general formula (X) are for example O-(7-aza-1H-benzotriazol-1-yl)-N,N,N,N'-tetramethyluronium hexafluorophosphate (HATU), dicyclohexylcarbodiimide or a combination of 1H-benzotria-1-ol and 1-ethyl-3-[3-(diemthylaminopropyl]carbodiimide hydrochloride.

Suitable organic bases for the amide coupling of benzoic acids of general formula (XIII) with amines of general formula (X) are for example 4-(dimethylamino)pyridine, N-ethyl-N,N-diisopropylamine or triethylamine.

Suitable solvents for the for the amide coupling of benzoic acids of general formula (XIII) with amines of general formula (X) are for example N,N-dimethylformamide, dichoromethane or tetrahydrofuran.

For coupling of the amide bond, other methods which are well known to the person skilled in the art are also suitable, such as a condensation between amine and acid using propanephosphonic acid anhydride (T3P) as coupling reagent.

In connection with the invention, formation of the compounds according to the invention of general formula (XV) were preferrably accomplished by in situ formation of acid chlorides of general formula (XIV) from benzoic acids of general formula (XIII) and subsequent reaction with amines of general formula (X).

(XV)+(IV)→(I):

Compounds according to the invention of general formula (I) can be prepared from halides of general formula (XV) and from triazolones of general formula (IV) using transition metals as catalysts.

Intermediates of general formula (XV) can be reacted with a suitable triazolone of general formula (IV), such as, for example 3-ethyl-4-methyl-1H-1,2,4-triazol-5(4H)-one, in the presence of a suitable base, such as, for example cesium carbonate, and a suitable palladium catalyst, such as for example (1E,4E)-1,5-diphenylpenta-1,4-dien-3-one-palladium, in the presence of a suitable ligand, such as for example (9,9-dimethyl-9H-xanthene-4,5-diyl)bis(diphenylphosphine), in a suitable solvent system, such as, for example, dioxane, in a temperature range from room temperature to the boiling point of the respective solvent, preferably the reaction is carried out at 100° C. to furnish compounds of general formula (I). Alternatively the following palladium catalysts can be used:

allylpalladium chloride dimer, dichlorobis(benzonitrile)palladium (II), palladium (II) acetate, palladium (II) chloride, tetrakis(triphenylphosphine)palladium (O), tris(dibenzylideneacetone)dipalladium (O), chloro(2'-amino-1,1'-biphenyl-2-yl)palladium(II) dimer, (2'-amino-1,1'-bipheny-2-yl)methanesulfonatopalladium(II) dimer, trans-di(p-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2-[(dimethylamino)methyl]phenyl}palladium, chloro[(1,2,3-N)-3-phenyl-2-propenyl][1,3-bis(2,6-di-iso-propylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]phenyl} palladium, {1,3-bis[2,6-di(propan-2-yl)phenyl]-2,3-dihydro-1H-imidazol-2-yl}(dichloro)(3-chloropyridine-kappaN)palladium, [1,3-bis(2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]-3,5-dimethoxyphenyl}palladium, dichloro[1,3-bis(2,6-di-3-pentylphenyl)imidazol-2-ylidene](3-chloropyridyl)palladium(II), dichloro(di-p-chloro)bis[1,3-bis(2,6-di-isopropylphenyl) imidazol-2-ylidene]dipalladium(II), 2-(2'-di-tert-butylphosphine)biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl]phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl)palladium(II), [2',6'-bis(propan-2-yloxy)biphenyl-2-yl](dicyclohexyl)phosphane-[2-(2-aminoethyl) phenyl](chloro)palladium, [2-(2-aminoethyl)phenyl](chloro){dicyclohexyl [2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2-amino-1,1'-biphenyl-2-yl)palladium(II), [2'-(azanidyl-kappaN)biphenyl-2-yl-kappaC2](chloro){dicyclohexyl [2',4',6'-tri(propan-2-yl)biphenyl-2-yl]-lambda5-phosphanyl}palladium, (2'-aminobi-phenyl-2-yl)(methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-[2-(2-aminoethyl) phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dimethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methane-sulfonato-kappaO)palladium-[2',6'-bis(propan-2-yloxy)biphenyl-2-yl](dicyclohexyl) phosphane, (2'-aminobiphenyl-2-yl)(methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonato-dicyclohexyl[2',4',6'-tri(propan-2-yl)biphenyl-2-yl]phosphane, dicyclohexyl[3,6-dimethoxy-2',4',6'-tri(propan-2-yl)biphenyl-2-yl]phosphane-(2'-aminobiphenyl-2-yl)(chloro)palladium, (2'-aminobiphenyl-2-yl)(methanesulfonato-kappaO)palladium-di-tert-butyl[3,6-dimethoxy-2',4',6'-tri(propan-2-yl)biphenyl-2-yl] phosphane, (2'-aminobiphenyl-2-yl)(methanesulfonato-kappaO)palladium-dicyclohexyl[3,6-dimethoxy-2',4',6'-tri (propan-2-yl)biphenyl-2-yl]phosphane or the following ligands:

racemic-2,2'-bis(diphenylphosphino)-1,1'-binaphthyl, rac-BINAP, 1,1'-bis(diphenyl-phosphino)ferrocene, bis (2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl)phosphine, di-tert-butyl (2',4',6'-triiso propylbiphenyl-2-yl)phosphine, dicyclohexyl(2',4',6'-triisopropylbiphenyl-2-yl) phosphine, di-tert-butyl(2',4',6'-triisopropyl-3-methoxy-6-methylbiphenyl-2-yl)phos-phine, di-tert-butyl(2',4',6'-triisopropyl-3,4,5,6-tetramethylbiphenyl-2-yl) phosphine, adamantan-1-yl(adamantan-2-yl)(2',4',6'-triisopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethyl-biphenyl-2-amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl (2',4',6'-tricyclohexyl-3,6-dimethoxybiphenyl-2-yl) phosphine, bis[3,5-bis(trifluoromethyl)phe-nyl] (2',4',6'-triisopropyl-3,6-dimethoxybiphenyl-2-yl) phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylbiphenyl-2-amine, 2'-(dicyclohexylphosphino)-N,N,N',N'-tetramethylbiphenyl-2,6-diamine, sodium 2'-(dicyclohexylphosphino)-2,6-diisopropylbiphenyl-4-sulfonate, sodium 2'-(dicyclohexylphosphino)-2,6-dimethoxybiphenyl-3-sulfonate, 1,1'-binaphthalen-2-yl(di-tert-butyl) phosphine, 1,3-bis(2,4,6-trimethylphenyl)-1,3-dihydro-2H-imidazol-2-ylidene, 1,3-bis[2,6-di(propan-2-yl)phenyl]-1,3-dihydro-2H-imidazol-2-ylidene.

Synthetic Route 3

Scheme 3: Route for the preparation of compounds of general formula (I) in which $R^1$, $R^2$, $R^3$, $R^4$ and $R^5$ have the meaning as given for general formula (I), supra.

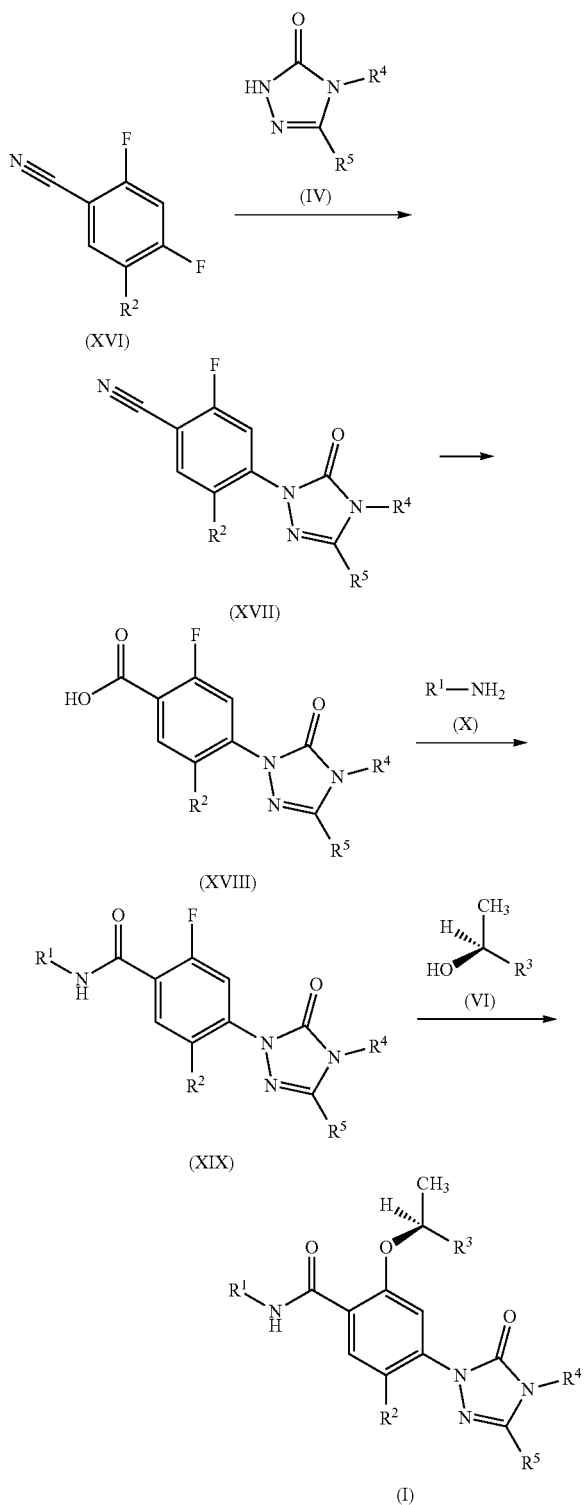

Compounds of general formulae (XVI), (IV), (VI) and (X) are either commercially available or can be prepared according to procedures available from the public domain, as understandable to the person skilled in the art. Specific examples are described in the Experimental Section.

Nitriles of general formula (XVII) can be prepared from nitriles of general formula (XVI) and triazolinones of general formula (IV) in the presence of a base. In connection with the method of the invention, the use of potassium carbonate as base in acetonitrile at 80° C. was preferable.

The formation of benzoates of general formula (XVIII) can be accomplished by hydrolysis of nitriles of general formula XVII using strong acids or bases. In connection with the method of the invention, the use of sodium hydroxide in ethanol at 85° C. was preferable.

The compounds of general formula (XIX) can be prepared by the reaction of the benzoic acids of general formula (XVIII) with amines of general formula (X) by amide coupling.

Suitable coupling reagents for the reaction of benzoic acids of general formula (XVIII) with amines of general formula (X) are for example O-(7-aza-1H-benzotriazol-1-yl)-N,N,N'-tetramethyluronium hexafluorophosphate (HATU), dicyclohexylcarbodiimide or a combination of 1H-benzotria-1-ol and 1-ethyl-3-[3-(diemthylaminopropyl] carbodiimide hydrochloride.

Suitable organic bases for the amide coupling of benzoic acids of general formula (XVIII) with amines of general formula (X) are for example 4-(dimethylamino)pyridine, N-ethyl-N,N-diisopropylamine, N-methylpyrollidine, or triethylamine.

Suitable solvents for the for the amide coupling of benzoic acids of general formula (XVIII) with amines of general formula (X) are for example N,N-dimethylformamide, dichoromethane or tetrahydrofuran.

For coupling of the amide bond, other methods which are well known to the person skilled in the art are also suitable, such as a condensation between amine and acid using propanephosphonic acid anhydride (T3P) as coupling reagent, or transformation of benzoic acids of general formula (XVIII) into their respective acid chlorides and subsequent reaction with amines of general formula (X) as described above.

In connection with the invention, formation of the compounds of general formula (XIX) were preferrably accomplished by HATU mediated amide coupling of benzoic acids of general formula (XVIII) and amines of general formula (X).

The formation of compounds of general formula (I) can be accomplished by reaction of amides of general formula (XIX) and alcohols of general formula (VI) in the presence of a base. Bases that can be employed for the reaction of amides of general formula (XIX) with alcohols of general formula (VI) are for example sodium hydride, sodium tert-butanolate, potassium tert-butanolate, or cesium carbonate. In connection with the method of the invention, sodium hydride was preferrably used as organic base.

Solvents that can be used for the reactions of tert-butyl benzoates of general formula (V) with alcohols of general formula (VI) are for example tetrahydrofuran, dimethyl sulfoxide and N,N-dimethylformamide. In connection with the method according to the invention N,N-dimethylformamide was preferrably used as solvent.

Reaction temperatures for the reactions of tert-butyl benzoates of general formula (V) with alcohols of general formula (VI) are for example ranging from room temperature to 80° C. In connection with the method of the invention, the reaction of alcohols of general formula (VI) with sodium hydride was preferrably performed at room temperature for 1h before addition of amides of formula (XIX) and subsequent heating of the reaction mixture to 80° C.

Suitable reaction times for the reaction of tert-butyl benzoates of general formula (V) with alcohols of general formula (VI) are ranging from 3h to several days.
Synthetic Route 4

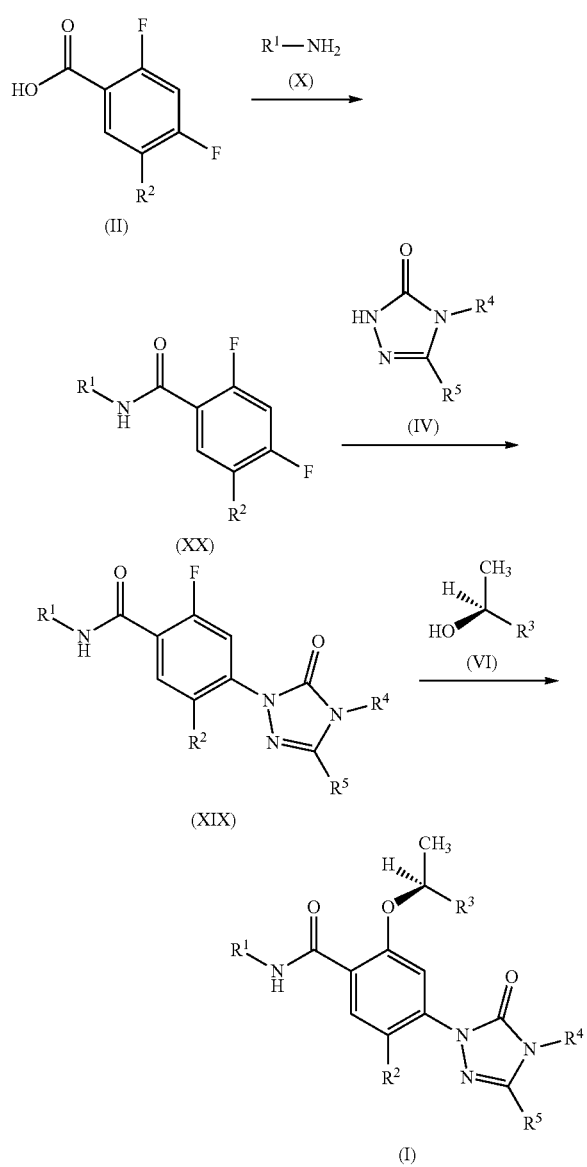

Scheme 4: Route for the preparation of compounds of general formula (I) in which $R^1$, $R^2$, $R^3$, $R^4$ and $R^5$ have the meaning as given for general formula (I), supra.

Compounds of general formulae (II), (IV), (VI) and (X) are either commercially available or can be prepared according to procedures available from the public domain, as understandable to the person skilled in the art. Specific examples are described in the Experimental Section.

Amides of general formula (XX) can be prepared by the reaction of the benzoic acids of general formula (II) with amines of general formula (X) by amide coupling.

Suitable coupling reagents for the reaction of benzoic acids of general formula (II) with amines of general formula (X) are for example O-(7-aza-1H-benzotriazol-1-yl)-N,N,N,N'-tetramethyluronium hexafluorophosphate (HATU), dicyclohexylcarbodiimide or a combination of 1H-benzotria-1-ol and 1-ethyl-3-[3-(diemthylaminopropyl]carbodiimide hydrochloride.

Suitable organic bases for the amide coupling of benzoic acids of general formula (II) with amines of general formula (X) are for example 4-(dimethylamino)pyridine, N-ethyl-N,N-diisopropylamine, N-methylpyrollidine, or triethylamine.

Suitable solvents for the for the amide coupling of benzoic acids of general formula (II) with amines of general formula (X) are for example N,N-dimethylformamide, dichoromethane or tetrahydrofuran.

For coupling of the amide bond, other methods which are well known to the person skilled in the art are also suitable, such as a condensation between amine and acid using propanephosphonic acid anhydride (T3P) as coupling reagent, or transformation of benzoic acids of general formula (II) into their respective acid chlorides and subsequent reaction with amines of general formula (X) as described above.

In connection with the invention, formation of the compounds of general formula (XX) were preferrably accomplished by HATU mediated amide coupling of benzoic acids of general formula (II) and amines of general formula (X).

Alternatively, amides of general formula (XX) can be prepared from benzoic acid derivatives of general formula (II) by in situ formation of the corresponding acid chlorides and subsequent reaction with amines of general formula (X).

In situ formation of acid chlorides from benzoic acids of general formular (II) can be accomplished, for example by using oxalyl chloride or thionyl chloride, both reagents used in the presence of catalytic amount of N,N-dimethylformamide.

(XX)+(IV)→(XIX):

The formation of compounds of general formula (XIX) can be accomplished by the reaction of triazolinones of general formula (IV) with amides of general formula (XX) in the presence of a base, such as potassium carbonate. In connection with the method of the invention, the use of 1,8-diazabicyclo[5.4.0]undec-7-ene as organic base in acetonitrile at 80° C. was preferable.

The formation of compounds of general formula (I) can be accomplished by reaction of amides of general formula (XIX) and alcohols of general formula (VI) in the presence of a base. Bases that can be employed for the reaction of amides of general formula (XIX) with alcohols of general formula (VI) are for example sodium hydride, sodium tert-butanolate, potassium tert-butanolate, or cesium carbonate. In connection with the method of the invention, sodium hydride was preferably used as organic base.

Solvents that can be used for the reactions of amides of general formula (XIX) with alcohols of general formula (VI) are for example tetrahydrofuran, dimethyl sulfoxide and N,N-dimethylformamide. In connection with the method according to the invention N,N-dimethylformamide was preferably used as solvent.

Reaction temperatures for the reactions of amides of general formula (XIX) with alcohols of general formula (VI) are for example ranging from room temperature to 140° C. In connection with the method of the invention, the reaction of alcohols of general formula (VI) with sodium hydride was preferably performed at room temperature for 1h before addition of amides of formula (XIX) and subsequent heating of the reaction mixture to 80° C.

Suitable reaction times for the reaction of amides of general formula (XIX) with alcohols of general formula (VI) are ranging from 3h to several days.

Synthetic Route 5

Scheme 5: Alternative route for the preparation of compounds of general formula (VIII) in which $R^2$, $R^3$, $R^4$ and $R^5$ have the meaning as given for general formula (I), supra, and A represents a chlorine, bromine or iodine atom.

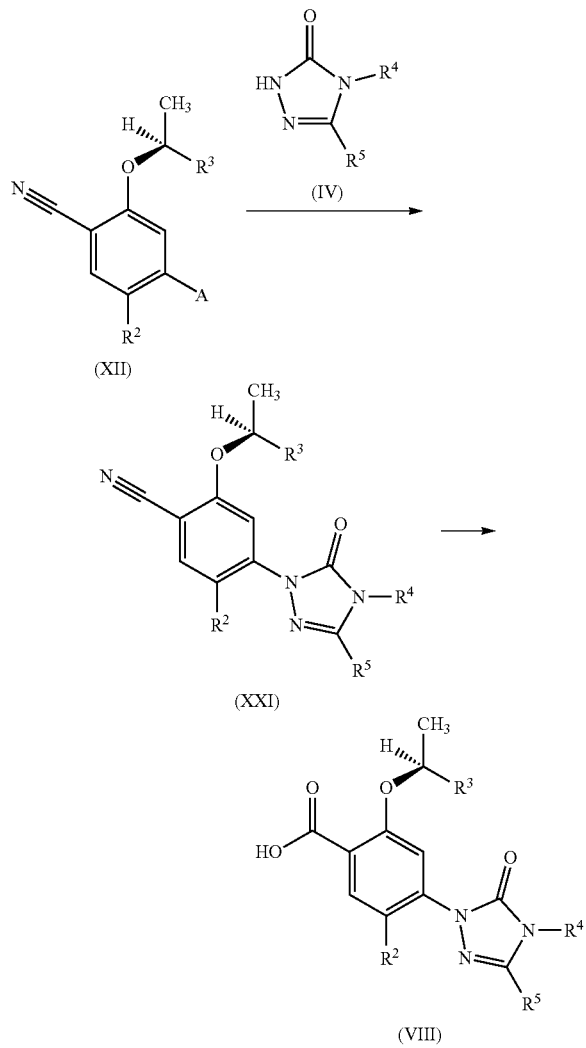

An alternative synthesis of compounds of formula (VIII) is described in scheme 5.

Compounds of general formula (XXI) can be prepared from halides of general formula (XII) and from triazolones of general formula (IV) using transition metals as catalysts.

The formation of benzoates of general formula (VIII) can be accomplished by hydrolysis of nitriles of general formula XXI using strong acids or bases. In connection with the method of the invention, the use of sulphuric acid, acetic acid and water at 120° C. was preferable.

The synthesis of compounds of general formula (XII) and the synthesis of compounds of general formula (I) from compounds of general formula (VIII) is described above.

The order of transformations exemplified in these schemes is therefore not intended to be limiting. In addition, interconversion of any of the substituents, $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

The resulting compounds of general formula (I) are optionally converted with corresponding (i) solvents and/or (ii) bases or acids to their solvates, salts and/or solvates of the salts, in which $R^1$, $R^2$, $R^3$, $R^4$ and $R^5$ have the meaning as given for general formula (I), supra.

In accordance with another aspect, the present invention provides methods of preparing compounds of general formula (I) as defined supra, said methods comprising the step of allowing an intermediate compound of general formula (VIII):

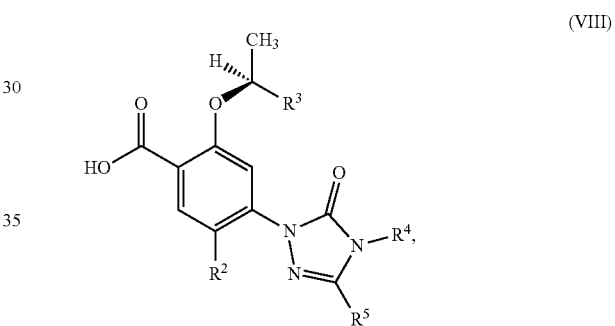

in which $R^2$, $R^3$, $R^4$ and $R^5$ are as defined for the compound of general formula (I) as defined supra, to react with a compound of general formula (X)

$$R^1-NH_2 \quad (X),$$

in which $R^1$ is as defined for the compound of general formula (I) as defined supra, thereby giving a compound of general formula (I):

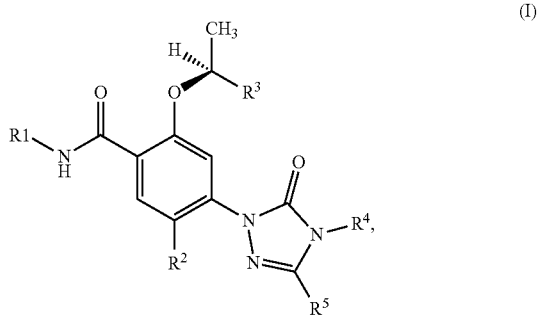

in which $R^1$, $R^2$, $R^3$, $R^4$ and $R^5$ are as defined supra.

In accordance with certain embodiments, the present invention provides methods of preparing compounds of general formula (I) as defined supra, said methods comprising the step of allowing an intermediate compound of general formula (IX):

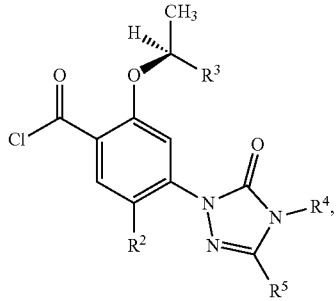

in which $R^2$, $R^3$, $R^4$ and $R^5$ are as defined for the compound of general formula (I) as defined supra,
to react with a compound of general formula (X):

  R¹—NH₂   (X), in which $R^1$ is as defined for the compound of general formula (I) as defined supra, thereby giving a compound of general formula (I):

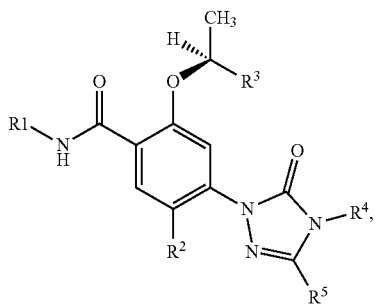

in which $R^1$, $R^2$, $R^3$, $R^4$ and $R^5$ are as defined supra.

In accordance with certain embodiments, the present invention provides methods of preparing compounds of general formula (I) as defined supra, said methods comprising the step of allowing an intermediate compound of general formula (VII)

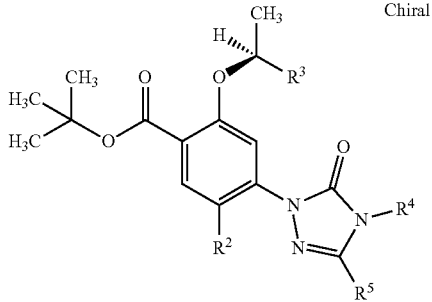

in which $R^2$, $R^3$, $R^4$ and $R^5$ are as defined for the compound of general formula (I) as defined supra, to be saponified resulting in a compound of general formula (VIII)

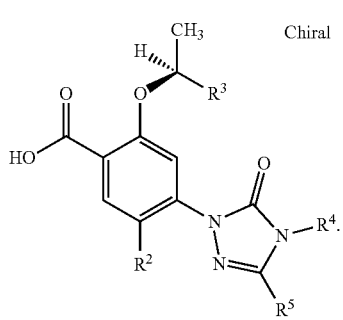

In accordance with certain embodiments, the present invention provides the intermediate compound of general formula (VIII)

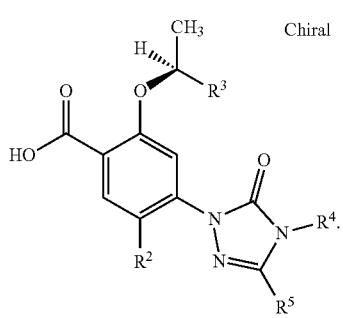

in which $R^2$, $R^3$, $R^4$ and $R^5$ are as defined for the compound of general formula (I) as defined supra, In accordance with certain embodiments, the present invention provides the use of the intermediate compound (VII) in which $R^2$, $R^3$, $R^4$ and $R^5$ are as defined for the compound of general formula (I) as defined supra for the production of a compound of general formula (I).

In accordance with further embodiments, the present invention provides methods of preparing compounds of general formula (I) as defined supra, said methods comprising the step of allowing an intermediate compound of general formula (XV):

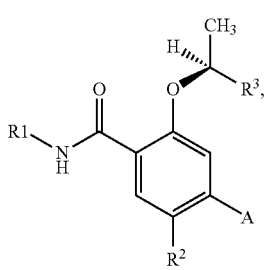

in which $R^1$, $R^2$ and $R^3$ are as defined for the compound of general formula (I) as defined supra, and A represents a chlorine, bromine or iodine atom, to react with a compound of general formula (IV):

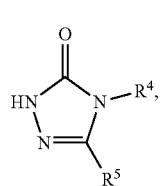
(IV)

in which R⁴ and R⁵ are as defined for the compound of general formula (I) as defined supra, thereby giving a compound of general formula (I):

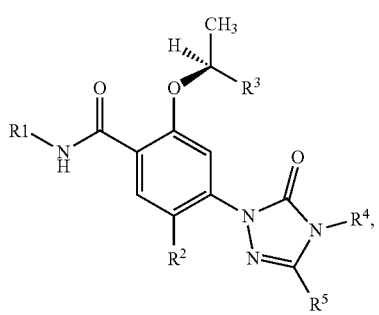
(I)

in which R¹, R², R³, R⁴ and R⁵ are as defined supra.

In accordance with other embodiments, the present invention provides methods of preparing compounds of general formula (I) as defined supra, said methods comprising the step of allowing an intermediate compound of general formula (XVIII)

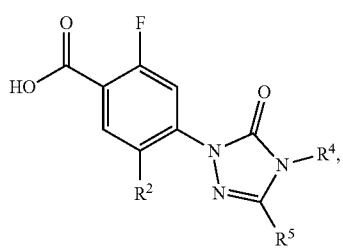
(XVIII)

in which R², R⁴ and R⁵ are as defined for the compound of general formula (I) as defined supra, to react with a compound of general formula (X):

R¹—NH₂  (X), in which R¹ is as defined for the compound of general formula (I) as defined supra, thereby giving a compound of general formula (XIX)

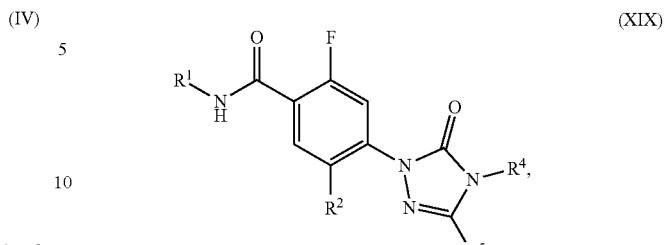
(XIX)

in which R¹, R², R⁴ and R⁵ are as defined supra.

In accordance with other embodiments, the present invention provides methods of preparing compounds of general formula (I) as defined supra, said methods comprising the step of allowing an intermediate compound of general formula (XX)

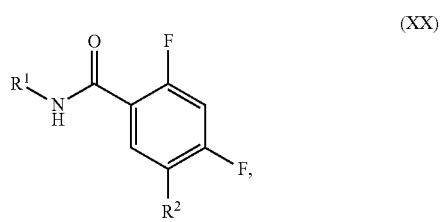
(XX)

in which R¹ and R² are as defined for the compound of general formula (I) as defined supra, to react with a compound of general formula (IV):

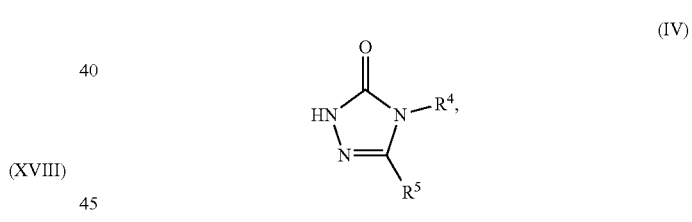
(IV)

in which R⁴ and R⁵ are as defined for the compound of general formula (I) as defined supra, thereby giving a compound of general formula (XIX):

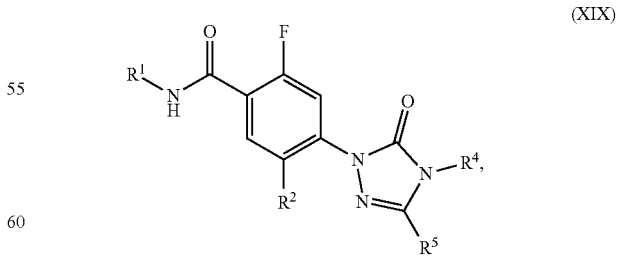
(XIX)

in which R¹, R², R⁴ and R⁵ are as defined for the compound of general formula (I) as defined supra.

In accordance with further embodiments, the present invention provides methods of preparing compounds of general formula (I) as defined supra, said methods comprising the step of allowing an intermediate compound of general formula (XIX)

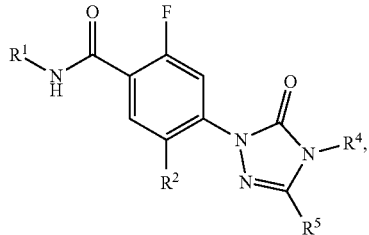
(XIX)

in which $R^1$, $R^2$, $R^4$ and $R^5$ are as defined for the compound of general formula (I) as defined supra,
to react with a compound of general formula (VI)

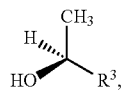
(VI)

in which $R^3$ is as defined for the compound of general formula (I) as defined supra, thereby giving a compound of general formula (I):

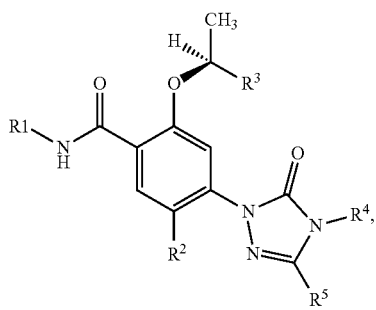
(I)

in which $R^1$, $R^2$, $R^3$, $R^4$ and $R^5$ are as defined supra.

In accordance with another aspect, the present invention provides methods of preparing compounds of general formula (I) as defined supra,
said methods comprise the step of allowing an intermediate compound of general formula (VIII)

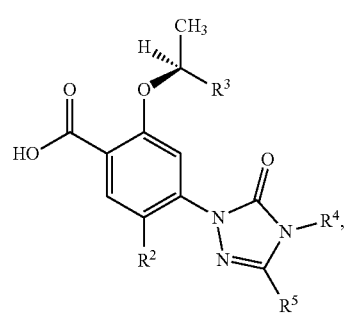
(VIII)

in which $R^2$, $R^3$, $R^4$ and $R^5$ are as defined for the compound of general formula (I) as defined supra,
to react with a compound of general formula (X)

$R^1$—$NH_2$ (X), in which $R^1$ is as defined for the compound of general formula (I) as defined supra, thereby giving a compound of general formula (I):

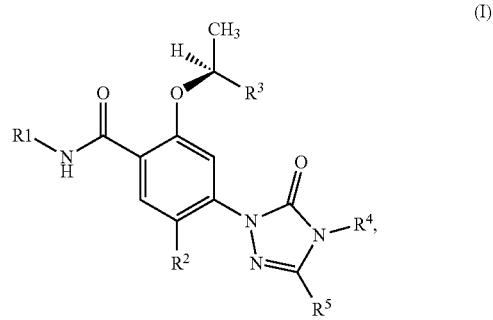
(I)

in which $R^1$, $R^2$, $R^3$, $R^4$ and $R^5$ are as defined supra,
then optionally converting said compound into solvates, salts and/or solvates of such salts using the corresponding (i) solvents and/or (ii) bases or acids.

In accordance with certain embodiments, the present invention provides methods of preparing compounds of general formula (I) as defined supra, said methods comprising the step of allowing an intermediate compound of general formula (IX)

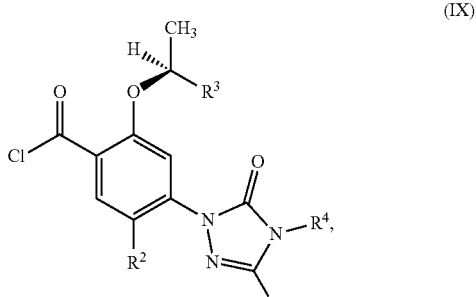
(IX)

in which $R^2$, $R^3$, $R^4$ and $R^5$ are as defined for the compound of general formula (I) as defined supra,
to react with a compound of general formula (X)

$R^1$—$NH_2$ (X), in which R¹ is as defined for the compound of general formula (I) as defined supra, thereby giving a compound of general formula (I):

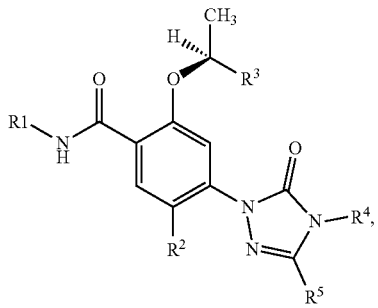

in which R¹, R², R³, R⁴ and R⁵ are as defined supra, then optionally converting said compound into solvates, salts and/or solvates of such salts using the corresponding (i) solvents and/or (ii) bases or acids.

In accordance with further embodiments, the present invention provides methods of preparing compounds of general formula (I) as defined supra, said methods comprising the step of allowing an intermediate compound of general formula (XV)

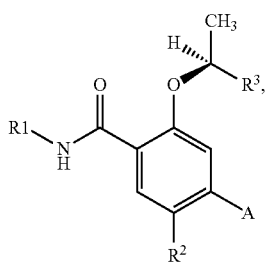

in which R¹, R² and R³ are as defined for the compound of general formula (I) as defined supra, and A represents a chlorine, bromine or iodine atom, to react with a compound of general formula (IV):

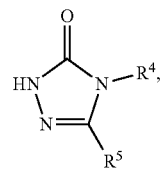

in which R⁴ and R⁵ are as defined for the compound of general formula (I) as defined supra, thereby giving a compound of general formula (I):

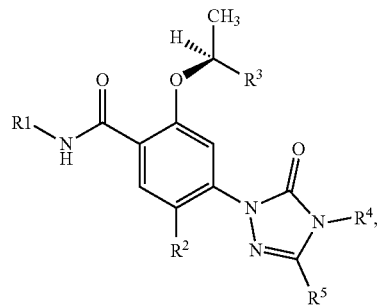

in which R¹, R², R³, R⁴ and R⁵ are as defined supra, then optionally converting said compound into solvates, salts and/or solvates of such salts using the corresponding (i) solvents and/or (ii) bases or acids.

In accordance with other embodiments, the present invention provides methods of preparing compounds of general formula (I) as defined supra, said methods comprising the step of allowing an intermediate compound of general formula (XIX)

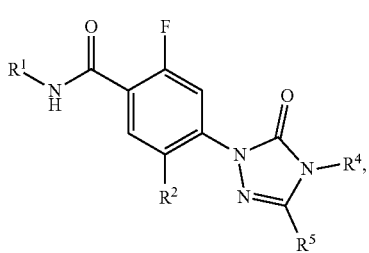

in which R¹, R², R⁴ and R⁵ are as defined for the compound of general formula (I) as defined supra, to react with a compound of general formula (VI):

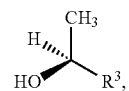

in which R³ is as defined for the compound of general formula (I) as defined supra, thereby giving a compound of general formula (I):

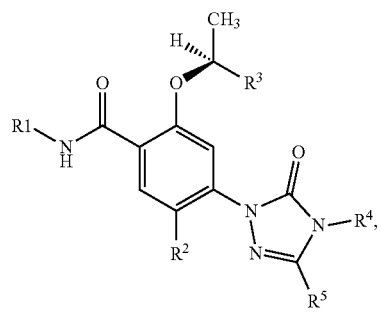

in which R¹, R², R³, R⁴ and R⁵ are as defined supra, then optionally converting said compound into solvates, salts and/or solvates of such salts using the corresponding (i) solvents and/or (ii) bases or acids.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (IV):

(IV), in which $R^4$ and $R^5$ are as defined for the compound of general formula (I) supra.

Furthermore, the invention provides the intermediate compounds of general formula (VI):

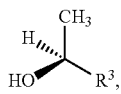
(VI)

in which $R^3$ is as defined for the compound of general formula (I) supra.

Particularly, the invention provides the intermediate compounds of general formula (VIII):

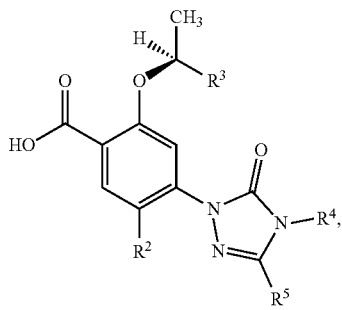
(VIII)

in which $R^2$, $R^3$, $R^4$ and $R^5$ are as defined for the compound of general formula (I) supra.

Particularly, the inventions provides the intermediate compounds of general formula (IX):

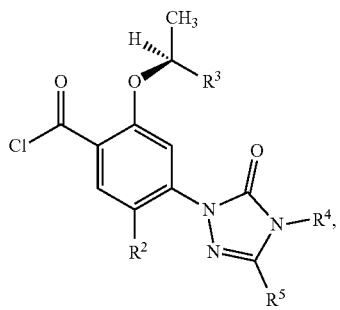
(IX)

in which $R^2$, $R^3$, $R^4$ and $R^5$ are as defined for the compound of general formula (I) supra.

Particularly, the inventions provides the intermediate compounds of general formula (XV):

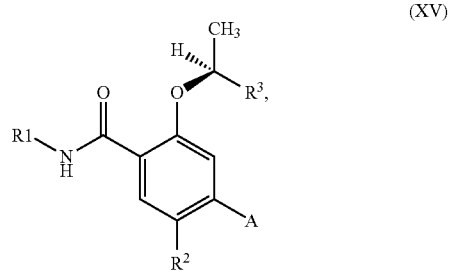
(XV)

in which $R^1$, $R^2$ and $R^3$ are as defined for the compound of general formula (I) supra, and A represents a chlorine, bromine or iodine atom.

Particularly, the inventions provides the intermediate compounds of general formula (XVIII):

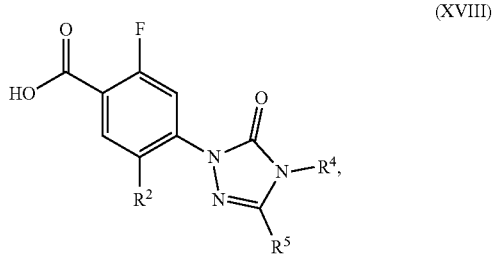
(XVIII)

in which $R^2$, $R^4$ and $R^5$ are as defined for the compound of general formula (I) supra.

Particularly, the invention provides the intermediate compounds of general formula (XIX):

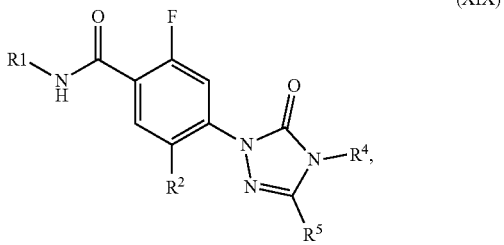
(XIX)

in which $R^1$, $R^2$, $R^4$ and $R^5$ are as defined for the compound of general formula (I) supra.

Particularly, the invention provides the intermediate compounds of general formula (XXI):

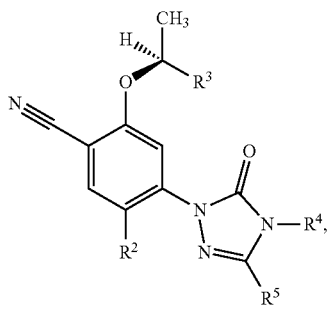

(XXI)

in which $R^2$, $R^3$, $R^4$ and $R^5$ are as defined for the compound of general formula (I) supra.

In accordance with another aspect, the present invention provides the use of said intermediate compounds for the preparation of a compound of general formula (I) as defined supra.

Particularly, the invention provides the use of intermediate compounds of general formula (IV):

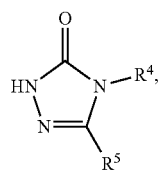

(IV)

in which $R^4$ and $R^5$ are as defined for the compound of general formula (I) supra, for the preparation of a compound of general formula (I) as defined supra.

Particularly, the invention provides the use of intermediate compounds of general formula (VI):

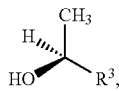

(VI)

in which $R^3$ is as defined for the compound of general formula (I) supra, for the preparation of a compound of general formula (I) as defined supra.

Particularly, the invention provides the use of intermediate compounds of general formula (VIII):

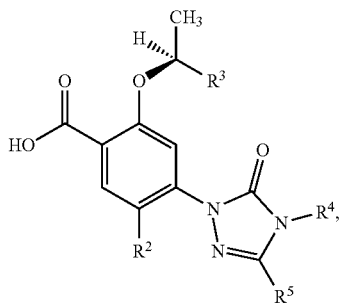

(VIII)

in which $R^2$, $R^3$, $R^4$ and $R^5$ are as defined for the compound of general formula (I) supra, for the preparation of a compound of general formula (I) as defined supra.

Particularly, the invention provides the use of intermediate compounds of general formula (IX):

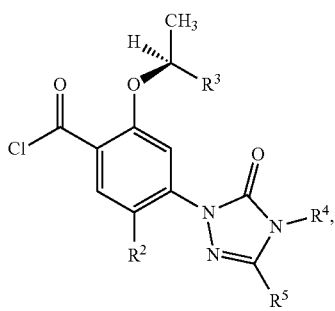

(IX)

in which $R^2$, $R^3$, $R^4$ and $R^5$ are as defined for the compound of general formula (I) supra, for the preparation of a compound of general formula (I) as defined supra.

Particularly, the invention provides the use of intermediate compounds of general formula (X):

$R^1$—$NH_2$     (X), in which $R^1$ is as defined for the compound of general formula (I) as defined supra, for the preparation of a compound of general formula (I) as defined supra.

Particularly, the invention provides the use of intermediate compounds of general formula (XV):

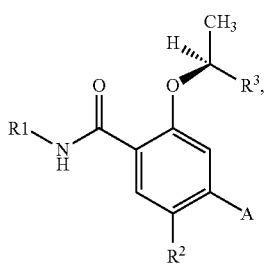

(XV)

in which $R^1$, $R^2$ and $R^3$ are as defined for the compound of general formula (I) supra, and A represents a chlorine, bromine or iodine atom, for the preparation of a compound of general formula (I) as defined supra.

Particularly, the invention provides the use of intermediate compounds of general formula (XVIII):

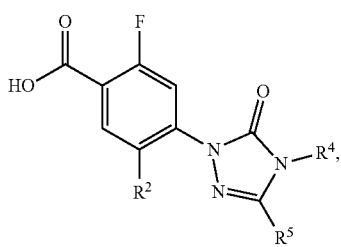

(XVIII)

in which $R^2$, $R^4$ and $R^5$ are as defined for the compound of general formula (I) supra, for the preparation of a compound of general formula (I) as defined supra.

Particularly, the invention provides the use of intermediate compounds of general formula (XIX):

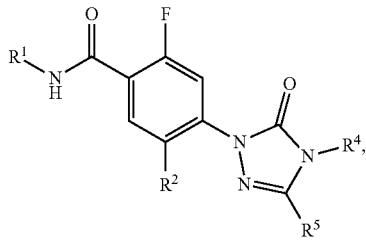

(XIX)

in which $R^1$, $R^2$, $R^4$ and $R^5$ are as defined for the compound of general formula (I) supra, for the preparation of a compound of general formula (I) as defined supra.

Particularly, the invention provides the use of intermediate compounds of general formula (XX):

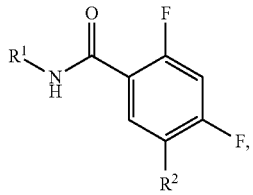

(XX)

in which $R^1$ and $R^2$ are as defined for the compound of general formula (I) as defined supra, for the preparation of a compound of general formula (I) as defined supra.

Particularly, the invention provides the use of intermediate compounds of general formula (XXI):

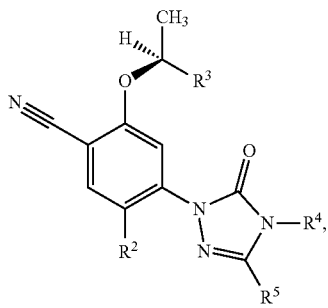

(XXI)

in which $R^2$, $R^3$, $R^4$ and $R^5$ are as defined for the compound of general formula (I) supra, for the preparation of a compound of general formula (I) as defined supra.

In one embodiment the present invention provides methods of preparing compounds of the present invention of general formula (I),

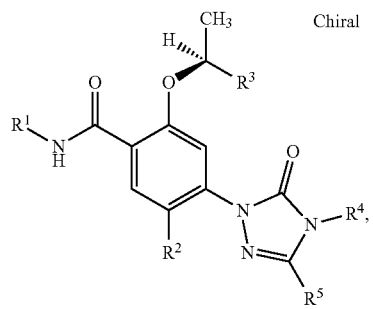

(I)

in which $R^1$, $R^2$, $R^3$ are as defined in any previous aspect and $R^4$ and $R^5$ are linked to one another in such a way that they jointly form together with the nitrogen atom and the carbon atom to which they are attached a 5 to 7 membered saturated or partially unsaturated heterocyclic ring that is substituted once with a hydroxy group, said methods comprising the step of reacting a compound of general formula (Ia)

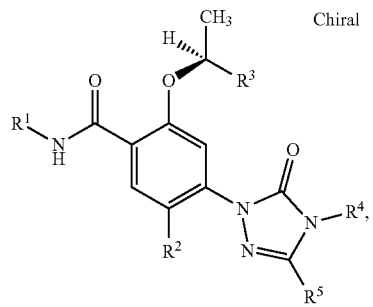

(Ia)

in which $R^1$, $R^2$, $R^3$ are as defined in any previous aspect and $R^4$ and $R^5$ are linked to one another in such a way that they jointly form a group selected from

*—$CH_2$—$X^1$—$X^2$—#,

*—$CH_2$—$X^1$—$X^2$—$X^3$—#,

*—$CH_2$—$X^1$—$X^2$—$X^3$—$X^4$—#, and $X^1$, $X^2$, $X^3$ and $X^4$ are —$CH_2$— in which groups "*" represents the point of attachment of $R^4$ to the rest of the molecule, and "#" represents the point of attachment of $R^5$ to the rest of the molecule, with a suitable microorganism, under suitable conditions and in a suitable medium.

In one embodiment the present invention provides methods of preparing compounds of the present invention of general formula (I),

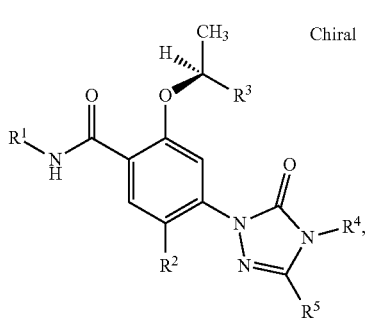

(I)

in which
R$^1$, R$^2$, R$^3$ are as defined in any previous aspect and
R$^4$ and R$^5$ are linked to one another in such a way that they jointly form a group
*—CH(OH)—X$^1$—X$^2$—#,
*—CH$_2$—CH(OH)—X$^2$ #,
*—CH(OH)—X$^1$—X$^2$—X$^3$—#,
*—CH$_2$—CH(OH)—X$^2$—X$^3$—#,
*—CH$_2$—X$^1$—CH(OH)—X$^3$—#,
*—CH═CH—CH(OH)—X$^3$—#,
*—CH(OH)—X$^1$—X$^2$—X$^3$—X$^4$—#,
*—CH$_2$—CH(OH)—X$^2$—X$^3$—X$^4$—#,
*—CH$_2$—X$^1$—CH(OH)—X$^3$—X$^4$—#,
*—CH$_2$—X$^1$—X$^2$—CH(OH)—X$^4$—#,
and X$^1$, X$^2$, X$^3$ and X$^4$ are —CH$_2$—.
in which groups "*" represents the point of attachment of R$^4$ to the rest of the molecule and "#" represents the point of attachment of R$^5$ to the rest of the molecule.
said methods comprising the step of reacting a compound of general formula (Ia)

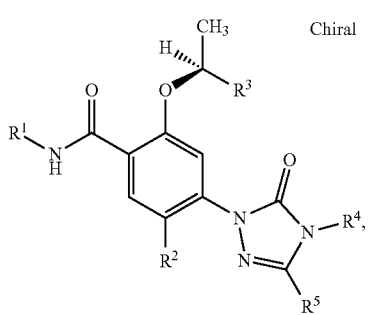

(Ia)

in which
R$^1$, R$^2$, R$^3$ are as defined in any previous aspect and
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
and X$^1$, X$^2$, X$^3$ and X$^4$ are —CH$_2$— in which groups "*" represents the point of attachment of R$^4$ to the rest of the molecule, and "#" represents the point of attachment of R$^5$ to the rest of the molecule,
with a suitable microorganism, under suitable conditions and in a suitable medium.

In one embodiment the present invention provides methods of preparing compounds of the present invention of general formula (I),

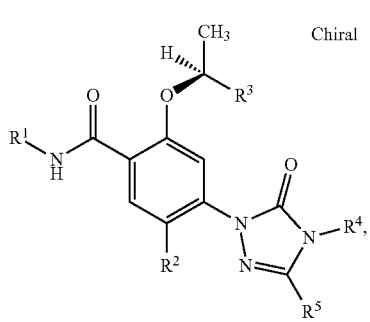

(I)

in which
R$^1$, R$^2$, R$^3$ are as defined in any previous aspect and
R$^4$ and R$^5$ are linked to one another in such a way that they jointly form a group
*—CH(OH)—X$^1$—X$^2$—#,
*—CH$_2$—CH(OH)—X$^2$ #,
*—CH(OH)—X$^1$—X$^2$—X$^3$—#,
*—CH$_2$—CH(OH)—X$^2$—X$^3$—#,
*—CH$_2$—X$^1$—CH(OH)—X$^3$—#,
*—CH═CH—CH(OH)—X$^3$—#,
*—CH(OH)—X$^1$—X$^2$—X$^3$—X$^4$—#,
*—CH$_2$—CH(OH)—X$^2$—X$^3$—X$^4$—#,
*—CH$_2$—X$^1$—CH(OH)—X$^3$—X$^4$—#,
*—CH$_2$—X$^1$—X$^2$—CH(OH)—X$^4$—#,
and X$^1$, X$^2$, X$^3$ and X$^4$ are —CH$_2$—.
in which groups "*" represents the point of attachment of R$^4$ to the rest of the molecule and "#" represents the point of attachment of R$^5$ to the rest of the molecule.
said methods comprising the step of reacting a compound of general formula (Ia)

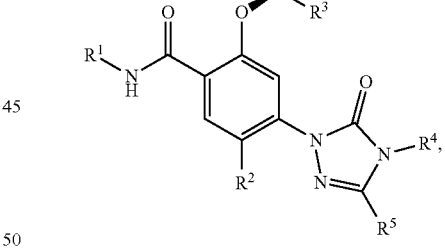

(Ia)

in which
R$^1$, R$^2$, R$^3$ are as defined in any previous aspect and
R$^4$ and R$^5$ are linked to one another in such a way that they jointly form a group selected from
*—CH$_2$—X$^1$—X$^2$—#,
*—CH$_2$—X$^1$—X$^2$—X$^3$—#,
*—CH$_2$—X$^1$—X$^2$—X$^3$—X$^4$—#,
and X$^1$, X$^2$, X$^3$ and X$^4$ are —CH$_2$—
in which groups "*" represents the point of attachment of R$^4$ to the rest of the molecule, and "#" represents the point of attachment of R$^5$ to the rest of the molecule,
with a modified *E. coli* or a fungus under suitable conditions and in a suitable medium.

In one embodiment the present invention provides methods of preparing compounds of the present invention of general formula (I), as defined in any previous aspect, said methods comprising the step of reacting a compound of general formula (Ia)

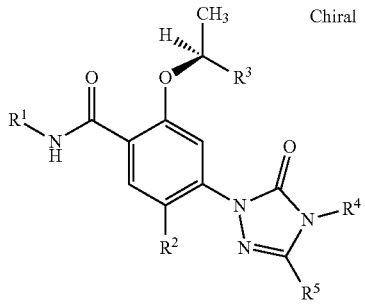

(Ia)

wherein

R¹, R² and R³ are as defined in any embodiment or aspect supra and

R⁴ and R⁵ are linked to one another in such a way that they jointly form a group selected from \*—CH₂—X¹—X²—#,
\*—CH₂—X¹—X²—X³—#,
\*—CH₂—X¹—X²—X³—X⁴—#,
and X¹, X², X³ and X⁴ are —CH₂— in which groups "\*" represents the point of attachment of R⁴ to the rest of the molecule, and "#" represents the point of attachment of R⁵ to the rest of the molecule, resulting in the following subgroups of compounds of general formula (Ia):

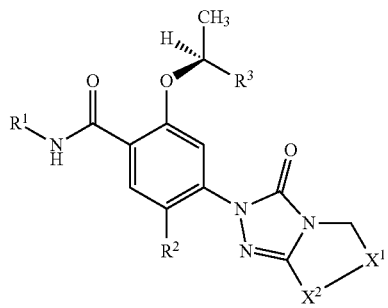

(Ia-1)

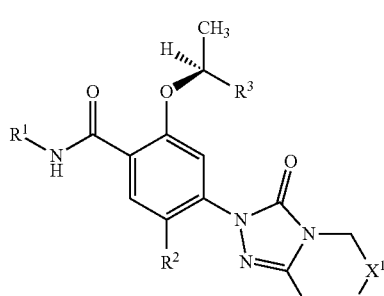

(Ia-2)

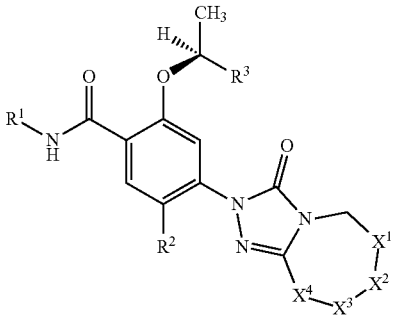

(Ia-3)

preferably a compound of formula (Ia-2), with a microorganism such as a e.g. a modified *E. coli* hosting a suitable plasmid, such as a nucleic acid sequence of Seq. ID. No.1 or Seq. ID. No.2, or a fungus and subsequently harvesting the culture and isolating the reaction product after a suitable reaction time to obtain a compound of formula (Ib)

wherein

R¹, R² and R³ are as defined in any embodiment or aspect supra and

R⁴ and R⁵ are linked to one another in such a way that they jointly form a group selected from \*—CH(OH)—X¹—X²—#,
\*—CH₂—CH(OH)—X²—#,
\*—CH(OH)—X¹—X²—X³—#,
\*—CH₂—CH(OH)—X²—X³—#,
\*—CH₂—X¹—CH(OH)—X³—#,
\*—CH=CH—CH(OH)—X³—#,
\*—CH(OH)—X¹—X²—X³—X⁴—#,
\*—CH₂—CH(OH)—X²—X³—X⁴—#,
\*—CH₂—X¹—CH(OH)—X³—X⁴—#,
\*—CH₂—X¹—X²—CH(OH)—X⁴—#,
and X¹, X², X³ and X⁴ are —CH₂—.

in which groups "\*" represents the point of attachment of R⁴ to the rest of the molecule, and "#" represents the point of attachment of R⁵ to the rest of the molecule.

In one embodiment the present invention provides methods of preparing compounds of the present invention of general formula (I), as defined in any previous aspect, said methods comprising the step of reacting a compound of general formula (Ia)

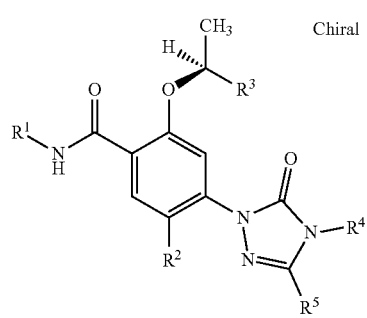

(Ia)

wherein

R¹, R² and R³ are as defined in any aspect or embodiment defined supra and

R⁴ and R⁵ are linked to one another in such a way that they jointly form a group selected from

*—CH₂—X¹—X²—#,
*—CH₂—X¹—X²—X³—#,
*—CH₂—X¹—X²—X³—X⁴—#,
and X¹, X², X³ and X⁴ are —CH₂—
in a suitable medium with a microorganism, such as a modified *E. coli* e.g. hosting certain modified plasmids, particularly those having the Seq ID No. 1 or Seq. ID No. 2, or a fungus such as e.g. *Nigrospora sphaerica* (ATCC 12772, CBS 98469) and
subsequently harvesting the culture and isolating the reaction product after a suitable reaction time to produce a compound of formula (Ib) wherein
R¹, R² and R³ are as defined in any aspect or embodiment supra and
R⁴ and R⁵ are linked to one another in such a way that they jointly form a group selected from
*—CH(OH)—X¹—X²—X³—#,
*—CH₂—CH(OH)—X²—X³—#,
*—CH₂—X¹—CH(OH)—X³—#,
*—CH═CH—CH(OH)—X³—#.

In one embodiment the process as described above further comprises subsequently harvesting the culture and isolating the reaction product after a suitable reaction time.

In another embodiment the present invention provides methods of preparing a compound of formula (I), wherein the suitable medium is a suitable nutrition solution comprising a buffer and an aqueous sugar solution.

In another embodiment the present invention provides methods of preparing a compound of formula (I), wherein the suitable medium is a suitable nutrition solution comprising a buffer such as an aqueous phosphatebuffer solution e.g. a potassiumdihydrogenphosphate/potassiumhydrogenphosphate buffer, a sodiumdihydrogenphosphate/sodiumhydrogenphosphate buffer, particularly a potassiumdihydrogenphosphate/potassiumhydrogenphosphate buffer and an aqueous sugar solution such as e.g. an aqueous glucose solution optionally further comprising an aqueous solution of a complexing agent such as e.g. ethylendiamintetraacetate.

In another embodiment the present invention provides methods of preparing a compound of formula (I), as disclosed supra and optionally further comprising aeration of the culture thus providing aerobic reaction conditions.

In another embodiment the present invention provides methods of preparing a compound of formula (I), as disclosed supra and further comprising the steps of harvesting the culture after a suitable reaction time such as e.g. 3-6h, particularly 3-4h and isolating the product.

In another embodiment the present invention provides methods of preparing a compound of formula (I), which are example compounds 293-296

293

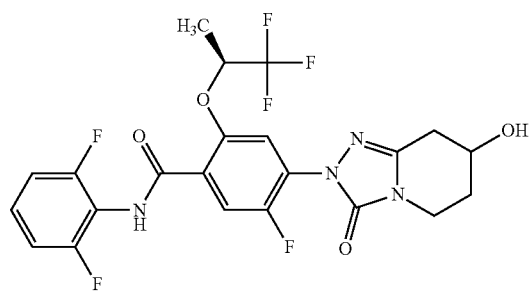

294

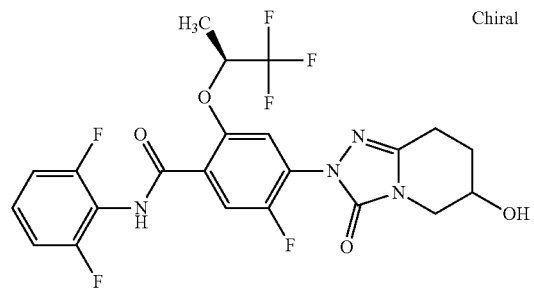

295

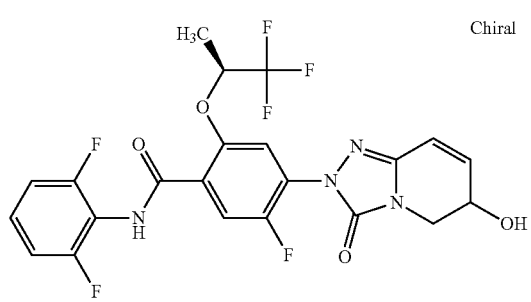

and

296

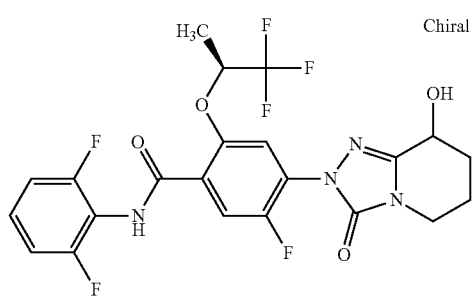

reacting a compound of formula (Ic)

(Ic)

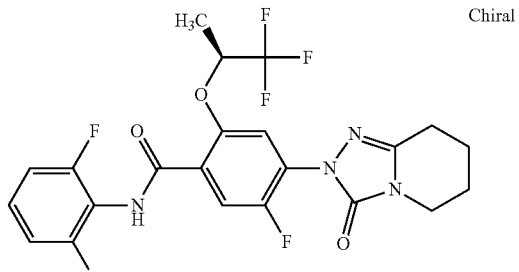

named N-(2,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide with *E. coli* DH5a LPSd pACYC_pel_POR_pETDuet_Δ3_CYP2C19 in a medium comprising a suitable buffer such as e.g. potassiumdihydrogenphosphate/potassiumhydrogenphosphate and an aqueous sugar solution such as e.g. glucose solution at a temperature range of 20-30° C., particularly 25°-30° C., the ranges including the lower and upper limit temperature, more particularly 27° C. under aerobic conditions and subsequently harvesting the culture and isolating the reaction product after a suitable reaction time, such as 3-6 h, particularly 3-4 h.

In a further embodiment the present invention provides methods of preparing a compound of formula (I), which are example compounds 293-296 under the conditions as described in example 293.

A further embodiment of the invention is the compound of formula (I) obtained by the method disclosed supra.

A further aspect of the invention is the nucleic acid sequence of Seq. ID. No.1., plasmid 1 of example 293.

Yet another aspect of the invention is the nucleic acid sequence of Seq ID. No.2, plasmid 2 of example 293.

A further aspect is the use of a plasmid of Seq. ID. No. 1 and/or Seq. ID. No.2 for the production of a mircoorganism suitable for a hydroxylation reaction, preferably the hydroxylation of a compound of formula (I), more preferably a compound of formula (Ia), even more preferably a compound of formula (Ia-2).

A further aspect is the use of nucleic acid sequence Seq. ID No. 1 or nucleic acid sequence Seq. ID No. 2
for the preparation of a microorganism suitable for the production of a compound of formula (I)
in which
$R^1$, $R^2$, $R^3$ are as defined in any previous aspect and
$R^4$ and $R^5$ are linked to one another in such a way that they jointly form together with the nitrogen atom and the carbon atom to which they are attached a 5 to 7 membered saturated or partially unsaturated heterocyclic ring that is substituted once with a hydroxy group,
more particularly, for the production of a compound of formula (I) in which
$R^1$, $R^2$, $R^3$ are as defined in any previous aspect and
$R^4$ and $R^5$ are linked to one another in such a way that they
jointly form a group selected from
*—CH(OH)—X$^1$—X$^2$—#,
*—CH$_2$—CH(OH)—X$^2$ #,
*—CH(OH)—X$^1$—X$^2$—X$^3$—#,
*—CH$_2$—CH(OH)—X$^2$—X$^3$—#,
*—CH$_2$—X$^1$—CH(OH)—X$^3$—#,
*—CH═CH—CH(OH)—X$^3$—#,
*—CH(OH)—X$^1$—X$^2$—X$^3$—X$^4$—#,
*—CH$_2$—CH(OH)—X$^2$—X$^3$—X$^4$—#,
*—CH$_2$—X$^1$—CH(OH)—X$^3$—X$^4$—#,
*—CH$_2$—X$^1$—X$^2$—CH(OH)—X$^4$—#,
and X$^1$, X$^2$, X$^3$ and X$^4$ are —CH$_2$—
in which groups "*" represents the point of attachment of $R^4$ to the rest of the molecule, and "#" represents the point of attachment of $R^5$ to the rest of the molecule.

A further aspect is the use of a plasmid of Seq. ID. No. 1 and/or Seq.D.no. 2 for the production of a mircoorganism suitable for the production of a compound of formula (I).

A further aspect is the use of a plasmid of Seq. ID. No. 1 and/or Seq. ID.no. 2 for the production of a mircoorganism suitable for the production of a compound of formula (I), more particularly a hydroxylated compound of formula (I), even more particularly a hydroxylated compound of formula (I) in which
$R^4$ and $R^5$ are linked to one another in such a way that they
jointly form a group selected from
*—CH(OH)—X$^1$—X$^2$—#,
*—CH$_2$—CH(OH)—X$^2$ #,
*—CH(OH)—X$^1$—X$^2$—X$^3$—#,
*—CH$_2$—CH(OH)—X$^2$—X$^3$—#,
*—CH$_2$—X$^1$—CH(OH)—X$^3$—#,
*—CH═CH—CH(OH)—X$^3$—#,
*—CH(OH)—X$^1$—X$^2$—X$^3$—X$^4$—#,
*—CH$_2$—CH(OH)—X$^2$—X$^3$—X$^4$—#,
*—CH$_2$—X$^1$—CH(OH)—X$^3$—X$^4$—#,
*—CH$_2$—X$^1$—X$^2$—CH(OH)—X$^4$—#,
and X$^1$, X$^2$, X$^3$ and X$^4$ are —CH$_2$—
in which groups "*" represents the point of attachment of $R^4$ to the rest of the molecule, and "#" represents the point of attachment of $R^5$ to the rest of the molecule.

Another aspect of the invention is a compound of formula (I), particularly a compound of formula (Ib) more particularly the compounds of examples 293-296 obtained by a method as described herein.

The present invention provides the use of the intermediate compounds of general formula (IV), (VI), (VIII), (IX), (X), (XV), (XVIII), (XIX) and (XXI) which are disclosed in the Example Section of this text, infra.

The present invention provides the intermediate compounds which are disclosed in the Example Section of this text, infra.

The present invention provides the intermediate compounds of general formula (IV), (VI), (VIII), (IX), (X), (XV), (XVIII), (XIX) and (XXI) which are disclosed in the Example Section of this text, infra.

The present invention provides any sub-combination within any embodiment or aspect of the present invention of intermediate compounds of general formula (IV), (VI), (VIII), (IX), (X), (XV), (XVIII), (XIX) and (XXI), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit DHODH and it is possible therefore that said compounds be used for the treatment or prophylaxis of diseases, preferably hyperproliferative and/or inflammatory disorders in humans and animals.

Compounds of the present invention can be utilized to inhibit the activity of DHODH. This method comprises administering to a mammal in need thereof, including a human, an effective amount of a compound of general formula (I) of the present invention, or a pharmaceutically acceptable salt, polymorph, metabolite, hydrate, solvate or ester thereof, for the treatment of hyperproliferative and/or inflammatory disorders.

Another aspect of the invention is a method of inhibiting proliferation of a cell, comprising contacting the cell with a compound of formula (I).

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include sarcomas, and haematological malignancies including but not limiting to leukemias, lymphomas, multiple myeolomas.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, gliosarcoma, osteosarcoma, malignant fibrous histiocytoma, lymphosarcoma, and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia, bisphenotypic B myelomonocytic leukemia, chronic lymphocytic leukemia, chronic myelogenous leukemia, chronic myeloid leukemia, chronic myelomonocytic leukemia (CMML), large granular lymphocytic leukemia, plasma cell leukemia, and also myelodysplastic syndrome (MDS), which can develop into an acute myeloid leukemia.

Inhibition of DHODH can also lead to differentiation of tumor initiating cells in hematological and solid cancers, especially leukemias.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

Another aspect of the invention is a method for controlling cancer in humans and animals by administering an effective amount of at least one compound of general formula (I) of the present invention, or a pharmaceutically acceptable salt, polymorph, metabolite, hydrate, solvate or ester thereof, or of a medicament, comprising at least one compound of general formula (I) of the present invention.

Another aspect of the invention is a method for controlling cancer (e.g., through treatment prophylaxis, etc.) in a subject (e.g., human, rat, etc.) by administering an effective amount of at least one compound of general formula (I), or a pharmaceutically acceptable salt, polymorph, metabolite, hydrate, solvate or ester thereof to the subject. In some embodiments, the subject may be administered a medicament, comprising at least one compound of general formula (I) and one or more pharmaceutically acceptable carriers, excipients, and/or diluents. In some embodiments, the method of treatment and/or prophylaxis of a hyperproliferative disorder in a subject may comprise administering to the subject an effective amount of a compound of general formula (I). The hyperproliferative disorder may be, for example, cancer (e.g. but not limited to lung cancer, acute myeloid leukemia, lymphoma, glioblastoma, prostate cancer, etc.).

A method of inhibiting dihydroorotate dehydrogenase activity in a cancer cell is also provided, wherein the method comprises contacting a cancer cell with a compound of general formula (I). The cancer cell may be in vitro or in vivo.

Another aspect of the invention is a method of treating lymphoma in a subject, the method comprising administering to the subject an effective amount of a compound of general formula (I).

A yet other aspect of the invention is a method of treating leukemia in a subject, the method comprising administering to the subject an effective amount of a compound of general formula (I).

In another aspect, the present invention provides the use of a compound of general formula (I) of the present invention, or a pharmaceutically acceptable salt, polymorph, metabolite, hydrate, solvate or ester thereof, for the preparation of a medicament for the treatment or prophylaxis of a disease.

In another aspect, the present invention provides methods of treating cancer, which cancer is selected from a solid tumor such as e.g. lung cancer, glioblastoma, and prostate cancer, leukemia such as e.g. acute myeloid leukemia and lymphoma.

In another aspect, the present invention provides methods of treating cancer, which cancer is selected from lung cancer, leukemia, lymphoma, glioblastoma, and prostate cancer.

In another aspect, the present invention provides methods of treating cancer, which cancer is selected from lung cancer, acute myeloid leukemia, lymphoma, glioblastoma, and prostate cancer.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from lung cancer, acute myeloid leukemia, lymphoma, glioblastoma, and prostate cancer.

In another aspect, the present invention provides methods of treating or preventing a disease or condition associated with inflammation, a metabolic disorder, infection or an immune disease or condition by administering to a subject having such a condition or disease, a therapeutically effective amount of a compound or composition of the invention.

In further embodiments, diseases or conditions, including chronic diseases, of humans or other species can be treated or prevented by inhibition of DHODH. These diseases or conditions include (1) inflammatory or allergic diseases such as systemic anaphylaxis and hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis and urticaria, (5) vasculitis, (6) spondyloarthropathies, (7) scleroderma, (8) asthma and respiratory allergic diseases such as allergic asthma, allergic rhinitis, allergic conjunctivitis, hypersensitivity lung diseases and the like, and (9) autoimmune diseases, such as arthritis (including rheumatoid and psoriatic), systemic lupus erythematosus, type I diabetes, glomerulonephritis and the like, (10) graft rejection (including allograft rejection and graft-v-host disease), (11) other diseases in which undesired inflammatory responses are to be inhibited, e.g., atherosclerosis, myositis, neurological disorders such as stroke, ischemic reperfusion injury, traumatic brain injury and closed-head injuries, neurodegenerative diseases (e.g., Parkinson's disease), multiple sclerosis, Alzheimer's disease, encephalitis, meningitis, osteoporosis, gout, hepatitis, nephritis, gall bladder disease, sepsis, sarcoidosis, conjunctivitis, otitis, chronic obstructive pulmonary disease, sinusitis and Behcet's syndrome, and (12) immune diseases or conditions.

In another aspect, the present invention provides methods of treating or preventing viral infections.

In yet another aspect, the present invention provides methods of treating or preventing Malaria.

These disorders have been well characterized in humans, but also exist with a similar etiology in other mammals, and can be treated by administering pharmaceutical compositions of the present invention.

If it is stated "preventing or treating" "treatment or prophylaxis" treating/treatment is preferred.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

In accordance with a further aspect, the present invention provides compounds of general formula (I), as described supra, or tautomers, N-oxides, and salts thereof, or salts of tautomers or N-oxides, particularly pharmaceutically acceptable salts thereof, or mixtures of same, for use in the treatment or prophylaxis of diseases, in particular hyperproliferative and/or inflammatory disorders.

In accordance with a further aspect, the present invention provides compounds of general formula (I), as described supra, or tautomers, N-oxides, and salts thereof, or salts of tautomers or N-oxides, for use in the treatment or prophylaxis of diseases, in particular hyperproliferative disorders, particularly benign hyperproliferative disorders, more particularly cancer.

The pharmaceutical activity of the compounds according to the invention can be explained by their activity as DHODH inhibitors.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, for the treatment or prophylaxis of diseases, in particular hyperproliferative and/or inflammatory disorders.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, for the treatment or prophylaxis of diseases, in particular hyperproliferative disorders, particularly benign hyperproliferative disorders, more particularly cancer.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, in a method of treatment or prophylaxis of diseases, in particular hyperproliferative and/or inflammatory disorders, particularly cancer.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, in a method of treatment or prophylaxis of diseases, in particular hyperproliferative disorders, particularly benign hyperproliferative disorders, more particularly cancer.

In accordance with a further aspect, the present invention provides the use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a medicament, for the prophylaxis or treatment of diseases, in particular hyperproliferative disorders, particularly benign hyperproliferative disorders, more particularly cancer.

In accordance with a further aspect, the present invention provides use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a pharmaceutical composition, for the prophylaxis or treatment of diseases, in particular hyperproliferative and/or inflammatory disorders.

In accordance with a further aspect, the present invention provides use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a pharmaceutical composition, preferably a medicament, for the prophylaxis or treatment of diseases, in particular hyperproliferative disorders, particularly benign hyperproliferative disorders, more particularly cancer.

In accordance with a further aspect, the present invention provides a method of treatment or prophylaxis of diseases, in particular hyperproliferative and/or inflammatory disorders, comprising administering an effective amount of a compound of general formula (I), as described supra, or a tautomer, an N-oxide, and a salt thereof, or a salt of a tautomer or an N-oxide, particularly a pharmaceutically acceptable salt thereof, or a mixture of same.

In accordance with a further aspect, the present invention provides a method of treatment or prophylaxis of diseases, in particular hyperproliferative disorders, particularly benign hyperproliferative disorders, more particularly cancer, comprising administering an effective amount of a compound of general formula (I), as described supra, or a tautomer, an N-oxide, and a salt thereof, or a salt of a tautomer or an N-oxide, particularly a pharmaceutically acceptable salt thereof, or a mixture of same.

In accordance with a further aspect, the present invention provides pharmaceutical compositions, in particular a medicament, comprising a compound of general formula (I), as described supra, or a tautomer, an N-oxide, and a salt thereof, or a salt of a tautomer or an N-oxide, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore provides pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity.

For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)),
ointment bases (for example petroleum jelly, paraffins, triglycerides, waxes, wool wax, wool wax alcohols, lanolin, hydrophilic ointment, polyethylene glycols),
bases for suppositories (for example polyethylene glycols, cacao butter, hard fat),
solvents (for example water, ethanol, isopropanol, glycerol, propylene glycol, medium chain-length triglycerides fatty oils, liquid polyethylene glycols, paraffins),
surfactants, emulsifiers, dispersants or wetters (for example sodium dodecyl sulfate), lecithin, phospholipids, fatty alcohols (such as, for example, Lanette®), sorbitan fatty acid esters (such as, for example, Span®),
polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
buffers, acids and bases (for example phosphates, carbonates, citric acid, acetic acid, hydrochloric acid, sodium hydroxide solution, ammonium carbonate, trometamol, triethanolamine),
isotonicity agents (for example glucose, sodium chloride),
adsorbents (for example highly-disperse silicas),
viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
flow regulators, lubricants, glidants and mould release agents (for example magnesium stearate, stearic acid, talc, highly-disperse silicas (such as, for example, Aerosil®)),
coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
capsule materials (for example gelatine, hydroxypropylmethylcellulose),
synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
plasticizers (for example polyethylene glycols, propylene glycol, glycerol, triacetine, triacetyl citrate, dibutyl phthalate),
penetration enhancers,
stabilisers (for example antioxidants such as, for example, ascorbic acid, ascorbyl palmitate, sodium ascorbate, butylhydroxyanisole, butylhydroxytoluene, propyl gallate),
preservatives (for example parabens, sorbic acid, thiomersal, benzalkonium chloride, chlorhexidine acetate, sodium benzoate),
colourants (for example inorganic pigments such as, for example, iron oxides, titanium dioxide),
flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention provides pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention provides a pharmaceutical combination, which comprises:
one or more first active ingredients, in particular compounds of general formula (I) as defined supra, and
one or more further active ingredients, in particular anti-cancer agents.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also provides such pharmaceutical combinations. For example, the compounds of the present invention can be combined with known anti-cancer agents.

Examples of anti-cancer agents include:
131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]- octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative and/or inflammatory disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg (e.g. about 0.5 mg to about 5 mg, about 5 mg to about 50 mg, about 50 mg to about 500 mg, about 500 mg to about 1500 mg, etc.) of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

In other embodiments of the invention the total amount of the active ingredient to be administered will generally range from 0.001 mg/kg to 200 mg/kg body weight per day, and preferably from 0.01 mg/kg to 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from 0.5 mg to 1500 mg of active ingredient, and can be administered one or more times per day or less than once a day.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), ..., $δ_i$ (intensity$_i$), ..., $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations

| Abbreviation | Meaning |
|---|---|
| aq. | aqueous |
| br | broad ($^1$H-NMR signal) |
| cat. | catalytic |
| CDCl$_3$ | deuterated chloroform |
| CI | chemical ionisation |
| d | doublet |
| DAD | diode array detector |
| DCM | dichloromethane |
| d | doublet |
| dd | double-doublet |
| ddd | double-doublet-doublet |
| DMF | N,N-dimethylformamide |
| DMSO | dimethylsulfoxide |
| ELSD | Evaporative Light Scattering Detector |
| eq. | equivalent |
| ESI | electrospray (ES) ionisation |
| h | hour(s) |
| HATU | 1-[bis(dimethylamino)methylene]-1H-1,2,3-triazolo[4,5-b]pyridinium 3-oxid hexafluorophosphate |
| HPLC | high performance liquid chromatography |
| LC-MS | liquid chromatography mass spectrometry |
| m | multiplet |
| min | minute(s) |
| MS | mass spectrometry |
| NMR | nuclear magnetic resonance spectroscopy: chemical shifts (δ) are given in ppm. The chemical shifts were corrected by setting the DMSO signal to 2.50 ppm unless otherwise stated. |
| p | pentet |
| q | quartet |
| r.t. or rt or RT | room temperature |
| rac | racemic |
| Rt | retention time (as measured either with HPLC or UPLC) in minutes |
| s | singlet |
| t | triplet |
| td | triple-doublet |
| UPLC | ultra performance liquid chromatography |

Other abbreviations have their meanings customary per se to the skilled person.

The various aspects and embodiments of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization.

In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Method A (HPLC-MS):

Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method B (HPLC-MS):

Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method C (HPLC-MS):

Instrument: Waters Acquity; MS: Waters ZQ; Column: Acquity BEH C18 1.7 μm, 50×2.1 mm; eluent A: water+0.1 vol % formic acid (99%), eluent B: acetonitrile; gradient:0-1.6 min 1-99% B, 1.8-2.0 min 99% B; temperature: 60° C.; flow: 0.8 ml/min; DAD scan: 210-400 nm

EXPERIMENTAL SECTION—INTERMEDIATES

Intermediate 1 tert-butyl 2,4,5-trifluorobenzoate

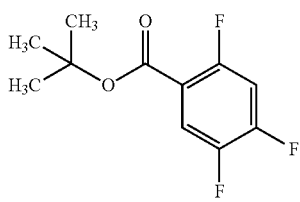 [SMILES: CC(C)(C)OC(=O)c1cc(F)c(F)cc1F]

Under argon, to a solution of 2,4,5-trifluorobenzoic acid (101 g, 574 mmol) in 2-methylpropan-2-01 (200 ml) was added N,N-dimethylpyridin-4-amine (35 g, 287 mmol). Subsequently, di-tert-butyl dicarbonate (200 ml, 860 mmol) was added in portions. The resulting mixture was stirred at ambient temperature for two days to yield a clear colorless solution. The reaction mixture was poured into an aqueous sodium carbonate solution (1 N, 1.5 l), and the resulting mixture was extracted with tert-butyl methyl ether (3×300 ml). The organic phases were concentrated and the observed crude product was purified by silica gel chromatography to yield tert-butyl 2,4,5-trifluorobenzoate (113 g, 85%) as white crystals.

$^1$H-NMR (400 MHz, DMSO-d6) δ[ppm]: 1.53 (s, 9H), 7.68 (m, 1H), 7.87 (m, 1H).

Intermediate 2 tert-butyl 2,5-difluoro-4-(3-oxo-5,6,7,8-tetrahydro[1,2,4]triazolo[4,3-a]pyridin-2(3H)-yl)benzoate

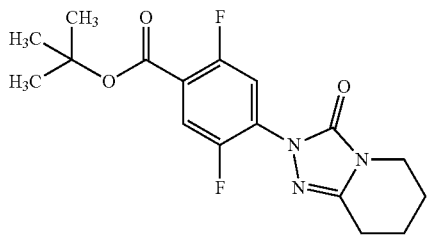 [SMILES: CC(C)(C)OC(=O)c1cc(F)c(-n2nc3n(c2=O)CCCC3)cc1F]

Under argon, to a solution of tert-butyl 2,4,5-trifluorobenzoate (intermediate 1) (50.0 g, 215 mmol) in acetonitrile (500 ml, 9.5 mol) was added 5,6,7,8-tetrahydro[1,2,4]triazolo[4,3-a]pyridin-3(2H)-one [CAS 118801-67-5] (33.0 g, 237 mmol), and potassium carbonate (59.5 g, 431 mmol). The reaction mixture was stirred under reflux for three days. The mixture was then cooled to room temperature, poured into water (2 l) and the mixture was extracted with tert-butyl methyl ether (3×500 ml). The organic phases were concentrated and the residue was purified twice by chromatography over silica gel to yield tert-butyl 2,5-difluoro-4-(3-oxo-5,6,7,8-tetrahydro[1,2,4]triazolo[4,3-a]pyridin-2(3H)-yl)benzoate 47.2 g (62%).

LC-MS (method A): $R_t$=1.22 min; MS (ESIpos): m/z=352.0 [M+H]$^+$ $^1$H-NMR (400 MHz, DMSO-d6) δ[ppm]: 1.54 (s, 9H), 1.73-1.92 (m, 4H), 2.70 (m, 2H), 3.56 (m, 2H), 7.61 (m, 1H), 7.78 (m, 1H).

Intermediate 3 tert-butyl 2,5-difluoro-4-(3-oxo-5,6-dihydro-3H-[1,2,4]triazolo[3,4-c][1,4]oxazin-2(8H)-yl)benzoate

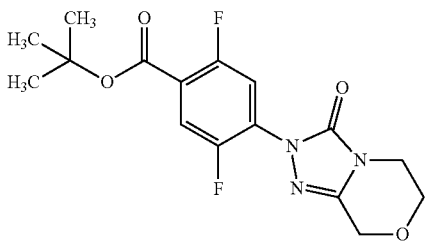 [SMILES: CC(C)(C)OC(=O)c1cc(F)c(-n2nc3n(c2=O)CCOC3)cc1F]

To a room temperature stirred solution of tert-butyl 2,4,5-trifluorobenzoate (intermediate 1) (1.16 g, 5.00 mmol) in anhydrous acetonitrile (12.5 ml) was added 2,5,6,8-tetrahydro-3H-[1,2,4]triazolo[3,4-c][1,4]oxazin-3-one [CAS 133365-36-3] (741 mg, 5.25 mmol) followed by dropwise addition of 1,8-diazabicyclo[5.4.0]undec-7-ene (1.52 ml, 10.0 mmol). Following complete addition, the resulting mixture was heated at 85° C. for 16 hours, cooled to room temperature and concentrated under reduced pressure to give a dark brown oil (3.52 g). The residue was purified by flash column chromatography to give a waxy white solid (1.35 g, 98% purity, 75%).

LC-MS (method A): $R_t$=1.15 min; MS (ESIpos): m/z=354.2 [M+H]$^+$ $^1$H-NMR (400 MHz, CHLOROFORM-d) δ [ppm]: 1.60 (s, 9H), 3.80 (dd, 2H), 4.08 (dd, 2H), 4.74 (s, 2H), 7.45 (dd, 1H), 7.73 (dd, 1H).

Intermediate 4 tert-butyl 2,5-difluoro-4-(3-oxo[1,2,4]triazolo[4,3-a]pyridin-2(3H)-yl)benzoate

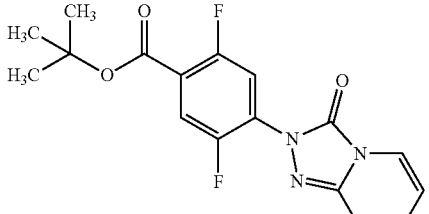

Tert-butyl 2,5-difluoro-4-(3-oxo[1,2,4]triazolo[4,3-a]pyridin-2(3H)-yl)benzoate was prepared as described for tert-butyl 2,5-difluoro-4-(3-oxo-5,6-dihydro-3H-[1,2,4]triazolo[3,4-c][1,4]oxazin-2(8H)-yl)benzoate (Intermediate 3) using tert-butyl 2,4,5-trifluorobenzoate (intermediate 1) and [1,2,4]triazolo[4,3-a]pyridin-3(2H)-one [CAS 6969-71-7] to yield the title compound (70%).

MS (ESIpos): m/z=348 [M+H]$^+$ $^1$H NMR (400 MHz, CDCl$_3$) δ [ppm] 1.60 (s, 9H), 6.55 (ddd, 1H), 7.13-7.21 (m, 2H), 7.53 (dd, 1H), 7.76 (d, 1H), 7.81 (td, 1H).

Intermediate 5

4-bromo-5-fluoro-2-{[(2S)-1,1,1-trifluoropropan-2-yl]oxy}benzonitrile

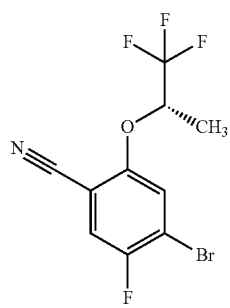 [SMILES: C[C@H](Oc1cc(Br)c(F)cc1C#N)C(F)(F)F]

To a stirred suspension of 4-bromo-2,5-difluorobenzonitrile (5.0 g, 22.9 mmol) and potassium carbonate (9.5 g, 68.8 mmol) in N,N-dimethylformamide (45.9 ml) was added (S)-1,1,1-trifluoropropanol [CAS 3539-97-7] dropwise (2.88 g, 25.2 mmol). The resulting mixture was heated at 55° C. for 15 hours and cooled to room temperature. Water (100 ml) was added to the mixture and extracted with diethyl ether (3×50 ml). The combined organic extracts were sequentially washed with water (2×100 ml), brine (100 ml), dried over magnesium sulfate, filtered and concentrated under reduced pressure to give an off white solid (6.93 g). The residue was purified by flash column chromatography to give the ether as a white crystalline solid (5.90 g, 97% purity, 80%).

LC-MS (method A): $R_t$=1.29 min; MS (ESIpos): m/z=312.0 [M+H]$^+$ $^1$H-NMR (400 MHz, CHLOROFORM-d) δ [ppm]: 1.511 (4.41), 1.531 (15.64), 1.533 (16.00), 1.548 (15.84), 1.550 (15.83), 4.566 (1.08), 4.581 (2.68), 4.597 (3.18), 4.612 (2.62), 4.626 (1.01), 7.194 (5.27), 7.207 (7.60), 7.220 (7.57).

Intermediate 6

4-bromo-2-{[(2S)-1,1,1-trifluoropropan-2-yl]oxy}benzonitrile

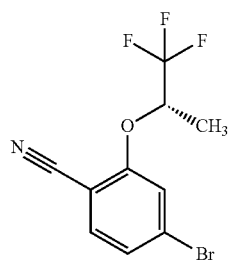 [SMILES: C[C@H](Oc1cc(Br)ccc1C#N)C(F)(F)F]

To a stirred suspension of 4-bromo-2-fluorobenzonitrile (5.00 g, 25.0 mmol) and potassium carbonate (10.4 g, 75.0 mmol) in N,N-dimethylformamide (50.0 ml) was added (S)-1,1,1-trifluoropropanol dropwise (3.14 g, 27.5 mmol). The resulting mixture was heated at 55° C. for two days and cooled to room temperature. Water (100 ml) was added to the mixture and extracted with diethyl ether (3×50 ml). The combined organic extracts were sequentially washed with water (2×100 ml), brine (100 ml), dried over magnesium sulfate, filtered and concentrated under reduced pressure to give a white solid 7.03 g (98% purity, 94%). The product was used directly in the next step without further purification.

LC-MS (method A): $R_t$=1.27 min; MS (ESIpos): m/z=294 [M+H]$^+$ $^1$H-NMR (500 MHz, CHLOROFORM-d) δ [ppm]: 1.368 (3.65), 1.415 (15.76), 1.427 (16.00), 1.428 (15.81), 1.984 (0.94), 4.525 (1.13), 4.538 (2.65), 4.550 (3.35), 4.562 (2.58), 4.574 (1.03), 7.019 (7.92), 7.022 (8.28), 7.073 (9.59), 7.089 (5.49), 7.092 (5.57), 7.105 (7.20), 7.108 (6.95).

Intermediate 7

2,5-difluoro-4-(3-oxo-5,6,7,8-tetrahydro[1,2,4]triazolo[4,3-a]pyridin-2(3H)-yl)benzonitrile

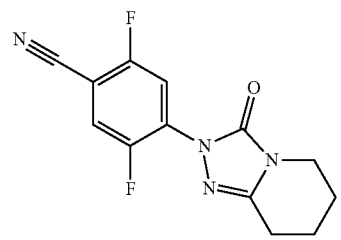 [SMILES: N#Cc1cc(F)c(-n2nc3n(c2=O)CCCC3)cc1F]

To a solution of 2,4,5-trifluorobenzonitrile (1.08 g, 6.9 mmol) and potassium carbonate (1.9 g, 13.8 mmol) in acetonitrile (25 ml) was added 5,6,7,8-tetrahydro[1,2,4]triazolo[4,3-a]pyridin-3(2H)-one [CAS 118801-67-5] (1.05 g, 7.6 mmol), and the mixture was heated under reflux overnight. The mixture was then cooled to room temperature, poured into water (150 ml), and extracted with dichloromethane (3×300 ml). The organic phases were dried over sodium sulfate, and concentrated under reduced pressure, and the residue was purified by flash chromatography to yield the title compound as an off-white solid (1.06 g, 56%).

LC-MS (method A): $R_t$=0.91 min; MS (ESIpos): m/z=277 [M+H]$^+$ $^1$H-NMR (400 MHz, CHLOROFORM-d) δ [ppm]: 1.194 (16.00), 1.896 (1.10), 1.898 (1.22), 1.905 (1.49), 1.914 (3.31), 1.920 (3.80), 1.926 (4.48), 1.936 (4.46), 1.941 (5.07), 1.944 (3.41), 1.953 (2.17), 1.957 (2.32), 1.978 (2.44), 1.982 (2.02), 1.992 (4.35), 1.997 (4.41), 2.008 (4.81), 2.013 (3.80), 2.019 (2.76), 2.022 (3.01), 2.028 (1.50), 2.035 (1.36), 2.050 (0.42), 2.776 (7.63), 2.793 (13.88), 2.808 (8.54), 3.218 (5.28), 3.691 (9.78), 3.707 (15.57), 3.722 (6.87), 7.448 (5.53), 7.462 (5.56), 7.472 (5.65), 7.486 (5.47), 7.644 (5.43), 7.658 (5.52), 7.667 (5.42), 7.682 (5.28).

Intermediate 8

2,5-difluoro-4-(3-oxo-5,6,7,8-tetrahydro[1,2,4]triazolo[4,3-a]pyridin-2(3H)-yl)benzoic acid

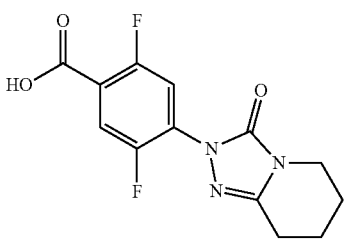 [SMILES: O=C(O)c1cc(F)c(-n2nc3n(c2=O)CCCC3)cc1F]

To a solution of 2,5-difluoro-4-(3-oxo-5,6,7,8-tetrahydro[1,2,4]triazolo[4,3-a]pyridin-2(3H)-yl)benzonitrile (intermediate 7) (4.3 g, 15.67 mmol) in ethanol (30 ml) was added aqueous sodium hydroxide (1 N, 300 ml) and the resulting suspension was heated to 85° C. for one hour. The resulting clear red solution was cooled to room temperature, adjusted to pH 1 with aqueous 1 N hydrochloric acid, and extracted with ethyl acetate. The organic phases were dried over sodium sulfate and concentrated under reduced pressure to yield a beige-brown solid (3.93 g, 85%), which was used for the next step.

LC-MS (method A): $R_t$=0.73 min; MS (ESIpos): m/z=296 [M+H]$^+$

Intermediate 9

5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzonitrile

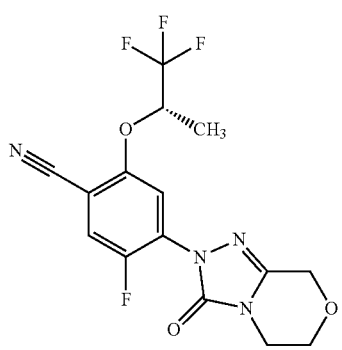

A mixture of 4-bromo-5-fluoro-2-{[(2S)-1,1,1-trifluoropropan-2-yl]oxy}benzonitrile (intermediate 5) (2.43 g, 7.79 mmol), 2,5,6,8-tetrahydro-3H-[1,2,4]triazolo[3,4-c][1,4]oxazin-3-one (1.0 g, 7.09 mmol), tris(dibenzylideneacetone)dipalladium(O) (195 mg, 0.21 mmol), 4,5-bis(diphenylphosphino)-9,9-dimethylxanthene (369 mg, 0.64 mmol) and cesium carbonate (3.46 g, 10.6 mmol) were placed under an argon atmosphere. To this mixture was then added argon sparged 1,4-dioxane (14.2 ml) after which the resulting mixture was heated at 105° C. for two days and then cooled to room temperature. The mixture was diluted with ethyl acetate, filtered through a Celite plug and concentrated under reduced pressure to give foamy dark orange solid (3.54 g). The residue was purified by flash column chromatography to give the title compound as a yellow solid (2.53 g, 98% purity, 94%).

LC-MS (method B): $R_t$=1.04 min; MS (ESIpos): m/z=373 [M+H]$^+$ $^1$H-NMR (400 MHz, CHLOROFORM-d) δ [ppm]: 1.526 (6.26), 1.542 (8.45), 1.544 (7.59), 3.713 (2.80), 3.726 (3.96), 3.729 (2.71), 3.740 (3.60), 3.999 (3.80), 4.009 (2.74), 4.012 (3.99), 4.025 (3.13), 4.607 (0.44), 4.623 (1.07), 4.638 (1.33), 4.653 (1.08), 4.673 (16.00), 7.338 (3.00), 7.353 (3.00), 7.381 (3.98), 7.405 (4.00).

Intermediate 10

5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzonitrile

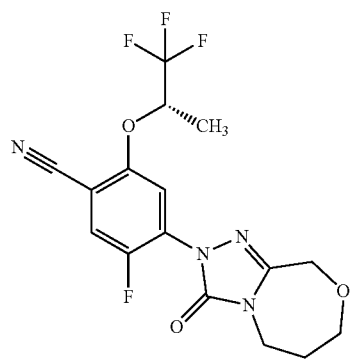 [SMILES: C[C@H](Oc1cc(-n2nc3n(c2=O)CCCOC3)c(F)cc1C#N)C(F)(F)F]

A mixture of 4-bromo-5-fluoro-2-{[(2S)-1,1,1-trifluoropropan-2-yl]oxy}benzonitrile (intermediate 5) (8.24 g, 26.4 mmol), 2,6,7,9-tetrahydro-3H,5H-[1,2,4]triazolo[3,4-c][1,4]oxazepin-3-one (intermediate 37) (3.72 g, 24.0 mmol), tris(dibenzylideneacetone)dipalladium(O) (659 mg, 720 μmol), 4,5-bis(diphenylphosphino)-9,9-dimethylxanthene (1.25 g, 2.16 mmol) and cesium carbonate (11.7 g, 36.0 mmol) were placed under an argon atmosphere. To this mixture was then added argon sparged 1,4-dioxane (48 ml) after which the resulting mixture was heated at 105° C. for two days and then cooled to room temperature. The mixture was diluted with ethyl acetate, filtered through a Celite plug and concentrated under reduced pressure to give a dark foam (3.54 g). The residue was purified by flash column chromatography to give the title compound as a off-white solid (8.56 g, 90%).

LC-MS (method A): $R_t$=1.07 min; MS (ESIpos): m/z=387.2 [M+H]$^+$ $^1$H-NMR (400 MHz, CHLOROFORM-d) δ [ppm]: 1.584 (3.78), 1.587 (1.48), 1.603 (6.18), 1.618 (6.41), 1.620 (6.42), 2.011 (0.70), 2.017 (0.65), 2.024 (1.24), 2.038 (1.84), 2.050 (1.28), 2.063 (0.74), 3.989 (2.42), 3.996 (1.08), 4.001 (1.79), 4.004 (1.76), 4.017 (2.33), 4.057 (2.76), 4.069 (2.30), 4.081 (2.72), 4.595 (16.00), 4.684 (0.45), 4.699 (1.08), 4.714 (1.33), 4.729 (1.04), 4.744 (0.41), 7.390 (3.04), 7.404 (3.01), 7.454 (4.08), 7.477 (4.04).

Intermediate 11

2-{[(2S)-1-(dimethylamino)propan-2-yl]oxy}-5-fluoro-4-(3-oxo-5,6,7,8-tetrahydro[1,2,4]triazolo-[4,3-a]pyridin-2(3H)-yl)benzonitrile

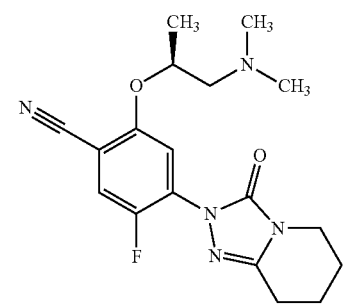 [SMILES: C[C@@H](CN(C)C)Oc1cc(-n2nc3n(c2=O)CCCC3)c(F)cc1C#N]

To a solution of (S)-(+)-1-dimethylamino-2-propanol (2.26 g, 25 mmol) in N,N-dimethylformamide (30 ml) was added sodium hydride (1.0 g, 60% purity, 25.1 mmol) and the suspension was stirred at room temperature for one hour. A solution of 2,5-difluoro-4-(3-oxo-5,6,7,8-tetrahydro[1,2,4]triazolo[4,3-a]pyridin-2(3H)-yl)benzonitrile (intermediate 7) (3.46 g, 12.5 mmol) in N,N-dimethylformamide (30 ml) was then added dropwise, and the reaction mixture was stirred for three hours, then poured into water, and extracted with ethyl acetate. The organic phases were washed with brine, dried over sodium sulfate and concentrated under reduced pressure. The residue was purified by flash chromatography to yield the title compound as a brown, foamy oil (2.1 g, 47%).

LC-MS (method A): $R_t$=0.52 min; MS (ESIpos): m/z=360.2 [M+H]$^+$

Intermediate 12

4-bromo-5-fluoro-2-{[(2S)-1,1,1-trifluoropropan-2-yl]oxy}benzoic Acid

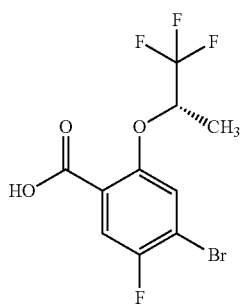 [SMILES: C[C@H](Oc1cc(Br)c(F)cc1C(=O)O)C(F)(F)F]

To a solution of 4-bromo-5-fluoro-2-{[(2S)-1,1,1-trifluoropropan-2-yl]oxy}benzonitrile (intermediate 5) (27.4 g, 87.9 mmol) in ethanol (90 ml) was added aqueous sodium hydroxide (2 N, 140 ml) and the resulting mixture was heated to 90° C. for 20 hours. The resulting solution was cooled to room temperature, diluted with water, and extracted with dichloromethane. The aqueous phase was acidified with 2 N aqueous hydrochloric acid (pH 2) upon which a white solid precipitated. The suspension was stirred for further 15 minutes, the solid was filtered off, washed with water and dried in vacuo. to yield an off-white solid (25.97 g, 89%), which was used for the next step without further purification.

LC-MS (method A): $R_t$=1.16 min; MS (ESIpos): m/z=331 [M+H]$^+$ $^1$H-NMR (400 MHz, DMSO-d6) δ[ppm]: 1.396 (15.96), 1.411 (16.00), 1.469 (0.69), 1.484 (0.45), 2.518 (3.48), 2.523 (2.36), 5.288 (1.19), 5.304 (2.89), 5.320 (3.73), 5.336 (2.70), 5.352 (1.05), 7.612 (11.35), 7.634 (11.12), 7.743 (7.88), 7.757 (7.91).

Intermediate 13

4-bromo-2-{[(2S)-1,1,1-trifluoropropan-2-yl]oxy}benzoic acid

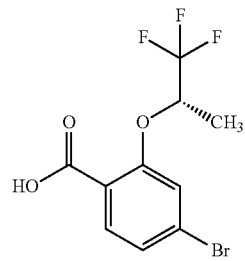 [SMILES: C[C@H](Oc1cc(Br)ccc1C(=O)O)C(F)(F)F]

To a solution of 4-bromo-2-{[(2S)-1,1,1-trifluoropropan-2-yl]oxy}benzonitrile (intermediate 6) (5.00 g, 17.0 mmol) in ethanol (18 ml) was added aqueous sodium hydroxide (2 N, 28 ml) and the resulting mixture was heated to 90° C. for 21 hours. The resulting solution was cooled to room temperature, diluted with water, and extracted with dichloromethane. The aqueous phase was acidified with 2 N aqueous hydrochloric acid (pH 2) upon which a white solid precipitated. The suspension was stirred for further 15 minutes, the solid was filtered off, washed with water and dried in vacuo. to yield white solid 4.76 g (89%), which was used for the next step without further purification.

LC-MS (method A): $R_t$=1.15 min; MS (ESIneg): m/z=311 [M−H]$^−$ $^1$H-NMR (400 MHz, DMSO-d6) δ[ppm]: 1.403 (15.87), 1.419 (16.00), 2.518 (2.74), 2.523 (1.80), 5.352 (1.13), 5.368 (2.86), 5.383 (3.71), 5.400 (2.72), 5.416 (1.03), 7.299 (6.49), 7.304 (6.51), 7.320 (6.97), 7.324 (7.05), 7.584 (13.85), 7.596 (8.97), 7.600 (8.84), 7.605 (12.52).

Intermediate 14

4-bromo-5-fluoro-2-{[(2S)-1,1,1-trifluoropropan-2-yl]oxy}benzoyl chloride

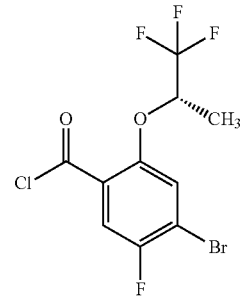 [SMILES: C[C@H](Oc1cc(Br)c(F)cc1C(=O)Cl)C(F)(F)F]

To a solution of 4-bromo-5-fluoro-2-{[(2S)-1,1,1-trifluoropropan-2-yl]oxy}benzoic acid (intermediate 12) (15.0 g, 45.3 mmol) in dichloromethane (230 ml) was added N,N-dimethylformamide (350 µl), followed by dropwise addition of ethanedioyl dichloride (4.7 ml, 54 mmol). The reaction mixture was stirred at room temperature for one hour, and concentrated under reduced pressure. The title compound was obtained as brown oil (15.84 g, quantitative), which was used for the next step without further purification. For analytic, a small amount of the product was treated with methanol, to yield the corresponding methyl ester, which was detected by LC-MS.

Intermediate 15

4-bromo-2-{[(2S)-1,1,1-trifluoropropan-2-yl]oxy}benzoyl chloride

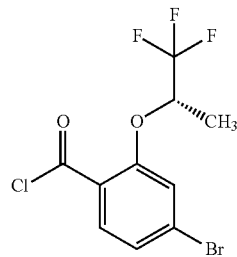 [SMILES: C[C@H](Oc1cc(Br)ccc1C(=O)Cl)C(F)(F)F]

To a solution of 4-bromo-2-{[(2S)-1,1,1-trifluoropropan-2-yl]oxy}benzoic acid (intermediate 13) (2.6 g, 8.3 mmol) in dichloromethane (42 ml) was added N,N-dimethylformamide (870 µl), followed by dropwise addition of ethanedioyl dichloride (870 µl, 10 mmol). The reaction mixture was stirred at room temperature for one hour, and concentrated under reduced pressure. The title compound was obtained as brown oil (15.84 g, quantitative), which was used for the next step without purification. For analytic, a small amount of the product was treated with methanol, to yield the corresponding methyl ester, which was detected by LC-MS.

LC-MS (method A) [methyl ester]: $R_t$=1.33 min; MS (ESIpos): m/z=327 [M+H]$^+$

Intermediate 16

5-fluoro-4-(3-oxo-5,6,7,8-tetrahydro[1,2,4]triazolo[4,3-a]pyridin-2(3H)-yl)-2-[(2S)-pentan-2-yloxy]benzoic Acid

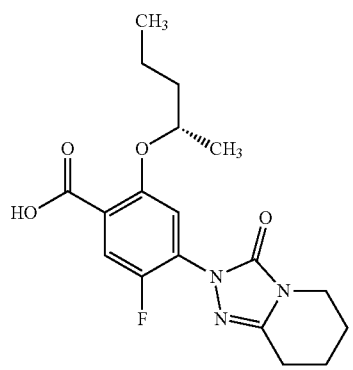 [SMILES: CCC[C@H](C)Oc1cc(-n2nc3n(c2=O)CCCC3)c(F)cc1C(=O)O]

To a −10° C. stirred solution of (S)-(+)-2-pentanol (1.16 g, 13.2 mmol) in anhydrous tetrahydrofuran (13.2 ml) was added a 1.0 M solution of potassium 1,1,1,3,3,3-hexamethyldisilazan-2-ide in tetrahydrofuran dropwise (7.20 ml, 7.20 mmol). The resulting mixture was then stirred at −10° C. for 1 hour, after which the resulting alkoxide solution was added dropwise to a stirred solution of tert-butyl 2,5-difluoro-4-(3-oxo-5,6,7,8-tetrahydro[1,2,4]triazolo[4,3-a]pyridin-2(3H)-yl)benzoate (intermediate 2) (2.11 g, 6.00 mmol) in anhydrous tetrahydrofuran (6.00 ml). The resulting orange solution was stirred at −10° C. for 2 hours and then concentrated under reduced pressure to give a orange solid. The residue was purified by flash column chromatography to give a mixture of esters as a colourless oil. The residue was suspended in a 4:1 ration of 1,4-dioxane/water (30.0 ml) after which lithium hydroxide (2.16 g, 90.0 mmol) was added in one portion. The resulting mixture was heated at 70° C. for 16 hours and cooled to room temperature. Water (20 ml) was added to the mixture followed by washing with diethyl ether (20 ml). The aqueous layer was acidified to pH 2.0 with concentrated hydrochloric acid and then extracted with diethyl ether (3×20 ml). The combined organic extracts were washed with brine (20 ml), dried over magnesium sulfate, filtered and concentrated under reduced pressure to give a cream solid. The residue was purified by flash column chromatography to give 5-fluoro-4-(3-oxo-5,6,7,8-tetrahydro[1,2,4]triazolo[4,3-a]pyridin-2(3H)-yl)-2-[(2S)-pentan-2-yloxy]benzoic acid as a cream solid (1.06 g, 48%).

LC-MS (method A): $R_t$=1.05 min; MS (ESIpos): m/z=364 [M+H]$^+$ $^1$H-NMR (400 MHz, CHLOROFORM-d) δ [ppm]: 0.958 (6.44), 0.976 (15.81), 0.983 (0.74), 0.995 (7.41), 1.002 (0.81), 1.400 (0.49), 1.418 (0.89), 1.426 (0.78), 1.435 (16.00), 1.444 (1.77), 1.450 (15.70), 1.459 (1.02), 1.462 (1.04), 1.471 (0.41), 1.478 (1.05), 1.484 (0.68), 1.490 (0.68), 1.497 (0.84), 1.504 (0.84), 1.509 (0.68), 1.516 (0.45), 1.523 (0.87), 1.542 (0.50), 1.675 (0.56), 1.689 (0.98), 1.700 (0.47), 1.704 (0.57), 1.710 (0.90), 1.714 (0.89), 1.724 (1.46), 1.728 (0.53), 1.734 (0.83), 1.739 (0.76), 1.749 (1.27), 1.763 (0.57), 1.811 (0.71), 1.825 (0.85), 1.827 (0.85), 1.837 (0.71), 1.841 (0.83), 1.846 (0.58), 1.851 (0.76), 1.853 (0.79), 1.860 (0.58), 1.862 (0.60), 1.867 (0.68), 1.872 (0.50), 1.876 (0.48), 1.888 (0.49), 1.902 (0.78), 1.910 (0.62), 1.919 (1.38), 1.926 (1.59), 1.931 (1.81), 1.942 (1.81), 1.946 (2.01), 1.959 (0.85), 1.962 (0.92), 1.984 (0.96), 1.990 (0.88), 1.999 (1.79), 2.003 (1.85), 2.014 (1.99), 2.019 (1.58), 2.028 (1.19), 2.042 (0.52), 2.793 (3.08), 2.808 (5.61), 2.825 (3.35), 3.701 (3.92), 3.712 (9.14), 3.717 (6.28), 3.732 (2.69), 4.674 (0.99), 4.689 (1.93), 4.704 (1.90), 4.720 (0.95), 5.308 (1.24), 7.464 (3.89), 7.478 (3.90), 8.012 (4.97), 8.040 (4.91), 11.113 (0.43).

Intermediate 17

5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid

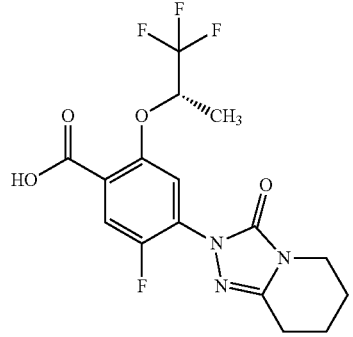 [SMILES: C[C@H](Oc1cc(-n2nc3n(c2=O)CCCC3)c(F)cc1C(=O)O)C(F)(F)F]

5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (S)-1,1,1-trifluoropropanol [CAS 3539-97-7]

(5.01 g, 44.0 mmol) and tert-butyl 2,5-difluoro-4-(3-oxo-5, 6,7,8-tetrahydro[1,2,4]triazolo[4,3-a]pyridin-2(3H)-yl)benzoate (intermediate 2) (7.03 g, 20.0 mmol) to yield the title compound, 7.15 g (98% purity, 90%).

LC-MS (method A): R$_t$=0.93 min; MS (ESIpos): m/z=390 [M+H]$^+$ $^1$H-NMR (400 MHz, CHLOROFORM-d) δ [ppm]: 1.578 (0.49), 1.607 (15.92), 1.623 (16.00), 1.908 (1.01), 1.923 (2.89), 1.935 (4.07), 1.950 (4.27), 1.966 (2.10), 1.988 (2.08), 2.007 (4.12), 2.018 (4.38), 2.032 (2.70), 2.046 (1.12), 2.054 (0.61), 2.798 (5.21), 2.814 (10.12), 2.830 (5.64), 3.709 (6.22), 3.725 (10.71), 3.739 (4.89), 4.821 (1.08), 4.836 (2.54), 4.851 (3.26), 4.866 (2.46), 4.882 (1.00), 7.504 (6.48), 7.519 (6.42), 7.954 (6.94), 7.981 (6.82).

Intermediate 18

5-fluoro-4-(3-oxo-5,6,7,8-tetrahydro[1,2,4]triazolo [4,3-a]pyridin-2(3H)-yl)-2-{[(2R)-1,1,1-trifluoropropan-2-yl]oxy}benzoic Acid

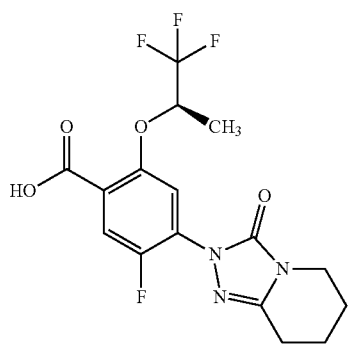 [SMILES: C[C@@H](Oc1cc(-n2nc3n(c2=O)CCCC3)c(F)cc1C(=O)O)C(F)(F)F]

5-fluoro-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzoic acid was prepared as described for 5-fluoro-4-(3-oxo-5,6,7,8-tetrahydro[1,2,4]triazolo[4,3-a]pyridin-2 (3H)-yl)-2-[(2S)-pentan-2-yloxy]benzoic acid (Intermediate 16), using (R)-1,1,1-trifluoropropanol [CAS 17628-73-8] (714 mg, 6.26 mmol) and tert-butyl 2,5-difluoro-4-(3-oxo-5,6,7,8-tetrahydro[1,2,4]triazolo[4,3-a]pyridin-2(3H)-yl) benzoate (intermediate 2) (1.0 g, 2.85 mmol) to yield the title compound, 800 mg (72%).

LC-MS (method A): R$_t$=0.92 min; MS (ESIpos): m/z=390 [M+H]$^+$ $^1$H-NMR (400 MHz, DMSO-d6) δ[ppm]: 1.400 (15.93), 1.416 (16.00), 1.512 (1.30), 1.769 (0.97), 1.784 (2.84), 1.796 (4.11), 1.810 (4.29), 1.823 (2.12), 1.864 (2.02), 1.878 (4.18), 1.889 (4.40), 1.903 (2.82), 1.917 (1.14), 2.083 (9.11), 2.326 (0.48), 2.683 (4.64), 2.699 (9.32), 2.715 (5.05), 3.549 (5.37), 3.564 (9.81), 3.579 (4.60), 5.184 (1.05), 5.200 (2.59), 5.216 (3.40), 5.232 (2.48), 5.248 (1.00), 7.481 (6.42), 7.497 (6.44), 7.645 (7.67), 7.671 (7.48), 13.231 (1.18).

Intermediate 19

2-[(1S)-1-cyclohexylethoxy]-5-fluoro-4-(3-oxo-5,6, 7,8-tetrahydro[1,2,4]triazolo[4,3-a]pyridin-2(3H)-yl) benzoic Acid

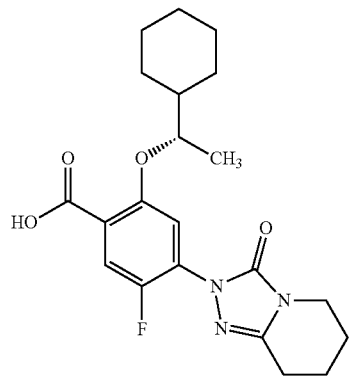 [SMILES: C[C@H](Oc1cc(-n2nc3n(c2=O)CCCC3)c(F)cc1C(=O)O)C1CCCCC1]

2-[(1S)-1-cyclohexylethoxy]-5-fluoro-4-(3-oxo-5,6,7,8-tetrahydro[1,2,4]triazolo[4,3-a]pyridin-2(3H)-yl)benzoic acid was prepared as described for 5-fluoro-4-(3-oxo-5,6,7, 8-tetrahydro[1,2,4]triazolo[4,3-a]pyridin-2(3H)-yl)-2-[(2S)-pentan-2-yloxy]benzoic acid (Intermediate 16), using (1S)-1-cyclohexylethanol (14.96 g, 116.7 mmol), tert-butyl 2,5-difluoro-4-(3-oxo-5,6,7,8-tetrahydro[1,2,4]triazolo[4,3-a] pyridin-2(3H)-yl)benzoate (intermediate 2) (20 g, 56.9 mmol) and to yield the title compound, and potassium 2-methylpropan-2-olate instead of potassium 1,1,1,3,3,3-hexamethyldisilazan-2-ide as base. The title compound was obtained as white solid, 13.03 g (57%).

LC-MS (method A): R$_t$=1.22 min; MS (ESIpos): m/z=404 [M+H]$^+$ $^1$H-NMR (400 MHz, DMSO-d6) δ[ppm]: −0.008 (0.83), 0.008 (0.90), 1.025 (0.44), 1.056 (1.55), 1.086 (2.87), 1.106 (2.47), 1.118 (3.29), 1.148 (3.68), 1.166 (15.87), 1.182 (16.00), 1.535 (1.26), 1.616 (1.40), 1.645 (1.48), 1.692 (4.71), 1.721 (4.07), 1.766 (0.90), 1.781 (2.33), 1.793 (3.31), 1.808 (3.63), 1.824 (2.93), 1.857 (2.93), 1.875 (3.52), 1.886 (3.49), 1.899 (2.18), 1.914 (0.86), 2.675 (3.71), 2.691 (7.09), 2.707 (3.89), 3.542 (4.20), 3.557 (7.48), 3.572 (3.50), 4.203 (0.54), 4.218 (1.95), 4.233 (2.74), 4.247 (1.91), 4.262 (0.51), 5.758 (0.53), 7.227 (4.58), 7.243 (4.56), 7.542 (5.25), 7.568 (5.18), 12.923 (4.84).

Intermediate 20

2-{[(2S)-1-(dimethylamino)propan-2-yl]oxy}-5-fluoro-4-(3-oxo-5,6,7,8-tetrahydro[1,2,4]triazolo[4, 3-a]pyridin-2(3H)-yl)benzoic Acid

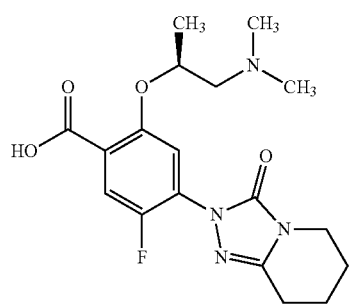 [SMILES: C[C@@H](CN(C)C)Oc1cc(-n2nc3n(c2=O)CCCC3)c(F)cc1C(=O)O]

To a solution of 2-{[(2S)-1-(dimethylamino)propan-2-yl]oxy}-5-fluoro-4-(3-oxo-5,6,7,8-tetrahydro[1,2,4]triazolo[4,3-a]pyridin-2(3H)-yl)benzonitrile (intermediate 11) (2.1 g, 5.84 mmol) in ethanol (12 ml) was added aqueous sodium hydroxide solution (120 ml, 1.0 M, 120 mmol), and the mixture was heated to 85° C. for seven hours. The mixture was then cooled to room temperature and extracted with ethyl acetate. The aqueous solution was then adjusted to pH 5 with 1 M aqueous hydrochloric acid and concentrated under reduced pressure. The residue was purified by reversed phase column chromatography (Biotage® SNAP ULTRA C18, water, acetonitrile 0-40%) to yield the product as a beige solid (1.9 g, 86%).

LC-MS (method B): $R_t$=0.51 min; MS (ESIneg): m/z=377 [M−H]⁻

¹H-NMR (400 MHz, CHLOROFORM-d) δ [ppm]: 1.497 (4.39), 1.513 (4.38), 1.909 (0.76), 1.921 (1.07), 1.936 (1.12), 1.993 (1.11), 2.003 (1.14), 2.595 (16.00), 2.766 (0.86), 2.772 (0.98), 2.781 (1.40), 2.797 (3.05), 2.812 (1.46), 3.115 (0.65), 3.143 (0.81), 3.174 (0.57), 3.689 (1.55), 3.704 (2.60), 3.718 (1.30), 4.599 (0.48), 7.289 (1.65), 7.304 (1.61), 7.724 (1.76), 7.751 (1.72).

Intermediate 21

5-fluoro-4-(3-oxo-5,6-dihydro-3H-[1,2,4]triazolo[3,4-c][1,4]oxazin-2(8H)-yl)-2-[(2S)-pentan-2-yloxy]benzoic Acid

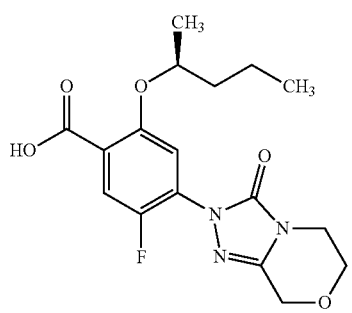 [SMILES: CCC[C@H](C)Oc1cc(-n2nc3n(c2=O)CCOC3)c(F)cc1C(=O)O]

5-fluoro-4-(3-oxo-5,6-dihydro-3H-[1,2,4]triazolo[3,4-c][1,4]oxazin-2(8H)-yl)-2-[(2S)-pentan-2-yloxy]benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (S)-pentan-2-ol (440 µl, 4.0 mmol) and tert-butyl 2,5-difluoro-4-(3-oxo-5,6-dihydro-3H-[1,2,4]triazolo[3,4-c][1,4]oxazin-2(8H)-yl)benzoate (intermediate 3) (650 mg, 1.84 mmol) to yield the title compound, 200 mg (30%).

LC-MS (method A): $R_t$=0.97 min; MS (ESIpos): m/z=366.2 [M+H]⁺

Intermediate 22 rac-2-{[(2S)-4-(dimethylamino)butan-2-yl]oxy}-5-fluoro-4-(3-oxo-5,6-dihydro-3H-[1,2,4]triazolo[3,4-c][1,4]oxazin-2(8H)-yl)benzoic Acid

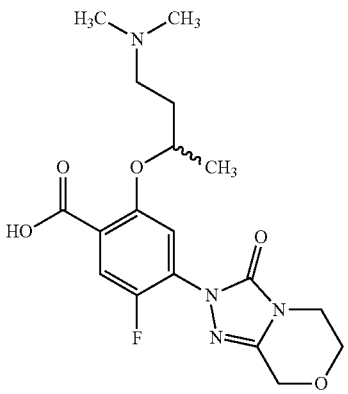 [SMILES: CC(CCN(C)C)Oc1cc(-n2nc3n(c2=O)CCOC3)c(F)cc1C(=O)O]

Rac-2-{[(2S)-4-(dimethylamino)butan-2-yl]oxy}-5-fluoro-4-(3-oxo-5,6-dihydro-3H-[1,2,4]triazolo[3,4-c][1,4]oxazin-2(8H)-yl)benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using rac-4-(dimethylamino)butan-2-ol (136 mg, 1.16 mmol) and tert-butyl 2,5-difluoro-4-(3-oxo-5,6-dihydro-3H-[1,2,4]triazolo[3,4-c][1,4]oxazin-2(8H)-yl)benzoate (intermediate 3) (200 mg, 0.566 mmol) to yield the title compound, 64 mg (52%).

LC-MS (method B): $R_t$=0.49 min; MS (ESIpos): m/z=395 [M+H]⁺

Intermediate 23 rac-5-fluoro-4-(3-oxo-5,6-dihydro-3H-[1,2,4]triazolo[3,4-c][1,4]oxazin-2(8H)-yl)-2-{[1-(pyrrolidin-1-yl)propan-2-yl]oxy}benzoic Acid

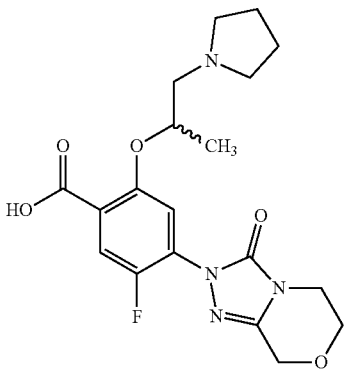 [SMILES: CC(CN1CCCC1)Oc1cc(-n2nc3n(c2=O)CCOC3)c(F)cc1C(=O)O]

5-fluoro-4-(3-oxo-5,6-dihydro-3H-[1,2,4]triazolo[3,4-c][1,4]oxazin-2(8H)-yl)-2-{[1-(pyrrolidin-1-yl)propan-2-yl]oxy}benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using rac-1-(pyrrolidin-1-yl)propan-2-ol (187 mg, 1.45 mmol) and tert-butyl 2,5-difluoro-4-(3-oxo-5,6-dihydro-3H-[1,2,4]triazolo[3,4-c][1,4]oxazin-2(8H)-yl)benzoate (intermediate 3) (250 mg, 0.707 mmol) to yield the title compound, 117 mg (41%).

LC-MS (method B): $R_t$=0.52 min; MS (ESIpos): m/z=407 [M+H]$^+$

Intermediate 24

5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzoic Acid

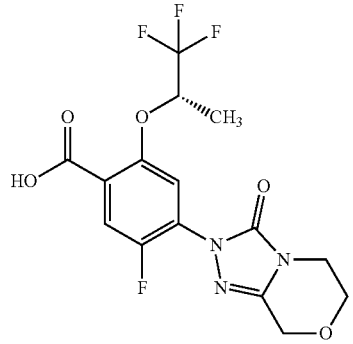 [SMILES: C[C@H](Oc1cc(-n2nc3n(c2=O)CCOC3)c(F)cc1C(=O)O)C(F)(F)F]

Method 1:

5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (S)-1,1,1-trifluoropropanol [CAS 3539-97-7] (461 mg, 4.0 mmol) and tert-butyl 2,5-difluoro-4-(3-oxo-5,6-dihydro-3H-[1,2,4]triazolo[3,4-c][1,4]oxazin-2(8H)-yl)benzoate (intermediate 3) (650 mg, 1.8 mmol) to yield the title compound, 356 mg (49%).

Method 2:

To a stirred suspension of 5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzonitrile (intermediate 9) (1.12 g, 3.0 mmol) in water (3.00 ml) was added concentrated sulfuric acid (8.40 ml, 158 mmol) and acetic acid (8.40 ml, 147 mmol). The resulting mixture was heated at 120° C. for 2 days and then cooled to room temperature. The mixture was poured onto ice water and extracted with diethyl ether (3×50 ml), after which the combined organic extracts were washed with 2.0 M aqueous sodium hydroxide (4×25 ml). The resulting aq. layer was acidified to pH 2.5 with concentrated aqueous hydrochloric acid and extracted with diethyl ether (3×50 ml). The combined organic extracts were dried over sodium sulfate, filtered and concentrated under reduced pressure to give the acid as an off white solid (1.07 g, 98% purity, 89%).

LC-MS (method A): $R_t$=0.84 min; MS (ESIpos): m/z=392 [M+H]$^+$ $^1$H-NMR (400 MHz, DMSO-d6) δ[ppm]: 1.400 (8.86), 1.416 (8.88), 1.513 (1.37), 2.083 (3.03), 2.326 (0.67), 2.331 (0.48), 2.518 (3.05), 2.522 (2.02), 2.668 (0.70), 2.673 (0.49), 3.653 (3.00), 3.666 (4.91), 3.680 (3.47), 4.016 (3.69), 4.030 (5.03), 4.043 (3.10), 4.736 (16.00), 5.177 (0.60), 5.193 (1.49), 5.209 (1.93), 5.225 (1.38), 5.241 (0.55), 7.484 (2.92), 7.499 (2.85), 7.640 (3.36), 7.666 (3.30).

Intermediate 25

5-fluoro-4-(3-oxo[1,2,4]triazolo[4,3-a]pyridin-2(3H)-yl)-2-{[(2S)-1,1,1-trifluoropropan-2-yl]oxy}benzoic Acid

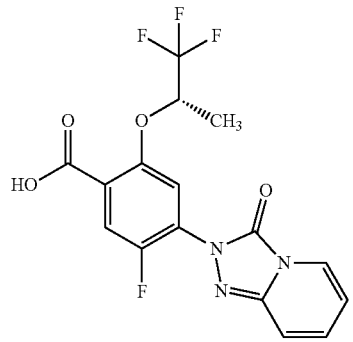 [SMILES: C[C@H](Oc1cc(-n2nc3ccccn3c2=O)c(F)cc1C(=O)O)C(F)(F)F]

5-fluoro-4-(3-oxo[1,2,4]triazolo[4,3-a]pyridin-2(3H)-yl)-2-{[(2S)-1,1,1-trifluoropropan-2-yl]oxy}benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (S)-1,1,1-trifluoropropanol [CAS 3539-97-7] and tert-butyl 2,5-difluoro-4-(3-oxo[1,2,4]triazolo[4,3-a]pyridin-2(3H)-yl)benzoate (intermediate 4).

Intermediate 26

5-fluoro-4-(3-oxo[1,2,4]triazolo[4,3-a]pyridin-2(3H)-yl)-2-[(2S)-pentan-2-yloxy]benzoic Acid

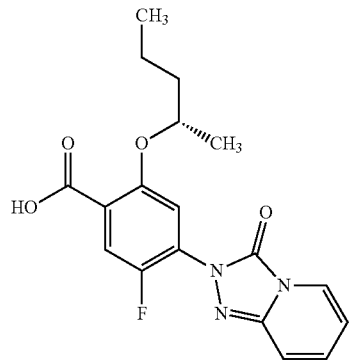 [SMILES: CCC[C@H](C)Oc1cc(-n2nc3ccccn3c2=O)c(F)cc1C(=O)O]

5-fluoro-4-(3-oxo[1,2,4]triazolo[4,3-a]pyridin-2(3H)-yl)-2-[(2S)-pentan-2-yloxy]benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (S)-pentan-2-ol and tert-butyl 2,5-difluoro-4-(3-oxo[1,2,4]triazolo[4,3-a]pyridin-2(3H)-yl)benzoate (intermediate 4).

MS (ESIneg): m/z=358 [M−H]$^-$ $^1$H NMR (400 MHz, CDCl$_3$) δ [ppm] 0.98 (t, 3H), 1.39-1.57 (m, 2H), 1.46 (d, 3H), 1.68-1.79 (m, 1H), 1.82-1.92 (m, 1H), 4.67-4.76 (m, 1H), 6.57 (ddd, 1H), 7.15-7.23 (m, 2H), 7.48 (d, 1H), 7.82 (td, 1H), 8.09 (d, 1H), 11.04 (br, 1H).

Intermediate 27

5-fluoro-4-(3-oxo[1,2,4]triazolo[4,3-a]pyridin-2(3H)-yl)-2-[(1S)-1-phenylethoxy]benzoic Acid

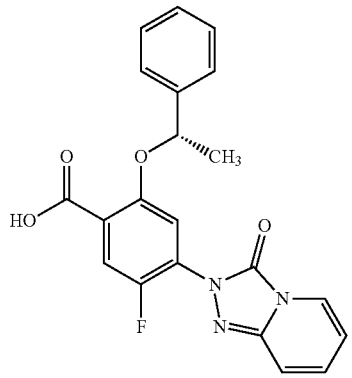 [SMILES: C[C@H](Oc1cc(-n2nc3ccccn3c2=O)c(F)cc1C(=O)O)c1ccccc1]

5-fluoro-4-(3-oxo[1,2,4]triazolo[4,3-a]pyridin-2(3H)-yl)-2-[(1S)-1-phenylethoxy]benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (1S)-1-phenylethanol and tert-butyl 2,5-difluoro-4-(3-oxo[1,2,4]triazolo[4,3-a]pyridin-2(3H)-yl)benzoate (intermediate 4).

MS (ESIneg): m/z=392 [M−H]⁻

¹H NMR (400 MHz, CDCl₃) δ [ppm] 1.83 (d, 3H), 5.63 (q, 1H), 6.55 (ddd, 1H), 7.11-7.22 (m, 2H), 7.29-7.41 (m, 5H), 7.44 (d, 1H), 7.79 (td, 1H), 8.05 (d, 1H), 11.04 (br, 1H).

Intermediate 28

5-fluoro-4-(3-oxo-5,6,7,8-tetrahydro[1,2,4]triazolo[4,3-a]pyridin-2(3H)-yl)-2-[(1S)-1-phenylethoxy]benzoic Acid

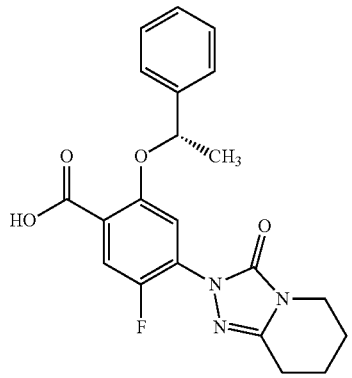 [SMILES: C[C@H](Oc1cc(-n2nc3n(c2=O)CCCC3)c(F)cc1C(=O)O)c1ccccc1]

5-fluoro-4-(3-oxo-5,6,7,8-tetrahydro[1,2,4]triazolo[4,3-a]pyridin-2(3H)-yl)-2-[(1S)-1-phenylethoxy]benzoic acid was prepared as described for 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (Intermediate 16), using (1S)-1-phenylethanol and tert-butyl 2,5-difluoro-4-(3-oxo-5,6,7,8-tetrahydro[1,2,4]triazolo[4,3-a]pyridin-2(3H)-yl)benzoate (intermediate 2).

MS (ESIpos): m/z=398 [M+H]⁺

¹H NMR (400 MHz, CDCl₃) δ [ppm] 1.80 (d, 3H), 1.86-1.94 (m, 2H), 1.94-2.02 (m, 2H), 2.76 (t, 2H), 3.65-3.71 (m, 2H), 5.61 (q, 1H), 7.30-7.40 (m, 5H), 7.45 (d, 1H), 7.98 (d, 1H).

Intermediate 29

5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzoic Acid

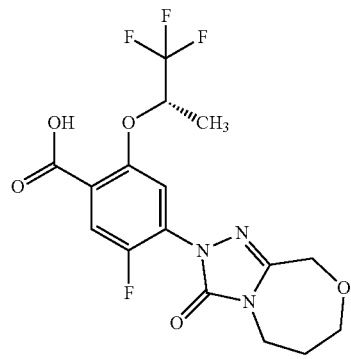 [SMILES: C[C@H](Oc1cc(-n2nc3n(c2=O)CCCOC3)c(F)cc1C(=O)O)C(F)(F)F]

To a stirred suspension of 5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzonitrile (intermediate 10) (2.61 g, 6.76 mmol) in water (6.76 ml) was added concentrated. sulfuric acid (18.9 ml) and acetic acid (18.9 ml). The resulting mixture was heated at 120° C. for two days and then cooled to room temperature. The mixture was poured onto ice water and extracted with diethyl ether (3×100 ml), after which the combined organic extracts were washed with 2.0 M aqueous sodium hydroxide (4×50 ml). The resulting aqueous layer was acidified to pH 2.5 with concentrated hydrochloric acid and extracted with diethyl ether (3×100 ml). The combined organic extracts were dried over sodium sulfate, filtered and concentrated under reduced pressure to give the acid as a beige solid (2.1 g, 85% purity, 65%). The material was used in the next step without further purification.

LC-MS (method A): R$_t$=0.89 min; MS (ESIpos): m/z=406 [M+H]⁺

¹H-NMR (400 MHz, CHLOROFORM-d) δ [ppm]: 0.817 (0.46), 0.837 (0.88), 0.842 (0.90), 0.849 (0.81), 0.858 (0.73), 0.887 (0.43), 1.262 (1.08), 1.293 (0.99), 1.379 (0.51), 1.624 (9.21), 1.640 (9.17), 2.019 (3.78), 2.032 (1.73), 2.045 (2.48), 2.057 (1.91), 2.065 (1.03), 2.070 (1.21), 3.709 (0.48), 3.723 (0.65), 3.737 (0.45), 4.001 (2.93), 4.016 (2.36), 4.028 (3.00), 4.041 (0.80), 4.062 (3.28), 4.075 (3.04), 4.087 (3.03), 4.609 (16.00), 4.694 (2.34), 4.821 (0.61), 4.837 (1.44), 4.852 (1.82), 4.868 (1.38), 4.883 (0.56), 7.445 (3.54), 7.459 (3.54), 7.473 (0.55), 7.488 (0.51), 7.971 (0.86), 7.977 (4.10), 7.998 (0.88), 8.003 (4.03).

Intermediate 30

4-bromo-N-(2,6-difluorophenyl)-5-fluoro-2-{[(2S)-1,1,1-trifluoropropan-2-yl]oxy}benzamide

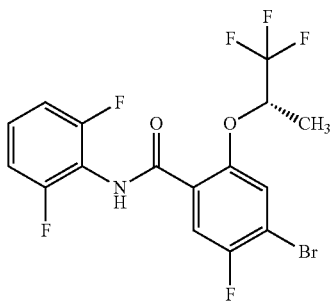 [SMILES: C[C@H](Oc1cc(Br)c(F)cc1C(=O)Nc1c(F)cccc1F)C(F)(F)F]

Under argon, a solution of 4-bromo-5-fluoro-2-{[(2S)-1,1,1-trifluoropropan-2-yl]oxy}benzoyl chloride (intermediate 14) (17.0 g, 48.6 mmol) in dichloromethane (200 ml) were added at room temperature to a solution of 2,6-difluoroaniline (5.8 ml, 54 mmol) and triethylamine (7.5 ml, 54 mmol) in dichloromethane (350 ml), and the mixture was stirred at room temperature for one hour. The reaction mixture was then concentrated under reduced pressure. The residue was dissolved in 150 ml of methanol and triturated with water (300 ml). The resulting solid was filtered, washed with water, and dried in vacuo to yield the title compound (20.6 g, 96%) as off-white solid.

LC-MS (method A): $R_t$=1.40 min; MS (ESIneg): m/z=440 [M–H]⁻

¹H-NMR (400 MHz, DMSO-d6) δ[ppm]: 1.147 (1.01), 1.165 (1.91), 1.184 (1.01), 1.339 (0.56), 1.356 (0.62), 1.394 (0.97), 1.411 (1.35), 1.430 (16.00), 1.446 (15.69), 1.486 (0.42), 2.331 (0.97), 2.518 (4.44), 2.522 (3.02), 2.673 (0.97), 5.366 (1.11), 5.383 (2.64), 5.399 (3.30), 5.415 (2.46), 5.430 (1.04), 7.183 (4.93), 7.203 (10.41), 7.224 (6.52), 7.367 (1.18), 7.382 (2.50), 7.403 (3.68), 7.419 (1.98), 7.424 (1.91), 7.440 (0.83), 7.555 (7.05), 7.576 (6.98), 7.808 (6.25), 7.822 (6.18), 9.886 (0.42), 9.918 (10.17).

Intermediate 31

4-bromo-N-(2-chloro-6-fluorophenyl)-5-fluoro-2-{[(2S)-1,1,1-trifluoropropan-2-yl]oxy}benzamide

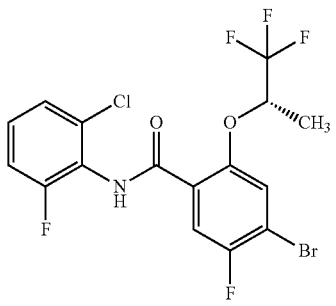

4-bromo-N-(2-chloro-6-fluorophenyl)-5-fluoro-2-{[(2S)-1,1,1-trifluoropropan-2-yl]oxy}benzamide was prepared as described for 4-bromo-N-(2,6-difluorophenyl)-5-fluoro-2-{[(2S)-1,1,1-trifluoropropan-2-yl]oxy}benzamide (Intermediate 30), using 4-bromo-5-fluoro-2-{[(2S)-1,1,1-trifluoropropan-2-yl]oxy}benzoyl chloride (intermediate 14) (10.6 g, 30.3 mmol) and 2-chloro-6-fluoroaniline (4.86 g, 33.4 mmol) to yield the title compound, 12.5 g (90%).

LC-MS (method A): $R_t$=1.44 min; MS (ESIpos): m/z=458 [M+H]⁺

¹H-NMR (400 MHz, DMSO-d6) δ[ppm]: 1.343 (1.25), 1.356 (1.38), 1.387 (1.01), 1.404 (1.10), 1.437 (16.00), 1.453 (15.85), 2.327 (0.96), 2.669 (0.99), 5.401 (1.31), 5.417 (2.76), 5.432 (3.40), 5.449 (2.53), 5.465 (1.17), 7.328 (1.83), 7.347 (4.04), 7.363 (2.55), 7.371 (2.93), 7.383 (2.30), 7.403 (4.05), 7.416 (5.56), 7.425 (9.27), 7.431 (9.39), 7.445 (2.51), 7.482 (0.62), 7.528 (5.87), 7.549 (5.79), 7.679 (0.57), 7.820 (5.53), 7.834 (5.48), 9.977 (10.39).

Intermediate 32

4-bromo-N-(2,6-difluorophenyl)-2-{[(2S)-1,1,1-trifluoropropan-2-yl]oxy}benzamide

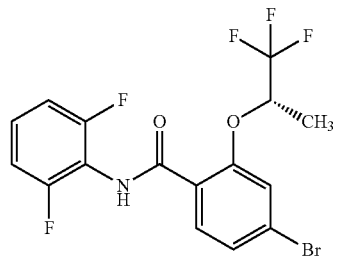 [SMILES: C[C@H](Oc1cc(Br)ccc1C(=O)Nc1c(F)cccc1F)C(F)(F)F]

4-bromo-N-(2,6-difluorophenyl)-2-{[(2S)-1,1,1-trifluoropropan-2-yl]oxy}benzamide was prepared as described for 4-bromo-N-(2,6-difluorophenyl)-5-fluoro-2-{[(2S)-1,1,1-trifluoropropan-2-yl]oxy}benzamide (Intermediate 30), using 4-bromo-2-{[(2S)-1,1,1-trifluoropropan-2-yl]oxy}benzoyl chloride (intermediate 15) (2.65 g, 7.99 mmol) and 2,6-difluoroaniline (950 μl, 8.8 mmol) to yield the title compound, 3.11 g (92%).

LC-MS (method A): $R_t$=1.36 min; MS (ESIpos): m/z=424 [M+H]⁺

¹H-NMR (400 MHz, DMSO-d6) δ[ppm]: 1.054 (0.42), 1.350 (0.40), 1.365 (0.42), 1.445 (16.00), 1.461 (15.92), 2.518 (4.30), 2.523 (2.73), 5.433 (1.17), 5.449 (2.71), 5.465 (3.50), 5.481 (2.57), 5.497 (1.09), 7.176 (4.91), 7.197 (10.19), 7.217 (6.29), 7.362 (4.96), 7.365 (4.80), 7.382 (7.32), 7.385 (6.93), 7.395 (4.03), 7.411 (2.04), 7.433 (0.82), 7.493 (7.91), 7.514 (5.84), 7.667 (8.70), 9.794 (12.87).

Intermediate 33

2,5-difluoro-N-(2-fluorophenyl)-4-(3-oxo-5,6,7,8-tetrahydro[1,2,4]triazolo[4,3-a]pyridin-2(3H)-yl)benzamide

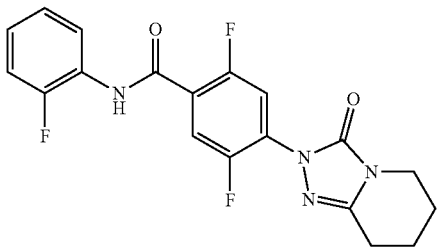 [SMILES: O=C(Nc1ccccc1F)c1cc(F)c(-n2nc3n(c2=O)CCCC3)cc1F]

To a solution of 2,5-difluoro-4-(3-oxo-5,6,7,8-tetrahydro[1,2,4]triazolo[4,3-a]pyridin-2(3H)-yl)benzoic acid (intermediate 8) (195 mg, 660 μmol) in N,N-dimethylformamide (5 ml) was added 1-[bis(dimethylamino)methylene]-1H-[1,2,3]triazolo[4,5-b]pyridin-1-ium 3-oxide hexafluorophosphate (HATU) (502 mg, 1.32 mmol), and the mixture was stirred at room temperature for 15 minutes. Then, 2-fluoroaniline (80.7 mg, 727 μmol) and N-ethyl-N-isopropylpropan-2-amine (350 μl, 2.0 mmol) were added subsequently, and the reaction mixture was stirred at room temperature for four hours. The reaction solution was directly subjected to reversed phase column chromatography (Biotage® SNAP ULTRA C18, water, acetonitrile 10-90%) to yield the product as a beige solid (110 mg, 43%).

LC-MS (method A): $R_t$=1.08 min; MS (ESIpos): m/z=389.8 [M+H]$^+$ $^1$H-NMR (400 MHz, DMSO-d6) δ[ppm]: 0.844 (0.47), 1.108 (8.91), 1.145 (0.50), 1.198 (0.42), 1.232 (0.92), 1.775 (1.68), 1.790 (4.64), 1.802 (6.53), 1.817 (6.65), 1.829 (3.29), 1.870 (3.21), 1.884 (6.59), 1.895 (7.01), 1.909 (4.27), 1.923 (1.68), 2.074 (7.34), 2.323 (1.28), 2.327 (1.68), 2.331 (1.23), 2.523 (4.80), 2.669 (1.90), 2.674 (1.59), 2.689 (7.65), 2.705 (15.02), 2.721 (8.15), 3.559 (9.08), 3.575 (16.00), 3.589 (7.23), 4.190 (0.84), 7.216 (1.90), 7.229 (5.00), 7.234 (5.72), 7.247 (6.51), 7.253 (7.20), 7.263 (4.94), 7.270 (4.22), 7.275 (5.36), 7.281 (2.23), 7.291 (5.31), 7.310 (2.29), 7.317 (4.75), 7.338 (2.32), 7.342 (1.95), 7.600 (3.24), 7.614 (3.60), 7.626 (3.55), 7.640 (3.24), 7.742 (3.55), 7.757 (3.80), 7.768 (3.80), 7.783 (3.49), 7.823 (2.18), 7.840 (3.85), 7.856 (2.12), 10.315 (8.04).

Intermediate 34

N-(2,6-difluorophenyl)-2,5-difluoro-4-(3-oxo-5,6,7,8-tetrahydro[1,2,4]triazolo[4,3-a]pyridin-2(3H)-yl)benzamide

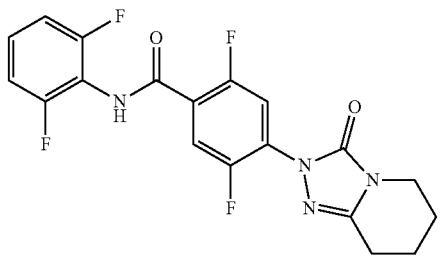 [SMILES: O=C(Nc1c(F)cccc1F)c1cc(F)c(-n2nc3n(c2=O)CCCC3)cc1F]

To a solution of 2,5-difluoro-4-(3-oxo-5,6,7,8-tetrahydro[1,2,4]triazolo[4,3-a]pyridin-2(3H)-yl)benzoic acid (intermediate 8) (195 mg, 660 μmol) in N,N-dimethylformamide (5 ml) was added 1-[bis(dimethylamino)methylene]-1H-[1,2,3]triazolo[4,5-b]pyridin-1-ium 3-oxide hexafluorophosphate (HATU) (502 mg, 1.32 mmol), and the mixture was stirred at room temperature for 15 minutes. Then, 2,6-difluoroaniline (93.8 mg, 727 μmol) and N-ethyl-N-isopropylpropan-2-amine (350 μl, 2.0 mmol) were added subsequently, and the reaction mixture was stirred at room temperature for four hours. The reaction solution was directly subjected to reversed phase column chromatography (Biotage® SNAP ULTRA C18, water, acetonitrile 10-90%) to yield the product as a beige solid (292 mg, 40% purity, 44% yield).

LC-MS (method A): $R_t$=0.99 min; MS (ESIpos): m/z=407.8 [M+H]$^+$

Intermediate 35

2,5-difluoro-N-(2-fluoro-6-methylphenyl)-4-(3-oxo-5,6,7,8-tetrahydro[1,2,4]triazolo[4,3-a]pyridin-2(3H)-yl)benzamide

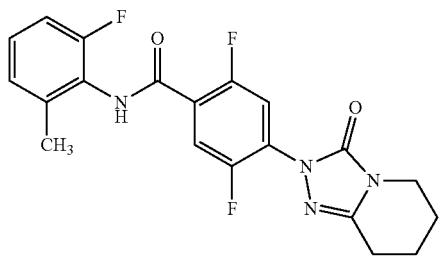 [SMILES: Cc1cccc(F)c1NC(=O)c1cc(F)c(-n2nc3n(c2=O)CCCC3)cc1F]

To a solution of 2,5-difluoro-4-(3-oxo-5,6,7,8-tetrahydro[1,2,4]triazolo[4,3-a]pyridin-2(3H)-yl)benzoic acid (intermediate 8) (1.4 g, 4.74 mmol) in N,N-dimethylformamide (110 ml) was added 1-[bis(dimethylamino)methylene]-1H-[1,2,3]triazolo[4,5-b]pyridin-1-ium 3-oxide hexafluorophosphate (HATU) (10.1 g, 26.6 mmol), and the mixture was stirred at room temperature for 15 minutes. Then, 2-fluoro-6-methylaniline (1.83 g, 14.6 mmol) and N-ethyl-N-isopropylpropan-2-amine (7.0 ml, 40 mmol) were added subsequently, and the reaction mixture was stirred at room temperature for four hours. The reaction solution was directly subjected to reversed phase column chromatography (Biotage® SNAP ULTRA C18, 0.1% aqueous ammonia, acetonitrile 1-100%) to yield the product as a beige solid (1.1 g, 57%).

LC-MS (method A): $R_t$=1.03 min; MS (ESIneg): m/z=403.3 [M–H]$^-$ $^1$H-NMR (400 MHz, CHLOROFORM-d) δ [ppm]: 1.273 (0.85), 1.290 (0.98), 1.316 (0.46), 1.579 (0.83), 1.907 (0.43), 1.914 (0.55), 1.923 (1.11), 1.930 (1.33), 1.934 (1.51), 1.946 (1.48), 1.950 (1.61), 1.962 (0.70), 1.966 (0.76), 1.986 (0.85), 1.990 (0.77), 2.000 (1.48), 2.005 (1.53), 2.016 (1.58), 2.021 (1.29), 2.030 (0.97), 2.044 (0.43), 2.203 (2.58), 2.336 (16.00), 2.796 (2.27), 2.813 (4.24), 2.829 (2.49), 3.710 (3.20), 3.725 (4.84), 3.740 (2.05), 7.001 (0.69), 7.023 (1.39), 7.046 (0.86), 7.072 (1.29), 7.091 (1.72), 7.190 (0.87), 7.204 (0.96), 7.210 (1.30), 7.224 (1.29), 7.230 (0.65), 7.243 (0.59), 7.625 (1.26), 7.639 (1.27), 7.655 (1.27), 7.670 (1.24), 7.974 (0.80), 8.012 (0.86), 8.020 (1.51), 8.036 (1.31), 8.047 (1.29), 8.064 (1.25).

Intermediate 36 tert-butyl 2-(4-[(2,6-difluorophenyl)carbamoyl]-2-fluoro-5-{[(2S)-1,1,1-trifluoropropan-2-yl]oxy}-phenyl)-3-oxo-2,3,5,6,8,9-hexahydro-7H-[1,2,4]triazolo[4,3-d][1,4]diazepine-7-carboxylate

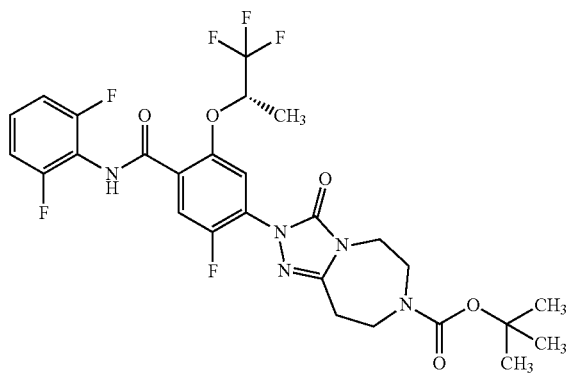 [SMILES: C[C@H](Oc1cc(-n2nc3n(c2=O)CCN(C(=O)OC(C)(C)C)CC3)c(F)cc1C(=O)Nc1c(F)cccc1F)C(F)(F)F]

4-bromo-N-(2,6-difluorophenyl)-5-fluoro-2-{[(2S)-1,1,1-trifluoropropan-2-yl]oxy}benzamide (intermediate 30) (100 mg, 226 µmol), tert-butyl 3-oxo-2,3,5,6,8,9-hexahydro-7H-[1,2,4]triazolo[4,3-d][1,4]diazepine-7-carboxylate [CAS 1424939-96-7] (86.3 mg, 339 µmol), tris(dibenzylideneacetone)dipalladium(O) (20.7 mg, 22.6 µmol), 4,5-bis(diphenylphosphino)-9,9-dimethylxanthene (39.3 mg, 67.8 µmol), and cesium carbonate (147 mg, 452 µmol) were placed in a microwave vial under argon. Degassed dioxane (2.0 ml) was added, the vial was capped and the mixture was heated to 110° C. for 40 hours. The resulting suspension was filtered over celite, the filter cake was washed with ethyl acetate, and the filtrate was reduced under reduced pressure. The residue was purified by preparative HPLC to yield the title compound as beige crystalline solid (67.2 mg, 90% purity, 43%).

LC-MS (method A): $R_t$=1.32 min; MS (ESIpos): m/z=616.2 [M+H]$^+$ $^1$H-NMR (400 MHz, DMSO-d6) δ[ppm]: 1.430 (1.97), 1.449 (16.00), 2.518 (1.77), 2.522 (1.16), 2.907 (0.55), 3.634 (0.66), 3.833 (0.70), 7.190 (0.52), 7.204 (0.70), 7.211 (1.04), 7.231 (0.64), 7.386 (0.40), 7.408 (0.40), 7.554 (0.62), 7.570 (1.11), 7.596 (0.67), 9.996 (1.53).

Intermediates 37-41 were prepared by methods described in the literature (the syntheses of similar triazolone derivatives are for example described in Chemische Berichte (1957), 90, 909-21; Journal of Medicinal Chemistry (1992), 35(1), 189-94; DE 19901846 A1).

Intermediate 37

2,6,7,9-tetrahydro-3H,5H-[1,2,4]triazolo[3,4-c][1,4]oxazepin-3-one

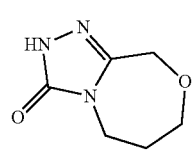 [SMILES: O=c1[nH]nc2n1CCCOC2]

Intermediate 38

5,6-dihydro[1,3]thiazolo[2,3-c][1,2,4]triazol-3(2H)-one

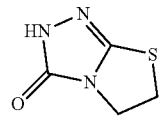

Intermediate 39

6,7-dihydro-5H-[1,2,4]triazolo[3,4-b][1,3]thiazin-3(2H)-one

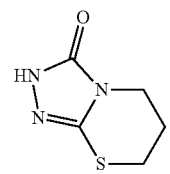

Intermediate 40

6,6-dimethyl-6,7-dihydro-5H-[1,2,4]triazolo[3,4-b][1,3]oxazin-3(2H)-one

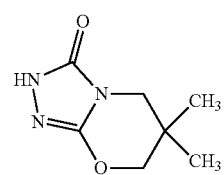

Intermediate 41

6,6-difluoro-5,6,7,8-tetrahydro[1,2,4]triazolo[4,3-a]pyridin-3(2H)-one

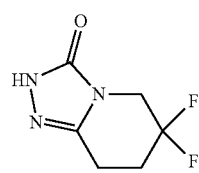

Intermediate 42

5-chloro-2-fluoro-4-(3-oxo-5,6,7,8-tetrahydro[1,2,4]triazolo[4,3-a]pyridin-2(3H)-yl)benzonitrile

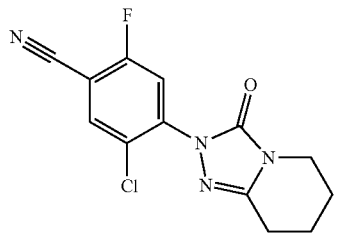 [SMILES: N#Cc1cc(Cl)c(-n2nc3n(c2=O)CCCC3)cc1F]

A mixture of 5-chloro-2,4-difluorobenzonitrile [CAS 146780-26-9] (540 mg, 3.11 mmol), 5,6,7,8-tetrahydro[1,2,4]triazolo[4,3-a]pyridin-3(2H)-one [CAS 118801-67-5] (476 mg, 3.42 mmol), and potassium carbonate (860 mg, 6.22 mmol) in acetonitrile (5.1 ml) was heated in an oil bath at 95° C. bath temperature for 3.5 hours. After cooling to room temperature, the mixture was poured into water, and the resulting mixture was extracted with dichloromethane. The organic fractions were dried over sodium sulfate and concentrated under reduced pressure to yield the crude product as yellow oil (1 g, 38%-UV), which was used in the next step without purification.

For analytical purpose, the reaction was repeated with 50.0 mg (288 µmol) of 5-chloro-2,4-difluorobenzonitrile, 5,6,7,8-tetrahydro[1,2,4]triazolo[4,3-a]pyridin-3(2H)-one (44.1 mg, 317 µmol), and potassium carbonate (79.6 mg, 576 µmol) in 0.4 ml acetonitrile under the same conditions. The crude material was purified by preparative HPLC (XBridge Prep C18 5µ OBD; solvents: water (+0.1% ammonia), acetonitrile; gradient 5%-95% acetonitrile in 10 min; flow: 30 ml/min) to afford 5-chloro-2-fluoro-4-(3-oxo-5,6,7,8-tetrahydro[1,2,4]triazolo[4,3-a]pyridin-2(3H)-yl)benzonitrile (16 mg, 19% yield, 100%-UV).

LC-MS (Method A): $R_t$=0.93 min; MS (ESIpos): m/z=293 [M+H]$^+$ $^1$H-NMR (500 MHz, DMSO-d6) δ[ppm]: −0.006 (0.53), 0.000 (13.44), 0.007 (0.47), 1.242 (0.55), 1.780 (1.49), 1.786 (1.73), 1.793 (4.36), 1.799 (4.35), 1.803 (5.95), 1.812 (4.83), 1.815 (6.38), 1.824 (2.21), 1.827 (2.42), 1.873 (2.41), 1.878 (2.20), 1.885 (5.83), 1.889 (5.08), 1.897 (6.55), 1.902 (4.54), 1.908 (4.03), 1.920 (1.58), 2.077 (1.08), 2.519 (1.18), 2.523 (0.96), 2.527 (0.73), 2.687 (8.10), 2.700 (15.19), 2.713 (7.92), 3.216 (0.91), 3.557 (8.68), 3.569 (16.00), 3.581 (7.93), 7.765 (10.96), 7.784 (11.13), 8.374 (10.26), 8.387 (10.04).

Intermediate 43

5-chloro-4-(3-oxo-5,6,7,8-tetrahydro[1,2,4]triazolo[4,3-a]pyridin-2(3H)-yl)-2-{[(2S)-1,1,1-tri-fluoropropan-2-yl]oxy}benzonitrile

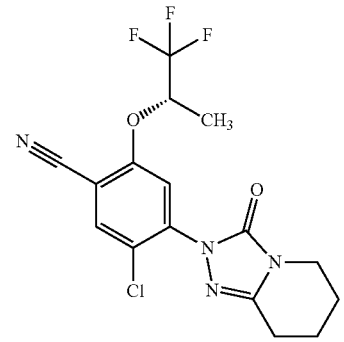 [SMILES: C[C@H](Oc1cc(-n2nc3n(c2=O)CCCC3)c(Cl)cc1C#N)C(F)(F)F]

To a solution of (2S)-1,1,1-trifluoropropan-2-ol (468 mg, 4.10 mmol) in tetrahydrofuran (5 ml) was added in portions sodium hydride (164 mg, 60% in mineral oil, 4.10 mmol) at 0° C. After stirring for 30 min, a solution of 5-chloro-2-fluoro-4-(3-oxo-5,6,7,8-tetrahydro[1,2,4]triazolo[4,3-a]pyridin-2(3H)-yl)benzonitrile (intermediate 42, crude product from previous step, 1.00 g, 38%-UV) and the mixture was stirred for 1.5 h at 0° C. The mixture was then poured into saturated aqueous sodium chloride (5 ml), and extracted with ethyl acetate. The organic fractions were dried over sodium sulfate and concentrated under reduced pressure. The crude product (1.16 g, 50%-UV) was used without purification.

LC-MS (Method A): $R_t$=1.12 min; MS (ESIpos): m/z=387 [M+H]$^+$

Intermediate 44

5-chloro-4-(3-oxo-5,6,7,8-tetrahydro[1,2,4]triazolo[4,3-a]pyridin-2(3H)-yl)-2-{[(2S)-1,1,1-tri-fluoropropan-2-yl]oxy}benzoic Acid

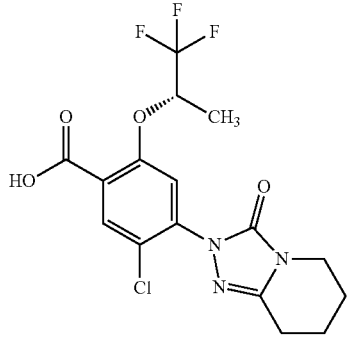 [SMILES: C[C@H](Oc1cc(-n2nc3n(c2=O)CCCC3)c(Cl)cc1C(=O)O)C(F)(F)F]

To a solution of 5-chloro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzonitrile (intermediate 43, crude product from previous step, 1.16 g, 50%-UV) in ethanol (90 ml) was added aqueous sodium hydroxide (62 ml, 1.0 M, 62 mmol) and the mixture was stirred at 80° C. for 2 d. After cooling to room temperature, the reaction mixture was extracted twice with ethyl acetate. The organic phase was discarded, and the aqueous phase was then adjusted to an acidic pH using 1 N aqueous hydrochloric acid and extracted with ethyl acetate. The organic phases were dried over sodium sulfate and concentrated under reduced pressure to yield the crude product (0.73 g, 80%-UV), which was used without further purification.

LC-MS (Method A): $R_t$=0.93 min; MS (ESIneg): m/z=404 [M–H]⁻

Intermediate 45 rac-tert-butyl N-[2-(5-bromo-2-cyano-4-fluoro-phenoxy)propyl]carbamate

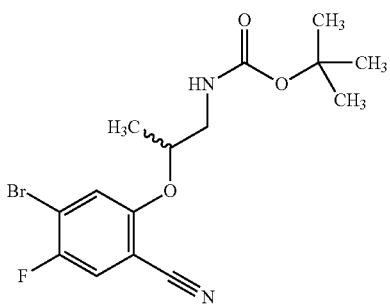 [SMILES: CC(CNC(=O)OC(C)(C)C)Oc1cc(Br)c(F)cc1C#N]

To a suspension of sodium hydride (4.04 g, 100 mmol, 60% purity) in THF (25 mL) was added tert-butyl N-(2-hydroxypropyl)carbamate (8.84 g, 50.5 mmol) at 0° C. The resulting mixture was stirred at 0° C. for 0.5 h, then a solution of 4-bromo-2,5-difluorobenzonitrile (10 g, 45.9 mmol) in THF (25 mL) was added. The mixture was stirred at 0° C. for 0.5 h. The reaction mixture was diluted with water and extracted with ethyl acetate. The combined organic layers were washed with brine, dried over sodium sulfate, filtered and concentrated under reduced pressure to give a residue, which was purified by column chromatography (silica gel, petroleum ether/ethyl acetate=50/1 to 10/1) to give the desired product (13 g, 34.8 mmol, 76% yield) as a white solid.

MS (M+H⁺): 397.1

¹H NMR (400 MHz, CDCl₃) [ppm]: 7.33-7.30 (t, J=6 Hz, 1H), 7.27-7.24 (t, J=6 Hz, 1H), 4.99 (s, 1H), 4.57 (s, 1H), 3.53-3.48 (m, 1H), 3.33-3.28 (m, 1H), 1.62-1.45 (q, 9H), 1.36-1.26 (m, 3H).

Intermediate 46 rac-4-bromo-2-[2-(tert-butoxycarbonylamino)-1-methyl-ethoxy]-5-fluoro-benzoic Acid

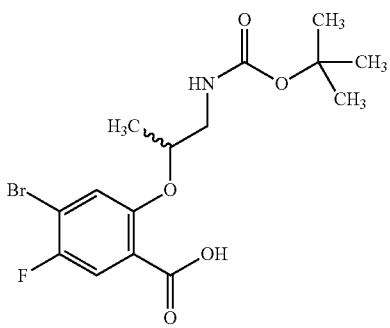 [SMILES: CC(CNC(=O)OC(C)(C)C)Oc1cc(Br)c(F)cc1C(=O)O]

To a solution of tert-butyl N-[2-(5-bromo-2-cyano-4-fluoro-phenoxy)propyl]carbamate (13 g, 34.8 mmol) in ethanol (60 mL) was added sodium hydroxide (5 M in water, 69.7 mL) at 25° C., the resulting mixture was stirred at 90° C. for 12 hrs. The reaction mixture was evaporated under vacuum, the residue was diluted with water (60 mL), acidified to pH=4-5 with aq. hydrochloric acid (1 N), extracted with ethyl acetate three times. The combined organic layers were washed with brine, dried over sodium sulfate, filtered, and concentrated under reduced pressure to give the desired product (11 g, crude) as a yellow oil, which was used in next step without further purification.

MS (M+H+): 336.2

¹H NMR (400 MHz, CDCl₃) δ [ppm]: 7.84-7.82 (d, J=8 Hz, 1H), 7.31-7.29 (d, J=8 Hz, 1H), 5.16 (s, 1H), 4.70 (s, 1H), 3.53-3.50 (m, 1H), 3.40-3.34 (m, 1H), 1.44-1.39 (t, J=10 Hz, 9H), 1.32-1.25 (m, 3H).

Intermediate 47 rac-tert-butyl (2-{5-bromo-2-[(2-chloro-6-fluorophenyl)carbamoyl]-4-fluorophenoxy}propyl) carbamate

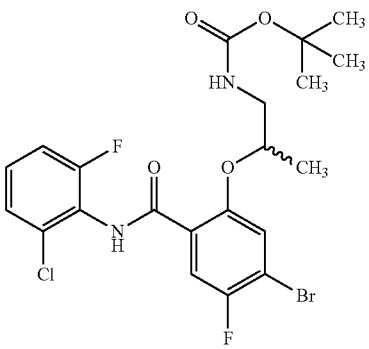 [SMILES: CC(CNC(=O)OC(C)(C)C)Oc1cc(Br)c(F)cc1C(=O)Nc1c(F)cccc1Cl]

Crude intermediate 46 (10 g, 25.5 mmol) and 2-chloro-6-fluoroaniline (3.71 g, 25.5 mmol) were suspended in pyridine (50 mL) was added phosphoryl chloride (15.6 g, 102 mmol, 9.5 mL) in one portion at 0° C. under nitrogen. The resulting mixture was stirred at 25° C. for 10 min. The reaction mixture was quenched by addition of water (300 mL) and extracted with ethyl acetate (300 mL×2). The combined organic layers were washed with brine (150 mL×2), dried over sodium sulfate, filtered and concentrated under reduced pressure. Column chromatography (silica gel, petroleum ether/ethyl acetate=50/1 to 5/1) afforded the desire product (8.22 g, 15.2 mmol, 59% yield, 96% purity).

MS (M+H⁺): 421.1

¹H NMR (400 MHz, CDCl₃) δ [ppm]: 9.46 (s, 1H), 8.06-8.03 (d, J=12 Hz, 1H), 7.31-7.28 (q, 2H), 7.26 (s, 1H), 7.25-7.13 (t, J=24 Hz, 1H), 4.92 (s, 1H), 4.78-4.73 (q, 1H), 3.50-3.47 (m, 2H), 1.58-1.42 (q, 3H), 1.38 (s, 9H).

EXPERIMENTAL SECTION—EXAMPLES

Example 1

N-(2,6-difluorophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

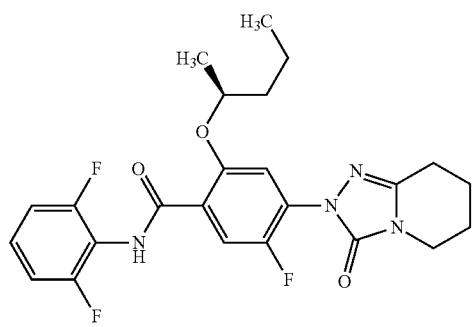 [SMILES: CCC[C@H](C)Oc1cc(-n2nc3n(c2=O)CCCC3)c(F)cc1C(=O)Nc1c(F)cccc1F]

To a 0° C. stirred solution of 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (intermediate 16) (100 mg, 275 µmol) and catalytic N,N-dimethylformamide in anhydrous dichloromethane (1.5 ml) was added oxalyl chloride (28 µl, 330 µmol). The resulting mixture was warmed to room temperature, stirred for 90 minutes and concentrated under reduced pressure. A solution of the residue in anhydrous dichloromethane (1.0 ml) was added dropwise to a 0° C. stirred solution of 2,6-difluoroaniline (39 mg, 303 µmol) and triethylamine (42 µl, 300 µmol) in anhydrous DCM (2.0 ml). Following complete addition, the mixture was warmed to room temperature and stirred for 1 hour. Aqueous 1.0 M hydrochloric acid was added to the mixture and extracted with dichloromethane. The combined organic extracts were washed with brine, dried (magnesium sulfate) and concentrated under reduced pressure. The residue was purified by flash column chromatography (hexanes/ethyl acetate) to give the desired product (111 mg, 85%).

MS (ESIpos): m/z=475 (M+H)$^+$ $^1$H NMR (300 MHz, CDCl$_3$) δ [ppm] 0.95 (t, 3H), 1.43 (d, 3H), 1.45-1.56 (m, 2H), 1.61-1.78 (m, 1H), 1.78-2.06 (m, 5H), 2.81 (t, 2H), 3.72 (t, 2H), 4.59-4.71 (m, 1H), 6.95-7.04 (m, 2H), 7.16-7.27 (m, 1H), 7.41 (d, 1H), 8.14 (d, 1H), 9.68 (s, 1H).

Examples 2-23 were prepared as described for example 1 from 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (intermediate 16) and the respective amines, as indicated. Products were purified by flash column chromatography or, if explicitly mentioned, by preparative HPLC.

Example 2

5-fluoro-N-(2-fluorophenyl)-4-(3-oxo-5,6,7,8-tetrahydro[1,2,4]triazolo[4,3-a]pyridin-2(3H)-yl)-2-[(2S)-pentan-2-yloxy]benzamide

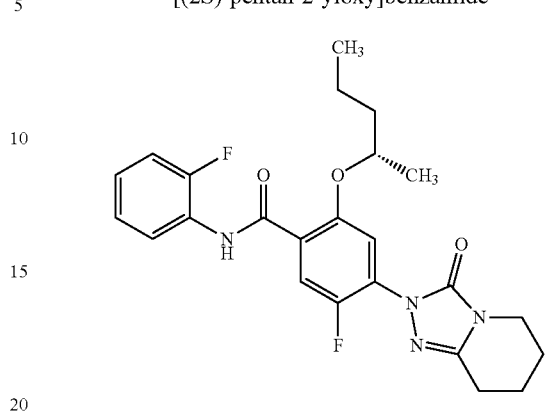

From intermediate 16 and 2-fluoroaniline.

LC-MS (method A): R$_t$=1.46 min; MS (ESIpos): m/z=457 [M+H]$^+$ $^1$H-NMR (400 MHz, DMSO-d6) δ[ppm]: 0.875 (6.76), 0.894 (16.00), 0.912 (7.62), 1.346 (11.35), 1.361 (11.28), 1.389 (1.11), 1.397 (1.00), 1.408 (1.06), 1.427 (0.96), 1.446 (0.91), 1.452 (0.92), 1.470 (0.90), 1.670 (1.13), 1.695 (0.88), 1.790 (2.28), 1.798 (2.94), 1.803 (3.29), 1.814 (3.07), 1.818 (3.31), 1.829 (1.73), 1.833 (1.63), 1.866 (1.21), 1.871 (1.23), 1.881 (2.35), 1.885 (2.56), 1.897 (2.70), 1.902 (2.20), 1.911 (1.61), 2.518 (1.69), 2.523 (1.18), 2.692 (3.05), 2.708 (6.06), 2.725 (3.28), 3.559 (3.63), 3.575 (6.53), 3.590 (2.88), 4.725 (0.82), 4.740 (1.56), 4.755 (1.53), 7.173 (1.45), 7.178 (1.33), 7.186 (1.38), 7.192 (1.85), 7.197 (1.30), 7.205 (1.32), 7.210 (1.26), 7.221 (1.64), 7.225 (1.93), 7.241 (2.22), 7.245 (2.44), 7.260 (0.98), 7.264 (0.94), 7.333 (1.53), 7.337 (1.50), 7.353 (1.33), 7.357 (1.44), 7.362 (1.62), 7.366 (1.53), 7.382 (1.18), 7.386 (1.16), 7.486 (3.45), 7.501 (3.41), 7.883 (4.33), 7.911 (4.28), 8.358 (1.21), 8.362 (1.26), 8.378 (2.31), 8.382 (2.25), 8.398 (1.19), 8.402 (1.12), 10.342 (3.06), 10.348 (2.99).

Example 3

5-fluoro-4-(3-oxo-5,6,7,8-tetrahydro[1,2,4]triazolo[4,3-a]pyridin-2(3H)-yl)-2-[(2S)-pentan-2-yloxy]-N-[3-(trifluoromethyl)phenyl]benzamide

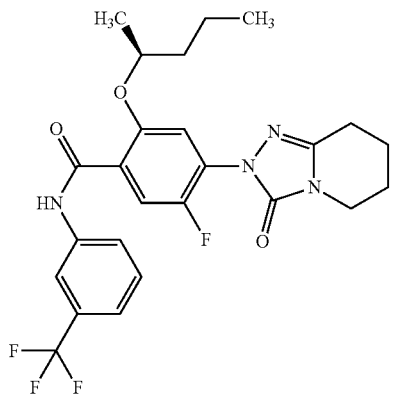 [SMILES: CCC[C@H](C)Oc1cc(-n2nc3n(c2=O)CCCC3)c(F)cc1C(=O)Nc1cccc(C(F)(F)F)c1]

From intermediate 16 and 3-(trifluoromethyl)aniline.

MS (ESIpos): m/z=507 (M+H)$^+$ $^1$H NMR (300 MHz, CDCl$_3$) δ [ppm] 1.00 (t, 3H), 1.47 (d, 3H), 1.49-1.57 (m, 2H), 1.64-2.05 (m, 6H), 2.81 (t, 2H), 3.72 (t, 2H), 4.60-4.73 (m, 1H), 7.35-7.42 (m, 2H), 7.49 (t, 1H), 7.86 (d, 1H), 7.93 (s, 1H), 8.15 (d, 1H), 10.4 (s, 1H).

Example 4

N-(1-acetylpiperidin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

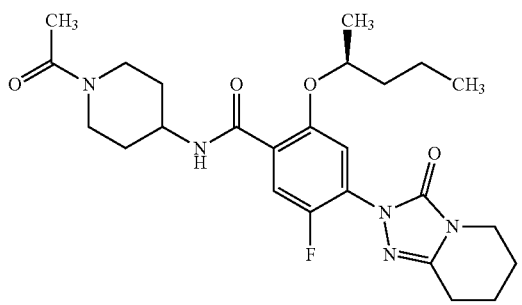 [SMILES: CCC[C@H](C)Oc1cc(-n2nc3n(c2=O)CCCC3)c(F)cc1C(=O)NC1CCN(C(C)=O)CC1]

From intermediate 16 and 1-(4-aminopiperidin-1-yl)ethanone.

The product was purified by preparative HPLC (X-Bridge Prep C18 5 μm OBD, 0.1% aqueous ammonia, acetonitrile).

LC-MS (method A): $R_t$=0.99 min; MS (ESIpos): m/z=488 [M+H]$^+$ $^1$H-NMR (400 MHz, CHLOROFORM-d) δ [ppm]: 0.935 (1.11), 0.946 (1.23), 0.953 (2.59), 0.964 (2.55), 0.972 (1.38), 0.982 (1.24), 1.361 (2.55), 1.375 (4.76), 1.390 (3.06), 1.404 (0.96), 1.423 (0.84), 1.432 (0.82), 1.448 (0.64), 1.461 (0.52), 1.626 (0.45), 1.646 (0.60), 1.652 (0.68), 1.660 (0.70), 1.676 (0.56), 1.684 (0.44), 1.908 (0.72), 1.916 (0.86), 1.920 (0.96), 1.932 (0.99), 1.936 (1.05), 1.948 (0.47), 1.952 (0.50), 1.972 (0.55), 1.988 (0.95), 1.993 (1.00), 2.003 (1.08), 2.009 (0.94), 2.016 (0.88), 2.031 (0.54), 2.133 (16.00), 2.783 (1.51), 2.800 (2.90), 2.815 (1.68), 2.874 (0.54), 3.253 (0.64), 3.259 (0.42), 3.694 (1.93), 3.709 (3.09), 3.724 (1.36), 3.791 (0.45), 4.516 (0.43), 4.541 (0.72), 4.556 (1.22), 4.572 (0.94), 4.587 (0.47), 7.292 (1.89), 7.307 (1.87), 8.044 (1.37), 8.073 (1.35), 8.163 (0.53), 8.177 (0.52).

Example 5

N-(3-chloropyridin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

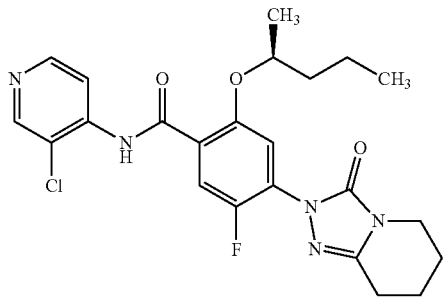 [SMILES: CCC[C@H](C)Oc1cc(-n2nc3n(c2=O)CCCC3)c(F)cc1C(=O)Nc1ccncc1Cl]

From intermediate 16 and 3-chloropyridin-4-amine.

The product was purified by preparative HPLC (X-Bridge Prep C18 5 μm OBD, 0.1% aqueous ammonia, acetonitrile).

LC-MS (method A): $R_t$=1.28 min; MS (ESIpos): m/z=474 [M+H]$^+$ $^1$H-NMR (400 MHz, CHLOROFORM-d) δ [ppm]: 0.929 (6.69), 0.947 (16.00), 0.965 (7.53), 1.259 (0.42), 1.282 (2.30), 1.391 (0.52), 1.409 (0.86), 1.416 (0.65), 1.424 (0.75), 1.427 (0.77), 1.435 (1.09), 1.442 (0.78), 1.452 (1.27), 1.462 (15.62), 1.471 (1.85), 1.477 (15.87), 1.489 (1.00), 1.496 (0.90), 1.501 (0.72), 1.509 (0.50), 1.515 (0.87), 1.529 (0.41), 1.534 (0.49), 1.665 (0.61), 1.679 (1.13), 1.689 (0.57), 1.694 (0.66), 1.699 (0.88), 1.704 (0.95), 1.714 (1.39), 1.719 (0.58), 1.724 (0.79), 1.728 (0.73), 1.739 (1.16), 1.753 (0.57), 1.914 (1.01), 1.926 (1.90), 1.931 (2.19), 1.939 (2.40), 1.944 (1.98), 1.948 (2.56), 1.952 (2.80), 1.956 (2.11), 1.961 (1.37), 1.965 (1.56), 1.969 (1.62), 1.979 (0.80), 1.990 (1.48), 2.004 (2.30), 2.009 (1.99), 2.019 (2.08), 2.024 (1.70), 2.034 (1.28), 2.047 (0.58), 2.803 (3.02), 2.819 (5.65), 2.836 (3.35), 3.713 (3.80), 3.729 (6.23), 3.744 (2.68), 4.655 (0.91), 4.671 (1.72), 4.687 (1.72), 4.703 (0.89), 7.467 (3.74), 7.481 (3.72), 8.101 (5.26), 8.130 (5.22), 8.463 (1.02), 8.476 (1.14), 8.589 (1.77), 8.626 (1.79), 8.640 (1.55), 10.429 (2.68).

Example 6

N-(2-chloro-6-fluorophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

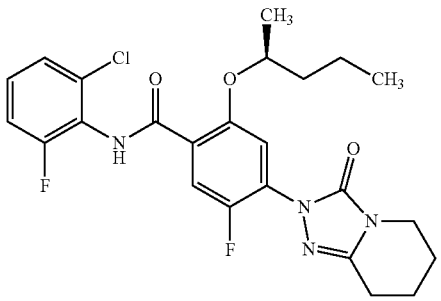 [SMILES: CCC[C@H](C)Oc1cc(-n2nc3n(c2=O)CCCC3)c(F)cc1C(=O)Nc1c(F)cccc1Cl]

From intermediate 16 and 2-chloro-6-fluoroaniline.

The product was purified by preparative HPLC (X-Bridge Prep C18 5 μm OBD, 0.1% aqueous ammonia, acetonitrile).

LC-MS (method A): $R_t$=1.35 min; MS (ESIpos): m/z=491 [M+H]$^+$ $^1$H-NMR (400 MHz, CHLOROFORM-d) δ [ppm]: 0.937 (6.73), 0.955 (16.00), 0.974 (7.56), 1.414 (0.59), 1.432 (1.21), 1.444 (15.10), 1.459 (15.32), 1.473 (0.81), 1.476 (0.89), 1.486 (0.68), 1.491 (0.81), 1.500 (0.77), 1.505 (0.72), 1.511 (0.80), 1.518 (0.84), 1.525 (0.90), 1.530 (0.75), 1.538 (0.54), 1.544 (0.93), 1.558 (0.50), 1.563 (0.58), 1.577 (0.46), 1.629 (1.09), 1.670 (0.75), 1.685 (1.13), 1.696 (0.58), 1.700 (0.71), 1.705 (0.93), 1.710 (0.91), 1.719 (1.45), 1.724 (0.61), 1.730 (0.84), 1.734 (0.80), 1.744 (1.16), 1.759 (0.54), 1.846 (0.69), 1.860 (0.87), 1.872 (0.75), 1.876 (0.88), 1.881 (0.68), 1.888 (0.87), 1.897 (0.77), 1.902 (1.02), 1.907 (1.03), 1.911 (1.08), 1.920 (2.00), 1.933 (2.11), 1.945 (2.04), 1.948 (2.17), 1.960 (0.98), 1.964 (1.01), 1.985 (1.07), 2.000 (1.96), 2.004 (2.05), 2.015 (2.16), 2.020 (1.77), 2.029 (1.29), 2.043 (0.53), 2.801 (3.05), 2.818 (5.83), 2.834 (3.34), 3.711 (3.77), 3.727 (6.13), 3.741 (2.72), 4.663 (1.01), 4.679 (1.98), 4.694 (1.95), 4.709 (0.96), 7.107 (1.11), 7.110 (1.15), 7.128 (1.92), 7.131 (2.59), 7.151 (1.69), 7.155 (1.72), 7.195 (1.24), 7.209 (1.23), 7.215 (2.50), 7.229 (2.53), 7.236 (1.58), 7.249 (1.61), 7.280 (2.67), 7.294 (1.25), 7.297 (1.90), 7.300 (1.30), 7.418 (3.77), 7.433 (3.71), 8.152 (5.03), 8.181 (4.88), 9.727 (3.12).

Example 7

5-fluoro-N-(2-methylphenyl)-4-(3-oxo-5,6,7,8-tetrahydro[1,2,4]triazolo[4,3-a]pyridin-2(3H)-yl)-2-[(2S)-pentan-2-yloxy]benzamide

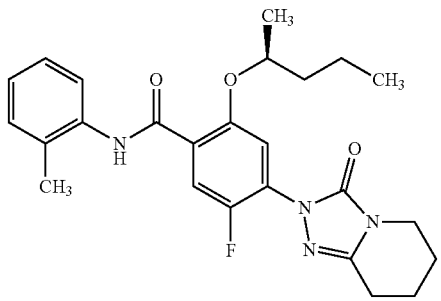 [SMILES: CCC[C@H](C)Oc1cc(-n2nc3n(c2=O)CCCC3)c(F)cc1C(=O)Nc1ccccc1C]

From intermediate 16 and o-toluidine.

The product was purified by preparative HPLC (X-Bridge Prep C18 5 μm OBD, 0.1% aqueous formic acid, acetonitrile).

LC-MS (method A): $R_t$=1.36 min; MS (ESIpos): m/z=453 [M+H]$^+$ $^1$H-NMR (400 MHz, CHLOROFORM-d) δ [ppm]: 0.929 (5.14), 0.947 (12.73), 0.965 (5.84), 1.419 (0.88), 1.426 (11.38), 1.442 (11.90), 1.452 (0.70), 1.459 (0.98), 1.473 (0.65), 1.478 (0.95), 1.484 (0.58), 1.492 (0.65), 1.497 (0.73), 1.503 (0.55), 1.516 (0.67), 1.582 (1.77), 1.640 (0.44), 1.655 (0.80), 1.670 (0.49), 1.674 (0.66), 1.679 (0.66), 1.689 (1.08), 1.695 (0.41), 1.699 (0.59), 1.704 (0.55), 1.714 (0.85), 1.728 (0.42), 1.819 (0.51), 1.833 (0.61), 1.836 (0.59), 1.845 (0.52), 1.849 (0.63), 1.853 (0.48), 1.858 (0.58), 1.861 (0.59), 1.867 (0.51), 1.874 (0.51), 1.879 (0.40), 1.895 (0.41), 1.908 (0.51), 1.913 (0.50), 1.922 (1.05), 1.929 (1.24), 1.934 (1.40), 1.945 (1.46), 1.949 (1.57), 1.961 (0.69), 1.965 (0.72), 1.986 (0.74), 1.992 (0.66), 2.001 (1.37), 2.006 (1.44), 2.016 (1.52), 2.021 (1.25), 2.031 (0.93), 2.044 (0.41), 2.355 (16.00), 2.801 (2.27), 2.817 (4.37), 2.833 (2.54), 3.712 (2.98), 3.727 (4.80), 3.743 (2.08), 4.637 (0.73), 4.652 (1.45), 4.668 (1.46), 4.683 (0.71), 7.098 (0.76), 7.102 (0.78), 7.117 (1.86), 7.120 (1.91), 7.135 (1.30), 7.138 (1.28), 7.232 (1.83), 7.252 (2.22), 7.290 (0.74), 7.404 (2.81), 7.419 (2.84), 8.010 (1.88), 8.028 (1.72), 8.030 (1.70), 8.167 (3.90), 8.196 (3.88), 9.656 (1.79).

Example 8

5-fluoro-N-(4-fluoro-2-methylphenyl)-4-(3-oxo-5,6,7,8-tetrahydro[1,2,4]triazolo[4,3-a]pyridin-2(3H)-yl)-2-[(2S)-pentan-2-yloxy]benzamide

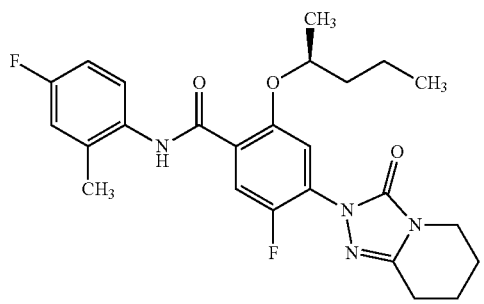 [SMILES: CCC[C@H](C)Oc1cc(-n2nc3n(c2=O)CCCC3)c(F)cc1C(=O)Nc1ccc(F)cc1C]

From intermediate 16 and 4-fluoro-2-methylaniline.

The product was purified by preparative HPLC (X-Bridge Prep C18 5 μm OBD, 0.1% aqueous formic acid, acetonitrile).

LC-MS (method A): $R_t$=1.36 min; MS (ESIpos): m/z=471 [M+H]$^+$ $^1$H-NMR (400 MHz, CHLOROFORM-d) δ [ppm]: 0.931 (4.92), 0.950 (12.09), 0.968 (5.64), 1.419 (0.81), 1.427 (11.60), 1.442 (11.68), 1.452 (0.73), 1.459 (0.90), 1.463 (0.75), 1.472 (0.67), 1.477 (0.95), 1.483 (0.60), 1.490 (0.62), 1.496 (0.78), 1.501 (0.52), 1.515 (0.65), 1.577 (5.23), 1.643 (0.40), 1.658 (0.73), 1.673 (0.45), 1.677 (0.64), 1.682 (0.62), 1.692 (1.04), 1.702 (0.57), 1.707 (0.53), 1.717 (0.83), 1.806 (0.49), 1.820 (0.62), 1.822 (0.61), 1.832 (0.50), 1.836 (0.61), 1.841 (0.47), 1.848 (0.59), 1.856 (0.50), 1.862 (0.51), 1.914 (0.44), 1.922 (1.01), 1.929 (1.20), 1.934 (1.36), 1.946 (1.39), 1.950 (1.52), 1.962 (0.66), 1.965 (0.71), 1.986 (0.71), 1.991 (0.64), 2.002 (1.34), 2.006 (1.40), 2.017 (1.50), 2.022 (1.23), 2.031 (0.91), 2.332 (16.00), 2.801 (2.22), 2.817 (4.18), 2.833 (2.46), 3.712 (2.81), 3.727 (4.58), 3.742 (2.00), 4.639 (0.72), 4.655 (1.44), 4.670 (1.44), 4.686 (0.70), 6.939 (2.37), 6.944 (1.08), 6.946 (1.12), 6.962 (1.97), 6.969 (1.21), 6.975 (1.03), 7.405 (2.76), 7.419 (2.77), 7.856 (1.10), 7.870 (1.32), 7.881 (1.32), 7.894 (1.10), 8.150 (3.76), 8.179 (3.68), 9.591 (1.88).

Example 9

5-fluoro-N-(5-fluoro-2-methylphenyl)-4-(3-oxo-5,6,7,8-tetrahydro[1,2,4]triazolo[4,3-a]pyridin-2(3H)-yl)-2-[(2S)-pentan-2-yloxy]benzamide

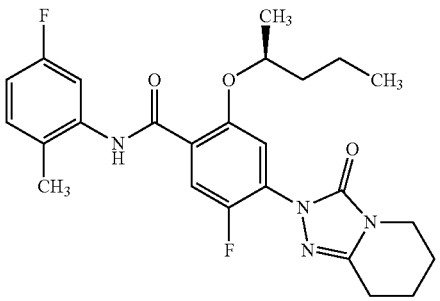 [SMILES: CCC[C@H](C)Oc1cc(-n2nc3n(c2=O)CCCC3)c(F)cc1C(=O)Nc1cc(F)ccc1C]

From intermediate 16 and 5-fluoro-2-methylaniline.

The product was purified by preparative HPLC (X-Bridge Prep C18 5 μm OBD, 0.1% aqueous ammonia, acetonitrile).

LC-MS (method A): $R_t$=1.40 min; MS (ESIneg): m/z=469 [M−H]$^-$ $^1$H-NMR (400 MHz, CHLOROFORM-d) δ [ppm]: 0.929 (6.51), 0.948 (16.00), 0.966 (7.35), 1.397 (0.48), 1.415 (0.87), 1.430 (14.73), 1.445 (14.06), 1.454 (1.16), 1.458 (1.00), 1.467 (0.87), 1.473 (1.17), 1.478 (0.79), 1.486 (0.79), 1.492 (0.99), 1.497 (0.66), 1.505 (0.45), 1.511 (0.83), 1.530 (0.47), 1.586 (8.72), 1.639 (0.55), 1.655 (0.99), 1.664 (0.46), 1.670 (0.59), 1.674 (0.83), 1.679 (0.78), 1.689 (1.31), 1.694 (0.50), 1.698 (0.70), 1.703 (0.66), 1.714 (1.07), 1.728 (0.49), 1.820 (0.60), 1.834 (0.76), 1.836 (0.73), 1.846 (0.64), 1.850 (0.74), 1.854 (0.59), 1.862 (0.71), 1.870 (0.61), 1.875 (0.63), 1.879 (0.50), 1.884 (0.50), 1.896 (0.51), 1.910 (0.64), 1.914 (0.62), 1.922 (1.30), 1.929 (1.54), 1.934 (1.72), 1.946 (1.77), 1.950 (1.91), 1.962 (0.83), 1.965 (0.88), 1.986 (0.91), 1.993 (0.83), 2.002 (1.69), 2.006 (1.78), 2.017 (1.90), 2.022 (1.54), 2.031 (1.13), 2.045 (0.48), 2.316 (15.27), 2.801 (2.86), 2.817 (5.28), 2.833 (3.11), 3.712 (3.54), 3.727 (5.83), 3.742 (2.50), 4.640 (0.90), 4.656 (1.79), 4.671 (1.80), 4.687 (0.87), 6.779 (1.00), 6.786 (1.08), 6.799 (1.92), 6.806 (2.07), 6.820 (1.12), 6.826 (1.17), 7.134 (1.45), 7.152 (1.58), 7.155 (1.47), 7.171 (1.27), 7.422 (3.43), 7.437 (3.47), 7.996 (1.87), 8.003 (1.86), 8.024 (1.89), 8.031 (1.84), 8.149 (4.55), 8.178 (4.52), 9.690 (2.14).

Example 10

5-fluoro-N-(4-methylpyridin-3-yl)-4-(3-oxo-5,6,7,8-tetrahydro[1,2,4]triazolo[4,3-a]pyridin-2(3H)-yl)-2-[(2S)-pentan-2-yloxy]benzamide

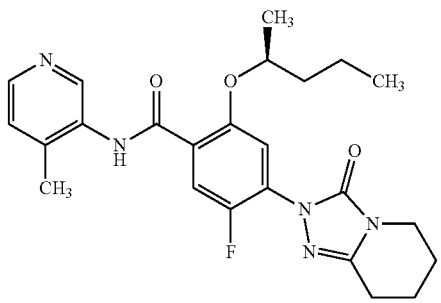 [SMILES: CCC[C@H](C)Oc1cc(-n2nc3n(c2=O)CCCC3)c(F)cc1C(=O)Nc1cnccc1C]

From intermediate 16 and 4-methylpyridin-3-amine.

The product was purified by preparative HPLC (X-Bridge Prep C18 5 μm OBD, 0.1% aqueous ammonia, acetonitrile).

LC-MS (method A): $R_t$=0.92 min; MS (ESIpos): m/z=454 $[M+H]^+$ $^1$H-NMR (400 MHz, CHLOROFORM-d) δ [ppm]: 0.940 (4.74), 0.958 (11.64), 0.977 (5.45), 1.261 (0.41), 1.430 (0.69), 1.444 (10.59), 1.459 (10.71), 1.470 (1.00), 1.484 (0.68), 1.489 (0.97), 1.494 (0.62), 1.503 (0.67), 1.508 (0.80), 1.513 (0.58), 1.522 (0.42), 1.527 (0.72), 1.546 (0.48), 1.560 (0.43), 1.605 (1.27), 1.660 (0.55), 1.675 (0.79), 1.684 (0.42), 1.689 (0.50), 1.694 (0.69), 1.699 (0.64), 1.709 (1.05), 1.714 (0.43), 1.719 (0.58), 1.723 (0.55), 1.734 (0.85), 1.813 (0.48), 1.827 (0.63), 1.839 (0.50), 1.843 (0.61), 1.847 (0.45), 1.854 (0.59), 1.862 (0.50), 1.868 (0.49), 1.917 (0.49), 1.925 (1.05), 1.933 (1.22), 1.937 (1.39), 1.948 (1.39), 1.952 (1.50), 1.964 (0.69), 1.969 (0.73), 1.990 (0.75), 1.996 (0.69), 2.005 (1.36), 2.009 (1.42), 2.020 (1.50), 2.025 (1.23), 2.034 (0.91), 2.048 (0.40), 2.352 (16.00), 2.805 (2.18), 2.820 (4.09), 2.837 (2.36), 3.714 (2.77), 3.729 (4.41), 3.744 (1.94), 4.659 (0.69), 4.674 (1.38), 4.690 (1.36), 4.705 (0.68), 7.185 (2.04), 7.197 (2.07), 7.437 (2.63), 7.451 (2.61), 8.158 (3.51), 8.187 (3.38), 8.350 (2.62), 8.362 (2.53), 9.056 (4.07), 9.699 (1.94).

Example 11

5-fluoro-N-(2-methoxy-4-methylpyridin-3-yl)-4-(3-oxo-5,6,7,8-tetrahydro[1,2,4]triazolo[4,3-a]pyridin-2(3H)-yl)-2-[(2S)-pentan-2-yloxy]benzamide

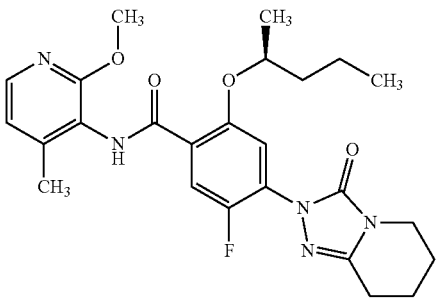 [SMILES: CCC[C@H](C)Oc1cc(-n2nc3n(c2=O)CCCC3)c(F)cc1C(=O)Nc1c(C)ccnc1OC]

From intermediate 16 and 2-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.26 min; MS (ESIpos): m/z=484 $[M+H]^+$ $^1$H-NMR (400 MHz, CHLOROFORM-d) δ [ppm]: 0.946 (2.63), 0.964 (6.58), 0.983 (2.99), 1.438 (5.62), 1.453 (5.79), 1.477 (0.40), 1.495 (0.44), 1.601 (1.14), 1.720 (0.54), 1.745 (0.43), 1.916 (0.46), 1.920 (0.54), 1.930 (0.75), 1.944 (0.72), 1.948 (0.78), 1.999 (0.67), 2.004 (0.72), 2.015 (0.75), 2.020 (0.62), 2.029 (0.46), 2.284 (9.26), 2.800 (1.13), 2.816 (2.12), 2.832 (1.25), 3.711 (1.45), 3.726 (2.32), 3.741 (1.02), 3.970 (16.00), 4.664 (0.73), 4.679 (0.72), 6.829 (1.38), 6.842 (1.43), 7.391 (1.43), 7.405 (1.44), 7.938 (1.92), 7.951 (1.85), 8.116 (1.95), 8.146 (1.95), 9.681 (1.15).

Example 12

N-(3,5-dimethylpyrazin-2-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

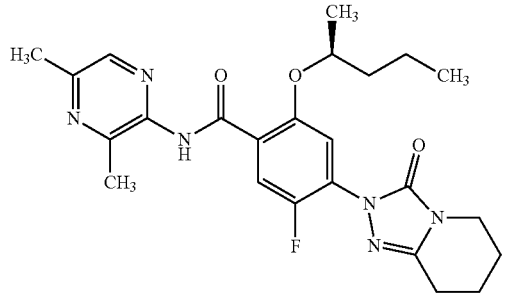

From intermediate 16 and 3,5-dimethylpyrazin-2-amine.

The product was purified by preparative HPLC (X-Bridge Prep C18 5 μm OBD, 0.1% aqueous formic acid, acetonitrile).

LC-MS (method A): $R_t$=1.15 min; MS (ESIpos): m/z=469 $[M+H]^+$ $^1$H-NMR (400 MHz, CHLOROFORM-d) δ [ppm]: 0.939 (4.46), 0.957 (10.95), 0.976 (5.06), 1.454 (9.68), 1.470

(10.05), 1.483 (0.51), 1.493 (0.84), 1.508 (0.70), 1.511 (0.66), 1.517 (0.51), 1.525 (0.64), 1.531 (0.64), 1.535 (0.53), 1.544 (0.44), 1.549 (0.74), 1.554 (0.44), 1.582 (2.57), 1.696 (0.64), 1.712 (0.40), 1.716 (0.57), 1.721 (0.54), 1.731 (0.90), 1.741 (0.52), 1.746 (0.48), 1.756 (0.76), 1.842 (0.45), 1.856 (0.56), 1.867 (0.46), 1.872 (0.54), 1.876 (0.41), 1.883 (0.52), 1.892 (0.44), 1.897 (0.47), 1.902 (0.43), 1.906 (0.62), 1.918 (0.80), 1.922 (0.95), 1.932 (1.30), 1.946 (1.26), 1.950 (1.33), 1.962 (0.60), 1.965 (0.62), 1.987 (0.65), 1.993 (0.60), 2.002 (1.20), 2.007 (1.25), 2.017 (1.33), 2.023 (1.07), 2.031 (0.79), 2.557 (14.74), 2.562 (16.00), 2.801 (1.88), 2.817 (3.63), 2.833 (2.09), 3.712 (2.44), 3.727 (3.93), 3.742 (1.71), 4.639 (0.63), 4.655 (1.26), 4.670 (1.24), 4.686 (0.61), 7.412 (2.47), 7.427 (2.45), 8.131 (3.31), 8.161 (3.30), 8.174 (3.72), 10.076 (1.90).

Example 13

5-fluoro-N-(5-methylpyrimidin-4-yl)-4-(3-oxo-5,6,7,8-tetrahydro[1,2,4]triazolo[4,3-a]pyridin-2(3H)-yl)-2-[(2S)-pentan-2-yloxy]benzamide

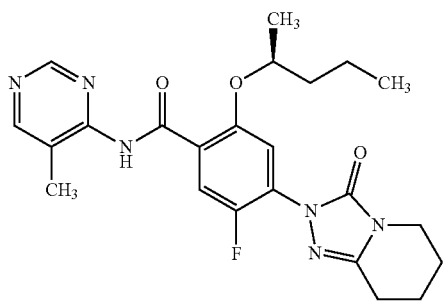 [SMILES: CCC[C@H](C)Oc1cc(-n2nc3n(c2=O)CCCC3)c(F)cc1C(=O)Nc1ncncc1C]

From intermediate 16 and 5-methylpyrimidin-4-amine.

The product was purified by preparative HPLC (X-Bridge Prep C18 5 μm OBD, 0.1% aqueous ammonia, acetonitrile).

LC-MS (method A): $R_t$=1.07 min; MS (ESIpos): m/z=455 [M+H]$^+$ $^1$H-NMR (400 MHz, CHLOROFORM-d) δ [ppm]: 0.950 (4.72), 0.968 (11.18), 0.986 (5.34), 1.464 (11.05), 1.480 (11.04), 1.490 (0.63), 1.498 (0.95), 1.513 (0.68), 1.516 (0.91), 1.523 (0.59), 1.531 (0.68), 1.537 (0.72), 1.542 (0.59), 1.550 (0.45), 1.556 (0.76), 1.570 (0.56), 1.575 (0.75), 1.594 (1.86), 1.694 (0.41), 1.708 (0.72), 1.723 (0.46), 1.728 (0.62), 1.733 (0.61), 1.743 (0.99), 1.747 (0.40), 1.753 (0.58), 1.758 (0.54), 1.768 (0.82), 1.866 (0.48), 1.880 (0.63), 1.891 (0.53), 1.896 (0.64), 1.900 (0.54), 1.908 (0.95), 1.915 (0.98), 1.922 (1.43), 1.931 (1.65), 1.936 (1.55), 1.947 (1.51), 1.951 (1.59), 1.955 (1.24), 1.963 (0.70), 1.967 (0.74), 1.988 (0.78), 2.003 (1.43), 2.008 (1.47), 2.018 (1.56), 2.023 (1.25), 2.032 (0.93), 2.047 (0.40), 2.318 (16.00), 2.802 (2.17), 2.818 (4.14), 2.834 (2.35), 2.877 (0.64), 3.101 (0.58), 3.712 (2.81), 3.727 (4.44), 3.742 (1.95), 4.648 (1.42), 4.663 (1.42), 4.679 (1.41), 4.694 (0.70), 7.437 (2.73), 7.452 (2.73), 8.114 (3.58), 8.143 (3.55), 8.560 (3.85), 8.929 (4.40), 10.249 (2.13).

Example 14

5-fluoro-N-(6-methoxy-4-methylpyridin-3-yl)-4-(3-oxo-5,6,7,8-tetrahydro[1,2,4]triazolo[4,3-a]pyridin-2(3H)-yl)-2-[(2S)-pentan-2-yloxy]benzamide

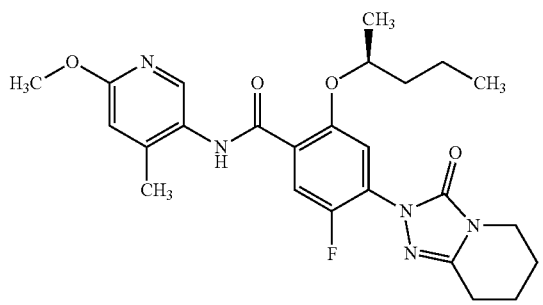 [SMILES: CCC[C@H](C)Oc1cc(-n2nc3n(c2=O)CCCC3)c(F)cc1C(=O)Nc1cnc(OC)cc1C]

From intermediate 16 and 6-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.24 min; MS (ESIpos): m/z=484 [M+H]$^+$ $^1$H-NMR (400 MHz, CHLOROFORM-d) δ [ppm]: 0.934 (2.43), 0.952 (6.05), 0.970 (2.77), 1.428 (5.60), 1.443 (5.62), 1.463 (0.45), 1.481 (0.42), 1.697 (0.53), 1.722 (0.43), 1.920 (0.49), 1.927 (0.58), 1.933 (0.65), 1.943 (0.67), 1.948 (0.72), 2.000 (0.64), 2.005 (0.68), 2.015 (0.72), 2.020 (0.59), 2.029 (0.44), 2.281 (7.18), 2.800 (1.03), 2.815 (2.00), 2.832 (1.16), 3.709 (1.33), 3.725 (2.13), 3.739 (0.96), 3.939 (16.00), 4.651 (0.69), 4.667 (0.70), 6.661 (2.10), 7.407 (1.34), 7.421 (1.33), 8.137 (1.86), 8.167 (1.77), 8.422 (2.61), 9.506 (1.09).

Example 15

5-fluoro-N-[2-methyl-6-(trifluoromethyl)phenyl]-4-(3-oxo-5,6,7,8-tetrahydro[1,2,4]triazolo[4,3-a]pyridin-2(3H)-yl)-2-[(2S)-pentan-2-yloxy]benzamide

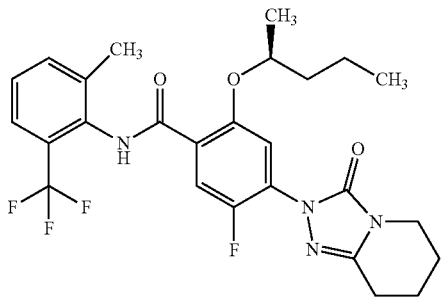 [SMILES: CCC[C@H](C)Oc1cc(-n2nc3n(c2=O)CCCC3)c(F)cc1C(=O)Nc1c(C)cccc1C(F)(F)F]

From intermediate 16 and 2-methyl-6-(trifluoromethyl)amine.

The product was purified by preparative HPLC (X-Bridge Prep C18 5 μm OBD, 0.1% aqueous ammonia, acetonitrile).

LC-MS (method A): $R_t$=1.41 min; MS (ESIpos): m/z=521 [M+H]$^+$ $^1$H-NMR (400 MHz, CHLOROFORM-d) δ [ppm]: 0.915 (1.53), 0.932 (2.74), 0.950 (1.66), 1.411 (3.45), 1.425 (3.35), 1.454 (0.92), 1.570 (9.08), 1.615 (0.46), 1.631 (0.81), 1.646

(0.51), 1.650 (0.74), 1.655 (0.65), 1.665 (1.14), 1.670 (0.48), 1.674 (0.62), 1.680 (0.58), 1.689 (0.91), 1.705 (0.42), 1.796 (0.47), 1.819 (0.52), 1.829 (0.48), 1.908 (0.47), 1.915 (0.61), 1.923 (1.32), 1.931 (1.57), 1.936 (1.76), 1.947 (1.79), 1.951 (1.92), 1.963 (0.84), 1.966 (0.88), 1.988 (0.94), 1.993 (0.86), 2.002 (1.72), 2.007 (1.81), 2.018 (1.88), 2.023 (1.53), 2.032 (1.13), 2.045 (0.48), 2.321 (16.00), 2.804 (2.80), 2.820 (5.25), 2.836 (3.03), 3.715 (3.64), 3.731 (5.74), 3.746 (2.48), 4.656 (0.81), 4.672 (1.63), 4.687 (1.62), 4.702 (0.79), 7.322 (1.03), 7.341 (2.38), 7.361 (1.47), 7.401 (3.23), 7.416 (3.19), 7.506 (2.05), 7.525 (1.64), 7.552 (2.05), 7.571 (1.71), 8.152 (3.39), 8.181 (3.40), 9.766 (0.50).

Example 16

N-[2-(difluoromethyl)phenyl]-5-fluoro-4-(3-oxo-5,6,7,8-tetrahydro[1,2,4]triazolo[4,3-a]pyridin-2(3H)-yl)-2-[(2S)-pentan-2-yloxy]benzamide

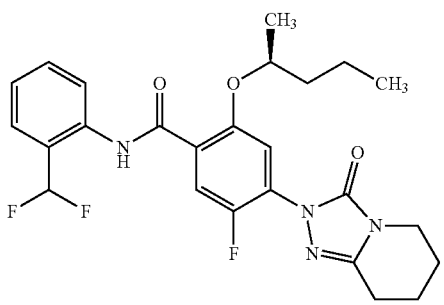 [SMILES: CCC[C@H](C)Oc1cc(-n2nc3n(c2=O)CCCC3)c(F)cc1C(=O)Nc1ccccc1C(F)F]

From intermediate 16 and 2-(difluoromethyl)aniline.

The product was purified by preparative HPLC (X-Bridge Prep C18 5 μm OBD, 0.1% aqueous formic acid, acetonitrile).

LC-MS (method A): $R_t$=1.35 min; MS (ESIpos): m/z=489 [M+H]$^+$ $^1$H-NMR (400 MHz, CHLOROFORM-d) δ [ppm]: 0.908 (6.25), 0.926 (15.09), 0.945 (7.37), 1.225 (0.41), 1.259 (0.70), 1.364 (0.46), 1.382 (0.80), 1.389 (0.59), 1.397 (0.77), 1.400 (0.83), 1.407 (1.25), 1.417 (12.87), 1.433 (12.64), 1.441 (1.71), 1.448 (0.86), 1.456 (0.90), 1.462 (0.95), 1.467 (0.71), 1.475 (0.53), 1.481 (0.87), 1.495 (0.42), 1.499 (0.48), 1.600 (16.00), 1.621 (1.11), 1.631 (0.54), 1.637 (0.64), 1.640 (0.80), 1.646 (0.79), 1.655 (1.18), 1.660 (0.54), 1.666 (0.67), 1.670 (0.64), 1.680 (0.92), 1.695 (0.44), 1.825 (0.54), 1.840 (0.72), 1.850 (0.62), 1.854 (0.73), 1.859 (0.62), 1.866 (0.72), 1.873 (0.66), 1.880 (0.63), 1.884 (0.52), 1.889 (0.50), 1.900 (0.61), 1.906 (0.57), 1.914 (0.95), 1.922 (1.46), 1.929 (1.73), 1.934 (1.94), 1.945 (1.97), 1.949 (2.11), 1.961 (0.96), 1.965 (1.00), 1.986 (1.02), 1.992 (0.95), 2.000 (1.90), 2.006 (2.01), 2.016 (2.10), 2.021 (1.73), 2.030 (1.28), 2.044 (0.54), 2.802 (3.02), 2.817 (5.72), 2.834 (3.25), 3.713 (3.70), 3.728 (6.16), 3.743 (2.70), 4.613 (0.79), 4.628 (1.58), 4.644 (1.59), 4.659 (0.79), 6.615 (1.84), 6.753 (3.62), 6.892 (1.75), 7.286 (1.13), 7.305 (2.40), 7.324 (1.44), 7.404 (3.60), 7.419 (3.60), 7.528 (1.21), 7.547 (2.08), 7.556 (2.52), 7.567 (1.24), 7.575 (2.03), 7.975 (2.34), 7.996 (2.11), 8.130 (4.67), 8.159 (4.69), 9.954 (2.50).

Example 17

N-(5-chloropyrimidin-4-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

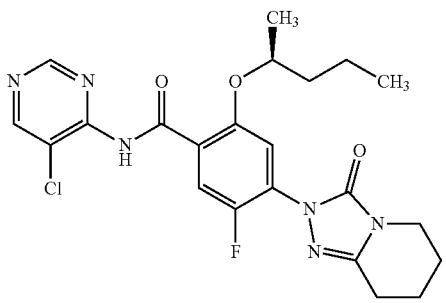 [SMILES: CCC[C@H](C)Oc1cc(-n2nc3n(c2=O)CCCC3)c(F)cc1C(=O)Nc1ncncc1Cl]

From intermediate 16 and 5-chloropyrimidin-4-amine.

The product was purified by preparative HPLC (X-Bridge Prep C18 5 μm OBD, 0.1% aqueous ammonia, acetonitrile).

LC-MS (method A): $R_t$=1.14 min; MS (ESIpos): m/z=475 [M+H]$^+$ $^1$H-NMR (400 MHz, CHLOROFORM-d) δ [ppm]: 0.931 (3.70), 0.950 (8.84), 0.969 (4.20), 1.261 (0.51), 1.416 (0.51), 1.432 (0.46), 1.435 (0.50), 1.442 (0.72), 1.450 (0.56), 1.461 (9.31), 1.476 (9.27), 1.486 (0.55), 1.494 (0.63), 1.500 (0.56), 1.505 (0.45), 1.518 (0.53), 1.575 (16.00), 1.582 (8.92), 1.679 (0.62), 1.699 (0.50), 1.704 (0.52), 1.714 (0.80), 1.724 (0.45), 1.728 (0.42), 1.739 (0.65), 1.908 (0.71), 1.917 (0.77), 1.925 (1.18), 1.934 (1.46), 1.939 (1.37), 1.948 (1.54), 1.952 (1.54), 1.956 (1.12), 1.964 (0.81), 1.968 (0.88), 1.982 (0.45), 1.989 (0.63), 2.003 (1.14), 2.009 (1.17), 2.019 (1.28), 2.024 (1.00), 2.033 (0.74), 2.803 (1.76), 2.819 (3.30), 2.835 (1.90), 3.712 (2.19), 3.727 (3.61), 3.742 (1.55), 4.662 (0.55), 4.678 (1.04), 4.693 (1.04), 4.709 (0.53), 7.473 (2.15), 7.488 (2.14), 8.140 (2.85), 8.169 (2.83), 8.669 (7.42), 9.008 (5.44), 10.680 (1.64).

Example 18

N-(3-chloropyridin-2-yl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

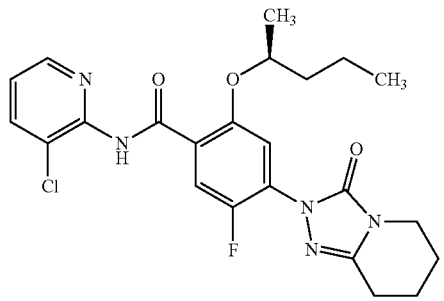 [SMILES: CCC[C@H](C)Oc1cc(-n2nc3n(c2=O)CCCC3)c(F)cc1C(=O)Nc1ncccc1Cl]

From intermediate 16 and 3-chloropyridin-2-amine.

The product was purified by preparative HPLC (X-Bridge Prep C18 5 μm OBD, 0.1% aqueous formic acid, acetonitrile).

LC-MS (method A): R$_t$=1.20 min; MS (ESIpos): m/z=474 [M+H]$^+$ $^1$H-NMR (400 MHz, CHLOROFORM-d) δ [ppm]: 0.920 (6.70), 0.939 (16.00), 0.957 (7.63), 1.257 (0.54), 1.399 (0.56), 1.410 (0.43), 1.417 (0.94), 1.425 (0.76), 1.432 (1.07), 1.443 (15.74), 1.459 (15.85), 1.467 (1.16), 1.476 (0.99), 1.481 (0.99), 1.486 (0.80), 1.493 (0.91), 1.500 (0.89), 1.506 (0.95), 1.511 (0.81), 1.519 (0.56), 1.525 (0.94), 1.539 (0.47), 1.544 (0.54), 1.655 (0.65), 1.670 (1.14), 1.681 (0.61), 1.685 (0.74), 1.690 (0.94), 1.695 (0.99), 1.704 (1.46), 1.710 (0.68), 1.715 (0.87), 1.719 (0.85), 1.730 (1.19), 1.744 (0.59), 1.879 (0.75), 1.893 (0.93), 1.896 (1.01), 1.905 (1.19), 1.909 (1.63), 1.918 (2.34), 1.930 (2.86), 1.935 (2.42), 1.941 (2.61), 1.944 (2.88), 1.956 (1.62), 1.961 (1.28), 1.969 (0.81), 1.982 (1.18), 1.988 (1.11), 1.997 (2.14), 2.002 (2.24), 2.013 (2.35), 2.017 (1.96), 2.026 (1.46), 2.040 (0.66), 2.797 (3.07), 2.814 (5.99), 2.829 (3.43), 3.709 (3.89), 3.725 (6.43), 3.740 (2.86), 4.643 (1.00), 4.659 (1.94), 4.674 (1.91), 4.690 (0.98), 7.095 (3.31), 7.106 (3.37), 7.114 (3.66), 7.126 (3.66), 7.406 (3.92), 7.421 (3.90), 7.760 (3.83), 7.765 (3.65), 7.780 (3.51), 7.784 (3.68), 8.181 (4.98), 8.210 (5.09), 8.481 (3.09), 8.486 (3.25), 8.493 (3.20), 8.498 (2.97), 10.484 (3.08).

Example 19

5-fluoro-4-(3-oxo-5,6,7,8-tetrahydro[1,2,4]triazolo[4,3-a]pyridin-2(3H)-yl)-2-[(2S)-pentan-2-yloxy]-N-[1-(pyrazin-2-yl)piperidin-4-yl]benzamide

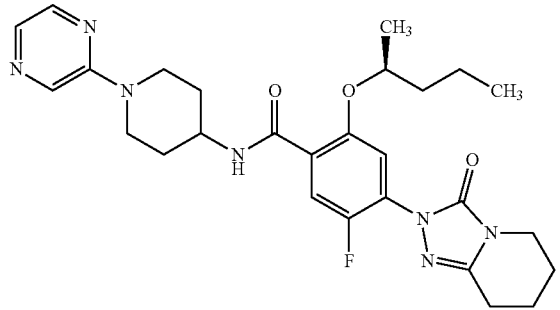 [SMILES: CCC[C@H](C)Oc1cc(-n2nc3n(c2=O)CCCC3)c(F)cc1C(=O)NC1CCN(c2cnccn2)CC1]

From intermediate 16 and 1-(pyrazin-2-yl)piperidin-4-amine.

The product was purified by preparative HPLC (X-Bridge Prep C18 5 µm OBD, 0.1% aqueous ammonia, acetonitrile).

LC-MS (method B): R$_t$=1.18 min; MS (ESIpos): m/z=524 [M+H]$^+$ $^1$H-NMR (400 MHz, CHLOROFORM-d) δ [ppm]: 0.894 (6.91), 0.913 (16.00), 0.931 (7.84), 1.357 (15.59), 1.372 (15.66), 1.384 (0.86), 1.393 (0.92), 1.395 (0.93), 1.403 (1.21), 1.410 (0.79), 1.421 (1.25), 1.430 (0.56), 1.438 (1.28), 1.443 (0.88), 1.449 (0.83), 1.457 (1.01), 1.463 (1.05), 1.467 (0.82), 1.482 (1.24), 1.495 (1.09), 1.501 (1.03), 1.521 (1.82), 1.528 (1.51), 1.552 (1.84), 1.572 (0.67), 1.580 (0.82), 1.590 (1.02), 1.604 (0.96), 1.614 (0.58), 1.618 (0.75), 1.625 (1.20), 1.628 (1.01), 1.639 (2.21), 1.650 (4.72), 1.663 (1.77), 1.678 (0.75), 1.698 (0.86), 1.712 (1.09), 1.724 (0.89), 1.729 (1.03), 1.733 (0.75), 1.740 (1.01), 1.749 (0.73), 1.754 (0.82), 1.758 (0.59), 1.763 (0.53), 1.774 (0.53), 1.891 (0.61), 1.906 (1.73), 1.918 (2.34), 1.930 (2.36), 1.934 (2.50), 1.950 (1.20), 1.971 (1.24), 1.986 (2.30), 1.990 (2.40), 2.001 (2.53), 2.006 (2.08), 2.014 (1.77), 2.029 (0.67), 2.179 (1.65), 2.187 (1.64), 2.202 (1.54), 2.211 (1.49), 2.782 (3.36), 2.798 (6.55), 2.814 (3.65), 3.142 (1.66), 3.149 (1.87), 3.170 (2.09), 3.176 (3.46), 3.182 (2.07), 3.204 (1.93), 3.211 (1.61), 3.692 (4.15), 3.707 (6.96), 3.722 (3.05), 4.236 (0.56), 4.261 (3.66), 4.271 (2.25), 4.281 (2.15), 4.293 (2.97), 4.531 (1.11), 4.546 (2.07), 4.561 (2.04), 4.576 (1.06), 7.288 (4.32), 7.302 (4.24), 7.844 (5.22), 7.851 (5.51), 8.058 (5.55), 8.068 (3.56), 8.072 (4.06), 8.074 (3.78), 8.079 (3.56), 8.088 (5.35), 8.184 (2.24), 8.195 (6.10), 8.198 (6.16).

Example 20

N-[1-(cyclopropylcarbonyl)piperidin-4-yl]-5-fluoro-4-(3-oxo-5,6,7,8-tetrahydro[1,2,4]triazolo[4,3-a]pyridin-2(3H)-yl)-2-[(2S)-pentan-2-yloxy]benzamide

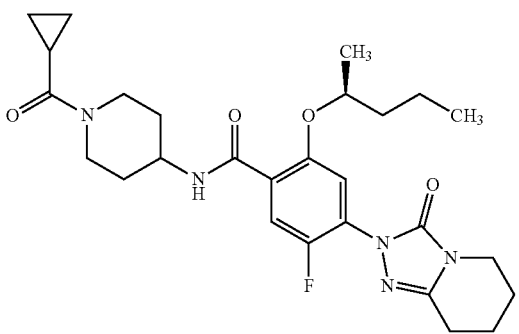 [SMILES: CCC[C@H](C)Oc1cc(-n2nc3n(c2=O)CCCC3)c(F)cc1C(=O)NC1CCN(C(=O)C2CC2)CC1]

From intermediate 16 and (4-aminopiperidin-1-yl)(cyclopropyl)methanone.

The product was purified by preparative HPLC (X-Bridge Prep C18 5 µm OBD, 0.1% aqueous formic acid, acetonitrile).

LC-MS (method B): R$_t$=1.12 min; MS (ESIpos): m/z=514 [M+H]$^+$ $^1$H-NMR (400 MHz, CHLOROFORM-d) δ [ppm]: 0.739 (2.24), 0.749 (8.60), 0.757 (9.81), 0.770 (8.61), 0.777 (10.19), 0.786 (2.76), 0.921 (6.84), 0.939 (13.91), 0.958 (10.83), 0.967 (11.75), 0.974 (9.50), 0.979 (11.09), 0.986 (8.74), 0.996 (2.88), 1.353 (11.57), 1.367 (12.46), 1.402 (4.89), 1.423 (5.15), 1.461 (3.04), 1.498 (0.88), 1.516 (0.48), 1.592 (0.85), 1.607 (1.46), 1.627 (1.89), 1.641 (2.60), 1.651 (1.80), 1.655 (1.67), 1.665 (2.00), 1.680 (0.97), 1.700 (1.40), 1.715 (2.14), 1.726 (1.82), 1.730 (2.06), 1.740 (3.55), 1.752 (4.51), 1.760 (4.46), 1.763 (3.17), 1.771 (6.46), 1.780 (2.57), 1.783 (3.26), 1.792 (3.20), 1.803 (1.33), 1.865 (9.27), 1.873 (2.21), 1.882 (2.04), 1.890 (4.00), 1.897 (4.77), 1.902 (5.26), 1.914 (5.46), 1.918 (5.68), 1.930 (2.67), 1.934 (2.75), 1.955 (2.83), 1.961 (2.75), 1.970 (5.28), 1.975 (5.53), 1.985 (5.99), 1.990 (5.16), 1.997 (4.69), 2.005 (2.88), 2.013 (2.73), 2.203 (1.47), 2.764 (7.72), 2.780 (14.85), 2.796 (8.44), 2.866 (0.99), 2.895 (1.68), 2.924 (1.02), 3.283 (1.01), 3.312 (1.67), 3.342 (0.98), 3.675 (9.57), 3.690 (16.00), 3.704 (6.90), 4.153 (1.54), 4.167 (1.65), 4.178 (2.27), 4.188 (2.49), 4.195 (2.83), 4.205 (2.81), 4.214 (2.18), 4.223 (2.36), 4.232 (1.77), 4.250 (0.95), 4.260 (0.48), 4.487 (1.54), 4.510 (1.86), 4.525 (3.68), 4.540 (5.10), 4.556 (4.74), 4.571 (2.42), 4.586 (0.53), 7.288 (9.79), 8.027 (11.72), 8.056 (11.80), 8.157 (4.23), 8.176 (4.12).

Example 21

5-fluoro-N-[1-(methylsulfonyl)piperidin-4-yl]-4-(3-oxo-5,6,7,8-tetrahydro[1,2,4]triazolo[4,3-a]-pyridin-2(3H)-yl)-2-[(2S)-pentan-2-yloxy]benzamide

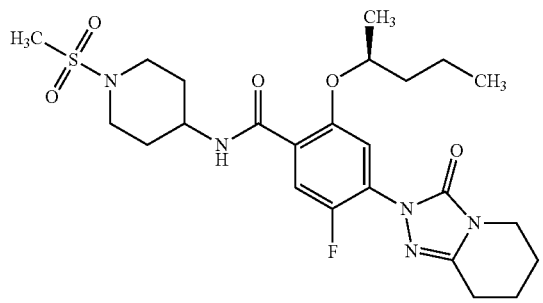 [SMILES: CCC[C@H](C)Oc1cc(-n2nc3n(c2=O)CCCC3)c(F)cc1C(=O)NC1CCN(S(C)(=O)=O)CC1]

From intermediate 16 and 1-(methylsulfonyl)piperidin-4-amine.

The product was purified by preparative HPLC (X-Bridge Prep C18 5 μm OBD, 0.1% aqueous formic acid, acetonitrile).

LC-MS (method A): $R_t$=1.07 min; MS (ESIpos): m/z=524 [M+H]$^+$ $^1$H-NMR (400 MHz, CHLOROFORM-d) δ [ppm]: 0.955 (2.98), 0.973 (7.37), 0.991 (3.43), 1.378 (6.54), 1.393 (6.64), 1.407 (0.42), 1.433 (0.51), 1.448 (0.49), 1.450 (0.53), 1.466 (0.61), 1.485 (0.46), 1.490 (0.44), 1.509 (0.44), 1.600 (1.54), 1.618 (0.94), 1.624 (1.00), 1.639 (0.55), 1.649 (0.47), 1.653 (0.49), 1.659 (0.66), 1.673 (0.67), 1.683 (0.41), 1.697 (0.53), 1.743 (0.46), 1.759 (0.42), 1.770 (0.41), 1.910 (0.68), 1.922 (0.91), 1.934 (0.93), 1.937 (0.99), 1.949 (0.46), 1.953 (0.47), 1.975 (0.49), 1.989 (0.89), 1.994 (0.95), 2.005 (0.99), 2.010 (0.81), 2.017 (0.64), 2.179 (0.63), 2.189 (0.64), 2.785 (1.37), 2.801 (2.70), 2.820 (16.00), 2.835 (0.78), 2.841 (0.81), 2.866 (1.36), 2.871 (1.29), 2.895 (0.79), 2.901 (0.66), 3.696 (1.69), 3.711 (2.82), 3.726 (1.24), 3.817 (1.00), 3.847 (0.93), 4.100 (0.43), 4.119 (0.43), 4.552 (0.44), 4.567 (0.85), 4.582 (0.85), 4.597 (0.43), 7.299 (1.76), 7.314 (1.72), 8.034 (2.31), 8.064 (2.24), 8.190 (0.77), 8.209 (0.76).

Example 22

5-fluoro-N-(1-methyl-2-oxopiperidin-(4R,S)-4-yl)-4-(3-oxo-5,6,7,8-tetrahydro[1,2,4]triazolo[4,3-a]pyridin-2(3H)-yl)-2-[(2S)-pentan-2-yloxy]benzamide, Mixture of Diastereomers

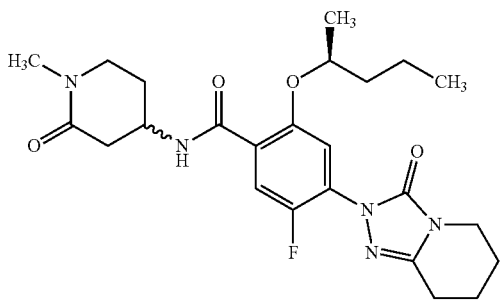 [SMILES: CCC[C@H](C)Oc1cc(-n2nc3n(c2=O)CCCC3)c(F)cc1C(=O)NC1CCN(C)C(=O)C1]

From intermediate 16 and rac-4-amino-1-methylpiperidin-2-one.

The product was purified by preparative HPLC (X-Bridge Prep C18 5 μm OBD, 0.1% aqueous formic acid, acetonitrile).

LC-MS (method A): $R_t$=0.97 min; MS (ESIpos): m/z=474 [M+H]$^+$ $^1$H-NMR (400 MHz, CHLOROFORM-d) δ [ppm]: 0.941 (1.17), 0.952 (1.22), 0.959 (2.87), 0.970 (2.72), 0.977 (1.37), 0.989 (1.22), 1.279 (16.00), 1.350 (2.40), 1.365 (4.96), 1.381 (2.72), 1.621 (1.15), 1.635 (0.69), 1.640 (0.47), 1.645 (0.41), 1.901 (0.44), 1.909 (0.70), 1.922 (0.96), 1.933 (0.88), 1.936 (0.88), 1.941 (0.69), 1.954 (0.45), 1.988 (0.66), 1.993 (0.68), 2.004 (0.72), 2.009 (0.58), 2.018 (0.42), 2.300 (0.45), 2.320 (0.41), 2.342 (0.48), 2.363 (0.48), 2.784 (1.03), 2.800 (2.04), 2.816 (1.52), 2.990 (7.27), 3.362 (0.42), 3.378 (0.78), 3.385 (0.42), 3.392 (0.44), 3.397 (0.44), 3.694 (1.26), 3.709 (2.09), 3.725 (0.90), 4.570 (0.43), 4.582 (0.41), 7.304 (1.27), 7.319 (1.24), 8.042 (1.74), 8.071 (1.70), 8.239 (0.55), 8.256 (0.53).

Example 23

5-fluoro-N-(1-methylpiperidin-4-yl)-4-(3-oxo-5,6,7,8-tetrahydro[1,2,4]triazolo[4,3-a]pyridin-2(3H)-yl)-2-[(2S)-pentan-2-yloxy]benzamide

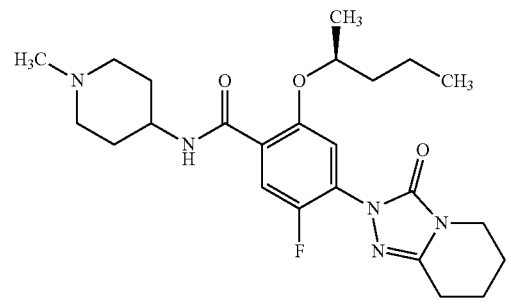 [SMILES: CCC[C@H](C)Oc1cc(-n2nc3n(c2=O)CCCC3)c(F)cc1C(=O)NC1CCN(C)CC1]

From intermediate 16 and 1-methylpiperidin-4-amine.

The product was purified by preparative HPLC (X-Bridge Prep C18 5 μm OBD, 0.1% aqueous ammonia, acetonitrile).

LC-MS (method B): $R_t$=1.11 min; MS (ESIpos): m/z=460 [M+H]$^+$ $^1$H-NMR (400 MHz, CHLOROFORM-d) δ [ppm]: 0.919 (4.45), 0.937 (10.63), 0.955 (5.06), 1.344 (9.61), 1.359 (9.80), 1.378 (0.64), 1.385 (0.48), 1.393 (0.54), 1.396 (0.55), 1.403 (0.72), 1.411 (0.52), 1.419 (0.61), 1.421 (0.73), 1.427 (0.48), 1.436 (0.59), 1.440 (0.67), 1.446 (0.53), 1.452 (0.54), 1.459 (0.60), 1.465 (0.65), 1.470 (0.51), 1.484 (0.66), 1.503 (0.64), 1.516 (0.55), 1.538 (1.01), 1.564 (1.07), 1.590 (0.80), 1.604 (0.81), 1.618 (0.46), 1.624 (0.67), 1.628 (0.54), 1.639 (0.96), 1.649 (0.59), 1.652 (0.56), 1.662 (0.75), 1.721 (0.48), 1.735 (0.63), 1.737 (0.61), 1.747 (0.53), 1.751 (0.62), 1.755 (0.48), 1.761 (0.58), 1.762 (0.58), 1.769 (0.45), 1.772 (0.47), 1.776 (0.49), 1.878 (0.52), 1.887 (1.10), 1.894 (1.33), 1.899 (1.48), 1.910 (1.51), 1.914 (1.58), 1.926 (0.75), 1.930 (0.78), 1.951 (0.81), 1.958 (0.79), 1.966 (1.50), 1.971 (1.55), 1.982 (1.65), 1.987 (1.37), 1.995 (1.08), 2.010 (0.77), 2.031 (1.40), 2.041 (1.27), 2.052 (1.16), 2.063 (1.19), 2.131 (0.68), 2.162 (1.17), 2.189 (0.67), 2.298 (16.00), 2.761 (2.44), 2.777 (4.83), 2.793 (3.09), 3.672 (2.59), 3.688 (4.25), 3.703 (1.92), 3.977 (0.48), 3.986 (0.46), 3.995 (0.48), 4.520 (0.68), 4.535

(1.29), 4.551 (1.27), 4.566 (0.65), 7.261 (2.67), 8.031 (3.34), 8.061 (3.30), 8.121 (1.02), 8.141 (1.00).

Examples 24-27 were prepared in analogy according to the general methods described above.

Example 24

N-(2-aminophenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

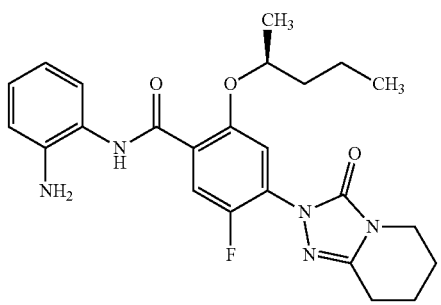 [SMILES: CCC[C@H](C)Oc1cc(-n2nc3n(c2=O)CCCC3)c(F)cc1C(=O)Nc1ccccc1N]

Example 25

5-fluoro-N-[2-(methylamino)phenyl]-4-(3-oxo-5,6,7,8-tetrahydro[1,2,4]triazolo[4,3-a]pyridin-2(3H)-yl)-2-[(2S)-pentan-2-yloxy]benzamide

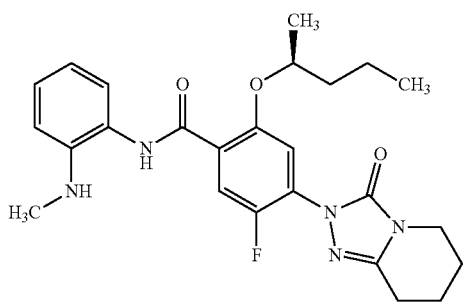 [SMILES: CCC[C@H](C)Oc1cc(-n2nc3n(c2=O)CCCC3)c(F)cc1C(=O)Nc1ccccc1NC]

Example 26

N-(2-amino-6-methylphenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

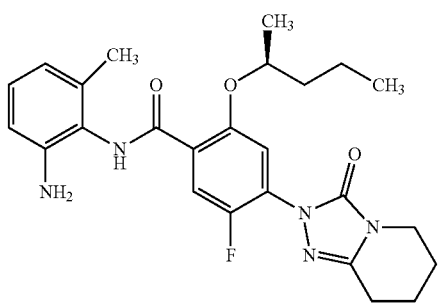 [SMILES: CCC[C@H](C)Oc1cc(-n2nc3n(c2=O)CCCC3)c(F)cc1C(=O)Nc1c(C)cccc1N]

MS (ESIpos): m/z=468.3 [M+H]+

¹H-NMR (400 MHz, DMSO-d6) δ[ppm]: −0.149 (0.42), -0.008 (4.72), 0.008 (3.65), 0.146 (0.42), 0.863 (4.75), 0.882 (11.10), 0.900 (5.34), 1.275 (9.68), 1.290 (9.59), 1.323 (0.45), 1.341 (0.71), 1.356 (0.71), 1.366 (0.89), 1.374 (0.68), 1.384 (0.89), 1.403 (0.83), 1.415 (0.71), 1.423 (0.74), 1.428 (0.80), 1.447 (0.80), 1.527 (0.42), 1.541 (0.68), 1.561 (0.74), 1.575 (1.04), 1.585 (0.71), 1.599 (0.77), 1.655 (0.53), 1.670 (0.74), 1.685 (0.77), 1.695 (0.71), 1.710 (0.62), 1.730 (0.42), 1.794 (1.42), 1.806 (2.02), 1.821 (2.08), 1.833 (1.04), 1.888 (2.08), 1.898 (2.14), 1.912 (1.31), 2.146 (16.00), 2.368 (1.10), 2.525 (2.49), 2.671 (0.45), 2.691 (2.32), 2.706 (4.63), 2.723 (2.43), 3.557 (2.70), 3.572 (4.78), 3.587 (2.20), 4.560 (0.77), 4.575 (1.45), 4.590 (1.45), 4.605 (0.74), 4.874 (1.37), 6.458 (2.05), 6.476 (2.20), 6.583 (2.05), 6.601 (2.35), 6.886 (1.96), 6.906 (3.06), 6.925 (1.57), 7.301 (3.00), 7.316 (2.91), 7.641 (3.62), 7.667 (3.56), 9.262 (4.36).

Example 27

N-(4-amino-2-methylphenyl)-5-fluoro-4-(3-oxo-5,6,7,8-tetrahydro[1,2,4]triazolo[4,3-a]pyridin-2(3H)-yl)-2-[(2S)-pentan-2-yloxy]benzamide

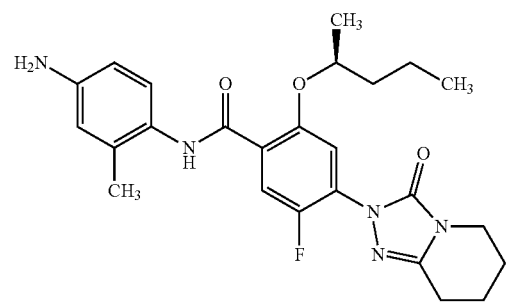 [SMILES: CCC[C@H](C)Oc1cc(-n2nc3n(c2=O)CCCC3)c(F)cc1C(=O)Nc1ccc(N)cc1C]

Example 28

5-fluoro-N-(2-fluoro-6-methylphenyl)-4-(3-oxo-5,6,7,8-tetrahydro[1,2,4]triazolo[4,3-a]pyridin-2(3H)-yl)-2-[(2S)-pentan-2-yloxy]benzamide

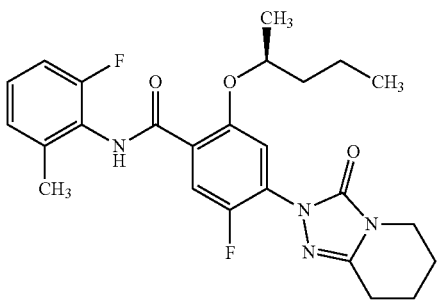 [SMILES: CCC[C@H](C)Oc1cc(-n2nc3n(c2=O)CCCC3)c(F)cc1C(=O)Nc1c(C)cccc1F]

Example 28 was prepared as described for example 1 from 5-fluoro-4-(3-oxo-5,6,7,8-tetrahydro[1,2,4]triazolo[4,3-a]pyridin-2(3H)-yl)-2-[(2S)-pentan-2-yloxy]benzoic acid (intermediate 16) and 2-fluoro-6-methylaniline.

The product was purified by preparative HPLC (X-Bridge Prep C18 5 μm OBD, 0.1% aqueous ammonia, acetonitrile).

LC-MS (method A): $R_t$=1.33 min; MS (ESIpos): m/z=471.3 [M+H]$^+$ $^1$H-NMR (400 MHz, CHLOROFORM-d) δ [ppm]: 0.936 (5.02), 0.954 (12.41), 0.972 (5.77), 1.430 (11.33), 1.445 (11.53), 1.458 (0.59), 1.466 (0.57), 1.469 (0.63), 1.477 (0.49), 1.484 (0.61), 1.491 (0.54), 1.496 (0.48), 1.503 (0.61), 1.510 (0.57), 1.516 (0.61), 1.522 (0.49), 1.535 (0.64), 1.582 (4.28), 1.655 (0.40), 1.670 (0.72), 1.684 (0.44), 1.689 (0.63), 1.695 (0.58), 1.704 (1.04), 1.715 (0.57), 1.719 (0.54), 1.729 (0.83), 1.811 (0.48), 1.825 (0.61), 1.837 (0.52), 1.841 (0.61), 1.846 (0.44), 1.853 (0.58), 1.860 (0.46), 1.867 (0.49), 1.902 (0.44), 1.912 (0.44), 1.921 (1.01), 1.928 (1.20), 1.933 (1.35), 1.945 (1.39), 1.948 (1.50), 1.960 (0.66), 1.964 (0.69), 1.985 (0.71), 1.991 (0.63), 2.000 (1.32), 2.005 (1.39), 2.015 (1.48), 2.020 (1.21), 2.029 (0.90), 2.326 (16.00), 2.801 (2.19), 2.817 (4.23), 2.833 (2.45), 3.711 (2.82), 3.727 (4.62), 3.741 (2.00), 4.641 (0.70), 4.656 (1.38), 4.671 (1.36), 4.687 (0.68), 6.986 (0.71), 7.006 (1.53), 7.031 (0.92), 7.060 (1.26), 7.080 (1.83), 7.151 (1.05), 7.164 (1.09), 7.171 (1.44), 7.185 (1.42), 7.190 (0.67), 7.204 (0.62), 7.399 (2.84), 7.414 (2.80), 8.131 (3.86), 8.160 (3.73), 9.562 (2.06).

Example 29

N-(2,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

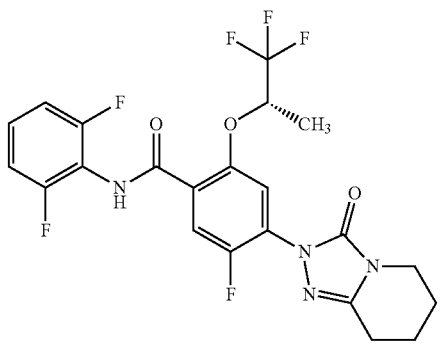 [SMILES: C[C@H](Oc1cc(-n2nc3n(c2=O)CCCC3)c(F)cc1C(=O)Nc1c(F)cccc1F)C(F)(F)F]

To a 0° C. stirred solution of 5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid (intermediate 17) (80.0 mg, 205 μmol) and catalytic N,N-dimethylformamide (3 drops) in anhydrous dichloromethane (1.5 ml) was added oxalyl chloride (21 μl, 250 μmol). The resulting mixture was warmed to room temperature, stirred for 90 minutes and concentrated under reduced pressure. A solution of the crude acid chloride in dichloromethane (1.0 ml) was then added dropwise to a 0° C. stirred solution of 2,6-difluoroaniline (29 mg, 226 μmol) and triethylamine (32 μl, 230 μmol) in anhydrous dichloromethane (2.0 ml). Following complete addition, the mixture was warmed to room temperature, stirred for 2 hours and concentrated under reduced pressure. The residue was dissolved in DMSO, filtered through a teflon filter and purified by reverse phase column chromatography (acetonitrile, 0.1% aqueous formic acid) to give the amide as a white solid (88 mg, 86%).

LC-MS (method A): $R_t$=1.19 min; MS (ESIneg): m/z=499 [M−H]$^-$ $^1$H-NMR (400 MHz, DMSO-d6) δ[ppm]: 1.035 (0.67), 1.052 (1.37), 1.070 (0.72), 1.428 (16.00), 1.444 (15.78), 1.512 (0.72), 1.795 (3.93), 1.807 (5.48), 1.818 (5.46), 1.822 (5.57), 1.835 (2.76), 1.875 (2.76), 1.890 (5.66), 1.900 (5.84), 1.905 (4.85), 1.914 (3.60), 1.929 (1.37), 2.331 (0.92), 2.518 (5.21), 2.522 (3.46), 2.673 (1.15), 2.678 (0.76), 2.696 (6.07), 2.712 (11.84), 2.729 (6.22), 3.561 (7.12), 3.577 (12.72), 3.591 (5.80), 5.272 (1.15), 5.287 (2.63), 5.304 (3.39), 5.319 (2.47), 5.335 (1.03), 7.187 (4.79), 7.208 (9.78), 7.228 (6.02), 7.367 (1.03), 7.382 (2.36), 7.403 (3.28), 7.424 (1.73), 7.440 (0.72), 7.541 (5.75), 7.560 (8.40), 7.585 (6.27), 9.985 (10.67).

Examples 30-112 were prepared as described for example 29 from 5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid (intermediate 17) and the respective amines, as indicated. Products were purified by flash column chromatography or, if explicitly mentioned, by preparative HPLC. Example 52 was prepared from example 51 by deprotection of the azetidine nitrogen, as described below.

Example 30

5-fluoro-4-(3-oxo-5,6,7,8-tetrahydro[1,2,4]triazolo[4,3-a]pyridin-2(3H)-yl)-N-[3-(trifluoromethyl)phenyl]-2-{[(2S)-1,1,1-trifluoropropan-2-yl]oxy}benzamide

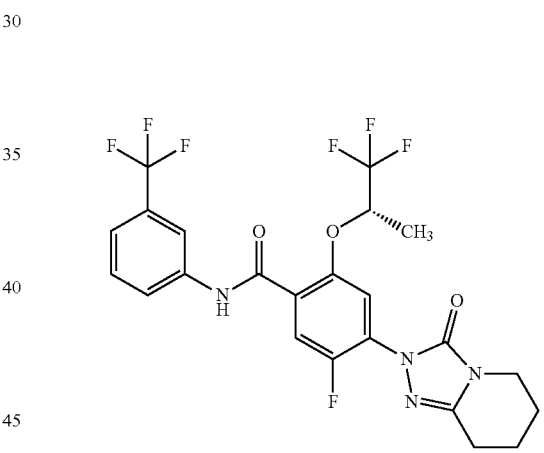

From intermediate 17 and 3-(trifluoromethyl)aniline.

MS (ESIpos): m/z=533 (M+H)$^+$ $^1$H-NMR (400 MHz, DMSO-d6) δ[ppm]: 0.851 (0.68), 1.172 (0.55), 1.233 (2.37), 1.404 (16.00), 1.420 (15.81), 1.796 (3.05), 1.808 (4.25), 1.823 (4.35), 1.835 (2.17), 1.890 (4.32), 1.901 (4.51), 1.929 (1.17), 1.987 (1.33), 2.006 (0.52), 2.322 (1.49), 2.326 (1.98), 2.331 (1.36), 2.522 (5.42), 2.537 (1.56), 2.664 (1.62), 2.669 (2.08), 2.673 (1.53), 2.697 (5.03), 2.713 (9.83), 2.730 (5.32), 3.562 (5.87), 3.577 (10.45), 3.592 (4.64), 5.246 (1.10), 5.262 (2.66), 5.278 (3.47), 5.294 (2.50), 5.309 (1.04), 7.464 (3.44), 7.483 (4.51), 7.527 (6.46), 7.542 (6.39), 7.587 (2.89), 7.607 (5.13), 7.626 (2.56), 7.652 (8.63), 7.678 (8.37), 7.835 (3.83), 7.856 (3.18), 8.173 (6.78), 10.616 (10.19).

Example 31

N-[2-chloro-4-(pentafluoro-lambda⁶-sulfanyl)phenyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

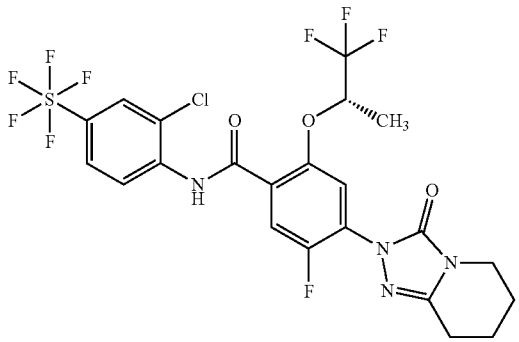 [SMILES: C[C@H](Oc1cc(-n2nc3n(c2=O)CCCC3)c(F)cc1C(=O)Nc1ccc(S(F)(F)(F)(F)F)cc1Cl)C(F)(F)F]

From intermediate 17 and 2-chloro-4-(pentafluoro-lambda6-sulfanyl)aniline.

LC-MS (method A): $R_t$=1.54 min; MS (ESIpos): m/z=625 [M+H]$^+$ $^1$H-NMR (400 MHz, CHLOROFORM-d) δ [ppm]: 1.421 (0.43), 1.623 (5.93), 1.656 (16.00), 1.673 (15.82), 1.914 (0.94), 1.929 (2.69), 1.941 (3.70), 1.953 (3.71), 1.957 (3.96), 1.969 (1.86), 1.972 (1.92), 1.994 (1.90), 2.000 (1.88), 2.009 (3.60), 2.014 (3.79), 2.024 (3.99), 2.029 (3.33), 2.038 (2.44), 2.052 (1.02), 2.805 (5.06), 2.821 (9.80), 2.838 (5.50), 3.713 (6.39), 3.729 (10.67), 3.744 (4.78), 4.879 (1.07), 4.895 (2.48), 4.910 (3.22), 4.926 (2.38), 4.941 (0.96), 7.542 (6.43), 7.556 (6.39), 7.708 (3.70), 7.715 (4.06), 7.732 (3.82), 7.738 (4.24), 7.839 (9.64), 7.845 (8.84), 8.086 (8.20), 8.114 (8.14), 8.727 (4.11), 8.750 (3.83), 9.870 (5.68).

Example 32

5-fluoro-N-(oxetan-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

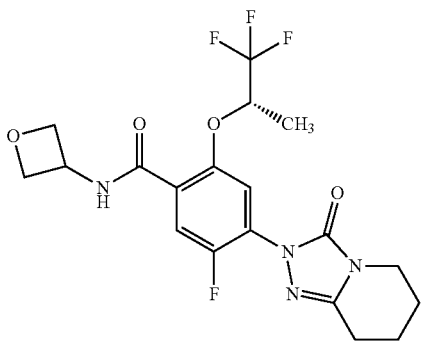 [SMILES: C[C@H](Oc1cc(-n2nc3n(c2=O)CCCC3)c(F)cc1C(=O)NC1COC1)C(F)(F)F]

From intermediate 17 and oxetan-3-amine.

LC-MS (method A): $R_t$=0.92 min; MS (ESIpos): m/z=445 [M+H]$^+$ $^1$H-NMR (400 MHz, CHLOROFORM-d) δ [ppm]: 1.631 (15.14), 1.647 (16.00), 1.902 (0.83), 1.909 (1.06), 1.918 (2.41), 1.925 (2.82), 1.930 (3.26), 1.941 (3.31), 1.945 (3.53), 1.957 (1.59), 1.961 (1.66), 1.983 (1.64), 1.989 (1.61), 1.998 (3.18), 2.003 (3.32), 2.014 (3.61), 2.019 (2.89), 2.028 (2.22), 2.042 (0.93), 2.624 (3.46), 2.715 (0.82), 2.790 (4.94), 2.805 (9.55), 2.822 (5.51), 2.993 (1.49), 3.697 (6.16), 3.713 (9.97), 3.728 (4.49), 4.392 (0.50), 4.563 (5.46), 4.580 (10.99), 4.596 (6.03), 4.839 (0.98), 4.854 (2.28), 4.870 (2.97), 4.885 (2.19), 4.900 (0.88), 4.977 (3.73), 4.981 (3.73), 4.995 (7.31), 4.998 (7.15), 5.013 (3.94), 5.016 (4.02), 5.201 (0.60), 5.219 (1.71), 5.235 (3.29), 5.253 (3.05), 5.269 (1.38), 7.391 (6.46), 7.405 (6.37), 8.033 (8.67), 8.062 (8.84), 8.104 (2.07), 8.121 (2.03).

Example 33

N-[2-(difluoromethyl)phenyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

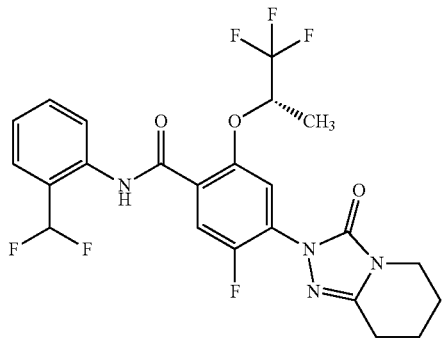 [SMILES: C[C@H](Oc1cc(-n2nc3n(c2=O)CCCC3)c(F)cc1C(=O)Nc1ccccc1C(F)F)C(F)(F)F]

From intermediate 17 and 2-(difluoromethyl)aniline.

LC-MS (method A): $R_t$=1.24 min; MS (ESIpos): m/z=515 [M+H]$^+$ $^1$H-NMR (400 MHz, CHLOROFORM-d) δ [ppm]: 1.625 (15.67), 1.641 (16.00), 1.710 (0.58), 1.905 (1.16), 1.920 (3.18), 1.932 (4.51), 1.944 (4.50), 1.947 (4.77), 1.959 (2.44), 1.963 (2.46), 1.985 (2.34), 2.004 (4.62), 2.015 (4.86), 2.028 (3.12), 2.043 (1.34), 2.316 (0.45), 2.796 (5.56), 2.812 (10.82), 2.829 (6.17), 3.705 (6.59), 3.721 (11.38), 3.735 (5.40), 4.864 (1.06), 4.880 (2.49), 4.895 (3.25), 4.911 (2.46), 4.926 (1.07), 6.614 (3.39), 6.753 (6.73), 6.891 (3.29), 7.302 (2.16), 7.320 (4.82), 7.339 (2.98), 7.485 (6.25), 7.499 (6.34), 7.525 (2.39), 7.547 (7.45), 7.568 (5.51), 7.919 (4.68), 7.938 (4.17), 8.098 (7.10), 8.127 (6.95), 9.384 (4.86).

Example 34

5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}-N-(1,3,5-trimethyl-1H-pyrazol-4-yl)benzamide

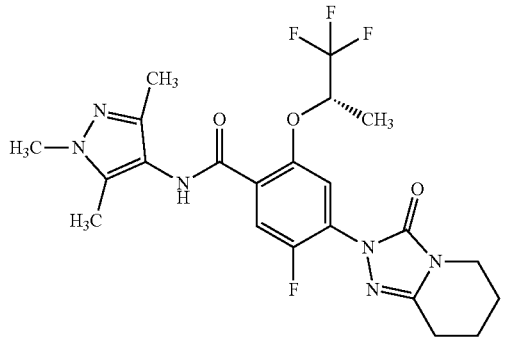 [SMILES: Cc1nn(C)c(C)c1NC(=O)c1cc(F)c(-n2nc3n(c2=O)CCCC3)cc1O[C@@H](C)C(F)(F)F]

From intermediate 17 and 1,3,5-trimethyl-1H-pyrazol-4-amine.

LC-MS (method A): $R_t$=0.97 min; MS (ESIpos): m/z=497 [M+H]$^+$ $^1$H-NMR (400 MHz, CHLOROFORM-d) δ [ppm]: 1.463 (4.62), 1.479 (4.72), 1.761 (1.74), 1.775 (1.78), 1.844 (1.99), 2.007 (16.00), 2.625 (1.74), 2.640 (3.09), 2.656 (1.75), 3.532 (1.92), 3.546 (3.26), 3.561 (2.02), 3.584 (9.16), 4.733 (0.76), 4.748 (0.98), 4.763 (0.75), 7.108 (1.50), 7.284 (1.71), 7.946 (2.04), 7.976 (1.77), 8.376 (1.94).

Example 35

N-(2-chloro-3-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

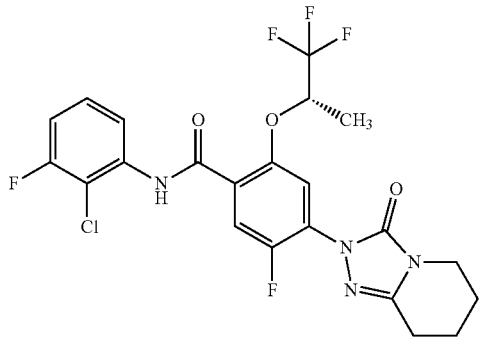 [SMILES: C[C@H](Oc1cc(-n2nc3n(c2=O)CCCC3)c(F)cc1C(=O)Nc1cccc(F)c1Cl)C(F)(F)F]

From intermediate 17 and 2-chloro-3-fluoroaniline.

LC-MS (method A): $R_t$=1.36 min; MS (ESIpos): m/z=517 [M+H]$^+$ $^1$H-NMR (400 MHz, CHLOROFORM-d) δ [ppm]: 1.571 (16.00), 1.657 (1.59), 1.673 (1.59), 2.807 (0.55), 2.822 (1.04), 2.839 (0.60), 3.716 (0.71), 3.731 (1.15), 3.746 (0.50), 6.975 (0.55), 6.979 (0.54), 7.295 (0.46), 7.310 (0.45), 7.515 (0.69), 7.529 (0.77), 8.099 (0.87), 8.128 (0.86), 8.357 (0.46), 8.378 (0.45), 9.748 (0.44).

Example 36

N-(2-chloro-4-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

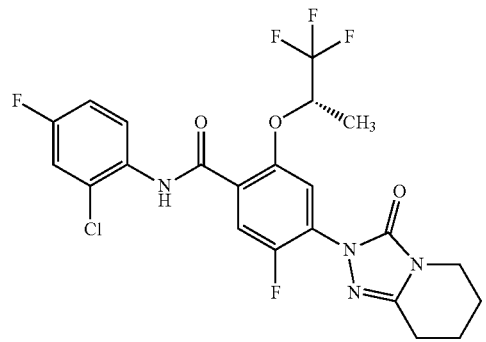 [SMILES: C[C@H](Oc1cc(-n2nc3n(c2=O)CCCC3)c(F)cc1C(=O)Nc1ccc(F)cc1Cl)C(F)(F)F]

From intermediate 17 and 2-chloro-4-fluoroaniline.

LC-MS (method A): $R_t$=1.35 min; MS (ESIpos): m/z=517 [M+H]$^+$ $^1$H-NMR (400 MHz, CHLOROFORM-d) δ [ppm]: 1.574 (16.00), 1.647 (3.49), 1.662 (3.53), 1.929 (0.58), 1.941 (0.79), 1.953 (0.78), 1.956 (0.86), 1.972 (0.41), 1.993 (0.40), 2.009 (0.76), 2.013 (0.80), 2.019 (1.12), 2.024 (0.87), 2.029 (0.70), 2.038 (0.53), 2.805 (1.20), 2.821 (2.28), 2.837 (1.33), 3.714 (1.55), 3.730 (2.55), 3.744 (1.11), 4.887 (0.57), 4.903 (0.74), 4.918 (0.55), 7.039 (0.48), 7.046 (0.53), 7.058 (0.53), 7.062 (0.56), 7.065 (0.61), 7.069 (0.61), 7.081 (0.49), 7.089 (0.54), 7.176 (1.26), 7.183 (1.16), 7.197 (1.25), 7.204 (1.15), 7.498 (1.48), 7.512 (1.50), 8.106 (1.91), 8.135 (1.83), 8.448 (0.98), 8.462 (1.01), 8.471 (0.99), 8.485 (0.94), 9.613 (1.04).

Example 37

5-fluoro-N-[2-methyl-3-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

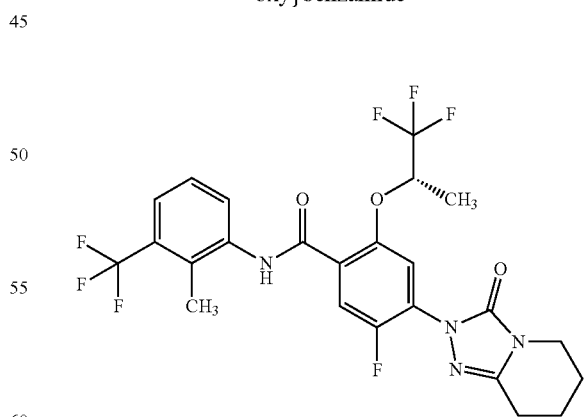

From intermediate 17 and 2-methyl-3-(trifluoromethyl)aniline.

LC-MS (method A): $R_t$=1.36 min; MS (ESIpos): m/z=547 [M+H]$^+$ $^1$H-NMR (400 MHz, CHLOROFORM-d) δ [ppm]: 1.577 (16.00), 1.644 (2.65), 1.660 (2.67), 1.933 (0.46), 1.945

(0.63), 1.956 (0.63), 1.960 (0.69), 2.013 (0.61), 2.018 (0.68), 2.028 (0.69), 2.033 (0.57), 2.042 (0.43), 2.407 (3.39), 2.810 (0.92), 2.826 (1.80), 2.842 (1.05), 3.717 (1.15), 3.733 (1.93), 3.748 (0.86), 4.927 (0.42), 4.942 (0.54), 4.958 (0.41), 5.310 (0.41), 7.360 (0.76), 7.380 (0.44), 7.497 (1.12), 7.511 (1.11), 7.535 (0.85), 7.555 (0.68), 7.983 (0.74), 8.003 (0.70), 8.153 (1.37), 8.181 (1.34), 9.136 (0.83).

Example 38

5-fluoro-N-[2-methyl-4-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

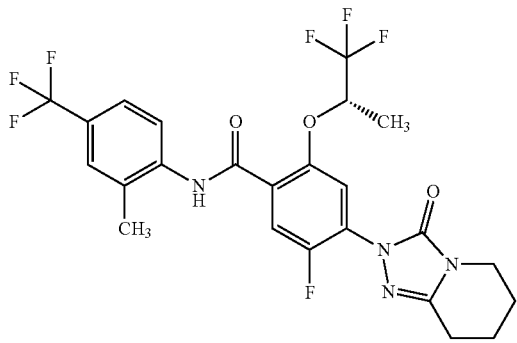 [SMILES: Cc1cc(C(F)(F)F)ccc1NC(=O)c1cc(F)c(-n2nc3n(c2=O)CCCC3)cc1O[C@@H](C)C(F)(F)F]

From intermediate 17 and 2-methyl-4-(trifluoromethyl)aniline.
LC-MS (method A): $R_t$=1.39 min; MS (ESIpos): m/z=547 [M+H]$^+$
$^1$H-NMR (400 MHz, CHLOROFORM-d) δ [ppm]: 1.572 (16.00), 1.628 (1.48), 1.644 (1.48), 2.374 (3.61), 2.809 (0.53), 2.825 (1.01), 2.841 (0.59), 3.717 (0.68), 3.732 (1.13), 3.748 (0.48), 7.499 (0.63), 7.507 (0.71), 7.522 (0.84), 8.132 (0.78), 8.161 (0.77), 8.185 (0.43), 8.206 (0.40), 9.156 (0.43).

Example 39

N-(2-chloro-3,5-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

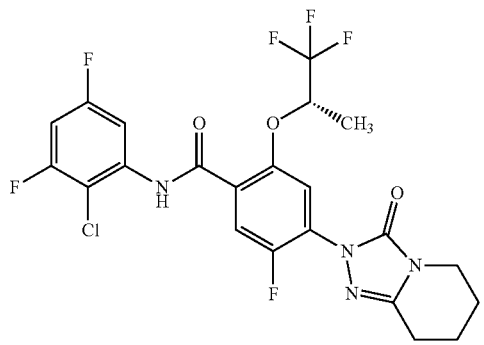

From intermediate 17 and 2-chloro-3,5-difluoroaniline.
LC-MS (method A): $R_t$=1.43 min; MS (ESIpos): m/z=535 [M+H]$^+$ $^1$H-NMR (400 MHz, CHLOROFORM-d) δ [ppm]: 1.571 (16.00), 1.657 (0.75), 1.674 (0.75), 2.823 (0.49), 3.731 (0.56), 8.076 (0.44), 8.105 (0.45).

Example 40

N-(3,5-dimethyl-1,2-oxazol-4-yl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

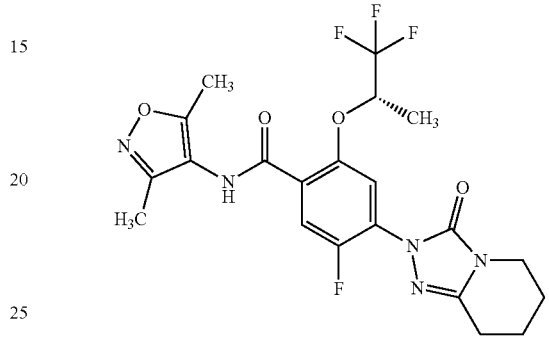

From intermediate 17 and 3,5-dimethyl-1,2-oxazol-4-amine.
LC-MS (method A): $R_t$=1.05 min; MS (ESIneg): m/z=482 [M−H]$^−$
$^1$H-NMR (400 MHz, CHLOROFORM-d) δ [ppm]: 1.599 (10.02), 1.656 (3.90), 1.672 (3.91), 1.931 (0.67), 1.938 (0.78), 1.943 (0.89), 1.954 (0.90), 1.958 (0.96), 1.970 (0.42), 1.974 (0.45), 1.997 (0.47), 2.002 (0.44), 2.011 (0.88), 2.018 (1.08), 2.026 (0.95), 2.032 (0.77), 2.041 (0.57), 2.204 (0.58), 2.235 (16.00), 2.378 (11.94), 2.806 (1.42), 2.822 (2.62), 2.839 (1.55), 3.712 (1.74), 3.727 (2.76), 3.743 (1.22), 4.919 (0.60), 4.934 (0.79), 4.949 (0.57), 7.477 (1.73), 7.491 (1.74), 8.123 (2.47), 8.152 (2.50), 8.553 (1.23).

Example 41

5-fluoro-N-(4-methyl-1,2-oxazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

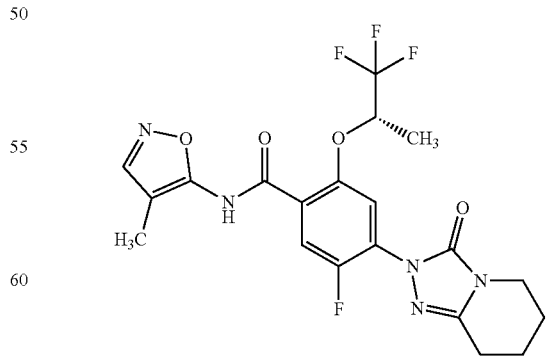

From intermediate 17 and 4-methyl-1,2-oxazol-5-amine.
LC-MS (method A): $R_t$=1.07 min; MS (ESIneg): m/z=468 [M−H]$^−$ ¹H-NMR (400 MHz, CHLOROFORM-d) δ [ppm]: 0.000 (3.05), 1.183 (0.56), 1.419 (1.13), 1.434 (1.18), 1.500 (16.00), 1.862 (0.90), 1.873 (0.57), 1.932 (0.69), 1.944 (0.57), 2.105 (0.45), 2.717 (0.52), 2.733 (0.95), 2.749 (0.56), 2.977 (0.62), 3.631 (0.62), 3.646 (1.02), 3.661 (0.44), 7.268 (0.40), 7.277 (0.41), 7.452 (0.42).

Example 42

5-fluoro-N-(4-methyl-1H-imidazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

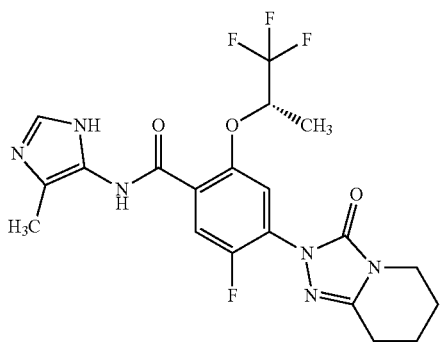 [SMILES: Cc1nc[nH]c1NC(=O)c1cc(F)c(-n2nc3n(c2=O)CCCC3)cc1O[C@@H](C)C(F)(F)F]

From intermediate 17 and 4-methyl-1H-imidazol-5-amine.

LC-MS (method A): R$_t$=0.78 min; MS (ESIpos): m/z=469.2 [M+H]⁺

¹H-NMR (400 MHz, CHLOROFORM-d) δ [ppm]: 1.184 (0.68), 1.533 (0.84), 1.549 (0.77), 1.580 (3.47), 1.589 (6.33), 1.595 (4.79), 1.605 (6.10), 1.852 (2.06), 1.863 (2.83), 1.878 (2.87), 1.895 (1.40), 1.937 (2.77), 1.948 (2.73), 1.961 (1.66), 1.975 (0.62), 2.159 (1.26), 2.294 (10.47), 2.373 (1.94), 2.378 (1.35), 2.401 (6.22), 2.571 (16.00), 2.726 (2.76), 2.741 (5.10), 2.757 (2.60), 2.924 (0.48), 3.629 (3.04), 3.635 (2.70), 3.645 (4.93), 3.650 (3.79), 3.659 (2.75), 3.728 (0.70), 4.805 (0.49), 4.821 (0.67), 4.837 (0.83), 4.852 (1.08), 4.868 (1.18), 4.883 (0.85), 6.931 (0.49), 7.386 (1.14), 7.401 (1.64), 7.406 (2.32), 7.420 (2.23), 7.453 (0.59), 7.744 (0.60), 7.917 (1.53), 7.945 (2.75), 8.019 (3.33), 8.031 (1.41), 8.059 (1.26), 8.164 (0.73), 8.187 (0.94), 9.012 (2.30), 9.047 (0.75), 9.433 (1.76).

Example 43

5-fluoro-N-(3-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

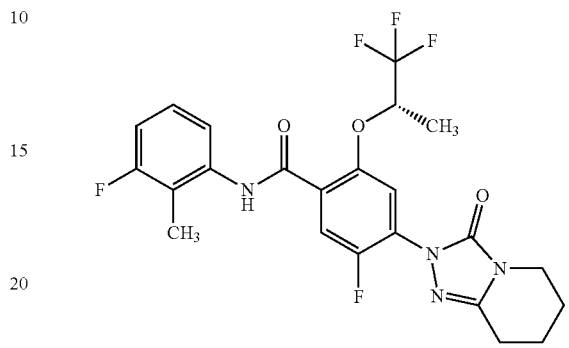

From intermediate 17 and 3-fluoro-2-methylaniline.

LC-MS (method A): R$_t$=1.27 min; MS (ESIpos): m/z=497 [M−H]⁺

¹H-NMR (400 MHz, CHLOROFORM-d) δ [ppm]: 1.504 (16.00), 1.554 (3.10), 1.570 (3.08), 1.854 (0.54), 1.866 (0.72), 1.877 (0.73), 1.881 (0.78), 1.934 (0.71), 1.939 (0.74), 1.949 (0.79), 1.954 (0.64), 1.963 (0.48), 2.142 (4.42), 2.146 (4.41), 2.730 (1.10), 2.747 (2.14), 2.762 (1.23), 3.638 (1.42), 3.654 (2.31), 3.669 (1.01), 4.824 (0.50), 4.840 (0.65), 4.855 (0.48), 6.833 (0.44), 6.855 (0.89), 6.877 (0.51), 7.133 (0.62), 7.149 (0.62), 7.407 (1.30), 7.422 (1.30), 7.605 (0.93), 7.625 (0.86), 8.061 (1.61), 8.091 (1.62), 9.008 (0.83).

Example 44

N-[2-(dimethylamino)ethyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

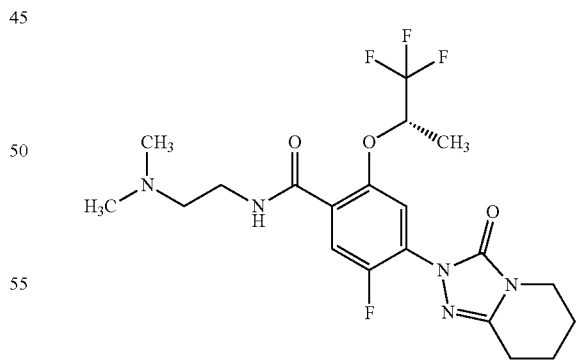

From intermediate 17 and N,N-dimethylethane-1,2-diamine.

LC-MS (method B): R$_t$=1.04 min; MS (ESIpos): m/z=459.8 [M+H]⁺

¹H-NMR (400 MHz, CHLOROFORM-d) δ [ppm]: 1.436 (0.45), 1.449 (0.75), 1.464 (0.62), 1.523 (13.22), 1.539 (13.33), 1.824 (0.94), 1.830 (1.22), 1.838 (2.56), 1.846 (3.02), 1.851 (3.46), 1.862 (3.45), 1.866 (3.76), 1.878 (1.73), 1.882 (1.83), 1.903 (1.86), 1.910 (1.81), 1.919 (3.39), 1.923 (3.56), 1.934 (3.73), 1.939 (3.12), 1.945 (2.26), 1.948 (2.32), 1.962 (1.07), 2.247 (0.41), 2.366 (16.00), 2.655 (2.48), 2.711 (5.18), 2.726 (9.50), 2.742 (5.45), 2.810 (1.37), 2.854 (1.32), 3.034 (1.50), 3.598 (2.63), 3.608 (2.70), 3.620 (7.79), 3.636 (10.88), 3.650 (4.81), 4.715 (0.99), 4.731 (2.28), 4.746 (3.01), 4.762 (2.20), 4.777 (0.89), 7.282 (6.13), 7.296 (6.17), 7.886 (1.28), 7.899 (2.19), 7.911 (1.23), 7.937 (6.99), 7.966 (6.77).

Example 45

5-fluoro-N-(1-methylpiperidin-4-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

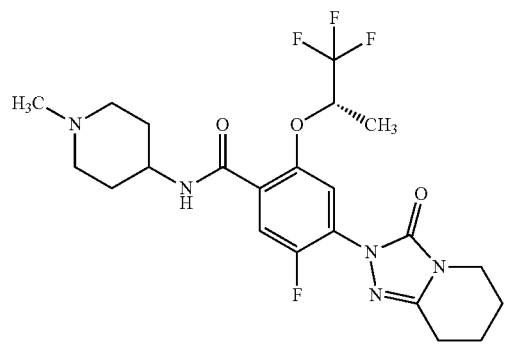 [SMILES: C[C@H](Oc1cc(-n2nc3n(c2=O)CCCC3)c(F)cc1C(=O)NC1CCN(C)CC1)C(F)(F)F]

From intermediate 17 and 1-methylpiperidin-4-amine.

LC-MS (method A): R$_t$=0.72 min; MS (ESIpos): m/z=486.1 [M+H]$^+$ $^1$H-NMR (400 MHz, CHLOROFORM-d) δ [ppm]: 1.510 (13.94), 1.526 (13.91), 1.647 (1.39), 1.671 (1.57), 1.824 (0.89), 1.831 (1.11), 1.839 (2.41), 1.847 (2.81), 1.852 (3.22), 1.863 (3.26), 1.867 (3.54), 1.879 (1.60), 1.883 (1.72), 1.905 (1.71), 1.911 (1.63), 1.920 (3.19), 1.925 (3.34), 1.935 (3.53), 1.940 (2.89), 1.949 (2.27), 1.963 (1.05), 1.994 (1.47), 2.010 (0.95), 2.032 (2.32), 2.068 (1.25), 2.254 (1.85), 2.345 (16.00), 2.550 (0.58), 2.712 (4.93), 2.728 (9.27), 2.744 (5.48), 2.811 (0.50), 2.893 (1.77), 2.918 (1.64), 3.033 (0.54), 3.619 (6.19), 3.635 (10.03), 3.650 (4.44), 3.919 (0.45), 3.936 (0.86), 3.945 (1.06), 3.954 (0.94), 3.963 (1.06), 3.973 (0.84), 3.990 (0.44), 4.713 (0.93), 4.728 (2.21), 4.743 (2.85), 4.759 (2.09), 4.774 (0.85), 7.273 (6.29), 7.287 (6.21), 7.434 (2.21), 7.453 (2.17), 7.968 (8.02), 7.997 (7.92).

Example 46

5-fluoro-4-(3-oxo-5,6,7,8-tetrahydro[1,2,4]triazolo[4,3-a]pyridin-2(3H)-yl)-N-[4-(trifluoromethyl)phenyl]-2-{[(2S)-1,1,1-trifluoropropan-2-yl]oxy}benzamide

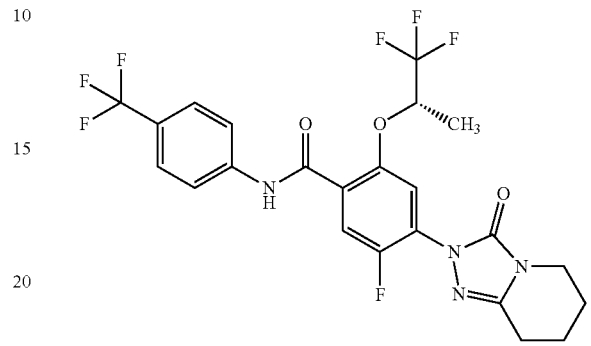

From intermediate 17 and 4-(trifluoromethyl)aniline.

LC-MS (method A): R$_t$=1.38 min; MS (ESIpos): m/z=533 [M+H]$^+$ $^1$H-NMR (500 MHz, CHLOROFORM-d) δ [ppm]: 1.513 (16.00), 1.585 (3.48), 1.599 (3.49), 1.857 (0.66), 1.862 (0.66), 1.867 (0.88), 1.875 (0.79), 1.879 (0.95), 1.936 (0.82), 1.941 (0.76), 1.948 (0.99), 1.953 (0.69), 1.960 (0.57), 2.732 (1.29), 2.745 (2.43), 2.758 (1.38), 3.638 (1.63), 3.651 (2.69), 3.663 (1.23), 4.853 (0.54), 4.865 (0.69), 4.877 (0.51), 7.406 (1.56), 7.417 (1.53), 7.550 (1.68), 7.567 (2.06), 7.711 (1.94), 7.728 (1.53), 8.089 (1.84), 8.113 (1.77), 9.557 (1.01).

Example 47

N-cyclopropyl-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

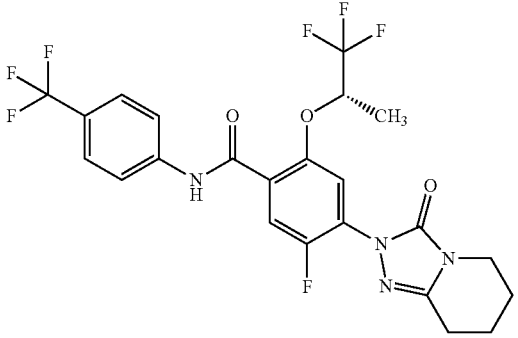 [SMILES: C[C@H](Oc1cc(-n2nc3n(c2=O)CCCC3)c(F)cc1C(=O)Nc1ccc(C(F)(F)F)cc1)C(F)(F)F]

From intermediate 17 and cyclopropanamine.

LC-MS (method A): R$_t$=1.04 min; MS (ESIpos): m/z=429.2 [M+H]$^+$ $^1$H-NMR (400 MHz, CHLOROFORM-d) δ [ppm]: 0.500 (0.91), 0.503 (0.94), 0.508 (0.86), 0.510 (0.93), 0.514 (0.96), 0.516 (0.89), 0.526 (0.42), 0.777 (0.46), 0.781 (1.02), 0.785 (1.02), 0.799 (1.23), 0.801 (0.76), 1.483 (2.67), 1.498 (2.76), 1.515 (16.00), 1.838 (0.43), 1.845 (0.49), 1.850 (0.58), 1.861 (0.58), 1.865 (0.64), 1.918 (0.57), 1.923 (0.59), 1.933

(0.64), 1.939 (0.51), 2.710 (0.94), 2.726 (1.77), 2.742 (1.04), 2.903 (0.61), 2.913 (0.60), 3.617 (1.19), 3.633 (1.90), 3.648 (0.85), 4.694 (0.45), 4.709 (0.59), 4.725 (0.43), 7.251 (1.25), 7.265 (1.21), 8.001 (1.54), 8.030 (1.52).

Example 48

N-(2-cyano-4-fluorophenyl)-5-fluoro-4-(3-oxo-5,6,7, 8-tetrahydro[1,2,4]triazolo[4,3-a]pyridin-2(3H)-yl)-2-{[(2S)-1,1,1-trifluoropropan-2-yl]oxy}benzamide

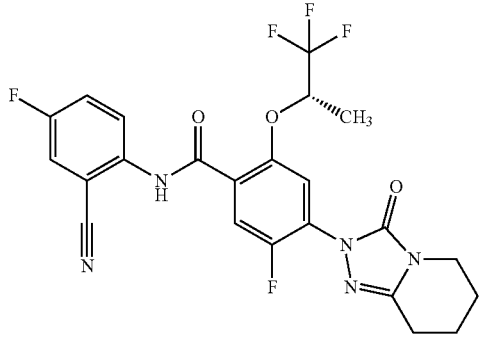 [SMILES: C[C@H](Oc1cc(-n2nc3n(c2=O)CCCC3)c(F)cc1C(=O)Nc1ccc(F)cc1C#N)C(F)(F)F]

From intermediate 17 and 2-amino-5-fluorobenzonitrile.
LC-MS (method A): $R_t$=1.21 min; MS (ESIpos): m/z=508 [M+H]$^+$
$^1$H-NMR (400 MHz, CHLOROFORM-d) δ [ppm]: 1.497 (16.00), 1.674 (1.05), 1.690 (1.06), 2.747 (0.72), 2.762 (0.42), 3.638 (0.48), 3.653 (0.79), 7.269 (0.42), 7.288 (0.41), 7.439 (0.50), 7.453 (0.55), 8.016 (0.63), 8.044 (0.64).

Example 49

N-(2-cyano-5-fluorophenyl)-5-fluoro-4-(3-oxo-5,6,7, 8-tetrahydro[1,2,4]triazolo[4,3-a]pyridin-2(3H)-yl)-2-{[(2S)-1,1,1-trifluoropropan-2-yl]oxy}benzamide

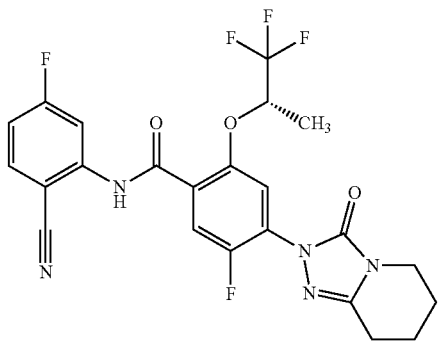 [SMILES: C[C@H](Oc1cc(-n2nc3n(c2=O)CCCC3)c(F)cc1C(=O)Nc1cc(F)ccc1C#N)C(F)(F)F]

From intermediate 17 and 2-amino-4-fluorobenzonitrile.
LC-MS (method A): $R_t$=1.25 min; MS (ESIpos): m/z=508 [M+H]$^+$
$^1$H-NMR (400 MHz, CHLOROFORM-d) δ [ppm]: 1.496 (16.00), 1.695 (1.63), 1.711 (1.65), 1.882 (0.41), 1.949 (0.40), 2.731 (0.60), 2.747 (1.13), 2.763 (0.67), 3.638 (0.72), 3.654 (1.21), 3.669 (0.52), 7.450 (0.81), 7.465 (0.77), 7.543 (0.55), 7.557 (0.56), 7.564 (0.54), 7.579 (0.52), 7.983 (1.04), 8.012 (1.02), 8.334 (0.47), 8.340 (0.50), 8.362 (0.48), 8.368 (0.47), 9.792 (0.48).

Example 50

N-(2-chloro-6-fluorophenyl)-5-fluoro-4-(3-oxo-5,6, 7,8-tetrahydro[1,2,4]triazolo[4,3-a]pyridin-2(3H)-yl)-2-{[(2S)-1,1,1-trifluoropropan-2-yl] oxy}benzamide

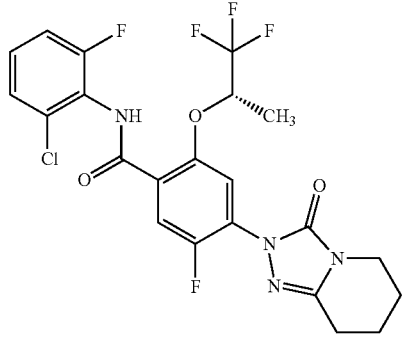 [SMILES: C[C@H](Oc1cc(-n2nc3n(c2=O)CCCC3)c(F)cc1C(=O)Nc1c(F)cccc1Cl)C(F)(F)F]

From intermediate 17 and 2-chloro-6-fluoroaniline.
LC-MS (method A): $R_t$=1.24 min; MS (ESIpos): m/z=517 [M+H]$^+$
$^1$H-NMR (400 MHz, CHLOROFORM-d) δ [ppm]: 1.260 (2.60), 1.566 (15.66), 1.651 (15.46), 1.667 (16.00), 1.914 (0.91), 1.920 (1.16), 1.928 (2.65), 1.936 (3.12), 1.941 (3.61), 1.953 (3.68), 1.956 (3.99), 1.960 (2.64), 1.968 (1.74), 1.972 (1.87), 1.993 (1.84), 1.999 (1.68), 2.009 (3.52), 2.014 (3.68), 2.024 (3.94), 2.030 (3.17), 2.035 (2.27), 2.038 (2.38), 2.045 (1.34), 2.052 (1.06), 2.807 (5.60), 2.824 (10.65), 2.840 (6.20), 3.713 (7.20), 3.729 (11.72), 3.744 (5.11), 4.918 (1.08), 4.934 (2.52), 4.949 (3.27), 4.964 (2.42), 4.979 (0.98), 7.006 (0.73), 7.109 (2.08), 7.112 (2.21), 7.129 (3.34), 7.133 (4.49), 7.136 (2.62), 7.152 (2.91), 7.156 (3.08), 7.216 (2.02), 7.230 (1.97), 7.237 (4.68), 7.250 (4.82), 7.257 (3.44), 7.281 (5.08), 7.285 (6.29), 7.288 (5.16), 7.302 (2.07), 7.305 (2.58), 7.308 (2.15), 7.502 (6.93), 7.516 (6.96), 7.528 (0.77), 8.170 (7.37), 8.199 (7.34), 9.033 (4.66).

Example 51 tert-butyl 3-{[5-fluoro-4-(3-oxo-5,6,7,8-tetrahydro [1,2,4]triazolo[4,3-a]pyridin-2(3H)-yl)-2-{[(2S)-1,1, 1-trifluoropropan-2-yl]oxy}benzoyl] amino}azetidine-1-carboxylate

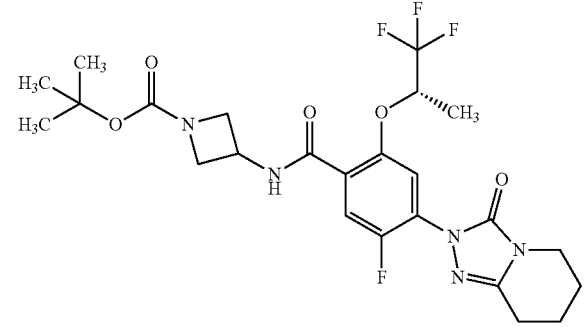 [SMILES: C[C@H](Oc1cc(-n2nc3n(c2=O)CCCC3)c(F)cc1C(=O)NC1CN(C(=O)OC(C)(C)C)C1)C(F)(F)F]

From intermediate 17 and tert-butyl 3-aminoazetidine-1-carboxylate.

LC-MS (method A): R$_t$=1.18 min; MS (ESIpos): m/z=544 [M+H]$^+$ $^1$H-NMR (400 MHz, DMSO-d6) δ[ppm]: 1.378 (16.00), 1.403 (1.63), 1.420 (1.61), 2.518 (0.78), 2.523 (0.58), 2.682 (0.48), 2.698 (0.94), 2.715 (0.51), 3.547 (0.56), 3.563 (1.01), 3.577 (0.44), 7.458 (0.74), 7.473 (0.73), 7.499 (0.96), 7.525 (0.93), 8.786 (0.50), 8.803 (0.49).

Example 52

N-(azetidin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

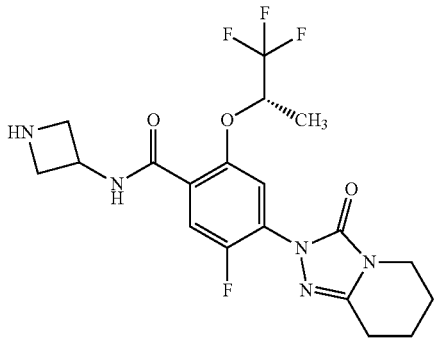 [SMILES: C[C@H](Oc1cc(-n2nc3n(c2=O)CCCC3)c(F)cc1C(=O)NC1CNC1)C(F)(F)F]

To a room temperature stirred solution of tert-butyl 3-{[5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoyl]amino}azetidine-1-carboxylate (example 51) (56.3 mg, 0.10 mmol, 1.00 eq.) in dichloromethane (0.50 ml) was added trifluoroacetic acid (0.12 ml). The resulting mixture was stirred at room temperature for 1 hour and then concentrated under reduced pressure to give a colourless oil. The residue was dissolved in DMSO, filtered through a teflon filter and purified by reverse phase column chromatography (15-55% acetonitrile, 0.1% aqueous ammonia) to give the title compound as an off white solid (13.7 mg, 28%).

LC-MS (method A): R$_t$=0.70 min; MS (ESIpos): m/z=444.4 [M+H]$^+$ $^1$H-NMR (400 MHz, CHLOROFORM-d) δ [ppm]: 0.000 (0.53), 0.811 (0.53), 1.149 (0.41), 1.158 (4.66), 1.165 (0.51), 1.175 (10.45), 1.184 (2.82), 1.193 (5.41), 1.209 (0.72), 1.227 (0.68), 1.543 (7.53), 1.560 (10.35), 1.567 (15.08), 1.583 (14.09), 1.827 (1.49), 1.843 (4.17), 1.854 (5.70), 1.866 (5.72), 1.870 (6.08), 1.882 (2.89), 1.886 (2.94), 1.909 (2.90), 1.914 (3.11), 1.923 (5.48), 1.928 (6.01), 1.939 (5.94), 1.943 (5.34), 1.950 (3.77), 1.957 (3.65), 1.966 (1.52), 1.978 (0.53), 1.994 (0.51), 2.557 (16.00), 2.646 (1.88), 2.668 (0.63), 2.715 (7.65), 2.731 (14.31), 2.747 (8.08), 2.875 (1.09), 2.923 (1.23), 2.949 (1.37), 3.053 (1.23), 3.456 (0.48), 3.621 (7.02), 3.629 (4.80), 3.636 (11.70), 3.646 (7.94), 3.651 (5.79), 3.664 (5.24), 3.681 (1.74), 3.728 (1.76), 3.742 (1.83), 3.750 (1.84), 3.763 (1.74), 3.888 (0.46), 3.901 (0.51), 3.913 (0.50), 3.927 (0.46), 4.019 (0.43), 4.031 (0.43), 4.044 (0.43), 4.092 (2.78), 4.259 (1.38), 4.267 (1.42), 4.279 (2.25), 4.286 (2.20), 4.301 (1.42), 4.308 (1.37), 4.326 (1.13), 4.339 (1.96), 4.363 (3.16), 4.387 (1.91), 4.412 (0.55), 4.513 (0.48), 4.727 (1.11), 4.742 (2.83), 4.758 (3.88), 4.774 (3.33), 4.791 (1.91), 4.811 (0.67), 4.859 (0.84), 4.877 (1.45), 4.895 (1.40), 4.912 (0.72), 6.931 (0.80), 7.309 (3.42), 7.318 (6.51), 7.323 (4.29), 7.332 (7.15), 7.346 (1.20), 7.454 (0.97), 7.876 (6.03), 7.904 (5.98), 7.936 (1.78), 7.945 (1.02), 7.955 (6.56), 7.974 (0.89), 7.984 (5.05), 8.106 (2.92), 8.123 (2.87), 8.287 (1.33).

Example 53

5-fluoro-N-(6-methoxy-2-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

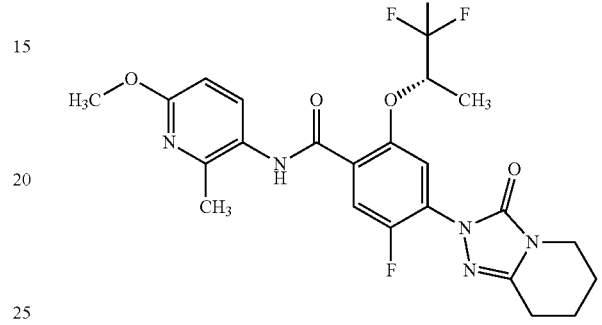

From intermediate 17 and 6-methoxy-2-methylpyridin-3-amine.

The product was purified by preparative HPLC (X-Bridge Prep C18 5 μm OBD, 0.1% aqueous formic acid, acetonitrile).

LC-MS (method A): R$_t$=1.24 min; MS (ESIneg): m/z=508 [M−H]$^−$ $^1$H-NMR (400 MHz, CHLOROFORM-d) δ [ppm]: 1.579 (0.96), 1.638 (3.37), 1.654 (3.40), 1.929 (0.54), 1.937 (0.63), 1.941 (0.73), 1.953 (0.75), 1.957 (0.81), 2.010 (0.72), 2.015 (0.77), 2.018 (0.99), 2.025 (0.81), 2.030 (0.66), 2.039 (0.49), 2.446 (9.49), 2.806 (1.15), 2.822 (2.19), 2.838 (1.29), 3.713 (1.47), 3.729 (2.42), 3.744 (1.05), 3.934 (16.00), 4.906 (0.55), 4.922 (0.73), 4.938 (0.52), 6.634 (1.37), 6.655 (1.41), 7.473 (1.49), 7.487 (1.49), 7.931 (1.72), 7.953 (1.62), 8.140 (1.97), 8.169 (1.91), 8.946 (1.11).

Example 54

5-fluoro-N-[1-(methylsulfonyl)piperidin-4-yl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

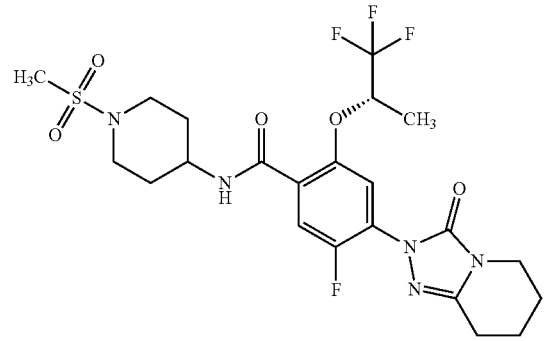 [SMILES: C[C@H](Oc1cc(-n2nc3n(c2=O)CCCC3)c(F)cc1C(=O)NC1CCN(S(C)(=O)=O)CC1)C(F)(F)F]

From intermediate 17 and 1-(methylsulfonyl)piperidin-4-amine.

The product was purified by preparative HPLC (X-Bridge Prep C18 5 μm OBD, 0.1% aqueous formic acid, acetonitrile).

LC-MS (method A): $R_t$=1.06 min; MS (ESIpos): m/z=551 [M+H]$^+$ $^1$H-NMR (400 MHz, CHLOROFORM-d) δ [ppm]: 1.595 (6.63), 1.612 (4.96), 1.630 (0.60), 1.639 (0.80), 1.918 (0.68), 1.930 (0.91), 1.941 (0.92), 1.945 (1.00), 1.957 (0.43), 1.962 (0.47), 1.984 (0.46), 1.990 (0.45), 1.998 (0.91), 2.003 (0.96), 2.014 (1.01), 2.017 (0.95), 2.028 (0.61), 2.140 (0.42), 2.165 (0.79), 2.791 (1.40), 2.806 (2.89), 2.817 (16.00), 2.822 (2.10), 2.838 (0.44), 2.845 (0.75), 2.850 (0.48), 2.874 (1.33), 2.898 (0.48), 2.904 (0.72), 3.698 (1.75), 3.713 (2.94), 3.728 (1.27), 3.801 (0.98), 3.832 (0.94), 4.093 (0.43), 4.111 (0.43), 4.817 (0.68), 4.832 (0.87), 4.847 (0.64), 7.362 (1.90), 7.376 (1.87), 7.549 (0.76), 7.567 (0.75), 8.050 (2.34), 8.079 (2.33).

Example 55

5-fluoro-N-(6-methoxy-4-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

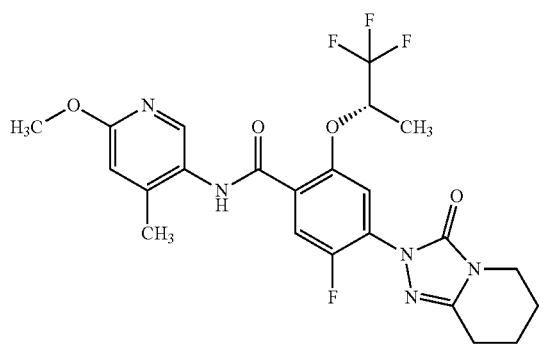 [SMILES: COc1cc(C)c(NC(=O)c2cc(F)c(-n3nc4n(c3=O)CCCC4)cc2O[C@@H](C)C(F)(F)F)cn1]

From intermediate 17 and 6-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.20 min; MS (ESIpos): m/z=511 [M+H]$^+$ $^1$H-NMR (400 MHz, CHLOROFORM-d) δ [ppm]: 1.599 (0.49), 1.637 (3.77), 1.653 (3.74), 1.927 (0.60), 1.935 (0.70), 1.939 (0.82), 1.951 (0.83), 1.955 (0.90), 1.971 (0.42), 1.993 (0.42), 2.008 (0.80), 2.013 (0.85), 2.017 (1.34), 2.023 (0.91), 2.028 (0.74), 2.037 (0.54), 2.261 (8.80), 2.805 (1.25), 2.820 (2.43), 2.836 (1.39), 3.711 (1.62), 3.726 (2.64), 3.741 (1.15), 3.940 (16.00), 4.896 (0.61), 4.911 (0.80), 4.927 (0.58), 6.666 (2.45), 7.473 (1.64), 7.488 (1.65), 8.132 (2.12), 8.161 (2.11), 8.335 (2.99), 8.875 (1.25).

Example 56

5-fluoro-N-(2-methoxy-4-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

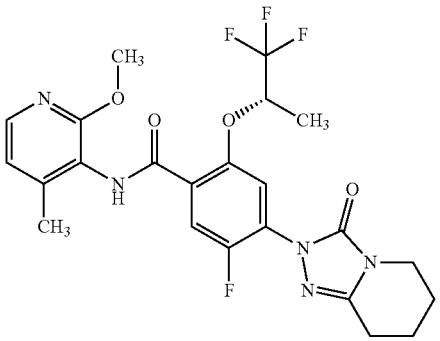 [SMILES: COc1nccc(C)c1NC(=O)c1cc(F)c(-n2nc3n(c2=O)CCCC3)cc1O[C@@H](C)C(F)(F)F]

From intermediate 17 and 2-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.22 min; MS (ESIneg): m/z=508 [M−H]$^-$ $^1$H-NMR (400 MHz, CHLOROFORM-d) δ [ppm]: 1.605 (0.71), 1.652 (3.93), 1.669 (3.92), 1.927 (0.63), 1.934 (0.73), 1.939 (0.86), 1.951 (0.86), 1.955 (0.94), 1.967 (0.40), 1.971 (0.44), 1.992 (0.44), 1.998 (0.41), 2.007 (0.84), 2.012 (0.89), 2.017 (0.63), 2.023 (0.94), 2.028 (0.76), 2.036 (0.57), 2.278 (11.08), 2.805 (1.33), 2.821 (2.56), 2.837 (1.48), 3.713 (1.74), 3.728 (2.82), 3.743 (1.22), 3.958 (16.00), 4.919 (0.64), 4.935 (0.83), 4.950 (0.60), 6.826 (1.67), 6.838 (1.71), 7.464 (1.73), 7.479 (1.68), 7.954 (2.20), 7.967 (2.13), 8.128 (2.21), 8.157 (2.19), 8.972 (1.33).

Example 57

N-(4,4-difluorocyclohexyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

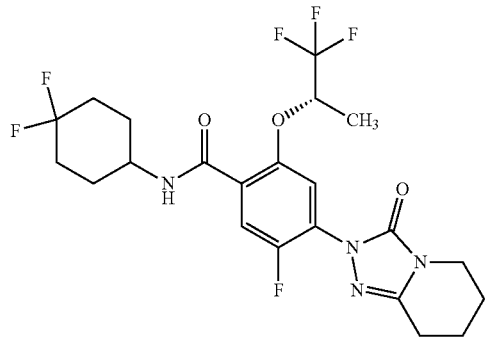 [SMILES: C[C@H](Oc1cc(-n2nc3n(c2=O)CCCC3)c(F)cc1C(=O)NC1CCC(F)(F)CC1)C(F)(F)F]

From intermediate 17 and 4,4-difluorocyclohexanamine.

The product was purified by preparative HPLC (X-Bridge Prep C18 5 μm OBD, 0.1% aqueous formic acid, acetonitrile).

LC-MS (method A): R$_t$=1.26 min; MS (ESIpos): m/z=507 [M+H]$^+$ $^1$H-NMR (400 MHz, CHLOROFORM-d) δ [ppm]: 1.261 (0.55), 1.580 (16.00), 1.589 (13.98), 1.605 (12.82), 1.626 (2.04), 1.650 (1.01), 1.847 (0.51), 1.881 (1.07), 1.903 (1.26), 1.909 (1.53), 1.918 (2.73), 1.925 (2.88), 1.930 (3.15), 1.941 (3.16), 1.945 (3.53), 1.957 (2.21), 1.961 (2.26), 1.984 (1.89), 1.989 (1.77), 1.998 (2.93), 2.003 (2.85), 2.014 (2.88), 2.019 (2.37), 2.028 (1.73), 2.042 (0.76), 2.100 (2.55), 2.120 (3.85), 2.142 (2.59), 2.174 (0.57), 2.791 (4.12), 2.806 (7.78), 2.823 (4.59), 3.698 (5.24), 3.713 (8.51), 3.728 (3.72), 4.084 (0.90), 4.102 (0.91), 4.796 (0.84), 4.811 (1.95), 4.827 (2.57), 4.842 (1.85), 4.857 (0.73), 7.357 (5.44), 7.372 (5.39), 7.498 (1.71), 7.517 (1.67), 7.529 (0.60), 8.055 (6.90), 8.084 (6.82).

Example 58

N-(1-ethylazetidin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

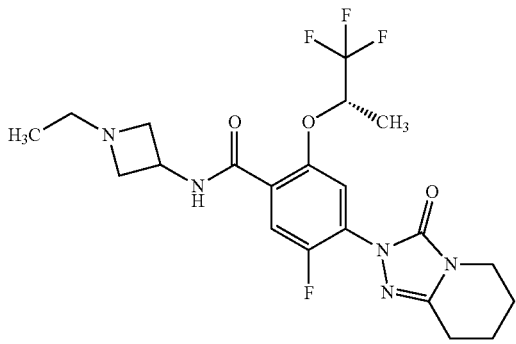 [SMILES: CCN1CC(NC(=O)c2cc(F)c(-n3nc4n(c3=O)CCCC4)cc2O[C@@H](C)C(F)(F)F)C1]

From intermediate 17 and 1-ethylazetidin-3-amine.

LC-MS (method A): R$_t$=0.75 min; MS (ESIpos): m/z=472 [M+H]$^+$ $^1$H-NMR (400 MHz, CHLOROFORM-d) [ppm]: 0.972 (7.23), 0.990 (16.00), 1.008 (7.51), 1.450 (0.44), 1.466 (0.47), 1.608 (10.98), 1.625 (11.42), 1.902 (0.62), 1.909 (0.81), 1.917 (1.78), 1.925 (2.14), 1.930 (2.38), 1.941 (2.49), 1.945 (2.59), 1.957 (1.13), 1.961 (1.20), 1.983 (1.22), 1.990 (1.23), 1.998 (2.38), 2.003 (2.44), 2.014 (2.59), 2.019 (2.08), 2.028 (1.53), 2.042 (0.63), 2.463 (1.44), 2.480 (4.24), 2.499 (4.10), 2.517 (1.32), 2.789 (3.85), 2.806 (7.19), 2.822 (5.32), 2.836 (2.60), 2.853 (1.44), 2.886 (2.16), 3.110 (2.62), 3.698 (4.87), 3.713 (8.03), 3.728 (3.47), 3.763 (2.51), 3.781 (4.08), 3.784 (4.03), 3.801 (2.45), 4.723 (1.31), 4.740 (2.43), 4.758 (2.40), 4.775 (1.22), 4.803 (0.72), 4.818 (1.70), 4.834 (2.21), 4.849 (1.61), 4.865 (0.65), 7.006 (0.41), 7.360 (4.90), 7.374 (4.76), 7.528 (0.42), 7.827 (1.52), 7.845 (1.50), 8.039 (6.09), 8.067 (5.99).

Example 59

N-[4-(dimethylamino)cyclohexyl]-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

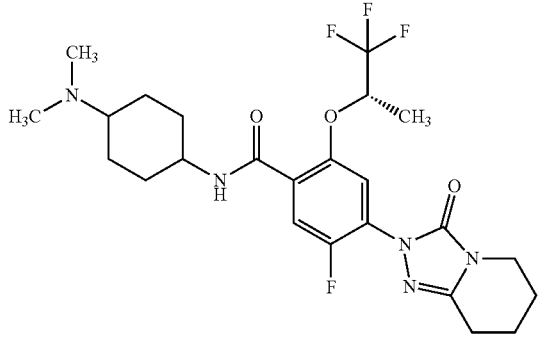 [SMILES: C[C@H](Oc1cc(-n2nc3n(c2=O)CCCC3)c(F)cc1C(=O)NC1CCC(N(C)C)CC1)C(F)(F)F]

From intermediate 17 and N,N-dimethylcyclohexane-1,4-diamine.

LC-MS (method A): R$_t$=0.77 min; MS (ESIneg): m/z=512 [M−H]$^-$ $^1$H-NMR (400 MHz, CHLOROFORM-d) δ [ppm]: 1.240 (0.49), 1.249 (0.55), 1.255 (0.58), 1.264 (0.58), 1.270 (0.59), 1.278 (0.61), 1.285 (0.61), 1.293 (0.57), 1.466 (0.83), 1.496 (0.79), 1.571 (4.85), 1.587 (4.91), 1.908 (0.81), 1.920 (1.12), 1.931 (1.13), 1.935 (1.21), 1.947 (0.55), 1.951 (0.57), 1.973 (0.57), 1.979 (0.56), 1.988 (1.10), 1.993 (1.16), 2.003 (1.24), 2.010 (1.73), 2.018 (0.88), 2.024 (0.66), 2.033 (0.87), 2.042 (0.84), 2.049 (0.80), 2.057 (0.72), 2.067 (0.73), 2.074 (0.74), 2.189 (0.88), 2.197 (0.91), 2.221 (0.88), 2.229 (0.82), 2.447 (16.00), 2.780 (1.59), 2.796 (3.13), 2.812 (1.77), 3.686 (1.98), 3.702 (3.36), 3.717 (1.47), 3.910 (0.50), 3.919 (0.40), 3.929 (0.50), 4.791 (0.78), 4.806 (1.00), 4.822 (0.73), 7.333 (2.17), 7.348 (2.13), 7.437 (0.91), 7.457 (0.89), 8.043 (2.63), 8.072 (2.57), 8.574 (2.09).

Example 60

N-(2-ethylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

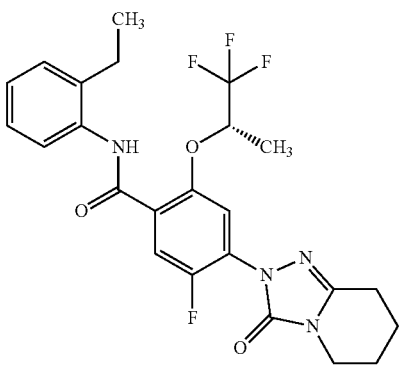 [SMILES: CCc1ccccc1NC(=O)c1cc(F)c(-n2nc3n(c2=O)CCCC3)cc1O[C@@H](C)C(F)(F)F]

From intermediate 17 and 2-ethylaniline.

LC-MS (method A): R$_t$=1.31 min; MS (ESIpos): m/z=493 [M+H]$^+$

¹H-NMR (400 MHz, CHLOROFORM-d) δ [ppm]: 1.226 (5.00), 1.245 (10.79), 1.264 (5.32), 1.579 (16.00), 1.619 (6.34), 1.635 (6.33), 1.928 (1.08), 1.941 (1.49), 1.956 (1.59), 1.972 (0.76), 1.993 (0.77), 2.009 (1.47), 2.014 (1.51), 2.024 (1.62), 2.038 (0.97), 2.052 (0.40), 2.639 (1.25), 2.657 (3.50), 2.676 (3.34), 2.695 (1.07), 2.805 (2.14), 2.822 (4.13), 2.838 (2.33), 3.715 (2.70), 3.730 (4.44), 3.745 (1.98), 4.871 (0.44), 4.887 (1.05), 4.903 (1.34), 4.918 (1.00), 7.188 (0.58), 7.204 (1.84), 7.223 (1.55), 7.226 (1.49), 7.257 (1.44), 7.295 (2.09), 7.471 (2.68), 7.485 (2.61), 7.814 (2.01), 7.834 (1.68), 8.139 (3.15), 8.167 (3.08), 9.016 (1.80).

Example 61

N-(2-chloro-6-methylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

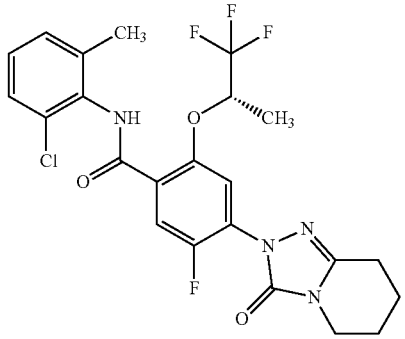 [SMILES: Cc1cccc(Cl)c1NC(=O)c1cc(F)c(-n2nc3n(c2=O)CCCC3)cc1O[C@@H](C)C(F)(F)F]

From intermediate 17 and 2-chloro-6-methylaniline.
LC-MS (method A): R$_t$=1.28 min; MS (ESIneg): m/z=511 [M−H]⁻

¹H-NMR (400 MHz, CHLOROFORM-d) δ [ppm]: 1.652 (6.60), 1.668 (6.61), 1.918 (0.48), 1.926 (1.08), 1.938 (1.46), 1.949 (1.45), 1.953 (1.58), 1.965 (0.69), 1.969 (0.75), 1.991 (0.75), 1.997 (0.71), 2.006 (1.43), 2.011 (1.50), 2.021 (1.58), 2.026 (1.27), 2.035 (0.95), 2.049 (0.40), 2.318 (16.00), 2.804 (2.17), 2.820 (4.13), 2.836 (2.38), 3.711 (2.69), 3.727 (4.55), 3.742 (1.96), 4.929 (0.43), 4.944 (1.03), 4.959 (1.33), 4.975 (0.98), 7.155 (0.85), 7.174 (2.83), 7.193 (3.57), 7.198 (1.99), 7.202 (2.55), 7.218 (0.76), 7.222 (0.52), 7.315 (1.63), 7.319 (1.67), 7.333 (1.20), 7.338 (1.22), 7.475 (2.72), 7.489 (2.72), 8.157 (3.48), 8.186 (3.42), 8.987 (2.03).

Example 62

N-(2-chloro-4-fluoro-6-methylphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

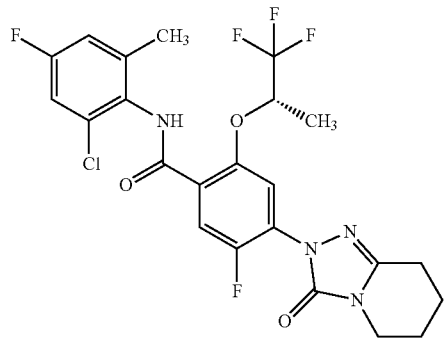 [SMILES: Cc1cc(F)cc(Cl)c1NC(=O)c1cc(F)c(-n2nc3n(c2=O)CCCC3)cc1O[C@@H](C)C(F)(F)F]

From intermediate 17 and 2-chloro-4-fluoro-6-methylaniline.
LC-MS (method A): R$_t$=1.30 min; MS (ESIpos): m/z=531 [M+H]⁺

¹H-NMR (400 MHz, CHLOROFORM-d) δ [ppm]: 1.576 (16.00), 1.653 (5.89), 1.669 (5.93), 1.930 (0.98), 1.942 (1.33), 1.954 (1.31), 1.957 (1.44), 1.973 (0.69), 1.995 (0.68), 2.010 (1.30), 2.014 (1.37), 2.025 (1.47), 2.030 (1.17), 2.039 (0.88), 2.310 (14.34), 2.807 (2.01), 2.824 (3.83), 2.840 (2.23), 3.715 (2.54), 3.730 (4.23), 3.745 (1.83), 4.927 (0.40), 4.942 (0.95), 4.958 (1.24), 4.973 (0.91), 6.935 (1.08), 6.941 (1.19), 6.957 (1.08), 6.964 (1.16), 7.073 (1.29), 7.080 (1.19), 7.093 (1.31), 7.100 (1.17), 7.479 (2.56), 7.493 (2.55), 8.144 (3.18), 8.172 (3.23), 8.885 (1.84).

Example 63

N-(2-chloro-4,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

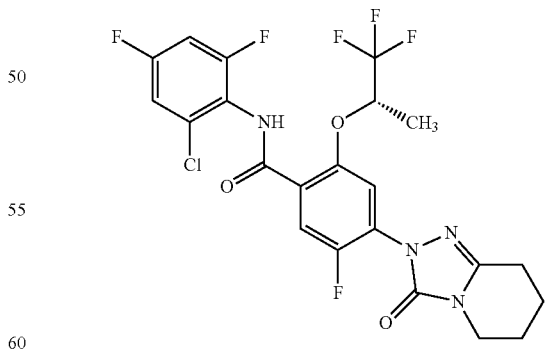

From intermediate 17 and 2-chloro-4,6-difluoroaniline.
LC-MS (method A): R$_t$=1.28 min; MS (ESIpos): m/z=535 [M+H]⁺

¹H-NMR (400 MHz, CHLOROFORM-d) δ [ppm]: 1.595 (9.60), 1.645 (15.98), 1.662 (16.00), 1.911 (0.94), 1.927 (2.68), 1.939 (3.69), 1.951 (3.67), 1.954 (3.96), 1.970 (1.88), 1.992 (1.88), 2.007 (3.61), 2.012 (3.78), 2.022 (4.01), 2.027 (3.24), 2.037 (2.42), 2.051 (1.01), 2.626 (0.75), 2.805 (5.37), 2.821 (10.44), 2.837 (5.90), 3.711 (6.68), 3.726 (11.35), 3.741 (4.92), 4.917 (1.06), 4.932 (2.48), 4.948 (3.22), 4.963 (2.38), 4.978 (0.96), 6.888 (2.03), 6.895 (2.27), 6.911 (2.80), 6.916 (2.94), 6.918 (2.89), 6.933 (2.04), 6.940 (2.18), 7.067 (2.50), 7.071 (2.82), 7.074 (2.87), 7.077 (2.61), 7.086 (2.64), 7.090 (2.78), 7.093 (2.89), 7.097 (2.37), 7.501 (6.61), 7.515 (6.57), 8.148 (7.17), 8.176 (7.23), 8.926 (5.40).

Example 64

5-fluoro-N-(4-fluoro-2,6-dimethylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

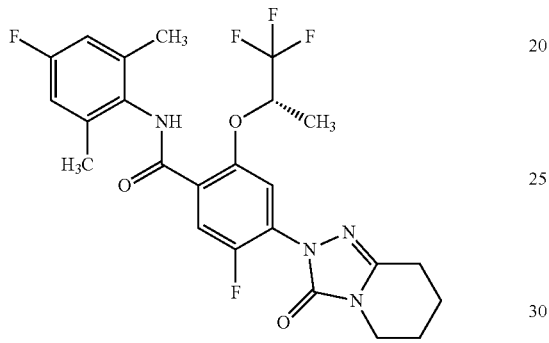

From intermediate 17 and 4-fluoro-2,6-dimethylaniline.
LC-MS (method A): $R_t$=1.28 min; MS (ESIpos): m/z=511 [M+H]$^+$ $^1$H-NMR (400 MHz, CHLOROFORM-d) δ [ppm]: 1.606 (1.52), 1.643 (3.27), 1.658 (3.29), 1.929 (0.54), 1.937 (0.62), 1.941 (0.72), 1.953 (0.73), 1.957 (0.80), 2.010 (0.71), 2.015 (0.74), 2.025 (0.79), 2.030 (0.64), 2.039 (0.48), 2.252 (16.00), 2.806 (1.16), 2.823 (2.17), 2.839 (1.28), 3.714 (1.48), 3.729 (2.41), 3.744 (1.04), 4.939 (0.53), 4.955 (0.69), 4.970 (0.50), 6.830 (2.17), 6.853 (2.15), 7.457 (1.45), 7.471 (1.46), 8.143 (1.96), 8.171 (1.93), 8.645 (0.92).

Example 65

N-(2-chloro-4-methylpyridin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

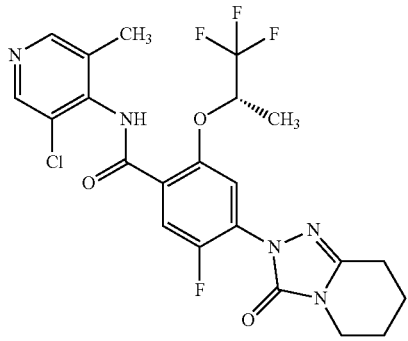 [SMILES: Cc1cncc(Cl)c1NC(=O)c1cc(F)c(-n2nc3n(c2=O)CCCC3)cc1O[C@@H](C)C(F)(F)F]

From intermediate 17 and 2-chloro-4-methylpyridin-3-amine.
LC-MS (method A): $R_t$=1.11 min; MS (ESIneg): m/z=512 [M−H]$^-$ $^1$H-NMR (400 MHz, CHLOROFORM-d) δ [ppm]: 1.586 (14.95), 1.677 (6.12), 1.693 (6.15), 1.933 (1.03), 1.945 (1.40), 1.956 (1.43), 1.960 (1.55), 1.976 (0.73), 1.998 (0.74), 2.013 (1.40), 2.017 (1.46), 2.028 (1.55), 2.033 (1.30), 2.042 (0.97), 2.056 (0.42), 2.349 (16.00), 2.810 (2.06), 2.827 (4.02), 2.843 (2.31), 3.717 (2.64), 3.732 (4.32), 3.748 (1.94), 4.950 (0.43), 4.965 (0.97), 4.981 (1.27), 4.996 (0.93), 7.192 (2.36), 7.204 (2.43), 7.509 (2.59), 7.523 (2.58), 8.149 (3.33), 8.178 (3.33), 8.212 (3.22), 8.224 (3.22), 9.132 (2.19).

Example 66

N-(2,4-dimethylpyridin-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

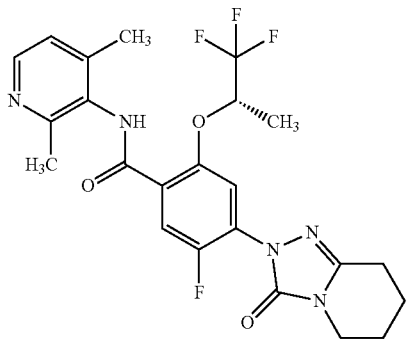 [SMILES: Cc1ccnc(C)c1NC(=O)c1cc(F)c(-n2nc3n(c2=O)CCCC3)cc1O[C@@H](C)C(F)(F)F]

From intermediate 17 and 2,4-dimethylpyridin-3-amine.
LC-MS (method A): $R_t$=0.81 min; MS (ESIpos): m/z=494 [M+H]$^+$ $^1$H-NMR (400 MHz, CHLOROFORM-d) δ [ppm]: 1.608 (9.87), 1.662 (6.35), 1.678 (6.30), 1.934 (1.08), 1.947 (1.51), 1.962 (1.62), 1.978 (0.81), 2.000 (0.77), 2.019 (1.54), 2.030 (1.61), 2.045 (1.02), 2.058 (0.44), 2.281 (14.78), 2.515 (16.00), 2.626 (2.90), 2.812 (2.01), 2.829 (3.91), 2.845 (2.27), 3.719 (2.48), 3.734 (4.23), 3.750 (1.93), 4.944 (0.43), 4.959 (0.98), 4.974 (1.27), 4.990 (0.92), 7.083 (2.08), 7.096 (2.10), 7.488 (2.53), 7.502 (2.50), 8.159 (3.07), 8.188 (3.08), 8.334 (2.74), 8.346 (2.63), 8.836 (2.11).

Example 67

5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}-N-(2,4,6-trimethylpyridin-3-yl)benzamide

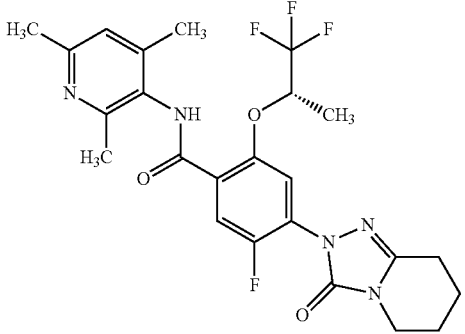 [SMILES: Cc1cc(C)c(NC(=O)c2cc(F)c(-n3nc4n(c3=O)CCCC4)cc2O[C@@H](C)C(F)(F)F)c(C)n1]

From intermediate 17 and 2,4,6-trimethylpyridin-3-amine.
LC-MS (method A): $R_t$=0.79 min; MS (ESIneg): m/z=506 [M–H]⁻
¹H-NMR (400 MHz, CHLOROFORM-d) δ [ppm]: 1.442 (7.39), 1.458 (7.49), 1.729 (2.46), 1.742 (2.56), 1.801 (2.53), 1.812 (2.60), 2.043 (15.52), 2.285 (16.00), 2.328 (15.22), 2.430 (0.46), 2.594 (2.48), 2.609 (4.67), 2.625 (2.61), 3.500 (2.78), 3.516 (4.81), 3.530 (2.46), 4.737 (0.56), 4.753 (1.22), 4.768 (1.56), 4.783 (1.18), 4.798 (0.52), 6.016 (0.59), 6.788 (4.69), 7.071 (1.94), 7.283 (2.70), 7.922 (2.73), 7.950 (2.73), 8.072 (1.90), 8.584 (3.19).

Example 68

N-(6-chloro-2,3-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

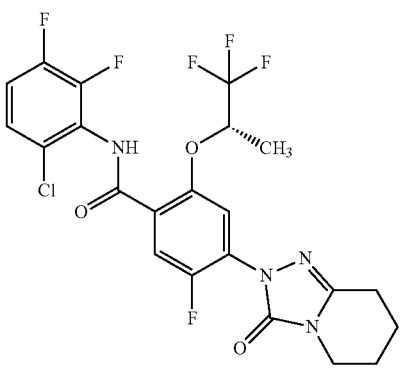 [SMILES: C[C@H](Oc1cc(-n2nc3n(c2=O)CCCC3)c(F)cc1C(=O)Nc1c(Cl)ccc(F)c1F)C(F)(F)F]

From intermediate 17 and 6-chloro-2,3-difluoroaniline.
LC-MS (method A): $R_t$=1.28 min; MS (ESIpos): m/z=535 [M+H]⁺
¹H-NMR (400 MHz, CHLOROFORM-d) δ [ppm]: 1.636 (4.25), 1.653 (16.00), 1.670 (15.48), 1.910 (1.06), 1.926 (2.96), 1.938 (4.26), 1.952 (4.46), 1.968 (2.29), 1.991 (2.20), 2.010 (4.36), 2.021 (4.58), 2.033 (2.92), 2.048 (1.20), 2.803 (4.90), 2.819 (9.54), 2.836 (5.29), 3.709 (5.79), 3.724 (9.99), 3.739 (4.77), 4.932 (1.04), 4.948 (2.42), 4.964 (3.13), 4.979 (2.35), 4.994 (0.98), 7.081 (1.26), 7.103 (3.33), 7.123 (3.55), 7.146 (1.94), 7.211 (2.32), 7.216 (2.47), 7.223 (2.75), 7.228 (2.62), 7.233 (2.05), 7.238 (1.92), 7.245 (1.84), 7.250 (1.72), 7.516 (5.83), 7.530 (5.84), 8.162 (6.02), 8.191 (6.02), 9.091 (5.61).

Example 69

5-fluoro-N-(2-methoxy-6-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

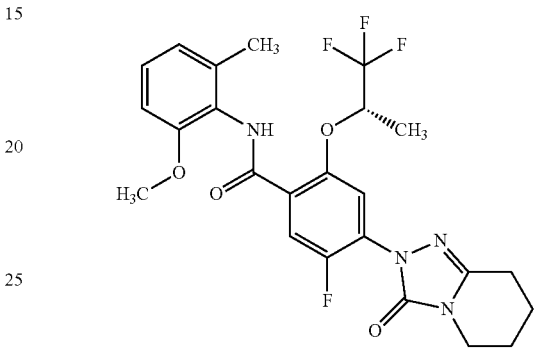

From intermediate 17 and 2-methoxy-6-methylaniline.
LC-MS (method A): $R_t$=1.25 min; MS (ESIneg): m/z=507 [M–H]⁻
¹H-NMR (400 MHz, CHLOROFORM-d) δ [ppm]: 1.720 (5.68), 1.736 (5.77), 2.008 (1.06), 2.020 (1.49), 2.035 (1.57), 2.047 (0.77), 2.051 (0.79), 2.073 (0.77), 2.092 (1.52), 2.103 (1.60), 2.116 (1.00), 2.131 (0.41), 2.375 (13.05), 2.886 (1.84), 2.902 (3.60), 2.918 (2.03), 3.795 (2.23), 3.810 (3.83), 3.825 (1.78), 3.906 (16.00), 5.003 (0.92), 5.018 (1.20), 5.033 (0.89), 6.880 (1.63), 6.901 (1.81), 6.975 (1.59), 6.994 (1.82), 7.250 (1.45), 7.290 (1.14), 7.363 (1.94), 7.532 (2.27), 7.547 (2.29), 8.229 (2.61), 8.258 (2.58), 8.977 (2.03).

Example 70

5-fluoro-N-(2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

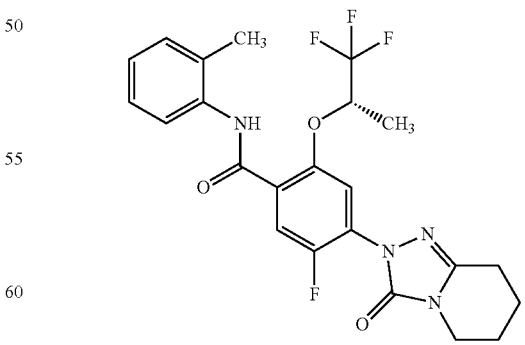

From intermediate 17 and o-toluidine.
MS (ESIpos): m/z=479 (M+H)⁺
¹H NMR (300 MHz, CDCl₃) δ [ppm] 1.62 (d, 3H), 1.86-2.06 (m, 4H), 2.31 (s, 3H), 2.81 (t, 2H), 3.71 (t, 2H), 4.82-4.97 (m, 1H), 7.13 (t, 1H), 7.20-7.30 (m, 2H), 7.46 (d, 1H), 7.89 (d, 1H), 8.14 (d, 1H), 9.02 (s, 1H).

Example 71

5-fluoro-N-(2-fluoro-6-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

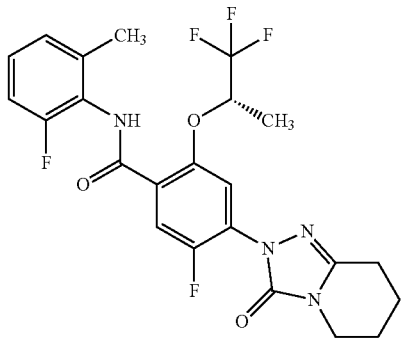

From intermediate 17 and 2-fluoro-6-methylaniline.

MS (ESIpos): m/z=497 (M+H)⁺

¹H NMR (300 MHz, CDCl₃) δ [ppm] 1.66 (d, 3H), 1.90-2.08 (m, 4H), 2.33 (s, 3H), 2.83 (t, 2H), 3.74 (t, 2H), 4.87-5.02 (m, 1H), 6.97-7.12 (m, 2H), 7.21 (dd, 1H), 7.50 (d, 1H), 8.17 (d, 1H), 8.18 (s, 1H).

Example 72

5-fluoro-N-(2-fluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

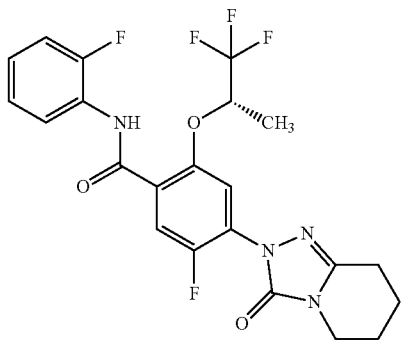 [SMILES: C[C@H](Oc1cc(-n2nc3n(c2=O)CCCC3)c(F)cc1C(=O)Nc1ccccc1F)C(F)(F)F]

From intermediate 17 and 2-fluoroaniline.

MS (ESIpos): m/z=483 (M+H)⁺

¹H NMR (300 MHz, CDCl₃) δ [ppm] 1.66 (d, 3H), 1.87-2.06 (m, 4H), 2.81 (t, 2H), 3.72 (t, 2H), 4.85-5.00 (m, 1H), 7.03-7.22 (m, 3H), 7.49 (d, 1H), 8.16 (d, 1H), 8.54 (td, 1H), 9.77 (s, 1H).

Example 73

5-fluoro-4-(3-oxo-5,6,7,8-tetrahydro[1,2,4]triazolo[4,3-a]pyridin-2(3H)-yl)-N-phenyl-2-{[(2S)-1,1,1-trifluoropropan-2-yl]oxy}benzamide

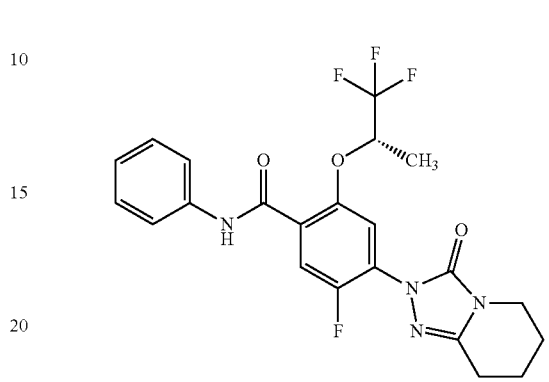

From intermediate 17 and aniline.

The product was purified by preparative HPLC (YMC Actus Triart C18 100×30 mm 5 μm, 0.1% aqueous formic acid, acetonitrile).

LC-MS (method C): R_t=1.25 min; MS (ESIpos): m/z=465 [M+H]⁺

Example 74

5-fluoro-N-(4-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

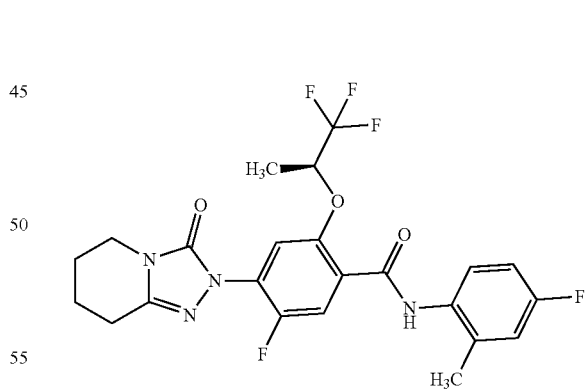

From intermediate 17 and 4-fluoro-2-methylaniline.

The product was purified by preparative HPLC (YMC Actus Triart C18 100×30 mm 5 μm, 0.1% aqueous formic acid, acetonitrile).

LC-MS (method C): R_t=1.26 min; MS (ESIpos): m/z=497 [M+H]⁺

Example 75

5-fluoro-4-(3-oxo-5,6,7,8-tetrahydro[1,2,4]triazolo[4,3-a]pyridin-2(3H)-yl)-N-(2,4,6-trifluorophenyl)-2-{[(2S)-1,1,1-trifluoropropan-2-yl]oxy}benzamide

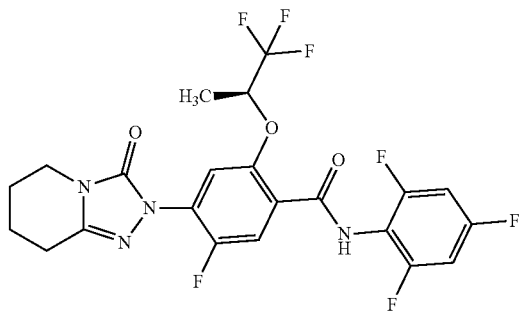 [SMILES: C[C@H](Oc1cc(-n2nc3n(c2=O)CCCC3)c(F)cc1C(=O)Nc1c(F)cc(F)cc1F)C(F)(F)F]

From intermediate 17 and 2,4,6-trifluoroaniline.

The product was purified by preparative HPLC (YMC Actus Triart C18 100×30 mm 5 μm, 0.1% aqueous formic acid, acetonitrile).

LC-MS (method C): $R_t$=1.23 min; MS (ESIpos): m/z=519 [M+H]$^+$

Example 76

5-fluoro-4-(3-oxo-5,6,7,8-tetrahydro[1,2,4]triazolo[4,3-a]pyridin-2(3H)-yl)-N-[2-(trifluoromethyl)phenyl]-2-{[(2S)-1,1,1-trifluoropropan-2-yl]oxy}benzamide

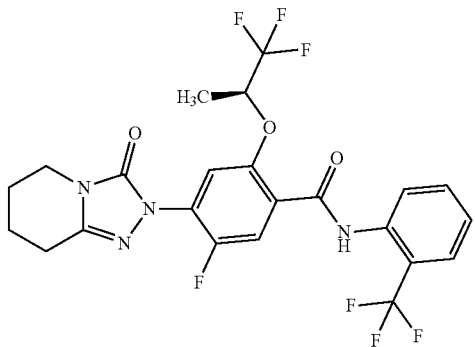 [SMILES: C[C@H](Oc1cc(-n2nc3n(c2=O)CCCC3)c(F)cc1C(=O)Nc1ccccc1C(F)(F)F)C(F)(F)F]

From intermediate 17 and 2-(trifluoromethyl)aniline.

The product was purified by preparative HPLC (YMC Actus Triart C18 100×30 mm 5 μm, 0.1% aqueous formic acid, acetonitrile).

LC-MS (method C): $R_t$=1.32 min; MS (ESIpos): m/z=533 [M+H]$^+$

Example 77

5-fluoro-N-(3-methylpyridin-2-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

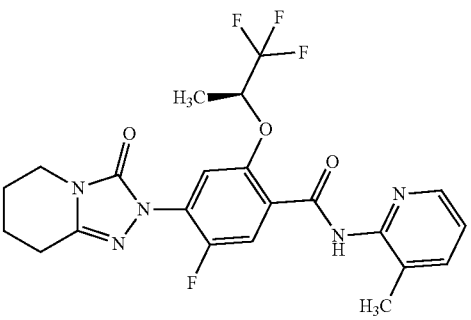 [SMILES: Cc1cccnc1NC(=O)c1cc(F)c(-n2nc3n(c2=O)CCCC3)cc1O[C@@H](C)C(F)(F)F]

From intermediate 17 and 3-methylpyridin-2-amine.

The product was purified by preparative HPLC (YMC Actus Triart C18 100×30 mm 5 μm, 0.1% aqueous formic acid, acetonitrile).

LC-MS (method C): $R_t$=1.00 min; MS (ESIpos): m/z=480 [M+H]$^+$

Example 78

N-(2-chlorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

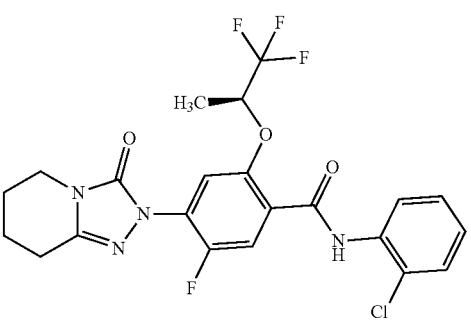 [SMILES: C[C@H](Oc1cc(-n2nc3n(c2=O)CCCC3)c(F)cc1C(=O)Nc1ccccc1Cl)C(F)(F)F]

From intermediate 17 and 2-chloroaniline.

The product was purified by preparative HPLC (YMC Actus Triart C18 100×30 mm 5 μm, 0.1% aqueous formic acid, acetonitrile).

LC-MS (method C): $R_t$=1.35 min; MS (ESIpos): m/z=500 [M+H]$^+$

Example 79

N-(2,6-dichlorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

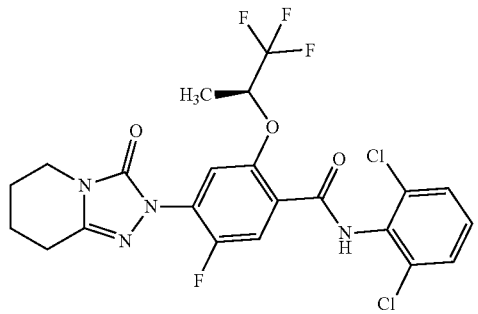 [SMILES: C[C@H](Oc1cc(-n2nc3n(c2=O)CCCC3)c(F)cc1C(=O)Nc1c(Cl)cccc1Cl)C(F)(F)F]

From intermediate 17 and 2,6-dichloroaniline.

The product was purified by preparative HPLC (YMC Actus Triart C18 100×30 mm 5 µm, 0.1% aqueous formic acid, acetonitrile).

LC-MS (method C): $R_t$=1.27 min; MS (ESIpos): m/z=534 [M+H]$^+$

Example 80

5-fluoro-N-(5-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

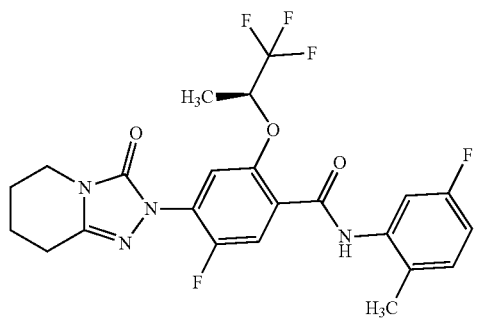 [SMILES: Cc1ccc(F)cc1NC(=O)c1cc(F)c(-n2nc3n(c2=O)CCCC3)cc1O[C@@H](C)C(F)(F)F]

From intermediate 17 and 5-fluoro-2-methylaniline.

The product was purified by preparative HPLC (YMC Actus Triart C18 100×30 mm 5 µm, 0.1% aqueous formic acid, acetonitrile).

LC-MS (method C): $R_t$=1.30 min; MS (ESIpos): m/z=497 [M+H]$^+$

Example 81

N-(2-cyano-3-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

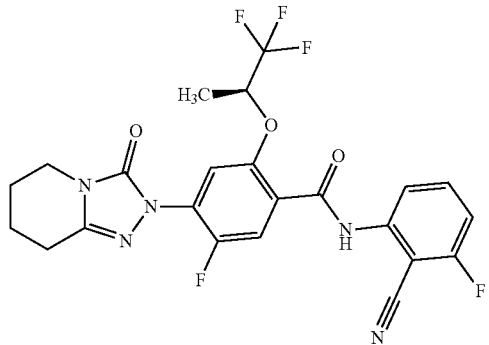 [SMILES: C[C@H](Oc1cc(-n2nc3n(c2=O)CCCC3)c(F)cc1C(=O)Nc1cccc(F)c1C#N)C(F)(F)F]

From intermediate 17 and 2-amino-6-fluorobenzonitrile.

The product was purified by preparative HPLC (YMC Actus Triart C18 100×30 mm 5 µm, 0.1% aqueous formic acid, acetonitrile).

LC-MS (method C): $R_t$=1.24 min; MS (ESIpos): m/z=508 [M+H]$^+$

Example 82

5-fluoro-N-(1-methyl-1H-pyrazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

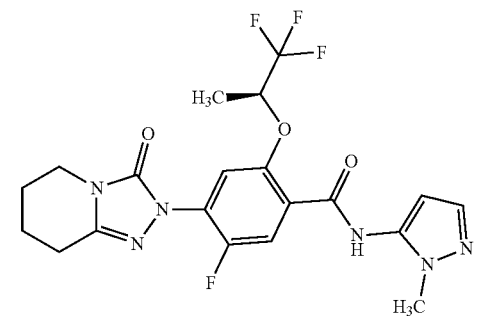 [SMILES: C[C@H](Oc1cc(-n2nc3n(c2=O)CCCC3)c(F)cc1C(=O)Nc1ccnn1C)C(F)(F)F]

From intermediate 17 and 1-methyl-1H-pyrazol-5-amine.

The product was purified by preparative HPLC (YMC Actus Triart C18 100×30 mm 5 µm, 0.1% aqueous formic acid, acetonitrile).

LC-MS (method C): $R_t$=0.99 min; MS (ESIpos): m/z=469 [M+H]$^+$

Example 83

5-fluoro-4-(3-oxo-5,6,7,8-tetrahydro[1,2,4]triazolo[4,3-a]pyridin-2(3H)-yl)-N-(tetrahydro-2H-pyran-4-yl)-2-{[(2S)-1,1,1-trifluoropropan-2-yl]oxy}benzamide

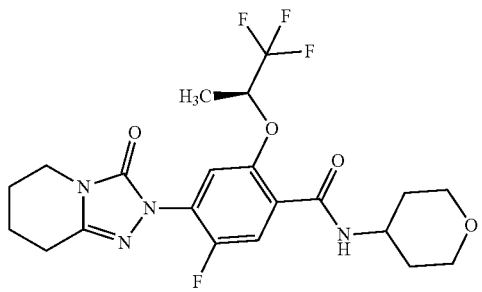 [SMILES: C[C@H](Oc1cc(-n2nc3n(c2=O)CCCC3)c(F)cc1C(=O)NC1CCOCC1)C(F)(F)F]

From intermediate 17 and tetrahydro-2H-pyran-4-amine.

The product was purified by preparative HPLC (YMC Actus Triart C18 100×30 mm 5 µm, 0.1% aqueous formic acid, acetonitrile).

LC-MS (method C): $R_t$=1.01 min; MS (ESIpos): m/z=473 [M+H]$^+$

Example 84

N-(2-chloro-5-fluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

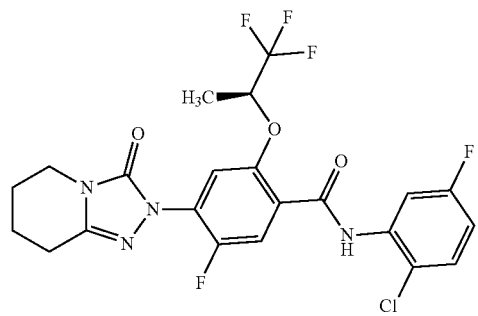 [SMILES: C[C@H](Oc1cc(-n2nc3n(c2=O)CCCC3)c(F)cc1C(=O)Nc1cc(F)ccc1Cl)C(F)(F)F]

From intermediate 17 and 2-chloro-5-fluoroaniline.

The product was purified by preparative HPLC (YMC Actus Triart C18 100×30 mm 5 µm, 0.1% aqueous formic acid, acetonitrile).

LC-MS (method C): $R_t$=1.41 min; MS (ESIpos): m/z=518 [M+H]$^+$

Example 85

5-fluoro-N-(4-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

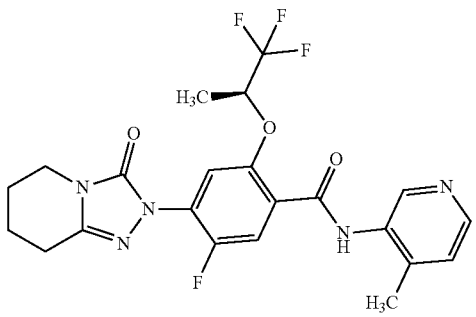 [SMILES: Cc1ccncc1NC(=O)c1cc(F)c(-n2nc3n(c2=O)CCCC3)cc1O[C@@H](C)C(F)(F)F]

From intermediate 17 and 4-methylpyridin-3-amine.

The product was purified by preparative HPLC (YMC Actus Triart C18 100×30 mm 5 µm, 0.1% aqueous formic acid, acetonitrile).

LC-MS (method C): $R_t$=0.83 min; MS (ESIpos): m/z=480 [M+H]$^+$

Example 86

5-fluoro-N-[2-methyl-5-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

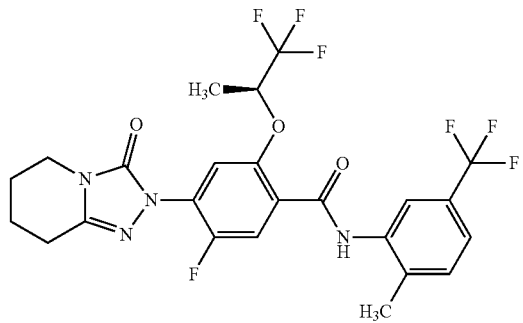 [SMILES: Cc1ccc(C(F)(F)F)cc1NC(=O)c1cc(F)c(-n2nc3n(c2=O)CCCC3)cc1O[C@@H](C)C(F)(F)F]

From intermediate 17 and 2-methyl-5-(trifluoromethyl)aniline.

The product was purified by preparative HPLC (YMC Actus Triart C18 100×30 mm 5 µm, 0.1% aqueous formic acid, acetonitrile).

LC-MS (method C): $R_t$=1.39 min; MS (ESIpos): m/z=547 [M+H]$^+$

Example 87

5-fluoro-N-(3-methylpyridin-4-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

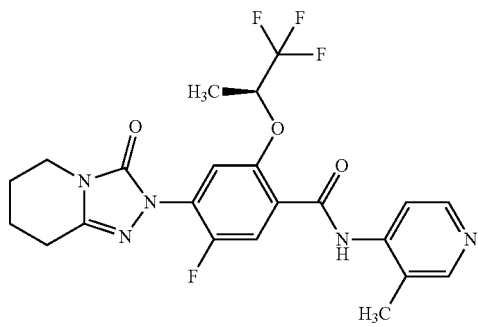 [SMILES: Cc1cnccc1NC(=O)c1cc(F)c(-n2nc3n(c2=O)CCCC3)cc1O[C@@H](C)C(F)(F)F]

From intermediate 17 and 3-methylpyridin-4-amine.

The product was purified by preparative HPLC (YMC Actus Triart C18 100×30 mm 5 μm, 0.1% aqueous formic acid, acetonitrile).

LC-MS (method C): $R_t$=0.78 min; MS (ESIpos): m/z=480 [M+H]$^+$

Example 88

5-fluoro-N-[2-methyl-6-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

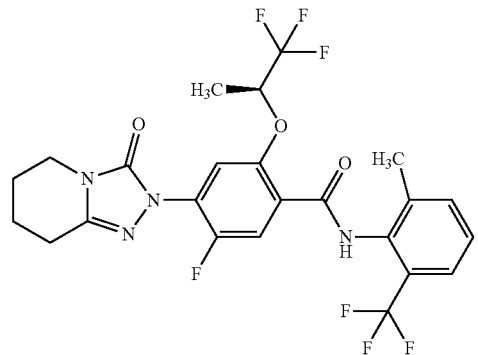 [SMILES: Cc1cccc(C(F)(F)F)c1NC(=O)c1cc(F)c(-n2nc3n(c2=O)CCCC3)cc1O[C@@H](C)C(F)(F)F]

From intermediate 17 and 2-methyl-6-(trifluoromethyl) aniline.

The product was purified by preparative HPLC (YMC Actus Triart C18 100×30 mm 5 μm, 0.1% aqueous formic acid, acetonitrile).

LC-MS (method C): $R_t$=1.31 min; MS (ESIpos): m/z=547 [M+H]$^+$

Example 89

N-(1,3-dimethyl-1H-pyrazol-4-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

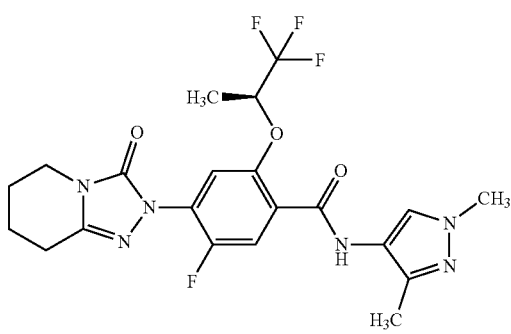 [SMILES: Cc1nn(C)cc1NC(=O)c1cc(F)c(-n2nc3n(c2=O)CCCC3)cc1O[C@@H](C)C(F)(F)F]

From intermediate 17 and 1,3-dimethyl-1H-pyrazol-4-amine.

The product was purified by preparative HPLC (YMC Actus Triart C18 100×30 mm 5 μm, 0.1% aqueous formic acid, acetonitrile).

LC-MS (method C): $R_t$=1.00 min; MS (ESIpos): m/z=483 [M+H]$^+$

Example 90

N-(1,4-dimethyl-1H-pyrazol-3-yl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

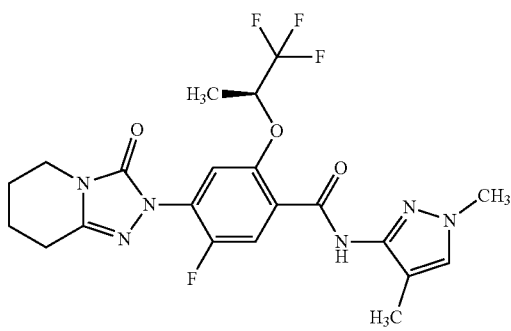 [SMILES: Cc1cn(C)nc1NC(=O)c1cc(F)c(-n2nc3n(c2=O)CCCC3)cc1O[C@@H](C)C(F)(F)F]

From intermediate 17 and 1,4-dimethyl-1H-pyrazol-3-amine.

The product was purified by preparative HPLC (YMC Actus Triart C18 100×30 mm 5 μm, 0.1% aqueous formic acid, acetonitrile).

LC-MS (method C): $R_t$=1.02 min; MS (ESIpos): m/z=483 [M+H]$^+$

Example 91

5-fluoro-N-(2-methylpyridin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

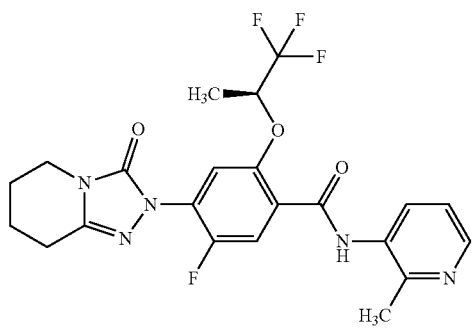 [SMILES: Cc1ncccc1NC(=O)c1cc(F)c(-n2nc3n(c2=O)CCCC3)cc1O[C@@H](C)C(F)(F)F]

From intermediate 17 and 2-methylpyridin-3-amine.

The product was purified by preparative HPLC (YMC Actus Triart C18 100×30 mm 5 µm, 0.1% aqueous formic acid, acetonitrile).

LC-MS (method C): $R_t$=0.83 min; MS (ESIpos): m/z=480 [M+H]$^+$

Example 92

5-fluoro-N-(2-hydroxy-2-methylpropyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

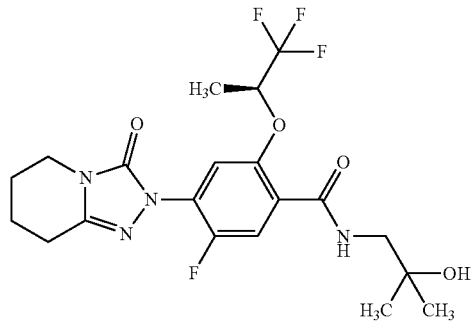 [SMILES: C[C@H](Oc1cc(-n2nc3n(c2=O)CCCC3)c(F)cc1C(=O)NCC(C)(C)O)C(F)(F)F]

From intermediate 17 and 1-amino-2-methylpropan-2-ol.

The product was purified by preparative HPLC (YMC Actus Triart C18 100×30 mm 5 µm, 0.1% aqueous formic acid, acetonitrile).

LC-MS (method C): $R_t$=0.96 min; MS (ESIpos): m/z=461 [M+H]$^+$

Example 93

5-fluoro-N-[2-(hydroxymethyl)-3-(trifluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

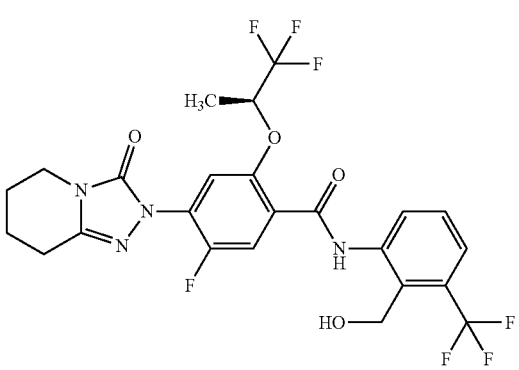 [SMILES: C[C@H](Oc1cc(-n2nc3n(c2=O)CCCC3)c(F)cc1C(=O)Nc1cccc(C(F)(F)F)c1CO)C(F)(F)F]

From intermediate 17 and [2-amino-6-(trifluoromethyl)phenyl]methanol.

The product was purified by preparative HPLC (YMC Actus Triart C18 100×30 mm 5 µm, 0.1% aqueous formic acid, acetonitrile).

LC-MS (method C): $R_t$=1.23 min; MS (ESIpos): m/z=563 [M+H]$^+$

Example 94

5-fluoro-N-[3-(hydroxymethyl) phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

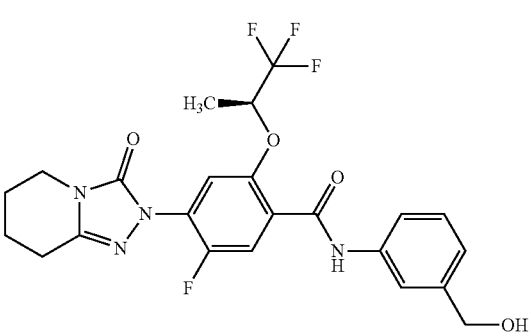 [SMILES: C[C@H](Oc1cc(-n2nc3n(c2=O)CCCC3)c(F)cc1C(=O)Nc1cccc(CO)c1)C(F)(F)F]

From intermediate 17 and (3-aminophenyl)methanol.

The product was purified by preparative HPLC (YMC Actus Triart C18 100×30 mm 5 µm, 0.1% aqueous formic acid, acetonitrile).

LC-MS (method C): $R_t$=1.06 min; MS (ESIpos): m/z=495 [M+H]$^+$

Example 95

5-fluoro-4-(3-oxo-5,6,7,8-tetrahydro[1,2,4]triazolo[4,3-a]pyridin-2(3H)-yl)-N-(quinolin-8-yl)-2-{[(2S)-1,1,1-trifluoropropan-2-yl]oxy}benzamide

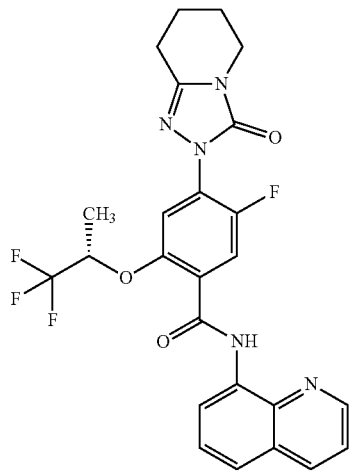 [SMILES: C[C@H](Oc1cc(-n2nc3n(c2=O)CCCC3)c(F)cc1C(=O)Nc1cccc2cccnc12)C(F)(F)F]

From intermediate 17 and quinolin-8-amine.

The product was purified by preparative HPLC (YMC Actus Triart C18 100×30 mm 5 μm, 0.1% aqueous formic acid, acetonitrile).

LC-MS (method C): $R_t$=1.39 min; MS (ESIpos): m/z=516 [M+H]$^+$

Example 96

5-fluoro-4-(3-oxo-5,6,7,8-tetrahydro[1,2,4]triazolo[4,3-a]pyridin-2(3H)-yl)-N-(quinolin-6-yl)-2-{[(2S)-1,1,1-trifluoropropan-2-yl]oxy}benzamide

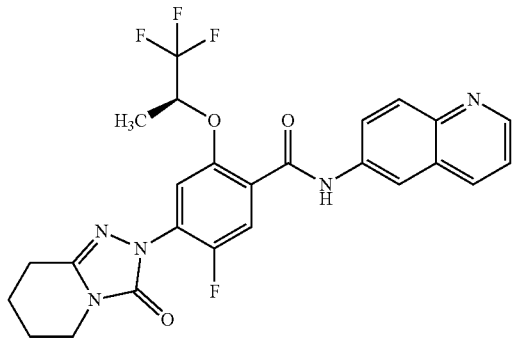 [SMILES: C[C@H](Oc1cc(-n2nc3n(c2=O)CCCC3)c(F)cc1C(=O)Nc1ccc2ncccc2c1)C(F)(F)F]

From intermediate 17 and quinolin-6-amine.

The product was purified by preparative HPLC (YMC Actus Triart C18 100×30 mm 5 μm, 0.1% aqueous formic acid, acetonitrile).

LC-MS (method C): $R_t$=0.96 min; MS (ESIpos): m/z=516 [M+H]$^+$

Example 97

3-{[5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoyl]amino}-4-methylbenzoic Acid

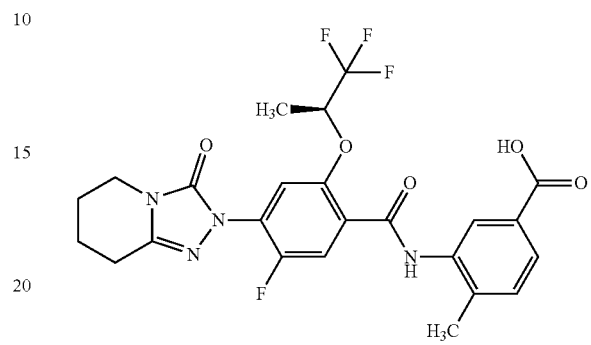

From intermediate 17 and 3-amino-4-methylbenzoic acid.

The product was purified by preparative HPLC (YMC Actus Triart C18 100×30 mm 5 μm, 0.1% aqueous formic acid, acetonitrile).

LC-MS (method C): $R_t$=1.10 min; MS (ESIpos): m/z=523 [M+H]$^+$

Example 98

5-fluoro-4-(3-oxo-5,6,7,8-tetrahydro[1,2,4]triazolo[4,3-a]pyridin-2(3H)-yl)-N-(quinolin-5-yl)-2-{[(2S)-1,1,1-trifluoropropan-2-yl]oxy}benzamide

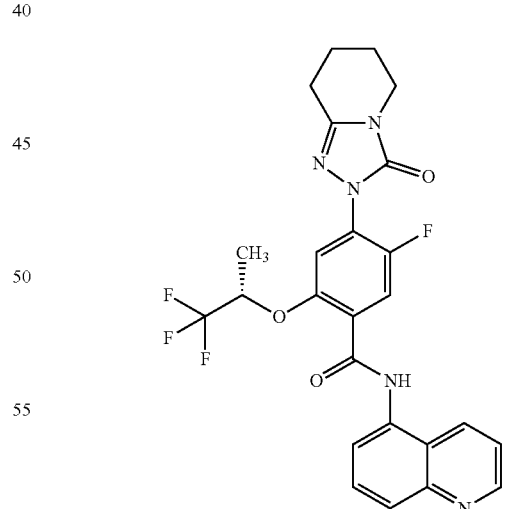

From intermediate 17 and quinolin-5-amine.

The product was purified by preparative HPLC (YMC Actus Triart C18 100×30 mm 5 μm, 0.1% aqueous formic acid, acetonitrile).

LC-MS (method C): $R_t$=0.96 min; MS (ESIpos): m/z=516 [M+H]$^+$

Example 99

5-fluoro-N-(2-methylquinolin-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

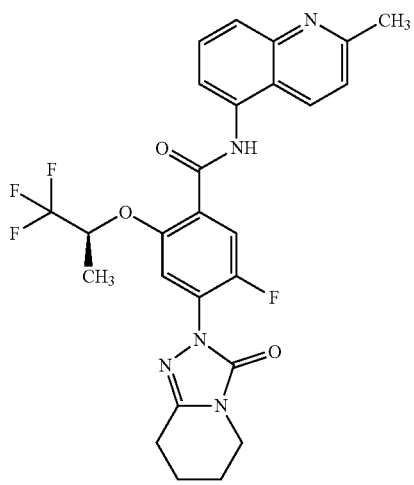 [SMILES: Cc1ccc2c(NC(=O)c3cc(F)c(-n4nc5n(c4=O)CCCC5)cc3O[C@@H](C)C(F)(F)F)cccc2n1]

From intermediate 17 and 2-methylquinolin-5-amine.

The product was purified by preparative HPLC (YMC Actus Triart C18 100×30 mm 5 μm, 0.1% aqueous formic acid, acetonitrile).

LC-MS (method C): $R_t$=0.89 min; MS (ESIpos): m/z=530 $[M+H]^+$

Example 100

5-fluoro-4-(3-oxo-5,6,7,8-tetrahydro[1,2,4]triazolo[4,3-a]pyridin-2(3H)-yl)-N-(quinolin-7-yl)-2-{[(2S)-1,1,1-trifluoropropan-2-yl]oxy}benzamide

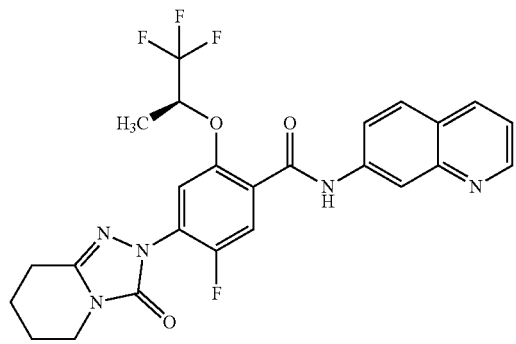 [SMILES: C[C@H](Oc1cc(-n2nc3n(c2=O)CCCC3)c(F)cc1C(=O)Nc1ccc2cccnc2c1)C(F)(F)F]

From intermediate 17 and quinolin-7-amine.

The product was purified by preparative HPLC (YMC Actus Triart C18 100×30 mm 5 μm, 0.1% aqueous formic acid, acetonitrile).

LC-MS (method C): $R_t$=0.93 min; MS (ESIpos): m/z=516 $[M+H]^+$

Example 101

5-fluoro-4-(3-oxo-5,6,7,8-tetrahydro[1,2,4]triazolo[4,3-a]pyridin-2(3H)-yl)-N-(3-sulfamoylphenyl)-2-{[(2S)-1,1,1-trifluoropropan-2-yl]oxy}benzamide

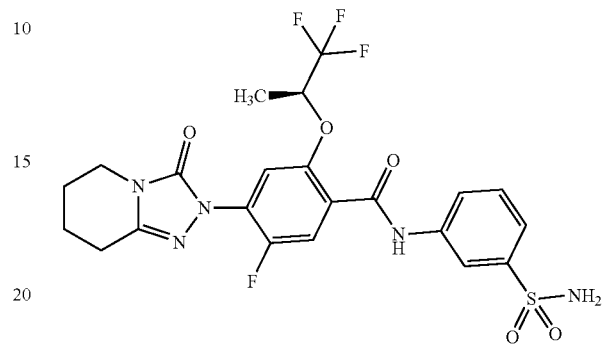

From intermediate 17 and 3-aminobenzenesulfonamide.

The product was purified by preparative HPLC (YMC Actus Triart C18 100×30 mm 5 μm, 0.1% aqueous formic acid, acetonitrile).

LC-MS (method C): $R_t$=1.02 min; MS (ESIpos): m/z=544 $[M+H]^+$

Example 102

5-fluoro-4-(3-oxo-5,6,7,8-tetrahydro[1,2,4]triazolo[4,3-a]pyridin-2(3H)-yl)-N-(7H-pyrrolo[2,3-d]pyrimidin-4-yl)-2-{[(2S)-1,1,1-trifluoropropan-2-yl]oxy}benzamide

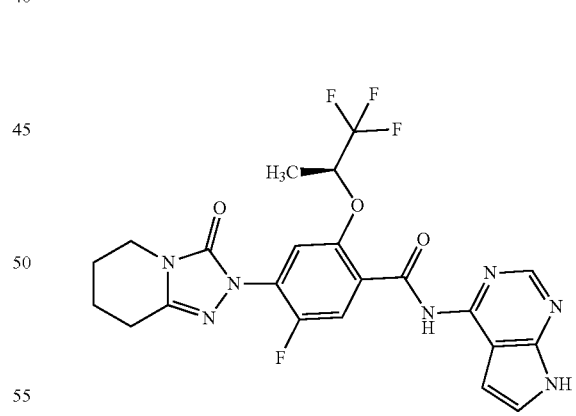

From intermediate 17 and 7H-pyrrolo[2,3-d]pyrimidin-4-amine

The product was purified by preparative HPLC (YMC Actus Triart C18 100×30 mm 5 μm, 0.1% aqueous formic acid, acetonitrile).

LC-MS (method C): $R_t$=0.96 min; MS (ESIpos): m/z=506 $[M+H]^+$

Example 103

5-fluoro-N-(2-methylquinolin-6-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

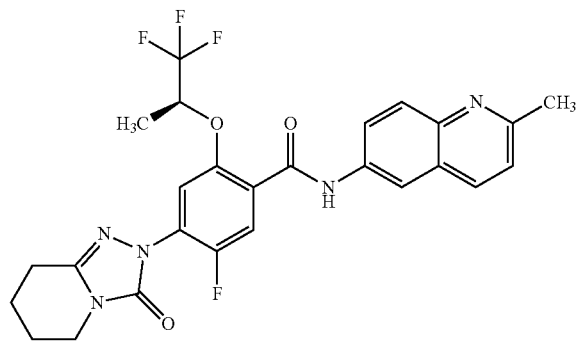 [SMILES: Cc1ccc2cc(NC(=O)c3cc(F)c(-n4nc5n(c4=O)CCCC5)cc3O[C@@H](C)C(F)(F)F)ccc2n1]

From intermediate 17 and 2-methylquinolin-6-amine.

The product was purified by preparative HPLC (YMC Actus Triart C18 100×30 mm 5 μm, 0.1% aqueous formic acid, acetonitrile).

LC-MS (method C): $R_t$=0.89 min; MS (ESIpos): m/z=530 [M+H]$^+$

Example 104

5-fluoro-N-(2-methyl-1,3-benzothiazol-6-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

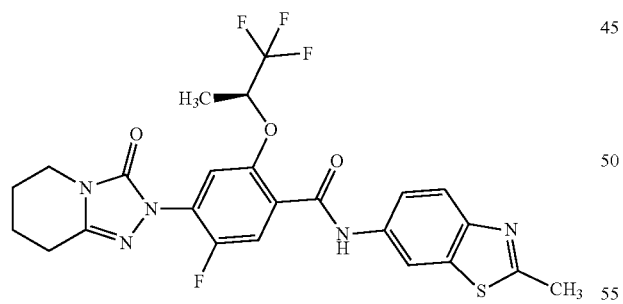

From intermediate 17 and 2-methyl-1,3-benzothiazol-6-amine.

The product was purified by preparative HPLC (YMC Actus Triart C18 100×30 mm 5 μm, 0.1% aqueous formic acid, acetonitrile).

LC-MS (method C): $R_t$=1.23 min; MS (ESIpos): m/z=536 [M+H]$^+$

Example 105

5-fluoro-N-(6-methyl-1H-indazol-5-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

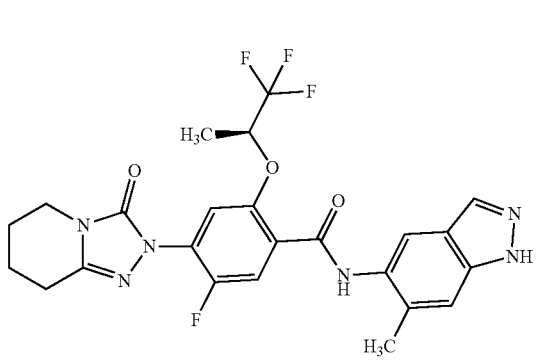 [SMILES: Cc1cc2[nH]ncc2cc1NC(=O)c1cc(F)c(-n2nc3n(c2=O)CCCC3)cc1O[C@@H](C)C(F)(F)F]

From intermediate 17 and 6-methyl-1H-indazol-5-amine.

The product was purified by preparative HPLC (YMC Actus Triart C18 100×30 mm 5 μm, 0.1% aqueous formic acid, acetonitrile).

LC-MS (method C): $R_t$=1.05 min; MS (ESIpos): m/z=519 [M+H]$^+$

Example 106

5-fluoro-N-(3-oxo-3,4-dihydro-2H-1,4-benzoxazin-7-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

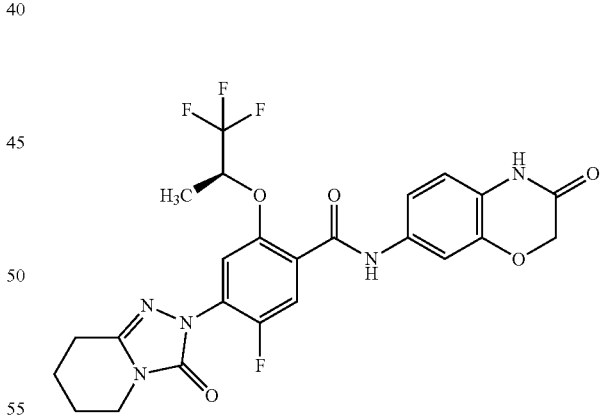

From intermediate 17 and 7-amino-2H-1,4-benzoxazin-3(4H)-one.

The product was purified by preparative HPLC (YMC Actus Triart C18 100×30 mm 5 μm, 0.1% aqueous formic acid, acetonitrile).

LC-MS (method C): $R_t$=1.03 min; MS (ESIpos): m/z=536 [M+H]$^+$

Example 107

N-(2,3-dimethoxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

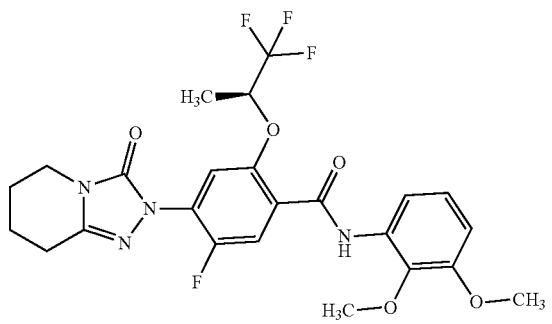 [SMILES: COc1cccc(NC(=O)c2cc(F)c(-n3nc4n(c3=O)CCCC4)cc2O[C@@H](C)C(F)(F)F)c1OC]

From intermediate 17 and 2,3-dimethoxyaniline.

The product was purified by preparative HPLC (YMC Actus Triart C18 100×30 mm 5 μm, 0.1% aqueous formic acid, acetonitrile).

LC-MS (method C): $R_t$=1.31 min; MS (ESIpos): m/z=525 [M+H]$^+$

Example 108

5-fluoro-N-(1H-indazol-7-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

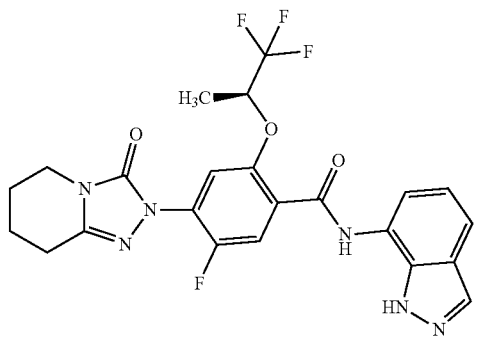 [SMILES: C[C@H](Oc1cc(-n2nc3n(c2=O)CCCC3)c(F)cc1C(=O)Nc1cccc2cn[nH]c12)C(F)(F)F]

From intermediate 17 and 1H-indazol-7-amine.

The product was purified by preparative HPLC (YMC Actus Triart C18 100×30 mm 5 μm, 0.1% aqueous formic acid, acetonitrile).

LC-MS (method C): $R_t$=1.15 min; MS (ESIpos): m/z=505 [M+H]$^+$

Example 109

5-fluoro-N-[1-(4-fluorophenyl)cyclopropyl]-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

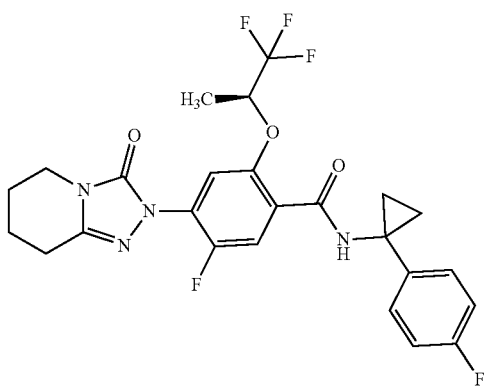 [SMILES: C[C@H](Oc1cc(-n2nc3n(c2=O)CCCC3)c(F)cc1C(=O)NC1(c2ccc(F)cc2)CC1)C(F)(F)F]

From intermediate 17 and 1-(4-fluorophenyl)cyclopropanamine.

The product was purified by preparative HPLC (YMC Actus Triart C18 100×30 mm 5 μm, 0.1% aqueous formic acid, acetonitrile).

LC-MS (method C): $R_t$=1.29 min; MS (ESIpos): m/z=523 [M+H]$^+$

Example 110

5-fluoro-N-(4-fluoro-3-hydroxy-1H-indazol-6-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

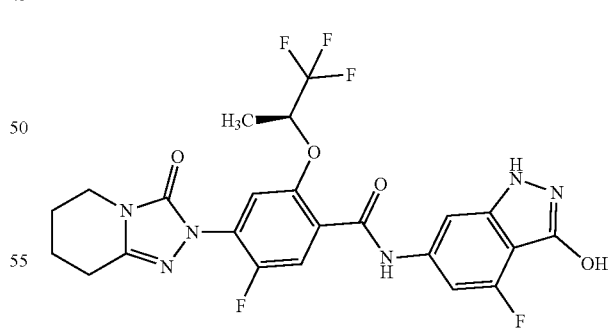

From intermediate 17 and 6-amino-4-fluoro-1H-indazol-3-ol.

The product was purified by preparative HPLC (YMC Actus Triart C18 100×30 mm 5 μm, 0.1% aqueous formic acid, acetonitrile).

LC-MS (method C): $R_t$=0.96 min; MS (ESIpos): m/z=539 [M+H]$^+$

Example 111

5-fluoro-N-[(1S,2S)-2-hydroxy-2,3-dihydro-1H-inden-1-yl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

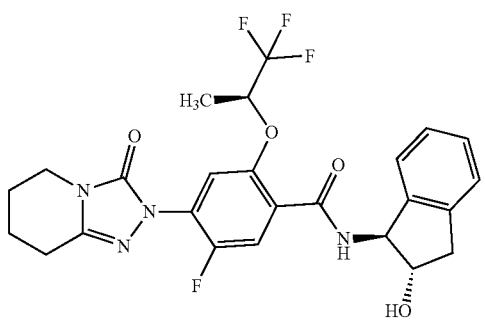 [SMILES: C[C@H](Oc1cc(-n2nc3n(c2=O)CCCC3)c(F)cc1C(=O)N[C@H]1c2ccccc2C[C@@H]1O)C(F)(F)F]

From intermediate 17 and (1S,2S)-1-aminoindan-2-ol.

The product was purified by preparative HPLC (YMC Actus Triart C18 100×30 mm 5 μm, 0.1% aqueous formic acid, acetonitrile).

LC-MS (method C): $R_t$=1.14 min; MS (ESIpos): m/z=521 [M+H]$^+$

Example 112

N-(3-carbamoyl-2-methylphenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

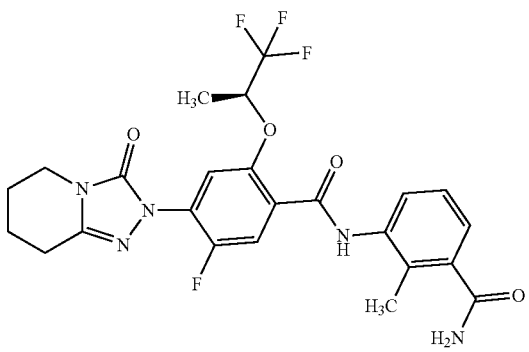 [SMILES: Cc1c(NC(=O)c2cc(F)c(-n3nc4n(c3=O)CCCC4)cc2O[C@@H](C)C(F)(F)F)cccc1C(N)=O]

From intermediate 17 and 3-amino-2-methylbenzamide.

The product was purified by preparative HPLC (YMC Actus Triart C18 100×30 mm 5 μm, 0.1% aqueous formic acid, acetonitrile).

LC-MS (method C): $R_t$=0.95 min; MS (ESIpos): m/z=522 [M+H]$^+$

Example 113

2-[(1S)-1-cyclohexylethoxy]-N-(1,1-dioxidotetrahydro-2H-thiopyran-4-yl)-5-fluoro-4-(3-oxo-5,6,7,8-tetrahydro[1,2,4]triazolo[4,3-a]pyridin-2(3H)-yl)benzamide

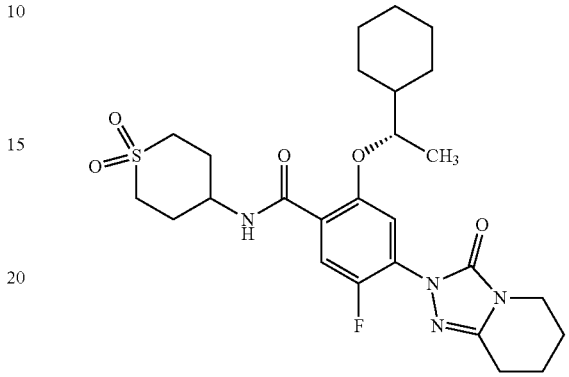

To a solution of 2-[(1S)-1-cyclohexylethoxy]-5-fluoro-4-(3-oxo-5,6,7,8-tetrahydro[1,2,4]triazolo[4,3-a]pyridin-2(3H)-yl)benzoic acid (intermediate 19) (100 mg, 248 μmol) in dichloromethane (1.0 ml) was added two drops of N,N-dimethylformamide. The solution was cooled to 0° C. and oxalyl chloride (34.6 mg, 273 μmol) was slowly added. The reaction was then warmed to room temperature and stirred for 90 minutes. The solvent was removed under reduced pressure and the residue was re-dissolved in dichloromethane (2.0 ml) and added dropwise to a cooled (0° C.) solution of tetrahydro-2H-thiopyran-4-amine 1,1-dioxide (40.7 mg, 273 μmol) and triethylamine (38 μl, 270 μmol) in dichloromethane (2.0 ml). The mixture was warmed to room temperature and stirred for one hour. Then, the solvent was removed under reduced pressure and the residue was purified by preparative HPLC (X-Bridge Prep C18 5 μm OBD, 0.1% aqueous formic acid, acetonitrile), to yield the title compound (90 mg, 67%) as a solid.

LC-MS (method A): $R_t$=1.13 min; MS (ESIpos): m/z=536 [M+H]$^+$ $^1$H-NMR (400 MHz, DMSO-d6) δ[ppm]: 0.993 (0.97), 1.001 (0.94), 1.024 (1.23), 1.031 (1.16), 1.073 (1.11), 1.080 (1.06), 1.103 (1.81), 1.109 (1.58), 1.132 (1.83), 1.159 (2.02), 1.192 (16.00), 1.207 (15.54), 1.220 (1.40), 1.228 (1.22), 1.559 (0.98), 1.566 (1.00), 1.573 (0.99), 1.624 (1.13), 1.658 (1.62), 1.702 (3.47), 1.732 (1.88), 1.770 (0.90), 1.779 (1.94), 1.786 (2.30), 1.791 (2.69), 1.802 (2.75), 1.806 (2.85), 1.818 (1.95), 1.822 (2.10), 1.855 (2.20), 1.859 (2.40), 1.869 (3.17), 1.874 (3.14), 1.884 (2.92), 1.890 (2.39), 1.899 (1.73), 1.905 (0.96), 1.966 (1.39), 1.978 (1.48), 1.994 (1.59), 2.003 (1.63), 2.019 (0.90), 2.149 (1.26), 2.158 (1.81), 2.164 (1.88), 2.173 (1.74), 2.178 (1.52), 2.183 (1.51), 2.188 (1.38), 2.193 (1.38), 2.198 (1.29), 2.208 (0.91), 2.540 (1.18), 2.672 (3.37), 2.688 (6.60), 2.704 (3.61), 3.090 (1.33), 3.098 (1.72), 3.127 (2.11), 3.133 (2.37), 3.141 (1.80), 3.279 (1.62), 3.308 (2.42), 3.342 (1.21), 3.539 (3.92), 3.554 (7.13), 3.568 (3.12), 4.149 (0.85), 4.155 (1.13), 4.165 (0.99), 4.175 (1.13), 4.282 (1.76), 4.297 (2.63), 4.312 (1.76), 7.240 (4.66), 7.256 (4.66), 7.501 (6.75), 7.528 (6.43), 8.224 (3.25), 8.244 (3.16).

Examples 114-138 were prepared as described for example 113 from 2-[(1S)-1-cyclohexylethoxy]-5-fluoro-4-(3-oxo-5,6,7,8-tetrahydro[1,2,4]triazolo[4,3-a]pyridin-2

(3H)-yl)benzoic acid (intermediate 19) and the respective amines, as indicated. Products were purified by flash column chromatography or, if explicitly mentioned, by preparative HPLC.

Example 114

2-[(1S)-1-cyclohexylethoxy]-N-(4,4-difluorocyclohexyl)-5-fluoro-4-(3-oxo-5,6,7,8-tetrahydro[1,2,4]triazolo[4,3-a]pyridin-2(3H)-yl)benzamide

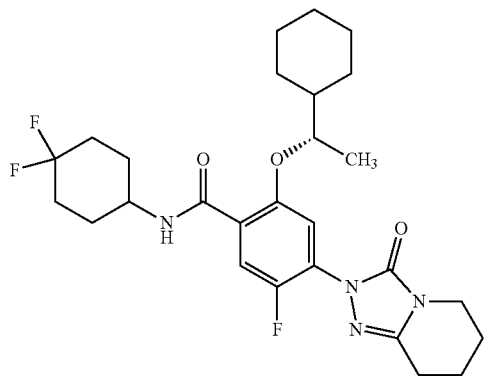 [SMILES: C[C@H](Oc1cc(-n2nc3n(c2=O)CCCC3)c(F)cc1C(=O)NC1CCC(F)(F)CC1)C1CCCCC1]

From intermediate 19 and 4,4-difluorocyclohexanamine.

The product was purified by preparative HPLC (X-Bridge Prep C18 5 μm OBD, 0.1% aqueous formic acid, acetonitrile).

LC-MS (method A): $R_t$=1.14 min; MS (ESIpos): m/z=522 [M+H]$^+$ $^1$H-NMR (400 MHz, DMSO-d6) δ[ppm]: 1.003 (0.99), 1.011 (0.95), 1.033 (1.26), 1.040 (1.18), 1.079 (1.06), 1.088 (1.21), 1.099 (1.04), 1.111 (1.53), 1.117 (1.48), 1.130 (1.44), 1.139 (1.44), 1.153 (2.22), 1.165 (1.46), 1.175 (1.73), 1.180 (1.94), 1.199 (16.00), 1.214 (15.48), 1.230 (1.11), 1.536 (1.92), 1.542 (2.21), 1.548 (2.02), 1.567 (2.68), 1.572 (2.53), 1.578 (2.19), 1.593 (1.26), 1.599 (1.19), 1.608 (1.15), 1.616 (1.06), 1.627 (1.17), 1.657 (1.54), 1.703 (3.79), 1.731 (1.93), 1.770 (0.95), 1.779 (2.01), 1.786 (2.40), 1.791 (2.75), 1.802 (2.79), 1.806 (2.90), 1.818 (1.58), 1.822 (1.64), 1.835 (1.43), 1.855 (1.92), 1.859 (2.16), 1.869 (3.64), 1.873 (3.75), 1.884 (3.24), 1.889 (2.77), 1.899 (2.47), 1.905 (2.30), 1.913 (2.32), 1.934 (2.76), 1.957 (2.22), 2.014 (2.22), 2.030 (2.85), 2.041 (2.37), 2.052 (1.84), 2.075 (0.84), 2.540 (1.46), 2.672 (3.45), 2.688 (6.74), 2.704 (3.68), 3.539 (4.39), 3.554 (7.73), 3.569 (3.86), 3.974 (0.93), 3.992 (0.91), 4.312 (1.77), 4.328 (2.63), 4.342 (1.75), 7.257 (4.67), 7.272 (4.65), 7.544 (7.00), 7.572 (6.60), 8.111 (3.23), 8.130 (3.16).

Example 115

2-[(1S)-1-cyclohexylethoxy]-5-fluoro-N-[2-methoxy-5-(trifluoromethyl)phenyl]-4-(3-oxo-5,6,7,8-tetrahydro[1,2,4]triazolo[4,3-a]pyridin-2(3H)-yl)benzamide

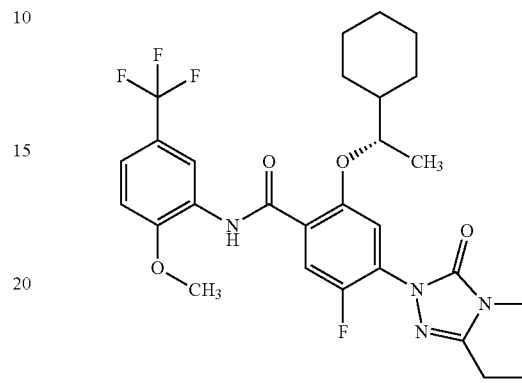

From intermediate 19 and 2-methoxy-5-(trifluoromethyl)aniline.

The product was purified by preparative HPLC (X-Bridge Prep C18 5 μm OBD, 0.1% aqueous formic acid, acetonitrile).

LC-MS (method A): $R_t$=1.59 min; MS (ESIpos): m/z=578 [M+H]$^+$ $^1$H-NMR (400 MHz, CHLOROFORM-d) δ [ppm]: 1.382 (6.95), 1.397 (6.77), 1.774 (1.31), 1.783 (1.65), 1.813 (1.01), 1.934 (1.00), 1.946 (1.03), 1.950 (1.11), 2.001 (1.35), 2.007 (1.43), 2.017 (1.25), 2.022 (0.96), 2.801 (1.54), 2.817 (2.95), 2.833 (1.69), 3.713 (1.92), 3.729 (3.21), 3.743 (1.39), 3.995 (16.00), 4.386 (1.00), 6.981 (1.43), 7.002 (1.61), 7.353 (0.93), 7.355 (0.99), 7.359 (1.06), 7.360 (1.14), 7.364 (2.07), 7.374 (1.03), 7.379 (2.67), 8.127 (2.63), 8.156 (2.60), 8.995 (1.83), 9.001 (1.79), 10.429 (1.57).

Example 116

2-[(1S)-1-cyclohexylethoxy]-5-fluoro-N-(6-methoxy-4-methylpyridin-3-yl)-4-(3-oxo-5,6,7,8-tetrahydro[1,2,4]triazolo[4,3-a]pyridin-2(3H)-yl)benzamide

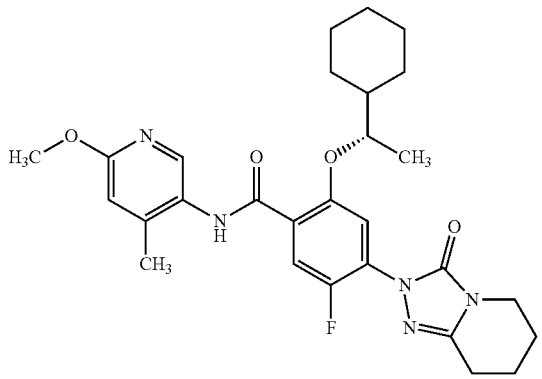 [SMILES: COc1cc(C)c(NC(=O)c2cc(F)c(-n3nc4n(c3=O)CCCC4)cc2O[C@@H](C)C2CCCCC2)cn1]

From intermediate 19 and 6-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.39 min; MS (ESIpos): m/z=525 [M+H]$^+$ $^1$H-NMR (400 MHz, CHLOROFORM-d) δ [ppm]: 1.368 (5.19), 1.383 (5.27), 1.612 (2.02), 1.948 (1.08), 2.273 (7.42), 2.274 (7.97), 2.800 (1.09), 2.817 (2.10), 2.832 (1.21), 3.710 (1.39), 3.725 (2.28), 3.740 (0.99), 3.939 (16.00), 6.665 (2.17), 6.667 (1.81), 7.384 (1.37), 7.399 (1.34), 8.128 (1.94), 8.157 (1.92), 8.341 (2.75), 9.497 (1.20).

Example 117

2-[(1S)-1-cyclohexylethoxy]-5-fluoro-N-(6-methoxy-2-methylpyridin-3-yl)-4-(3-oxo-5,6,7,8-tetrahydro[1,2,4]triazolo[4,3-a]pyridin-2(3H)-yl)benzamide

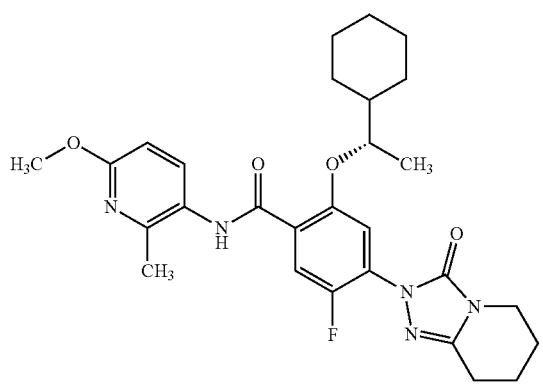 [SMILES: COc1ccc(NC(=O)c2cc(F)c(-n3nc4n(c3=O)CCCC4)cc2O[C@@H](C)C2CCCCC2)c(C)n1]

From intermediate 19 and 6-methoxy-2-methylpyridin-3-amine.

The product was purified by preparative HPLC (X-Bridge Prep C18 5 μm OBD, 0.1% aqueous formic acid, acetonitrile).

LC-MS (method A): $R_t$=1.43 min; MS (ESIpos): m/z=525 [M+H]$^+$ $^1$H-NMR (400 MHz, CHLOROFORM-d) δ [ppm]: 1.371 (4.50), 1.386 (4.74), 2.468 (8.80), 2.801 (1.00), 2.817 (1.92), 2.834 (1.12), 3.712 (1.28), 3.727 (2.08), 3.742 (0.91), 3.931 (16.00), 6.634 (1.22), 6.655 (1.25), 7.381 (1.26), 7.395 (1.24), 7.996 (1.68), 8.018 (1.56), 8.134 (1.80), 8.164 (1.75), 9.556 (1.07).

Example 118

2-[(1S)-1-cyclohexylethoxy]-5-fluoro-N-(2-methoxy-4-methylpyridin-3-yl)-4-(3-oxo-5,6,7,8-tetrahydro[1,2,4]triazolo[4,3-a]pyridin-2(3H)-yl)benzamide

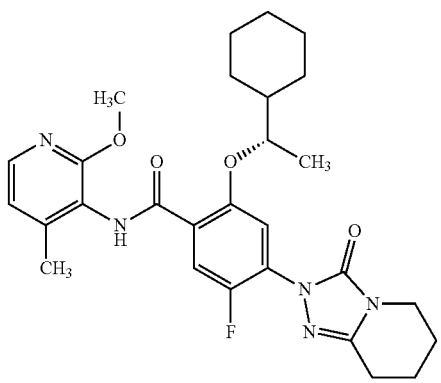 [SMILES: COc1nccc(C)c1NC(=O)c1cc(F)c(-n2nc3n(c2=O)CCCC3)cc1O[C@@H](C)C1CCCCC1]

From intermediate 19 and 2-methoxy-4-methylpyridin-3-amine.

The product was purified by preparative HPLC (X-Bridge Prep C18 5 μm OBD, 0.1% aqueous formic acid, acetonitrile).

LC-MS (method A): $R_t$=1.41 min; MS (ESIpos): m/z=525 [M+H]$^+$ $^1$H-NMR (400 MHz, CHLOROFORM-d) δ [ppm]: 1.371 (5.34), 1.387 (5.54), 1.620 (1.18), 2.014 (1.13), 2.282 (9.70), 2.800 (1.15), 2.817 (2.25), 2.832 (1.31), 3.711 (1.49), 3.726 (2.44), 3.741 (1.08), 3.959 (16.00), 6.830 (1.47), 6.843 (1.52), 7.371 (1.46), 7.386 (1.44), 7.943 (1.98), 7.956 (1.95), 8.122 (2.03), 8.151 (2.05), 9.606 (1.27).

Example 119

2-[(1S)-1-cyclohexylethoxy]-N-[3-(dimethylcarbamoyl)phenyl]-5-fluoro-4-(3-oxo-5,6,7,8-tetrahydro[1,2,4]triazolo[4,3-a]pyridin-2(3H)-yl)benzamide

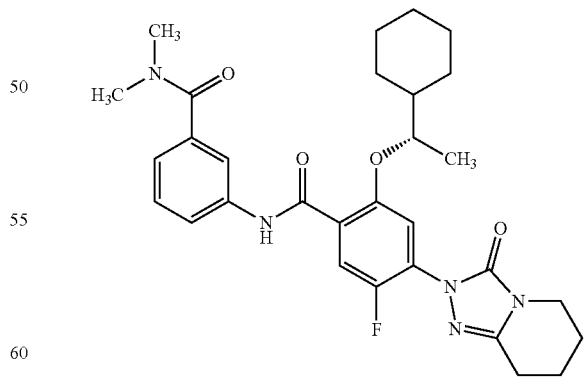

From intermediate 19 and 3-amino-N,N-dimethylbenzamide.

The product was purified by preparative HPLC (X-Bridge Prep C18 5 μm OBD, 0.1% aqueous formic acid, acetonitrile).

LC-MS (method A): R$_t$=1.28 min; MS (ESIpos): m/z=551 [M+H]$^+$ $^1$H-NMR (400 MHz, CHLOROFORM-d) δ [ppm]: 1.133 (1.32), 1.140 (1.25), 1.155 (1.32), 1.164 (1.60), 1.178 (1.01), 1.190 (1.85), 1.217 (1.15), 1.267 (1.06), 1.276 (1.38), 1.284 (1.35), 1.290 (1.18), 1.297 (1.04), 1.307 (1.12), 1.315 (1.03), 1.390 (15.78), 1.406 (16.00), 1.627 (3.39), 1.734 (1.25), 1.741 (1.39), 1.749 (1.08), 1.778 (1.29), 1.796 (3.56), 1.825 (2.88), 1.919 (1.59), 1.926 (1.87), 1.931 (2.14), 1.943 (2.23), 1.946 (2.38), 1.950 (1.66), 1.959 (1.08), 1.963 (1.14), 1.984 (1.73), 1.990 (1.96), 1.998 (2.92), 2.004 (2.75), 2.014 (2.89), 2.019 (2.75), 2.026 (2.31), 2.028 (2.29), 2.798 (3.31), 2.813 (6.43), 2.830 (3.67), 3.039 (6.90), 3.129 (6.84), 3.709 (4.18), 3.724 (6.99), 3.739 (3.00), 4.418 (1.58), 4.433 (2.34), 4.449 (1.50), 7.196 (1.92), 7.199 (2.71), 7.202 (2.04), 7.215 (2.44), 7.219 (3.37), 7.221 (2.32), 7.362 (4.22), 7.377 (4.26), 7.389 (2.80), 7.409 (4.80), 7.428 (2.76), 7.584 (1.98), 7.587 (2.30), 7.590 (2.27), 7.592 (2.17), 7.604 (1.64), 7.607 (1.75), 7.610 (1.96), 7.613 (1.73), 7.818 (3.10), 7.822 (4.79), 7.827 (3.01), 8.125 (5.73), 8.154 (5.81), 10.181 (3.75).

Example 120

2-[(1S)-1-cyclohexylethoxy]-5-fluoro-N-[1-(methylsulfonyl)piperidin-4-yl]-4-(3-oxo-5,6,7,8-tetrahydro[1,2,4]triazolo[4,3-a]pyridin-2(3H)-yl)benzamide

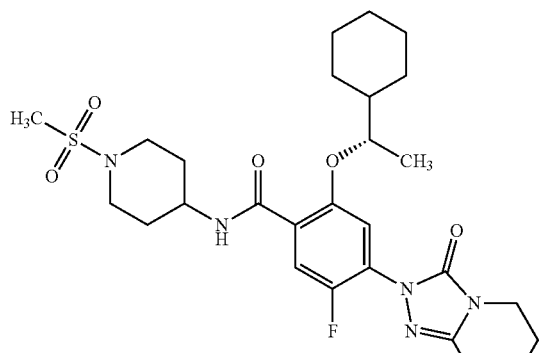

From intermediate 19 and 1-(methylsulfonyl)piperidin-4-amine.

The product was purified by preparative HPLC (X-Bridge Prep C18 5 μm OBD, 0.1% aqueous formic acid, acetonitrile).

LC-MS (method A): R$_t$=1.20 min; MS (ESIpos): m/z=565 [M+H]$^+$ $^1$H-NMR (400 MHz, CHLOROFORM-d) δ [ppm]: 1.315 (6.10), 1.331 (6.01), 1.615 (2.10), 1.909 (0.97), 1.916 (1.07), 1.921 (1.07), 1.933 (1.05), 1.936 (1.19), 2.784 (1.27), 2.800 (2.49), 2.816 (3.13), 2.819 (16.00), 2.851 (1.75), 2.857 (1.27), 3.695 (1.59), 3.710 (2.66), 3.725 (1.16), 4.347 (1.00), 7.291 (1.61), 8.035 (2.20), 8.065 (2.20).

Example 121

2-[(1S)-1-cyclohexylethoxy]-5-fluoro-N-(5-methoxy-4-methylpyridin-3-yl)-4-(3-oxo-5,6,7,8-tetrahydro[1,2,4]triazolo[4,3-a]pyridin-2(3H)-yl)benzamide

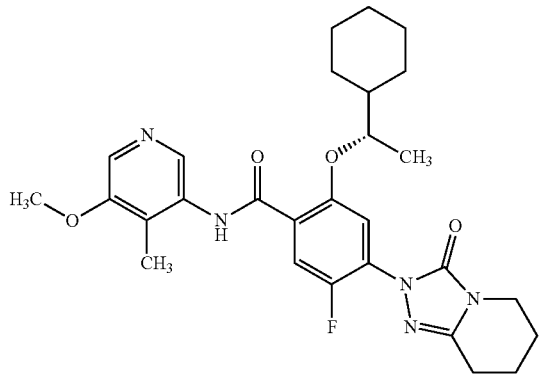 [SMILES: COc1cncc(NC(=O)c2cc(F)c(-n3nc4n(c3=O)CCCC4)cc2O[C@@H](C)C2CCCCC2)c1C]

From intermediate 19 and 5-methoxy-4-methylpyridin-3-amine.

The product was purified by preparative HPLC (X-Bridge Prep C18 5 μm OBD, 0.1% aqueous ammonia, acetonitrile).

LC-MS (method A): R$_t$=1.20 min; MS (ESIpos): m/z=524 [M+H]$^+$ $^1$H-NMR (400 MHz, CHLOROFORM-d) δ [ppm]: 1.298 (6.59), 1.313 (6.91), 1.683 (1.19), 1.868 (1.13), 1.873 (1.32), 1.924 (1.17), 1.930 (1.08), 1.940 (1.06), 2.150 (14.84), 2.726 (1.50), 2.742 (2.88), 2.758 (1.65), 3.634 (1.87), 3.650 (3.14), 3.665 (1.32), 3.893 (16.00), 4.360 (1.00), 7.338 (1.81), 7.353 (1.81), 8.042 (3.18), 8.063 (2.46), 8.093 (2.49), 8.677 (2.37), 9.646 (1.54).

Example 122

2-[(1S)-1-cyclohexylethoxy]-5-fluoro-N-[6-(morpholin-4-yl)pyridazin-3-yl]-4-(3-oxo-5,6,7,8-tetrahydro[1,2,4]triazolo[4,3-a]pyridin-2(3H)-yl)benzamide

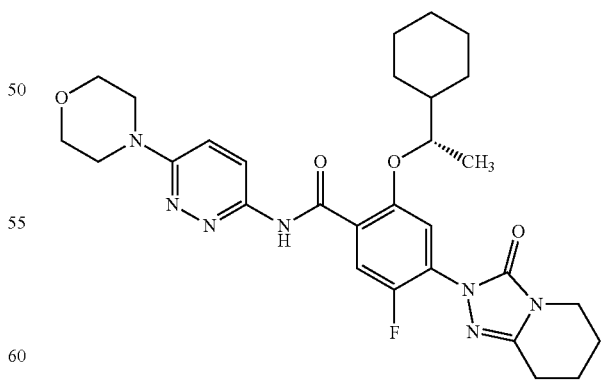

From intermediate 19 and 6-(morpholin-4-yl)pyridazin-3-amine.

The product was purified by preparative HPLC (X-Bridge Prep C18 5 μm OBD, 0.1% aqueous formic acid, acetonitrile).

LC-MS (method A): $R_t$=1.30 min; MS (ESIpos): m/z=567 [M+H]$^+$ $^1$H-NMR (400 MHz, CHLOROFORM-d) δ [ppm]: 1.085 (1.31), 1.095 (1.47), 1.117 (2.32), 1.123 (2.56), 1.137 (1.05), 1.147 (2.08), 1.155 (2.37), 1.160 (1.99), 1.168 (0.99), 1.183 (0.93), 1.191 (0.91), 1.259 (1.62), 1.290 (2.08), 1.323 (1.66), 1.409 (15.58), 1.425 (16.00), 1.674 (1.14), 1.704 (1.04), 1.749 (2.09), 1.756 (2.11), 1.781 (3.03), 1.799 (1.96), 1.808 (1.87), 1.831 (1.06), 1.839 (0.99), 1.847 (1.01), 1.925 (1.94), 1.933 (2.50), 1.938 (2.97), 1.948 (3.79), 1.952 (3.95), 1.964 (1.87), 1.968 (1.89), 1.989 (2.19), 2.003 (2.58), 2.009 (2.71), 2.018 (3.20), 2.024 (2.38), 2.034 (1.68), 2.805 (3.84), 2.820 (7.56), 2.837 (4.22), 3.709 (6.23), 3.717 (10.39), 3.720 (10.18), 3.732 (14.91), 3.747 (3.82), 3.882 (8.63), 3.896 (9.39), 3.906 (6.47), 4.405 (1.64), 4.421 (2.51), 4.437 (1.63), 7.006 (0.57), 7.301 (2.87), 7.381 (4.86), 7.395 (4.80), 8.046 (6.81), 8.076 (6.86), 8.737 (3.23), 8.762 (3.05), 11.073 (1.18).

Example 123

2-[(1S)-1-cyclohexylethoxy]-5-fluoro-N-(5-methoxypyrimidin-4-yl)-4-(3-oxo-5,6,7,8-tetrahydro[1,2,4]triazolo[4,3-a]pyridin-2(3H)-yl)benzamide

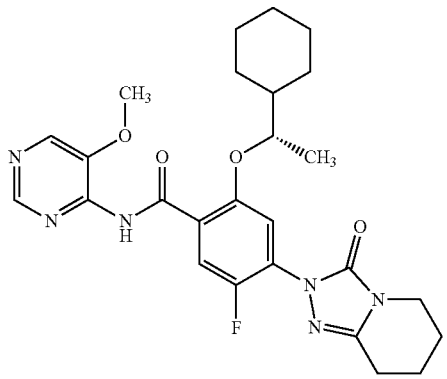 [SMILES: COc1cncnc1NC(=O)c1cc(F)c(-n2nc3n(c2=O)CCCC3)cc1O[C@@H](C)C1CCCCC1]

From intermediate 19 and 6-(morpholin-4-yl)pyridazin-3-amine.

The product was purified by preparative HPLC (X-Bridge Prep C18 5 μm OBD, 0.1% aqueous formic acid, acetonitrile).

LC-MS (method A): $R_t$=1.14 min; MS (ESIpos): m/z=511 [M+H]$^+$ $^1$H-NMR (400 MHz, CHLOROFORM-d) δ [ppm]: 1.031 (0.48), 1.038 (0.47), 1.067 (0.83), 1.098 (0.74), 1.132 (0.50), 1.163 (0.59), 1.185 (0.91), 1.205 (0.83), 1.213 (0.58), 1.228 (0.66), 1.237 (0.70), 1.245 (0.41), 1.258 (0.53), 1.383 (7.29), 1.399 (7.32), 1.688 (1.41), 1.727 (0.48), 1.747 (0.94), 1.754 (1.09), 1.779 (1.74), 1.803 (1.09), 1.918 (0.84), 1.925 (1.01), 1.930 (1.15), 1.941 (1.29), 1.945 (1.44), 1.957 (1.07), 1.960 (1.06), 1.983 (0.98), 1.988 (1.04), 1.997 (1.42), 2.012 (1.24), 2.017 (1.02), 2.026 (0.74), 2.796 (1.71), 2.812 (3.28), 2.829 (1.90), 3.707 (2.10), 3.722 (3.52), 3.737 (1.52), 4.033 (16.00), 4.392 (0.75), 4.408 (1.10), 4.424 (0.72), 7.390 (2.08), 7.405 (2.06), 8.140 (2.99), 8.169 (2.95), 8.263 (2.87), 8.772 (4.28), 10.731 (1.73).

Example 124

2-[(1S)-1-cyclohexylethoxy]-5-fluoro-N-(2-methoxypyrimidin-5-yl)-4-(3-oxo-5,6,7,8-tetrahydro[1,2,4]triazolo[4,3-a]pyridin-2(3H)-yl)benzamide

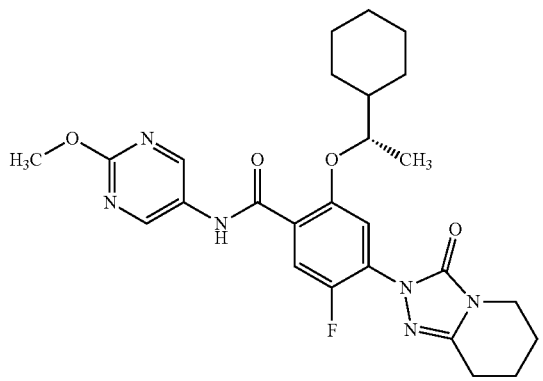 [SMILES: COc1ncc(NC(=O)c2cc(F)c(-n3nc4n(c3=O)CCCC4)cc2O[C@@H](C)C2CCCCC2)cn1]

From intermediate 19 and 2-methoxypyrimidin-5-amine.

The product was purified by preparative HPLC (X-Bridge Prep C18 5 μm OBD, 0.1% aqueous formic acid, acetonitrile).

LC-MS (method A): $R_t$=1.29 min; MS (ESIpos): m/z=512 [M+H]$^+$ $^1$H-NMR (400 MHz, CHLOROFORM-d) δ [ppm]: 1.393 (5.54), 1.409 (5.64), 2.801 (1.12), 2.817 (2.12), 2.834 (1.25), 3.712 (1.40), 3.728 (2.35), 3.743 (1.00), 4.045 (16.00), 7.393 (1.42), 7.408 (1.42), 8.121 (2.01), 8.150 (1.97), 8.866 (10.12), 10.079 (1.31).

Example 125

2-[(1S)-1-cyclohexylethoxy]-N-(4,6-dimethoxypyrimidin-5-yl)-5-fluoro-4-(3-oxo-5,6,7,8-tetrahydro[1,2,4]triazolo[4,3-a]pyridin-2(3H)-yl)benzamide

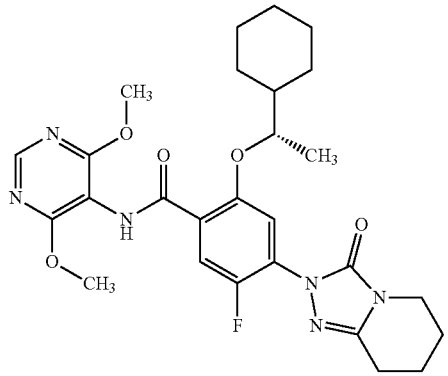 [SMILES: COc1ncnc(OC)c1NC(=O)c1cc(F)c(-n2nc3n(c2=O)CCCC3)cc1O[C@@H](C)C1CCCCC1]

From intermediate 19 and 4,6-dimethoxypyrimidin-5-amine.

The product was purified by preparative HPLC (X-Bridge Prep C18 5 μm OBD, 0.2% aqueous ammonia, acetonitrile).

LC-MS (method B): $R_t$=1.33 min; MS (ESIpos): m/z=541 [M+H]$^+$ $^1$H-NMR (400 MHz, CHLOROFORM-d) δ [ppm]: 1.205 (0.43), 1.359 (2.94), 1.375 (2.89), 1.662 (0.91), 1.767 (0.61), 1.792 (0.60), 1.925 (0.45), 1.937 (0.46), 1.940 (0.49), 1.977 (0.43), 1.991 (0.52), 1.997 (0.56), 2.007 (0.67), 2.012 (0.64), 2.018 (0.40), 2.794 (0.66), 2.810 (1.31), 2.825 (0.74), 3.703 (0.83), 3.718 (1.41), 3.733 (0.61), 4.020 (16.00), 4.419 (0.50), 7.360 (0.82), 7.374 (0.83), 8.107 (1.03), 8.136 (1.03), 8.380 (2.30), 9.304 (0.82).

Example 126

2-[(1S)-1-cyclohexylethoxy]-N-(3,5-dimethylpyrazin-2-yl)-5-fluoro-4-(3-oxo-5,6,7,8-tetrahydro[1,2,4]triazolo[4,3-a]pyridin-2(3H)-yl)benzamide

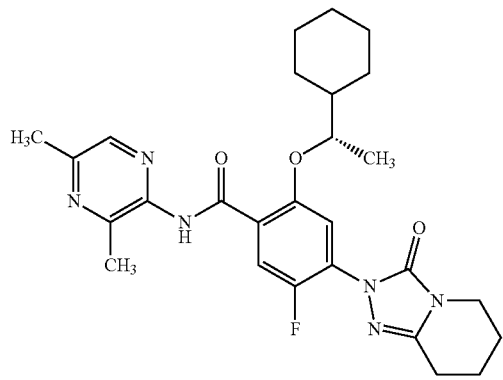 [SMILES: Cc1cnc(NC(=O)c2cc(F)c(-n3nc4n(c3=O)CCCC4)cc2O[C@@H](C)C2CCCCC2)c(C)n1]

From intermediate 19 and 3,5-dimethylpyrazin-2-amine.

The product was purified by preparative HPLC (X-Bridge Prep C18 5 μm OBD, 0.1% aqueous formic acid, acetonitrile).

LC-MS (method A): $R_t$=1.32 min; MS (ESIpos): m/z=510 [M+H]$^+$ $^1$H-NMR (400 MHz, CHLOROFORM-d) δ [ppm]: 1.126 (0.59), 1.157 (0.53), 1.181 (0.45), 1.203 (0.77), 1.228 (0.75), 1.234 (0.66), 1.243 (0.52), 1.251 (0.51), 1.260 (0.75), 1.274 (0.41), 1.396 (4.90), 1.412 (4.84), 1.702 (0.48), 1.745 (0.55), 1.770 (0.98), 1.785 (0.74), 1.795 (0.81), 1.908 (0.54), 1.923 (0.84), 1.935 (0.96), 1.947 (0.93), 1.951 (0.98), 1.966 (0.77), 1.987 (0.60), 2.002 (1.07), 2.007 (1.07), 2.018 (0.89), 2.023 (0.70), 2.032 (0.51), 2.565 (16.00), 2.803 (1.09), 2.819 (2.09), 2.836 (1.18), 3.713 (1.36), 3.729 (2.24), 3.744 (0.98), 4.427 (0.52), 4.442 (0.74), 4.457 (0.49), 7.394 (1.34), 7.409 (1.33), 8.122 (1.70), 8.151 (1.71), 8.172 (1.55), 10.087 (1.09).

Example 127

2-[(1S)-1-cyclohexylethoxy]-5-fluoro-N-(6-methoxypyrazin-2-yl)-4-(3-oxo-5,6,7,8-tetrahydro[1,2,4]triazolo[4,3-a]pyridin-2(3H)-yl)benzamide

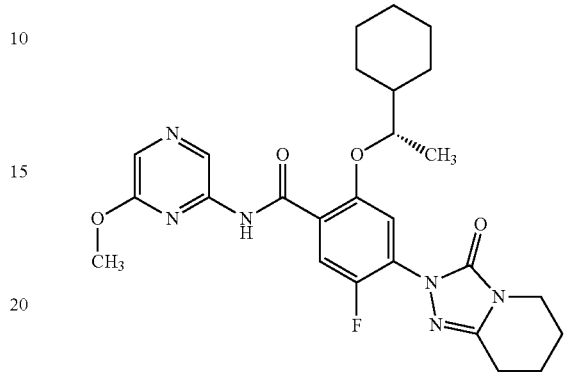

From intermediate 19 and 6-methoxypyrazin-2-amine.

The product was purified by preparative HPLC (X-Bridge Prep C18 5 μm OBD, 0.1% aqueous formic acid, acetonitrile).

LC-MS (method A): $R_t$=1.47 min; MS (ESIpos): m/z=511 [M+H]$^+$ $^1$H-NMR (400 MHz, CHLOROFORM-d) δ [ppm]: 1.174 (0.85), 1.205 (1.29), 1.232 (1.01), 1.250 (0.49), 1.261 (0.74), 1.405 (6.24), 1.421 (6.21), 1.622 (0.41), 1.692 (0.43), 1.722 (0.42), 1.782 (0.82), 1.805 (0.78), 1.815 (0.79), 1.830 (0.48), 1.839 (0.54), 1.850 (0.55), 1.874 (0.41), 1.925 (0.64), 1.933 (0.75), 1.937 (0.83), 1.948 (0.85), 1.952 (0.91), 1.964 (0.42), 1.968 (0.45), 1.990 (0.47), 2.005 (1.03), 2.010 (1.16), 2.019 (1.17), 2.025 (0.94), 2.035 (0.74), 2.040 (0.60), 2.047 (0.57), 2.803 (1.29), 2.820 (2.44), 2.836 (1.42), 3.714 (1.66), 3.729 (2.70), 3.744 (1.15), 3.953 (16.00), 4.458 (0.57), 4.473 (0.83), 4.489 (0.55), 7.414 (1.62), 7.428 (1.59), 8.043 (3.93), 8.143 (2.27), 8.172 (2.20), 9.260 (3.63), 10.567 (1.22).

Example 128

2-[(1S)-1-cyclohexylethoxy]-5-fluoro-N-(3-methoxypyrazin-2-yl)-4-(3-oxo-5,6,7,8-tetrahydro[1,2,4]triazolo[4,3-a]pyridin-2(3H)-yl)benzamide

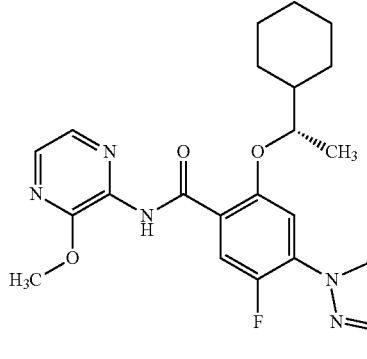

From intermediate 19 and 3-methoxypyrazin-2-amine.

The product was purified by preparative HPLC (X-Bridge Prep C18 5 μm OBD, 0.1% aqueous formic acid, acetonitrile).

LC-MS (method A): $R_t$=1.34 min; MS (ESIpos): m/z=512 [M+H]$^+$ $^1$H-NMR (400 MHz, CHLOROFORM-d) δ [ppm]: 1.036 (0.79), 1.041 (0.60), 1.049 (0.57), 1.079 (0.89), 1.112 (0.97), 1.135 (0.55), 1.143 (0.58), 1.166 (0.70), 1.192 (1.34), 1.221 (0.88), 1.229 (0.71), 1.252 (0.86), 1.259 (0.80), 1.278 (3.86), 1.296 (0.56), 1.397 (6.33), 1.412 (6.33), 1.682 (0.57), 1.713 (0.66), 1.748 (0.72), 1.756 (0.69), 1.791 (2.14), 1.817 (1.64), 1.903 (0.41), 1.919 (1.04), 1.931 (1.47), 1.946 (1.63), 1.962 (1.17), 1.983 (1.86), 2.002 (2.29), 2.012 (2.41), 2.040 (0.58), 2.798 (1.63), 2.814 (3.19), 2.830 (1.79), 3.710 (1.95), 3.725 (3.34), 3.740 (1.56), 4.091 (16.00), 4.400 (0.78), 4.416 (1.16), 4.431 (0.77), 7.374 (1.89), 7.389 (1.90), 7.837 (1.71), 7.844 (1.91), 8.064 (1.59), 8.071 (1.60), 8.156 (2.14), 8.185 (2.12), 10.658 (1.61).

Example 129

2-[(1S)-1-cyclohexylethoxy]-5-fluoro-N-(6-methoxypyridazin-3-yl)-4-(3-oxo-5,6,7,8-tetrahydro[1,2,4]triazolo[4,3-a]pyridin-2(3H)-yl)benzamide

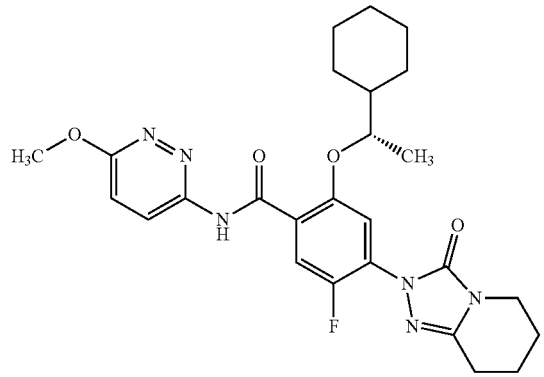 [SMILES: COc1ccc(NC(=O)c2cc(F)c(-n3nc4n(c3=O)CCCC4)cc2O[C@@H](C)C2CCCCC2)nn1]

From intermediate 19 and 6-methoxypyridazin-3-amine.

The product was purified by preparative HPLC (X-Bridge Prep C18 5 μm OBD, 0.1% aqueous formic acid, acetonitrile).

LC-MS (method A): $R_t$=1.40 min; MS (ESIpos): m/z=511 [M+H]$^+$ $^1$H-NMR (400 MHz, CHLOROFORM-d) δ [ppm]: 1.149 (0.81), 1.181 (0.83), 1.445 (5.28), 1.461 (5.44), 1.946 (0.73), 1.950 (0.78), 2.002 (0.83), 2.007 (0.87), 2.017 (1.07), 2.023 (0.90), 2.802 (1.11), 2.818 (2.14), 2.834 (1.23), 3.713 (1.43), 3.729 (2.30), 3.744 (1.01), 4.127 (16.00), 4.436 (0.88), 7.036 (1.70), 7.059 (1.69), 7.061 (1.63), 7.387 (1.42), 7.402 (1.42), 8.105 (1.96), 8.135 (1.92), 8.587 (2.83), 8.610 (2.65), 10.991 (1.13).

Example 130

2-[(1S)-1-cyclohexylethoxy]-N-(5,6-dimethylpyrimidin-4-yl)-5-fluoro-4-(3-oxo-5,6,7,8-tetrahydro[1,2,4]triazolo[4,3-a]pyridin-2(3H)-yl)benzamide

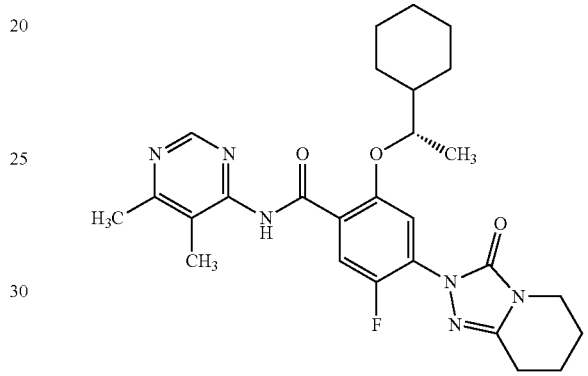

From intermediate 19 and 5,6-dimethylpyrimidin-4-amine.

The product was purified by preparative HPLC (X-Bridge Prep C18 5 μm OBD, 0.1% aqueous formic acid, acetonitrile).

LC-MS (method A): $R_t$=1.28 min; MS (ESIpos): m/z=509 [M+H]$^+$ $^1$H-NMR (400 MHz, CHLOROFORM-d) δ [ppm]: 1.121 (0.74), 1.129 (0.69), 1.152 (1.26), 1.179 (1.50), 1.206 (1.45), 1.212 (1.37), 1.224 (0.79), 1.239 (1.12), 1.247 (1.04), 1.255 (1.08), 1.263 (1.35), 1.271 (1.08), 1.278 (0.96), 1.287 (0.80), 1.294 (0.76), 1.302 (0.67), 1.369 (0.96), 1.385 (1.02), 1.406 (11.40), 1.421 (11.11), 1.681 (0.88), 1.713 (0.91), 1.729 (0.64), 1.737 (0.66), 1.744 (0.66), 1.773 (2.00), 1.798 (2.32), 1.908 (0.46), 1.924 (1.28), 1.936 (1.70), 1.947 (1.79), 1.951 (1.88), 1.967 (1.14), 1.988 (1.42), 2.007 (2.32), 2.017 (2.31), 2.029 (1.16), 2.047 (0.47), 2.238 (16.00), 2.598 (11.14), 2.803 (2.48), 2.812 (1.16), 2.819 (4.69), 2.836 (2.72), 3.713 (3.07), 3.720 (0.91), 3.728 (5.05), 3.743 (2.21), 4.428 (1.08), 4.444 (1.61), 4.459 (1.06), 7.408 (2.90), 7.423 (2.92), 8.093 (4.16), 8.121 (4.04), 8.787 (4.14), 10.250 (1.31).

Example 131

2-[(1S)-1-cyclohexylethoxy]-5-fluoro-N-(4-methylpyrimidin-5-yl)-4-(3-oxo-5,6,7,8-tetrahydro[1,2,4]triazolo[4,3-a]pyridin-2(3H)-yl)benzamide

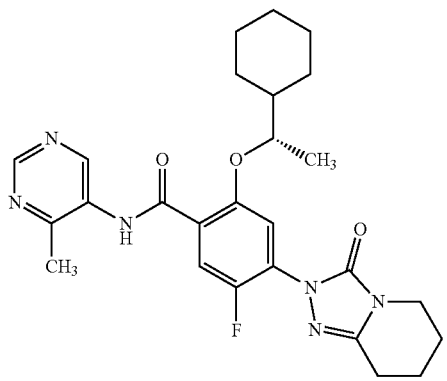 [SMILES: Cc1ncncc1NC(=O)c1cc(F)c(-n2nc3n(c2=O)CCCC3)cc1O[C@@H](C)C1CCCCC1]

From intermediate 19 and 4-methylpyrimidin-5-amine.

The product was purified by preparative HPLC (X-Bridge Prep C18 5 μm OBD, 0.1% aqueous formic acid, acetonitrile).

LC-MS (method A): $R_t$=1.21 min; MS (ESIpos): m/z=495 [M+H]$^+$ $^1$H-NMR (400 MHz, CHLOROFORM-d) δ [ppm]: 1.036 (0.42), 1.068 (0.56), 1.074 (0.56), 1.100 (0.64), 1.123 (0.52), 1.132 (0.68), 1.138 (0.62), 1.145 (0.54), 1.153 (0.63), 1.161 (0.61), 1.183 (0.82), 1.214 (0.85), 1.245 (0.91), 1.254 (0.71), 1.261 (1.29), 1.399 (6.46), 1.414 (6.67), 1.595 (5.20), 1.695 (0.72), 1.715 (0.83), 1.723 (0.94), 1.731 (0.86), 1.740 (0.94), 1.754 (0.86), 1.762 (0.97), 1.776 (1.24), 1.804 (0.62), 1.928 (0.80), 1.941 (1.05), 1.952 (1.19), 1.956 (1.36), 1.968 (0.97), 1.993 (0.94), 1.999 (0.97), 2.007 (1.26), 2.013 (1.16), 2.023 (1.10), 2.028 (0.92), 2.037 (0.67), 2.580 (16.00), 2.809 (1.55), 2.824 (2.90), 2.840 (1.64), 3.102 (0.42), 3.717 (1.93), 3.733 (3.14), 3.748 (1.38), 4.447 (0.69), 4.463 (1.02), 4.479 (0.65), 7.445 (1.85), 7.459 (1.84), 8.139 (2.52), 8.168 (2.48), 8.935 (3.62), 9.325 (2.90), 9.764 (1.57).

Example 132

2-[(1S)-1-cyclohexylethoxy]-N-(2,4-dimethylpyrimidin-5-yl)-5-fluoro-4-(3-oxo-5,6,7,8-tetrahydro[1,2,4]triazolo[4,3-a]pyridin-2(3H)-yl)benzamide

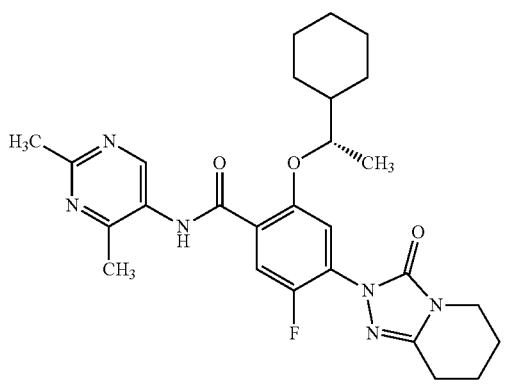 [SMILES: Cc1ncc(NC(=O)c2cc(F)c(-n3nc4n(c3=O)CCCC4)cc2O[C@@H](C)C2CCCCC2)c(C)n1]

From intermediate 19 and 2,4-dimethylpyrimidin-5-amine.

The product was purified by preparative HPLC (X-Bridge Prep C18 5 μm OBD, 0.2% aqueous ammonia, acetonitrile).

LC-MS (method B): $R_t$=1.23 min; MS (ESIpos): m/z=509 [M+H]$^+$ $^1$H-NMR (400 MHz, CHLOROFORM-d) δ [ppm]: 1.060 (0.45), 1.066 (0.45), 1.114 (0.60), 1.142 (0.76), 1.177 (0.77), 1.210 (0.75), 1.217 (0.47), 1.240 (0.71), 1.260 (0.69), 1.388 (6.64), 1.404 (6.66), 1.618 (1.40), 1.688 (0.69), 1.701 (0.68), 1.710 (0.75), 1.717 (0.87), 1.725 (0.80), 1.736 (0.72), 1.749 (0.69), 1.768 (1.15), 1.798 (0.60), 1.925 (0.73), 1.937 (1.02), 1.948 (1.30), 1.952 (1.44), 1.964 (0.77), 1.990 (0.90), 2.004 (1.01), 2.009 (1.01), 2.019 (1.04), 2.024 (0.85), 2.033 (0.62), 2.527 (16.00), 2.725 (12.54), 2.805 (1.47), 2.820 (2.85), 2.836 (1.62), 3.713 (1.89), 3.729 (3.04), 3.744 (1.33), 4.438 (0.67), 4.454 (1.00), 4.470 (0.64), 7.428 (1.78), 7.443 (1.78), 8.131 (2.56), 8.160 (2.52), 9.102 (3.75), 9.689 (1.62).

Example 133

2-[(1S)-1-cyclohexylethoxy]-5-fluoro-N-(3-methylpyrazin-2-yl)-4-(3-oxo-5,6,7,8-tetrahydro[1,2,4]triazolo[4,3-a]pyridin-2(3H)-yl)benzamide

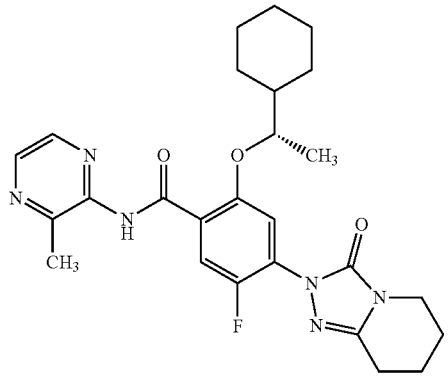 [SMILES: Cc1nccnc1NC(=O)c1cc(F)c(-n2nc3n(c2=O)CCCC3)cc1O[C@@H](C)C1CCCCC1]

From intermediate 19 and 3-methylpyrazin-2-amine.

The product was purified by preparative HPLC (X-Bridge Prep C18 5 μm OBD, 0.1% aqueous formic acid, acetonitrile).

LC-MS (method A): $R_t$=1.24 min; MS (ESIpos): m/z=495 [M+H]$^+$ $^1$H-NMR (400 MHz, CHLOROFORM-d) δ [ppm]: 1.102 (0.63), 1.110 (0.58), 1.133 (1.08), 1.140 (0.90), 1.156 (0.59), 1.164 (1.04), 1.171 (0.94), 1.181 (0.59), 1.194 (0.60), 1.204 (1.17), 1.209 (1.14), 1.218 (0.53), 1.233 (1.23), 1.242 (0.93), 1.249 (0.86), 1.264 (0.90), 1.273 (0.67), 1.281 (0.60), 1.289 (0.49), 1.405 (9.32), 1.421 (9.40), 1.623 (0.60), 1.673 (0.71), 1.706 (0.72), 1.714 (0.61), 1.722 (0.42), 1.730 (0.41), 1.737 (0.50), 1.743 (0.69), 1.760 (1.44), 1.766 (1.62), 1.780 (1.73), 1.789 (1.61), 1.798 (1.24), 1.924 (0.97), 1.932 (1.16), 1.937 (1.31), 1.948 (1.34), 1.952 (1.44), 1.968 (0.90), 1.988 (1.12), 1.994 (0.91), 2.009 (1.88), 2.018 (1.86), 2.033 (0.88), 2.608 (16.00), 2.805 (2.03), 2.820 (3.89), 2.837 (2.21), 3.714 (2.51), 3.730 (4.21), 3.744 (1.81), 4.435 (0.96), 4.450 (1.39), 4.465 (0.92), 7.408 (2.54), 7.423 (2.52), 8.126 (3.34), 8.155 (3.34), 8.298 (1.88), 8.304 (2.07), 8.389 (2.50), 8.395 (2.21), 10.183 (2.08).

Example 134

2-[(1S)-1-cyclohexylethoxy]-5-fluoro-N-(5-methylpyrimidin-4-yl)-4-(3-oxo-5,6,7,8-tetrahydro[1,2,4]triazolo[4,3-a]pyridin-2(3H)-yl)benzamide

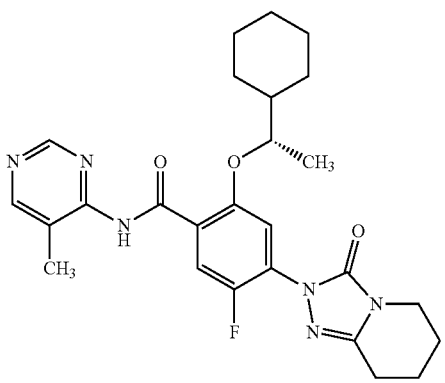 [SMILES: Cc1cncnc1NC(=O)c1cc(F)c(-n2nc3n(c2=O)CCCC3)cc1O[C@@H](C)C1CCCCC1]

From intermediate 19 and 5-methylpyrimidin-4-amine.
The product was purified by preparative HPLC (X-Bridge Prep C18 5 μm OBD, 0.2% aqueous ammonia, acetonitrile).
LC-MS (method B): $R_t$=1.22 min; MS (ESIpos): m/z=495 [M+H]$^+$
$^1$H-NMR (400 MHz, CHLOROFORM-d) δ [ppm]: 1.110 (0.74), 1.118 (0.66), 1.141 (1.27), 1.148 (0.99), 1.165 (1.10), 1.172 (1.23), 1.188 (1.05), 1.195 (1.14), 1.202 (0.80), 1.217 (0.89), 1.221 (0.90), 1.238 (0.85), 1.245 (0.97), 1.253 (0.88), 1.263 (0.93), 1.270 (0.82), 1.276 (0.71), 1.285 (0.60), 1.294 (0.52), 1.402 (9.98), 1.418 (9.92), 1.700 (2.07), 1.729 (0.56), 1.736 (0.54), 1.764 (1.73), 1.772 (1.75), 1.788 (1.89), 1.911 (0.52), 1.920 (1.08), 1.927 (1.31), 1.932 (1.46), 1.943 (1.49), 1.947 (1.59), 1.963 (0.98), 1.983 (1.28), 2.004 (2.04), 2.014 (2.19), 2.025 (1.01), 2.042 (0.40), 2.313 (16.00), 2.799 (2.16), 2.815 (4.15), 2.831 (2.34), 3.097 (0.64), 3.708 (2.76), 3.723 (4.43), 3.739 (1.96), 4.423 (1.02), 4.438 (1.51), 4.454 (0.98), 7.409 (2.73), 7.424 (2.70), 8.099 (3.71), 8.128 (3.65), 8.562 (4.24), 8.910 (4.80), 10.247 (2.28).

Example 135

2-[(1S)-1-cyclohexylethoxy]-5-fluoro-N-(4-methylpyridazin-3-yl)-4-(3-oxo-5,6,7,8-tetrahydro[1,2,4]triazolo[4,3-a]pyridin-2(3H)-yl)benzamide

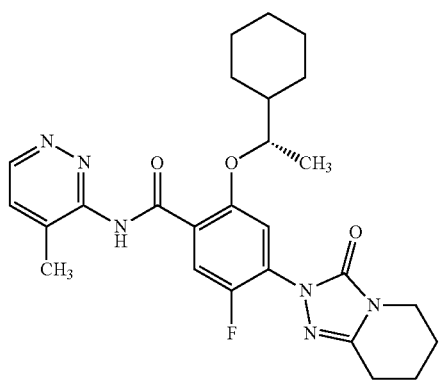 [SMILES: Cc1ccnnc1NC(=O)c1cc(F)c(-n2nc3n(c2=O)CCCC3)cc1O[C@@H](C)C1CCCCC1]

From intermediate 19 and 4-methylpyridazin-3-amine.
The product was purified by preparative HPLC (X-Bridge Prep C18 5 μm OBD, 0.1% aqueous formic acid, acetonitrile).
LC-MS (method A): $R_t$=1.19 min; MS (ESIpos): m/z=495 [M+H]$^+$
$^1$H-NMR (400 MHz, CHLOROFORM-d) δ [ppm]: 1.100 (0.44), 1.129 (1.24), 1.158 (1.74), 1.190 (1.61), 1.223 (1.78), 1.227 (1.79), 1.240 (1.27), 1.249 (1.61), 1.263 (2.61), 1.271 (2.03), 1.294 (1.33), 1.302 (1.23), 1.326 (0.48), 1.433 (13.98), 1.448 (13.80), 1.664 (3.93), 1.765 (2.70), 1.800 (3.50), 1.829 (1.51), 1.911 (0.65), 1.926 (1.69), 1.939 (2.22), 1.950 (2.30), 1.953 (2.42), 1.969 (1.17), 1.991 (1.46), 2.005 (3.08), 2.010 (3.13), 2.020 (2.83), 2.026 (2.45), 2.035 (2.34), 2.398 (16.00), 2.807 (3.36), 2.823 (6.46), 2.839 (3.67), 3.717 (4.19), 3.732 (7.02), 3.747 (3.04), 4.440 (1.41), 4.456 (2.03), 4.470 (1.36), 7.006 (0.53), 7.420 (5.35), 7.435 (5.86), 7.529 (0.58), 8.093 (5.55), 8.121 (5.47), 8.971 (2.05), 8.983 (2.01), 10.558 (2.28).

Example 136

2-[(1S)-1-cyclohexylethoxy]-5-fluoro-N-(5-fluoropyrimidin-4-yl)-4-(3-oxo-5,6,7,8-tetrahydro[1,2,4]triazolo[4,3-a]pyridin-2(3H)-yl)benzamide

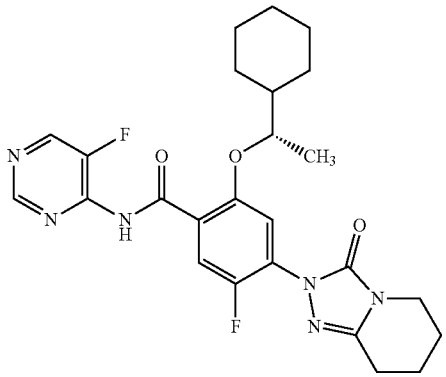 [SMILES: C[C@H](Oc1cc(-n2nc3n(c2=O)CCCC3)c(F)cc1C(=O)Nc1ncncc1F)C1CCCCC1]

From intermediate 19 and 5-fluoropyrimidin-4-amine.
The product was purified by preparative HPLC (X-Bridge Prep C18 5 μm OBD, 0.1% aqueous formic acid, acetonitrile).
LC-MS (method A): $R_t$=1.27 min; MS (ESIneg): m/z=497 [M−H]$^-$
$^1$H-NMR (400 MHz, CHLOROFORM-d) δ [ppm]: 1.059 (1.01), 1.067 (0.98), 1.088 (1.15), 1.097 (1.31), 1.111 (1.20), 1.119 (1.05), 1.128 (0.99), 1.136 (1.24), 1.142 (1.47), 1.149 (1.34), 1.157 (0.71), 1.173 (1.01), 1.180 (1.48), 1.188 (0.73), 1.204 (0.55), 1.211 (0.91), 1.233 (0.84), 1.240 (0.84), 1.256 (1.15), 1.264 (1.62), 1.271 (1.51), 1.277 (1.29), 1.287 (1.08), 1.295 (1.23), 1.303 (1.12), 1.308 (1.03), 1.316 (0.63), 1.327 (0.40), 1.400 (16.00), 1.415 (15.57), 1.634 (2.45), 1.691 (1.18), 1.722 (1.07), 1.784 (3.55), 1.796 (2.87), 1.803 (2.96), 1.907 (0.59), 1.914 (0.78), 1.922 (1.74), 1.929 (2.09), 1.934 (2.34), 1.946 (2.42), 1.950 (2.61), 1.962 (1.49), 1.966 (1.81), 1.986 (1.79), 1.993 (1.57), 2.002 (3.11), 2.007 (3.37), 2.016 (3.58), 2.022 (2.33), 2.028 (1.53), 2.031 (1.57), 2.045 (0.67), 2.801 (3.70), 2.817 (7.06), 2.834 (4.10), 3.710 (4.73), 3.726 (7.62), 3.741 (3.34), 4.435 (1.55), 4.451 (2.33), 4.467 (1.52), 7.430 (4.52), 7.444 (4.54), 8.145 (6.44), 8.174 (6.34), 8.551 (5.33), 8.558 (5.23), 8.890 (5.58), 8.895 (5.48), 10.794 (2.81).

Example 137

2-[(1S)-1-cyclohexylethoxy]-5-fluoro-N-[3-(morpholin-4-yl)pyrazin-2-yl]-4-(3-oxo-5,6,7,8-tetrahydro[1,2,4]triazolo[4,3-a]pyridin-2(3H)-yl)benzamide

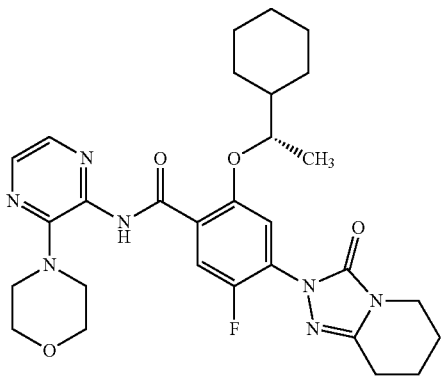 [SMILES: C[C@H](Oc1cc(-n2nc3n(c2=O)CCCC3)c(F)cc1C(=O)Nc1nccnc1N1CCOCC1)C1CCCCC1]

From intermediate 19 and 3-(morpholin-4-yl)pyrazin-2-amine.

The product was purified by preparative HPLC (X-Bridge Prep C18 5 μm OBD, 0.1% aqueous formic acid, acetonitrile).

LC-MS (method A): $R_t$=1.27 min; MS (ESIneg): m/z=564 [M−H]$^-$ $^1$H-NMR (400 MHz, CHLOROFORM-d) δ [ppm]: 1.016 (0.54), 1.048 (1.86), 1.079 (2.64), 1.109 (2.34), 1.123 (2.56), 1.154 (2.83), 1.180 (2.10), 1.213 (1.21), 1.245 (0.63), 1.261 (0.97), 1.369 (3.14), 1.385 (4.62), 1.390 (15.80), 1.406 (16.00), 1.637 (2.07), 1.667 (2.27), 1.695 (2.32), 1.729 (3.97), 1.737 (4.24), 1.760 (3.18), 1.833 (0.43), 1.912 (2.02), 1.926 (2.99), 1.938 (3.99), 1.950 (4.06), 1.953 (3.87), 1.965 (1.59), 1.991 (1.56), 2.005 (2.95), 2.011 (2.96), 2.021 (3.20), 2.026 (2.57), 2.035 (1.88), 2.049 (0.77), 2.803 (3.99), 2.812 (2.63), 2.819 (7.65), 2.828 (1.57), 2.835 (4.32), 3.273 (0.95), 3.285 (1.46), 3.306 (2.14), 3.319 (2.79), 3.328 (2.15), 3.359 (2.03), 3.368 (2.80), 3.382 (2.35), 3.403 (1.46), 3.414 (1.01), 3.704 (0.96), 3.716 (5.16), 3.731 (8.33), 3.746 (3.55), 3.784 (0.71), 3.792 (1.12), 3.812 (4.20), 3.821 (7.47), 3.826 (6.26), 3.830 (6.33), 3.836 (7.10), 3.845 (3.71), 3.865 (0.89), 3.873 (0.54), 4.354 (0.44), 4.369 (1.73), 4.385 (2.60), 4.400 (1.73), 4.415 (0.45), 4.485 (0.41), 7.006 (0.48), 7.390 (4.67), 7.405 (4.61), 7.449 (0.81), 7.463 (0.79), 7.529 (1.08), 8.014 (1.32), 8.041 (1.08), 8.072 (5.79), 8.079 (8.31), 8.107 (8.60), 8.113 (6.24), 8.156 (6.14), 8.185 (6.20), 10.210 (3.81).

Example 138

2-[(1S)-1-cyclohexylethoxy]-N-(4,6-dimethylpyrimidin-5-yl)-5-fluoro-4-(3-oxo-5,6,7,8-tetrahydro[1,2,4]triazolo[4,3-a]pyridin-2(3H)-yl)benzamide

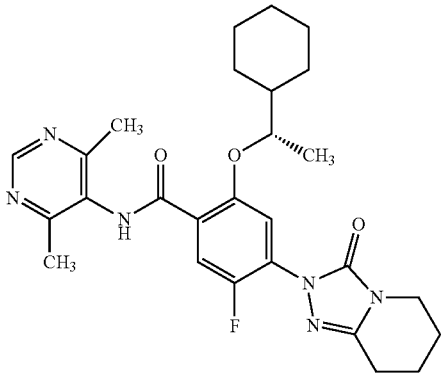 [SMILES: Cc1ncnc(C)c1NC(=O)c1cc(F)c(-n2nc3n(c2=O)CCCC3)cc1O[C@@H](C)C1CCCCC1]

From intermediate 19 and 4,6-dimethylpyrimidin-5-amine.

The product was purified by preparative HPLC (X-Bridge Prep C18 5 μm OBD, 0.1% aqueous formic acid, acetonitrile).

LC-MS (method A): $R_t$=1.18 min; MS (ESIpos): m/z=509 [M+H]$^+$ $^1$H-NMR (400 MHz, CHLOROFORM-d) δ [ppm]: 1.388 (3.64), 1.404 (3.60), 1.588 (0.60), 1.720 (0.64), 1.756 (0.60), 1.930 (0.52), 1.942 (0.79), 1.953 (0.67), 1.957 (0.70), 1.973 (0.52), 2.009 (0.53), 2.014 (0.57), 2.024 (0.58), 2.029 (0.49), 2.506 (16.00), 2.810 (0.81), 2.826 (1.58), 2.843 (0.89), 3.719 (1.03), 3.734 (1.69), 3.750 (0.75), 4.495 (0.55), 7.433 (1.00), 7.447 (0.99), 8.127 (1.39), 8.156 (1.37), 8.909 (2.11), 9.558 (0.93).

Examples 139-147 were prepared in analogy according to the general methods described above.

Example 139

N-(3-amino-2-methylphenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

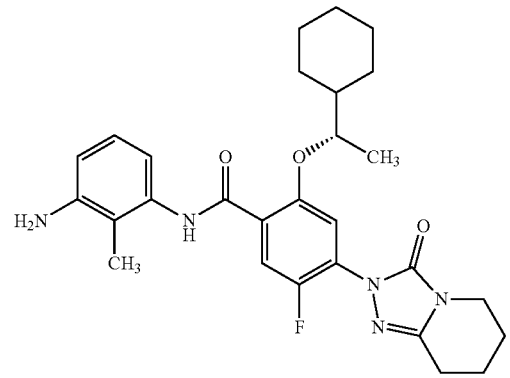 [SMILES: Cc1c(N)cccc1NC(=O)c1cc(F)c(-n2nc3n(c2=O)CCCC3)cc1O[C@@H](C)C1CCCCC1]

301

Example 140

N-[4-amino-2-(trifluoromethyl)phenyl]-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

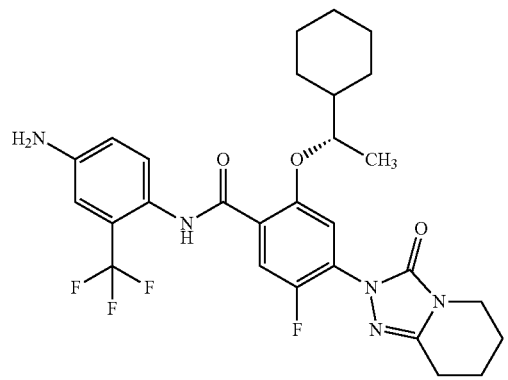 [SMILES: C[C@H](Oc1cc(-n2nc3n(c2=O)CCCC3)c(F)cc1C(=O)Nc1ccc(N)cc1C(F)(F)F)C1CCCCC1]

Example 141

2-[(1S)-1-cyclohexylethoxy]-5-fluoro-N-(2-methyl-4-sulfamoylphenyl)-4-(3-oxo-5,6,7,8-tetrahydro[1,2,4]triazolo[4,3-a]pyridin-2(3H)-yl)benzamide

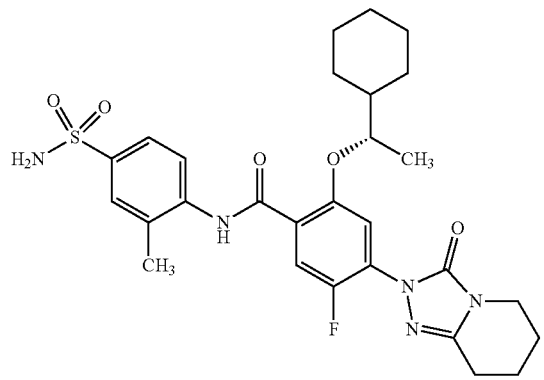 [SMILES: Cc1cc(S(N)(=O)=O)ccc1NC(=O)c1cc(F)c(-n2nc3n(c2=O)CCCC3)cc1O[C@@H](C)C1CCCCC1]

302

Example 142

N-[2-(aminomethyl)-6-methylphenyl]-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

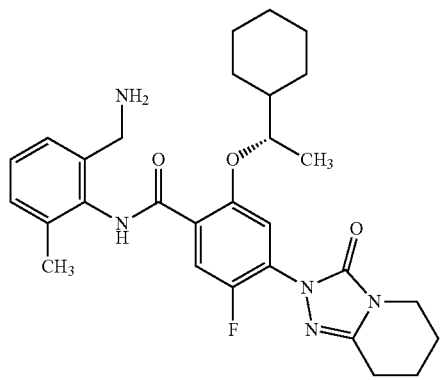 [SMILES: Cc1cccc(CN)c1NC(=O)c1cc(F)c(-n2nc3n(c2=O)CCCC3)cc1O[C@@H](C)C1CCCCC1]

Example 143

Methyl 2-({2-[(1R)-1-cyclohexylethoxy]-5-fluoro-4-(3-oxo-5,6,7,8-tetrahydro[1,2,4]triazolo[4,3-a]pyridin-2(3H)-yl)benzoyl}amino)-3-methylbenzoate

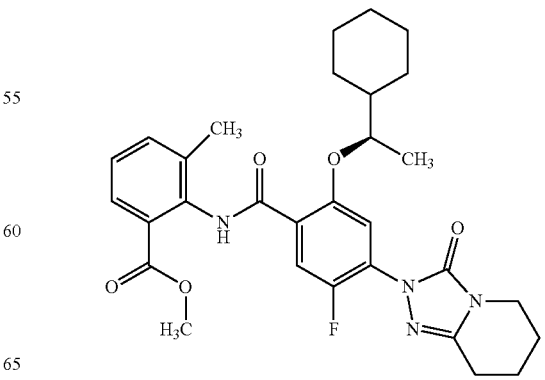

Example 144

2-[(1R)-1-cyclohexylethoxy]-N-(2,3-dihydro-1H-isoindol-4-yl)-5-fluoro-4-(3-oxo-5,6,7,8-tetrahydro[1,2,4]triazolo[4,3-a]pyridin-2(3H)-yl)benzamide

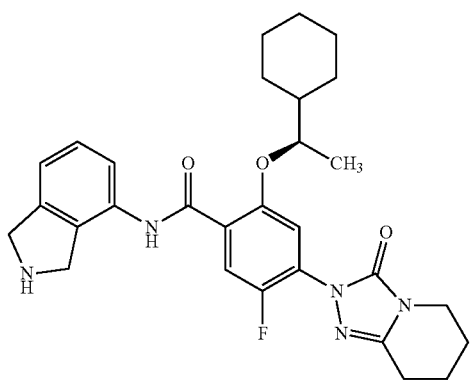 [SMILES: C[C@@H](Oc1cc(-n2nc3n(c2=O)CCCC3)c(F)cc1C(=O)Nc1cccc2c1CNC2)C1CCCCC1]

Example 145

N-(5-amino-3-methylpyridin-2-yl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

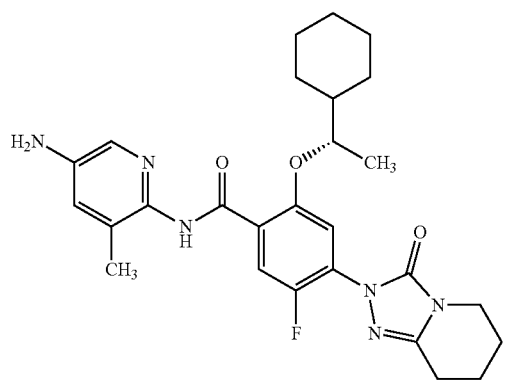 [SMILES: Cc1cc(N)cnc1NC(=O)c1cc(F)c(-n2nc3n(c2=O)CCCC3)cc1O[C@@H](C)C1CCCCC1]

Example 146

2-({2-[(1S)-1-cyclohexylethoxy]-5-fluoro-4-(3-oxo-5,6,7,8-tetrahydro[1,2,4]triazolo[4,3-a]pyridin-2(3H)-yl)benzoyl}amino)-3-methylbenzoic Acid

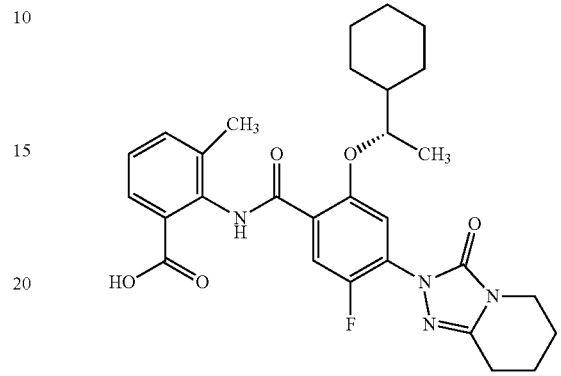

Example 147 tert-butyl 4-({2-[(1S)-1-cyclohexylethoxy]-4-(3-oxo-5,6,7,8-tetrahydro[1,2,4]triazolo[4,3-a]-pyridin-2(3H)-yl)benzoyl}amino)-3-methylbenzoate

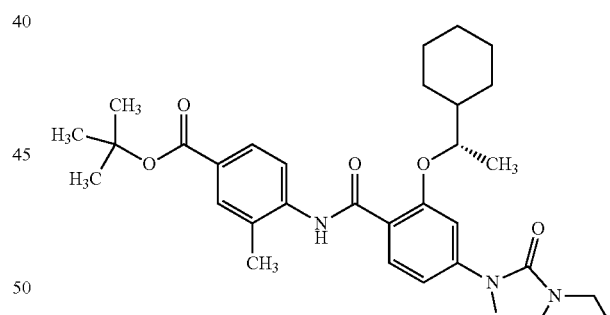

Examples 148-179 were prepared as described for example 113 from 2-[(1S)-1-cyclohexylethoxy]-5-fluoro-4-(3-oxo-5,6,7,8-tetrahydro[1,2,4]triazolo[4,3-a]pyridin-2(3H)-yl)benzoic acid (intermediate 19) and the respective amines, as indicated. Products were purified by flash column chromatography or, if explicitly mentioned, by preparative HPLC.

Example 148

2-[(1S)-1-cyclohexylethoxy]-5-fluoro-N-(2-fluorophenyl)-4-(3-oxo-5,6,7,8-tetrahydro[1,2,4]-triazolo[4,3-a]pyridin-2(3H)-yl)benzamide

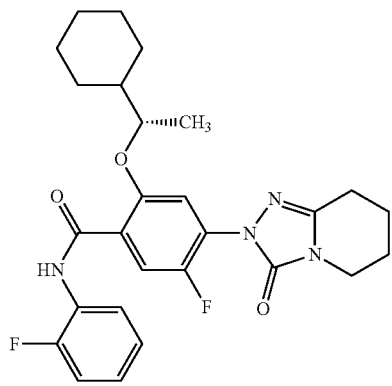 [SMILES: C[C@H](Oc1cc(-n2nc3n(c2=O)CCCC3)c(F)cc1C(=O)Nc1ccccc1F)C1CCCCC1]

From intermediate 19 and 2-fluoroaniline.

MS (ESIpos): m/z=497 (M+H)+

$^1$H NMR (400 MHz, CDCl$_3$) δ [ppm] 0.96-1.21 (m, 3H), 1.21-1.35 (m, 2H), 1.38 (d, 3H), 1.65-1.86 (m, 5H), 1.89-1.97 (m, 2H), 1.97-2.04 (m, 3H), 2.81 (t, 2H), 3.72 (t, 2H), 4.35-4.44 (m, 1H), 7.03-7.21 (m, 3H), 7.36 (d, 1H), 8.16 (d, 1H), 8.61 (td, 1H), 10.4 (s, 1H).

Example 149

2-[(1S)-1-cyclohexylethoxy]-5-fluoro-N-(2-fluorophenyl)-4-(3-oxo-5,6,7,8-tetrahydro[1,2,4]-triazolo[4,3-a]pyridin-2(3H)-yl)benzamide

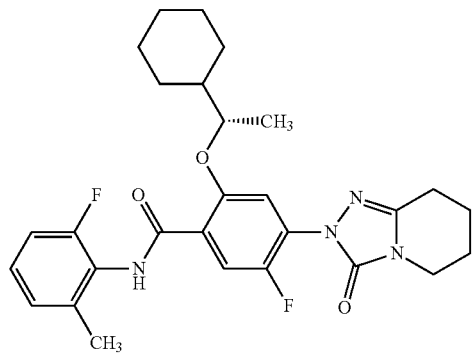 [SMILES: Cc1cccc(F)c1NC(=O)c1cc(F)c(-n2nc3n(c2=O)CCCC3)cc1O[C@@H](C)C1CCCCC1]

From intermediate 19 and 2-fluoro-6-methylaniline.

MS (ESIpos): m/z=511 (M+H)+

$^1$H NMR (400 MHz, CDCl$_3$) δ [ppm] 0.97-1.31 (m, 5H), 1.37 (d, 3H), 1.62-1.80 (m, 5H), 1.89-2.05 (m, 5H), 2.31 (s, 3H), 2.81 (t, 2H), 3.72 (t, 2H), 4.38-4.47 (m, 1H), 7.00 (td, 1H), 7.06 (d, 1H), 7.17 (dd, 1H), 7.38 (d, 1H), 8.14 (d, 1H), 9.52 (s, 1H).

Example 150

2-[(1S)-1-cyclohexylethoxy]-5-fluoro-4-(3-oxo-5,6,7,8-tetrahydro[1,2,4]triazolo[4,3-a]pyridin-2(3H)-yl)-N-[3-(trifluoromethyl)phenyl]benzamide

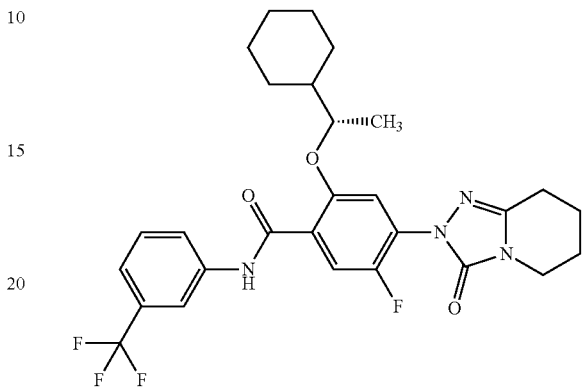

From intermediate 19 and 3-(trifluoromethyl)aniline.

MS (ESIpos): m/z=547 (M+H)+

$^1$H NMR (400 MHz, CDCl$_3$) δ [ppm] 1.06-1.36 (m, 5H), 1.40 (d, 3H), 1.68-1.86 (5H, m), 1.88-1.97 (2H, m), 1.97-2.07 (m, 3H), 2.81 (t, 2H), 3.72 (t, 2H), 4.40-4.48 (m, 1H), 7.37-7.41 (m, 2H), 7.49 (t, 1H), 7.88-7.93 (m, 2H), 8.14 (d, 1H), 10.3 (s, 1H).

Example 151

2-[(1S)-1-cyclohexylethoxy]-N-(2,6-difluorophenyl)-5-fluoro-4-(3-oxo-5,6,7,8-tetrahydro[1,2,4]triazolo[4,3-a]pyridin-2(3H)-yl)benzamide

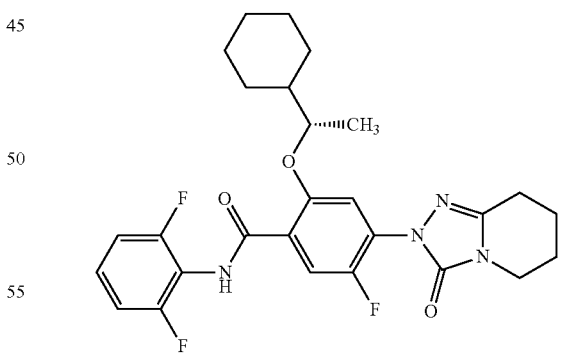

From intermediate 19 and 2,6-difluoroaniline.

MS (ESIpos): m/z=515 (M+H)+

$^1$H NMR (400 MHz, CDCl$_3$) δ [ppm] 0.97-1.33 (m, 5H), 1.38 (d, 3H), 1.64-1.82 (m, 5H), 1.89-1.96 (m, 2H), 1.96-2.05 (m, 3H), 2.81 (t, 2H), 3.71 (t, 2H), 4.38-4.46 (m, 1H), 6.96-7.04 (m, 2H), 7.17-7.25 (m, 1H), 7.39 (d, 1H), 8.14 (d, 1H), 9.63 (s, 1H).

Example 152

2-[(1S)-1-cyclohexylethoxy]-5-fluoro-N-(4-fluoro-2-methylphenyl)-4-(3-oxo-5,6,7,8-tetrahydro[1,2,4]triazolo[4,3-a]pyridin-2(3H)-yl)benzamide

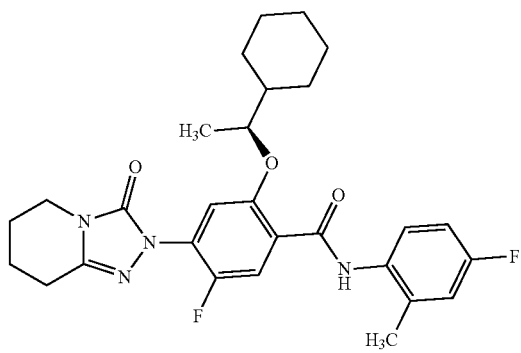 [SMILES: Cc1cc(F)ccc1NC(=O)c1cc(F)c(-n2nc3n(c2=O)CCCC3)cc1O[C@@H](C)C1CCCCC1]

From intermediate 19 and 4-fluoro-2-methylaniline.

The product was purified by preparative HPLC (YMC Actus Triart C18 100×30 mm 5 μm, 0.1% aqueous formic acid, acetonitrile).

LC-MS (method C): $R_t$=1.52 min; MS (ESIpos): m/z=511 [M+H]$^+$

Example 153

2-[(1S)-1-cyclohexylethoxy]-5-fluoro-4-(3-oxo-5,6,7,8-tetrahydro[1,2,4]triazolo[4,3-a]pyridin-2(3H)-yl)-N-(2,4,6-trifluorophenyl)benzamide

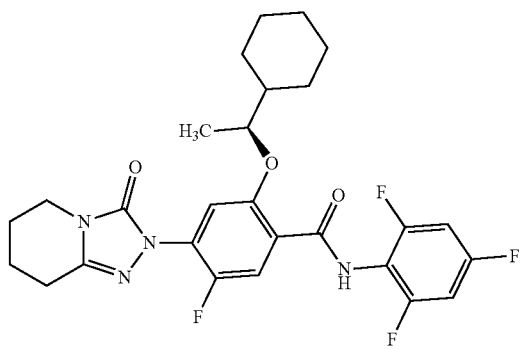 [SMILES: C[C@H](Oc1cc(-n2nc3n(c2=O)CCCC3)c(F)cc1C(=O)Nc1c(F)cc(F)cc1F)C1CCCCC1]

From intermediate 19 and 2,4,6-trifluoroaniline.

The product was purified by preparative HPLC (YMC Actus Triart C18 100×30 mm 5 μm, 0.1% aqueous formic acid, acetonitrile).

LC-MS (method C): $R_t$=1.50 min; MS (ESIpos): m/z=533 [M+H]$^+$

Example 154

2-[(1S)-1-cyclohexylethoxy]-5-fluoro-N-(3-fluoro-2-methylphenyl)-4-(3-oxo-5,6,7,8-tetrahydro[1,2,4]triazolo[4,3-a]pyridin-2(3H)-yl)benzamide

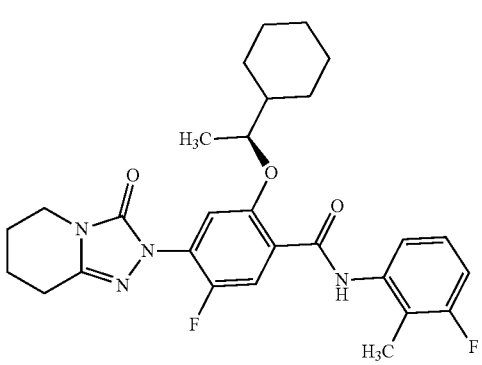 [SMILES: Cc1c(F)cccc1NC(=O)c1cc(F)c(-n2nc3n(c2=O)CCCC3)cc1O[C@@H](C)C1CCCCC1]

From intermediate 19 and 3-fluoro-2-methylaniline.

The product was purified by preparative HPLC (YMC Actus Triart C18 100×30 mm 5 μm, 0.1% aqueous formic acid, acetonitrile).

LC-MS (method C): $R_t$=1.55 min; MS (ESIpos): m/z=511 [M+H]$^+$

Example 155

2-[(1S)-1-cyclohexylethoxy]-5-fluoro-4-(3-oxo-5,6,7,8-tetrahydro[1,2,4]triazolo[4,3-a]pyridin-2(3H)-yl)-N-[2-(trifluoromethyl)phenyl]benzamide

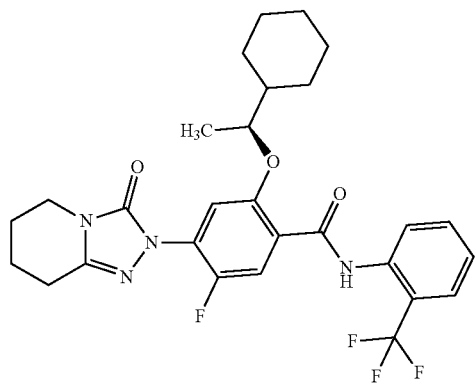 [SMILES: C[C@H](Oc1cc(-n2nc3n(c2=O)CCCC3)c(F)cc1C(=O)Nc1ccccc1C(F)(F)F)C1CCCCC1]

From intermediate 19 and 1-methyl-2-(trifluoromethyl)benzene.

The product was purified by preparative HPLC (YMC Actus Triart C18 100×30 mm 5 μm, 0.1% aqueous formic acid, acetonitrile).

LC-MS (method C): $R_t$=1.58 min; MS (ESIpos): m/z=547 [M+H]$^+$

Example 156

2-[(1S)-1-cyclohexylethoxy]-5-fluoro-N-(3-methylpyridin-2-yl)-4-(3-oxo-5,6,7,8-tetrahydro-[1,2,4]triazolo[4,3-a]pyridin-2(3H)-yl)benzamide

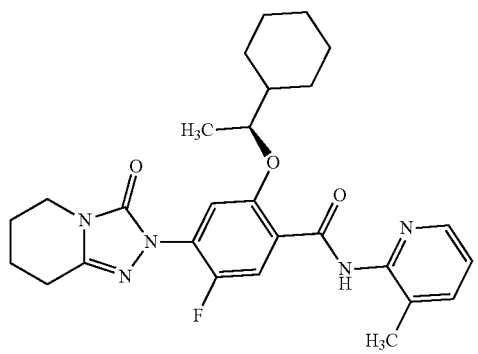 [SMILES: Cc1cccnc1NC(=O)c1cc(F)c(-n2nc3n(c2=O)CCCC3)cc1O[C@@H](C)C1CCCCC1]

From intermediate 19 and 2,3-dimethylpyridine.

The product was purified by preparative HPLC (YMC Actus Triart C18 100×30 mm 5 μm, 0.1% aqueous formic acid, acetonitrile).

LC-MS (method C): $R_t$=1.26 min; MS (ESIpos): m/z=494 [M+H]$^+$

Example 157

2-[(1S)-1-cyclohexylethoxy]-N-(2,6-dichlorophenyl)-5-fluoro-4-(3-oxo-5,6,7,8-tetrahydro-[1,2,4]triazolo[4,3-a]pyridin-2(3H)-yl)benzamide

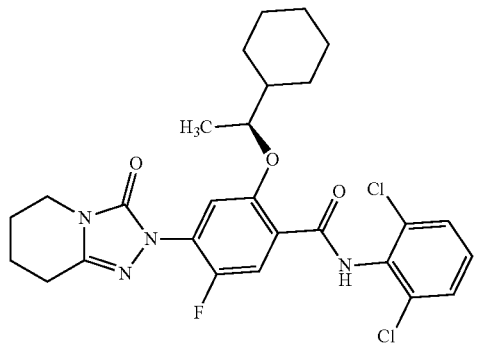 [SMILES: C[C@H](Oc1cc(-n2nc3n(c2=O)CCCC3)c(F)cc1C(=O)Nc1c(Cl)cccc1Cl)C1CCCCC1]

From intermediate 19 and 1,3-dichloro-2-methylbenzene.

The product was purified by preparative HPLC (YMC Actus Triart C18 100×30 mm 5 μm, 0.1% aqueous formic acid, acetonitrile).

LC-MS (method C): $R_t$=1.54 min; MS (ESIpos): m/z=548 [M+H]$^+$

Example 158

2-[(1S)-1-cyclohexylethoxy]-5-fluoro-N-(5-fluoro-2-methylphenyl)-4-(3-oxo-5,6,7,8-tetrahydro-[1,2,4]triazolo[4,3-a]pyridin-2(3H)-yl)benzamide

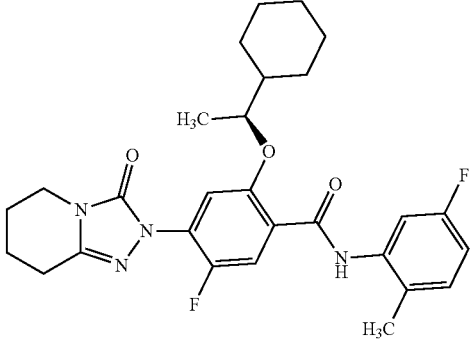 [SMILES: Cc1ccc(F)cc1NC(=O)c1cc(F)c(-n2nc3n(c2=O)CCCC3)cc1O[C@@H](C)C1CCCCC1]

From intermediate 19 and 5-fluoro-2-methylaniline.

The product was purified by preparative HPLC (YMC Actus Triart C18 100×30 mm 5 μm, 0.1% aqueous formic acid, acetonitrile).

LC-MS (method C): $R_t$=1.56 min; MS (ESIpos): m/z=511 [M+H]$^+$

Example 159

2-[(1S)-1-cyclohexylethoxy]-N-(2,4-difluorophenyl)-5-fluoro-4-(3-oxo-5,6,7,8-tetrahydro-[1,2,4]triazolo[4,3-a]pyridin-2(3H)-yl)benzamide

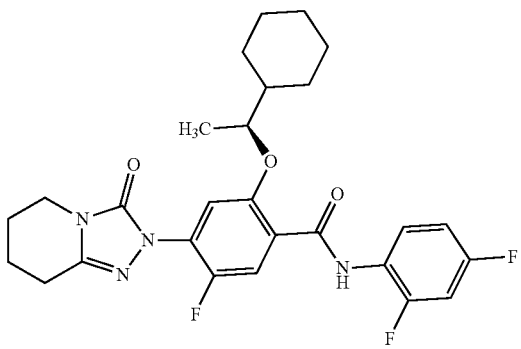 [SMILES: C[C@H](Oc1cc(-n2nc3n(c2=O)CCCC3)c(F)cc1C(=O)Nc1ccc(F)cc1F)C1CCCCC1]

From intermediate 19 and 2,4-difluoroaniline.

The product was purified by preparative HPLC (YMC Actus Triart C18 100×30 mm 5 μm, 0.1% aqueous formic acid, acetonitrile).

LC-MS (method C): $R_t$=1.60 min; MS (ESIpos): m/z=515 [M+H]$^+$

Example 160

2-[(1S)-1-cyclohexylethoxy]-N-[2-(dimethylamino)ethyl]-5-fluoro-4-(3-oxo-5,6,7,8-tetrahydro-[1,2,4]triazolo[4,3-a]pyridin-2(3H)-yl)benzamide

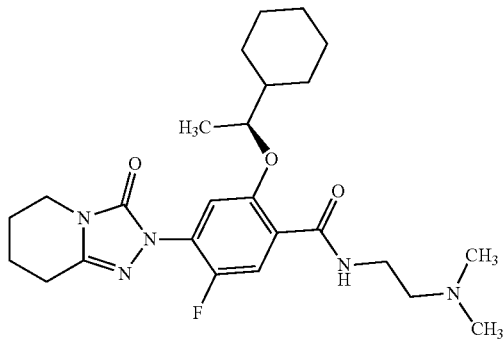 [SMILES: C[C@H](Oc1cc(-n2nc3n(c2=O)CCCC3)c(F)cc1C(=O)NCCN(C)C)C1CCCCC1]

From intermediate 19 and N,N-dimethylethane-1,2-diamine.

The product was purified by preparative HPLC (YMC Actus Triart C18 100×30 mm 5 µm, 0.1% aqueous formic acid, acetonitrile).

LC-MS (method C): $R_t$=0.86 min; MS (ESIpos): m/z=474 [M+H]$^+$

Example 161

2-[(1S)-1-cyclohexylethoxy]-5-fluoro-N-[2-fluoro-6-(trifluoromethyl)phenyl]-4-(3-oxo-5,6,7,8-tetrahydro[1,2,4]triazolo[4,3-a]pyridin-2(3H)-yl)benzamide

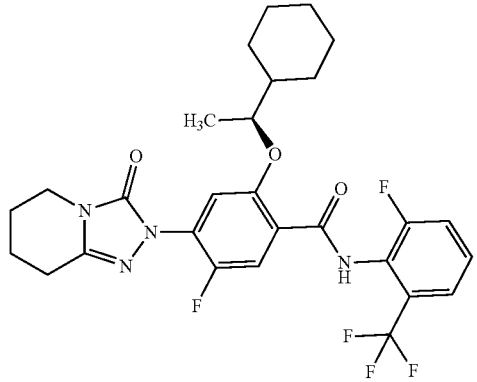 [SMILES: C[C@H](Oc1cc(-n2nc3n(c2=O)CCCC3)c(F)cc1C(=O)Nc1c(F)cccc1C(F)(F)F)C1CCCCC1]

From intermediate 19 and 2-fluoro-6-(trifluoromethyl)aniline.

The product was purified by preparative HPLC (YMC Actus Triart C18 100×30 mm 5 µm, 0.1% aqueous formic acid, acetonitrile).

LC-MS (method C): $R_t$=1.53 min; MS (ESIpos): m/z=565 [M+H]$^+$

Example 162

2-[(1S)-1-cyclohexylethoxy]-5-fluoro-N-(1-methyl-1H-pyrazol-5-yl)-4-(3-oxo-5,6,7,8-tetrahydro[1,2,4]triazolo[4,3-a]pyridin-2(3H)-yl)benzamide

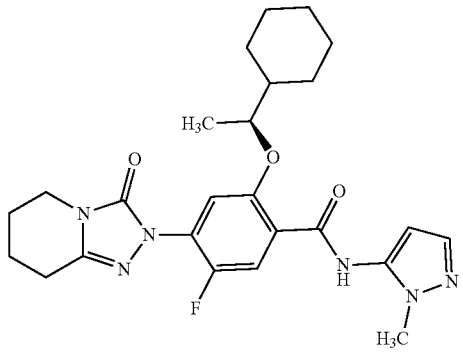 [SMILES: C[C@H](Oc1cc(-n2nc3n(c2=O)CCCC3)c(F)cc1C(=O)Nc1ccnn1C)C1CCCCC1]

From intermediate 19 and 1-methyl-1H-pyrazol-5-amine.

The product was purified by preparative HPLC (YMC Actus Triart C18 100×30 mm 5 µm, 0.1% aqueous formic acid, acetonitrile).

LC-MS (method C): $R_t$=1.24 min; MS (ESIpos): m/z=483 [M+H]$^+$

Example 163

2-[(1S)-1-cyclohexylethoxy]-5-fluoro-4-(3-oxo-5,6,7,8-tetrahydro[1,2,4]triazolo[4,3-a]pyridin-2(3H)-yl)-N-(tetrahydro-2H-pyran-4-yl)benzamide

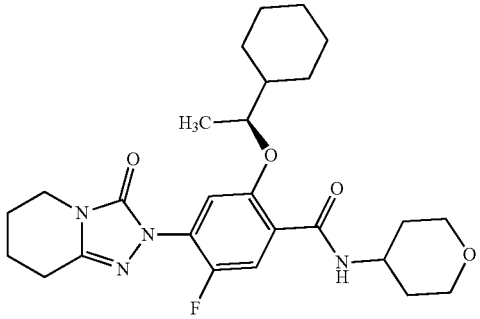 [SMILES: C[C@H](Oc1cc(-n2nc3n(c2=O)CCCC3)c(F)cc1C(=O)NC1CCOCC1)C1CCCCC1]

From intermediate 19 and tetrahydro-2H-pyran-4-amine.

The product was purified by preparative HPLC (YMC Actus Triart C18 100×30 mm 5 µm, 0.1% aqueous formic acid, acetonitrile).

LC-MS (method C): $R_t$=1.27 min; MS (ESIpos): m/z=487 [M+H]$^+$

Example 164

N-(2-cyano-4-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide

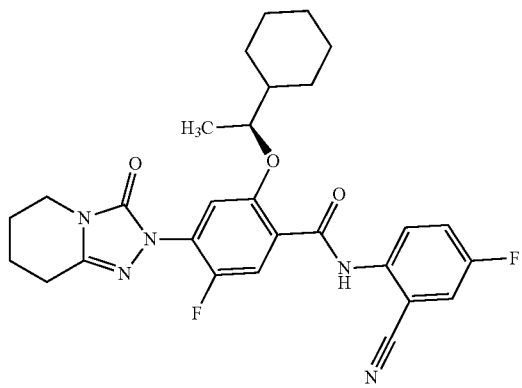 [SMILES: C[C@H](Oc1cc(-n2nc3n(c2=O)CCCC3)c(F)cc1C(=O)Nc1ccc(F)cc1C#N)C1CCCCC1]

From intermediate 19 and 2-amino-5-fluorobenzonitrile.

The product was purified by preparative HPLC (YMC Actus Triart C18 100×30 mm 5 μm, 0.1% aqueous formic acid, acetonitrile).

LC-MS (method C): $R_t$=1.49 min; MS (ESIpos): m/z=522 [M+H]$^+$

Example 165

N-(2-chloro-5-fluorophenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

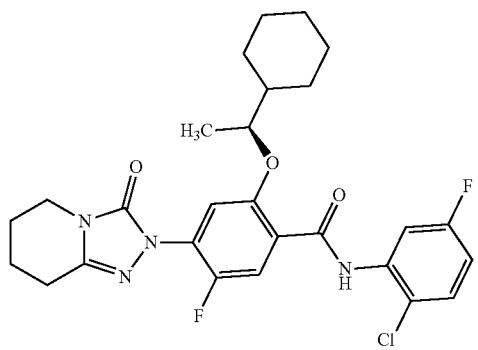 [SMILES: C[C@H](Oc1cc(-n2nc3n(c2=O)CCCC3)c(F)cc1C(=O)Nc1cc(F)ccc1Cl)C1CCCCC1]

From intermediate 19 and 2-chloro-5-fluoroaniline.

The product was purified by preparative HPLC (YMC Actus Triart C18 100×30 mm 5 μm, 0.1% aqueous formic acid, acetonitrile).

LC-MS (method C): $R_t$=1.67 min; MS (ESIpos): m/z=532 [M+H]$^+$

Example 166

2-[(1S)-1-cyclohexylethoxy]-5-fluoro-N-(4-methylpyridin-3-yl)-4-(3-oxo-5,6,7,8-tetrahydro-[1,2,4]triazolo[4,3-a]pyridin-2(3H)-yl)benzamide

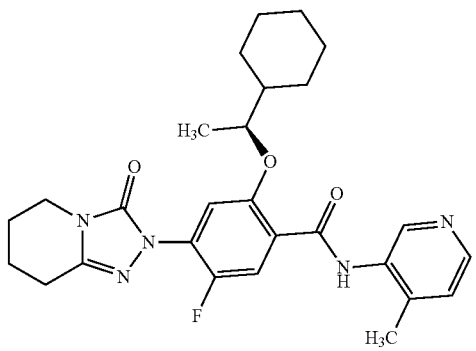 [SMILES: Cc1ccncc1NC(=O)c1cc(F)c(-n2nc3n(c2=O)CCCC3)cc1O[C@@H](C)C1CCCCC1]

From intermediate 19 and 4-methylpyridin-3-amine.

The product was purified by preparative HPLC (YMC Actus Triart C18 100×30 mm 5 μm, 0.1% aqueous formic acid, acetonitrile).

LC-MS (method C): $R_t$=1.08 min; MS (ESIpos): m/z=494 [M+H]$^+$

Example 167

2-[(1S)-1-cyclohexylethoxy]-5-fluoro-N-[2-methyl-5-(trifluoromethyl)phenyl]-4-(3-oxo-5,6,7,8-tetrahydro[1,2,4]triaolo[4,3-a]pyridin-2(3H)-yl)benzamide

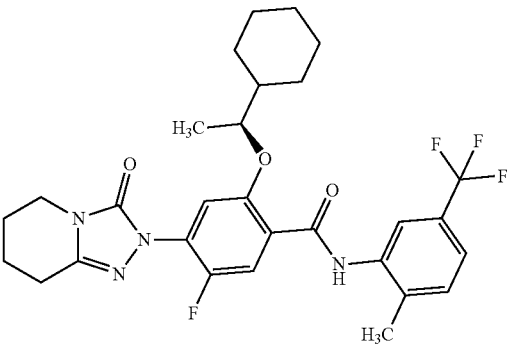 [SMILES: Cc1ccc(C(F)(F)F)cc1NC(=O)c1cc(F)c(-n2nc3n(c2=O)CCCC3)cc1O[C@@H](C)C1CCCCC1]

From intermediate 19 and 2-methyl-5-(trifluoromethyl)aniline.

The product was purified by preparative HPLC (YMC Actus Triart C18 100×30 mm 5 μm, 0.1% aqueous formic acid, acetonitrile).

LC-MS (method C): $R_t$=1.62 min; MS (ESIpos): m/z=561 [M+H]$^+$

Example 168

2-[(1S)-1-cyclohexylethoxy]-5-fluoro-N-(3-methylpyridin-4-yl)-4-(3-oxo-5,6,7,8-tetrahydro-[1,2,4]triazolo[4,3-a]pyridin-2(3H)-yl)benzamide

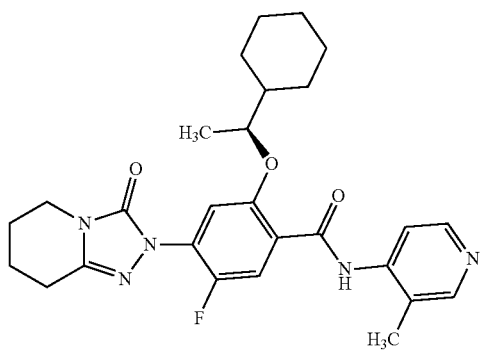 [SMILES: Cc1cnccc1NC(=O)c1cc(F)c(-n2nc3n(c2=O)CCCC3)cc1O[C@@H](C)C1CCCCC1]

From intermediate 19 and 3-methylpyridin-4-amine.

The product was purified by preparative HPLC (YMC Actus Triart C18 100×30 mm 5 µm, 0.1% aqueous formic acid, acetonitrile).

LC-MS (method C): $R_t$=0.96 min; MS (ESIpos): m/z=494 [M+H]$^+$

Example 169

N-(2-chloro-6-fluorophenyl)-2-[(1S)-1-cyclohexylethoxy]-5-fluoro-4-(3-oxo-5,6,7,8-tetrahydro[1,2,4]triazolo[4,3-a]pyridin-2(3H)-yl)benzamide

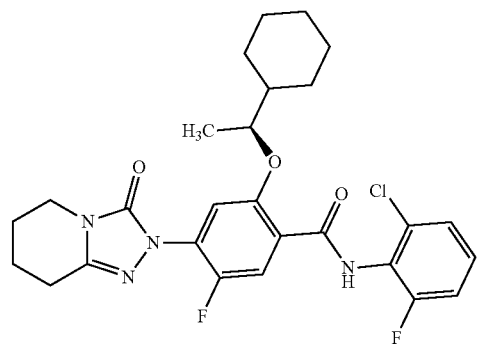 [SMILES: C[C@H](Oc1cc(-n2nc3n(c2=O)CCCC3)c(F)cc1C(=O)Nc1c(F)cccc1Cl)C1CCCCC1]

From intermediate 19 and 2-chloro-6-fluoroaniline.

The product was purified by preparative HPLC (YMC Actus Triart C18 100×30 mm 5 µm, 0.1% aqueous formic acid, acetonitrile).

LC-MS (method C): $R_t$=1.51 min; MS (ESIpos): m/z=532 [M+H]$^+$

Example 170

2-[(1S)-1-cyclohexylethoxy]-5-fluoro-N-[2-methyl-3-(trifluoromethyl)phenyl]-4-(3-oxo-5,6,7,8-tetrahydro[1,2,4]triazolo[4,3-a]pyridin-2(3H)-yl)benzamide

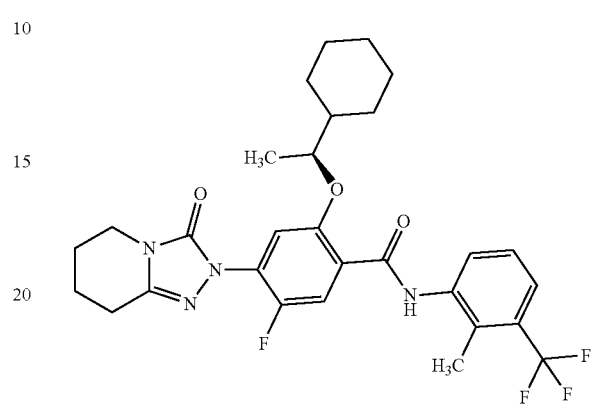

From intermediate 19 and 2-methyl-3-(trifluoromethyl)aniline.

The product was purified by preparative HPLC (YMC Actus Triart C18 100×30 mm 5 µm, 0.1% aqueous formic acid, acetonitrile).

LC-MS (method C): $R_t$=1.62 min; MS (ESIpos): m/z=561 [M+H]$^+$

Example 171

2-[(1S)-1-cyclohexylethoxy]-5-fluoro-N-[2-methyl-4-(trifluoromethyl)phenyl]-4-(3-oxo-5,6,7,8-tetrahydro[1,2,4]triazolo[4,3-a]pyridin-2(3H)-yl)benzamide

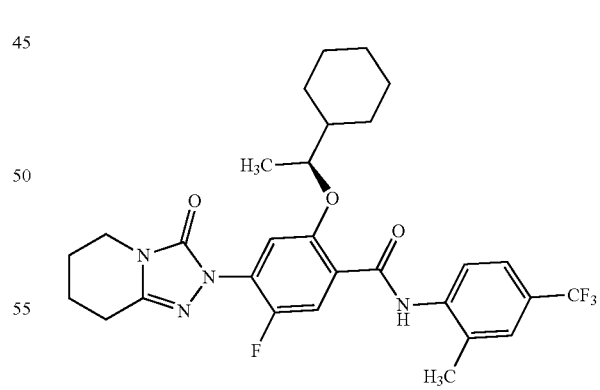

From intermediate 19 and 2-methyl-4-(trifluoromethyl)aniline.

The product was purified by preparative HPLC (YMC Actus Triart C18 100×30 mm 5 µm, 0.1% aqueous formic acid, acetonitrile).

LC-MS (method C): $R_t$=1.64 min; MS (ESIpos): m/z=561 [M+H]$^+$

Example 172

N-(2-chloro-3-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide

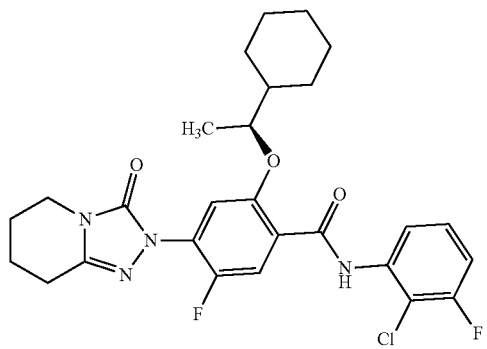 [SMILES: C[C@H](Oc1cc(-n2nc3n(c2=O)CCCC3)c(F)cc1C(=O)Nc1cccc(F)c1Cl)C1CCCCC1]

From intermediate 19 and 2-chloro-3-fluoroaniline.

The product was purified by preparative HPLC (YMC Actus Triart C18 100×30 mm 5 μm, 0.1% aqueous formic acid, acetonitrile).

LC-MS (method C): $R_t$=1.64 min; MS (ESIpos): m/z=532 [M+H]$^+$

Example 173

2-[(1S)-1-cyclohexylethoxy]-N-(1,3-dimethyl-1H-pyrazol-4-yl)-5-fluoro-4-(3-oxo-5,6,7,8-tetrahydro[1,2,4]triazolo[4,3-a]pyridin-2(3H)-yl)benzamide

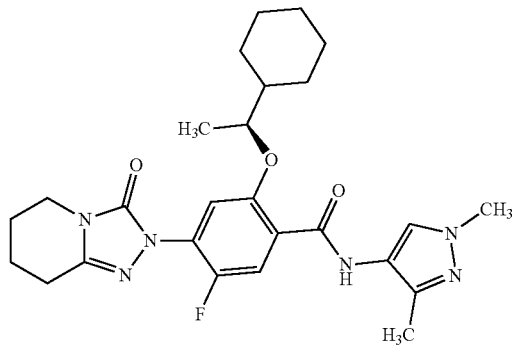 [SMILES: Cc1nn(C)cc1NC(=O)c1cc(F)c(-n2nc3n(c2=O)CCCC3)cc1O[C@@H](C)C1CCCCC1]

From intermediate 19 and 1,3-dimethyl-1H-pyrazol-4-amine.

The product was purified by preparative HPLC (YMC Actus Triart C18 100×30 mm 5 μm, 0.1% aqueous formic acid, acetonitrile).

LC-MS (method C): $R_t$=1.25 min; MS (ESIpos): m/z=497 [M+H]$^+$

Example 174

2-[(1S)-1-cyclohexylethoxy]-5-fluoro-N-(1-methylpiperidin-4-yl)-4-(3-oxo-5,6,7,8-tetrahydro-[1,2,4]triazolo[4,3-a]pyridin-2(3H)-yl)benzamide

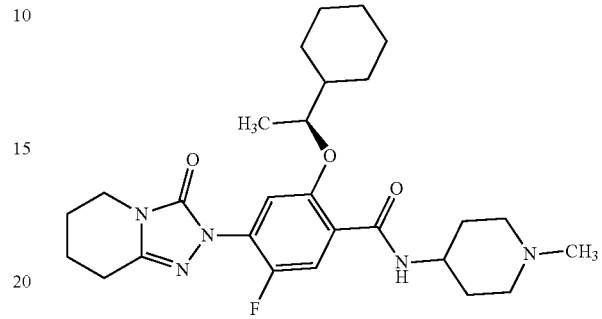

From intermediate 19 and 1-methylpiperidin-4-amine.

The product was purified by preparative HPLC (YMC Actus Triart C18 100×30 mm 5 μm, 0.1% aqueous formic acid, acetonitrile).

LC-MS (method C): $R_t$=0.85 min; MS (ESIpos): m/z=500 [M+H]$^+$

Example 175

2-[(1S)-1-cyclohexylethoxy]-N-(1,4-dimethyl-1H-pyrazol-3-yl)-5-fluoro-4-(3-oxo-5,6,7,8-tetrahydro[1,2,4]triazolo[4,3-a]pyridin-2(3H)-yl)benzamide

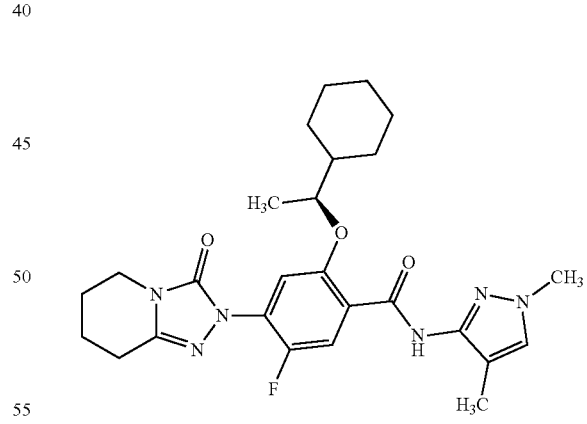

From intermediate 19 and 1,4-dimethyl-1H-pyrazol-3-amine.

The product was purified by preparative HPLC (YMC Actus Triart C18 100×30 mm 5 μm, 0.1% aqueous formic acid, acetonitrile).

LC-MS (method C): $R_t$=1.29 min; MS (ESIpos): m/z=497 [M+H]$^+$

Example 176

2-[(1S)-1-cyclohexylethoxy]-5-fluoro-N-(2-hydroxy-2-methylpropyl)-4-(3-oxo-5,6,7,8-tetrahydro-[1,2,4]triazolo[4,3-a]pyridin-2(3H)-yl)benzamide

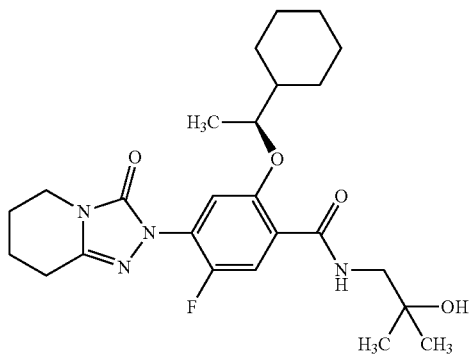 [SMILES: C[C@H](Oc1cc(-n2nc3n(c2=O)CCCC3)c(F)cc1C(=O)NCC(C)(C)O)C1CCCCC1]

From intermediate 19 and 1-amino-2-methylpropan-2-ol.

The product was purified by preparative HPLC (YMC Actus Triart C18 100×30 mm 5 µm, 0.1% aqueous formic acid, acetonitrile).

LC-MS (method C): $R_t$=1.21 min; MS (ESIpos): m/z=475 [M+H]$^+$

Example 177

2-[(1S)-1-cyclohexylethoxy]-5-fluoro-N-[2-(hydroxymethyl)-3-(trifluoromethyl)phenyl]-4-(3-oxo-5,6,7,8-tetrahydro[1,2,4]triazolo[4,3-a]pyridin-2(3H)-yl)benzamide

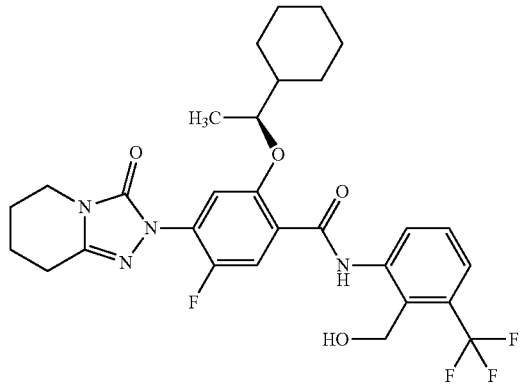 [SMILES: C[C@H](Oc1cc(-n2nc3n(c2=O)CCCC3)c(F)cc1C(=O)Nc1cccc(C(F)(F)F)c1CO)C1CCCCC1]

From intermediate 19 and [2-amino-6-(trifluoromethyl)phenyl]methanol.

The product was purified by preparative HPLC (YMC Actus Triart C18 100×30 mm 5 µm, 0.1% aqueous formic acid, acetonitrile).

LC-MS (method C): $R_t$=1.45 min; MS (ESIpos): m/z=577 [M+H]$^+$

Example 178

2-[(1S)-1-cyclohexylethoxy]-5-fluoro-N-(5-methyl-1,2-oxazol-4-yl)-4-(3-oxo-5,6,7,8-tetrahydro-[1,2,4]triazolo[4,3-a]pyridin-2(3H)-yl)benzamide

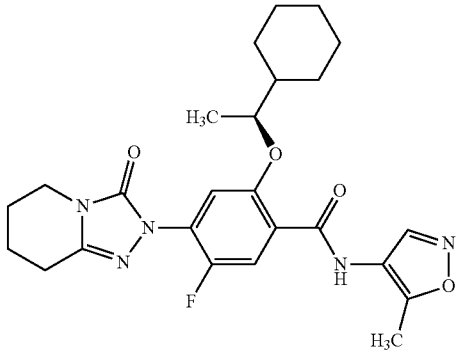 [SMILES: Cc1oncc1NC(=O)c1cc(F)c(-n2nc3n(c2=O)CCCC3)cc1O[C@@H](C)C1CCCCC1]

From intermediate 19 and 5-methyl-1,2-oxazol-4-amine.

The product was purified by preparative HPLC (YMC Actus Triart C18 100×30 mm 5 µm, 0.1% aqueous formic acid, acetonitrile).

LC-MS (method C): $R_t$=1.33 min; MS (ESIpos): m/z=484 [M+H]$^+$

Example 179

N-(2-chloro-4-fluorophenyl)-2-[(1S)-1-cyclohexylethoxy]-5-fluoro-4-(3-oxo-5,6,7,8-tetrahydro-[1,2,4]triazolo[4,3-a]pyridin-2(3H)-yl)benzamide

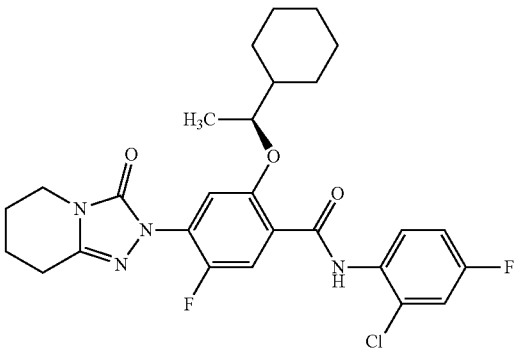 [SMILES: C[C@H](Oc1cc(-n2nc3n(c2=O)CCCC3)c(F)cc1C(=O)Nc1ccc(F)cc1Cl)C1CCCCC1]

From intermediate 19 and 2-chloro-4-fluoroaniline.

The product was purified by preparative HPLC (YMC Actus Triart C18 100×30 mm 5 µm, 0.1% aqueous formic acid, acetonitrile).

LC-MS (method C): $R_t$=1.64 min; MS (ESIpos): m/z=532 [M+H]$^+$

Example 180

N-(2-chloro-6-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

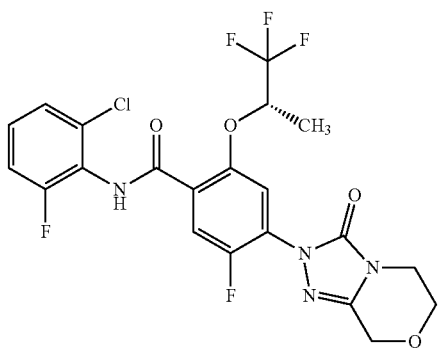 [SMILES: C[C@H](Oc1cc(-n2nc3n(c2=O)CCOC3)c(F)cc1C(=O)Nc1c(F)cccc1Cl)C(F)(F)F]

To a 0° C. stirred solution of 5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzoic acid (intermediate 24) (74.3 mg, 190 μmol) and DMF (3 drops) in anhydrous dichloromethane (0.95 ml) was added oxalyl chloride dropwise (28.9 mg, 0.23 mmol). The resulting mixture was warmed to room temperature, stirred for one hour and concentrated under reduced pressure. A solution of the crude acid chloride in dichloromethane (0.63 ml) was then added dropwise to a 0° C. stirred solution of 2-chloro-6-fluoraniline (30.4 mg, 0.21 mmol) and triethylamine (21.1 mg, 0.21 mmol) in dichloromethane (0.70 ml). Following complete addition, the mixture was warmed to room temperature and stirred for one hour. Aqueous hydrochloric acid (1.0 M, 10 ml) was added to the residue and extracted with dichloromethane (3×10 ml). The combined organic extracts were washed with brine (10 ml), dried over magnesium sulfate, filtered and concentrated under reduced pressure to give a pale yellow oil. The residue was purified by reverse phase column chromatography (acetonitrile, 0.1% aqueous formic acid) to give the amide as a white solid (73.3 mg, 66%).

LC-MS (method A): $R_t$=1.18 min; MS (ESIpos): m/z=519 [M+H]$^+$ $^1$H-NMR (400 MHz, CHLOROFORM-d) δ [ppm]: 1.572 (8.35), 1.659 (7.01), 1.676 (7.05), 3.807 (2.84), 3.820 (4.22), 3.834 (3.51), 4.086 (3.74), 4.098 (3.02), 4.100 (4.34), 4.113 (2.89), 4.772 (16.00), 4.911 (0.46), 4.927 (1.09), 4.942 (1.41), 4.958 (1.09), 4.973 (0.42), 7.112 (0.89), 7.116 (0.94), 7.133 (1.48), 7.136 (1.96), 7.140 (1.10), 7.155 (1.20), 7.159 (1.25), 7.222 (0.85), 7.235 (0.84), 7.242 (1.98), 7.256 (2.11), 7.263 (2.04), 7.285 (2.13), 7.290 (2.75), 7.305 (0.88), 7.309 (1.07), 7.312 (0.89), 7.463 (2.95), 7.477 (2.96), 8.182 (3.04), 8.212 (3.06), 9.021 (2.04).

Examples 181-243 were prepared in analogy to example 180 from the respective carboxylic acids and the respective amines, as indicated. Products were purified by flash column chromatography or, if explicitly mentioned, by preparative HPLC.

Example 181

5-fluoro-N-(6-methoxy-4-methylpyridin-3-yl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

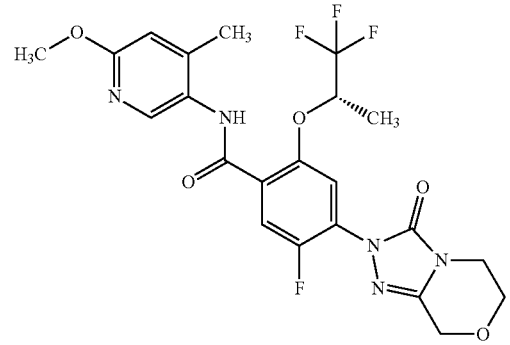 [SMILES: COc1cc(C)c(NC(=O)c2cc(F)c(-n3nc4n(c3=O)CCOC4)cc2O[C@@H](C)C(F)(F)F)cn1]

From Intermediate 24 and 6-methoxy-4-methylpyridin-3-amine.

LC-MS (method A): $R_t$=1.07 min; MS (ESIpos): m/z=512 [M–H]$^+$ $^1$H-NMR (400 MHz, CHLOROFORM-d) δ [ppm]: 1.589 (0.76), 1.647 (4.45), 1.663 (4.41), 2.019 (0.46), 2.266 (9.79), 3.806 (1.68), 3.819 (2.50), 3.833 (2.13), 3.949 (16.00), 4.086 (2.25), 4.097 (1.77), 4.101 (2.57), 4.114 (1.78), 4.770 (9.83), 4.889 (0.68), 4.905 (0.87), 4.920 (0.65), 6.676 (2.54), 7.439 (1.87), 7.454 (1.85), 8.146 (2.51), 8.174 (2.44), 8.343 (3.08), 8.868 (1.38).

Example 182

5-fluoro-N-(4-methylpyridin-3-yl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

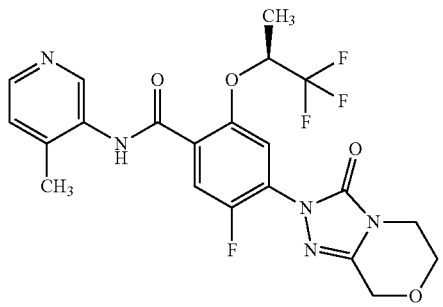 [SMILES: Cc1ccncc1NC(=O)c1cc(F)c(-n2nc3n(c2=O)CCOC3)cc1O[C@@H](C)C(F)(F)F]

From Intermediate 24 and 4-methylpyridin-3-amine.
The product was purified by preparative HPLC (Chromatorex C18 125×30 mm 10 μm, 0.1% aqueous ammonia, acetonitrile).

LC-MS (method B): $R_t$=0.96 min; MS (ESIneg): m/z=480 [M–H]$^-$ $^1$H-NMR (400 MHz, DMSO-d6) δ[ppm]: 1.076 (2.64), 1.094 (2.55), 1.435 (6.35), 1.451 (6.32), 1.996 (1.77), 2.085 (0.54), 2.280 (16.00), 2.331 (0.50), 2.518 (3.12), 2.523 (2.07), 2.674 (0.48), 2.950 (5.52), 3.670 (2.13), 3.683 (3.60), 3.697 (2.44), 4.032 (2.62), 4.046 (3.73), 4.058 (2.18), 4.754 (10.85), 5.311 (0.41), 5.327 (1.01), 5.343 (1.28), 5.359 (0.94), 7.312 (2.44), 7.324 (2.48), 7.571 (2.59), 7.585 (2.57), 7.686 (3.14), 7.698 (0.80), 7.711 (3.14), 8.304 (3.42), 8.316 (3.37), 8.572 (5.57), 10.014 (3.83).

Example 183

N-(2,6-difluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

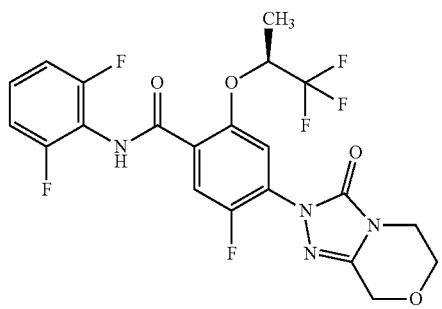 [SMILES: C[C@H](Oc1cc(-n2nc3n(c2=O)CCOC3)c(F)cc1C(=O)Nc1c(F)cccc1F)C(F)(F)F]

From Intermediate 24 and 2,6-difluoroaniline.
The product was purified by preparative HPLC (Chromatorex C18 125×30 mm 10 μm, 0.1% aqueous formic acid, acetonitrile).
LC-MS (method A): $R_t$=1.13 min; MS (ESIpos): m/z=503 [M+H]$^+$
$^1$H-NMR (400 MHz, DMSO-d6) δ[ppm]: 1.432 (8.16), 1.448 (8.08), 2.084 (16.00), 2.327 (0.50), 2.523 (1.83), 2.531 (0.50), 2.669 (0.47), 3.668 (3.16), 3.681 (5.53), 3.695 (3.55), 4.029 (3.95), 4.043 (5.85), 4.056 (3.34), 4.752 (14.13), 5.265 (0.57), 5.280 (1.33), 5.296 (1.72), 5.312 (1.27), 5.328 (0.52), 7.191 (2.47), 7.212 (5.08), 7.232 (3.16), 7.372 (0.57), 7.388 (1.25), 7.409 (1.77), 7.425 (0.97), 7.430 (0.96), 7.446 (0.41), 7.573 (3.33), 7.584 (5.08), 7.608 (3.29), 10.008 (3.86).

Example 184

5-fluoro-N-(2-fluoro-6-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

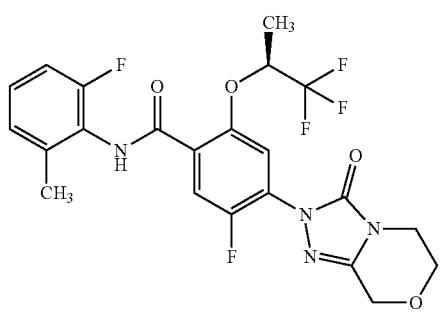 [SMILES: Cc1cccc(F)c1NC(=O)c1cc(F)c(-n2nc3n(c2=O)CCOC3)cc1O[C@@H](C)C(F)(F)F]

From Intermediate 24 and 2-fluoro-6-methylaniline.
The product was purified by preparative HPLC (Chromatorex C18 125×30 mm 10 μm, 0.1% aqueous formic acid, acetonitrile).

LC-MS (method A): $R_t$=1.16 min; MS (ESIpos): m/z=499 [M+H]$^+$
$^1$H-NMR (400 MHz, DMSO-d6) δ[ppm]: 1.431 (7.00), 1.447 (7.01), 2.085 (5.21), 2.272 (16.00), 2.518 (2.28), 2.523 (1.65), 3.669 (2.26), 3.682 (3.84), 3.696 (2.61), 4.031 (2.78), 4.045 (4.01), 4.058 (2.37), 4.753 (12.11), 5.307 (0.44), 5.323 (1.10), 5.339 (1.43), 5.356 (1.02), 5.759 (1.00), 7.100 (0.91), 7.117 (2.32), 7.121 (2.26), 7.134 (2.50), 7.143 (1.39), 7.227 (1.08), 7.241 (1.18), 7.247 (1.56), 7.261 (1.20), 7.266 (0.77), 7.281 (0.63), 7.566 (6.67), 7.580 (3.00), 7.590 (3.68), 9.828 (4.20).

Example 185

5-fluoro-N-(2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

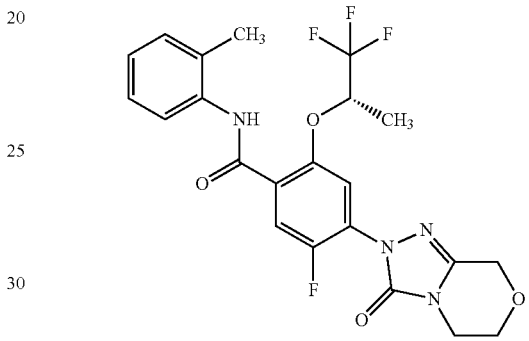

From Intermediate 24 and o-toluidine.
LC-MS (method A): $R_t$=1.21 min; MS (ESIpos): m/z=481 [M+H]$^+$
$^1$H-NMR (400 MHz, CHLOROFORM-d) δ [ppm]: 1.201 (8.19), 1.218 (16.00), 1.235 (8.73), 1.580 (1.03), 1.629 (0.64), 1.645 (0.64), 2.321 (1.57), 3.461 (2.72), 3.479 (8.01), 3.496 (7.46), 3.514 (2.60), 4.100 (0.40), 4.770 (1.47).

Example 186

N-(2,6-dichlorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

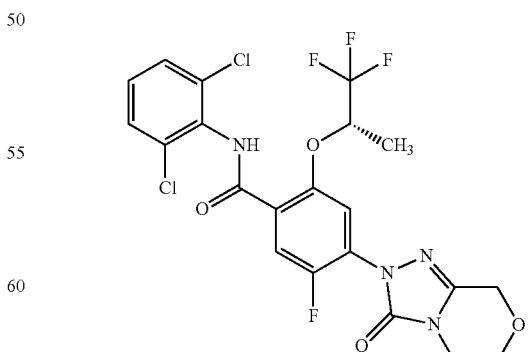

From Intermediate 24 and 2,6-dichloroaniline.
LC-MS (method A): $R_t$=1.22 min; MS (ESIpos): m/z=535 [M+H]$^+$ ¹H-NMR (500 MHz, CHLOROFORM-d) δ [ppm]: 1.512 (12.67), 1.524 (12.83), 3.655 (5.00), 3.664 (8.25), 3.674 (5.40), 3.934 (5.57), 3.944 (8.21), 3.954 (4.80), 4.616 (16.00), 4.783 (1.04), 4.795 (2.13), 4.807 (2.67), 4.819 (2.06), 4.830 (0.98), 7.065 (2.09), 7.081 (4.28), 7.097 (2.87), 7.121 (4.39), 7.312 (4.64), 7.322 (4.44), 8.032 (3.80), 8.055 (3.79), 8.922 (5.01).

Example 187

N-(2-chloro-6-methylphenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

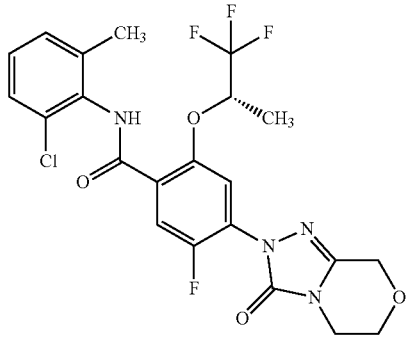 [SMILES: C[C@H](Oc1cc(-n2nc3n(c2=O)CCOC3)c(F)cc1C(=O)Nc1c(Cl)cccc1Cl)C(F)(F)F]

From Intermediate 24 and 2-chloro-6-methylaniline.
LC-MS (method A): R$_t$=1.23 min; MS (ESIpos): m/z=515 [M+H]⁺

¹H-NMR (500 MHz, CHLOROFORM-d) δ [ppm]: 1.735 (6.96), 1.749 (7.00), 2.080 (0.70), 2.396 (16.00), 3.870 (2.70), 3.880 (4.17), 3.891 (3.27), 4.149 (3.28), 4.160 (4.25), 4.170 (2.78), 4.833 (12.96), 5.011 (0.46), 5.023 (1.08), 5.036 (1.39), 5.048 (1.03), 5.061 (0.42), 7.239 (0.98), 7.255 (3.10), 7.279 (2.25), 7.281 (2.64), 7.294 (0.96), 7.353 (1.66), 7.395 (1.85), 7.398 (1.84), 7.410 (1.51), 7.413 (1.45), 7.520 (2.83), 7.531 (2.84), 8.240 (3.29), 8.263 (3.33), 9.058 (2.51).

Example 188

N-(2-chloro-4-fluoro-6-methylphenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

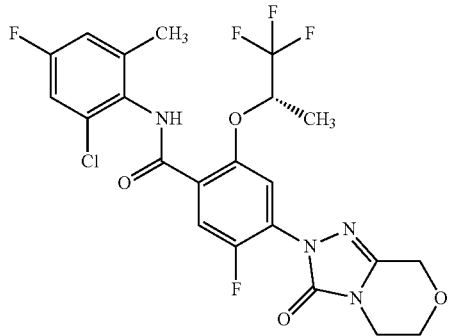

From Intermediate 24 and 2-chloro-4-fluoro-6-methylaniline.
LC-MS (method A): R$_t$=1.25 min; MS (ESIneg): m/z=531 [M−H]⁻

¹H-NMR (500 MHz, CHLOROFORM-d) δ [ppm]: 1.657 (7.02), 1.670 (7.36), 2.010 (0.44), 2.306 (16.00), 3.801 (2.85), 3.811 (4.07), 3.822 (3.42), 4.081 (3.56), 4.092 (4.15), 4.103 (2.90), 4.762 (14.32), 4.926 (0.45), 4.939 (1.06), 4.951 (1.36), 4.963 (1.00), 4.975 (0.40), 6.935 (1.25), 6.941 (1.36), 6.953 (1.27), 6.959 (1.34), 7.073 (1.50), 7.078 (1.42), 7.089 (1.51), 7.094 (1.37), 7.440 (2.95), 7.452 (2.90), 8.149 (3.65), 8.171 (3.51), 8.874 (2.19).

Example 189

N-(2-chloro-4,6-difluorophenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

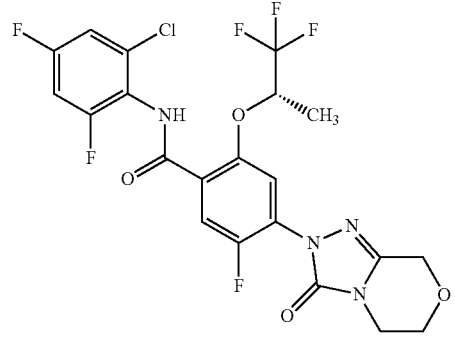 [SMILES: C[C@H](Oc1cc(-n2nc3n(c2=O)CCOC3)c(F)cc1C(=O)Nc1c(F)cc(F)cc1Cl)C(F)(F)F]

From Intermediate 24 and 2-chloro-4,6-difluoroaniline.
LC-MS (method A): R$_t$=1.23 min; MS (ESIpos): m/z=537 [M+H]⁺

¹H-NMR (500 MHz, CHLOROFORM-d) δ [ppm]: 1.618 (2.57), 1.654 (7.69), 1.667 (7.60), 3.804 (3.07), 3.814 (4.58), 3.825 (3.69), 4.085 (3.92), 4.096 (4.65), 4.106 (3.17), 4.766 (16.00), 4.914 (0.54), 4.927 (1.14), 4.939 (1.44), 4.951 (1.08), 4.963 (0.43), 6.895 (0.93), 6.901 (1.02), 6.914 (1.29), 6.918 (1.37), 6.931 (0.95), 6.937 (0.98), 7.072 (1.14), 7.077 (1.47), 7.081 (1.21), 7.088 (1.21), 7.093 (1.46), 7.097 (1.10), 7.464 (3.02), 7.475 (2.99), 8.161 (3.32), 8.183 (3.26), 8.913 (2.62).

Example 190

5-fluoro-N-(4-fluoro-2-methylphenyl)-4-(3-oxo-5,6-dihydro-3H-[1,2,4]triazolo[3,4-c][1,4]oxazin-2(8H)-yl)-2-{[(2S)-1,1,1trifluoropropan-2-yl]oxy}benzamide

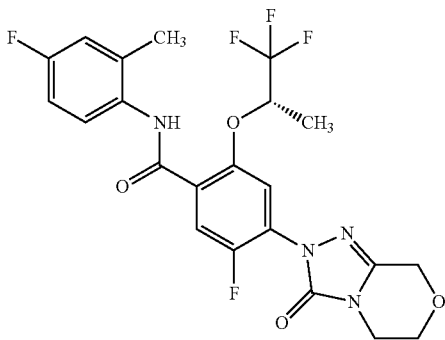 [SMILES: Cc1cc(F)ccc1NC(=O)c1cc(F)c(-n2nc3n(c2=O)CCOC3)cc1O[C@@H](C)C(F)(F)F]

From Intermediate 24 and 4-fluoro-2-methylaniline.
LC-MS (method A): R$_t$=1.18 min; MS (ESIpos): m/z=499 [M+H]$^+$
$^1$H-NMR (500 MHz, CHLOROFORM-d) δ [ppm]: 1.047 (0.59), 1.466 (7.05), 1.480 (7.07), 1.526 (0.70), 2.131 (16.00), 3.632 (2.72), 3.642 (4.20), 3.653 (3.23), 3.913 (3.33), 3.925 (4.31), 3.935 (2.80), 4.593 (12.98), 4.714 (0.47), 4.727 (1.11), 4.739 (1.47), 4.751 (1.06), 4.764 (0.44), 6.764 (0.54), 6.770 (0.95), 6.786 (3.95), 6.803 (3.10), 7.106 (2.57), 7.281 (2.79), 7.559 (1.06), 7.570 (1.34), 7.576 (1.12), 7.586 (1.18), 7.973 (3.21), 7.996 (3.20), 8.784 (2.24).

Example 191

5-fluoro-N-(5-fluoro-2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

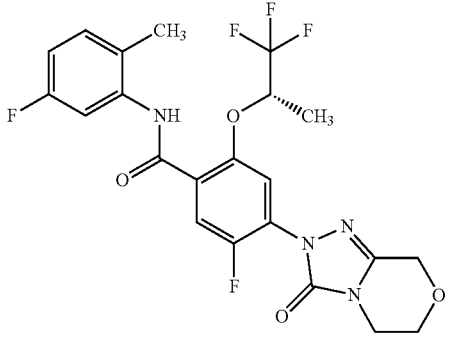 [SMILES: Cc1ccc(F)cc1NC(=O)c1cc(F)c(-n2nc3n(c2=O)CCOC3)cc1O[C@@H](C)C(F)(F)F]

From Intermediate 24 and 5-fluoro-2-methylaniline.
LC-MS (method A): R$_t$=1.26 min; MS (ESIpos): m/z=499 [M+H]$^+$
$^1$H-NMR (500 MHz, CHLOROFORM-d) δ [ppm]: 1.625 (7.46), 1.638 (7.49), 1.667 (0.69), 2.010 (0.50), 2.276 (14.37), 3.798 (3.15), 3.808 (4.50), 3.819 (3.76), 4.080 (4.03), 4.089 (3.35), 4.091 (4.61), 4.101 (3.31), 4.759 (16.00), 4.869 (0.51), 4.882 (1.19), 4.893 (1.52), 4.906 (1.20), 4.919 (0.46), 6.807 (0.90), 6.812 (0.98), 6.824 (1.76), 6.829 (1.83), 6.840 (1.01), 6.846 (1.01), 7.150 (1.37), 7.163 (1.53), 7.166 (1.44), 7.179 (1.23), 7.456 (3.10), 7.467 (3.06), 7.875 (1.63), 7.880 (1.66), 7.896 (1.67), 7.901 (1.61), 8.125 (3.49), 8.147 (3.56), 9.049 (2.13).

Example 192

5-fluoro-N-[2-methyl-6-(trifluoromethyl)phenyl]-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

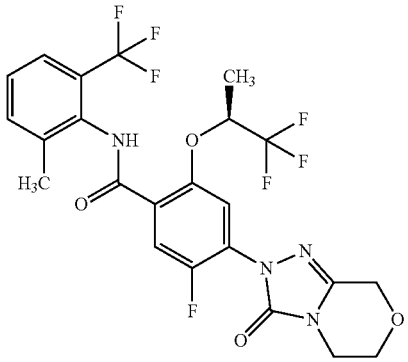 [SMILES: Cc1cccc(C(F)(F)F)c1NC(=O)c1cc(F)c(-n2nc3n(c2=O)CCOC3)cc1O[C@@H](C)C(F)(F)F]

From Intermediate 24 and 2-methyl-6-(trifluoromethyl)aniline.
LC-MS (method A): R$_t$=1.18 min; MS (ESIpos): m/z=549 [M+H]$^+$
$^1$H-NMR (500 MHz, CHLOROFORM-d) δ [ppm]: 1.640 (2.42), 1.651 (2.43), 1.672 (2.39), 2.200 (8.34), 2.325 (16.00), 3.800 (2.97), 3.811 (4.44), 3.821 (3.63), 4.078 (3.97), 4.089 (4.62), 4.099 (3.28), 4.140 (0.55), 4.761 (15.84), 4.929 (0.48), 4.941 (1.13), 4.953 (1.45), 4.965 (1.08), 4.977 (0.43), 6.698 (0.49), 6.713 (1.00), 6.729 (0.54), 7.201 (0.80), 7.215 (0.75), 7.318 (0.83), 7.334 (0.84), 7.341 (1.05), 7.356 (2.33), 7.371 (1.40), 7.440 (3.15), 7.450 (3.08), 7.511 (2.01), 7.526 (1.66), 7.554 (2.01), 7.570 (1.73), 8.168 (0.75), 8.190 (0.74).

Example 193

N-[2-(difluoromethyl)phenyl]-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

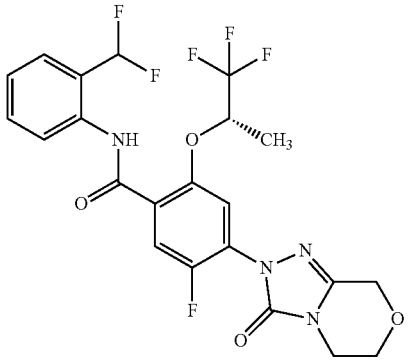 [SMILES: C[C@H](Oc1cc(-n2nc3n(c2=O)CCOC3)c(F)cc1C(=O)Nc1ccccc1C(F)F)C(F)(F)F]

From Intermediate 24 and 2-(difluoromethyl)aniline.
LC-MS (method A): R$_t$=1.20 min; MS (ESIpos): m/z=517 [M+H]$^+$ ¹H-NMR (500 MHz, CHLOROFORM-d) δ [ppm]: 1.633 (7.89), 1.647 (8.28), 2.620 (0.41), 3.801 (3.22), 3.811 (4.97), 3.821 (3.82), 4.080 (4.09), 4.091 (5.05), 4.101 (3.38), 4.761 (16.00), 4.858 (0.51), 4.870 (1.18), 4.883 (1.54), 4.895 (1.15), 4.908 (0.53), 6.640 (1.65), 6.750 (3.26), 6.861 (1.55), 7.308 (1.06), 7.324 (2.31), 7.339 (1.36), 7.455 (3.09), 7.466 (3.04), 7.533 (1.06), 7.549 (4.62), 7.564 (3.35), 7.933 (2.12), 7.949 (1.94), 8.113 (3.35), 8.135 (3.35), 9.379 (2.25).

Example 194

N-(2-chloro-3,6-difluorophenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

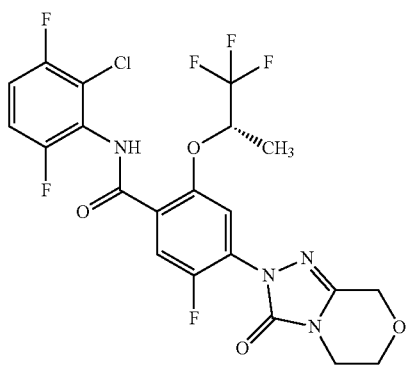 [SMILES: C[C@H](Oc1cc(-n2nc3n(c2=O)CCOC3)c(F)cc1C(=O)Nc1c(F)ccc(F)c1Cl)C(F)(F)F]

From Intermediate 24 and 2-chloro-3,6-difluoroaniline.

LC-MS (method A): R$_t$=1.21 min; MS (ESIpos): m/z=535 [M+H]$^+$

¹H-NMR (500 MHz, CHLOROFORM-d) δ [ppm]: 1.618 (2.41), 1.664 (7.49), 1.677 (7.43), 2.622 (0.78), 3.805 (3.02), 3.816 (4.41), 3.826 (3.63), 4.086 (3.90), 4.094 (3.26), 4.097 (4.53), 4.107 (3.15), 4.768 (16.00), 4.927 (0.48), 4.939 (1.13), 4.951 (1.43), 4.964 (1.07), 4.976 (0.43), 7.094 (0.41), 7.102 (2.02), 7.107 (1.94), 7.112 (1.96), 7.118 (3.90), 7.121 (1.79), 7.128 (2.15), 7.132 (1.88), 7.477 (3.19), 7.488 (3.08), 8.173 (3.34), 8.196 (3.27), 9.064 (2.29).

Example 195

5-fluoro-N-(3-fluoro-2-methylphenyl)-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

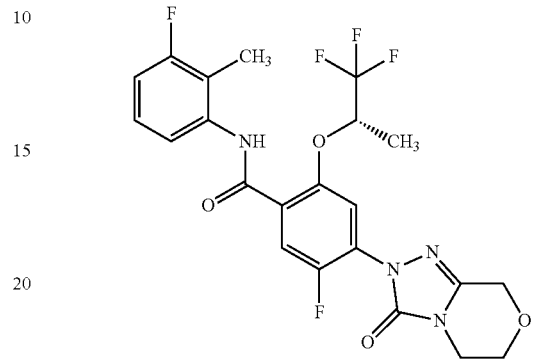

From Intermediate 24 and 3-fluoro-2-methylaniline.

LC-MS (method A): R$_t$=1.24 min; MS (ESIpos): m/z=499 [M+H]$^+$

¹H-NMR (500 MHz, CHLOROFORM-d) δ [ppm]: 1.454 (7.49), 1.467 (7.52), 1.824 (1.58), 2.035 (10.57), 2.039 (10.63), 3.611 (3.16), 3.621 (4.59), 3.632 (3.81), 3.893 (4.07), 3.905 (4.72), 3.915 (3.36), 4.573 (16.00), 4.706 (0.51), 4.718 (1.22), 4.730 (1.51), 4.743 (1.13), 4.756 (0.45), 6.730 (1.14), 6.747 (2.23), 6.765 (1.26), 7.009 (0.75), 7.025 (1.51), 7.038 (1.52), 7.054 (0.71), 7.094 (2.16), 7.281 (3.07), 7.493 (2.38), 7.510 (2.19), 7.954 (3.66), 7.977 (3.54), 8.894 (2.40).

Example 196

5-fluoro-4-(3-oxo-5,6-dihydro-3H-[1,2,4]triazolo[3,4-c][1,4]oxazin-2(8H)-yl)-N-(2,4,6-trifluoro-phenyl)-2-{[(2S)-1,1,1-trifluoropropan-2-yl]oxy}benzamide

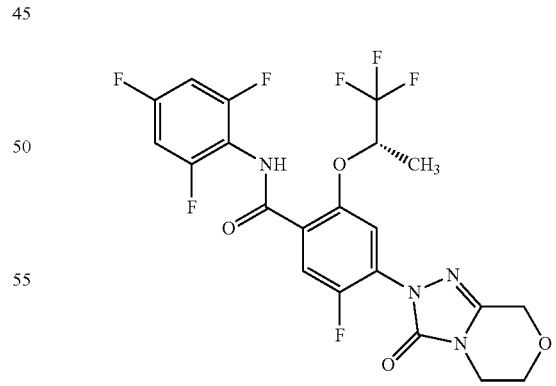

From Intermediate 24 and 2,4,6-trifluoroaniline.

LC-MS (method A): R$_t$=1.18 min; MS (ESIpos): m/z=519 [M+H]$^+$

¹H-NMR (400 MHz, CHLOROFORM-d) δ [ppm]: 1.645 (7.52), 1.661 (7.40), 2.016 (3.38), 3.801 (2.97), 3.814 (4.46), 3.817 (3.24), 3.827 (3.72), 4.082 (3.87), 4.093 (3.20), 4.096 (4.54), 4.109 (3.09), 4.766 (16.00), 4.881 (0.48), 4.896

(1.12), 4.912 (1.44), 4.927 (1.08), 4.943 (0.45), 6.772 (1.14), 6.777 (2.61), 6.785 (0.48), 6.796 (3.50), 6.798 (3.48), 6.810 (0.51), 6.817 (2.76), 6.822 (1.13), 7.459 (3.11), 7.473 (3.08), 8.140 (3.54), 8.169 (3.53), 8.846 (2.50).

Example 197

N-(2,6-dichloro-4-fluorophenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

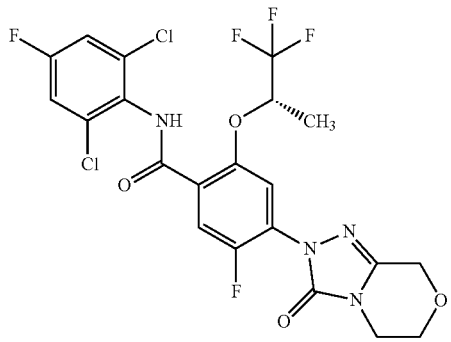 [SMILES: C[C@H](Oc1cc(-n2nc3n(c2=O)CCOC3)c(F)cc1C(=O)Nc1c(Cl)cc(F)cc1Cl)C(F)(F)F]

From Intermediate 24 and 2,6-dichloro-4-fluoroaniline.
LC-MS (method A): R$_t$=1.26 min; MS (ESIpos): m/z=553 [M+H]$^+$
$^1$H-NMR (400 MHz, CHLOROFORM-d) δ [ppm]: 1.578 (16.00), 1.660 (6.41), 1.676 (6.62), 3.807 (2.38), 3.820 (3.89), 3.834 (3.08), 4.087 (3.02), 4.101 (4.08), 4.114 (2.58), 4.771 (12.23), 4.923 (0.42), 4.939 (1.02), 4.955 (1.35), 4.969 (1.01), 4.985 (0.43), 7.202 (6.80), 7.221 (6.95), 7.462 (2.56), 7.476 (2.59), 8.168 (2.91), 8.196 (2.92), 8.971 (2.37).

Example 198

N-(4,5-difluoro-2-methylphenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

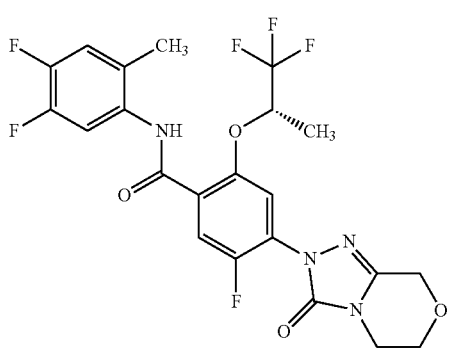 [SMILES: Cc1cc(F)c(F)cc1NC(=O)c1cc(F)c(-n2nc3n(c2=O)CCOC3)cc1O[C@@H](C)C(F)(F)F]

From Intermediate 24 and 4,5-difluoro-2-methylaniline.
LC-MS (method A): R$_t$=1.27 min; MS (ESIpos): m/z=517 [M+H]$^+$
$^1$H-NMR (400 MHz, CHLOROFORM-d) δ [ppm]: 1.629 (7.16), 1.644 (11.48), 2.259 (13.55), 3.798 (2.87), 3.811 (4.36), 3.825 (3.59), 4.081 (3.82), 4.092 (3.22), 4.095 (4.45), 4.108 (3.06), 4.761 (16.00), 4.870 (0.52), 4.886 (1.19), 4.901 (1.54), 4.917 (1.13), 4.932 (0.46), 7.005 (1.22), 7.026 (1.35), 7.032 (1.35), 7.053 (1.21), 7.452 (3.11), 7.467 (3.07), 7.854 (1.50), 7.873 (1.58), 7.884 (1.57), 7.904 (1.51), 8.122 (3.76), 8.151 (3.76), 8.984 (2.18).

Example 199

5-fluoro-N-[2-methyl-4-(trifluoromethyl)phenyl]-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

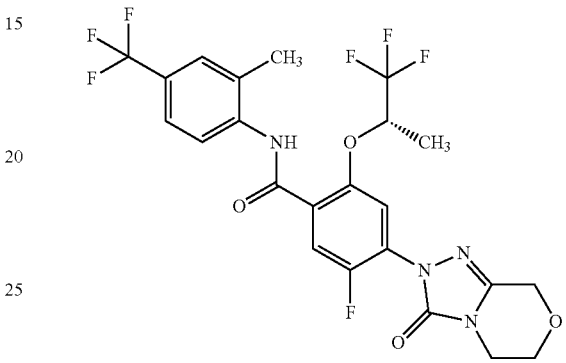

From Intermediate 24 and 2-methyl-4-(trifluoromethyl)aniline.
LC-MS (method A): R$_t$=1.37 min; MS (ESIpos): m/z=549 [M+H]$^+$
$^1$H-NMR (400 MHz, CHLOROFORM-d) δ [ppm]: 1.615 (5.42), 1.636 (6.64), 1.651 (6.69), 2.375 (16.00), 3.805 (2.71), 3.818 (4.12), 3.820 (3.03), 3.832 (3.51), 4.086 (3.71), 4.097 (2.93), 4.100 (4.26), 4.112 (2.98), 4.768 (15.76), 4.877 (0.45), 4.893 (1.09), 4.908 (1.42), 4.924 (1.05), 4.939 (0.43), 7.474 (2.92), 7.488 (3.03), 7.501 (2.85), 7.516 (1.45), 7.537 (1.39), 8.140 (3.29), 8.169 (3.27), 8.183 (2.01), 8.204 (1.84), 9.144 (2.03).

Example 200

N-(2-chloro-5-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

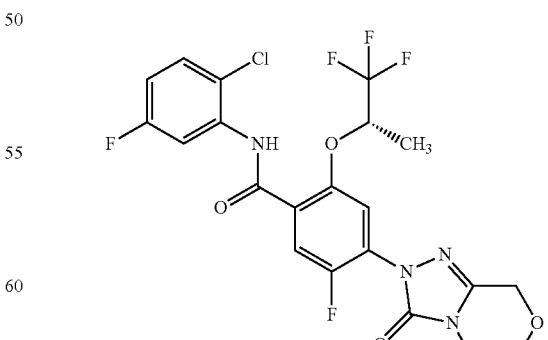

From Intermediate 24 and 2-chloro-5-fluoroaniline
LC-MS (method A): R$_t$=1.36 min; MS (ESIneg): m/z=517 [M−H]$^-$.

¹H-NMR (400 MHz, CHLOROFORM-d) δ [ppm]: 1.632 (3.35), 1.656 (7.36), 1.672 (7.40), 3.801 (2.95), 3.814 (4.44), 3.817 (3.14), 3.827 (3.70), 4.081 (3.86), 4.091 (3.09), 4.095 (4.58), 4.107 (3.19), 4.763 (16.00), 4.850 (0.51), 4.865 (1.20), 4.881 (1.57), 4.897 (1.15), 4.912 (0.47), 6.804 (1.19), 6.812 (1.31), 6.822 (1.26), 6.826 (1.41), 6.830 (1.42), 6.834 (1.47), 6.845 (1.29), 6.852 (1.38), 7.351 (2.42), 7.365 (2.43), 7.373 (2.34), 7.387 (2.22), 7.482 (3.21), 7.496 (3.23), 8.091 (4.10), 8.120 (4.07), 8.418 (2.00), 8.425 (2.01), 8.445 (2.02), 8.452 (1.99), 9.751 (1.99).

Example 201

5-fluoro-N-(4-fluoro-2,6-dimethylphenyl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

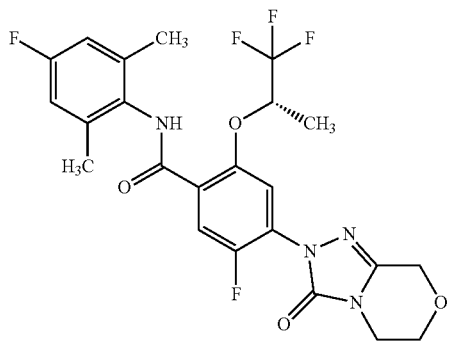 [SMILES: Cc1cc(F)cc(C)c1NC(=O)c1cc(F)c(-n2nc3n(c2=O)CCOC3)cc1O[C@@H](C)C(F)(F)F]

From Intermediate 24 and 4-fluoro-2,6-dimethylaniline.
LC-MS (method A): $R_t$=1.23 min; MS (ESIpos): m/z=513 [M+H]⁺
¹H-NMR (400 MHz, CHLOROFORM-d) δ [ppm]: 1.644 (3.44), 1.660 (3.50), 2.248 (16.00), 3.793 (1.21), 3.805 (1.97), 3.819 (1.50), 4.074 (1.59), 4.088 (2.05), 4.101 (1.29), 4.758 (6.48), 4.933 (0.56), 4.948 (0.73), 4.964 (0.54), 6.825 (2.24), 6.848 (2.24), 7.419 (1.51), 7.433 (1.52), 8.140 (1.58), 8.169 (1.56), 8.637 (1.09).

Example 202

N-(2-chloro-4-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

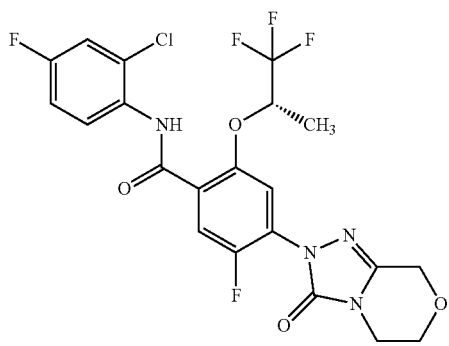 [SMILES: C[C@H](Oc1cc(-n2nc3n(c2=O)CCOC3)c(F)cc1C(=O)Nc1ccc(F)cc1Cl)C(F)(F)F]

From Intermediate 24 and 2-chloro-4-fluoroaniline.
LC-MS (method A): $R_t$=1.32 min; MS (ESIneg): m/z=517 [M+H]⁺

¹H-NMR (400 MHz, CHLOROFORM-d) δ [ppm]: 0.842 (0.76), 0.849 (0.72), 1.261 (0.69), 1.293 (0.67), 1.584 (12.78), 1.655 (6.46), 1.672 (6.45), 3.807 (2.75), 3.819 (4.01), 3.822 (2.89), 3.833 (3.56), 4.085 (3.77), 4.096 (2.90), 4.099 (4.19), 4.112 (2.96), 4.768 (16.00), 4.860 (0.46), 4.876 (1.05), 4.891 (1.39), 4.907 (1.02), 4.922 (0.41), 7.042 (0.89), 7.049 (1.02), 7.062 (0.99), 7.065 (1.07), 7.069 (1.16), 7.072 (1.17), 7.084 (0.93), 7.092 (1.04), 7.179 (2.51), 7.186 (2.21), 7.200 (2.56), 7.207 (2.28), 7.468 (2.86), 7.481 (2.83), 8.117 (3.64), 8.147 (3.54), 8.451 (1.95), 8.464 (1.94), 8.473 (1.90), 8.488 (1.84), 9.605 (1.93).

Example 203

N-(2-cyano-4-fluorophenyl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

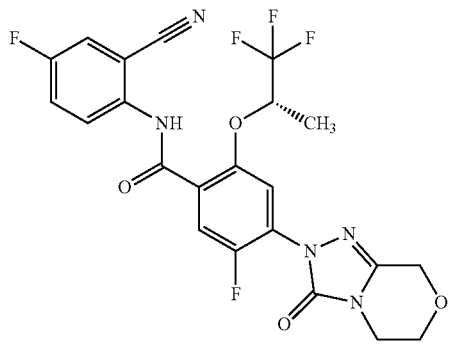 [SMILES: C[C@H](Oc1cc(-n2nc3n(c2=O)CCOC3)c(F)cc1C(=O)Nc1ccc(F)cc1C#N)C(F)(F)F]

From Intermediate 24 and 2-amino-5-fluorobenzonitrile.
LC-MS (method A): $R_t$=1.17 min; MS (ESIpos): m/z=510 [M+H]⁺

¹H-NMR (400 MHz, CHLOROFORM-d) δ [ppm]: 1.610 (1.66), 1.755 (6.55), 1.772 (6.62), 2.016 (0.58), 3.803 (2.77), 3.816 (4.06), 3.819 (2.87), 3.830 (3.45), 4.084 (3.72), 4.095 (2.95), 4.098 (4.20), 4.110 (2.94), 4.767 (16.00), 4.860 (0.45), 4.876 (1.05), 4.891 (1.37), 4.907 (1.00), 4.922 (0.40), 7.341 (1.11), 7.348 (2.45), 7.352 (1.88), 7.360 (1.44), 7.367 (2.47), 7.371 (1.91), 7.374 (1.49), 7.381 (0.88), 7.393 (1.19), 7.401 (0.78), 7.480 (3.06), 7.494 (3.09), 8.101 (3.86), 8.129 (3.83), 8.423 (1.38), 8.435 (1.41), 8.445 (1.35), 8.457 (1.34), 9.741 (2.16).

Example 204

5-fluoro-N-(2-methoxy-4-methylpyridin-3-yl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

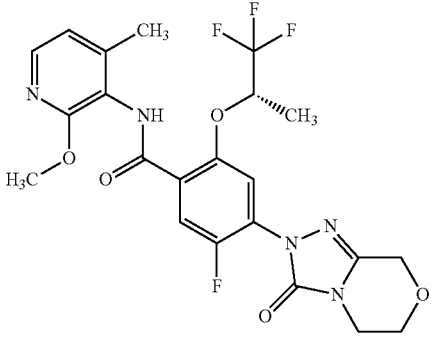

From Intermediate 24 and 2-methoxy-4-methylpyridin-3-amine.

LC-MS (method A): $R_t$=1.10 min; MS (ESIneg): m/z=510 [M+H]$^+$ $^1$H-NMR (400 MHz, CHLOROFORM-d) δ [ppm]: 1.656 (3.88), 1.672 (3.93), 2.010 (1.01), 2.273 (10.82), 3.798 (1.46), 3.811 (2.26), 3.825 (1.82), 3.956 (16.00), 4.077 (1.92), 4.088 (1.73), 4.091 (2.33), 4.104 (1.52), 4.762 (7.99), 4.913 (0.63), 4.928 (0.82), 4.943 (0.61), 6.824 (1.63), 6.837 (1.66), 7.426 (1.68), 7.440 (1.69), 7.953 (2.05), 7.967 (2.04), 8.135 (2.05), 8.163 (2.06), 8.960 (1.38).

Example 205

N-(4-chloro-2-methylpyridin-3-yl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

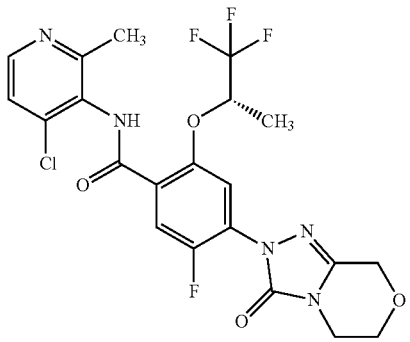 [SMILES: Cc1nccc(Cl)c1NC(=O)c1cc(F)c(-n2nc3n(c2=O)CCOC3)cc1O[C@@H](C)C(F)(F)F]

From Intermediate 24 and 4-chloro-2-methylpyridin-3-amine.

LC-MS (method A): $R_t$=0.99 min; MS (ESIpos): m/z=516 [M+H]$^+$ $^1$H-NMR (400 MHz, CHLOROFORM-d) δ [ppm]: 1.675 (5.82), 1.691 (5.88), 2.017 (0.50), 2.574 (16.00), 2.719 (0.49), 3.810 (2.35), 3.823 (3.44), 3.826 (2.47), 3.837 (3.00), 4.090 (3.16), 4.100 (2.50), 4.103 (3.53), 4.117 (2.49), 4.774 (13.95), 4.957 (0.91), 4.972 (1.18), 4.988 (0.85), 7.321 (2.24), 7.334 (2.29), 7.472 (2.56), 7.486 (2.55), 8.091 (0.59), 8.172 (3.42), 8.201 (3.38), 8.379 (2.74), 8.392 (2.66), 9.046 (2.06).

Example 206

N-(2-chloro-4-methylpyridin-3-yl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

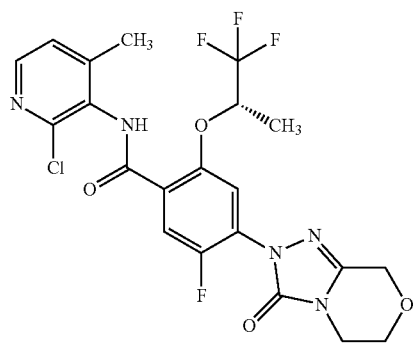 [SMILES: Cc1ccnc(Cl)c1NC(=O)c1cc(F)c(-n2nc3n(c2=O)CCOC3)cc1O[C@@H](C)C(F)(F)F]

From Intermediate 24 and 2-chloro-4-methylpyridin-3-amine.

LC-MS (method A): $R_t$=1.04 min; MS (ESIpos): m/z=516 [M+H]$^+$ $^1$H-NMR (400 MHz, CHLOROFORM-d) δ [ppm]: 1.681 (5.98), 1.696 (5.99), 2.013 (2.42), 2.346 (16.00), 3.805 (2.42), 3.817 (3.57), 3.820 (2.60), 3.831 (3.03), 4.084 (3.25), 4.095 (2.62), 4.098 (3.63), 4.111 (2.57), 4.768 (13.88), 4.958 (0.94), 4.973 (1.22), 4.988 (0.88), 7.194 (2.25), 7.206 (2.29), 7.468 (2.62), 7.481 (2.60), 8.036 (0.44), 8.156 (3.46), 8.184 (3.45), 8.212 (3.12), 8.224 (3.06), 9.121 (2.17).

Example 207

N-(2-chloro-4,6-dimethylpyridin-3-yl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

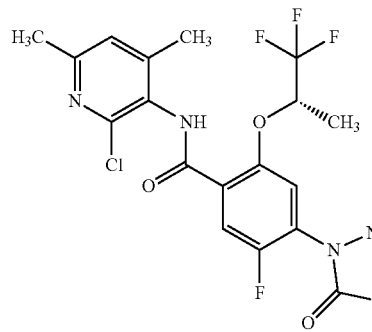

From Intermediate 24 and 2-chloro-4,6-dimethylpyridin-3-amine.

LC-MS (method A): $R_t$=1.11 min; MS (ESIneg): m/z=528 [M−H]$^−$

Example 208

N-(2,4-dimethylpyridin-3-yl)-5-fluoro-4-(3-oxo-5,6-dihydro-3H-[1,2,4]triazolo[3,4-c][1,4]oxazin-2(8H)-yl)-2-{[(2S)-1,1,1-trifluoropropan-2-yl]oxy}benzamide

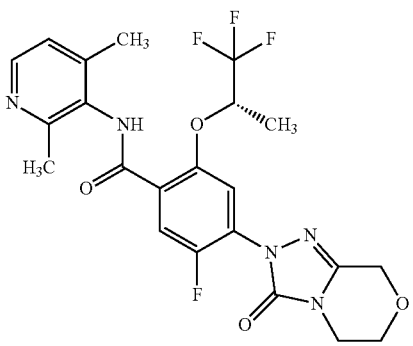 [SMILES: Cc1ccnc(C)c1NC(=O)c1cc(F)c(-n2nc3n(c2=O)CCOC3)cc1O[C@@H](C)C(F)(F)F]

From Intermediate 24 and 2,4-dimethylpyridin-3-amine.
LC-MS (method A): $R_t$=0.73 min; MS (ESIpos): m/z=496 [M+H]$^+$ $^1$H-NMR (400 MHz, CHLOROFORM-d) δ [ppm]: 1.671 (6.70), 1.687 (6.81), 1.795 (0.64), 2.295 (15.58), 2.533 (16.00), 3.812 (2.68), 3.824 (3.93), 3.827 (2.79), 3.838 (3.35), 4.092 (3.56), 4.103 (2.85), 4.106 (4.01), 4.119 (2.85), 4.776 (15.04), 4.939 (0.44), 4.955 (1.03), 4.970 (1.36), 4.985 (0.98), 5.001 (0.40), 7.115 (1.84), 7.128 (1.88), 7.454 (2.90), 7.468 (2.89), 8.172 (3.93), 8.200 (3.86), 8.345 (2.84), 8.358 (2.77), 8.839 (2.13).

Example 209

5-fluoro-N-(2-methoxy-6-methylphenyl)-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

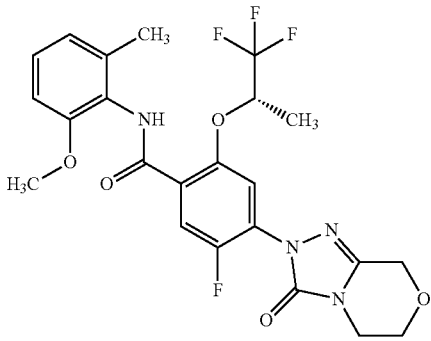

From Intermediate 24 and 2-methoxy-6-methylaniline.
LC-MS (method A): $R_t$=1.19 min; MS (ESIpos): m/z=511 [M+H]$^+$ $^1$H-NMR (400 MHz, CHLOROFORM-d) δ [ppm]: 1.637 (4.76), 1.653 (4.83), 2.283 (11.55), 3.798 (1.85), 3.812 (3.58), 3.818 (16.00), 3.824 (2.91), 4.076 (2.24), 4.090 (2.88), 4.103 (1.82), 4.762 (8.99), 4.900 (0.77), 4.915 (1.01), 4.931 (0.75), 6.793 (1.33), 6.813 (1.47), 6.887 (1.31), 6.906 (1.49), 7.164 (1.31), 7.184 (2.04), 7.204 (1.03), 7.407 (2.00), 7.421 (2.00), 8.150 (2.41), 8.179 (2.39), 8.871 (1.60).

Example 210

N-(6-chloro-2,3-difluorophenyl)-5-fluoro-4-(3-oxo-5,6-dihydro-3H-[1,2,4]triazolo[3,4-c]-[1,4]oxazin-2(8H)-yl)-2-{[(2S)-1,1,1-trifluoropropan-2-yl]oxy}benzamide

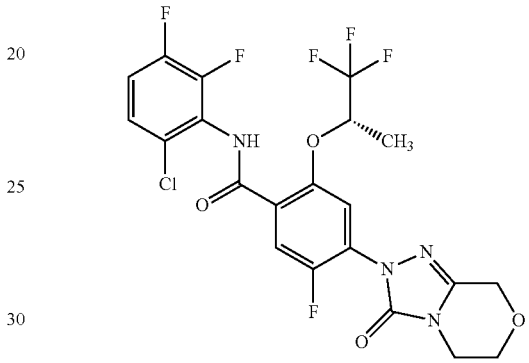

From Intermediate 24 and 6-chloro-2,3-difluoroaniline.
LC-MS (method A): $R_t$=1.22 min; MS (ESIpos): m/z=537 [M+H]$^+$ $^1$H-NMR (400 MHz, CHLOROFORM-d) δ [ppm]: 1.566 (16.00), 1.666 (4.53), 1.682 (4.58), 3.808 (1.78), 3.821 (2.75), 3.835 (2.22), 4.088 (2.30), 4.103 (2.82), 4.116 (1.84), 4.774 (9.28), 4.938 (0.72), 4.953 (0.94), 4.969 (0.71), 7.090 (0.45), 7.113 (1.12), 7.133 (1.16), 7.136 (0.85), 7.155 (0.72), 7.218 (0.76), 7.224 (0.79), 7.230 (0.92), 7.236 (0.85), 7.241 (0.66), 7.247 (0.65), 7.253 (0.72), 7.259 (0.81), 7.481 (1.90), 7.495 (1.91), 8.183 (2.21), 8.212 (2.18), 9.079 (1.53).

Example 211

5-fluoro-N-(6-methoxy-4-methylpyridin-3-yl)-4-(3-oxo-5,6-dihydro-3H-[1,2,4]triazolo[3,4-c]-[1,4]oxazin-2(8H)-yl)-2-[(2S)-pentan-2-yloxy]benzamide

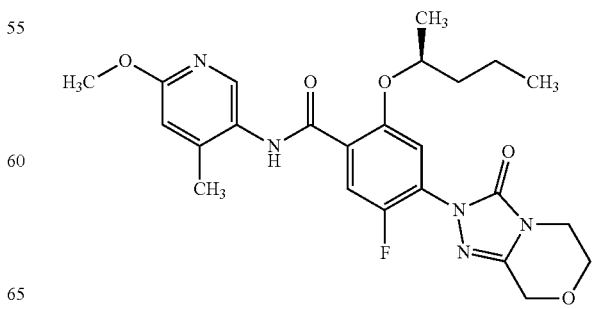

From Intermediate 21 and 6-methoxy-4-methylpyridin-3-amine.

The product was purified by preparative HPLC (Chromatorex C18 125×30 mm 10 μm, 0.1% aqueous formic acid, acetonitrile).

LC-MS (method A): $R_t$=1.20 min; MS (ESIneg): m/z=484 [M−H]⁻

¹H-NMR (400 MHz, DMSO-d6) δ[ppm]: 0.858 (2.70), 0.876 (6.35), 0.894 (3.04), 1.292 (5.45), 1.306 (5.50), 1.371 (0.52), 1.390 (0.57), 1.404 (0.61), 1.423 (0.47), 1.428 (0.44), 1.447 (0.45), 1.582 (0.41), 1.597 (0.55), 1.621 (0.43), 1.693 (0.41), 1.709 (0.41), 2.210 (0.59), 2.250 (9.42), 2.518 (1.10), 2.522 (0.71), 3.659 (1.35), 3.672 (2.28), 3.686 (1.59), 3.835 (16.00), 3.866 (1.04), 4.022 (1.70), 4.036 (2.38), 4.048 (1.42), 4.560 (0.41), 4.575 (0.77), 4.591 (0.77), 4.743 (6.99), 6.777 (2.95), 7.371 (1.65), 7.386 (1.64), 7.673 (2.19), 7.699 (2.11), 8.193 (3.65), 9.668 (2.60).

Example 212

N-(2-chloro-6-fluorophenyl)-5-fluoro-4-(3-oxo-5,6-dihydro-3H-[1,2,4]triazolo[3,4-c][1,4]oxazin-2(8H)-yl)-2-[(2S)-pentan-2-yloxy]benzamide

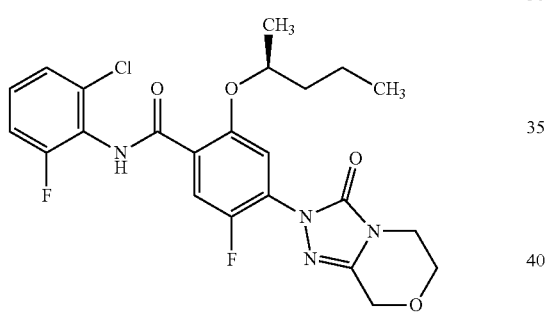

The product was purified by preparative HPLC (Chromatorex C18 125×30 mm 10 μm, 0.1% aqueous formic acid, acetonitrile).

From Intermediate 21 and 2-chloro-6-fluoroaniline.

LC-MS (method A): $R_t$=1.30 min; MS (ESIpos): m/z=493 [M+H]⁺

¹H-NMR (400 MHz, DMSO-d6) δ[ppm]: 0.860 (6.38), 0.878 (15.05), 0.897 (7.24), 0.921 (0.42), 1.290 (0.75), 1.311 (8.08), 1.325 (8.15), 1.351 (1.04), 1.369 (0.96), 1.376 (1.07), 1.391 (1.01), 1.408 (1.04), 1.427 (0.89), 1.440 (0.87), 1.446 (0.93), 1.465 (0.89), 1.484 (0.54), 1.560 (0.47), 1.574 (0.76), 1.595 (0.91), 1.607 (1.11), 1.619 (0.89), 1.632 (0.79), 1.741 (0.51), 1.756 (0.75), 1.771 (0.85), 1.815 (0.47), 2.084 (1.18), 2.250 (0.71), 2.518 (3.68), 2.523 (2.36), 3.662 (3.26), 3.674 (5.56), 3.688 (3.73), 3.834 (1.16), 4.022 (4.19), 4.036 (5.89), 4.049 (3.47), 4.597 (0.75), 4.612 (1.38), 4.627 (1.35), 4.642 (0.73), 4.724 (0.88), 4.748 (16.00), 7.338 (0.82), 7.358 (2.07), 7.377 (1.45), 7.382 (1.75), 7.406 (2.04), 7.421 (4.15), 7.441 (4.64), 7.447 (3.87), 7.463 (1.29), 7.662 (2.75), 7.688 (2.69), 9.843 (6.16).

Example 213

5-fluoro-N-(2-fluoro-6-methylphenyl)-4-(3-oxo[1,2,4]triazolo[4,3-a]pyridin-2(3H)-yl)-2-{[(2S)-1,1,1-trifluoropropan-2-yl]oxy}benzamide

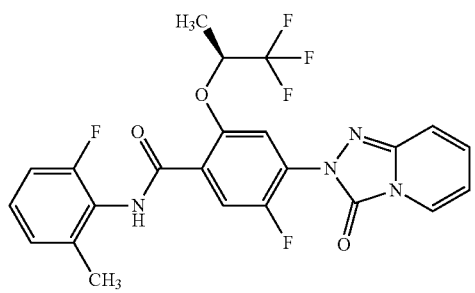 [SMILES: Cc1cccc(F)c1NC(=O)c1cc(F)c(-n2nc3ccccn3c2=O)cc1O[C@@H](C)C(F)(F)F]

From Intermediate 25 and 2-fluoro-6-methylaniline.

MS (ESIpos): m/z=493 (M+H)⁺

¹H NMR (400 MHz, CHLOROFORM-d) δ [ppm] 8.87 (s, 1H), 8.22 (d, 1H), 7.83 (dt, 1H), 7.49 (d, 1H), 7.25-7.13 (m, 3H), 7.12-6.95 (m, 2H), 6.59 (ddd, 1H), 4.95 (p, 1H), 2.32 (s, 3H), 1.67 (d, 3H).

Example 214

5-fluoro-N-(2-fluorophenyl)-4-(3-oxo[1,2,4]triazolo[4,3-a]pyridin-2(3H)-yl)-2-{[(2S)-1,1,1-trifluoropropan-2-yl]oxy}benzamide

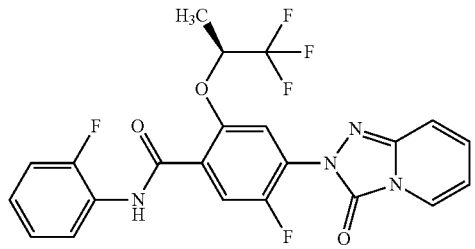 [SMILES: C[C@H](Oc1cc(-n2nc3ccccn3c2=O)c(F)cc1C(=O)Nc1ccccc1F)C(F)(F)F]

From Intermediate 25 and 2-fluoroaniline.

MS (ESIpos): m/z=479 (M+H)⁺

¹H NMR (400 MHz, CHLOROFORM-d) δ [ppm] 9.78 (s, 1H), 8.55 (t, 1H), 8.24 (d, 1H), 7.83 (dd, 1H), 7.51 (d, 1H), 7.25-7.13 (m, 6H), 7.13-7.06 (m, 2H), 6.59 (ddd, 1H), 4.95 (p, 1H), 1.68 (d, 3H).

Example 215

N-(2,6-difluorophenyl)-5-fluoro-4-(3-oxo-5,6-dihydro-3H-[1,2,4]triazolo[3,4-c][1,4]oxazin-2(8H)-yl)-2-[(2S)-pentan-2-yloxy]benzamide

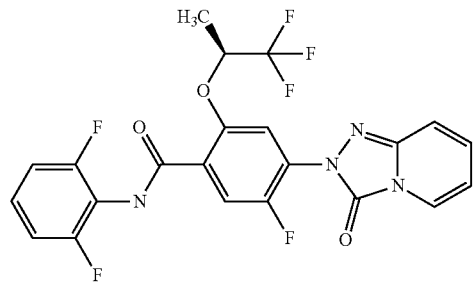 [SMILES: C[C@H](Oc1cc(-n2nc3ccccn3c2=O)c(F)cc1C(=O)Nc1c(F)cccc1F)C(F)(F)F]

From Intermediate 25 and 2,6-difluoroaniline.

MS (ESIpos): m/z=497 (M+H)⁺

¹H NMR (400 MHz, CHLOROFORM-d) δ [ppm] 8.97 (s, 1H), 8.23 (d, 1H), 7.83 (dd, 1H), 7.51 (d, 1H), 7.23 (d, 22H), 7.01 (t, 2H), 6.59 (ddd, 1H), 4.94 (p, 1H), 1.66 (d, 3H).

Example 216

5-fluoro-4-(3-oxo[1,2,4]triazolo[4,3-a]pyridin-2(3H)-yl)-2-[(2S)-pentan-2-yloxy]-N-[3-(trifluoromethyl)phenyl]benzamide

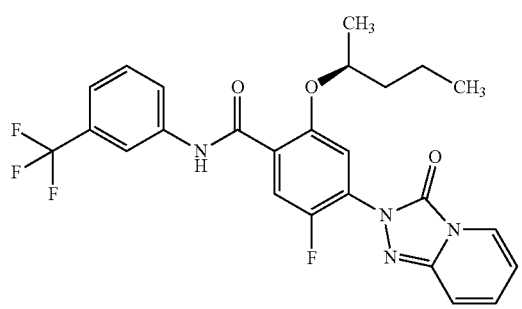 [SMILES: CCC[C@H](C)Oc1cc(-n2nc3ccccn3c2=O)c(F)cc1C(=O)Nc1cccc(C(F)(F)F)c1]

From Intermediate 26 and 3-(trifluoromethyl)aniline.

MS (ESIpos): m/z=503 (M+H)⁺

¹H NMR (300 MHz, CDCl₃) δ [ppm] 1.00 (t, 3H), 1.42-1.67 (m, 2H) 1.49 (d, 3H), 1.72-1.86 (m, 1H), 1.87-2.00 (m, 1H), 4.63-4.76 (m, 1H), 6.57 (dd, 1H), 7.17-7.22 (m, 2H), 7.36-7.45 (m, 2H), 7.50 (t, 1H), 7.80-7.89 (m, 2H), 7.94 (s, 1H), 8.22 (d, 1H), 10.34 (s, 1H).

Example 217

5-fluoro-N-(2-fluoro-6-methylphenyl)-4-(3-oxo[1,2,4]triazolo[4,3-a]pyridin-2(3H)-yl)-2-[(2S)-pentan-2-yloxy]benzamide

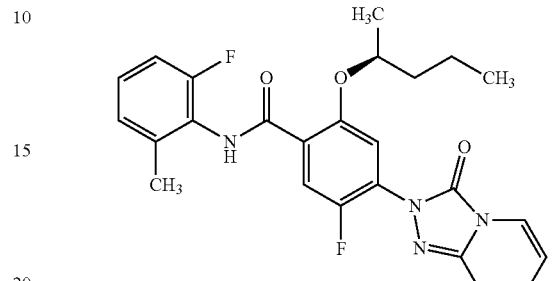

From Intermediate 26 and 2-fluoro-6-methylaniline.

MS (ESIpos): m/z=467 (M+H)⁺

¹H NMR (300 MHz, CDCl₃) δ [ppm] 0.95 (t, 3H), 1.36-1.58 (m, 2H) 1.45 (d, 3H), 1.63-1.78 (m, 1H), 1.80-1.94 (m, 1H), 2.33 (s, 3H), 4.62-4.73 (m, 1H), 6.53-6.60 (m, 1H), 7.01 (t, 1H), 7.07 (d, 1H), 7.13-7.24 (m, 3H), 7.43 (d, 1H), 7.84 (td, 1H), 8.20 (d, 1H), 9.56 (s, 1H).

Example 218

5-fluoro-N-(2-fluorophenyl)-4-(3-oxo[1,2,4]triazolo[4,3-a]pyridin-2(3H)-yl)-2-[(2S)-pentan-2-yloxy]benzamide

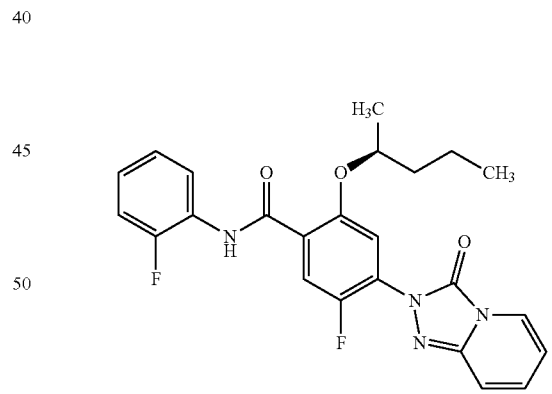

From Intermediate 26 and 2-fluoroaniline.

MS (ESIpos): m/z=453 (M+H)⁺

¹H NMR (300 MHz, CDCl₃) δ [ppm] 0.96 (t, 3H), 1.35-1.60 (m, 2H) 1.47 (d, 3H), 1.66-1.79 (m, 1H), 1.88-2.03 (m, 1H), 4.62-4.75 (m, 1H), 6.57 (dd, 1H), 7.03-7.23 (m, 5H), 7.42 (d, 1H), 7.84 (td, 1H), 8.24 (d, 1H), 8.63 (dt, 1H), 10.48 (s, 1H).

Example 219

5-fluoro-N-(2-methylphenyl)-4-(3-oxo[1,2,4]triazolo[4,3-a]pyridin-2(3H)-yl)-2-[(2S)-pentan-2-yloxy]benzamide

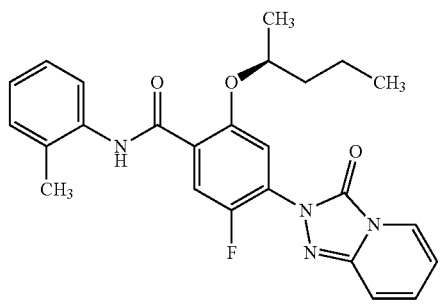 [SMILES: CCC[C@H](C)Oc1cc(-n2nc3ccccn3c2=O)c(F)cc1C(=O)Nc1ccccc1C]

From Intermediate 26 and o-toluidine.

MS (ESIpos): m/z=449 (M+H)$^+$ $^1$H NMR (300 MHz, CDCl$_3$) δ [ppm] 0.95 (t, 3H), 1.37-1.57 (m, 2H) 1.45 (d, 3H), 1.62-1.76 (m, 1H), 1.80-1.95 (m, 1H), 2.36 (s, 3H), 4.61-4.73 (m, 1H), 6.54-6.60 (m, 1H), 7.12 (dt, 1H), 7.18-7.21 (m, 2H), 7.22-7.31 (m, 2H), 7.43 (d, 1H), 7.84 (td, 1H), 8.02 (d, 1H), 8.24 (d, 1H), 9.65 (s, 1H).

Example 220

N-(2,6-difluorophenyl)-5-fluoro-4-(3-oxo[1,2,4]triazolo[4,3-a]pyridin-2(3H)-yl)-2-[(2S)-pentan-2-yloxy]benzamide

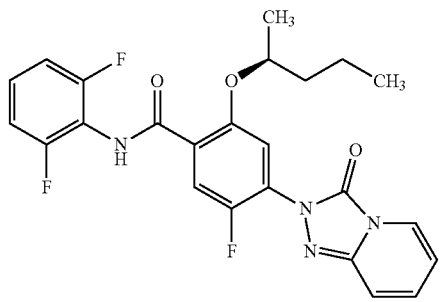 [SMILES: CCC[C@H](C)Oc1cc(-n2nc3ccccn3c2=O)c(F)cc1C(=O)Nc1c(F)cccc1F]

From Intermediate 26 and 2,6-difluoroaniline.

MS (ESIpos): m/z=471 (M+H)$^+$ $^1$H NMR (300 MHz, CDCl$_3$) δ [ppm] 0.96 (t, 3H), 1.37-1.57 (m, 2H) 1.46 (d, 3H), 1.64-1.79 (m, 1H), 1.81-1.96 (m, 1H), 4.61-4.74 (m, 1H), 6.53-6.60 (m, 1H), 6.96-7.06 (m, 2H), 7.15-7.29 (m, 3H), 7.43 (d, 1H), 7.83 (td, 1H), 8.21 (d, 1H), 9.68 (s, 1H).

Example 221

5-fluoro-N-(2-fluoro-6-methylphenyl)-4-(3-oxo[1,2,4]triazolo[4,3-a]pyridin-2(3H)-yl)-2-[(1S)-1-phenylethoxy]benzamide

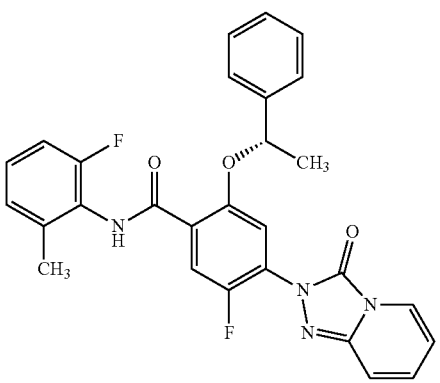 [SMILES: Cc1cccc(F)c1NC(=O)c1cc(F)c(-n2nc3ccccn3c2=O)cc1O[C@@H](C)c1ccccc1]

From Intermediate 27 and 2-fluoro-6-methylaniline.

MS (ESIpos): m/z=501 (M+H)$^+$ $^1$H NMR (300 MHz, CDCl$_3$) δ [ppm] 1.81 (d, 3H), 2.32 (s, 3H), 5.62 (q, 1H), 6.54 (dd, 1H), 6.98-7.10 (m, 2H), 7.13-7.45 (m, 9H), 7.80 (td, 1H), 8.18 (d, 1H), 9.62 (s, 1H).

Example 222

N-(2,6-difluorophenyl)-5-fluoro-4-(3-oxo[1,2,4]triazolo[4,3-a]pyridin-2(3H)-yl)-2-[(1S)-1-phenylethoxy]benzamide

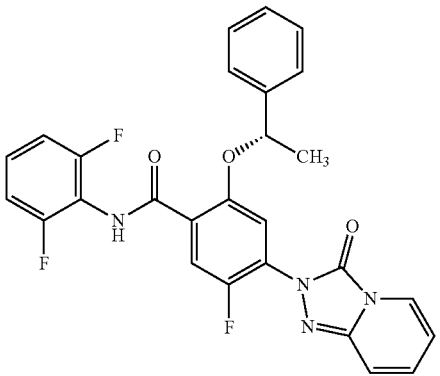 [SMILES: C[C@H](Oc1cc(-n2nc3ccccn3c2=O)c(F)cc1C(=O)Nc1c(F)cccc1F)c1ccccc1]

From Intermediate 27 and 2,6-difluoroaniline.

MS (ESIpos): m/z=505 (M+H)$^+$ $^1$H NMR (300 MHz, CDCl$_3$) δ [ppm] 1.82 (d, 3H), 5.62 (q, 1H), 6.54 (dd, 1H), 6.98-7.07 (m, 2H), 7.13-7.18 (m, 2H), 7.19-7.45 (m, 7H), 7.79 (td, 1H), 8.18 (d, 1H), 9.74 (s, 1H).

Example 223

5-fluoro-N-(2-fluorophenyl)-4-(3-oxo[1,2,4]triazolo[4,3-a]pyridin-2(3H)-yl)-2-[(1S)-1-phenylethoxy]benzamide

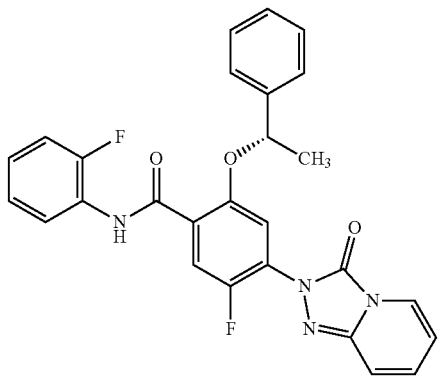 [SMILES: C[C@H](Oc1cc(-n2nc3ccccn3c2=O)c(F)cc1C(=O)Nc1ccccc1F)c1ccccc1]

From Intermediate 27 and 2-fluoroaniline.
MS (ESIpos): m/z=487 (M+H)+
$^1$H NMR (300 MHz, CDCl$_3$) δ [ppm] 1.86 (d, 3H), 5.62 (q, 1H), 6.53 (dd, 1H), 7.05-7.44 (m, 11H), 7.79 (td, 1H), 8.20 (d, 1H), 8.65 (dt, 1H), 10.55 (s, 1H).

Example 224

5-fluoro-N-(2-methylphenyl)-4-(3-oxo-5,6,7,8-tetrahydro[1,2,4]triazolo[4,3-a]pyridin-2(3H)-yl)-2-[(1S)-1-phenylethoxy]benzamide

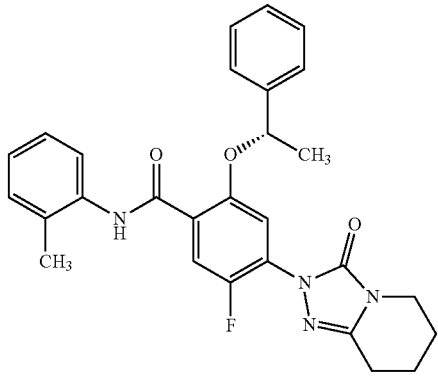 [SMILES: Cc1ccccc1NC(=O)c1cc(F)c(-n2nc3n(c2=O)CCCC3)cc1O[C@@H](C)c1ccccc1]

From Intermediate 28 and o-toluidine.
MS (ESIpos): m/z=487 (M+H)+
$^1$H NMR (300 MHz, CDCl$_3$) δ [ppm] 1.78 (d, 3H), 1.84-2.02 (m, 4H), 2.20 (s, 3H), 2.77 (t, 2H), 3.69 (t, 2H), 5.62 (q, 1H), 7.07-7.14 (m, 1H), 7.17-7.22 (m, 1H), 7.23-7.41 (m, 7H), 8.02 (d, 1H), 8.15 (d, 1H), 9.66 (s, 1H).

Example 225

5-fluoro-4-(3-oxo-5,6,7,8-tetrahydro[1,2,4]triazolo[4,3-a]pyridin-2(3H)-yl)-2-[(1S)-1-phenylethoxy]-N-[3-(trifluoromethyl)phenyl]benzamide

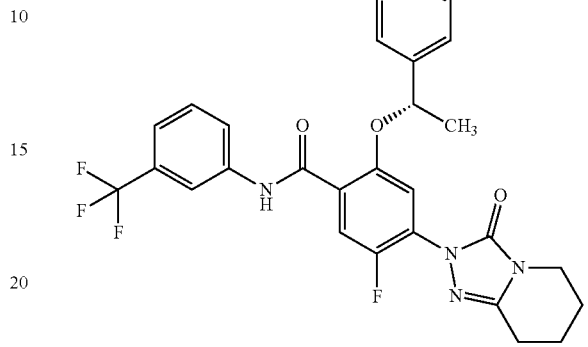

From Intermediate 28 and 3-(trifluoromethyl)aniline.
MS (ESIpos): m/z=541 (M+H)+
$^1$H NMR (300 MHz, CDCl$_3$) δ [ppm] 1.86 (d, 3H), 1.88-2.04 (m, 4H), 2.79 (t, 2H), 3.70 (t, 2H), 5.61 (q, 1H), 7.32-7.49 (m, 8H), 7.67 (s, 1H), 7.77 (d, 1H), 8.13 (d, 1H), 10.2 (s, 1H).

Example 226

5-fluoro-N-(2-methylphenyl)-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

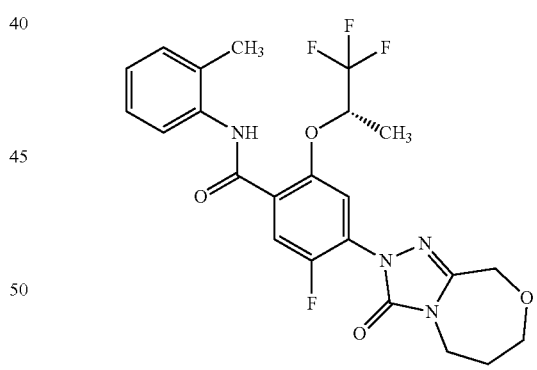

From Intermediate 29 and o-toluidine.
LC-MS (method A): R$_t$=1.24 min; MS (ESIpos): m/z=495 [M+H]+
$^1$H-NMR (400 MHz, CHLOROFORM-d) δ [ppm]: 1.627 (6.76), 1.643 (6.70), 2.015 (1.54), 2.021 (0.72), 2.034 (1.36), 2.047 (1.95), 2.059 (1.37), 2.072 (0.70), 2.320 (16.00), 4.005 (2.37), 4.017 (1.90), 4.019 (1.90), 4.031 (2.29), 4.064 (2.68), 4.076 (2.49), 4.089 (2.54), 4.613 (13.95), 4.868 (0.48), 4.884 (1.09), 4.899 (1.43), 4.914 (1.03), 4.930 (0.42), 7.125 (0.70), 7.128 (0.76), 7.147 (1.88), 7.162 (1.38), 7.166 (1.35), 7.242 (2.22), 7.249 (1.37), 7.261 (1.53), 7.287 (0.76), 7.402 (2.86), 7.416 (2.87), 7.885 (2.00), 7.905 (1.72), 8.149 (3.58), 8.177 (3.55), 9.022 (1.83).

Example 227

5-fluoro-N-(2-fluoro-6-methylphenyl)-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

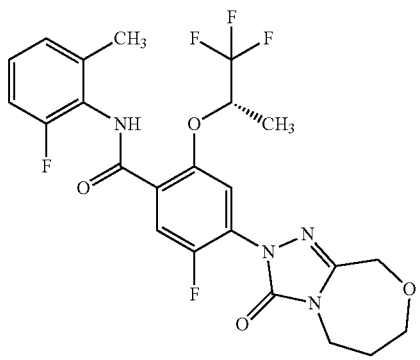 [SMILES: Cc1cccc(F)c1NC(=O)c1cc(F)c(-n2nc3n(c2=O)CCCOC3)cc1O[C@@H](C)C(F)(F)F]

From Intermediate 29 and 2-fluoro-6-methylaniline.
LC-MS (method A): $R_t$=1.22 min; MS (ESIpos): m/z=513 [M+H]$^+$
$^1$H-NMR (400 MHz, CHLOROFORM-d) δ [ppm]: 1.649 (6.36), 1.665 (6.38), 2.015 (0.99), 2.020 (0.65), 2.033 (1.26), 2.046 (1.85), 2.059 (1.31), 2.072 (0.67), 2.314 (16.00), 2.628 (0.56), 4.004 (2.24), 4.016 (1.83), 4.031 (2.21), 4.064 (2.56), 4.076 (2.37), 4.088 (2.50), 4.615 (13.93), 4.898 (0.43), 4.913 (1.00), 4.929 (1.31), 4.945 (0.96), 6.991 (0.76), 7.012 (1.53), 7.035 (0.95), 7.063 (1.34), 7.082 (1.82), 7.171 (0.99), 7.185 (1.05), 7.191 (1.44), 7.205 (1.39), 7.211 (0.72), 7.224 (0.64), 7.404 (2.82), 7.417 (2.84), 8.155 (3.59), 8.183 (3.51), 8.864 (2.01).

Example 228

N-(2-chloro-6-fluorophenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

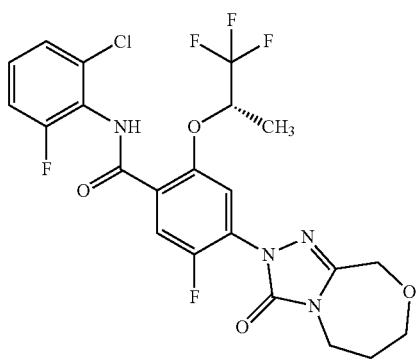 [SMILES: C[C@H](Oc1cc(-n2nc3n(c2=O)CCCOC3)c(F)cc1C(=O)Nc1c(F)cccc1Cl)C(F)(F)F]

From Intermediate 29 and 2-chloro-6-fluoroaniline.
LC-MS (method A): $R_t$=1.23 min; MS (ESIpos): m/z=533 [M+H]$^+$
$^1$H-NMR (400 MHz, CHLOROFORM-d) δ [ppm]: 1.660 (8.08), 1.676 (8.12), 2.025 (0.84), 2.038 (1.70), 2.050 (2.45), 2.063 (1.75), 2.076 (0.88), 4.008 (2.75), 4.020 (2.31), 4.023 (2.31), 4.034 (2.71), 4.067 (3.17), 4.079 (3.09), 4.092 (3.03), 4.619 (16.00), 4.912 (0.54), 4.927 (1.25), 4.943 (1.62), 4.958 (1.20), 4.974 (0.49), 7.112 (0.98), 7.115 (1.06), 7.132 (1.69), 7.135 (2.25), 7.138 (1.30), 7.155 (1.38), 7.159 (1.40), 7.221 (0.95), 7.234 (0.93), 7.241 (2.15), 7.254 (2.22), 7.262 (1.93), 7.285 (2.42), 7.288 (3.20), 7.307 (1.27), 7.311 (1.05), 7.427 (3.39), 7.441 (3.36), 8.179 (3.32), 8.208 (3.34), 9.022 (2.47).

Example 229

N-[2-(difluoromethyl)phenyl]-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

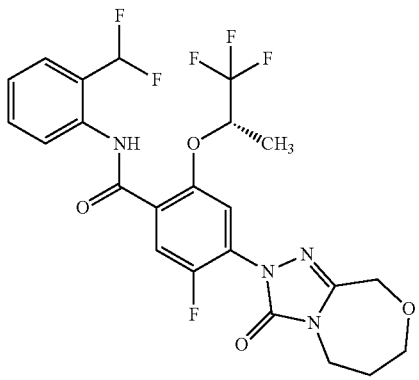 [SMILES: C[C@H](Oc1cc(-n2nc3n(c2=O)CCCOC3)c(F)cc1C(=O)Nc1ccccc1C(F)F)C(F)(F)F]

From Intermediate 29 and 2-(difluoromethyl)aniline.
LC-MS (method A): $R_t$=1.23 min; MS (ESIpos): m/z=531 [M+H]$^+$
$^1$H-NMR (400 MHz, CHLOROFORM-d) δ [ppm]: 1.633 (8.00), 1.650 (7.36), 2.018 (0.79), 2.031 (1.59), 2.044 (2.31), 2.056 (1.65), 2.069 (0.84), 4.001 (2.65), 4.014 (2.20), 4.016 (2.20), 4.028 (2.61), 4.061 (3.03), 4.073 (2.91), 4.086 (2.92), 4.611 (16.00), 4.855 (0.48), 4.870 (1.14), 4.886 (1.47), 4.901 (1.11), 4.916 (0.46), 6.612 (1.68), 6.751 (3.35), 6.889 (1.63), 7.306 (0.93), 7.324 (2.10), 7.343 (1.29), 7.420 (3.07), 7.434 (3.04), 7.529 (1.00), 7.549 (4.40), 7.568 (3.14), 7.931 (1.94), 7.951 (1.76), 8.108 (3.60), 8.136 (3.50), 9.380 (2.06).

Example 230

5-fluoro-N-(2-methoxy-4-methylpyridin-3-yl)-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

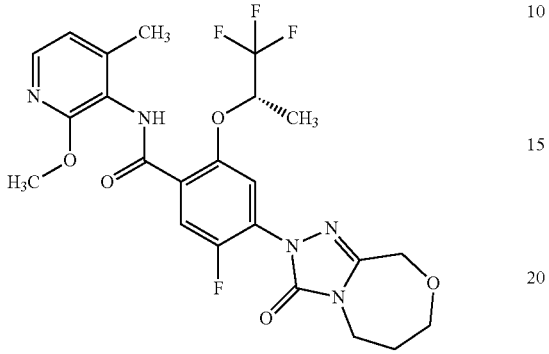

From Intermediate 29 and 2-methoxy-4-methylpyridin-3-amine.

LC-MS (method A): $R_t$=1.09 min; MS (ESIneg): m/z=524 [M−H]⁻

¹H-NMR (400 MHz, CHLOROFORM-d) δ [ppm]: 1.583 (0.47), 1.632 (0.48), 1.660 (4.31), 1.676 (4.25), 2.017 (1.16), 2.023 (0.46), 2.037 (0.87), 2.049 (1.24), 2.061 (0.88), 2.074 (0.44), 2.126 (0.87), 2.277 (11.34), 2.629 (0.52), 3.960 (16.00), 3.977 (1.50), 4.007 (1.42), 4.019 (1.20), 4.033 (1.43), 4.065 (1.65), 4.078 (1.59), 4.091 (1.52), 4.617 (8.14), 4.915 (0.65), 4.931 (0.84), 4.946 (0.62), 6.827 (1.72), 6.840 (1.73), 7.393 (1.74), 7.407 (1.72), 7.957 (2.23), 7.970 (2.10), 8.136 (2.13), 8.164 (2.07), 8.963 (1.46).

Example 231

N-(2,6-dichlorophenyl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

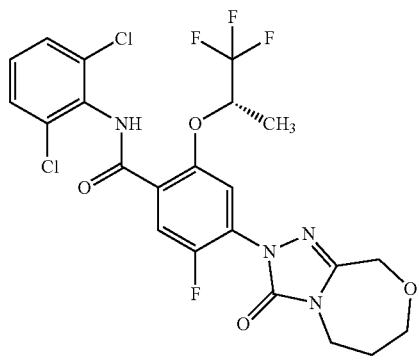

From Intermediate 29 and 2,6-dichloroaniline.

The product was purified by reverse phase column chromatography (0.1% aqueous formic acid, acetonitrile).

LC-MS (method A): $R_t$=1.26 min; MS (ESIpos): m/z=549 [M+H]⁺

¹H-NMR (400 MHz, CHLOROFORM-d) δ [ppm]: 1.661 (9.55), 1.677 (8.61), 2.017 (1.63), 2.023 (0.81), 2.037 (1.57), 2.049 (2.31), 2.061 (1.63), 2.074 (0.83), 4.007 (2.63), 4.019 (2.13), 4.021 (2.14), 4.033 (2.59), 4.065 (3.04), 4.078 (2.87), 4.090 (2.92), 4.617 (16.00), 4.926 (0.51), 4.941 (1.22), 4.957 (1.58), 4.972 (1.18), 4.988 (0.47), 7.211 (1.95), 7.231 (3.26), 7.251 (2.88), 7.419 (11.00), 7.439 (9.09), 8.179 (3.72), 8.207 (3.63), 9.072 (2.64).

Example 232

N-(2-chloro-4-fluoro-6-methylphenyl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

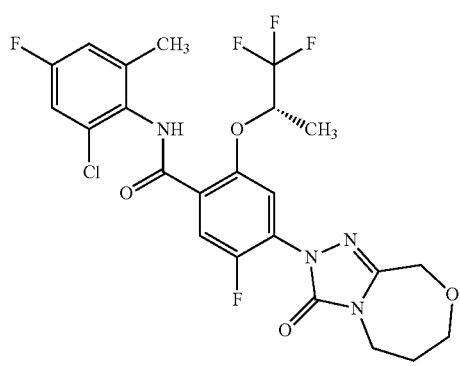 [SMILES: Cc1cc(F)cc(Cl)c1NC(=O)c1cc(F)c(-n2nc3n(c2=O)CCCOC3)cc1O[C@@H](C)C(F)(F)F]

From Intermediate 29 and 2-chloro-4-fluoro-6-methylaniline.

The product was purified by reverse phase column chromatography (0.1% aqueous formic acid, acetonitrile).

LC-MS (method A): $R_t$=1.29 min; MS (ESIneg): m/z=545 [M−H]⁻

¹H-NMR (400 MHz, CHLOROFORM-d) δ [ppm]: 1.656 (7.01), 1.672 (7.02), 2.011 (0.83), 2.017 (0.80), 2.031 (1.55), 2.043 (2.16), 2.055 (1.53), 2.068 (0.74), 2.306 (16.00), 4.001 (2.48), 4.015 (2.14), 4.027 (2.34), 4.060 (2.75), 4.073 (2.71), 4.085 (2.54), 4.598 (0.54), 4.603 (1.21), 4.611 (13.04), 4.922 (0.46), 4.938 (1.08), 4.953 (1.40), 4.969 (1.03), 4.984 (0.41), 6.932 (1.25), 6.939 (1.40), 6.955 (1.27), 6.962 (1.37), 7.070 (1.49), 7.077 (1.40), 7.090 (1.52), 7.097 (1.36), 7.402 (2.87), 7.416 (2.84), 8.143 (3.47), 8.171 (3.52), 8.875 (2.31).

Example 233

N-(2-chloro-6-methylphenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

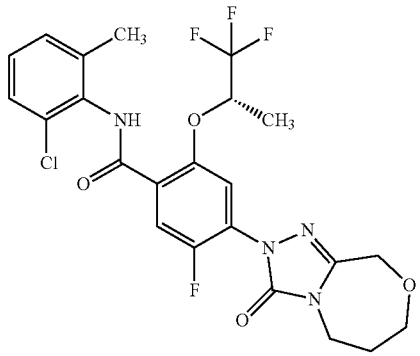 [SMILES: Cc1cccc(Cl)c1NC(=O)c1cc(F)c(-n2nc3n(c2=O)CCCOC3)cc1O[C@@H](C)C(F)(F)F]

From Intermediate 29 and 2-chloro-6-methylaniline.

The product was purified by reverse phase column chromatography (Chromatorex C18 10 µm, 0.1% aqueous formic acid, acetonitrile).

LC-MS (method A): $R_t$=1.26 min; MS (ESIpos): m/z=529 [M+H]$^+$ $^1$H-NMR (400 MHz, CHLOROFORM-d) δ [ppm]: 1.658 (6.92), 1.674 (6.94), 2.012 (1.83), 2.018 (0.73), 2.032 (1.41), 2.044 (2.05), 2.056 (1.48), 2.070 (0.74), 2.318 (16.00), 4.003 (2.29), 4.015 (1.98), 4.029 (2.29), 4.062 (2.51), 4.074 (2.61), 4.086 (2.46), 4.613 (11.95), 4.924 (0.43), 4.940 (1.05), 4.955 (1.36), 4.970 (1.01), 4.985 (0.41), 7.158 (0.79), 7.177 (2.68), 7.196 (3.65), 7.204 (2.74), 7.219 (0.82), 7.316 (1.70), 7.321 (1.71), 7.335 (1.28), 7.339 (1.28), 7.402 (2.72), 7.416 (2.71), 8.163 (3.23), 8.191 (3.18), 8.977 (2.28).

Example 234

N-(2-chloro-4,6-difluorophenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

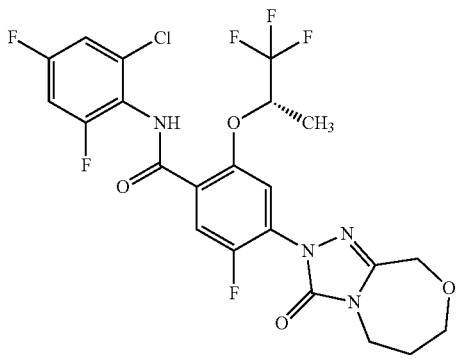 [SMILES: C[C@H](Oc1cc(-n2nc3n(c2=O)CCCOC3)c(F)cc1C(=O)Nc1c(F)cc(F)cc1Cl)C(F)(F)F]

From Intermediate 29 and 2-chloro-4,6-difluoroaniline.

The product was purified by reverse phase column chromatography (0.1% aqueous formic acid, acetonitrile).

LC-MS (method A): $R_t$=1.26 min; MS (ESIpos): m/z=551 [M+H]$^+$ $^1$H-NMR (400 MHz, CHLOROFORM-d) δ [ppm]: 1.622 (1.96), 1.652 (9.37), 1.667 (9.40), 2.019 (0.97), 2.033 (2.05), 2.044 (2.93), 2.056 (2.15), 2.070 (1.03), 4.002 (3.18), 4.015 (2.87), 4.028 (3.20), 4.062 (3.46), 4.074 (3.77), 4.087 (3.38), 4.613 (16.00), 4.911 (0.59), 4.927 (1.40), 4.942 (1.82), 4.957 (1.36), 4.972 (0.56), 6.889 (1.05), 6.896 (1.17), 6.912 (1.61), 6.917 (1.75), 6.933 (1.09), 6.940 (1.17), 7.067 (1.32), 7.073 (1.86), 7.079 (1.40), 7.088 (1.40), 7.093 (1.88), 7.098 (1.32), 7.424 (3.60), 7.438 (3.60), 8.153 (3.80), 8.181 (3.78), 8.916 (3.39).

Example 235

5-fluoro-N-[2-methyl-6-(trifluoromethyl)phenyl]-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

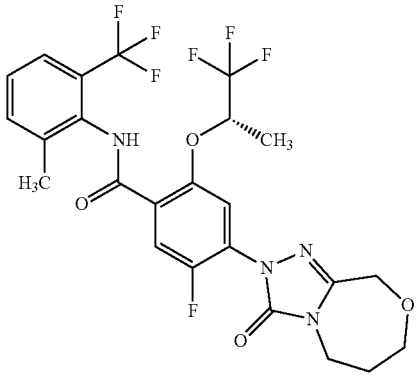 [SMILES: Cc1cccc(C(F)(F)F)c1NC(=O)c1cc(F)c(-n2nc3n(c2=O)CCCOC3)cc1O[C@@H](C)C(F)(F)F]

From Intermediate 29 and 2-methyl-6-(trifluoromethyl)aniline.

The product was purified by reverse phase column chromatography (0.1% aqueous formic acid, acetonitrile).

LC-MS (method A): $R_t$=1.30 min; MS (ESIpos): m/z=563 [M+H]$^+$ $^1$H-NMR (400 MHz, CHLOROFORM-d) δ [ppm]: 1.533 (0.71), 1.549 (0.75), 1.604 (3.81), 1.640 (3.52), 1.655 (3.37), 2.023 (0.94), 2.037 (1.88), 2.048 (2.56), 2.060 (1.80), 2.073 (0.83), 2.326 (16.00), 4.007 (2.87), 4.020 (2.59), 4.033 (2.62), 4.065 (3.08), 4.077 (3.23), 4.089 (2.78), 4.608 (1.67), 4.616 (12.95), 4.922 (0.49), 4.937 (1.16), 4.953 (1.50), 4.968 (1.11), 4.983 (0.45), 7.338 (1.02), 7.357 (2.33), 7.377 (1.48), 7.399 (3.00), 7.412 (2.98), 7.511 (2.17), 7.530 (1.74), 7.554 (2.16), 7.573 (1.77), 8.163 (1.12), 8.191 (1.10).

Example 236

N-(2,6-dichloro-4-fluorophenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

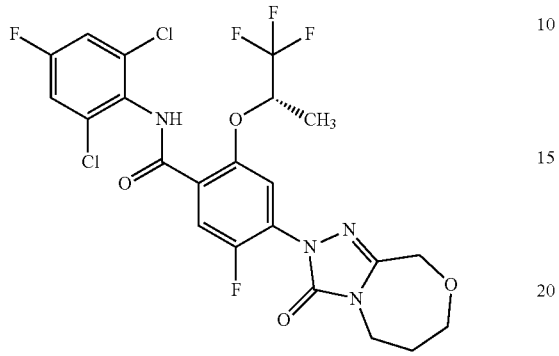

From Intermediate 29 and 2,6-dichloro-4-fluoroaniline.
The product was purified by reverse phase column chromatography (0.1% aqueous formic acid, acetonitrile).
LC-MS (method A): $R_t$=1.29 min; MS (ESIpos): m/z=567 [M+H]$^+$
$^1$H-NMR (400 MHz, CHLOROFORM-d) δ [ppm]: 1.532 (0.51), 1.548 (0.52), 1.605 (2.70), 1.657 (7.33), 1.674 (7.43), 2.016 (0.51), 2.022 (0.80), 2.035 (1.57), 2.048 (2.22), 2.060 (1.57), 2.073 (0.80), 4.005 (2.58), 4.017 (2.09), 4.019 (2.14), 4.031 (2.46), 4.064 (3.01), 4.077 (2.76), 4.089 (2.78), 4.608 (1.52), 4.615 (16.00), 4.925 (0.49), 4.940 (1.15), 4.956 (1.50), 4.971 (1.12), 4.986 (0.45), 7.198 (10.53), 7.218 (10.12), 7.423 (3.20), 7.437 (3.20), 8.159 (4.00), 8.188 (4.08), 8.972 (2.62).

Example 237

5-fluoro-N-(4-fluoro-2,6-dimethylphenyl)-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

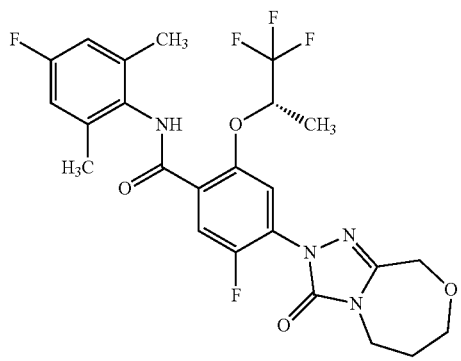

From Intermediate 29 and 4-fluoro-2,6-dimethylaniline.
The product was purified by reverse phase column chromatography (0.1% aqueous formic acid, acetonitrile).
LC-MS (method A): $R_t$=1.26 min; MS (ESIpos): m/z=527 [M+H]$^+$ $^1$H-NMR (400 MHz, CHLOROFORM-d) δ [ppm]: 1.603 (3.10), 1.650 (3.46), 1.666 (3.46), 2.037 (0.73), 2.049 (1.05), 2.061 (0.75), 2.253 (16.00), 4.007 (1.19), 4.022 (1.01), 4.034 (1.17), 4.067 (1.33), 4.079 (1.32), 4.091 (1.27), 4.617 (6.53), 4.934 (0.55), 4.950 (0.70), 4.965 (0.53), 6.832 (2.23), 6.854 (2.22), 7.381 (1.44), 7.395 (1.43), 8.150 (1.79), 8.179 (1.77), 8.635 (1.05).

Example 238

N-(4-chloro-2-methylpyridin-3-yl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

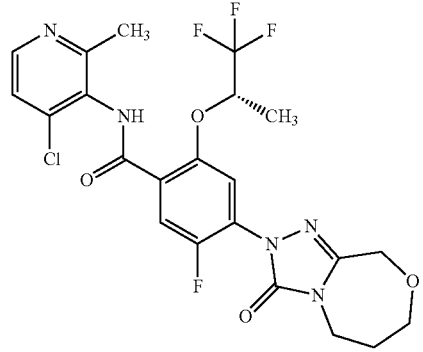

From Intermediate 29 and 4-chloro-2-methylpyridin-3-amine.
The product was purified by reverse phase column chromatography (Chromatorex C18 10 μm, 0.1% aqueous formic acid, acetonitrile).
LC-MS (method A): $R_t$=1.03 min; MS (ESIpos): m/z=530 [M+H]$^+$ $^1$H-NMR (400 MHz, CHLOROFORM-d) δ [ppm]: 1.682 (7.70), 1.698 (7.71), 2.019 (0.85), 2.030 (0.99), 2.044 (1.84), 2.055 (2.55), 2.067 (1.84), 2.081 (0.94), 2.500 (0.40), 2.665 (8.57), 4.013 (2.72), 4.026 (2.35), 4.039 (2.65), 4.072 (3.15), 4.084 (3.11), 4.097 (2.97), 4.623 (16.00), 4.953 (0.47), 4.968 (1.09), 4.984 (1.40), 4.999 (1.04), 5.014 (0.42), 7.454 (4.21), 7.468 (3.35), 7.529 (0.41), 8.167 (4.09), 8.195 (4.12), 8.411 (1.92), 8.425 (1.88), 9.122 (2.05).

Example 239

N-(2-chloro-4-methylpyridin-3-yl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

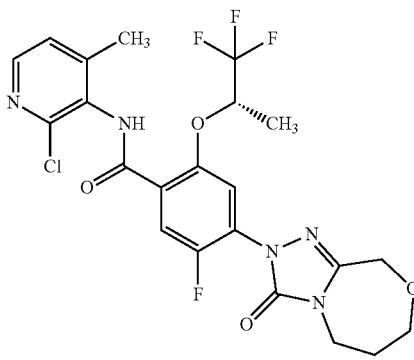 [SMILES: Cc1ccnc(Cl)c1NC(=O)c1cc(F)c(-n2nc3n(c2=O)CCCOC3)cc1O[C@@H](C)C(F)(F)F]

From Intermediate 29 and 2-chloro-4-methylpyridin-3-amine.

The product was purified by reverse phase column chromatography (0.1% aqueous formic acid, acetonitrile).

LC-MS (method A): $R_t$=1.08 min; MS (ESIneg): m/z=528 [M−H]⁻

¹H-NMR (400 MHz, CHLOROFORM-d) δ [ppm]: 1.613 (0.48), 1.629 (0.53), 1.684 (5.61), 1.700 (5.68), 2.016 (1.37), 2.052 (1.84), 2.349 (16.00), 4.010 (1.87), 4.023 (1.83), 4.036 (1.91), 4.068 (2.32), 4.081 (2.47), 4.093 (2.31), 4.620 (11.21), 4.959 (0.75), 4.974 (0.98), 4.990 (0.74), 7.196 (1.58), 7.207 (1.65), 7.433 (2.10), 7.447 (2.13), 8.157 (3.76), 8.184 (3.78), 8.215 (1.40), 8.227 (1.41), 9.123 (2.16).

Example 240

N-(2-chloro-4,6-dimethylpyridin-3-yl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

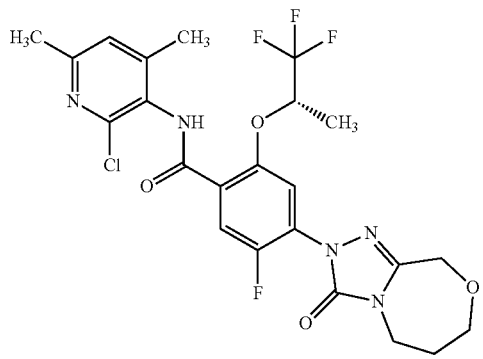 [SMILES: Cc1cc(C)c(NC(=O)c2cc(F)c(-n3nc4n(c3=O)CCCOC4)cc2O[C@@H](C)C(F)(F)F)c(Cl)n1]

From Intermediate 29 and 2-chloro-4,6-dimethylpyridin-3-amine.

The product was purified by reverse phase column chromatography (0.1% aqueous formic acid, acetonitrile).

LC-MS (method A): $R_t$=1.14 min; MS (ESIneg): m/z=542 [M−H]⁻

¹H-NMR (400 MHz, CHLOROFORM-d) δ [ppm]: 1.670 (8.31), 1.686 (8.36), 2.011 (2.57), 2.043 (3.09), 2.054 (2.31), 2.299 (15.28), 2.531 (12.01), 4.001 (3.22), 4.014 (3.15), 4.027 (3.22), 4.060 (3.64), 4.073 (4.08), 4.085 (3.55), 4.611 (16.00), 4.932 (0.52), 4.946 (1.21), 4.962 (1.58), 4.977 (1.19), 4.992 (0.50), 7.060 (3.90), 7.418 (3.53), 7.432 (3.52), 8.040 (0.58), 8.142 (5.13), 8.170 (5.21), 9.026 (3.03).

Example 241

N-(2,4-dimethylpyridin-3-yl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

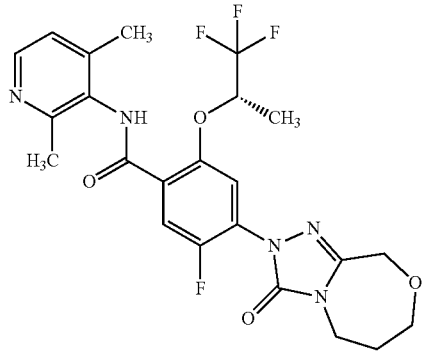 [SMILES: Cc1ccnc(C)c1NC(=O)c1cc(F)c(-n2nc3n(c2=O)CCCOC3)cc1O[C@@H](C)C(F)(F)F]

From Intermediate 29 and 2,4-dimethylpyridin-3-amine.

The product was purified by reverse phase column chromatography (0.1% aqueous formic acid, acetonitrile).

LC-MS (method A): $R_t$=0.80 min; MS (ESIpos): m/z=510 [M+H]⁺

¹H-NMR (400 MHz, CHLOROFORM-d) δ [ppm]: 1.641 (3.60), 1.670 (7.51), 1.686 (6.85), 2.030 (0.63), 2.044 (1.25), 2.056 (1.80), 2.068 (1.29), 2.081 (0.65), 2.284 (14.66), 2.517 (16.00), 2.628 (3.85), 4.014 (2.01), 4.026 (1.68), 4.041 (1.98), 4.072 (2.29), 4.084 (2.22), 4.098 (2.19), 4.623 (12.19), 4.954 (0.91), 4.969 (1.20), 4.984 (0.89), 7.006 (0.43), 7.091 (1.99), 7.103 (2.01), 7.411 (2.57), 7.425 (2.54), 7.529 (0.45), 8.128 (0.45), 8.171 (3.30), 8.198 (3.19), 8.340 (2.78), 8.353 (2.73), 8.828 (2.01).

Example 242

5-fluoro-N-(2-methoxy-6-methylphenyl)-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

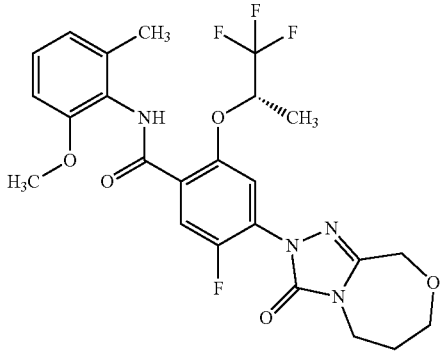

From Intermediate 29 and 2-methoxy-6-methylaniline.

The product was purified by reverse phase column chromatography (0.1% aqueous formic acid, acetonitrile).

LC-MS (method A): $R_t$=1.23 min; MS (ESIpos): m/z=525 $[M+H]^+$ $^1$H-NMR (400 MHz, CHLOROFORM-d) δ [ppm]: 1.636 (4.51), 1.652 (4.58), 2.008 (1.69), 2.012 (0.50), 2.026 (0.94), 2.038 (1.32), 2.049 (0.96), 2.062 (0.47), 2.282 (11.94), 3.817 (16.00), 3.996 (1.45), 4.010 (1.28), 4.022 (1.41), 4.056 (1.66), 4.069 (1.70), 4.081 (1.61), 4.607 (8.30), 4.903 (0.70), 4.919 (0.90), 4.934 (0.68), 6.791 (1.26), 6.811 (1.39), 6.885 (1.27), 6.904 (1.45), 7.162 (1.27), 7.183 (1.99), 7.202 (1.00), 7.373 (1.87), 7.387 (1.85), 8.144 (2.67), 8.172 (2.64), 8.875 (1.62).

Example 243

N-(6-chloro-2,3-difluorophenyl)-5-fluoro-4-(3-oxo-6,7-dihydro-3H,5H-[1,2,4]triazolo[3,4-c]-[1,4]oxazepin-2(9H)-yl)-2-{[(2S)-1,1,1-trifluoropropan-2-yl]oxy}benzamide

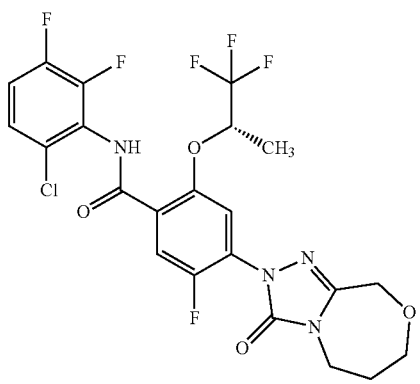 [SMILES: C[C@H](Oc1cc(-n2nc3n(c2=O)CCCOC3)c(F)cc1C(=O)Nc1c(Cl)ccc(F)c1F)C(F)(F)F]

From Intermediate 29 and 6-chloro-2,3-difluoroaniline.
The product was purified by reverse phase column chromatography (0.1% aqueous formic acid, acetonitrile).

LC-MS (method A): $R_t$=1.26 min; MS (ESIpos): m/z=551 $[M+H]^+$ $^1$H-NMR (400 MHz, CHLOROFORM-d) δ [ppm]: 1.636 (0.42), 1.664 (7.49), 1.680 (7.54), 2.018 (1.00), 2.025 (0.83), 2.038 (1.59), 2.050 (2.16), 2.062 (1.52), 2.076 (0.77), 4.008 (2.44), 4.022 (2.01), 4.034 (2.39), 4.067 (2.92), 4.079 (2.71), 4.092 (2.75), 4.619 (16.00), 4.926 (0.48), 4.941 (1.13), 4.957 (1.46), 4.972 (1.07), 4.988 (0.43), 7.088 (0.79), 7.107 (0.99), 7.110 (1.88), 7.130 (2.08), 7.134 (1.38), 7.153 (1.31), 7.216 (1.41), 7.222 (1.31), 7.228 (1.64), 7.234 (1.40), 7.239 (1.09), 7.245 (1.01), 7.251 (1.11), 7.256 (1.03), 7.442 (3.17), 7.456 (3.19), 8.177 (4.04), 8.205 (3.89), 9.081 (2.44).

Example 244

N-(2,6-difluorophenyl)-5-fluoro-4-(3-oxo-6,7-dihydro-5H-[1,2,4]triazolo[3,4-b][1,3]oxazin-2(3H)-yl)-2-{[(2S)-1,1,1-trifluoropropan-2-yl]oxy}benzamide

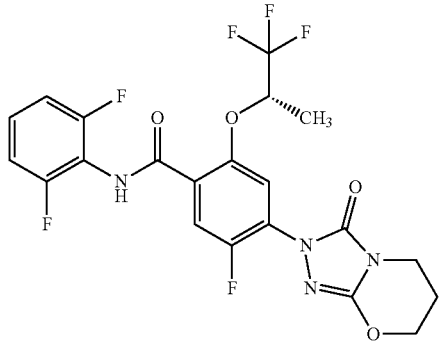 [SMILES: C[C@H](Oc1cc(-n2nc3n(c2=O)CCCO3)c(F)cc1C(=O)Nc1c(F)cccc1F)C(F)(F)F]

A solution of 4-bromo-N-(2,6-difluorophenyl)-5-fluoro-2-{[(2S)-1,1,1-trifluoropropan-2-yl]oxy}benzamide (intermediate 30) (100 mg, 226 μmol), 6,7-dihydro-5H-[1,2,4]triazolo[3,4-b][1,3]oxazin-3(2H)-one (CAS 133365-37-4) (47.9 mg, 339 μmol), tris(dibenzylideneacetone)dipalladium (O) (20.7 mg, 22.6 μmol), 4,5-bis(diphenylphosphino)9,9-dimethylxanthene (39.3 mg, 67.8 μmol), and cesium carbonate (147 mg, 452 μmol) in dimethyl sulfoxide was heated to 110° C. for seventeen hours. The mixture was filtered over celite, the filter cake was washed with ethyl acetate, and the combined filtrate was concentrated under reduced pressure. The residue was purified by by preparative HPLC (X-Bridge Prep C18 5 μm, 0.1% aqueous formic acid, acetonitrile) to yield the title compound as light yellow solid 54.0 mg (97% purity, 46% yield).

LC-MS (method A): $R_t$=1.14 min; MS (ESIpos): m/z=503 $[M+H]^+$ $^1$H-NMR (400 MHz, DMSO-d6) δ[ppm]: 1.137 (0.72), 1.232 (0.96), 1.427 (16.00), 1.442 (16.00), 2.084 (1.05), 2.123 (1.93), 2.137 (5.55), 2.150 (6.91), 2.164 (5.71), 2.178 (1.93), 2.322 (1.77), 2.326 (2.41), 2.331 (1.77), 2.453 (0.80), 2.522 (6.91), 2.664 (1.77), 2.668 (2.41), 2.673 (1.69), 3.288 (1.05), 3.292 (0.80), 3.673 (6.59), 3.688 (13.51), 3.703 (6.19), 4.442 (7.64), 4.456 (9.89), 4.468 (7.40), 5.260 (1.13), 5.276 (2.65), 5.292 (3.30), 5.309 (2.49), 5.324 (1.05), 5.758 (1.85), 7.188 (4.82), 7.208 (10.05), 7.228 (6.19), 7.368 (1.29), 7.385 (2.57), 7.405 (3.46), 7.426 (2.09), 7.442 (1.05), 7.492 (5.95), 7.507 (5.87), 7.544 (6.43), 7.568 (6.27), 9.950 (14.71).

Examples 245-257 were prepared in analogy to example 244 from the respective aryl bromides and the respective triazolone derivative, as indicated.

Example 245

N-(2,6-difluorophenyl)-5-fluoro-4-(8-methyl-3-oxo-5,6,7,8-tetrahydro[1,2,4]triazolo[4,3-a]-pyrimidin-2(3H)-yl)-2-{[(2S)-1,1,1-trifluoropropan-2-yl]oxy}benzamide

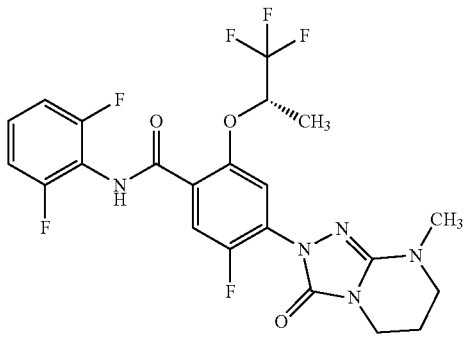 [SMILES: C[C@H](Oc1cc(-n2nc3n(c2=O)CCCN3C)c(F)cc1C(=O)Nc1c(F)cccc1F)C(F)(F)F]

From intermediate 30 and 8-methyl-5,6,7,8-tetrahydro[1,2,4]triazolo[4,3-a]pyrimidin-3(2H)-one (CAS 425706-28-1).

LC-MS (method A): $R_t$=1.17 min; MS (ESIpos): m/z=516 [M+H]$^+$ $^1$H-NMR (400 MHz, DMSO-d6) δ[ppm]: 1.432 (3.75), 1.447 (3.73), 2.019 (0.42), 2.033 (1.19), 2.047 (1.62), 2.061 (1.25), 2.076 (0.43), 2.084 (0.40), 2.518 (2.12), 2.522 (1.48), 2.754 (0.61), 2.876 (16.00), 3.221 (1.71), 3.235 (2.27), 3.249 (1.64), 3.564 (1.59), 3.579 (3.07), 3.594 (1.52), 5.261 (0.62), 5.277 (0.81), 5.293 (0.59), 7.189 (1.14), 7.209 (2.41), 7.230 (1.51), 7.385 (0.59), 7.405 (0.84), 7.422 (0.59), 7.426 (0.54), 7.499 (1.39), 7.517 (2.25), 7.543 (1.52), 9.895 (3.63).

Example 246

N-(2,6-difluorophenyl)-5-fluoro-4-(3-oxo-5,6-dihydro[1,3]thiazolo[2,3-c][1,2,4]triazol-2(3H)-yl)-2-{[(2S)-1,1,1-trifluoropropan-2-yl]oxy}benzamide

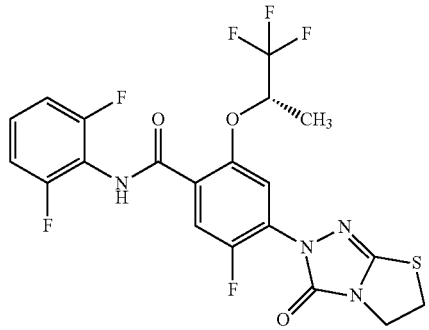 [SMILES: C[C@H](Oc1cc(-n2nc3n(c2=O)CCS3)c(F)cc1C(=O)Nc1c(F)cccc1F)C(F)(F)F]

From intermediate 30 and 5,6-dihydro[1,3]thiazolo[2,3-c][1,2,4]triazol-3(2H)-one (intermediate 38).

LC-MS (method A): $R_t$=1.19 min; MS (ESIpos): m/z=505 [M+H]$^+$ $^1$H-NMR (400 MHz, DMSO-d6) δ[ppm]: 1.137 (0.63), 1.382 (0.93), 1.398 (1.23), 1.427 (16.00), 1.443 (15.90), 1.525 (6.17), 2.084 (6.10), 2.331 (1.43), 2.518 (8.73), 2.522 (5.53), 2.539 (0.77), 2.673 (1.40), 3.452 (3.43), 3.936 (3.47), 3.941 (3.80), 3.956 (11.37), 3.973 (10.07), 4.018 (9.50), 4.035 (9.70), 4.050 (3.37), 4.055 (2.93), 5.274 (1.17), 5.290 (2.63), 5.305 (3.37), 5.321 (2.50), 5.337 (1.03), 5.748 (1.57), 5.758 (2.80), 7.188 (4.80), 7.209 (10.03), 7.229 (6.20), 7.348 (0.57), 7.369 (1.57), 7.386 (2.53), 7.406 (3.57), 7.427 (2.37), 7.443 (1.20), 7.554 (6.90), 7.560 (8.63), 7.568 (6.83), 7.585 (6.57), 9.979 (14.40).

Example 247

N-(2,6-difluorophenyl)-5-fluoro-4-(3-oxo-6,7-dihydro-3H,5H-[1,2,4]triazolo[3,4-c][1,4]oxazepin-2(9H)-yl)-2-{[(2S)-1,1,1-trifluoropropan-2-yl]oxy}benzamide

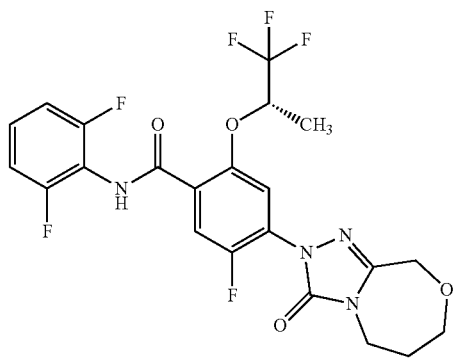 [SMILES: C[C@H](Oc1cc(-n2nc3n(c2=O)CCCOC3)c(F)cc1C(=O)Nc1c(F)cccc1F)C(F)(F)F]

From intermediate 30 and 2,6,7,9-tetrahydro-3H,5H-[1,2,4]triazolo[3,4-c][1,4]oxazepin-3-one (intermediate 37).

LC-MS (method A): $R_t$=1.17 min; MS (ESIpos): m/z=517 [M+H]$^+$ $^1$H-NMR (400 MHz, DMSO-d6) δ[ppm]: 1.137 (0.66), 1.430 (9.62), 1.446 (9.54), 1.882 (3.57), 2.084 (4.92), 2.518 (5.90), 2.522 (3.86), 2.673 (0.89), 3.922 (4.07), 3.934 (4.07), 3.947 (3.97), 3.969 (4.20), 3.981 (4.92), 3.993 (3.97), 4.606 (16.00), 5.293 (0.64), 5.308 (1.56), 5.324 (1.99), 5.340 (1.48), 5.355 (0.58), 5.758 (1.43), 7.190 (2.87), 7.211 (5.96), 7.231 (3.72), 7.371 (0.69), 7.387 (1.48), 7.408 (2.10), 7.424 (1.25), 7.445 (0.52), 7.579 (4.07), 7.603 (6.23), 7.616 (3.76), 10.000 (8.44).

Example 248

N-(2,6-difluorophenyl)-5-fluoro-4-(3-oxo-6,7,8,9-tetrahydro-3H-[1,2,4]triazolo[4,3-a]azepin-2(5H)-yl)-2-{[(2S)-1,1,1-trifluoropropan-2-yl]oxy}benzamide

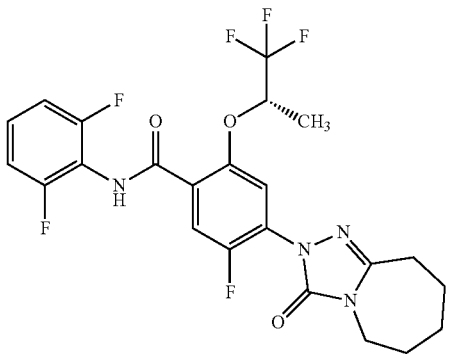 [SMILES: C[C@H](Oc1cc(-n2nc3n(c2=O)CCCCC3)c(F)cc1C(=O)Nc1c(F)cccc1F)C(F)(F)F]

From intermediate 30 and 2,5,6,7,8,9-hexahydro-3H-[1,2,4]triazolo[4,3-a]azepin-3-one (CAS 27182-43-0).

LC-MS (method A): $R_t$=1.27 min; MS (ESIpos): m/z=515 [M+H]$^+$ $^1$H-NMR (500 MHz, DMSO-d6) δ[ppm]: 1.236 (0.52), 1.432 (16.00), 1.445 (15.91), 1.646 (6.57), 1.691 (10.32), 1.811 (5.58), 2.084 (0.42), 2.358 (2.11), 2.361 (2.86), 2.365 (2.30), 2.518 (8.96), 2.522 (6.52), 2.539 (1.17), 2.631 (2.16), 2.635 (2.91), 2.638 (2.25), 2.756 (6.52), 2.768 (6.05), 2.778 (6.24), 3.362 (0.66), 3.776 (6.38), 5.301 (1.08), 5.314 (2.49), 5.326 (3.28), 5.339 (2.39), 5.351 (1.03), 5.759 (0.99), 7.156 (0.52), 7.171 (0.89), 7.194 (4.74), 7.211 (9.57), 7.227 (5.82), 7.353 (1.03), 7.371 (3.61), 7.384 (5.87), 7.392 (6.33), 7.407 (3.80), 7.424 (2.16), 7.437 (0.99), 7.470 (0.84), 7.479 (1.08), 7.487 (1.27), 7.497 (0.75), 7.562 (6.19), 7.574 (6.85), 7.581 (8.54), 7.859 (0.89), 7.875 (0.84), 9.978 (13.75), 10.210 (0.42).

Example 249

N-(2,6-difluorophenyl)-5-fluoro-4-(3-oxo[1,2,4]triazolo[4,3-a]pyrazin-2(3H)-yl)-2-{[(2S)-1,1,1-trifluoropropan-2-yl]oxy}benzamide

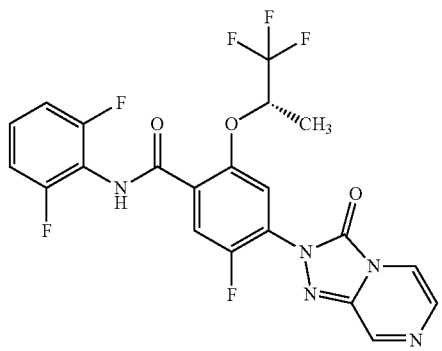 [SMILES: C[C@H](Oc1cc(-n2nc3cnccn3c2=O)c(F)cc1C(=O)Nc1c(F)cccc1F)C(F)(F)F]

From intermediate 30 and [1,2,4]triazolo[4,3-a]pyrazin-3(2H)-one (CAS 53975-75-0).

LC-MS (method A): $R_t$=1.17 min; MS (ESIpos): m/z=498 [M+H]$^+$ $^1$H-NMR (400 MHz, DMSO-d6) δ[ppm]: 1.137 (0.81), 1.232 (0.49), 1.449 (13.73), 1.465 (13.73), 1.906 (0.81), 2.084 (11.86), 2.336 (1.38), 2.518 (16.00), 2.522 (10.72), 2.539 (1.38), 2.678 (1.30), 3.283 (0.41), 3.371 (0.89), 5.242 (1.06), 5.258 (2.36), 5.274 (2.92), 5.290 (2.11), 5.305 (0.81), 7.202 (4.30), 7.222 (8.69), 7.242 (5.52), 7.381 (1.06), 7.397 (2.11), 7.418 (3.01), 7.435 (1.54), 7.439 (1.62), 7.455 (0.73), 7.642 (9.75), 7.654 (10.15), 7.680 (6.09), 7.704 (8.20), 7.715 (5.36), 7.998 (5.93), 8.002 (5.85), 8.010 (5.60), 8.014 (5.44), 9.056 (8.61), 9.061 (8.28), 10.106 (9.75).

Example 250

N-(2,6-difluorophenyl)-5-fluoro-4-(3-oxo-6,7-dihydro-5H-[1,2,4]triazolo[3,4-b][1,3]thiazin-2(3H)-yl)-2-{[(2S)-1,1,1-trifluoropropan-2-yl]oxy}benzamide

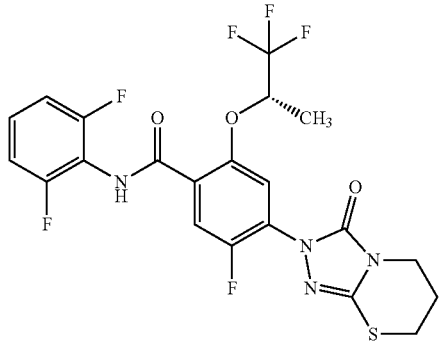

From intermediate 30 and 6,7-dihydro-5H-[1,2,4]triazolo[3,4-b][1,3]thiazin-3(2H)-one (intermediate 39).

LC-MS (method A): $R_t$=1.22 min; MS (ESIpos): m/z=519 [M+H]$^+$ $^1$H-NMR (400 MHz, DMSO-d6) δ[ppm]: 1.427 (7.80), 1.443 (7.64), 1.647 (0.82), 2.074 (16.00), 2.216 (2.42), 2.228 (3.38), 2.241 (2.53), 2.327 (0.87), 2.669 (0.84), 3.221 (3.81), 3.234 (3.84), 3.248 (3.49), 3.564 (0.46), 3.693 (3.23), 3.708 (5.12), 3.723 (2.99), 5.282 (0.59), 5.298 (1.28), 5.314 (1.63), 5.330 (1.20), 5.345 (0.52), 7.189 (2.42), 7.210 (4.79), 7.230 (3.02), 7.346 (0.70), 7.364 (1.58), 7.386 (2.14), 7.407 (1.88), 7.427 (1.52), 7.443 (0.98), 7.549 (2.96), 7.568 (4.22), 7.594 (3.00), 9.987 (6.52).

Example 251

N-(2,6-difluorophenyl)-4-(6,6-dimethyl-3-oxo-6,7-dihydro-5H-[1,2,4]triazolo[3,4-b][1,3]oxazin-2(3H)-yl)-5-fluoro-2-{[(2S)-1,1,1-trifluoropropan-2-yl]oxy}benzamide

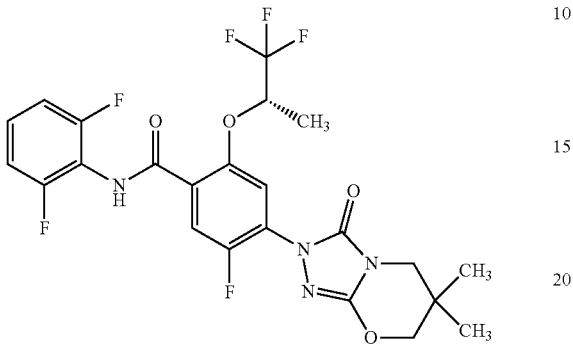

From intermediate 30 and 6,6-dimethyl-6,7-dihydro-5H-[1,2,4]triazolo[3,4-b][1,3]oxazin-3(2H)-one (intermediate 40).

LC-MS (method A): $R_t$=1.25 min; MS (ESIpos): m/z=531 [M+H]$^+$ $^1$H-NMR (400 MHz, DMSO-d6) δ[ppm]: 1.080 (16.00), 1.430 (2.47), 1.446 (2.47), 2.518 (2.20), 2.523 (1.57), 3.464 (4.00), 4.154 (4.37), 5.312 (0.52), 5.758 (1.46), 7.189 (0.76), 7.209 (1.56), 7.230 (0.97), 7.385 (0.45), 7.406 (0.54), 7.531 (0.95), 7.546 (1.91), 7.572 (1.03), 9.949 (2.24).

Example 252

4-(6,6-difluoro-3-oxo-5,6,7,8-tetrahydro[1,2,4]triazolo[4,3-a]pyridin-2(3H)-yl)-N-(2,6-difluoro-phenyl)-5-fluoro-2-{[(2S)-1,1,1-trifluoropropan-2-yl]oxy}benzamide

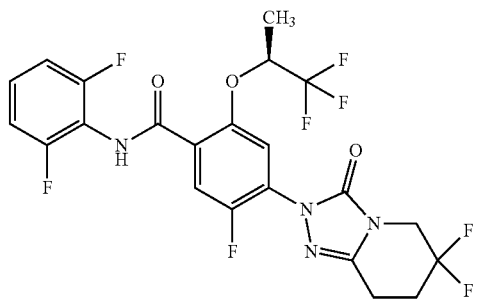 [SMILES: C[C@H](Oc1cc(-n2nc3n(c2=O)CC(F)(F)CC3)c(F)cc1C(=O)Nc1c(F)cccc1F)C(F)(F)F]

From intermediate 30 and 6,6-difluoro-5,6,7,8-tetrahydro[1,2,4]triazolo[4,3-a]pyridin-3(2H)-one (intermediate 41).

LC-MS (method A): $R_t$=1.25 min; MS (ESIpos): m/z=537 [M+H]$^+$ $^1$H-NMR (400 MHz, DMSO-d6) δ[ppm]: 1.429 (16.00), 1.445 (15.89), 1.717 (0.89), 2.074 (1.68), 2.327 (2.32), 2.424 (1.54), 2.442 (3.29), 2.459 (5.29), 2.539 (2.14), 2.669 (2.07), 2.729 (3.79), 2.810 (0.43), 2.888 (4.36), 2.962 (6.14), 2.979 (11.50), 2.996 (5.29), 4.058 (4.96), 4.089 (9.86), 4.121 (4.75), 5.275 (1.11), 5.290 (2.61), 5.306 (3.32), 5.321 (2.50), 5.337 (1.07), 6.875 (0.46), 6.916 (0.50), 7.191 (4.71), 7.212 (10.00), 7.232 (6.43), 7.329 (0.50), 7.349 (0.82), 7.388 (3.29), 7.409 (3.93), 7.426 (2.75), 7.569 (5.93), 7.588 (8.29), 7.614 (6.32), 7.662 (0.57), 7.705 (0.64), 7.951 (0.75), 10.014 (4.89).

Example 253

N-(2,6-difluorophenyl)-5-fluoro-4-(3-oxo[1,2,4]triazolo[4,3-b]pyridazin-2(3H)-yl)-2-{[(2S)-1,1,1-trifluoropropan-2-yl]oxy}benzamide

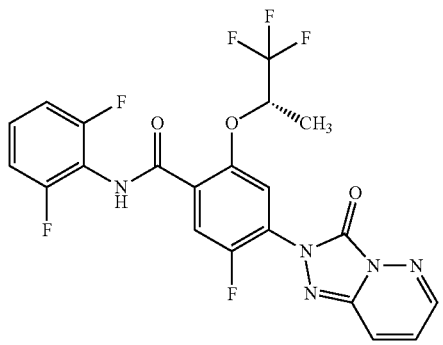 [SMILES: C[C@H](Oc1cc(-n2nc3cccnn3c2=O)c(F)cc1C(=O)Nc1c(F)cccc1F)C(F)(F)F]

From intermediate 30 and [1,2,4]triazolo[4,3-b]pyridazin-3(2H)-one (CAS 33050-35-0).

LC-MS (method A): $R_t$=1.14 min; MS (ESIpos): m/z=498 [M+H]$^+$ $^1$H-NMR (400 MHz, DMSO-d6) δ[ppm]: 1.137 (1.07), 1.233 (1.15), 1.448 (9.81), 1.464 (9.73), 1.907 (0.74), 2.084 (13.69), 2.115 (0.41), 2.332 (2.97), 2.336 (1.32), 2.518 (16.00), 2.522 (10.56), 2.539 (1.07), 2.669 (4.21), 2.673 (3.05), 2.678 (1.32), 5.259 (0.74), 5.274 (1.57), 5.290 (1.98), 5.306 (1.48), 5.322 (0.58), 5.758 (11.22), 7.201 (2.97), 7.221 (6.10), 7.242 (3.88), 7.255 (4.62), 7.265 (4.04), 7.279 (4.04), 7.289 (4.45), 7.381 (0.66), 7.396 (1.48), 7.418 (2.06), 7.438 (1.07), 7.454 (0.49), 7.658 (4.04), 7.682 (4.12), 7.707 (3.71), 7.721 (3.63), 7.939 (3.71), 7.942 (3.79), 7.963 (3.55), 7.966 (3.30), 8.372 (4.45), 8.375 (4.37), 8.382 (4.54), 8.385 (4.12), 10.085 (7.01).

Example 254

2-(4-[(2,6-difluorophenyl)carbamoyl]-2-fluoro-5-{[(2S)-1,1,1-trifluoropropan-2-yl]oxy}phenyl)-3-oxo-2,3,5,6,7,8-hexahydro[1,2,4]triazolo[4,3-a]pyridine-8-(R,S)-carboxylic acid, mixture of diastereomers

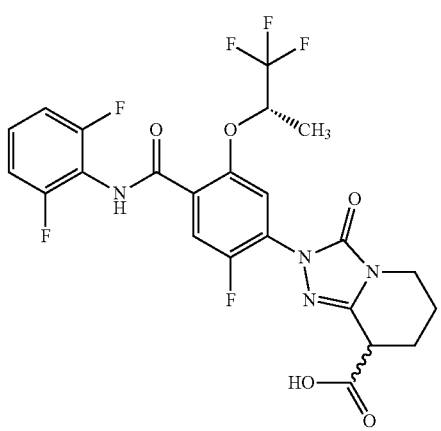 [SMILES: C[C@H](Oc1cc(-n2nc3n(c2=O)CCCC3C(=O)O)c(F)cc1C(=O)Nc1c(F)cccc1F)C(F)(F)F]

From intermediate 30 and rac-3-oxo-2,3,5,6,7,8-hexahydro[1,2,4]triazolo[4,3-a]pyridine-8carboxylic acid (CAS 1432681-89-4).

LC-MS (method A): $R_t$=1.06 min; MS (ESIpos): m/z=498 [M+H]$^+$ $^1$H-NMR (400 MHz, DMSO-d6) δ[ppm]: 1.421 (7.84), 1.435 (13.20), 1.449 (7.69), 1.914 (3.73), 1.928 (5.59), 1.943 (4.58), 2.066 (3.96), 2.080 (5.13), 2.095 (3.65), 2.322 (3.03), 2.326 (4.12), 2.331 (3.11), 2.539 (16.00), 2.664 (3.11), 2.668 (4.19), 2.673 (3.18), 3.513 (2.25), 3.530 (2.87), 3.546 (3.18), 3.561 (3.65), 3.577 (2.17), 3.622 (2.02), 3.635 (3.73), 3.650 (2.80), 3.666 (2.41), 3.680 (1.24), 3.824 (2.49), 3.838 (4.58), 3.852 (2.41), 5.299 (1.79), 5.315 (2.25), 5.326 (1.79), 7.190 (4.35), 7.211 (8.85), 7.231 (5.51), 7.371 (1.01), 7.387 (2.25), 7.407 (3.18), 7.423 (1.86), 7.547 (4.97), 7.556 (4.97), 7.574 (6.83), 7.599 (5.90), 7.621 (1.79), 7.641 (1.01), 9.998 (7.22), 10.003 (7.15).

Example 255

2-(4-[(2-chloro-6-fluorophenyl)carbamoyl]-2-fluoro-5-{[(2S)-1,1,1-trifluoropropan-2-yl]oxy}phenyl)-3-oxo-2,3,5,6,7,8-hexahydro[1,2,4]triazolo[4,3-a]pyridine-8-(R,S)-carboxylic Acid, Mixture of Diastereomers

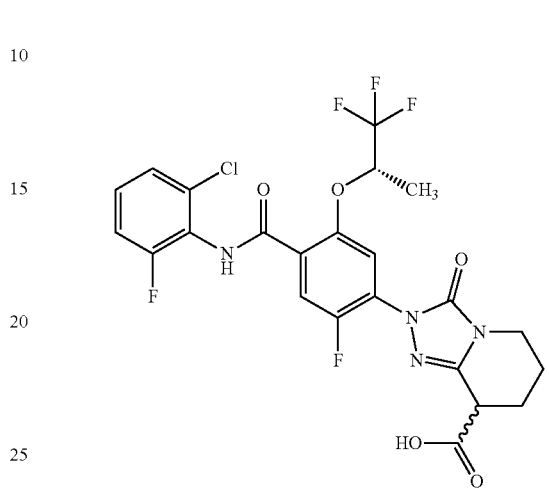

From intermediate 31 and rac-3-oxo-2,3,5,6,7,8-hexahydro[1,2,4]triazolo[4,3-a]pyridine-8-carboxylic acid (CAS 1432681-89-4).

LC-MS (method A): $R_t$=1.11 min; MS (ESIpos): m/z=561 [M+H]$^+$ $^1$H-NMR (400 MHz, DMSO-d6) δ[ppm]: 1.428 (3.62), 1.441 (5.29), 1.455 (3.34), 1.931 (2.09), 2.083 (16.00), 2.322 (2.23), 2.326 (2.92), 2.331 (2.23), 2.522 (7.93), 2.539 (1.39), 2.665 (2.37), 2.669 (3.06), 2.673 (2.23), 3.538 (0.97), 3.552 (1.11), 3.568 (1.25), 3.637 (1.39), 3.653 (0.97), 3.668 (0.83), 3.843 (0.97), 3.857 (1.81), 5.326 (0.83), 5.342 (0.97), 5.755 (6.68), 7.355 (1.53), 7.371 (0.97), 7.378 (1.11), 7.388 (0.83), 7.408 (1.53), 7.421 (1.81), 7.433 (3.06), 7.438 (3.62), 7.551 (3.76), 7.575 (2.92), 10.062 (3.48).

Example 256

2-(4-[(2-chloro-6-fluorophenyl)carbamoyl]-2-fluoro-5-{[(2S)-1,1,1-trifluoropropan-2-yl]oxy}phenyl)-3-oxo-2,3,5,6,7,8-hexahydro[1,2,4]triazolo[4,3-a]pyridine-6-(R,S)-carboxylic Acid, Mixture of Diastereomers

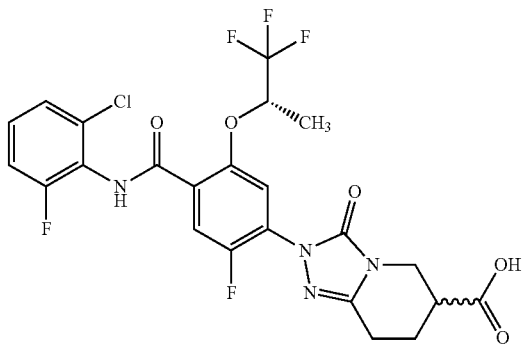 [SMILES: C[C@H](Oc1cc(-n2nc3n(c2=O)CC(C(=O)O)CC3)c(F)cc1C(=O)Nc1c(F)cccc1Cl)C(F)(F)F]

From intermediate 31 and rac-3-oxo-2,3,5,6,7,8-hexahydro[1,2,4]triazolo[4,3-a]pyridine-6-carboxylic acid (CAS 1432680-45-9).

LC-MS (method A): $R_t$=1.14 min; MS (ESIpos): m/z=561 [M+H]$^+$ $^1$H-NMR (400 MHz, DMSO-d6) δ[ppm]: 1.137 (0.53), 1.232 (1.26), 1.432 (3.97), 1.448 (3.97), 1.967 (0.46), 1.988 (0.60), 2.001 (0.46), 2.085 (3.83), 2.157 (0.53), 2.323 (2.98), 2.327 (4.10), 2.331 (2.91), 2.518 (16.00), 2.523 (10.51), 2.540 (1.06), 2.665 (3.04), 2.669 (4.17), 2.673 (2.98), 2.734 (0.66), 2.750 (1.26), 2.770 (0.79), 2.793 (0.53), 3.046 (0.46), 3.659 (0.60), 3.678 (0.60), 3.689 (0.99), 3.708 (0.99), 3.751 (0.79), 3.764 (0.86), 3.782 (0.46), 3.796 (0.46), 5.333 (0.53), 5.348 (0.66), 5.363 (0.53), 5.759 (6.08), 7.335 (0.46), 7.353 (0.93), 7.370 (0.60), 7.377 (0.73), 7.407 (0.93), 7.421 (1.06), 7.431 (1.92), 7.438 (2.38), 7.452 (0.46), 7.540 (1.45), 7.565 (1.92), 7.573 (1.45), 10.053 (3.37).

Example 257

N-(2,6-difluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

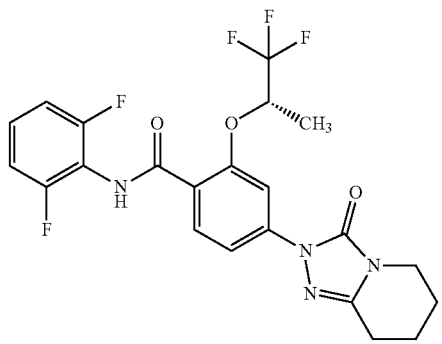 [SMILES: C[C@H](Oc1cc(-n2nc3n(c2=O)CCCC3)ccc1C(=O)Nc1c(F)cccc1F)C(F)(F)F]

From intermediate 32 and 5,6,7,8-tetrahydro[1,2,4]triazolo[4,3-a]pyridin-3(2H)-one.

LC-MS (method A): $R_t$=1.25 min; MS (ESIneg): m/z=481 [M−H]$^−$ $^1$H-NMR (400 MHz, DMSO-d6) δ[ppm]: 1.138 (0.43), 1.231 (0.38), 1.432 (1.08), 1.447 (1.13), 1.489 (15.78), 1.504 (15.73), 1.556 (4.63), 1.646 (2.96), 1.794 (3.93), 1.806 (5.66), 1.817 (5.93), 1.882 (5.98), 1.893 (5.87), 2.084 (3.61), 2.349 (2.10), 2.443 (0.43), 2.518 (8.78), 2.523 (5.93), 2.541 (1.29), 2.718 (6.30), 2.734 (12.93), 2.750 (6.84), 3.317 (2.21), 3.376 (1.13), 3.565 (7.70), 3.581 (13.85), 3.596 (6.09), 5.272 (1.13), 5.288 (2.64), 5.304 (3.45), 5.319 (2.59), 5.336 (1.13), 5.758 (2.26), 7.180 (4.85), 7.200 (9.86), 7.221 (6.20), 7.373 (3.18), 7.385 (4.26), 7.395 (5.71), 7.409 (2.26), 7.430 (0.97), 7.478 (0.54), 7.489 (0.59), 7.570 (0.59), 7.587 (0.65), 7.711 (3.77), 7.732 (7.27), 7.772 (6.73), 7.792 (3.56), 7.828 (7.92), 7.854 (0.59), 7.874 (0.48), 8.296 (0.59), 9.685 (16.00).

Example 258

N-(2,6-difluorophenyl)-5-fluoro-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide

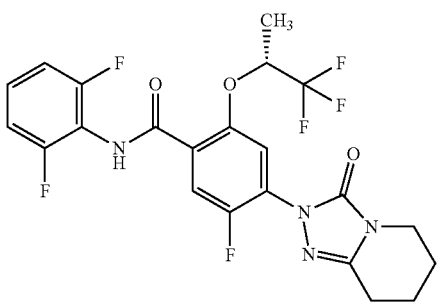 [SMILES: C[C@@H](Oc1cc(-n2nc3n(c2=O)CCCC3)c(F)cc1C(=O)Nc1c(F)cccc1F)C(F)(F)F]

To a solution of 5-fluoro-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzoic acid (intermediate 18) (100 mg, 257 μmol) in dichloromethane (1 ml) was added 1-chloro-N,N,2-trimethylprop-1-en-1-amine (100 μl, 770 μmol) and the solution was stirred at room temperature for thirty minutes. Then, pyridine (100 μl, 1.3 mmol) and a solution of 2,6-difluoroaniline (55 μl, 510 μmol) in dichloromethane (1 ml) were added subsequently and the reaction was stirred for one hour at room temperature. The reaction mixture was concentrated under reduced pressure and the residue was purified by preparative HPLC (X-Bridge Prep C18 5 μm, 0.1% aqueous formic acid, acetonitrile) to yield the title compound as white solid (83 mg, 98% purity, 63%).

LC-MS (method A): $R_t$=1.19 min; MS (ESIpos): m/z=501 [M+H]$^+$ $^1$H-NMR (400 MHz, DMSO-d6) δ[ppm]: 1.428 (16.00), 1.444 (16.00), 1.795 (3.75), 1.807 (5.19), 1.822 (5.33), 1.834 (2.59), 1.875 (2.59), 1.889 (5.33), 1.900 (5.48), 1.913 (3.46), 1.928 (1.30), 2.518 (6.92), 2.523 (4.76), 2.674 (1.44), 2.696 (5.77), 2.712 (11.53), 2.728 (6.05), 3.289 (0.86), 3.385 (0.72), 3.388 (0.72), 3.561 (6.92), 3.577 (12.54), 3.591 (5.62), 5.270 (1.15), 5.286 (2.59), 5.302 (3.32), 5.318 (2.45), 5.333 (1.01), 7.189 (4.90), 7.209 (10.09), 7.229 (6.34), 7.370 (1.15), 7.385 (2.45), 7.406 (3.46), 7.422 (1.73), 7.427 (1.87), 7.443 (0.72), 7.542 (6.05), 7.560 (9.23), 7.585 (6.77), 9.986 (8.22).

Examples 259-260 were prepared as described for example 258 from intermediate 18 and the respective amines, as indicated.

Example 259

5-fluoro-N-(2-fluoro-6-methylphenyl)-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide

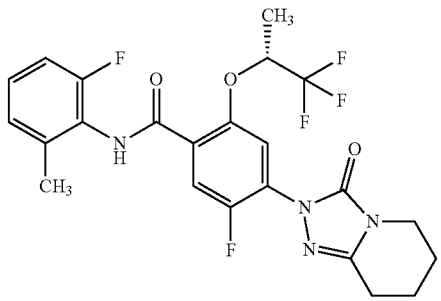 [SMILES: Cc1cccc(F)c1NC(=O)c1cc(F)c(-n2nc3n(c2=O)CCCC3)cc1O[C@H](C)C(F)(F)F]

From intermediate 18 and 2-fluoro-6-methylaniline.
LC-MS (method A): $R_t$=1.22 min; MS (ESIpos): m/z=497 [M+H]$^+$
$^1$H-NMR (400 MHz, DMSO-d6) δ[ppm]: 1.429 (7.04), 1.445 (7.00), 1.782 (0.45), 1.797 (1.26), 1.809 (1.73), 1.821 (1.75), 1.824 (1.77), 1.836 (0.87), 1.878 (0.88), 1.892 (1.80), 1.902 (1.84), 1.916 (1.11), 1.931 (0.43), 2.271 (16.00), 2.518 (0.99), 2.523 (0.63), 2.699 (2.09), 2.715 (4.12), 2.730 (2.18), 3.564 (2.48), 3.579 (4.38), 3.594 (1.92), 5.316 (0.46), 5.332 (1.11), 5.348 (1.44), 5.364 (1.04), 5.380 (0.40), 7.100 (0.93), 7.116 (2.35), 7.120 (2.28), 7.133 (2.52), 7.143 (1.42), 7.226 (1.11), 7.240 (1.21), 7.246 (1.58), 7.260 (1.22), 7.266 (0.77), 7.280 (0.65), 7.538 (3.17), 7.545 (4.27), 7.552 (3.11), 7.569 (3.69), 9.810 (4.16).

Example 260

5-fluoro-N-(2-fluorophenyl)-4-(3-oxo-5,6,7,8-tetrahydro[1,2,4]triazolo[4,3-a]pyridin-2(3H)-yl)-2-{[(2R)-1,1,1-trifluoropropan-2-yl]oxy}benzamide

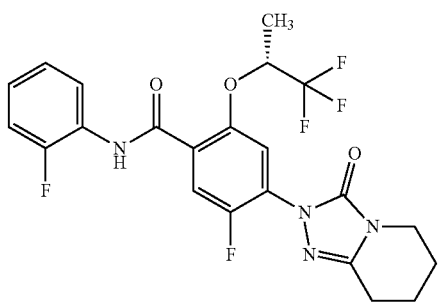 [SMILES: C[C@@H](Oc1cc(-n2nc3n(c2=O)CCCC3)c(F)cc1C(=O)Nc1ccccc1F)C(F)(F)F]

From intermediate 18 and 2-fluoroaniline.
LC-MS (method A): $R_t$=1.29 min; MS (ESIpos): m/z=483 [M+H]$^+$
$^1$H-NMR (400 MHz, DMSO-d6) δ[ppm]: 1.470 (16.00), 1.486 (15.97), 1.796 (3.46), 1.808 (4.90), 1.823 (5.00), 1.836 (2.48), 1.877 (2.43), 1.891 (5.02), 1.902 (5.19), 1.915 (3.20), 1.930 (1.23), 2.518 (5.17), 2.523 (3.39), 2.699 (5.52), 2.715 (10.83), 2.731 (5.81), 3.564 (6.48), 3.580 (11.55), 3.594 (5.26), 5.387 (1.08), 5.404 (2.59), 5.420 (3.37), 5.435 (2.47), 5.451 (0.99), 7.188 (0.74), 7.202 (2.23), 7.208 (2.74), 7.216 (5.36), 7.219 (6.08), 7.226 (7.55), 7.237 (5.33), 7.240 (5.26), 7.253 (1.42), 7.295 (2.71), 7.301 (2.45), 7.314 (2.04), 7.322 (2.98), 7.329 (1.73), 7.333 (1.80), 7.341 (1.25), 7.346 (1.68), 7.588 (6.24), 7.602 (6.13), 7.728 (7.09), 7.754 (7.02), 8.057 (2.09), 8.063 (1.88), 8.077 (3.68), 8.082 (3.10), 8.089 (1.94), 8.101 (1.87), 10.024 (9.27).

Example 261

5-fluoro-N-(2-fluorophenyl)-4-(3-oxo-5,6,7,8-tetrahydro[1,2,4]triazolo[4,3-a]pyridin-2(3H)-yl)-2-[(1S)-1-phenylethoxy]benzamide

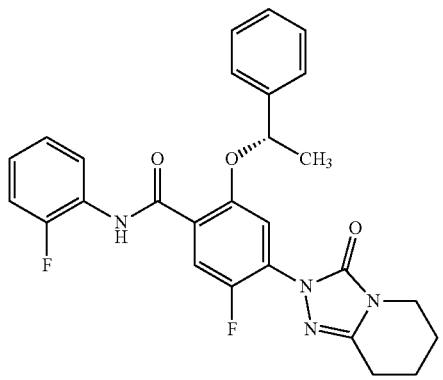 [SMILES: C[C@H](Oc1cc(-n2nc3n(c2=O)CCCC3)c(F)cc1C(=O)Nc1ccccc1F)c1ccccc1]

To a solution of 2,5-difluoro-N-(2-fluorophenyl)-4-(3-oxo-5,6,7,8-tetrahydro[1,2,4]triazolo[4,3-a]pyridin-2(3H)-yl)benzamide (intermediate 33) (62.0 mg, 160 µmol) in N,N-dimethylformamide (1.3 ml) were added (1S)-1-phenylethanol (58.5 mg, 479 µmol) and cesium carbonate (156 mg, 479 µmol) and the mixture was stirred at 100° C. for four hours. After cooling to room temperature, brine (5 ml) was added and the mixture was extracted with ethyl acetate (3×5 ml). The combined organic phases were dried over magnesium sulfate, concentrated under reduced pressure and the residue was purified by preparative HPLC (X-Bridge Prep C18 5 µm OBD, 0.1% aqueous formic acid, acetonitrile) to yield the title compound as white solid (28 mg, 98% purity, 35%).

LC-MS (method A): $R_t$=1.43 min; MS (ESIpos): m/z=492 [M+H]$^+$
$^1$H-NMR (400 MHz, DMSO-d6) δ[ppm]: 1.108 (9.31), 1.684 (15.15), 1.700 (15.18), 1.750 (1.42), 1.765 (3.80), 1.777 (5.46), 1.788 (5.41), 1.792 (5.57), 1.804 (2.86), 1.844 (2.84), 1.859 (5.73), 1.869 (5.78), 1.874 (4.94), 1.883 (3.58), 1.898 (1.40), 2.327 (0.75), 2.523 (2.55), 2.645 (6.08), 2.661 (12.21), 2.677 (6.69), 3.522 (6.93), 3.537 (12.37), 3.552 (5.73), 5.755 (1.35), 5.770 (4.13), 5.786 (4.09), 5.801 (1.28), 7.183 (0.99), 7.188 (1.12), 7.196 (1.21), 7.202 (3.06), 7.207 (2.87), 7.215 (2.89), 7.221 (3.97), 7.226 (2.92), 7.234 (3.16), 7.240 (4.13), 7.247 (4.30), 7.261 (5.84), 7.266 (5.54), 7.276 (7.46), 7.281 (4.36), 7.291 (3.67), 7.294 (5.51), 7.298 (3.49), 7.330 (8.96), 7.341 (11.41), 7.345 (10.26), 7.349 (16.00), 7.355 (11.25), 7.367 (9.58), 7.385 (2.44), 7.389 (2.35), 7.439 (12.21), 7.457 (8.32), 7.808 (7.39), 7.836 (7.18), 8.301 (2.35), 8.305 (2.45), 8.321 (4.36), 8.325 (4.31), 8.340 (2.24), 8.345 (2.12), 10.402 (6.71), 10.407 (6.65).

Example 262

N-(2,6-difluorophenyl)-5-fluoro-4-(3-oxo-5,6,7,8-tetrahydro[1,2,4]triazolo[4,3-a]pyridin-2(3H)-yl)-2-[(1S)-1-phenylethoxy]benzamide

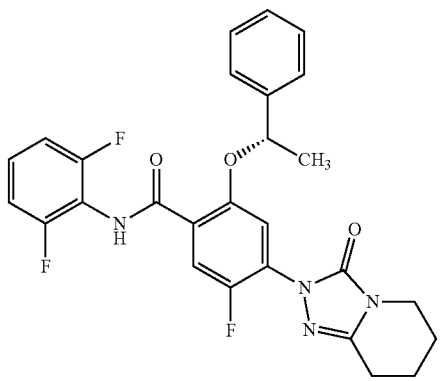 [SMILES: C[C@H](Oc1cc(-n2nc3n(c2=O)CCCC3)c(F)cc1C(=O)Nc1c(F)cccc1F)c1ccccc1]

To a solution of (1S)-1-phenylethanol (53.4 mg, 437 µmol) in N,N-dimethylformamide (1.2 ml) was added sodium hydride (17.5 mg, 60% dispersion in mineral oil, 437 µmol) and the reaction mixture was stirred at room temperature for one hour. Then, (N-(2,6-difluorophenyl)-2,5-difluoro-4-(3-oxo-5,6,7,8-tetrahydro[1,2,4]triazolo[4,3-a]pyridin-2(3H)-yl)benzamide (60 mg, 146 µmol) (intermediate 34) in N,N-dimethylformamide (0.5 ml) was added and the mixture was stirred at 80° C. for three hours. After cooling to room temperature, brine (5 ml) was added and the mixture was extracted with ethyl acetate (3×5 ml). The combined organic phases were dried over magnesium sulfate, concentrated under reduced pressure and the residue was purified by preparative HPLC (X-Bridge Prep C18 5 µm OBD, 0.1% aqueous formic acid, acetonitrile) to yield the title compound as white solid (7 mg, 97% purity, 9%).

LC-MS (method A): $R_t$=1.31 min; MS (ESIneg): m/z=507 [M−H]⁻

¹H-NMR (400 MHz, DMSO-d6) δ[ppm]: 0.860 (0.50), 0.967 (1.86), 1.031 (0.50), 1.047 (0.50), 1.107 (5.71), 1.145 (1.74), 1.209 (0.99), 1.232 (1.74), 1.353 (0.37), 1.388 (0.37), 1.594 (7.57), 1.610 (7.57), 1.768 (1.86), 1.780 (2.48), 1.795 (2.73), 1.862 (2.60), 1.872 (2.85), 2.318 (1.61), 2.323 (3.60), 2.327 (5.09), 2.332 (3.60), 2.337 (1.49), 2.518 (16.00), 2.523 (11.29), 2.647 (2.73), 2.664 (8.56), 2.669 (6.70), 2.673 (4.71), 2.679 (4.47), 2.697 (0.87), 2.713 (0.37), 3.291 (0.74), 3.373 (0.37), 3.504 (1.12), 3.522 (3.35), 3.538 (5.95), 3.552 (2.85), 3.565 (0.99), 4.190 (0.50), 5.646 (1.74), 5.663 (1.74), 7.219 (2.48), 7.240 (5.21), 7.249 (2.23), 7.260 (6.20), 7.268 (5.21), 7.273 (3.84), 7.285 (3.10), 7.322 (4.22), 7.341 (6.82), 7.359 (3.10), 7.391 (0.62), 7.407 (1.24), 7.428 (1.86), 7.449 (1.12), 7.465 (5.09), 7.483 (3.60), 7.573 (2.85), 7.600 (2.85), 9.955 (7.19).

Examples 263-267 were prepared as described for example 262 from the respective difluorobenzamide derivatives and the respective alcohols, as indicated.

Example 263

5-fluoro-N-(2-fluoro-6-methylphenyl)-4-(3-oxo-5,6,7,8-tetrahydro[1,2,4]triazolo[4,3-a]pyridin-2(3H)-yl)-2-[(1S)-1-phenylethoxy]benzamide

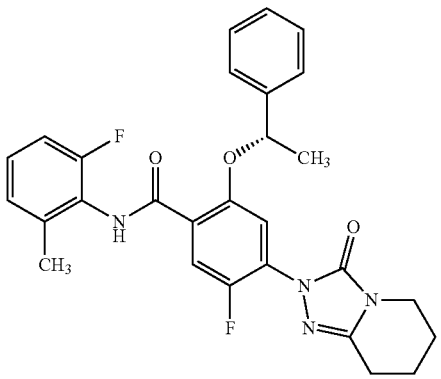 [SMILES: Cc1cccc(F)c1NC(=O)c1cc(F)c(-n2nc3n(c2=O)CCCC3)cc1O[C@@H](C)c1ccccc1]

From intermediate 35 and (1S)-1-phenylethanol.

LC-MS (method A): $R_t$=1.30 min; MS (ESIpos): m/z=505 [M+H]⁺

¹H-NMR (400 MHz, DMSO-d6) δ[ppm]: 0.968 (0.56), 1.028 (0.60), 1.043 (0.61), 1.108 (4.21), 1.145 (0.41), 1.209 (0.46), 1.591 (6.83), 1.607 (6.79), 1.767 (1.12), 1.779 (1.52), 1.794 (1.60), 1.806 (0.83), 1.845 (0.76), 1.860 (1.64), 1.871 (1.64), 1.884 (1.02), 1.899 (0.41), 2.293 (16.00), 2.323 (0.50), 2.327 (0.71), 2.332 (0.50), 2.518 (1.88), 2.523 (1.37), 2.644 (1.83), 2.660 (3.88), 2.669 (1.31), 2.677 (2.15), 3.520 (2.21), 3.535 (3.97), 3.550 (1.74), 5.628 (0.45), 5.643 (1.55), 5.659 (1.57), 5.675 (0.43), 7.133 (1.75), 7.152 (3.22), 7.170 (1.16), 7.209 (2.76), 7.224 (2.78), 7.244 (1.09), 7.249 (0.61), 7.252 (0.96), 7.257 (1.32), 7.264 (1.95), 7.270 (2.61), 7.276 (1.72), 7.285 (1.45), 7.289 (1.98), 7.292 (1.12), 7.297 (0.68), 7.326 (2.76), 7.345 (4.69), 7.363 (2.18), 7.466 (4.18), 7.484 (3.29), 7.488 (2.36), 7.549 (3.69), 7.575 (3.55), 9.803 (3.93).

Example 264

5-fluoro-N-(2-fluoro-6-methylphenyl)-2-{[(2R,3R)-3-hydroxybutan-2-yl]oxy}-4-(3-oxo-5,6,7,8-tetrahydro[1,2,4]triazolo[4,3-a]pyridin-2(3H)-yl)benzamide

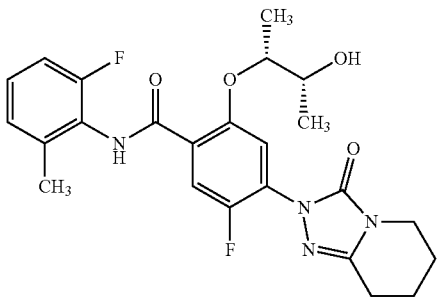 [SMILES: Cc1cccc(F)c1NC(=O)c1cc(F)c(-n2nc3n(c2=O)CCCC3)cc1O[C@H](C)[C@@H](C)O]

From intermediate 35 and (2R,3R)-butane-2,3-diol.

LC-MS (method A): $R_t$=1.04 min; MS (ESIpos): m/z=473 [M+H]⁺

¹H-NMR (400 MHz, DMSO-d6) δ[ppm]: 1.108 (16.00), 1.124 (0.43), 1.141 (0.40), 1.273 (0.41), 1.289 (0.41), 2.269 (1.07), 2.693 (0.92), 3.576 (0.42), 4.189 (1.37).

Example 265

2-{[(2S)-1-(dimethylamino)propan-2-yl]oxy}-5-fluoro-N-(2-fluoro-6-methylphenyl)-4-(3-oxo-5,6,7,8-tetrahydro[1,2,4]triazolo[4,3-a]pyridin-2(3H)-yl)benzamide

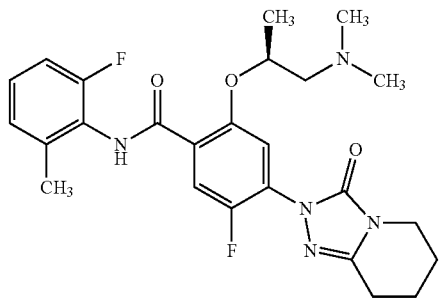 [SMILES: Cc1cccc(F)c1NC(=O)c1cc(F)c(-n2nc3n(c2=O)CCCC3)cc1O[C@@H](C)CN(C)C]

From intermediate 35 and (2S)-1-(dimethylamino)propan-2-ol.

LC-MS (method A): $R_t$=0.74 min; MS (ESIpos): m/z=486 [M+H]⁺

¹H-NMR (400 MHz, DMSO-d6) δ[ppm]: 1.108 (16.00), 1.370 (3.52), 1.385 (3.55), 1.792 (0.46), 1.804 (0.64), 1.819 (0.66), 1.882 (0.63), 1.887 (0.68), 1.898 (0.79), 1.911 (0.43), 2.022 (12.64), 2.253 (6.24), 2.285 (0.46), 2.295 (0.51), 2.318 (0.62), 2.327 (0.69), 2.518 (0.69), 2.523 (0.45), 2.658 (0.51), 2.680 (0.58), 2.692 (1.47), 2.694 (1.25), 2.712 (1.91), 2.728 (0.85), 3.301 (0.55), 3.559 (0.94), 3.575 (1.66), 3.590 (0.74), 4.196 (0.66), 7.127 (0.98), 7.146 (1.47), 7.228 (0.44), 7.242 (0.47), 7.248 (0.61), 7.262 (0.51), 7.441 (1.14), 7.455 (1.12), 7.647 (1.53), 7.674 (1.47), 10.530 (1.44).

Example 266

2-{[(2R)-1-(dimethylamino)propan-2-yl]oxy}-5-fluoro-N-(2-fluoro-6-methylphenyl)-4-(3-oxo-5,6,7,8-tetrahydro[1,2,4]triazolo[4,3-a]pyridin-2(3H)-yl)benzamide

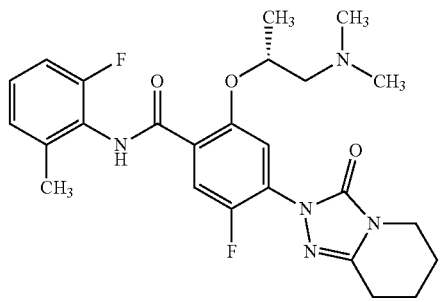 [SMILES: Cc1cccc(F)c1NC(=O)c1cc(F)c(-n2nc3n(c2=O)CCCC3)cc1O[C@H](C)CN(C)C]

From intermediate 35 and (2R)-1-(dimethylamino)propan-2-ol.

LC-MS (method A): $R_t$=0.68 min; MS (ESIpos): m/z=486 [M+H]⁺

¹H-NMR (400 MHz, DMSO-d6) δ[ppm]: 1.108 (16.00), 1.371 (0.58), 1.386 (0.58), 2.021 (2.22), 2.253 (1.09), 2.693 (0.42), 4.190 (0.61).

Example 267

5-fluoro-N-(2-fluoro-6-methylphenyl)-4-(3-oxo-5,6,7,8-tetrahydro[1,2,4]triazolo[4,3-a]pyridin-2(3H)-yl)-2-{[(2S)-1-(pyrrolidin-1-yl)propan-2-yl]oxy}benzamide

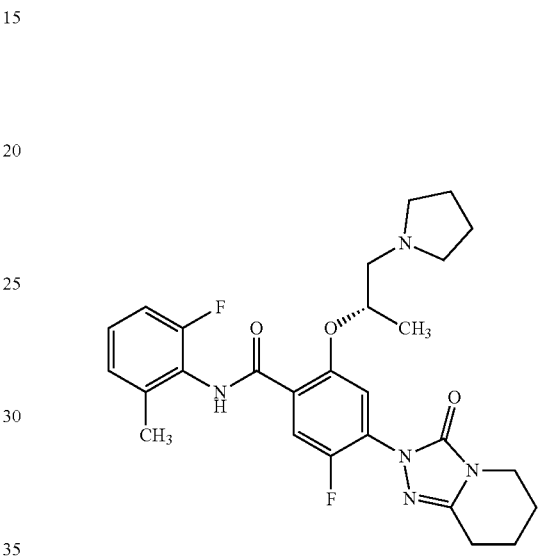

From intermediate 35 and (2S)-1-(pyrrolidin-1-yl)propan-2-ol.

LC-MS (method B): $R_t$=1.30 min; MS (ESIneg): m/z=510 [M−H]⁻

¹H-NMR (400 MHz, CHLOROFORM-d) δ [ppm]: 0.133 (1.05), 1.263 (2.49), 1.323 (0.95), 1.335 (1.19), 1.339 (1.19), 1.354 (0.91), 1.359 (1.00), 1.379 (0.47), 1.464 (0.47), 1.484 (1.01), 1.489 (0.87), 1.513 (11.32), 1.528 (11.00), 1.599 (1.41), 1.912 (0.49), 1.920 (1.08), 1.927 (1.30), 1.933 (1.44), 1.943 (1.49), 1.947 (1.60), 1.959 (0.71), 1.963 (0.75), 1.984 (0.78), 1.990 (0.69), 1.998 (1.42), 2.003 (1.49), 2.014 (1.56), 2.019 (1.30), 2.028 (0.95), 2.042 (0.41), 2.254 (0.71), 2.274 (1.40), 2.289 (1.65), 2.309 (0.93), 2.327 (16.00), 2.364 (1.17), 2.372 (1.24), 2.395 (1.33), 2.404 (1.27), 2.425 (0.92), 2.444 (1.69), 2.459 (1.37), 2.480 (0.66), 2.799 (2.32), 2.815 (4.36), 2.831 (2.58), 3.053 (1.20), 3.077 (1.33), 3.084 (1.19), 3.109 (1.15), 3.708 (2.90), 3.724 (4.83), 3.739 (2.09), 4.548 (0.45), 4.556 (0.62), 4.563 (0.57), 4.572 (0.90), 4.580 (0.56), 4.587 (0.61), 4.596 (0.43), 6.957 (0.77), 6.978 (1.59), 7.001 (0.96), 7.038 (1.38), 7.057 (1.92), 7.134 (1.01), 7.148 (1.08), 7.155 (1.44), 7.168 (1.42), 7.174 (0.69), 7.188 (0.63), 7.362 (2.98), 7.376 (2.98), 7.960 (3.79), 7.988 (3.75), 10.744 (2.04).

Example 268

N-[2-(difluoromethyl)phenyl]-2-{[(2S)-1-(dimethyl-amino)propan-2-yl]oxy}-5-fluoro-4-(3-oxo-5,6,7,8-tetrahydro[1,2,4]triazolo[4,3-a]pyridin-2(3H)-yl)benzamide

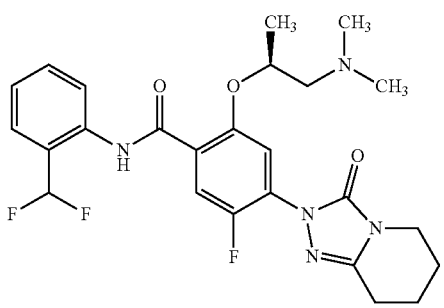 [SMILES: C[C@@H](CN(C)C)Oc1cc(-n2nc3n(c2=O)CCCC3)c(F)cc1C(=O)Nc1ccccc1C(F)F]

To a solution of 2-{[(2S)-1-(dimethylamino)propan-2-yl]oxy}-5-fluoro-4-(3-oxo-5,6,7,8-tetrahydro[1,2,4]triazolo[4,3-a]pyridin-2(3H)-yl)benzoic acid (intermediate 20) (100 mg, 264 μmol) in N,N-dimethylformamide (5 ml) was added 1-[bis(dimethylamino)methylene]-1H-[1,2,3]triazolo[4,5-b]pyridin-1-ium 3-oxide hexafluorophosphate (HATU) (201 mg, 529 μmol) and the mixture was stirred at room temperature for 15 minutes. Then, 2-(difluoromethyl)aniline hydrochloride (94.9 mg, 529 μmol) and N,N-diisopropylethylamine (280 μl, 1.6 mmol) were added and the reaction was stirred at room temperature for three hours. The crude reaction solution was subjected to preparative HPLC (X-Bridge Prep C18 5 μm OBD, 0.1% aqueous ammonia, acetonitrile) to yield the title compound (60 mg, 45%).

LC-MS (method B): $R_t$=1.23 min; MS (ESIpos): m/z=504 [M+H]$^+$ $^1$H-NMR (400 MHz, CHLOROFORM-d) δ [ppm]: 1.474 (5.30), 1.490 (5.28), 1.600 (2.88), 1.921 (0.64), 1.934 (0.89), 1.948 (0.95), 1.965 (0.45), 1.985 (0.46), 2.004 (0.90), 2.015 (0.96), 2.029 (0.59), 2.110 (16.00), 2.285 (0.57), 2.294 (0.61), 2.317 (0.67), 2.327 (0.65), 2.769 (0.65), 2.792 (0.81), 2.800 (1.77), 2.815 (2.55), 2.824 (0.86), 2.832 (1.47), 3.709 (1.58), 3.724 (2.65), 3.739 (1.19), 4.613 (0.44), 6.725 (0.79), 6.864 (1.51), 7.003 (0.75), 7.338 (0.49), 7.357 (1.11), 7.376 (0.68), 7.421 (1.64), 7.436 (1.63), 7.501 (0.45), 7.520 (0.92), 7.539 (0.51), 7.626 (1.10), 7.638 (1.14), 7.657 (0.92), 8.013 (1.90), 8.042 (1.87), 10.669 (1.08).

Examples 269-278 were prepared as described for example 268 from the respective benzoic acid derivatives and the respective amines, as indicated.

Example 269

2-{[(2S)-1-(dimethylamino)propan-2-yl]oxy}-5-fluoro-N-(4-fluoro-2-methylphenyl)-4-(3-oxo-5,6,7,8-tetrahydro[1,2,4]triazolo[4,3-a]pyridin-2(3H)-yl)benzamide

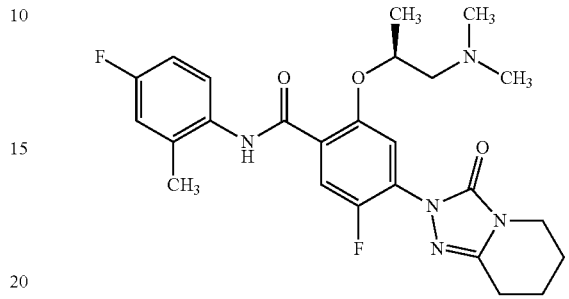

From intermediate 20 and 4-fluoro-2-methylaniline.

LC-MS (method B): $R_t$=1.23 min; MS (ESIpos): m/z=486 [M+H]$^+$ $^1$H-NMR (400 MHz, CHLOROFORM-d) δ [ppm]: 1.473 (4.17), 1.488 (4.19), 1.603 (2.03), 1.920 (0.45), 1.932 (0.63), 1.943 (0.69), 1.947 (0.69), 1.999 (0.61), 2.004 (0.63), 2.014 (0.68), 2.028 (0.42), 2.111 (16.00), 2.291 (0.61), 2.301 (0.68), 2.315 (6.67), 2.323 (0.90), 2.333 (0.70), 2.731 (0.64), 2.754 (0.65), 2.764 (0.56), 2.786 (0.58), 2.798 (0.94), 2.814 (1.81), 2.830 (1.02), 3.707 (1.15), 3.722 (1.90), 3.737 (0.85), 6.916 (0.45), 6.924 (0.64), 6.949 (0.65), 6.956 (0.45), 6.972 (0.60), 6.979 (0.44), 7.392 (1.24), 7.407 (1.23), 7.447 (0.61), 7.460 (0.63), 7.468 (0.59), 7.482 (0.56), 8.010 (1.45), 8.039 (1.44), 10.336 (0.86).

Example 270

2-{[(2S)-1-(dimethylamino)propan-2-yl]oxy}-5-fluoro-N-(5-fluoro-2-methylphenyl)-4-(3-oxo-5,6,7,8-tetrahydro[1,2,4]triazolo[4,3-a]pyridin-2(3H)-yl)benzamide

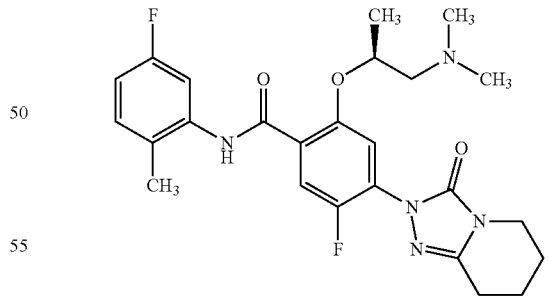

From intermediate 20 and 5-fluoro-2-methylaniline.

LC-MS (method B): $R_t$=1.26 min; MS (ESIpos): m/z=486 [M+H]$^+$ $^1$H-NMR (400 MHz, CHLOROFORM-d) δ [ppm]: 1.468 (5.82), 1.483 (5.75), 1.602 (3.25), 1.920 (0.60), 1.933 (0.83), 1.944 (0.83), 1.947 (0.90), 1.963 (0.43), 1.984 (0.49), 2.000 (0.81), 2.004 (0.85), 2.015 (0.91), 2.029 (0.55), 2.152 (16.00), 2.301 (7.13), 2.330 (0.56), 2.341 (0.57), 2.363 (0.66), 2.373 (0.63), 2.735 (0.71), 2.757 (0.73), 2.767 (0.63), 2.789 (0.70), 2.798 (1.28), 2.814 (2.43), 2.831 (1.37), 3.708 (1.56), 3.723 (2.57), 3.738 (1.15), 6.820 (0.41), 6.826 (0.46), 6.840 (0.85), 6.847 (0.92), 6.861 (0.48), 6.868 (0.49), 7.155 (0.68), 7.171 (0.75), 7.176 (0.70), 7.192 (0.61), 7.428 (1.65), 7.442 (1.64), 7.544 (0.78), 7.551 (0.79), 7.570 (0.79), 7.577 (0.78), 8.044 (1.88), 8.073 (1.86), 10.214 (0.91).

Example 271

2-{[(2S)-1-(dimethylamino)propan-2-yl]oxy}-5-fluoro-N-(4-methylpyridin-3-yl)-4-(3-oxo-5,6,7,8-tetrahydro[1,2,4]triazolo[4,3-a]pyridin-2(3H)-yl)benzamide

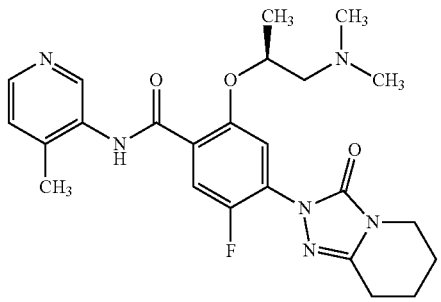

From intermediate 20 and 4-methylpyridin-3-amine.
LC-MS (method B): $R_t$=0.99 min; MS (ESIpos): m/z=469 [M+H]$^+$
$^1$H-NMR (400 MHz, CHLOROFORM-d) δ [ppm]: 1.494 (5.60), 1.509 (5.68), 1.653 (2.09), 1.922 (0.67), 1.934 (0.93), 1.946 (0.94), 1.949 (1.00), 1.965 (0.48), 1.986 (0.48), 2.006 (0.95), 2.016 (1.01), 2.030 (0.62), 2.111 (16.00), 2.279 (0.65), 2.287 (0.65), 2.311 (0.73), 2.320 (0.73), 2.341 (10.04), 2.758 (0.70), 2.783 (0.77), 2.791 (0.75), 2.800 (1.37), 2.816 (3.14), 2.833 (1.48), 3.709 (1.62), 3.724 (2.77), 3.739 (1.24), 4.597 (0.58), 7.197 (1.39), 7.209 (1.43), 7.412 (1.74), 7.426 (1.73), 7.993 (1.89), 8.022 (1.92), 8.366 (1.83), 8.379 (1.82), 8.608 (3.02), 10.662 (1.14).

Example 272

2-{[(2S)-1-(dimethylamino)propan-2-yl]oxy}-N-(3,5-dimethylpyrazin-2-yl)-5-fluoro-4-(3-oxo-5,6,7,8-tetrahydro[1,2,4]triazolo[4,3-a]pyridin-2(3H)-yl)benzamide

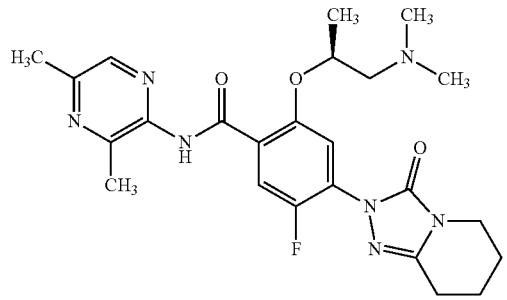 [SMILES: Cc1cnc(NC(=O)c2cc(F)c(-n3nc4n(c3=O)CCCC4)cc2O[C@@H](C)CN(C)C)c(C)n1]

From intermediate 20 and 3,5-dimethylpyrazin-2-amine.
LC-MS (method B): $R_t$=1.02 min; MS (ESIpos): m/z=484 [M+H]$^+$ $^1$H-NMR (400 MHz, CHLOROFORM-d) δ [ppm]: 1.496 (5.32), 1.511 (5.37), 1.640 (0.98), 1.920 (0.71), 1.932 (0.98), 1.947 (1.05), 1.963 (0.50), 1.984 (0.51), 2.003 (1.00), 2.014 (1.05), 2.028 (0.64), 2.120 (16.00), 2.274 (0.65), 2.282 (0.73), 2.306 (0.77), 2.314 (0.74), 2.554 (9.81), 2.562 (10.77), 2.798 (1.36), 2.814 (2.80), 2.830 (1.49), 2.843 (0.77), 2.850 (0.66), 2.875 (0.65), 3.707 (1.63), 3.722 (2.76), 3.737 (1.22), 4.589 (0.56), 7.399 (1.72), 7.413 (1.71), 7.957 (1.89), 7.986 (1.89), 8.171 (2.73), 11.249 (1.26).

Example 273

2-{[(2S)-1-(dimethylamino)propan-2-yl]oxy}-5-fluoro-N-(6-methoxy-4-methylpyridin-3-yl)-4-(3-oxo-5,6,7,8-tetrahydro[1,2,4]triazolo[4,3-a]pyridin-2(3H)-yl)benzamide

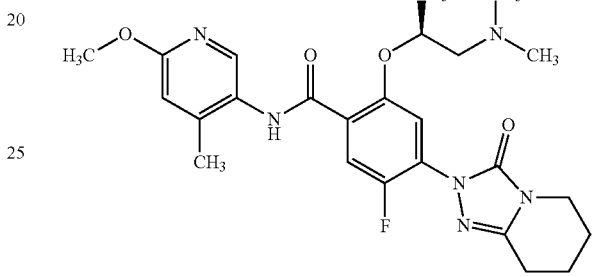

From intermediate 20 and 6-methoxy-4-methylpyridin-3-amine.
LC-MS (method B): $R_t$=1.12 min; MS (ESIpos): m/z=499 [M+H]$^+$
$^1$H-NMR (400 MHz, CHLOROFORM-d) δ [ppm]: 1.482 (4.25), 1.497 (4.28), 1.659 (1.33), 1.916 (0.49), 1.928 (0.67), 1.939 (0.69), 1.943 (0.73), 1.995 (0.65), 2.000 (0.68), 2.010 (0.72), 2.015 (0.60), 2.024 (0.44), 2.104 (16.00), 2.262 (0.80), 2.271 (7.61), 2.294 (0.73), 2.303 (0.70), 2.735 (0.63), 2.759 (0.65), 2.767 (0.57), 2.794 (1.20), 2.810 (1.92), 2.826 (1.07), 3.703 (1.19), 3.718 (2.02), 3.733 (0.90), 3.874 (0.53), 3.926 (11.06), 4.569 (0.47), 6.661 (1.99), 7.383 (1.33), 7.397 (1.36), 7.966 (1.57), 7.994 (1.53), 8.091 (2.43), 10.536 (1.13).

Example 274

2-{[(2S)-1-(dimethylamino)propan-2-yl]oxy}-5-fluoro-N-(4-methylpyridazin-3-yl)-4-(3-oxo-5,6,7,8-tetrahydro[1,2,4]triazolo[4,3-a]pyridin-2(3H)-yl)benzamide

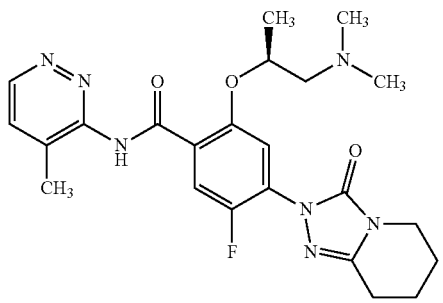 [SMILES: Cc1ccnnc1NC(=O)c1cc(F)c(-n2nc3n(c2=O)CCCC3)cc1O[C@@H](C)CN(C)C]

From intermediate 20 and 4-methylpyridazin-3-amine.
LC-MS (method B): $R_t$=0.90 min; MS (ESIpos): m/z=470 [M+H]$^+$ $^1$H-NMR (400 MHz, CHLOROFORM-d) δ [ppm]: 1.282 (16.00), 1.509 (1.84), 1.525 (1.86), 2.171 (1.13), 2.381 (2.30), 2.819 (0.70), 2.836 (0.41), 3.712 (0.50), 3.727 (0.77), 7.424 (0.48), 7.438 (0.48), 7.923 (0.50), 7.951 (0.49), 8.947 (0.63), 8.960 (0.61).

Example 275

2-{[(2S)-1-(dimethylamino)propan-2-yl]oxy}-5-fluoro-N-(2-methoxy-4-methylpyridin-3-yl)-4-(3-oxo-5,6,7,8-tetrahydro[1,2,4]triazolo[4,3-a]pyridin-2(3H)-yl)benzamide

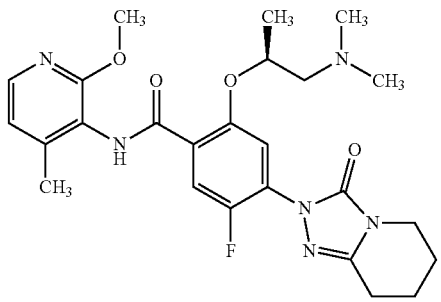 [SMILES: COc1nccc(C)c1NC(=O)c1cc(F)c(-n2nc3n(c2=O)CCCC3)cc1O[C@@H](C)CN(C)C]

From intermediate 20 and 2-methoxy-4-methylpyridin-3-amine.
LC-MS (method B): $R_t$=1.11 min; MS (ESIpos): m/z=499 [M+H]$^+$ $^1$H-NMR (400 MHz, CHLOROFORM-d) δ [ppm]: 1.479 (5.44), 1.494 (5.36), 1.591 (3.64), 1.921 (0.55), 1.928 (0.66), 1.933 (0.74), 1.945 (0.76), 1.948 (0.83), 2.000 (0.73), 2.005 (0.76), 2.015 (0.80), 2.020 (0.67), 2.029 (0.49), 2.127 (5.59), 2.289 (9.73), 2.800 (1.32), 2.808 (0.60), 2.815 (2.31), 2.832 (1.34), 3.709 (1.53), 3.724 (2.49), 3.739 (1.08), 3.966 (16.00), 6.822 (1.45), 6.835 (1.47), 7.385 (1.25), 7.400 (1.25), 7.943 (1.92), 7.956 (1.89), 7.978 (2.10), 8.007 (2.09), 10.367 (0.56).

Example 276

2-{[(2S)-1-(dimethylamino)propan-2-yl]oxy}-5-fluoro-N-(2-methylphenyl)-4-(3-oxo-5,6,7,8-tetrahydro[1,2,4]triazolo[4,3-a]pyridin-2(3H)-yl)benzamide

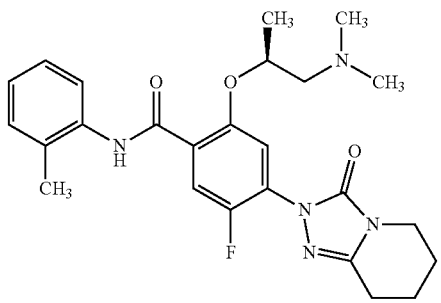 [SMILES: Cc1ccccc1NC(=O)c1cc(F)c(-n2nc3n(c2=O)CCCC3)cc1O[C@@H](C)CN(C)C]

From intermediate 20 and o-toluidine.
LC-MS (method B): $R_t$=1.21 min; MS (ESIpos): m/z=468 [M+H]$^+$ $^1$H-NMR (400 MHz, CHLOROFORM-d) δ [ppm]: 1.261 (2.04), 1.471 (6.60), 1.487 (6.67), 1.590 (12.40), 1.923 (1.43), 1.929 (2.04), 1.941 (1.69), 1.945 (2.37), 1.949 (2.12), 1.961 (1.11), 1.986 (1.14), 2.001 (2.17), 2.017 (2.19), 2.027 (1.38), 2.155 (2.74), 2.342 (16.00), 2.626 (13.58), 2.720 (0.46), 2.781 (1.79), 2.798 (3.48), 2.816 (4.71), 2.832 (2.54), 3.697 (1.92), 3.710 (3.65), 3.712 (3.76), 3.725 (5.21), 3.740 (2.01), 7.006 (1.06), 7.128 (0.70), 7.144 (2.01), 7.162 (1.44), 7.166 (1.38), 7.222 (1.09), 7.241 (4.26), 7.259 (3.18), 7.413 (1.46), 7.428 (1.46), 7.452 (1.06), 7.466 (1.03), 7.476 (1.01), 7.490 (0.98), 7.528 (1.11), 7.649 (1.64), 7.663 (1.67), 7.672 (1.29), 7.687 (1.03), 8.044 (0.88), 8.072 (0.86).

Example 277 rac-2-{[4-(dimethylamino)butan-2-yl]oxy}-5-fluoro-N-(2-fluoro-6-methylphenyl)-4-(3-oxo-5,6-dihydro-3H-[1,2,4]triazolo[3,4-c][1,4]oxazin-2(8H)-yl)benzamide

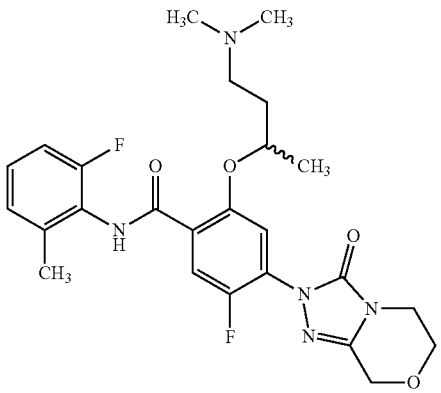 [SMILES: Cc1cccc(F)c1NC(=O)c1cc(F)c(-n2nc3n(c2=O)CCOC3)cc1OC(C)CCN(C)C]

From intermediate 22 and 2-fluoro-6-methylaniline.
LC-MS (method B): $R_t$=1.14 min; MS (ESIpos): m/z=502 [M+H]$^+$ $^1$H-NMR (400 MHz, CHLOROFORM-d) δ [ppm]: 0.000 (0.60), 1.007 (2.18), 1.162 (1.63), 1.229 (2.62), 1.250 (14.10), 1.267 (1.43), 1.484 (6.89), 1.499 (7.10), 2.113 (2.61), 2.257 (0.68), 2.287 (16.00), 2.314 (0.70), 2.790 (10.53), 3.206 (1.04), 3.225 (1.65), 3.244 (0.92), 3.768 (2.24), 3.780 (3.49), 3.795 (2.69), 4.051 (2.94), 4.061 (2.75), 4.065 (3.56), 4.077 (2.35), 4.739 (12.57), 4.757 (0.82), 4.771 (0.78), 4.786 (0.45), 6.947 (0.73), 6.969 (1.38), 6.973 (1.26), 6.992 (0.88), 7.064 (1.35), 7.083 (1.86), 7.148 (0.95), 7.163 (1.02), 7.168 (1.35), 7.182 (1.29), 7.188 (0.69), 7.203 (0.60), 7.356 (2.24), 7.370 (2.24), 7.495 (0.44), 8.011 (3.22), 8.039 (3.17), 9.058 (2.34).

Example 278 rac-5-fluoro-N-(2-fluoro-6-methylphenyl)-4-(3-oxo-5,6-dihydro-3H-[1,2,4]triazolo[3,4-c][1,4]oxazin-2(8H)-yl)-2-{[1-(pyrrolidin-1-yl)propan-2-yl]oxy}benzamide

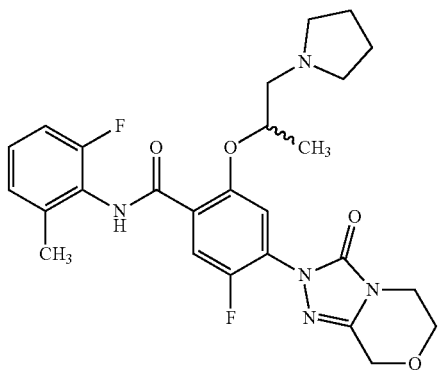 [SMILES: Cc1cccc(F)c1NC(=O)c1cc(F)c(-n2nc3n(c2=O)CCOC3)cc1OC(C)CN1CCCC1]

From intermediate 23 and 2-fluoro-6-methylaniline.

LC-MS (method B): $R_t$=1.27 min; MS (ESIpos): m/z=514 [M+H]$^+$ $^1$H-NMR (400 MHz, CHLOROFORM-d) δ [ppm]: 0.134 (3.48), 0.888 (0.66), 1.262 (7.42), 1.290 (0.45), 1.327 (1.01), 1.339 (1.19), 1.358 (0.93), 1.518 (8.47), 1.533 (8.12), 1.586 (2.79), 2.279 (1.26), 2.293 (1.41), 2.328 (16.00), 2.369 (0.75), 2.377 (0.76), 2.400 (0.84), 2.408 (0.83), 2.429 (0.77), 2.447 (1.42), 2.462 (1.21), 3.064 (0.64), 3.088 (0.83), 3.120 (0.60), 3.801 (2.82), 3.814 (4.27), 3.828 (3.43), 4.080 (3.64), 4.091 (3.07), 4.094 (4.36), 4.107 (2.92), 4.566 (0.64), 4.766 (14.33), 6.960 (0.82), 6.982 (1.68), 7.006 (1.17), 7.042 (1.27), 7.061 (1.77), 7.140 (0.91), 7.154 (1.00), 7.160 (1.30), 7.174 (1.28), 7.180 (0.64), 7.194 (0.55), 7.334 (1.43), 7.348 (1.43), 7.971 (1.88), 7.999 (1.85), 10.754 (1.46).

Example 279

N-(2,6-difluorophenyl)-5-fluoro-4-(3-oxo-6,7,8,9-tetrahydro-3H-[1,2,4]triazolo[4,3-d][1,4]diazepin-2(5H)-yl)-2-{[(2S)-1,1,1-trifluoropropan-2-yl]oxy}benzamide, Salt with Hydrochloric Acid

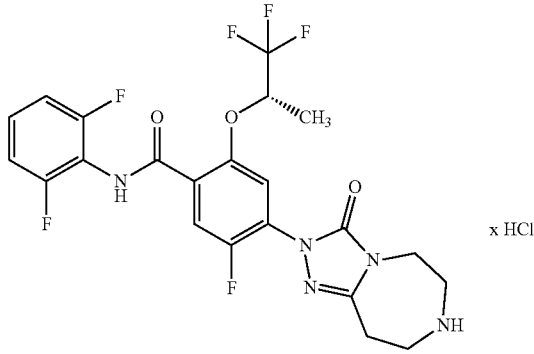 [SMILES: C[C@H](Oc1cc(-n2nc3n(c2=O)CCNCC3)c(F)cc1C(=O)Nc1c(F)cccc1F)C(F)(F)F]

Intermediate 36 was treated with a solution of hydrochloric acid in dioxane (4 M, 1 ml) and the mixture was stirred at room temperature for two hours. The resulting suspension was concentrated under reduced pressure to obtain the title compound as yellow solid (53 mg, 95% purity, 91%)

LC-MS (method A): $R_t$=0.89 min; MS (ESIneg): m/z=514 [M−H]$^−$ $^1$H-NMR (400 MHz, DMSO-d6) δ[ppm]: 1.231 (0.70), 1.268 (0.64), 1.434 (13.39), 1.450 (13.32), 1.671 (0.89), 1.907 (0.57), 2.323 (2.61), 2.327 (3.63), 2.331 (2.61), 2.387 (0.76), 2.518 (16.00), 2.523 (10.65), 2.665 (2.68), 2.669 (3.70), 2.673 (2.61), 3.164 (4.14), 3.180 (4.53), 3.188 (5.04), 3.445 (4.65), 3.565 (14.02), 3.589 (0.45), 4.081 (5.04), 4.101 (4.72), 5.239 (0.89), 5.254 (2.17), 5.271 (2.74), 5.287 (2.04), 5.302 (0.83), 5.762 (0.57), 7.020 (3.38), 7.148 (3.95), 7.196 (4.33), 7.216 (8.67), 7.236 (5.48), 7.275 (3.44), 7.341 (0.45), 7.377 (1.27), 7.393 (2.80), 7.414 (3.63), 7.430 (1.85), 7.434 (1.85), 7.451 (0.76), 7.526 (5.23), 7.541 (5.23), 7.595 (5.80), 7.619 (5.61), 9.431 (3.76), 10.024 (12.56).

Example 280

N-(2,6-difluorophenyl)-5-fluoro-4-[(8R,S)-8-hydroxy-3-oxo-5,6,7,8-tetrahydro[1,2,4]triazolo[4,3-a]pyridin-2(3H)-yl]-2-{[(2S)-1,1,1-trifluoropropan-2-yl]oxy}benzamide, mixture of diastereomers

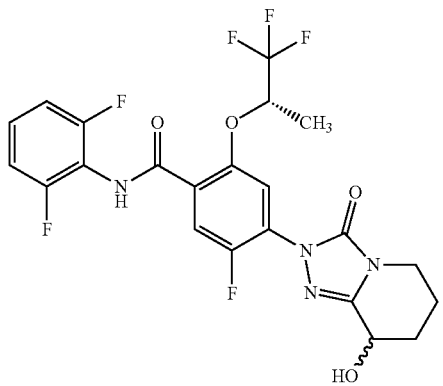 [SMILES: C[C@H](Oc1cc(-n2nc3n(c2=O)CCCC3O)c(F)cc1C(=O)Nc1c(F)cccc1F)C(F)(F)F]

Sulfuric acid (1.0 M, 4 ml) was added to a mixture of N-(2,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide (example 29) (100 mg, 200 µmol), 2-methylpropan-2-ol (4.0 ml) and cerium(4+) disulfate (266 mg, 799 µmol). The mixture was stirred at room temperature over night. Additional cerium(4+) disulfate (266 mg, 799 µmol) was added, and the mixture was stirred at 50° C. over night, after which further cerium(4+) disulfate (266 mg, 799 µmol) was added. The mixture was again stirred at 50° C. over night. The mixture was neutralized with saturated aqueous sodium hydrogen carbonate solution. The resulting precipitate was filtered and washed with water. The filtrate was extracted once with dichloromethane and twice with ethyl acetate. The combined org. layers were washed with brine, filtered via a water-repellent filter and concentrated in vacuo. Methanol (20 ml) was added and the suspension was stirred at room temperature before the insolubles were filtered. The filtrate was concentrated in vacuo and submitted to the preparative HPLC (X-Bridge Prep C18 5 µm, 0.1% aqueous formic acid, acetonitrile) to yield the title compound (4.6 mg, 4%)

LC-MS (method A): $R_t$=1.06 min; MS (ESIpos): m/z=517.4 [M+H]$^+$

¹H-NMR (600 MHz, METHANOL-d4) δ [ppm]: −0.006 (2.70), 0.005 (2.26), 1.285 (0.95), 1.555 (1.83), 1.567 (16.00), 1.578 (15.09), 1.922 (0.48), 1.933 (0.95), 1.951 (1.99), 1.969 (3.57), 1.974 (3.57), 1.988 (1.75), 2.003 (0.79), 2.006 (0.79), 2.013 (0.52), 2.064 (1.19), 2.072 (1.55), 2.082 (1.79), 2.090 (2.06), 2.099 (1.11), 2.107 (1.03), 2.203 (0.95), 2.220 (1.43), 2.225 (1.75), 2.228 (1.63), 2.237 (1.31), 2.241 (1.15), 2.250 (0.87), 2.259 (0.48), 2.656 (0.75), 2.778 (0.60), 2.788 (0.99), 2.799 (0.52), 3.608 (1.19), 3.616 (1.43), 3.621 (1.35), 3.629 (2.74), 3.637 (1.95), 3.641 (1.99), 3.649 (1.63), 3.674 (0.67), 3.684 (1.07), 3.698 (1.75), 3.708 (3.18), 3.718 (2.26), 3.729 (1.95), 3.738 (0.87), 4.629 (0.56), 4.762 (2.42), 4.770 (4.61), 4.780 (2.50), 5.144 (0.91), 5.152 (1.99), 5.163 (2.54), 5.173 (1.91), 5.184 (0.83), 6.480 (0.75), 6.495 (0.79), 7.086 (5.36), 7.100 (10.08), 7.114 (6.03), 7.355 (0.95), 7.365 (2.14), 7.369 (2.02), 7.379 (3.53), 7.389 (1.91), 7.393 (1.87), 7.403 (0.83), 7.495 (0.56), 7.504 (0.56), 7.531 (6.00), 7.540 (5.92), 7.677 (0.64), 7.694 (0.95), 7.703 (5.48), 7.719 (5.40), 7.894 (1.03).

Example 281

5-chloro-N-(2,6-difluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

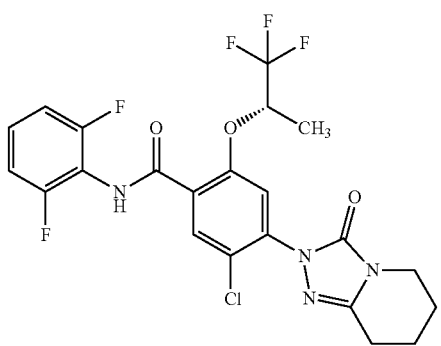 [SMILES: C[C@H](Oc1cc(-n2nc3n(c2=O)CCCC3)c(Cl)cc1C(=O)Nc1c(F)cccc1F)C(F)(F)F]

Two a solution of S-5-chloro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid (intermediate 44, crude product from previous step, 50.0 mg, 80%-UV) in dichloromethane (3.6 ml) was added two drops of N,N-dimethylformamide followed by oxalyl chloride (11 µl, 140 µmol) at 0° C. The cooling bath was removed and the mixture was stirred for 90 min at room temperature. The solution was concentrated under reduced pressure and subsequently dried in an oil pump vacuum. 2,6-difluoroaniline (17.5 mg, 136 µmol) was dissolved in 2 ml dichloromethane and triethylamine (19 µl, 140 µmol) was added. The solution was cooled to 0° C. and a solution of the pre-formed acid chloride in 2 ml dichloromethane was slowly added. The mixture was stirred at room temperature for 1 h. The reaction mixture was then concentrated under reduced pressure and purified by preparative HPLC (XBridge Prep C18 5µ OBD; solvents: water (+0.1% ammonia), acetonitrile; gradient 5%-95% acetonitrile in 10 min; flow: 30 ml/min) to yield the desired product (28 mg, 99%-UV, 25% over 4 steps).

LC-MS (Method B): $R_t$=1.20 min; MS (ESIpos): m/z=517 [M+H]$^+$

¹H-NMR (400 MHz, CHLOROFORM-d) δ [ppm]: 0.860 (0.55), 0.870 (0.43), 0.879 (0.72), 0.895 (0.71), 0.922 (0.53), 0.927 (1.46), 0.940 (0.83), 0.944 (3.23), 0.950 (0.51), 0.960 (1.88), 0.972 (0.90), 1.019 (0.78), 1.031 (0.46), 1.041 (8.50), 1.048 (0.63), 1.079 (0.45), 1.090 (2.26), 1.097 (0.71), 1.111 (6.27), 1.118 (1.28), 1.141 (0.89), 1.160 (0.42), 1.195 (3.10), 1.263 (2.68), 1.282 (6.27), 1.300 (5.25), 1.352 (0.80), 1.373 (0.65), 1.458 (0.46), 1.492 (0.42), 1.534 (1.80), 1.570 (7.51), 1.645 (15.68), 1.661 (16.00), 1.813 (0.57), 1.885 (0.52), 1.919 (1.01), 1.937 (3.98), 1.949 (3.72), 1.960 (3.78), 1.964 (4.01), 1.976 (1.93), 1.981 (1.96), 2.001 (1.97), 2.016 (3.69), 2.020 (3.84), 2.031 (4.06), 2.036 (3.37), 2.045 (2.53), 2.059 (1.13), 2.140 (0.77), 2.166 (0.73), 2.800 (5.39), 2.816 (10.39), 2.832 (6.01), 3.309 (1.03), 3.719 (6.74), 3.735 (11.20), 3.750 (5.09), 3.893 (0.45), 4.026 (0.55), 4.891 (1.09), 4.906 (2.56), 4.921 (3.31), 4.937 (2.50), 4.952 (1.07), 5.317 (0.51), 6.986 (1.31), 6.993 (5.45), 7.013 (10.68), 7.032 (7.20), 7.218 (1.28), 7.233 (3.81), 7.244 (14.74), 7.254 (4.79), 7.261 (2.47), 7.291 (1.17), 7.529 (0.53), 8.443 (14.21), 8.889 (5.04).

Examples 282-283 were prepared and purified by preparative HPLC as described for example 281 from 5-chloro-4-(3-oxo-5,6,7,8-tetrahydro[1,2,4]triazolo[4,3-a]pyridin-2 (3H)-yl)-2-{[(2S)-1,1,1-trifluoropropan-2-yl]oxy}benzoic acid (intermediate 44) and the respective amines, as indicated.

Example 282

5-chloro-N-(2-chloro-6-fluorophenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

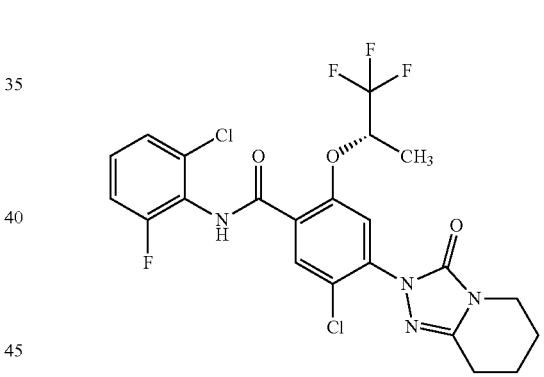

The title compound was prepared from intermediate 44 and 2-chloro-6-fluoroaniline.

LC-MS (Method B): $R_t$=1.24 min; MS (ESIpos): m/z=533 [M+H]$^+$

¹H-NMR (400 MHz, CHLOROFORM-d) δ [ppm]: 0.888 (0.47), 0.896 (0.48), 0.927 (0.76), 0.944 (0.70), 0.960 (1.10), 1.041 (4.61), 1.091 (0.44), 1.111 (1.18), 1.195 (0.83), 1.263 (3.22), 1.283 (3.83), 1.300 (3.16), 1.352 (0.74), 1.375 (0.46), 1.440 (0.52), 1.459 (0.92), 1.477 (0.61), 1.534 (1.58), 1.567 (9.20), 1.652 (15.71), 1.668 (16.00), 1.920 (1.01), 1.938 (2.95), 1.950 (3.81), 1.965 (4.07), 1.982 (2.02), 2.002 (2.00), 2.021 (3.92), 2.032 (4.11), 2.046 (2.56), 2.060 (1.02), 2.167 (0.45), 2.802 (5.17), 2.818 (9.99), 2.834 (5.58), 3.310 (0.67), 3.721 (6.23), 3.737 (10.60), 3.751 (4.86), 4.915 (1.10), 4.931 (2.55), 4.946 (3.31), 4.961 (2.52), 4.976 (1.03), 5.319 (0.45), 7.006 (0.55), 7.111 (1.90), 7.114 (2.14), 7.134 (4.56), 7.154 (2.66), 7.158 (2.85), 7.220 (1.79), 7.234 (2.61), 7.241 (5.08), 7.249 (14.50), 7.254 (6.38), 7.261 (4.84), 7.288 (7.08), 7.307 (2.79), 7.529 (0.53), 8.459 (12.91), 8.941 (4.90).

Example 283

5-chloro-N-[1-(4-fluorophenyl)cyclopropyl]-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

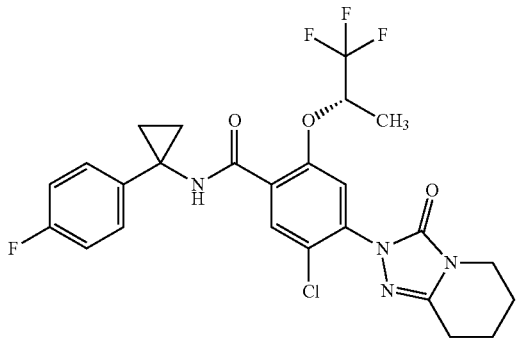 [SMILES: C[C@H](Oc1cc(-n2nc3n(c2=O)CCCC3)c(Cl)cc1C(=O)NC1(c2ccc(F)cc2)CC1)C(F)(F)F]

The title compound was prepared from intermediate 44 and 1-(4-fluorophenyl)cyclopropan-1-amine.

LC-MS (Method B): $R_t$=1.26 min; MS (ESIpos): m/z=539 [M+H]$^+$ $^1$H-NMR (400 MHz, CHLOROFORM-d) δ [ppm]: 1.041 (2.22), 1.194 (1.20), 1.262 (0.95), 1.282 (13.05), 1.302 (16.00), 1.307 (8.97), 1.327 (0.48), 1.412 (0.65), 1.533 (0.48), 1.571 (10.56), 1.587 (11.30), 1.906 (0.51), 1.913 (0.68), 1.922 (1.46), 1.929 (1.78), 1.934 (1.98), 1.945 (2.01), 1.949 (2.15), 1.961 (0.97), 1.965 (1.02), 1.986 (1.04), 1.992 (0.96), 2.000 (1.95), 2.006 (2.04), 2.016 (2.15), 2.021 (1.75), 2.030 (1.30), 2.044 (0.54), 2.780 (3.06), 2.796 (5.97), 2.812 (3.36), 3.056 (0.64), 3.699 (3.89), 3.715 (6.37), 3.730 (2.82), 4.783 (0.63), 4.799 (1.47), 4.814 (1.91), 4.830 (1.40), 4.845 (0.57), 6.957 (0.42), 6.965 (4.12), 6.970 (1.33), 6.982 (1.57), 6.987 (8.68), 6.992 (1.52), 7.003 (1.42), 7.009 (4.67), 7.017 (0.49), 7.118 (9.55), 7.312 (0.50), 7.319 (4.77), 7.325 (1.75), 7.333 (4.90), 7.336 (1.94), 7.341 (4.41), 7.349 (1.65), 7.355 (4.18), 8.027 (3.02), 8.297 (12.49).

Example 284

5-chloro-N-[2-(difluoromethyl)phenyl]-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

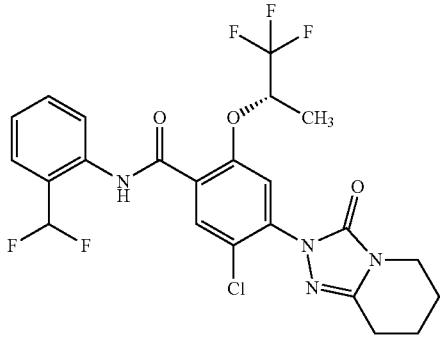 [SMILES: C[C@H](Oc1cc(-n2nc3n(c2=O)CCCC3)c(Cl)cc1C(=O)Nc1ccccc1C(F)F)C(F)(F)F]

5-Chloro-4-(3-oxo-5,6,7,8-tetrahydro[1,2,4]triazolo[4,3-a]pyridin-2(3H)-yl)-2-{[(2S)-1,1,1-tri-fluoropropan-2-yl]oxy}benzoic acid (intermediate 44, crude product from previous step, 50.0 mg, 80%-UV) was dissolved in N,N-dimethylformamide and to this solution was added 1-[bis(dimethylamino)methylene]-1H-[1,2,3]triazolo[4,5-b]pyridin-1-ium 3-oxide hexafluorophosphate (HATU) (93.7 mg, 246 μmol). After stirring for 20 min at room temperature, 2-(difluoromethyl)aniline (35.3 mg, 246 μmol) and N,N-diisopropylethylamine (260 μl, 1.5 mmol) were added subsequently and the mixture was stirred overnight. The reaction mixture was then concentrated under reduced pressure and the residue was purified by preparative HPLC (XBridge Prep C18 5μ OBD; solvents: water (+0.1% ammonia), acetonitrile; gradient 5%-95% acetonitrile in 10 min; flow: 30 ml/min) to yield the desired product (13 mg, 99%-UV, 12% over 4 steps).

LC-MS (Method B): $R_t$=1.25 min; MS (ESIpos): m/z=531 [M+H]$^+$ $^1$H-NMR (400 MHz, CHLOROFORM-d) δ [ppm]: 0.134 (1.01), 0.878 (0.42), 0.888 (0.43), 0.894 (0.48), 0.927 (0.99), 1.041 (6.11), 1.188 (0.67), 1.195 (1.43), 1.205 (1.41), 1.210 (1.87), 1.214 (1.88), 1.227 (1.91), 1.230 (1.88), 1.263 (3.75), 1.283 (4.75), 1.300 (3.96), 1.439 (1.22), 1.455 (1.24), 1.516 (0.46), 1.534 (1.52), 1.574 (16.00), 1.628 (14.86), 1.644 (15.04), 1.924 (1.21), 1.939 (3.05), 1.951 (4.03), 1.963 (3.99), 1.966 (4.25), 1.982 (2.23), 2.002 (2.32), 2.018 (4.61), 2.033 (4.26), 2.047 (2.61), 2.061 (1.08), 2.315 (0.57), 2.701 (2.70), 2.775 (0.47), 2.791 (1.15), 2.801 (5.44), 2.817 (10.51), 2.833 (5.96), 3.039 (0.65), 3.706 (0.60), 3.723 (7.23), 3.738 (11.46), 3.753 (5.14), 4.862 (0.99), 4.877 (2.36), 4.892 (3.07), 4.908 (2.32), 4.923 (0.99), 6.607 (3.41), 6.744 (6.76), 6.883 (3.24), 7.062 (0.96), 7.251 (13.32), 7.309 (2.12), 7.327 (4.52), 7.346 (2.82), 7.535 (2.19), 7.551 (7.27), 7.570 (5.49), 7.647 (0.91), 7.941 (3.99), 7.962 (3.86), 8.387 (15.06), 9.283 (4.26).

Examples 285-289 were prepared and purified by preparative HPLC as described for example 284 from 5-chloro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzoic acid (intermediate 44) and the respective amines, as indicated.

Example 285

5-chloro-N-(4-methylpyridazin-3-yl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

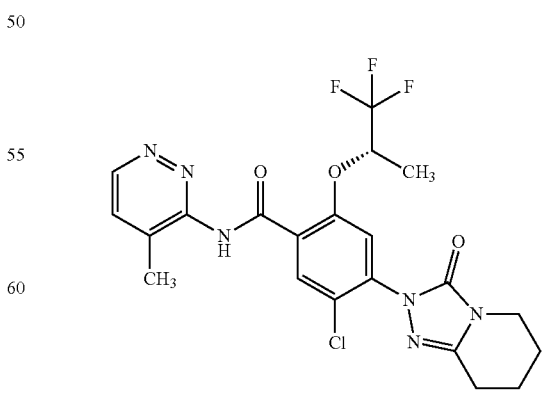

The title compound was prepared from intermediate 44 and 4-methylpyridazin-3-amine.

LC-MS (Method B): R$_t$=0.92 min; MS (ESIpos): m/z=497 [M+H]$^+$ $^1$H-NMR (400 MHz, CHLOROFORM-d) δ [ppm]: 1.216 (0.43), 1.261 (0.78), 1.589 (5.57), 1.698 (5.73), 1.715 (5.79), 1.933 (0.55), 1.941 (1.18), 1.948 (1.44), 1.953 (1.60), 1.965 (1.67), 1.969 (1.77), 1.981 (0.84), 1.984 (0.86), 2.005 (0.86), 2.020 (1.57), 2.025 (1.67), 2.035 (1.75), 2.040 (1.47), 2.050 (1.08), 2.063 (0.47), 2.102 (0.41), 2.375 (16.00), 2.805 (2.47), 2.812 (1.20), 2.820 (4.82), 2.836 (2.74), 3.724 (3.13), 3.739 (5.23), 3.754 (2.31), 4.903 (0.89), 4.919 (1.15), 4.934 (0.86), 7.407 (2.31), 7.410 (2.40), 7.420 (2.42), 7.422 (2.41), 7.939 (0.43), 8.125 (0.44), 8.393 (5.22), 8.986 (2.31), 8.998 (2.26), 9.714 (2.07).

Example 286

5-chloro-N-(6-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

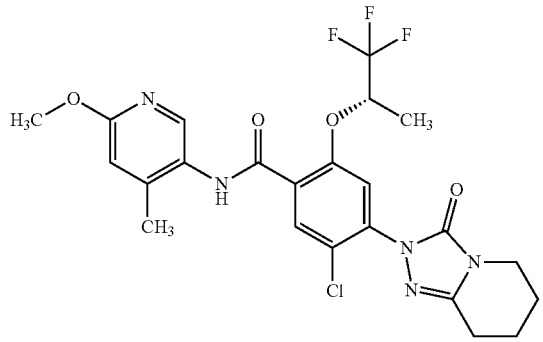 [SMILES: COc1cc(C)c(NC(=O)c2cc(Cl)c(-n3nc4n(c3=O)CCCC4)cc2O[C@@H](C)C(F)(F)F)cn1]

The title compound was prepared from intermediate 44 and 6-methoxy-4-methylpyridin-3-amine.

LC-MS (Method B): R$_t$=1.15 min; MS (ESIpos): m/z=526 [M+H]$^+$ $^1$H-NMR (400 MHz, CHLOROFORM-d) δ [ppm]: 1.041 (1.11), 1.262 (0.78), 1.282 (7.59), 1.299 (0.78), 1.590 (2.70), 1.637 (4.20), 1.652 (4.21), 1.938 (0.66), 1.950 (0.92), 1.962 (0.93), 1.965 (1.01), 1.981 (0.50), 2.002 (0.49), 2.022 (0.96), 2.032 (1.01), 2.037 (0.85), 2.046 (0.63), 2.256 (9.96), 2.800 (1.30), 2.816 (2.58), 2.833 (1.48), 3.720 (1.63), 3.735 (2.76), 3.751 (1.25), 3.941 (16.00), 4.896 (0.65), 4.911 (0.84), 4.926 (0.63), 6.668 (2.71), 7.223 (3.89), 8.327 (3.31), 8.415 (4.84), 8.768 (1.49).

Example 287

5-chloro-N-(2-methoxy-4-methylpyridin-3-yl)-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

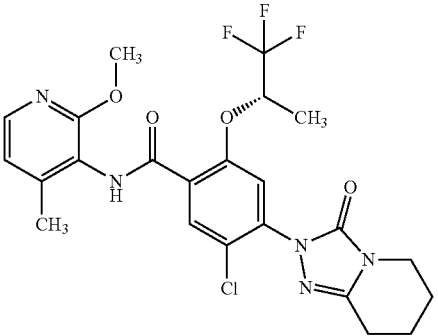

The title compound was prepared from intermediate 44 and 2-methoxy-4-methylpyridin-3-amine.

LC-MS (Method B): R$_t$=1.16 min; MS (ESIpos): m/z=526 [M+H]$^+$ $^1$H-NMR (400 MHz, CHLOROFORM-d) δ [ppm]: 1.041 (1.53), 1.252 (0.49), 1.262 (0.71), 1.282 (13.71), 1.300 (1.08), 1.587 (4.93), 1.652 (4.45), 1.669 (4.56), 1.939 (0.75), 1.951 (1.04), 1.966 (1.13), 1.982 (0.57), 2.002 (0.57), 2.022 (1.10), 2.032 (1.14), 2.046 (0.72), 2.277 (12.02), 2.802 (1.41), 2.818 (2.85), 2.834 (1.63), 3.722 (1.83), 3.738 (3.05), 3.753 (1.40), 3.960 (16.00), 4.916 (0.70), 4.931 (0.92), 4.947 (0.69), 6.828 (1.83), 6.841 (1.91), 7.228 (4.06), 7.958 (2.27), 7.970 (2.19), 8.410 (5.04), 8.880 (1.58).

Example 288

5-chloro-N-(4-fluoro-2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

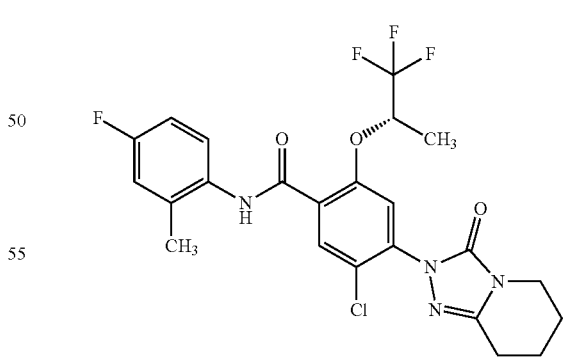

The title compound was prepared from intermediate 44 and 4-fluoro-2-methylaniline.

LC-MS (Method B): R$_t$=1.26 min; MS (ESIpos): m/z=513 [M+H]$^+$ $^1$H-NMR (400 MHz, CHLOROFORM-d) δ [ppm]: 0.133 (0.56), 0.927 (0.71), 1.041 (5.52), 1.195 (0.52), 1.262 (1.62), 1.282 (6.14), 1.300 (3.56), 1.534 (0.97), 1.585 (4.34), 1.626

(6.65), 1.642 (6.75), 1.939 (1.08), 1.951 (1.53), 1.966 (1.65), 1.982 (0.82), 2.003 (0.78), 2.018 (1.54), 2.023 (1.56), 2.033 (1.65), 2.047 (1.02), 2.061 (0.45), 2.294 (16.00), 2.800 (2.10), 2.817 (4.21), 2.833 (2.41), 3.722 (2.64), 3.737 (4.48), 3.752 (2.08), 4.880 (0.44), 4.895 (1.06), 4.911 (1.37), 4.926 (1.05), 4.941 (0.43), 6.933 (0.43), 6.940 (0.92), 6.958 (3.27), 6.979 (2.91), 7.228 (6.08), 7.714 (0.99), 7.721 (0.49), 7.728 (1.00), 7.732 (1.02), 7.739 (1.02), 7.751 (0.87), 8.415 (7.35), 8.845 (1.95).

Example 289

5-chloro-N-(2-methylphenyl)-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

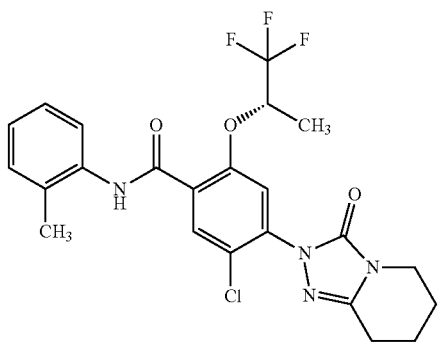 [SMILES: Cc1ccccc1NC(=O)c1cc(Cl)c(-n2nc3n(c2=O)CCCC3)cc1O[C@@H](C)C(F)(F)F]

The title compound was prepared from intermediate 44 and 2-methylaniline.

LC-MS (Method B): $R_t$=1.25 min; MS (ESIpos): m/z=495 [M+H]$^+$ $^1$H-NMR (400 MHz, CHLOROFORM-d) δ [ppm]: 0.000 (1.18), 0.844 (0.43), 1.007 (2.62), 1.063 (0.47), 1.078 (0.46), 1.160 (2.87), 1.229 (3.13), 1.248 (0.51), 1.265 (1.74), 1.499 (0.51), 1.541 (2.06), 1.558 (0.93), 1.585 (6.44), 1.602 (6.50), 1.895 (0.47), 1.904 (1.03), 1.911 (1.27), 1.916 (1.42), 1.927 (1.46), 1.932 (1.57), 1.943 (0.71), 1.947 (0.74), 1.968 (0.75), 1.973 (0.69), 1.983 (1.39), 1.987 (1.47), 1.998 (1.56), 2.003 (1.29), 2.012 (0.96), 2.026 (0.42), 2.280 (16.00), 2.766 (2.23), 2.782 (4.25), 2.799 (2.50), 3.688 (2.85), 3.704 (4.64), 3.718 (2.07), 4.839 (0.43), 4.855 (1.03), 4.870 (1.36), 4.886 (0.99), 4.901 (0.41), 7.094 (0.69), 7.097 (0.73), 7.113 (1.65), 7.116 (1.81), 7.131 (1.37), 7.134 (1.34), 7.200 (6.41), 7.209 (2.25), 7.218 (1.35), 7.224 (1.53), 7.228 (1.65), 7.256 (0.81), 7.843 (1.92), 7.864 (1.67), 8.389 (8.46), 8.878 (1.71).

Example 290

N-(2,6-difluoro-4-hydroxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide Step A: Synthesis of N-(2,6-difluoro-4-methoxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide

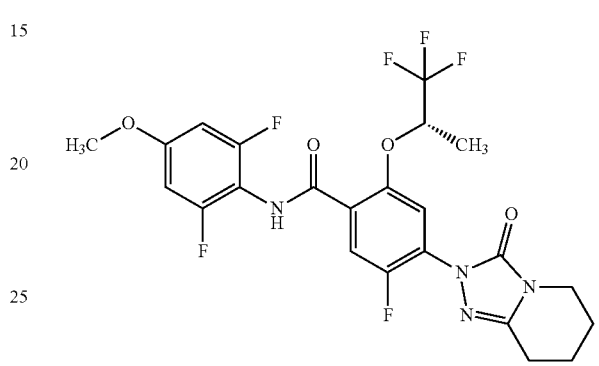

Synthesized analogously to Example 1 from intermediate 17 and 2,6-difluoro-4-methoxyaniline.

LC-MS (method A): $R_t$=1.23 min; MS (ESIpos): m/z=531.1 [M+H]$^+$ $^1$H-NMR (400 MHz, DMSO-d6) δ[ppm]: 1.424 (5.64), 1.439 (5.73), 1.794 (1.15), 1.806 (1.64), 1.820 (1.67), 1.834 (0.86), 1.889 (1.68), 1.900 (1.73), 2.084 (4.50), 2.669 (0.41), 2.695 (1.73), 2.711 (3.36), 2.727 (1.83), 3.560 (1.94), 3.576 (3.46), 3.590 (1.69), 3.801 (16.00), 5.272 (0.90), 5.289 (1.16), 5.304 (0.86), 6.843 (3.22), 6.867 (3.33), 7.530 (2.57), 7.535 (3.15), 7.545 (2.43), 7.561 (2.48), 9.736 (3.97).

Step B

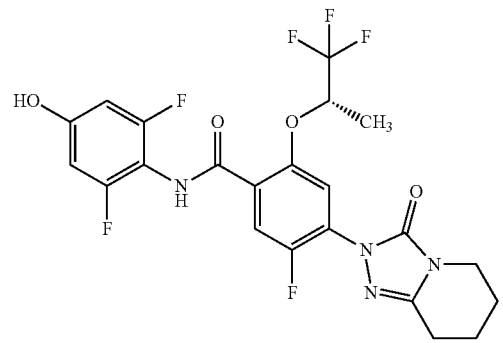 [SMILES: C[C@H](Oc1cc(-n2nc3n(c2=O)CCCC3)c(F)cc1C(=O)Nc1c(F)cc(O)cc1F)C(F)(F)F]

The product from Step A (320 mg, 603 μmol) was dissolved in dichloromethane (9.0 ml, 140 mmol) under an atmosphere of argon and cooled to −20° C. A solution of boron tribromide in dichloromethane (2.4 ml, 1.0 M, 2.4 mmol) was added dropwise. The mixture was stirred at 0° C. for 4h and at 6° C. for an additional 60h. The mixture was quenched at 0° C. with a mixture of methanol and water. The phases were separated and the aqueous phase was extracted once more with dichloromethane. The combined organic phases were washed with brine, dried over sodium sulfate and concentrated. HPLC purification yielded the desired product 82.0 mg (97% purity, 26% yield).

LC-MS (method C): $R_t$=1.07 min; MS (ESIpos): m/z=517 [M+H]$^+$ $^1$H-NMR (400 MHz, DMSO-d6) δ[ppm]: 1.418 (9.52), 1.434 (9.57), 1.793 (1.69), 1.805 (2.43), 1.820 (2.50), 1.833 (1.22), 1.888 (2.48), 1.899 (2.56), 2.084 (16.00), 2.327 (0.99), 2.522 (2.98), 2.669 (1.09), 2.694 (2.73), 2.709 (5.45), 2.725 (2.90), 3.558 (3.17), 3.574 (5.70), 3.589 (2.61), 5.249 (0.62), 5.265 (1.49), 5.282 (1.96), 5.297 (1.42), 5.313 (0.55), 6.539 (5.60), 6.562 (5.70), 7.515 (5.04), 7.521 (4.29), 7.536 (4.57), 7.540 (5.18), 9.611 (6.85), 10.432 (0.42).

Example 291

N-(2,6-difluoro-3-hydroxyphenyl)-5-fluoro-4-(3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

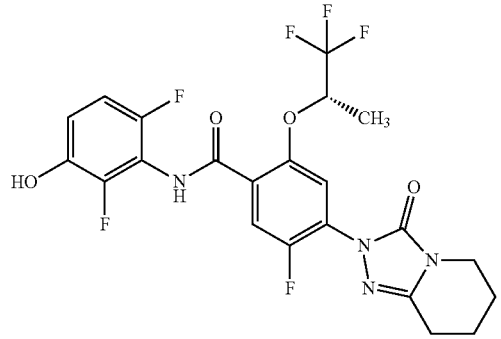 [SMILES: C[C@H](Oc1cc(-n2nc3n(c2=O)CCCC3)c(F)cc1C(=O)Nc1c(F)ccc(O)c1F)C(F)(F)F]

Synthesized analogously to Example 290 from N-(2,6-difluoro-3-methoxyphenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide which was synthesized analogously to Example 1 from intermediate 17 and 2,6-difluoro-3-methoxyaniline.

LC-MS (Method A): $R_t$=1.07 min; MS (ESIpos): m/z=517 [M+H]$^+$ $^1$H-NMR (400 MHz, DMSO-d6) δ[ppm]: 1.232 (0.51), 1.426 (11.47), 1.442 (11.41), 1.795 (2.60), 1.807 (3.69), 1.821 (3.79), 1.834 (1.87), 1.875 (1.84), 1.890 (3.82), 1.900 (3.97), 1.913 (2.46), 1.928 (0.96), 2.084 (3.32), 2.518 (3.59), 2.523 (2.44), 2.696 (4.05), 2.712 (7.98), 2.728 (4.21), 3.561 (4.74), 3.577 (8.55), 3.591 (3.91), 3.856 (0.46), 5.264 (0.78), 5.280 (1.88), 5.296 (2.42), 5.312 (1.76), 5.328 (0.73), 5.759 (1.03), 6.868 (0.88), 6.881 (1.08), 6.891 (2.24), 6.903 (2.33), 6.913 (1.82), 6.926 (1.60), 6.951 (2.14), 6.973 (2.99), 6.996 (1.12), 7.536 (4.66), 7.547 (6.38), 7.571 (4.71), 9.920 (16.00).

Example 292

N-(2,6-difluorophenyl)-5-fluoro-4-(8-imino-3,8-dioxo-5,6,7,8-tetrahydro-8λ$^6$-[1,2,4]triazolo-[3,4-b][1,3]thiazin-2(3H)-yl)-2-{[(2S)-1,1,1-trifluoropropan-2-yl]oxy}benzamide

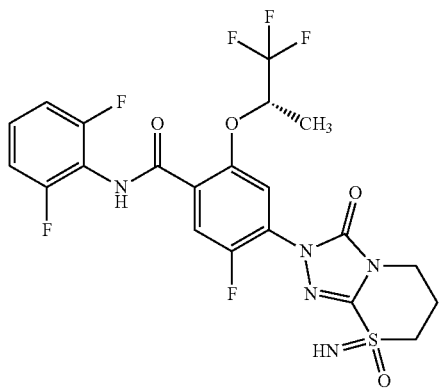 [SMILES: C[C@H](Oc1cc(-n2nc3n(c2=O)CCCS3(=N)=O)c(F)cc1C(=O)Nc1c(F)cccc1F)C(F)(F)F]

Following a procedure by Tota et al. (Chem. Commun. 2017, 53, 348-351)N-(2,6-difluorophenyl)-5-fluoro-4-(3-oxo-6,7-dihydro-5H-[1,2,4]triazolo[3,4-b][1,3]thiazin-2(3H)-yl)-2-{[(2S)-1,1,1-trifluoropropan-2-yl]oxy}benzamide (Example 250, 43.0 mg, 82.9 μmol) was dissolved in methanol (500 μl). Ammonium carbamate (19.4 mg, 249 μmol) was added followed by (diacetoxyiodo)benzene (53.4 mg, 166 μmol). The mixture was stirred at room temperature for 4h. The reaction mixture was filtered and purified by prepHPLC to yield the desired product 24.0 mg (95% purity, 50% yield).

LC-MS (Method A): $R_t$=1.09 min; MS (ESIpos): m/z=550 [M+H]$^+$ $^1$H-NMR (400 MHz, DMSO-d6) δ[ppm]: 1.137 (1.59), 1.232 (0.76), 1.432 (8.88), 1.438 (9.29), 1.448 (9.71), 1.453 (8.65), 1.522 (1.29), 2.085 (12.59), 2.116 (0.71), 2.327 (3.47), 2.331 (2.47), 2.336 (1.12), 2.518 (14.88), 2.523 (9.82), 2.669 (3.47), 2.673 (2.47), 2.678 (1.12), 2.729 (3.41), 2.889 (4.12), 3.452 (0.94), 3.530 (0.71), 3.543 (1.24), 3.564 (1.76), 3.580 (2.41), 3.593 (1.53), 3.611 (1.71), 3.623 (2.65), 3.640 (1.82), 3.661 (1.53), 3.674 (0.76), 3.773 (4.71), 3.787 (8.76), 3.802 (4.47), 5.270 (0.82), 5.286 (1.88), 5.301 (2.41), 5.316 (1.82), 5.333 (0.76), 5.760 (16.00), 5.924 (7.65), 7.195 (4.18), 7.215 (8.71), 7.235 (5.41), 7.374 (0.94), 7.390 (2.12), 7.411 (2.76), 7.427 (1.65), 7.447 (0.71), 7.605 (4.65), 7.619 (4.82), 7.631 (6.35), 7.656 (5.94), 7.950 (0.47), 10.067 (10.41).

Example 293

N-(2,6-difluorophenyl)-5-fluoro-4-(7-hydroxy-3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

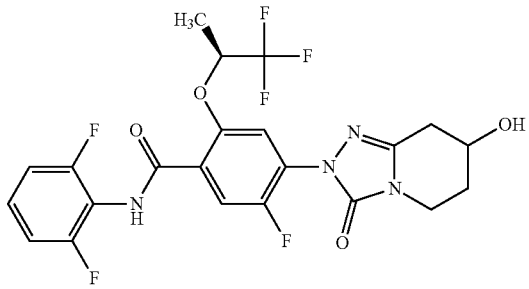 [SMILES: C[C@H](Oc1cc(-n2nc3n(c2=O)CCC(O)C3)c(F)cc1C(=O)Nc1c(F)cccc1F)C(F)(F)F]

LIST OF ABBREVIATIONS

ATP adenosine triphosphate
BSA bovine serum albumin
CYP Cytochrome P450 enzyme
DNA deoxyribonucleic acid
dNTP deoxynucleoside triphosphate
Δ deletion from amino acid
EDTA Ethylenediaminetetraacetate
HMFM Hogness Modified Freezing medium
LB Luria-Bertani broth
LPSd lipopolysaccharide deficient
mod modified
OD550 optical density at 550 nm
PCR polymerase chain reaction
pelB pelB Leader sequence from thr vector pET22b+
POR human cytochrome p450 oxidoreductase
rpm rotation per minute
SAP shrimp alkaline phosphatase The company GENE Bridges/Heidelberg performed a knockout of the gene rfaP of *Escherichia coli* DH5α providing the strain *Escherichia coli* DH5α LPSd.

Culture media were prepared in demineralized water and sterilized at 121° C. for 20 minutes or sterile filtered. All solutions were prepared with MilliQ water and sterile filtered, unless otherwise described. All preparations were performed under sterile conditions.

Luria-Bertani broth (LB) medium: 10 g/L bacto tryptone, 5 g/L bacto yeast extract, 10 g/L sodium chloride.

Luria-Bertani broth agar: 10 g/L bacto tryptone, 5 g/L bacto yeast extract, 10 g/L sodium chloride, 15 g/L agar, 50 mg/L ampicillin, 17 mg/L chloramphenicol.

10× Hogness Modified Freezing medium (HMFM): aqueous solution of 0.27M $KH_2PO_4$(monopotassiumphosphate), 0.13M $K_2HPO_4$, 68 mM $(NH_4)_2SO_4$, 4 mM $MgSO4$, 15 mM trisodium citrate, 36 w/v % glycerol.

2 fold yeast tryptone (2YT) medium: 16 g/L bacto tryptone, 10 g/L bacto yeast extract, 5 g/L sodium chloride.

Plasmid 1: pACYC_pelB_POR:

The pACYC_pelB_POR-plasmid is a derivate of the commercially available pACYC(Duet)-plasmid of the company Novagen. To generate this plasmid two fragments, pACYC_mod and pelB_POR were ligated.

Creation of the pelB_POR Fragment:

The human NAPDH hemoprotein reductase (POR) was amplified via two primer containing the restriction sites BamHI (GAGGATCCGATGGGAGACTCCCACGTG) (SEQ ID NO: 3) and SalI (GAGAGTCGACCTAGCTCCACACGTCCAG) (SEQ ID NO: 4) out of the plasmid pMPSV-CMV::hOR. pMPSV-CMV::hOR plasmid (1 μL) was mixed with MilliQ water (51.5 μL), expand buffer with MgCl2 (7.5 μL), dNTPs (6 μL), Taq-Expand (1 μL), forward primer (4 μL) and reverse primer (4 μL). The PCR was performed according to the following procedure: 1) 94° C. for 5 minutes, 2) 94° C. for 30 seconds, 3) 60° C. for 30 seconds, 4) 72° C. for 90 seconds, 5) go back to step 2 (30 cycles), 6) 72° C. for 5 minutes, 7) 15° C. forever. To combine the POR with an upstream pelB-sequence, the POR has to be cloned into the empty vector pET22b+. As well as the amplified PCR fragment the empty vector pET22b+, provided by the company Novagen, was digested with the restriction enzymes BamHI and SalI. The first digestion was performed with BamHI. Either the empty vector pET22b+ or the amplified PCR fragment (30 μL) was mixed with 10× buffer NEB3.1 (4 μl), BSA solution (10 mg/mL, 0.4 μL), BamHI restriction enzyme (1 μL) and MilliQ water (5 μL). After incubation at 37° C. for 1 hour the reaction was stopped by incubating for 20 minutes at 65° C. The digested PCR fragment and empty vector pET22b+ were purified via the QIAquick PCR Purification kit from Qiagen. Afterwards the second digestion was performed with SalI. Either the BamHI digested empty vector pET22b+ or the BamHI digested PCR fragment (30 μL) was mixed with 10× buffer NEB3.1 (4 μl), BSA solution (10 mg/mL, 0.4 μL), SalI restriction enzyme (1 μL) and MilliQ water (5 μL). After incubation at 37° C. for 1 hour the reaction was stopped by incubating for 20 minutes at 65° C. For the double-digested vector a dephosphorylation with a shrimp alkaline phosphatase followed. The double-digested empty vector pET22b+(40 μL) was mixed with 10×SAP buffer (5 μl), SAP enzyme (2 μL) and MilliQ water (3 μL). After incubation at 37° C. for 30 minutes the reaction was stopped by incubating for 20 minutes at 65° C. The double-digested PCR fragment and the dephosphorylated double-digested empty vector were purified via the QIAquick PCR Purification kit from Qiagen. Afterwards a gel extraction with the QIAquick Gel Extraction Kit from Qiagen followed. The ligation of the double-digested POR and the double-digested pET22b+-vector was performed with T4 DNA Ligase. Cut vector (1 μL) was mixed with PCR product (1 μL), 10× Ligase buffer with 10 mM ATP (1.5 μL), T4 DNA Ligase (1 μL) and MilliQ water (10.5 μL). After incubation for 30 minutes at room temperature the ligated DNA was purified by ethanol precipitation. Ligated DNA (15 μL) was mixed with glycogen (1 μL), ammonium acetate (7.5 μL) and 100% ethanol (37.5 μL). After 5 minutes at room temperature a centrifugation at 14000 rpm for 5 minutes was used to precipitate the DNA. The supernatant was removed and the DNA washed with 75% ethanol (100 μL), before the DNA was air-dried and resuspended in MilliQ water (12 μL). The ligated DNA was digested with the restriction enzymes NdeI und XhoI. The first digestion was performed with NdeI. The ligated DNA (30 μL) was mixed with 10× buffer NEB4 (4 μl), NdeI restriction enzyme (1 μL) and MilliQ water (5 μL). After incubation at 37° C. for 1 hour the reaction was stopped by incubating for 20 minutes at 65° C. The digested vector was purified via the QIAquick PCR Purification kit from Qiagen. Afterwards the second digestion was performed with XhoI. The NdeI digested DNA (30 μL) was mixed with 10× buffer NEB4 (4 μl), BSA solution (10 mg/mL, 0.4 μL), XhoI restriction enzyme (1 µL) and MilliQ water (5 µL). After incubation at 37° C. for 1 hour the reaction was stopped by incubating for 20 minutes at 65° C. The double-digested DNA was purified via the QIAquick PCR Purification kit from Qiagen. Afterwards a gel extraction with the QIAquick Gel Extraction Kit from Qiagen followed to isolate the pelB_POR fragment.

Creation of the pACYC_mod Fragment:

To change the upstream promoter of the pACYC(Duet)-vector, the pACYC(Duet)-vector as well as the pCW_CYP1A2 vector, provided by the company Oxford Biomedical Research, was digested with the restriction enzymes MluI and XhoI.

The first digestion was performed with MluI. Either the pACYC(Duet)-vector or the pCW_CYP1A2 vector (30 µL) was mixed with 10× buffer NEB3.1 (4 µl), BSA solution (10 mg/mL, 0.4 µL), MluI restriction enzyme (1 µL) and MilliQ water (5 µL). After incubation at 37° C. for 1 hour the reaction was stopped by incubating for 20 minutes at 65° C. The digested vector was purified via the QIAquick PCR Purification kit from Qiagen. Afterwards the second digestion was performed with XhoI. Either the MluI digested pACYC(Duet)-vector or the MluI digested pCW_CYP1A2 (30 µL) was mixed with 10× buffer NEB3.1 (4 µl), BSA solution (10 mg/mL, 0.4 µL), XhoI restriction enzyme (1 µL) and MilliQ water (5 µL). After incubation at 37° C. for 1 hour the reaction was stopped by incubating for 20 minutes at 65° C. For the double-digested pACYC(Duet)-vector a dephosphorylation with a shrimp alkaline phosphatase followed. The double-digested pACYC(Duet) vector (40 µL) was mixed with 10×SAP buffer (5 µl), SAP enzyme (2 µL) and MilliQ water (3 µL). After incubation at 37° C. for 30 minutes the reaction was stopped by incubating for 20 minutes at 65° C. The double-digested CYP1A2 fragment and the dephosphorylated double-digested pACYC(Duet) vector were purified via the QIAquick PCR Purification kit from Qiagen. Afterwards a gel extraction with the QIAquick Gel Extraction Kit from Qiagen followed. The ligation of the double-digested CYP1A2 fragment and the double-digested pACYC(Duet)-vector was performed with T4 DNA Ligase. The cut vector (1 µL) was mixed with cut CYP1A2 fragment (1 µL), 10× Ligase buffer with 10 mM ATP (1.5 µL), T4 DNA Ligase (1 µL) and MilliQ water (10.5 µL). After incubation for 30 minutes at room temperature the ligated DNA was purified by ethanol precipitation. Ligated DNA (15 µL) was mixed with glycogen (1 µL), ammonium acetate (7.5 µL) and 100% ethanol (37.5 µL). After 5 minutes at room temperature a centrifugation at 14000 rpm for 5 minutes was used to precipitate the DNA. The supernatant was removed and the DNA washed with 75% ethanol (100 µL), before the DNA was air-dried and resuspended in MilliQ water (12 µL). The ligated DNA was digested with the restriction enzymes NdeI und XhoI. The first digestion was performed with NdeI. The ligated DNA (30 µL) was mixed with 10× buffer NEB4 (4 µl), NdeI restriction enzyme (1 µL) and MilliQ water (5 µL). After incubation at 37° C. for 1 hour the reaction was stopped by incubating for 20 minutes at 65° C. The digested vector was purified via the QIAquick PCR Purification kit from Qiagen. Afterwards the second digestion was performed with XhoI. The NdeI digested DNA (30 µL) was mixed with 10× buffer NEB4 (4 µl), BSA solution (10 mg/mL, 0.4 µL), XhoI restriction enzyme (1 µL) and MilliQ water (5 µL). After incubation at 37° C. for 1 hour the reaction was stopped by incubating for 20 minutes at 65° C. Afterwards the double-digested pACYC_mod-vector was a dephosphorylated with a shrimp alkaline phosphatase. The vector (40 µL) was mixed with 10× SAP buffer (5 µl), SAP enzyme (2 µL) and MilliQ water (3 µL). After incubation at 37° C. for 30 minutes the reaction was stopped by incubating for 20 minutes at 65° C. It followed a PCR purification via the QIAquick PCR Purification kit from Qiagen. Afterwards a gel extraction with the QIAquick Gel Extraction Kit from Qiagen followed to isolate the pACYC_mod fragment with modified promotor.

Assembly of the pACYC_pelB_POR Plasmid:

The pelB_POR fragment (1 µL) was mixed with pACYC_mod fragment (1 µL), 10×Ligase buffer with 10 mM ATP (1.5 µL), T4 DNA Ligase (1 µL) and MilliQ water (10.5 µL). After incubation for 30 minutes at room temperature the ligated DNA was purified by ethanol precipitation. Ligated DNA (15 µL) was mixed with glycogen (1 µL), ammonium acetate (7.5 µL) and 100% ethanol (37.5 µL). After 5 minutes at room temperature a centrifugation at 14000 rpm for 5 minutes was used to precipitate the DNA. The supernatant was removed and the DNA washed with 75% ethanol (100 µL), before the DNA was air-dried and resuspended in MilliQ water (12 µL).

The analysis of the gene sequence of pACYC_pelB_POR at LGC Genomics GmbH:

Seq. ID No. 1

```
ggccgcggcaaagccgttttccataggctccgcccccctgacaagcatc
acgaaatctgacgctcaaatcagtggtggcgaaacccgacaggactata
aagataccaggcgtttccccctggcggctccctcgtgcgctctcctgtt
cctgcctttcggtttaccggtgtcattccgctgttatggccgcgtttgt
ctcattccacgcctgacactcagttccgggtaggcagttcgctccaagc
tggactgtatgcacgaaccccccgttcagtccgaccgctgcgccttatc
cggtaactatcgtcttgagtccaacccggaaagacatgcaaaagcacca
ctggcagcagccactggtaattgatttagaggagttagtcttgaagtca
tgcgccggttaaggctaaactgaaaggacaagttttggtgactgcgctc
ctccaagccagttacctcggttcaaagagttggtagctcagagaacctt
cgaaaaaccgccctgcaaggcggttttttcgttttcagagcaagagatt
acgcgcagaccaaaacgatctcaagaagatcatcttattaatcagataa
aatatttctagatttcagtgcaatttatctcttcaaatgtagcacctga
agtcagccccatacgatataagttgtaattctcatgttagtcatgcccc
gcgcccaccggaaggagctgactgggttgaaggctcaagggcatcgg
tcgagatcccggtgcctaatgagtgagctaacttacattaattgcgttg
cgctcactgcccgctttccagtcgggaaacctgtcgtgccagctgcatt
aatgaatcggccaacgcgcgggagaggcggtttgcgtattgggcgcca
gggtggttttcttttcaccagtgagacgggcaacagctgattgccctt
caccgcctggccctgagagagttgcagcaagcggtccacgctggtttgc
cccagcaggcgaaaatcctgtttgatggtggttaacggcgggatataac
atgagctgtcttcggtatcgtcgtatcccactaccgagatgtccgcacc
aacgcgcagcccggactcggtaatggcgcgcattgcgcccagcgccatc
tgatcgttggcaaccagcatcgcagtgggaacgatgccctcattcagca
tttgcatggtttgttgaaaaccggacatggcactccagtcgccttcccg
ttccgctatcggctgaatttgattgcgagtgagatatttatgccagcca
```

-continued gccagacgcagacgcgccgagacagaacttaatgggcccgctaacagcg cgatttgctggtgacccaatgcgaccagatgctccacgcccagtcgcgt accgtcttcatgggagaaaataatactgttgatgggtgtctggtcagag acatcaagaaataacgccggaacattagtgcaggcagcttccacagcaa tggcatcctggtcatccagcggatagttaatgatcagcccactgacgcg ttgcgcgagaagattgtgcaccgccgctttacaggcttcgacgccgctt cgttctaccatcgacaccaccacgctggcacccagttgatcggcgcgag atttaatcgccgcgacaatttgcgacggcgcgtgcagggccagactgga ggtggcaacgccaatcagcaacgactgtttgcccgccagttgttgtgcc acgcggttgggaatgtaattcagctccgccatcgccgcttccactttttt cccgcgttttcgcagaaacgtggctggcctggttcaccacgcgggaaac ggtctgataagagacaccggcatactctgcgacatcgtataacgttact ggtttcacattcaccaccctgaattgactctcttccgggcgctatcatg ccataccgcgaaaggttttgcaccattcgatggtgtcctggcacgacag gtttcccgactggaaagcgggcagtgagcgcaacgcaattaatgtaagt tagctcactcattaggcacccaggctttacactttatgcttccggctc gtataatgtgtggaattgtgagcggataacaatttcacacaggaaacag gatcgatccatcgatgagcttactccccatcccctgttgacaattaat catcggctcgtataatgtgtggaattgtgagcggataacaatttcacac aggaaacaggatcagcttactccccatcccctgttgacaattaatcat cggctcgtataatgtgtggaattgtgagcggataacaatttcacacagg aaacaggatccatcgatgcttaggaggtcatatgaaatacctgctgccg accgctgctgctggtctgctgctcctcgctgcccagccggcgatggcca tggatatcggaattaattcggatccgatgggagactccacgtggacac cagctccaccgtgtccgaggcggtggccgaagaagtatctcttttcagc atgacggacatgattctgttttcgctcatcgtgggtctcctaacctact ggttcctctttagaaagaaaaagaagaagtccccgagttcaccaaaat tcagacattgacctcctctgtcagagagagcagctttgtggaaaagatg aagaaaacggggaggaacatcatcgtgttctacggctcccagacgggga ctgcagaggagtttgccaaccgcctgtccaaggacgcccaccgctacgg gatgcgaggcatgtcagcggaccctgaggagtatgacctggccgacctg agcagcctgccagagatcgacaacgccctggtggttttctgcatggcca cctacggtgaggagacccaccgacaatgcccaggacttctacgactg gctgcaggagacagacgtggatctctctggggtcaagttcgcggtgttt ggtcttgggaacaagacctacgagcacttcaatgccatgggcaagtacg tggacaagcggctggagcagctcggcgcccagcgcatctttgagctggg gttgggcgacgacgatgggaacttggaggaggacttcatcacctggcga gagcagttctggccgccgtgtgtgaacactttggggtggaagccactg gcgaggagtccagcattcgccagtacgagcttgtggtccacaccgacat agatgcggccaaggtgtacatggggggagatgggccggctgaagagctac -continued gagaaccagaagccccctttgatgccaagaatccgttcctggctgcag tcaccaccaaccggaagctgaaccagggaaccgagcgccacctcatgca cctggaattggacatctcggactccaaaatcaggtatgaatctggggac cacgtggctgtgtacccagccaacgactctgctctcgtcaaccagctgg gcaaaatcctgggtgccgacctggacgtcgtcatgtccctgaacaacct ggatgaggagtccaacaagaagcacccattcccgtgccctacgtcctac cgcacggccctcacctactacctggacatcaccaacccgccgcgtacca acgtgctgtacgagctggcgcagtacgcctcggagccctcggagcagga gctgctgcgcaagatggcctcctcctccggcgagggcaaggagctgtac ctgagctgggtggtggaggcccggaggcacatcctggccatcctgcagg actgcccgtccctgcggccccccatcgaccacctgtgtgagctgctgcc gcgcctgcaggcccgctactactccatcgcctcatcctccaaggtccac cccaactctgtgcacatctgtgcggtggttgtgggagtacgagaccaagg ccggccgcatcaacaagggcgtggccaccaactggctgcgggccaagga gcctgccggggagaacggcggccgtgcgctggtgcccatgttcgtgcgc aagtcccagttccgcctgcccttcaaggccaccacgcctgtcatcatgg tgggccccggcaccggggtggcacccttcataggcttcatccaggagcg ggcctggctgcgacagcagggcaaggaggtgggggagacgctgctgtac tacggctgccgccgctcagatgaggactacctgtaccgggaggagctgg cgcagttccacagggacggtgcgctcacccagctcaacgtggccttctc ccggggagcagtcccacaaggtctacgtccagcacctgctaaagcaagac cgagagcacctgtggaagttgatcgaaggcggtgcccacatctacgtct gtggggatgcacggaacatggccagggatgtgcagaacaccttctacga catcgtggctgagctcgggggccatggagcacgcgcaggcggtggactac atcaagaaactgatgaccaagggccgctactccctggacgtgtggagct aggtcgacaagcttgcggccgcactcgagtctggtaaagaaaccgctgc tgcgaaatttgaacgccagcacatggactcgtctactagcgcagcttaa ttaacctaggctgctgccaccgctgagcaataactagcataacccttg gggcctctaaacgggtcttgaggggttttttgctgaaacctcaggcatt tgagaagcacacggtcacactgcttccggtagtcaataaaccggtaaac cagcaatagacataagcggctatttaacgaccctgccctgaaccgacga ccgggtcgaatttgctttcgaatttctgccattcatccgcttattatca cttattcaggcgtagcaaccaggcgtttaagggcaccaataactgcctt aaaaaaattacgccccgccctgccactcatcgcagtactgttgtaattc attaagcattctgccgacatggaagccatcacaaacggcatgatgaacc tgaatcgccagcggcatcagcaccttgtcgccttgcgtataatatttgc ccatagtgaaaacgggggcgaagaagttgtccatattggccacgtttaa atcaaaactggtgaaactcacccagggattggctgagacgaaaaacata ttctcaataaaccctttagggaaataggccaggttttcaccgtaacacg ccacatcttgcgaatatatgtgtagaaactgccggaaatcgtcgtggta ttcactccagagcgatgaaaacgtttcagtttgctcatggaaaacggtg -continued

```
taacaagggtgaacactatcccatatcaccagctcaccgtctttcattg ccatacggaactccggatgagcattcatcaggcgggcaagaatgtgaat aaaggccggataaaacttgtgcttattttctttacggtctttaaaaag gccgtaatatccagctgaacggtctggttataggtacattgagcaactg actgaaatgcctcaaaatgttctttacgatgccattgggatatatcaac ggtggtatatccagtgattttttctccattttagcttccttagctcctg aaaatctcgataactcaaaaaatacgcccggtagtgatcttatttcatt atggtgaaagttggaacctcttacgtgccgatcaacgtctcattttcgc caaaagttggcccagggcttcccggtatcaacagggacaccaggattta tttattctgcgaagtgatcttccgtcacaggtatttattcggcgcaaag tgcgtcgggtgatgctgccaacttactgatttagtgtatgatggtgttt ttgaggtgctccagtggcttctgtttctatcagctgtccctcctgttca gctactgacggggtggtgcgtaacggcaaaagcaccgccggacatcagc gctagcggagtgtatactggcttactatgttggcactgatgagggtgtc agtgaagtgcttcatgtggcaggagaaaaaaggctgcaccggtgcgtca gcagaatatgtgatacaggatatattccgcttcctcgctcactgactcg ctacgctcggtcgttcgactgcggcgagcggaaatggcttacgaacggg gcggagatttcctggaagatgccaggaagatacttaacagggaagtgag ag
```

Plasmid 2: pETDuet_Δ3_CYP2C19:

The pETDuet_Δ3_CYP2C19-plasmid is a derivate of the commercially available pETDuet-1-plasmid of the company Novagen. To generate this plasmid two fragments, pETDuet_mod and Δ3_CYP2C19 were ligated.

Creation of the Δ3_CYP2C19 Fragment:

The human monooxygenase CYP2C19 was amplified via two primer containing the restriction sites NdeI (CCATC-GATCATATGGCTCGACAATCTTCTGGACGAG-GAAAACTCCCT) (SEQ ID NO: 5) and XhoI (ATTGA-GACTCGAGTCAGACAGGAATGAAGCACA) (SEQ ID NO: 6) out of the plasmid pBLUESCRIPTS SK+_2C19. Using the forward primer containing the NdeI restriction site the first 20 amino acids of the CYP2C19 enzymes were deleted und lead to the Δ3_CYP2C19 fragment.

pBLUESCRIPTS SK+_2C19 (1 µL) was mixed with MilliQ water (51.5 µL), expand buffer with MgCl2 (7.5 µL), dNTPs (6 µL), Taq-Expand (1 µL), forward primer (4 µL) and reverse primer (4 µL). The PCR was performed after following program: 1) 94° C. for 5 minutes, 2) 94° C. for 30 seconds, 3) 60° C. for 30 seconds, 4) 72° C. for 90 seconds, 5) go back to step 2 (30 cycles), 6) 72° C. for 5 minutes, 7) 15° C. forever. The amplified PCR fragment was then digested with the restriction enzymes NdeI and XhoI. The first digestion was performed with NdeI. The amplified 25 PCR fragment (30 µL) was mixed with 10× buffer NEB4 (4 µl), NdeI restriction enzyme (1 µL) and MilliQ water (5 µL). After incubation at 37° C. for 1 hour the reaction was stopped by incubating for 20 minutes at 65° C. The digested PCR fragment was purified via the QIAquick PCR Purification kit from Qiagen. Afterwards the second digestion was performed with XhoI.

The NdeI digested PCR fragment (30 µL) was mixed with 10× buffer NEB4 (4 µl), BSA solution (10 mg/mL, 0.4 µL), XhoI restriction enzyme (1 µL) and MilliQ water (5 µL). After incubation at 37° C. for 1 hour the reaction was stopped by incubating for 20 minutes at 65° C. The double-digested PCR fragment was purified via the QIAquick PCR Purification kit from Qiagen. Afterwards a gel extraction with the QIAquick Gel Extraction Kit from Qiagen followed to isolated the Δ3_CYP2C19 fragment.

Creation of the pETDuet_mod Fragment:

To change the upstream promotor of the pETDuet-1-vector, the pETDuet-1-vector as well as the pCW_CYP1A2 vector, provided by the company Oxford Biomedical Research, was digested with the restriction enzymes MluI and XhoI.

The first digestion was performed with MluI. Either the pETDuet-1-vector or the pCW_CYP1A2 vector (30 µL) was mixed with 10× buffer NEB4 (4 µl), BSA solution (10 mg/mL, 0.4 µL), MluI restriction enzyme (1 µL) and MilliQ water (5 µL). After incubation at 37° C. for 1 hour the reaction was stopped by incubating for 20 minutes at 65° C. The digested vector was purified via the QIAquick PCR Purification kit from Qiagen. Afterwards the second digestion was performed with XhoI. Either the MluI digested pETDuet-1-vector or the MluI digested pCW_CYP1A2 (30 µL) was mixed with 10× buffer NEB4 (4 µl), BSA solution (10 mg/mL, 0.4 µL), XhoI restriction enzyme (1 µL) and MilliQ water (5 µL). After incubation at 37° C. for 1 hour the reaction was stopped by incubating for 20 minutes at 65° C. For the double-digested pETDuet-1-vector a dephosphorylation with a shrimp alkaline phosphatase followed. The double-digested pETDuet-1 vector (40 µL) was mixed with 10×SAP buffer (5 µl), SAP enzyme (2 µL) and milliQ water (3 µL). After incubation at 37° C. for 30 minutes the reaction was stopped by incubating for 20 minutes at 65° C. The double-digested CYP1A2 fragment and the dephosphorylated double-digested pETDuet-1 vector were purified via the QIAquick PCR Purification kit from Qiagen. Afterwards a gel extraction with the QIAquick Gel Extraction Kit from Qiagen followed. The ligation of the double-digested CYP1A2 fragment and the double-digested pETDuet-1-vector was performed with T4 DNA Ligase. The cut vector (1 µL) was mixed with cut CYP1A2 fragment (1 µL), 10× Ligase buffer with 10 mM ATP (1.5 µL), T4 DNA Ligase (1 µL) and MilliQ water (10.5 µL). After incubation for 30 minutes at room temperature the ligated DNA was purified by ethanol precipitation. Ligated DNA (15 µL) was mixed with glycogen (1 µL), ammonium acetate (7.5 µL) and 100% ethanol (37.5 µL). After 5 minutes at room temperature a centrifugation at 14000 rpm for 5 minutes was used to precipitate the DNA. The supernatant was removed and the DNA washed with 75% ethanol (100 µL), before the DNA was air-dried and resuspended in MilliQ water (12 µL). The ligated DNA was digested with the restriction enzymes NdeI und XhoI. The first digestion was performed with NdeI. The ligated DNA (30 µL) was mixed with 10× buffer NEB4 (4 µl), NdeI restriction enzyme (1 µL) and MilliQ water (5 µL). After incubation at 37° C. for 1 hour the reaction was stopped by incubating for 20 minutes at 65° C. The digested vector was purified via the QIAquick PCR Purification kit from Qiagen. Afterwards the second digestion was performed with XhoI. The NdeI digested DNA (30 µL) was mixed with 10× buffer NEB4 (4 µl), BSA solution (10 mg/mL, 0.4 µL), XhoI restriction enzyme (1 µL) and MilliQ water (5 µL). After incubation at 37° C. for 1 hour the reaction was stopped by incubating for 20 minutes at 65° C. Afterwards the double-digested pETDuet_mod-vector was a dephosphorylated with a shrimp alkaline phosphatase. The vector (40 µL) was mixed with 10×SAP buffer (5 µl), SAP enzyme (2 μL) and milliQ water (3 μL). After incubation at 37° C. for 30 minutes the reaction was stopped by incubating for 20 minutes at 65° C. It followed a PCR purification via the QIAquick PCR Purification kit from Qiagen. Afterwards a gel extraction with the QIAquick Gel Extraction Kit from Qiagen followed to isolate the pETDuet_mod fragment with modified promotor.

Assembly of the pETDuet_Δ3_CYP2C19 Plasmid:

The Δ3_CYP2C19 fragment (1 μL) was mixed with pETDuet_mod fragment (1 μL), 10× Ligase buffer with 10 mM ATP (1.5 μL), T4 DNA Ligase (1 μL) and MilliQ water (10.5 μL). After incubation for 30 minutes at room temperature the ligated DNA was purified by ethanol precipitation. Ligated DNA (15 μL) was mixed with glycogen (1 μL), ammonium acetate (7.5 μL) and 100% ethanol (37.5 μL). After 5 minutes at room temperature a centrifugation at 14000 rpm for 5 minutes was used to precipitate the DNA. The supernatant was removed and the DNA washed with 75% ethanol (100 μL), before the DNA was air-dried and resuspended in MilliQ water (12 μL).

The analysis of the gene sequence of pETDuet_delta3_CYP2C19 at LGC Genomics GmbH:

Seq. ID. No. 2
ttgaagcatttatcagggttattgtctcatgagcggatacatatttgaa tgtatttagaaaaataaacaaataggtcatgaccaaaatcccttaacgt gagttttcgttccactgagcgtcagaccccgtagaaaagatcaaaggat cttcttgagatccttttttttctgcgcgtaatctgctgcttgcaaacaaa aaaaccaccgctaccagcggtggtttgtttgccggatcaagagctacca actcttttttccgaaggtaactggcttcagcagagcgcagataccaaata ctgtccttctagtgtagccgtagttaggccaccacttcaagaactctgt agcaccgctacatacctcgctctgctaatcctgttaccagtggctgct gccagtggcgataagtcgtgtcttaccgggttggactcaagacgatagt taccggataaggcgcagcggtcgggctgaacgggggttcgtgcacaca gcccagcttggagcgaacgacctacaccgaactgagatacctacagcgt gagctatgagaaagcgccacgcttcccgaagggagaaaggcggacaggt atccggtaagcggcagggtcggaacaggagagcgcacgagggagcttcc agggggaaacgcctggtatctttatagtcctgtcgggtttcgccacctc tgacttgagcgtcgattttgtgatgctcgtcagggggggcggagcctat ggaaaaacgccagcaacgcggccttttacggttcctggccttttgctg gccttttgctcacatgttctttcctgcgttatcccctgattctgtggat aaccgtattaccgcctttgagtgagctgataccgctcgccgcagccgaa cgaccgagcgcagcgagtcagtgagcgaggaagcggaagagcgcctgat gcggtattttctccttacgcatctgtgcggtatttcacaccgcaatggt gcactctcagtacaatctgctctgatgccgcatagttaagccagtatac actccgctatcgctacgtgactgggtcatggctgcgccccgacacccgc caacaccgctgacgcgccctgacgggcttgtctgctcccggcatccgc ttacagacaagctgtgaccgtctccgggagctgcatgtgtcagaggttt tcaccgtcatcaccgaaacgcgcgaggcagctgcggtaaagctcatcag cgtggtcgtgaagcgattcacagatgtctgcctgttcatccgcgtccag ctcgttgagtttctccagaagcgttaatgtctggcttctgataaagcgg gccatgttaagggcggttttttcctgtttggtcactgatgcctccgtgta aggggatttctgttcatgggggtaatgataccgatgaaacgagagagg atgctcacgatacgggttactgatgatgaacatgcccggttactggaac gttgtgagggtaaacaactggcggtatggatgcggcgggaccagagaaa aatcactcagggtcaatgccagcgcttcgttaatacagatgtaggtgtt ccacagggtagccagcagcatcctgcgatgcagatccggaacataatgg tgcagggcgctgacttccgcgtttccagactttacgaaacacggaaacc gaagaccattcatgttgttgctcaggtcgcagacgttttgcagcagcag tcgcttcacgttcgctcgcgtatcggtgattcattctgctaaccagtaa ggcaaccccgccagcctagccgggtcctcaacgacaggagcacgatcat gctagtcatgcccgcgcccaccggaaggagctgactgggttgaaggct ctcaagggcatcggtcgagatcccggtgcctaatgagtgagctaactta cattaattgcgttgcgctcactgcccgctttccagtcgggaaacctgtc gtgccagctgcattaatgaatcggccaacgcgcggggagaggcggtttg cgtattgggcgccagggtggtttttcttttcaccagtgagacgggcaaca gctgattgcccttcaccgcctggccctgagagagttgcagcaagcggtc cacgctggtttgccccagcaggcgaaaatcctgtttgatggtggttaac ggcgggatataacatgagctgtcttcggtatcgtcgtatcccactaccg agatgtccgcaccaacgcgcagcccggactcggtaatgcgcgcattgc gcccagcgccatctgatcgttggcaaccagcatcgcagtgggaacgatg ccctcattcagcatttgcatggtttgttgaaaaccggacatggcactcc agtcgccttcccgttccgctatcggctgaatttgattgcgagtgagata tttatgccagccagccagacgcagacgcgccgagacagaacttaatggg cccgctaacagcgcgatttgctggtgacccaatgcgaccagatgctcca cgcccagtcgcgtaccgtcttcatgggagaaaataatactgttgatggg tgtctggtcagagacatcaagaaataacgccggaacattagtgcaggca gcttccacagcaatggcatcctggtcatccagcggatagttaatgatca gcccactgacgcgttgcgcgagaagattgtgcaccgccgctttacaggc ttcgacgccgcttcgttctaccatcgacaccaccacgctggcacccagt tgatcggcgcgagatttaatcgccgcgacaatttgcgacggcgcgtgca gggccagactggaggtggcaacgccaatcagcaacgactgtttgcccgc cagttgttgtgccacgcggttgggaatgtaattcagctccgccatcgcc gcttccacttttttcccgcgttttcgcagaaacgtggctggcctggttca ccacgcgggaaacggtctgataagagacaccggcatactctgcgacatc gtataacgttactggtttcacattcaccaccctgaattgactctcttcc gggcgctatcatgccataccgcgaaaggttttgcaccattcgatggtgt cctggcacgacaggtttcccgactggaaagcgggcagtgagcgcaacgc aattaatgtaagttagctcactcattaggcaccccaggctttacacttt atgcttccggctcgtataatgtgtggaattgtgagcggataacaatttc -continued

```
acacaggaaacaggatcgatccatcgatgagcttactccccatccccct
gttgacaattaatcatcggctcgtataatgtgtggaattgtgagcggat
aacaatttcacacaggaaacaggatcagcttactccccatcccctgtt
gacaattaatcatcggctcgtataatgtgtggaattgtgagcggataac
aatttcacacaggaaacaggatccatcgatgcttaggaggtcatatggc
tcgacaatcttctggacgaggaaaactccctcctggccccactcctctc
ccagtgattggaaatatcctacagatagatattaaggatgtcagcaaat
ccttaaccaatctctcaaaaatctatggccctgtgttcactctgtattt
tggcctggaacgcatggtggtgctgcatggatatgaagtggtgaaggaa
gccctgattgatcttggagaggagttttctggaagaggccatttccac
tggctgaaagagctaacagaggatttggaatcgttttcagcaatggaaa
gagatggaaggagatccggcgtttctccctcatgacgctgcggaatttt
gggatggggaagaggagcattgaggaccgtgttcaagaggaagcccgct
gccttgtggaggagttgagaaaaaccaaggcttcaccctgtgatccac
tttcatcctgggctgtgctccctgcaatgtgatctgctccattattttc
cagaaacgtttcgattataaagatcagcaatttcttaacttgatggaaa
aattgaatgaaaacatcaggattgtaagcaccccctggatccagatatg
caataattttcccactatcattgattatttcccgggaacccataacaaa
ttacttaaaaaccttgcttttatggaaagtgatattttggagaaagtaa
aagaacaccaagaatcgatggacatcaacaaccctcgggactttattga
ttgcttcctgatcaaaatggagaaggaaaagcaaaaccaacagtctgaa
ttcactattgaaaacttggtaatcactgcagctgacttacttggagctg
ggacagagacaacaagcacaaccctgagatatgctctccttctcctgct
gaagcacccagaggtcacagctaaagtccaggaagagattgaacgtgtc
attggcagaaaccggagcccctgcatgcaggacaggggccacatgccct
acacagatgctgtggtgcacgaggtccagagatacatcgacctcatccc
caccagcctgcccatgcagtgacctgtgacgttaaattcagaaactac
ctcattcccaagggcacaaccatattaacttccctcacttctgtgctac
atgacaacaaagaatttcccaacccagagatgtttgaccctcgtcactt
tctggatgaaggtggaaattttaagaaaagtaactacttcatgcctttc
tcagcaggaaaacggatttgtgtgggagagggcctggcccgcatggagc
tgttttattcctgaccttcattttacagaactttaacctgaaatctct
gattgacccaaaggaccttgacacaactcctgttgtcaatggatttgct
tctgtcccgcccttctatcagctgtgcttcattcctgtctgactcgagt
ctggtaaagaaaccgctgctgcgaaatttgaacgccagcacatggactc
gtctactagcgcagcttaattaacctaggctgctgccaccgctgagcaa
taactagcataaccccttggggcctctaaacgggtcttgaggggtttttt
gctgaaaggaggaactatatccggattggcgaatgggacgcgccctgta
gcggcgcattaagcgcggcgggtgtggtggttacgcgcagcgtgaccgc
tacacttgccagcgccctagcgcccgctccttttcgctttcttcccttcc
tttctcgccacgttcgccggctttccccgtcaagctctaaatcggggc
```

-continued

```
tccctttagggttccgatttagtgctttacggcacctcgaccccaaaaa
acttgattagggtgatggttcacgtagtgggccatcgccctgatagacg
gttttttcgccctttgacgttggagtccacgttctttaatagtggactct
tgttccaaactggaacaacactcaaccctatctcggtctattcttttga
tttataagggattttgccgatttcggcctattggttaaaaaatgagctg
atttaacaaaatttaacgcgaattttaacaaaatattaacgtttacaa
tttctggcggcacgatggcatgagattatcaaaaggatcttcacctag
atccttttaaattaaaaatgaagttttaaatcaatctaaagtatatatg
agtaaacttggtctgacagttaccaatgcttaatcagtgaggcacctat
ctcagcgatctgtctatttcgttcatccatagttgcctgactccccgtc
gtgtagataactacgatacgggagggcttaccatctggccccagtgctg
caatgataccgcgagacccacgctcaccggctccagatttatcagcaat
aaaccagccagccggaagggccgagcgcagaagtggtcctgcaacttta
tccgcctccatccagtctattaattgttgccgggaagctagagtaagta
gttcgccagttaatagtttgcgcaacgttgttgccattgctacaggcat
cgtggtgtcacgctcgtcgtttggtatggcttcattcagctccggttcc
caacgatcaaggcgagttacatgatccccatgttgtgcaaaaaagcgg
ttagctccttcggtcctccgatcgttgtcagaagtaagttggccgcagt
gttatcactcatggttatggcagcactgcataattctcttactgtcatg
ccatccgtaagatgcttttctgtgactggtgagtactcaaccaagtcat
tctgagaatagtgtatgcggcgaccgagttgctcttgccggcgtcaat
acgggataataccgcgccacatagcagaactttaaaagtgctcatcatt
ggaaaacgttcttcggggcgaaaactctcaaggatcttaccgctgttga
gatccagttcgatgtaacccactcgtgcacccaactgatcttcagcatc
ttttactttcaccagcgtttctgggtgagcaaaaacaggaaggcaaaat
gccgcaaaaaagggaataagggcgacacggaaatgttgaatactcatac
tcttcctttttcaatcatga
```

Generation of Chemo-Competent E. coli DH5a LPSd Cells:

Luria-Bertani broth medium (5 mL) was inoculated with 2 μl of the strain E. coli DH5a LPSd which was stored as glycerol culture. This culture was shaken at 37° C. and 165 rpm overnight. The overnight culture (1 mL) was used to inoculate Luria-Bertani broth medium (25 mL). The culture was shaken at 37° C. and 175 rpm. After 2 hours, the OD550 was 0.4, whereupon the culture was chilled in ice for 10 minutes and subsequently subjected to centrifugation at 4° C. and 4000 rpm for 10 minutes. The supernatant was discarded and the cell pellet was suspended in a cold and sterile aqueous solution of calcium chloride, CaCl$_2$ (5 mL, 0.1 M). The mixture was subjected to centrifugation at 4° C. and 4000 rpm for 10 minutes. The supernatant was discarded and the cell pellet was suspended in a cold and sterile aqueous solution of calciumchloride, CaCl$_2$ (1 mL, 0.1 M). The chemo-competent cells were aliquoted a 200 μL.

Transformation of Chemo-Competent E. coli DH5a LPSd Cells:

Plasmid 1 (2.5 μL) and plasmid 2 (2.5 μL) were added to chemo-competent E. coli DH5a LPSd cells (200 μL) and the suspension was chilled in ice for 30 minutes. Luria-Bertani broth medium (0.5 mL, 37° C.) was added and the culture was shaken at 37° C. and 800 rpm for 1 hour and subsequently subjected to centrifugation at 4000 rpm for 3 minutes. The cells were placed on Luria-Bertani broth agar plates with ampicillin (50 mg/L) and chloramphenicol (17 mg/L) and incubated at 37° C. overnight. The E. coli DH5a LPSd cells harbouring the plasmids were stored in 96 micro-titer plates. To a mixture of 10×HMFM medium (2 mL) and 2YT medium (18 mL) ampicillin (50 mg/L) and chloramphenicol (17 mg/L) were added. Each well of the micro-titer plate containing 200 µL media was inoculated with a single colony of the agar plate. The microtiter plates were shaken at 37° C. and 800 rpm for 16 hours and subsequently stored at −80° C. until further use.

Cultivation of E. coli DH5α LPSd A_pel_POR_D_d3_2C19 and Protein Expression:

Oxford trace metal solution (1 L): aqueous solution of iron(III) chloride, $FeCl_3$ hexahydrate (27 g/L), $ZnCl2$ (1.31 g/L), cobalt(II) chloride, $CoCl_2$ hexahydrate (2.87 g/L), copper(II) chloride, dihydrate $CuCl_2 \times 2H_2O$ (1.27 g/L), boric acid, $H_3BO_3$ (0.5 g/L), calcium chloride$CaCl_2$ dihydrate (1.32 g/L), sodium molybdate$Na_2MoO_4$ dihydrate (2.35 g/L) and hydrochloric acid (37%, 100 mL).

Media of the preculture: tryptone (16 g/L), sodium chloride (10 g/L) und yeast extract (10 g/L) in water adjusted to pH 7.2 to 7.4 with aqueous sodium hydroxide solution (16%). The media was sterilized at 121° C. for 20 minutes. Afterwards ampicillin (50 mg/L) and chloramphenicol (17 mg/L) were added.

Two precultures (100 mL each) were inoculated with the Escherichia coli DH5a LPSd strain (50 µL) containing the desired plasmids and were shaken at 37° C. and 165 rpm. These precultures (100 mL) were used to inoculate two 10 L steel fermenter. The cultivation media was prepared in the fermenters. Tryptone (12 g/L), yeast extract (24 g/L), predigested beef extract (2 g/L), KH2PO4 (2.2 g/L), K2HPO4 (9.4 g/L) and glycerol (87%, 4.6 g/L) were dissolved in demineralized water (8.7 L) and sterilized for 20 minutes at 121° C. in the fermenter. Afterwards ampicillin (0.5 g) in water (20 mL), chloramphenicol (0.17 g) in ethanol (20 mL), riboflavin (10 mg) in water (20 mL), thiamine hydrochloride (3.37 g) in water (10 mL) and Oxford trace metal solution (2.5 mL) were added. After the inoculation of the first fermenter (17 hours old preculture), the inoculated culture was stirred at 315 rpm at 37° C. with an aeration rate of 3.3 L/min at pH 6.6 which was regulated by addition of aqueous sodium hydroxide solution (16%) or aqueous phosphoric acid solution (16%). After 3 hours, an OD550 of 0.9 was reached, the temperature was decreased to 25° C. within 15 minutes and isopropyl p-D-thiogalactopyranoside (2.38 g) in water (40 mL) and aminolevulinic acid (838 mg) in water (40 mL) were added to start the protein expression. After 9 hours the aqueous phosphoric acid solution (16%) was substituted for an aqueous glucose solution (50%) for pH regulation. After additional 12 hours the cells (206 g) were harvested by centrifugation, suspended in buffer (206 mL; KH2PO4 (4 g/L), K2HPO4 (12.3 g/L), glycerol (4% (v/v)), glucose (5% (w/v)), EDTA (0.5 mM)), frozen in liquid nitrogen and stored at −80° C. until further use in aliquots of 2×150 mL, 2×40 mL und 5×1 mL. The second 10 L steel fermenter was inoculated with the second preculture (16 hours old). The inoculated culture was stirred at 315 rpm at 37° C. with an aeration rate of 3.3 L/min at pH 6.6 which was regulated by addition of aqueous sodium hydroxide solution (16%) and aqueous phosphoric acid solution (16%). After 3 hours, the OD550 was 0.93, the temperature was decreased to 25° C. for 15 minutes, then isopropyl p-D-thiogalactopyranoside (2.38 g) in water (40 mL) and aminolevulinic acid (838 mg) in water (40 mL) were added. After 11.5 hours the aqueous phosphoric acid solution (16%) was substituted for an aqueous glucose solution (50%) for pH regulation. After additional 9.5 hours the cells (176 g) were harvested by centrifugation, suspended in buffer (176 mL; KH2PO4 (4 g/L), K2HPO4 (12.3 g/L), glycerol (4% (v/v)), glucose (5% (w/v)), EDTA (0.5 mM)), frozen in liquid nitrogen and stored at −80° C. until further use in aliquots of 2×150 mL, 2 ×40 mL und 5×1 mL.

Biotransformation with E. coli DH5a LPSd pACYC_pelFPOR_pETDuet_Δ3_CYP2C19:

To a 20 L steel fermenter which contained KH2PO4 (80 g), K2HPO4 (246 g), synperonic (2 mL), demineralized water (19.2 L), aqueous glucose solution (50%, 400 mL) and aqueous EDTA solution (0.5 M, 20 mL)N-(2,6-difluorophenyl)-5-fluoro-4-(3-oxo-5,6,7,8-tetrahydro[1,2,4]triazolo[4,3-a]pyridin-2(3H)-yl)-2-{[(2S)-1,1,1-trifluoropropan-2-yl]oxy}benzamide (500 mg, 999 µmol) dissolved in DMF (40 mL) was added and the culture was stirred at 215 rpm at 27° C. with an aeration rate of 6.6 L/min. Cells in buffer (760 mL) were added and the culture was stirred at an oxygen partial pressure of 50% regulated by the stirring rate of up to 800 rpm. After 3 hours and 40 minutes the culture was harvested by extraction with 3-methylbutan-2-one. The organic layer was concentrated to give 2.28 g of an oil which was dissolved in a mixture of methanol/water (14/1), was washed with hexane and was concentrated to give 1.51 g of an oil. The crude product was further purified by flash chromatography using silica gel (dichloromethane/methanol gradient) and by preparative HPLC to give the title compound (57.6 mg, 11% yield).

Preparative HPLC Method:

Instrument: Waters Autopurification system; column: Waters XBrigde C18 5µ 100×30 mm; eluent A: water+0.1 vol-% formic acid (99%), eluent B: acetonitrile; gradient: 0.00-0.50 min 10% B (25 →70 mL/min), 0.51-12.50 min 19-39% B (70 mL/min), DAD scan: 210-400 nm.

Analytical HPLC Method:

Instrument: Waters Acquity UPLCMS SingleQuad; column: Acquity UPLC BEH C18 1.7 µm, 50×2.1 mm; eluent A: water+0.1 vol-% formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Analytical HPLC: $R_t$=1.02 min.

LC-MS: $R_t$=0.99 min; MS (ESIpos): m/z=517 [M+H]$^+$ $^1$H-NMR (600 MHz, DMSO-d6) δ[ppm]: 0.000 (4.64), 0.970 (0.69), 1.111 (16.00), 1.147 (0.44), 1.234 (0.49), 1.435 (8.20), 1.445 (8.18), 1.971 (1.67), 1.980 (3.21), 1.987 (2.99), 1.996 (1.55), 2.519 (0.74), 2.522 (0.71), 2.525 (0.56), 2.654 (1.27), 2.662 (1.31), 2.682 (1.71), 2.690 (1.62), 2.860 (1.84), 2.867 (2.06), 2.888 (1.62), 2.895 (1.48), 3.327 (0.50), 3.574 (0.56), 3.586 (0.93), 3.595 (1.27), 3.606 (1.51), 3.619 (1.00), 3.637 (1.08), 3.646 (2.18), 3.655 (1.43), 3.666 (1.12), 3.675 (0.55), 4.205 (0.96), 4.227 (1.83), 5.306 (2.57), 5.314 (1.85), 5.326 (1.68), 5.336 (1.20), 5.347 (0.51), 7.196 (2.40), 7.209 (4.63), 7.223 (2.77), 7.381 (0.45), 7.392 (1.05), 7.405 (1.56), 7.416 (0.93), 7.555 (2.80), 7.565 (3.03), 7.571 (3.28), 7.588 (2.93), 8.319 (1.92), 9.996 (3.60).

Example 294

N-(2,6-difluorophenyl)-5-fluoro-4-(6-hydroxy-3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

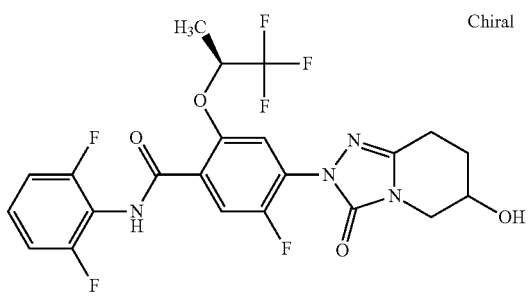 [SMILES: C[C@H](Oc1cc(-n2nc3n(c2=O)CC(O)CC3)c(F)cc1C(=O)Nc1c(F)cccc1F)C(F)(F)F]

For the preparation of the title compound see Example 293. Preparative HPLC (method see Example 293) gave the title compound (36.9 mg, 7% yield).

Analytical HPLC: $R_t$=1.03 min.

LC-MS: $R_t$=1.01 min; MS (ESIpos): m/z=517 [M+H]$^+$ $^1$H-NMR (600 MHz, DMSO-d6) δ[ppm]: −0.005 (0.49), 0.000 (10.71), 0.971 (0.94), 1.111 (16.00), 1.148 (0.62), 1.211 (0.46), 1.234 (0.72), 1.435 (8.50), 1.445 (8.38), 1.853 (0.43), 1.864 (0.58), 1.872 (1.10), 1.876 (1.11), 1.883 (1.11), 1.886 (0.98), 1.890 (1.02), 1.893 (0.93), 1.900 (0.80), 1.920 (0.58), 1.929 (1.35), 1.938 (1.48), 1.948 (0.95), 1.960 (0.73), 2.517 (1.01), 2.521 (0.95), 2.524 (0.76), 2.693 (0.70), 2.701 (1.08), 2.710 (0.78), 2.722 (1.26), 2.729 (1.77), 2.739 (1.01), 2.800 (0.99), 2.810 (1.26), 2.817 (1.08), 2.828 (1.62), 2.838 (0.76), 2.845 (0.74), 2.856 (0.60), 3.498 (1.41), 3.503 (1.48), 3.519 (2.03), 3.524 (1.94), 3.606 (2.25), 3.612 (2.50), 3.627 (1.73), 3.633 (1.61), 4.194 (0.78), 4.231 (1.97), 5.296 (0.67), 5.306 (1.44), 5.317 (2.18), 5.327 (3.21), 7.195 (2.50), 7.209 (4.79), 7.223 (2.84), 7.381 (0.49), 7.392 (1.13), 7.406 (1.66), 7.416 (1.00), 7.555 (2.93), 7.565 (3.39), 7.570 (3.57), 7.586 (2.95), 8.318 (1.63), 9.987 (3.71).

Example 295

N-(2,6-difluorophenyl)-5-fluoro-4-(6-hydroxy-3-oxo-5,6-dihydro[1,2,4]triazolo[4,3-a]pyridin-2(3H)-yl)-2-{[(2S)-1,1,1-trifluoropropan-2-yl]oxy}benzamide

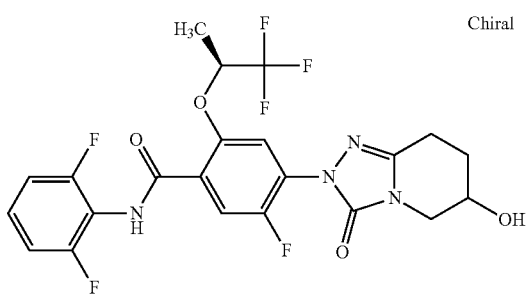 [SMILES: C[C@H](Oc1cc(-n2nc3n(c2=O)CC(O)CC3)c(F)cc1C(=O)Nc1c(F)cccc1F)C(F)(F)F]

For the preparation of the title compound see Example 293. Preparative HPLC gave the title compound (42.7 mg, 8% yield).

Preparative HPLC Method:

Instrument: Waters Autopurification system; column: Waters XBrigde C18 5µ 100×30 mm; Eluent A: water+0.2 Vol-% aqueous ammonia (32%), Eluent B: methanol; Gradient: 0.00-0.50 min 20% B (25 →70 mL/min), 0.51-7.50 min 39-59% B (70 mL/min), DAD scan: 210-400 nm.

Analytical HPLC Method:

Instrument: Waters Acquity UPLCMS SingleQuad; column: Acquity UPLC BEH C18 1.7 µm, 50×2.1 mm; Eluent A: water+0.2 Vol-% aqueous ammonia (32%), Eluent B: methanol; Gradient: 0-1.6 min 1-99% B, 1.6-2.0 min 99% B; flow 0.8 mL/min; temperature: 60° C.; DAD scan: 210-400 nm.

Analytical HPLC: $R_t$=1.32 min.

LC-MS: $R_t$=1.03 min; MS (ESIpos): m/z=515 [M+H]$^+$ $^1$H-NMR (600 MHz, DMSO-d6) δ[ppm]: 0.000 (14.44), 0.842 (0.43), 0.855 (0.68), 1.111 (1.15), 1.235 (3.80), 1.441 (14.33), 1.451 (14.18), 1.844 (0.41), 2.388 (0.45), 2.616 (0.47), 3.510 (0.58), 3.681 (2.18), 3.689 (2.29), 3.703 (3.02), 3.711 (2.95), 3.811 (3.07), 3.820 (3.36), 3.832 (2.34), 3.841 (2.28), 3.854 (0.52), 4.294 (0.42), 4.302 (0.42), 4.583 (3.20), 5.297 (1.17), 5.307 (2.21), 5.317 (2.74), 5.327 (2.08), 5.731 (1.45), 6.537 (0.89), 6.554 (16.00), 6.576 (0.71), 7.201 (4.58), 7.214 (8.87), 7.227 (5.24), 7.387 (0.93), 7.400 (2.17), 7.411 (3.17), 7.422 (1.92), 7.436 (0.71), 7.572 (0.61), 7.581 (0.76), 7.597 (5.56), 7.603 (6.18), 7.613 (9.32), 10.018 (5.03).

Example 296

N-(2,6-difluorophenyl)-5-fluoro-4-(8-hydroxy-3-oxo-5,6,7,8-tetrahydro[1,2,4]triazolo[4,3-a]-pyridin-2(3H)-yl)-2-{[(2S)-1,1,1-trifluoropropan-2-yl]oxy}benzamide

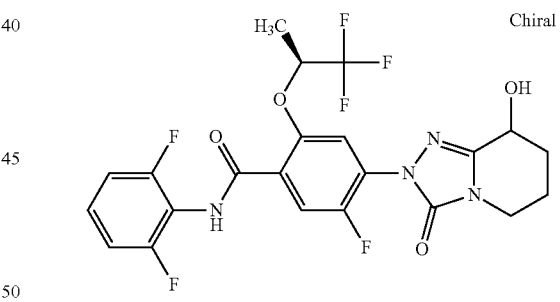

For the preparation of the title compound see Example 293. Preparative HPLC (method see Example 295) gave the title compound (124 mg, 24% yield).

Analytical HPLC: $R_t$=1.29 min.

LC-MS: $R_t$=1.00 min; MS (ESIpos): m/z=517 [M+H]$^+$ $^1$H-NMR (600 MHz, DMSO-d6) δ[ppm]: 0.000 (3.79), 1.113 (16.00), 1.237 (0.47), 1.442 (3.57), 1.452 (3.57), 1.841 (0.52), 1.849 (0.99), 1.858 (0.85), 1.871 (0.51), 1.938 (0.50), 1.946 (0.48), 2.545 (0.64), 3.515 (0.65), 3.523 (0.46), 3.529 (0.47), 3.616 (0.72), 3.626 (0.53), 3.636 (0.52), 4.651 (0.74), 4.658 (0.72), 5.289 (0.51), 5.300 (0.67), 5.311 (0.49), 5.947 (0.70), 5.955 (0.69), 7.192 (1.08), 7.205 (2.08), 7.219 (1.24), 7.394 (0.46), 7.397 (0.43), 7.407 (0.71), 7.571 (1.28), 7.581 (1.43), 7.585 (1.49), 7.602 (1.27), 8.310 (1.10), 10.004 (1.56).

Example 297 rac-tert-butyl[2-{2-[(2-chloro-6-fluorophenyl)carbamoyl]-4-fluoro-5-(3-oxo-5,6,7,8-tetrahydro-[1,2,4]triazolo[4,3-a]pyridin-2(3H)-yl)phenoxy}propyl] carbamate

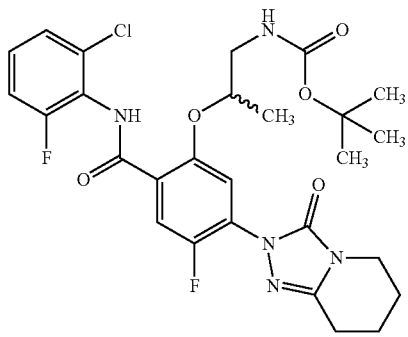 [SMILES: CC(CNC(=O)OC(C)(C)C)Oc1cc(-n2nc3n(c2=O)CCCC3)c(F)cc1C(=O)Nc1c(F)cccc1Cl]

Prepared analogously to Example 244 from Intermediate 47 and 5,6,7,8-tetrahydro[1,2,4]triazolo[4,3-a]pyridin-3(2H)-one LC-MS (Method B): $R_t$=1.24 min; MS (ESIneg): m/z=576 [M−H]⁻

¹H-NMR (400 MHz, DMSO-d6) δ[ppm]: 1.215 (0.72), 1.244 (2.67), 1.261 (16.00), 1.298 (0.50), 1.790 (0.57), 1.802 (0.80), 1.817 (0.82), 1.871 (0.41), 1.885 (0.84), 1.897 (0.85), 1.909 (0.52), 2.074 (3.12), 2.084 (0.43), 2.518 (0.75), 2.523 (0.49), 2.690 (0.90), 2.706 (1.76), 2.722 (0.93), 3.260 (0.41), 3.556 (1.06), 3.571 (1.90), 3.586 (0.85), 7.143 (0.48), 7.342 (0.64), 7.361 (0.44), 7.365 (0.44), 7.393 (0.43), 7.399 (0.59), 7.413 (0.67), 7.426 (0.97), 7.441 (1.73), 7.458 (0.43), 7.462 (0.43), 7.710 (0.68), 7.737 (0.65), 9.779 (1.57).

Example 298 rac-2-{[1-aminopropan-2-yl]oxy}-N-(2-chloro-6-fluorophenyl)-5-fluoro-4-(3-oxo-5,6,7,8-tetrahydro[1,2,4]triazolo[4,3-a]pyridin-2(3H)-yl)benzamide, salt with hydrochloric acid

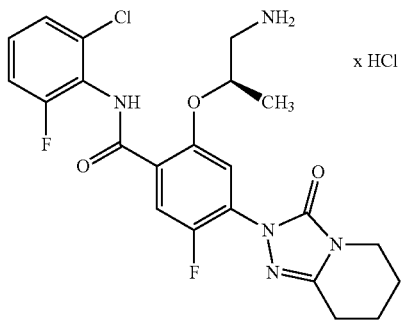 [SMILES: C[C@H](CN)Oc1cc(-n2nc3n(c2=O)CCCC3)c(F)cc1C(=O)Nc1c(F)cccc1Cl]

Rac-tert-butyl [2-{2-[(2-chloro-6-fluorophenyl)carbamoyl]-4-fluoro-5-(3-oxo-5,6,7,8-tetrahydro-[1,2,4]triazolo[4,3-a]pyridin-2(3H)-yl)phenoxy}propyl]carbamate (Example 297, 75.0 mg, 130 μmol) was dissolved in dioxane (2.0 ml). A solution of hydrochloric acid in dioxane was added (320 μl, 4.0 M, 1.3 mmol) and the mixture was stirred at room temperature overnight. The reaction mixture was concentrated to yield the desired product (42.0 mg, 95% purity, 60% yield).

LC-MS (Method A): $R_t$=0.78 min; MS (ESIpos): m/z=478 [M+H]⁺

¹H-NMR (400 MHz, DMSO-d6) δ[ppm]: 1.154 (0.46), 1.172 (0.76), 1.301 (16.00), 1.317 (15.62), 1.352 (0.46), 1.798 (3.08), 1.810 (4.37), 1.825 (4.45), 1.837 (2.17), 1.893 (4.48), 1.907 (4.83), 1.987 (1.41), 2.331 (1.48), 2.518 (9.84), 2.522 (6.04), 2.673 (1.67), 2.697 (5.05), 2.713 (9.88), 2.729 (5.32), 3.094 (1.52), 3.115 (1.67), 3.127 (2.93), 3.149 (2.85), 3.190 (3.04), 3.198 (3.46), 3.223 (1.86), 3.231 (1.56), 3.378 (0.65), 3.564 (5.89), 3.580 (10.41), 3.594 (4.67), 4.823 (1.98), 7.351 (1.75), 7.355 (1.94), 7.372 (3.65), 7.375 (4.22), 7.393 (2.74), 7.399 (3.00), 7.413 (2.01), 7.426 (2.28), 7.433 (3.99), 7.447 (4.14), 7.453 (3.34), 7.465 (9.62), 7.469 (8.63), 7.485 (2.66), 7.490 (2.66), 7.498 (5.32), 7.512 (5.09), 7.646 (0.46), 7.674 (6.16), 7.700 (5.70), 8.080 (1.94).

EXPERIMENTAL SECTION—BIOLOGICAL ASSAYS

The following table 2 lists the abbreviations used herein, in particular in the Biological Assays part of the Experimental Section:

TABLE 2

| Abbreviations | |
|---|---|
| Abbreviation | Meaning |
| ATCC | American Type Culture Collection |
| DDK | name of a polypeptide tag |
| DHODH | Dihydroorotate Dehydrogenase |
| ATP | adensoin triphosphate |
| BSA | bovine serum albumin |
| CYP | cytochrom P450 enzyme |
| Δ | deletion from amino acid |
| DNA | desoxyribonucleic acid |
| DMSO | dimethylsulfoxide |
| dNTP | desoxynucleoside triphosphate |
| EDTA | ethylendiamintetraacetate |
| h | hour(s) |
| HMFM | Hogness Modified Freezing Medium |
| IC₅₀ | half maximal inhibitory concentration |
| LB | Luria-Bertani broth |
| LPSd | lipopolysaccharide deficient |
| μM | micromolar |
| mM | millimolar |
| mod. | modified |
| MTP | microtiter plate |
| MYC | name of a polypeptide tag |
| μl | microliter |
| nM | nanomolar |
| OD550 | optical density at 550 nm |
| PBS | Phosphate Buffered Saline |
| pelB | pelB Leadersequence from vector pET22b+ |
| PCR | polymerase chain reaction |
| POR | human NAPDH hemoprotein reductase |
| rpm | rotation per minute |
| RPMI | Roswell Park Memorial Institute |
| rt | room temperature |
| SAP | shrimp alkaline phosphatase |
| THP | cell line name |
| Triton X | name of a detergent |
| Tris | tris(hydroxymethyl)aminomethane |

Examples were tested in selected biological assays one or more times. When tested more than once, data are reported as either average values or as median values, wherein
the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: DHODH Enzymatic Assay-1

The enzymatic assay couples DHODH activity with bleaching of the dye 2,6-dichlorophenolindophenol (DCIP) (Knecht and Loffler, 1998; Miller et al., 1968). The assay was conducted in buffer containing 50 mM Tris, 0.1% Triton X-100, 150 mM potassium chloride, 2 nM DHODH, 1 mM dihydroorotate, 0.1 mM decylubiquinone, 0.06 mM DCIP, and 2% DMSO at pH 8.0 at 32 degree celsius. The reaction was initiated by addition of substrates. Enzyme activity was monitored kinetically by the reduction in DCIP absorbance at 600 nm. Purified recombinant human DHODH enzyme was purchased from Novus (cat. no. NBP1-98916). Other chemicals were purchased from Sigma-Aldrich. Absorbance measurements were obtained using a BMG clarion star plate-reading spectrophotometer.

In Vitro Assay 2: DHODH Enzymatic Assay-2

The enzymatic assay couples DHODH activity with bleaching of the dye 2,6-Dichlorophenolindophenol (DCIP) (Knecht and Loffler, 1998; Miller et al., 1968). The assay was conducted in aqueous buffer containing 50 mM Tris, 0.1% Triton X-100, 150 mM potassium chloride, 0.4 µg/mL DHODH, 1 mM dihydroorotate, 0.1 mM decylubiquinone, 0.06 mM DCIP, and 0.17% DMSO at pH 8.0 at room temperature. Compounds were added via pin transfer or via D300 digital dispenser, and the reaction was initiated by addition of substrates. Enzyme activity was monitored kinetically by the reduction in DCIP absorbance at 600 nm. Purified recombinant human DHODH (full-length, C-terminal MYC/DDK-tag) enzyme was purchased from Origene (cat. no. TP039034). Other chemicals, including leflunomide and teriflunomide, were purchased from Sigma-Aldrich. Absorbance measurements were obtained using a Molecular Devices Spectramax M5 plate-reading spectrophotometer.

In Vitro Assay 3: H460 (Lung Cancer)

Alamar Blue:

4000 cells/well of NCI-H460 cells were seeded in 90% RPMI 1640 (Invitrogen, #22400-089) and 10% fetal bovine serum (Invitrogen, #10099-141) and Penicillin/Streptomycin in 96 well plates. The next day, cells were incubated with different concentrations of test compounds for 72h. Cellular viability was analysed incubating cells with 12 µl of Alamar Blue (Invitrogen) per well for 2 hours at 37° C. Finally the plate was analysed using excitation wavelength: 544 nm and emission wavelength: 590 nm.

CellTiter-Glo®:

250 cells/well of NCI-H460 cells were seeded in 90% RPMI 1640 (Invitrogen, #22400-089) and 10% fetal bovine serum (Invitrogen, #10099-141) and Penicillin/Streptomycin in 96 well plates. The next day, cells were incubated with different concentrations of test compounds for 72h. Cellular viability was analyzed using CellTiter-Glo® Luminescent Cell Viability Assay (Promega, #G7572) according to manufacturer's instructions.

In Vitro Assay 4: THP-1 Proliferation Assay-1 (AML)

2000 cells/well of THP-1 cells were seeded in RPMI 1640 with Glutamax (Gibco, #11875-093) and 10% fetal calf serum (Biochrom, #S0615) in 384-well plates. The next day, cells were incubated with different concentrations of test compounds for 72h. Cellular viability was analyzed using CellTiter-Glo® Luminescent Cell Viability Assay (Promega, #G7570) according to manufacturer's instructions.

TABLE 3

IC50 values of examples in in vitro assays 1-4

| Example No. | in vitro assay 1: DHODH enzymatic assay 1 $IC_{50}$ [mol/l] (mean values) | in vitro assay 2: DHODH enzymatic assay 2 $IC_{50}$ [nmol/l] (mean values) | in vitro assay 3: H460 (lung cancer) $IC_{50}$ [nmol/l] (mean values) | in vitro assay 4: THP-1 proliferation assay (AML) $IC_{50}$ [mol/l] |
|---|---|---|---|---|
| 1 | 1.00 E−8 | 2.0 | | 7.85 E−9 |
| 2 | 2.18 E−7 | 30.0 | | 8.76 E−8 |
| 3 | 2.30 E−7 | 33.0 | | 8.92 E−8 |
| 4 | 5.90 E−6 | | | |
| 5 | 1.70 E−7 | | | 1.47 E−7 |
| 6 | 1.00 E−9 | | | 6.52 E−10 |
| 7 | 1.13 E−8 | 3.0 | 0.5 | |
| 8 | 4.50 E−9 | | | 4.38 E−9 |
| 9 | 1.60 E−8 | | | 4.99 E−9 |
| 10 | 1.70 E−8 | | | 3.59 E−8 |
| 11 | 5.80 E−9 | | | 5.96 E−9 |
| 12 | 6.50 E−7 | | | |
| 13 | 1.90 E−7 | | | |
| 14 | 1.20 E−8 | | | 1.36 E−8 |
| 15 | 2.70 E−9 | | | 8.36 E−10 |
| 16 | 5.10 E−9 | | | 3.00 E−9 |
| 17 | 3.10 E−7 | | | |
| 18 | 3.50 E−8 | | | 2.18 E−8 |
| 19 | 9.00 E−8 | | | 2.32 E−7 |
| 20 | 4.50 E−7 | | | |
| 21 | 8.50 E−7 | | | |
| 22 | 8.00 E−6 | | | |
| 23 | 6.00 E−6 | | | |
| 24 | | 57.8 | 2.4 | |
| 25 | | 1.5E3 | 2.9 | |
| 26 | 9.00 E−9 | 11.0 | 1.2 | |
| 27 | 1.70 E−9 | 1.8 | 2.0 | |
| 28 | 9.25 E−8 | 2.0 | | |
| 29 | 2.80 E−8 | 3.0 | | 3.25 E−8 |
| 30 | 4.75 E−7 | 141.0 | | 9.26 E−8 |
| 31 | 1.50 E−6 | | | |
| 32 | 3.00 E−5 | | | |
| 33 | 7.25 E−9 | | | 1.85 E−8 |
| 34 | 4.30 E−7 | | | |
| 35 | 3.90 E−8 | | | |
| 36 | 4.00 E−8 | | | 3.12 E−8 |
| 37 | 5.00 E−8 | | | |
| 38 | 8.50 E−8 | | | |
| 39 | 1.50 E−7 | | | |
| 40 | 1.70 E−7 | | | |
| 41 | 2.10 E−7 | | | |
| 42 | 4.60 E−7 | | | |
| 43 | 2.00 E−8 | | | 2.91 E−8 |
| 44 | 4.50 E−6 | | | |
| 45 | 3.00 E−5 | | | |
| 46 | 6.00 E−7 | | | |
| 47 | 1.60 E−6 | | | |
| 48 | 1.10 E−7 | | | 1.70 E−7 |
| 49 | 2.20 E−7 | | | |
| 50 | 3.50 E−9 | | | 5.01 E−9 |
| | 3.40 E−9 | | | |
| | 5.50 E−9 | | | |
| | 4.50 E−9 | | | |
| | 5.50 E−9 | | | |
| | <5.00 E−9 | | | |
| | 3.30 E−9 | | | |
| 51 | 1.40 E−6 | | | |
| 52 | 8.50 E−6 | | | |
| 53 | 2.90 E−7 | | | |

TABLE 3-continued

IC50 values of examples in in vitro assays 1-4

| Example No. | in vitro assay 1: DHODH enzymatic assay 1 $IC_{50}$ [mol/l] (mean values) | in vitro assay 2: DHODH enzymatic assay 2 $IC_{50}$ [nmol/l] (mean values) | in vitro assay 3: H460 (lung cancer) $IC_{50}$ [nmol/l] (mean values) | in vitro assay 4: THP-1 proliferation assay (AML) $IC_{50}$ [mol/l] |
|---|---|---|---|---|
| 54 | 8.00 E−6 | | | |
| 55 | 5.43 E−8 | | | 1.15 E−7 |
| 56 | 1.78 E−8 | | | 3.15 E−8 |
| 57 | 2.20 E−7 | | | |
| 58 | 2.80 E−6 | | | |
| 59 | 6.80 E−6 | | | |
| 60 | 1.40 E−8 | | | 1.45 E−8 |
| 61 | 2.00 E−9 | | | 7.86 E−10 |
| 62 | 3.00 E−9 | | | >1.00 E−5 |
| 63 | 8.50 E−9 | | | 1.03 E−8 |
| 64 | 4.30 E−9 | | | |
| 65 | 1.50 E−8 | | | 2.59 E−8 |
| 66 | 9.00 E−8 | | | 2.92 E−7 |
| 67 | 1.20 E−7 | | | |
| 68 | 9.00 E−9 | | | 1.23 E−8 |
| 69 | 6.00 E−9 | | | 5.85 E−9 |
| 70 | 1.15 E−8 | 1.0E5 | | 1.04 E−8 |
| 71 | 6.33 E−9 | 2.0 | | 6.04 E−9 |
| 72 | 4.85 E−7 | 235.0 | | |
| 73 | 1.20 E−7 | | | |
| 74 | 1.10 E−8 | | | 2.40 E−8 |
| 75 | 4.30 E−8 | | | 1.81 E−8 |
| 76 | 9.50 E−9 | | | 1.62 E−8 |
| 77 | 1.70 E−7 | | | |
| 78 | 1.70 E−8 | | | 2.57 E−8 |
| 79 | <5.00 E−9 | | | 8.33 E−11 |
| | 2.10 E−9 | | | <5.00 E−12 |
| | 2.50 E−9 | | | |
| 80 | 1.50 E−8 | | | 2.13 E−8 |
| 81 | 1.60 E−7 | | | |
| 82 | 9.00 E−7 | | | |
| 83 | 2.50 E−6 | | | |
| 84 | 9.60 E−8 | | | 3.96 E−8 |
| 85 | 7.50 E−8 | | | 8.55 E−7 |
| 86 | 3.50 E−8 | | | 2.03 E−8 |
| 87 | 2.00 E−7 | | | |
| 88 | <5.00 E−9 | | | 7.78 E−9 |
| | 5.00 E−9 | | | |
| 89 | 2.50 E−6 | | | |
| 90 | 3.00 E−7 | | | |
| 91 | 2.50 E−7 | | | |
| 92 | 1.80 E−6 | | | |
| 93 | 1.80 E−6 | | | |
| 94 | 2.40 E−6 | | | |
| 95 | 1.50 E−6 | | | |
| 96 | 3.00 E−5 | | | |
| 97 | 3.00 E−5 | | | |
| 98 | 3.80 E−6 | | | |
| 99 | 2.20 E−7 | | | |
| 100 | 6.50 E−6 | | | |
| 101 | 3.00 E−5 | | | |
| 102 | 8.50 E−7 | | | |
| 103 | 4.50 E−6 | | | |
| 104 | 3.10 E−6 | | | |
| 105 | 4.50 E−8 | | | 1.61 E−7 |
| 106 | 1.60 E−7 | | | |
| 107 | 1.80 E−7 | | | |
| 108 | 2.20 E−6 | | | |
| 109 | 5.50 E−8 | | | 1.31 E−7 |
| 110 | 3.00 E−5 | | | |
| 111 | 5.00 E−7 | | | |
| 112 | 3.00 E−7 | | | |
| 113 | 1.50 E−6 | | | |
| 114 | 3.90 E−8 | | | 2.43 E−8 |
| 115 | 1.00 E−6 | | | |
| 116 | 3.30 E−9 | | | |
| 117 | 2.00 E−8 | | | |
| 118 | 2.50 E−9 | | | |
| 119 | 1.00 E−7 | | | |
| 120 | 2.50 E−8 | | | 6.21 E−7 |
| 121 | 5.00 E−8 | | | |
| 122 | 2.20 E−7 | | | |
| 123 | 8.00 E−7 | | | |
| 124 | 2.30 E−7 | | | |
| 125 | 8.00 E−8 | | | >1.00 E−5 |
| 126 | 6.50 E−8 | | | 2.66 E−7 |
| 127 | 3.00 E−7 | | | |
| 128 | 1.50 E−7 | | | |
| 129 | 7.00 E−7 | | | |
| 130 | 3.50 E−7 | | | |
| 131 | 1.80 E−7 | | | |
| 132 | 2.00 E−7 | | | |
| 133 | 7.50 E−8 | | | |
| 134 | 1.80 E−8 | | | 4.38 E−8 |
| 135 | 2.90 E−9 | | | 2.52 E−8 |
| 136 | 1.90 E−7 | | | |
| 137 | 5.00 E−7 | | | |
| 138 | 4.90 E−8 | | | 1.04 E−7 |
| 139 | | 2.4E3 | 2.4 | |
| 140 | 5.00 E−9 | 127.9 | 0.8 | |
| 141 | 4.47 E−8 | 111.5 | 75.0 | |
| 142 | 1.43 E−8 | 80.0 | 18.7 | |
| 143 | | 175.4 | 5.3 | |
| 144 | 1.50 E−7 | 468.8 | 185.8 | |
| 145 | | 2.0E4 | 8.2 | |
| 146 | | 2.5E3 | 229.7 | |
| 147 | 5.00 E−8 | 30.1 | 6.0 | |
| 148 | 6.50 E−8 | 29.0 | | 1.60 E−8 |
| 149 | 6.25 E−9 | 2.0 | | 4.49 E−9 |
| 150 | 2.10 E−7 | 64.0 | | |
| 151 | 1.20 E−8 | 3.0 | | 2.35 E−9 |
| 152 | <5.00 E−9 | | | 4.66 E−9 |
| | 3.20 E−9 | | | |
| 153 | 2.00 E−8 | | | 1.12 E−8 |
| 154 | 1.70 E−8 | | | 7.88 E−9 |
| 155 | 6.05 E−9 | | | 3.52 E−9 |
| 156 | 9.50 E−9 | | | 6.49 E−9 |
| 157 | <5.00 E−9 | | | 2.73 E−10 |
| | 2.70 E−9 | | | |
| 158 | 6.85 E−9 | | | 1.19 E−9 |
| 159 | 1.80 E−7 | | | |
| 160 | 4.00 E−7 | | | |
| 161 | 3.60 E−8 | | | |
| 162 | 2.30 E−8 | | | 3.45 E−8 |
| 163 | 9.00 E−8 | | | 1.81 E−7 |
| 164 | 2.50 E−8 | | | 1.59 E−8 |
| 165 | 4.00 E−8 | | | 1.11 E−8 |
| 166 | <5.00 E−9 | | | 6.30 E−9 |
| | 4.00 E−9 | | | |
| 167 | 2.00 E−8 | | | 1.05 E−8 |
| 168 | 1.60 E−8 | | | 9.59 E−7 |
| 169 | <5.00 E−9 | | | 9.69 E−10 |
| | 2.60 E−9 | | | |
| 170 | 2.35 E−8 | | | 1.22 E−8 |
| 171 | 2.00 E−8 | | | 5.33 E−9 |
| 172 | 2.00 E−7 | | | |
| 173 | 1.60 E−7 | | | |
| 174 | 7.50 E−7 | | | |
| 175 | 1.60 E−8 | | | 1.28 E−8 |
| 176 | 1.50 E−7 | | | |
| 177 | 9.00 E−8 | | | 8.84 E−7 |
| 178 | 4.10 E−8 | | | 3.98 E−8 |
| 179 | 3.00 E−8 | | | 6.73 E−9 |
| 180 | 1.20 E−8 | | | 1.38 E−8 |
| 181 | 3.15 E−7 | | | 8.02 E−7 |
| 182 | 7.00 E−7 | | | 1.20 E−6 |
| 183 | 7.00 E−8 | | | 9.24 E−8 |
| 184 | 3.00 E−8 | | | 3.64 E−8 |
| 185 | 4.50 E−8 | | | 5.65 E−8 |
| 186 | 5.30 E−9 | | | 5.21 E−9 |

TABLE 3-continued

IC50 values of examples in in vitro assays 1-4

| Example No. | in vitro assay 1: DHODH enzymatic assay 1 $IC_{50}$ [mol/l] (mean values) | in vitro assay 2: DHODH enzymatic assay 2 $IC_{50}$ [nmol/l] (mean values) | in vitro assay 3: H460 (lung cancer) $IC_{50}$ [nmol/l] (mean values) | in vitro assay 4: THP-1 proliferation assay (AML) $IC_{50}$ [mol/l] |
|---|---|---|---|---|
| 187 | 7.00 E−9 | | | 1.65 E−8 |
| 188 | 9.00 E−9 | | | 7.40 E−8 |
| 189 | 4.00 E−8 | | | 8.75 E−8 |
| 190 | 6.00 E−8 | | | 2.79 E−8 |
| 191 | 7.50 E−8 | | | 2.63 E−7 |
| 192 | 1.60 E−8 | | | 5.48 E−9 |
| 193 | 6.00 E−8 | | | 8.77 E−8 |
| 194 | 3.20 E−8 | | | 3.72 E−8 |
| 195 | 1.90 E−7 | | | 9.37 E−8 |
| 196 | 2.10 E−7 | | | |
| 197 | 7.00 E−9 | | | 6.04 E−9 |
| 198 | 2.30 E−7 | | | |
| 199 | 6.00 E−7 | | | |
| 200 | 4.50 E−7 | | | |
| 201 | 3.20 E−8 | | | 3.41 E−8 |
| 202 | 2.50 E−7 | | | |
| 203 | 1.00 E−6 | | | |
| 204 | 1.00 E−7 | | | 2.25 E−7 |
| 205 | 1.70 E−7 | | | |
| 206 | 1.00 E−7 | | | 2.05 E−7 |
| 207 | 6.00 E−8 | | | 3.19 E−7 |
| 208 | 5.60 E−7 | | | |
| 209 | 2.50 E−8 | | | 3.42 E−8 |
| 210 | 4.60 E−8 | | | 4.22 E−8 |
| 211 | 7.50 E−8 | | | 6.62 E−8 |
| 212 | 1.10 E−8 | | | 4.62 E−9 |
| 213 | 1.95 E−8 | | | 3.03 E−8 |
| 214 | 3.50 E−7 | | | |
| 215 | 6.10 E−8 | | | 9.37 E−8 |
| 216 | 1.75 E−6 | 1.2E3 | | |
| 217 | 1.70 E−8 | 5.0 | | 7.23 E−9 |
| 218 | 3.55 E−7 | 748.0 | | |
| 219 | 1.41 E−7 | 6.0 | | 1.42 E−8 |
| 220 | 5.00 E−8 | 26.0 | | 2.87 E−8 |
| 221 | 4.78 E−7 | 29.0 | | |
| 222 | 1.20 E−7 | 55.0 | | |
| 223 | 4.50 E−6 | 3.8E3 | | |
| 224 | 2.30 E−8 | 1.0 | | |
| 225 | 1.35 E−6 | 561.0 | | |
| 226 | 1.80 E−8 | | | 2.11 E−8 |
| 227 | 1.00 E−8 | | | 1.46 E−8 |
| 228 | 3.00 E−9 | | | 5.48 E−9 |
| 229 | 2.30 E−8 | | | 2.54 E−8 |
| 230 | 3.00 E−8 | | | 4.65 E−8 |
| 231 | 3.00 E−9 | | | 1.51 E−9 |
| 232 | 2.90 E−9 | | | 4.13 E−9 |
| 233 | 3.20 E−9 | | | 2.33 E−9 |
| 234 | 1.50 E−8 | | | 1.36 E−8 |
| 235 | 5.00 E−9 | | | 4.74 E−9 |
| 236 | 4.10 E−9 | | | 1.60 E−9 |
| 237 | 7.50 E−9 | | | 8.47 E−9 |
| 238 | 9.00 E−8 | | | 3.90 E−7 |
| 239 | 2.50 E−8 | | | 3.97 E−8 |
| 240 | 2.30 E−8 | | | 2.19 E−8 |
| 241 | 2.50 E−7 | | | |
| 242 | 9.00 E−9 | | | 5.24 E−9 |
| 243 | 1.80 E−8 | | | 1.13 E−8 |
| 244 | 3.00 E−7 | | | |
| 245 | 5.80 E−8 | | | 6.47 E−8 |
| 246 | 1.00 E−7 | | | |
| 247 | 3.08 E−8 | | | 2.66 E−8 |
| 248 | 1.50 E−8 | | | 3.19 E−8 |
| 249 | 2.00 E−7 | | | |
| 250 | 1.60 E−7 | | | |
| 251 | 3.00 E−5 | | | |
| 252 | 1.50 E−7 | | | |
| 253 | 1.30 E−6 | | | |
| 254 | 2.00 E−7 | | | 1.11 E−6 |
| 255 | 6.00 E−8 | | | 4.14 E−7 |
| 256 | 3.00 E−5 | | | |
| 257 | 1.60 E−8 | | | 2.22 E−8 |
| 258 | 2.50 E−7 | | | |
| 259 | 1.00 E−7 | | | |
| 260 | 1.00 E−6 | | | |
| 261 | 5.17 E−7 | 285.0 | | |
| 262 | 1.83 E−8 | 5.0 | | 7.55 E−9 |
| 263 | 1.27 E−8 | 5.0 | | 3.28 E−9 |
| 264 | 7.00 E−6 | | | |
| 265 | 1.83 E−8 | | | 2.38 E−8 |
| 266 | 4.00 E−7 | | | |
| 267 | 1.80 E−8 | | | 2.67 E−8 |
| 268 | 2.50 E−8 | | | 4.18 E−8 |
| 269 | 3.00 E−8 | | | 4.12 E−8 |
| 270 | 2.50 E−8 | | | 3.79 E−8 |
| 271 | 1.40 E−7 | | | |
| 272 | 3.00 E−5 | | | |
| 273 | 1.50 E−7 | | | |
| 274 | 1.00 E−6 | | | |
| 275 | 8.00 E−8 | | | 1.33 E−7 |
| 276 | 1.60 E−8 | | | 2.75 E−8 |
| 277 | 8.00 E−6 | | | |
| 278 | 9.50 E−8 | | | |
| 279 | 1.10 E−6 | | | |
| 280 | 1.60 E−8 | | | 8.59 E−9 |
| 281 | 2.40 E−7 | | | |
| 282 | 4.00 E−8 | | | |
| 283 | 5.00 E−7 | | | |
| 284 | 1.30 E−7 | | | |
| 285 | 8.00 E−6 | | | |
| 286 | 7.00 E−7 | | | |
| 287 | 2.00 E−7 | | | |
| 288 | 2.80 E−7 | | | |
| 289 | 1.80 E−7 | | | |
| 290 | 3.40 E−9 | | | 7,35 E−9 |
| 291 | 1.50 E−8 | | | 6,09 E−7 |
| 292 | 4.50 E−6 | | | |
| 293 | 1,40 E−6 | | | |
| 294 | 1,00 E−6 | | | |
| 295 | 1,00 E−6 | | | |
| 296 | 7,00 E−8 | | | |
| 297 | 6.80 E−7 | | | |
| 298 | 1.60 E−6 | | | |

In accordance with further embodiments, the present invention provides compounds of general formula (I), that inhibit DHODH as described in in vitro assay 1 with an $IC_{50} \leq 50$ nM.

In accordance with further embodiments, the present invention provides compounds of general formula (I), that inhibit DHODH as described in in vitro assay 1 with an $IC_{50} \leq 15$ nM.

In Vitro Assay 5: THP-1 Proliferation Assay-2

Tumor and normal cells are cultivated in their respective media (ATCC recommended media). On day 1 of the assay, adherent cells are detached from the culture vessels by trypsinization. Suspension cells are centrifuged at 300×g and resuspended in fresh media. Cells are seeded at densities of 300-1000 cells/30 µL/well in the inner wells of white 384-well plates (Perkin Elmer). The outer wells of each plate are filled with 60 µL PBS/well to reduce evaporation. One plate is used for treatment of cells, the second plate is the start plate. All plates are incubated at 37° C., 5% $CO_2$ for 24 hrs. On day 2, 30 µL/well of CellTiter Glow (CTG, Promega) is added to the start plate, the plate is shaken at rt for 10 min on a laboratory plate shaker and then the plate is read in a Infinite M200 Pro MTP Reader (Tecan, Luminescence, 0.1s). Compounds from a 10 mM stock (in DMSO) are added in triplicates to the treatment plate in tenfold dilutions (from $1E^{-6}M$ to $1E^{-12}M$) with a HP D300 Digital Dispenser (the dispenser adds substances to wells in nanoliter volumes, therefore any volume added with this device does not count toward the final volume in the well). For rescue/specificity experiments with uridine, 100 μM uridine/well (diluted from a 10 mM stock solution in DMSO; Sigma-Aldrich) are added with the HP D300 Digital Dispenser. Treatment plates are incubated for a further 72 hrs at 37° C., 5% carbon dioxide, On day 5 of the assay, 30 μL/well of CellTiter Glow (CTG, Promega) is added to the treatment plate, the plate is shaken at rt for 10 min on a laboratory plate shaker and then the plate is read in a Infinite M200 Pro MTP Reader (Tecan, Luminescence, 0.1s).

In Vitro Assay 6: SUDHL-10 Proliferation Assay (Lymphoma)

2000 cells/well of SUDHL-10 cells were seeded in RPMI 1640 with Glutamax (Gibco, #11875-093) and 10% fetal calf serum (Biochrom, #S0615) in 384-well plates. The next day, cells were incubated with different concentrations of test compounds for 72h. Cellular viability was analyzed using CellTiter-Glo® Luminescent Cell Viability Assay (Promega, #G7570) according to manufacturer's instructions.

TABLE 4

$IC_{50}$ values of examples in in vitro assay 6

| Example No. | in vitro assay 6: SUDHL10 $IC_{50}$ [mol/l] (mean values) |
|---|---|
| 30 | 9.53 E-9 |
| 181 | 8.71 E-8 |
| 220 | 1.75 E-9 |

In Vitro Assay 7: xCelligence Proliferation Assay (HCT116 (Colorectal Carcinoma, A498 (Kidney Carcinoma), Panc1 (Pancreas Carcinoma) Cell Lines)

Impedance measurement is a dimensionless parameter termed Cell Index (CI) which is derived as a relative change in measured electrical impedance caused by an increase of cell number on the bottom of the cell culture well.

To determine CI, 2000 cells/well are seeded into 96-well E-plates. Cells are placed in the Real-Time Cell Analyzer (RTCA) station (ACEA Biosciences) and incubated for 24h. Subsequently, compounds are added at concentrations as indicated and cells are replaced in the Real-Time Cell Analyzer (RTCA) station and analyzed until cells reach confluency. Impedance is measured every 60 min. Cell index is determined by the xCelligence software and presented as CI over time.

In Vitro Assay 8: U-87 MG Proliferation Assay (Glioblastoma)

U-87 MG cells are plated in MEM Earle's medium+10% FCS with 4000 cells/well in a 96-well microtiter plate (d-1). Compound is added at d0. Cell number is determined by Alamar Blue staining (2h) at d0 and d3. Fluorescence is determined in Victor3 (Excitation 530 nm; emission 590 nm). C0 is defined as the signal measured at d4 for cells without treatment (0.1% DMSO). CI is defined as the signal measured at d0.

TABLE 5

$IC_{50}$ values of examples in in vitro assay 8

| Example No. | in vitro assay 8: U-87 MG $IC_{50}$ [mol/l] (mean values) |
|---|---|
| 30 | 2.2 E-6 |

In Vitro Assay 9: Colo 205 Proliferation Assay (Colorectal Carcinoma)

COLO 205 cells are plated in RPM1640 medium with stable glutamine+10% FCS+10 mM Hepes+1 mM Natriumpyruvat+1×Non Essential Amino Acids with 4000 cells/well in a 96-well microtiter plate (d-1). Compound is added at d0. Cell number is determined by Alamar Blue staining (2h) at d0 and d3. Fluorescence is determined in Victor3 (Excitation 530 nm; emission 590 nm). C0 is defined as the signal measured at d4 for cells without treatment (0.1% DMSO). CI is defined as the signal measured at d0.

In Vitro Assay 10: MKN-45 Proliferation Assay (Gastric Cancer)

MKN-45 cells are plated in RPMI1640 medium with stable glutamine+20% FCS with 4000 cells/well in a 96-well microtiter plate (d-1). Compound is added at d0. Cell number is determined by Alamar Blue staining (2h) at d0 and d3. Fluorescence is determined in Victor3 (Excitation 530 nm; emission 590 nm). C0 is defined as the signal measured at d4 for cells without treatment (0.1% DMSO). CI is defined as the signal measured at d0.

In Vitro Assay 11: MIA PaCa2 Proliferation Assay (Pancreatic Carcinoma)

MIA PaCa 2 cells are plated in DMEM/HAMS F12 medium+10% FCS+2.5% Horse Serum with 4000 cells/well in a 96-well microtiter plate (d-1). Compound is added at d0. Cell number is determined by Alamar Blue staining (2h) at d0 and d3. Fluorescence is determined in Victor3 (Excitation 530 nm; emission 590 nm). C0 is defined as the signal measured at d4 for cells without treatment (0.1% DMSO). $C_1$ is defined as the signal measured at d0.

In Vitro Assay 12: DU 145 Proliferation Assay (Prostate Cancer)

DU 145 cells are plated in DMEM/HAMS F12 medium+10% FCS with 4000 cells/well in a 96-well microtiter plate (d-1). Compound is added at d0. Cell number is determined by Alamar Blue staining (2h) at d0 and d3. Fluorescence is determined in Victor3 (Excitation 530 nm; emission 590 nm). C0 is defined as the signal measured at d4 for cells without treatment (0.1% DMSO). CI is defined as the signal measured at d0.

TABLE 6

$IC_{50}$ values of examples in in vitro assay 12

| Example No. | in vitro assay 12: DU 145 $IC_{50}$ [mol/l] (mean values) |
|---|---|
| 30 | 3.5 E-7 |

Assay 13: MOLM 13 Differentiation Assay (AML)

20000 cells per well of MOLM 13 cells are seeded in RPMI 1640 with Glutamax (Gibco, #11875-093) and 10% fetal calf serum (Biochrom, #S0615) and incubated with different concentrations of test compounds for 96h. After treatment for 10 min with Human TruStain FcX, (Biolegend, #422302) or BD Human Fc Block (#564220) at RT, cells are incubated with 2 μg/ml APC anti-mouse/human CD11b Antibody (Biolegend, Cat #101212) for 30 min at 4° C. Cells are analyzed by Fluorescence-activating cell sorting (FACS) (BD FACS Canto, BD Biosciences).

Assay 14: Cancer Cell Proliferation Panel

The CellTiter-Blue® Cell Viability Assay (#G8081, Promega) is used according to manufacturer's instructions. Briefly, cells are harvested from exponential phase cultures, counted and plated in 96-well flat-bottom microtiter plates at a cell density of 4,000-60,000 cells/well depending on the cell line's growth rate. After a 24 h recovery period to allow the cells to resume exponential growth, 10 μl of culture medium (four control wells/plate) or of culture medium with test compound are added. The compound is applied at 10 concentrations in duplicate in half-log increments up to 30 μM and treatment is continued for three days. After three days treatment of cells, 20 μl/well CellTiter-Blue® reagent is added. Following an incubation period of up to four hours, fluorescence (FU) is measured by using the Enspire Multimode Plate Reader (excitation λ=531 nm, emission λ=615 nm).

For calculations, the mean values of duplicate/quadruplicate (untreated control) data are used.

The invention claimed is:

1. A pharmaceutical combination comprising:
one or more first active ingredients of general formula (I)

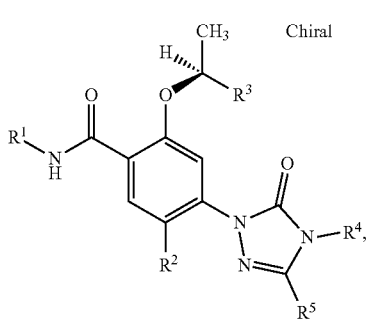

(I)

in which
R$^1$ represents a group selected from
a C$_1$-C$_8$-alkyl group, which is optionally substituted with a group selected from
C$_3$-C$_8$-cycloalkyl, phenyl and monocyclic or bicyclic heteroaryl,
wherein said phenyl substituent is optionally substituted, one, two or three times with one or more substituents independently selected from a halogen atom, a C$_1$-C$_3$-alkyl group, a C$_1$-C$_4$-haloalkyl group, a C$_1$-C$_3$-alkoxy group and a hydroxy group,
a C$_2$-C$_8$-haloalkyl group,
a C$_3$-C$_8$-cycloalkyl group, which is optionally substituted, one or two times, each substituent independently selected from a halogen atom, a hydroxy group, a phenyl group and a —N(R$^7$)(R$^8$) group,
wherein said phenyl substituent is optionally substituted, one, two or three times, each substituent independently selected from a halogen atom, a C$_1$-C$_3$-alkyl group, a C$_1$-C$_4$-haloalkyl group, a C$_1$-C$_3$-alkoxy group and a hydroxy group,
a C$_2$-C$_6$-cyanoalkyl group,
a C$_2$-C$_6$-hydroxyalkyl group,
a (C$_2$-C$_6$-hydroxyalkyl)-O—(C$_2$-C$_6$-alky)- group,
a —(C$_2$-C$_6$-alkyl)-N(R$^7$)(R$^8$) group,
a —(C$_1$-C$_6$-alkyl)-C(=O)N(R$^7$)(R$^8$) group,
a 4- to 7-membered, optionally unsaturated, heterocyclic group, which is connected to the rest of the molecule via a carbon atom, and which is optionally substituted one or two times, each substituent independently selected from a $C_1$-$C_3$-alkyl group, a 5- to 6-membered heteroaryl group, a -C(=O)O($C_1$-$C_4$-alkyl) group, a —C(=O)($C_1$-$C_6$-alkyl) group, a —C(=O)($C_3$-$C_6$-cycloalkyl) group, a —S(=O)$_2$($C_1$-$C_6$-alkyl) group and a oxo (=O) group, wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$),), —SH, —S—($C_1$-$C_6$-alkyl), —S—($C_2$-$C_6$-alkenyl), —S(=O)$_2$N(R$^7$)(R$^8$), —S(=O)$_2$($C_1$-$C_6$-alkyl), —S(=O)$_2$—O—($C_2$-$C_6$-alkenyl), —S(=O)(=NR$^{14}$)($C_1$-$C_3$-alkyl), —N(O)$_2$, —P(=O)($C_1$-$C_3$-alkyl)$_2$ and SF$_5$, or wherein two vicinal substituents of said phenyl groups may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$) and a monocyclic or bicyclic heteroaryl group which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, cyano, —C(=O)OR$^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$), $R^2$ represents a hydrogen atom or a halogen atom,
$R^3$ represents a group selected from
a $C_1$-$C_6$-alkyl group,
a $C_3$-$C_8$-cycloalkyl group,
a $C_1$-$C_6$-haloalkyl group,
a $C_1$-$C_6$-hydroxyalkyl group,
a $C_2$-$C_6$-alkenyl group,
a $C_2$-$C_6$-alkinyl group,
a $C_4$-$C_8$-cycloalkenyl group,
a ($C_1$-$C_6$-alkyl)-N(R$^7$)R$^8$ group,
a —($C_1$-$C_6$-alkyl)-N(H)C(=O)R$^6$ group,
a —($C_1$-$C_6$-alkyl)-N(H)C(=O)OR$^{15}$ group, a —($C_1$-$C_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and wherein said 4- to 7-membered nitrogen containing heterocycloalkyl group is optionally substituted with a $C_1$-$C_3$-alkyl group,
and
a phenyl group,
which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$), $R^4$ and $R^5$ jointly form an optionally unsaturated, heterocyclic ring A of partial formula (i)

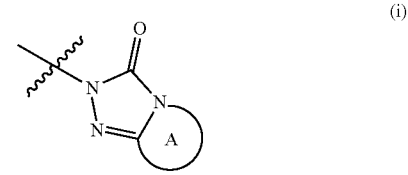

(i)

whereby ring A in addition to the two mandatory atoms, the nitrogen atom and the carbon atom bridging the two rings, bears additional 3 to 6 members selected from —O—, —S—, —S(=O)—, —S(=O)$_2$—, —S(=O)(=NR$^{14}$)—, —N=, —N(R$^7$)—, —C(=O)—, —C(=O)—, —CH=, —CR$^{11}$=, —C(R$^{12}$)$_2$—, —C(H)(R$^{13}$)—, $R^6$ represents a hydrogen atom or a group selected from
a $C_1$-$C_6$-alkyl group and a benzyl group,
$R^7$ and $R^8$ represent, independently from each occurrence, a hydrogen atom or a group selected from
a $C_1$-$C_6$-alkyl group, a $C_2$-$C_6$-alkenyl group, a $C_2$-$C_6$-hydroxyalkyl group, a haloalkyl group, a aryl group, a ($C_1$-$C_6$-alkyl)-aryl group, and a —($C_2$-$C_6$-alkyl)-N(R$^9$)(R$^{10}$) group, or $R^7$ and $R^8$ together with the nitrogen to which they are attached represent a
nitrogen containing 4- to 7-membered heterocycloalkyl group,
wherein said 4- to 7-membered nitrogen containing heterocycloalkyl group is optionally substituted with a group selected from
$C_1$-$C_6$-alkyl, —S—($C_1$-$C_6$-alkyl), —S—($C_2$-$C_6$-alkenyl), —S(=O)$_2$($C_1$-$C_3$-alkyl), —S(=O)$_2$—($C_2$-$C_6$-alkenyl), and —C(=O)OR$^6$ —, $R^9$ and $R^{10}$ represent, independently from each occurrence, a hydrogen atom or a $C_1$-$C_3$-alkyl group,
or
$R^9$ and $R^{10}$ together with the nitrogen to which they are attached represent a
nitrogen containing 4- to 7-membered heterocycloalkyl group, $R^{11}$ represents, independently from each occurrence a hydrogen atom, a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$ —, hydroxy, —SH, —S—($C_1$-$C_6$-alkyl), —S—($C_2$-$C_6$-alkenyl), S(=O)$_2$ ($C_1$-$C_6$-alkyl), —S(=O)$_2$—($C_2$-$C_6$-alkenyl), —N(O)$_2$, and —N(R$^7$)(R$^8$)

$R^{12}$ represents, independently from each occurrence, a hydrogen atom, a halogen atom or a $C_1$-$C_3$-alkyl group, $R^{13}$ represents a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$ —, hydroxy, —SH, —S—($C_1$-$C_6$-alkyl), —S—($C_2$-$C_6$-alkenyl), S(=O)$_2$—($C_1$-$C_6$-alkyl), —S(=O)$_2$—($C_2$-$C_6$-alkenyl), —N(O)$_2$, and —N(R$^7$)(R$^8$), $R^{14}$ represents a hydrogen atom or a group selected from a cyano group and a —C(=O)($C_1$-$C_3$-haloalkyl) group, $R^{15}$ represents a group selected from a $C_1$-$C_6$-alkyl group and a benzyl group, or a tautomer, an N-oxide, or a salt thereof, or a salt of a tautomer or an N-oxide of said compound, and one or more further active ingredients.

2. The pharmaceutical combination according to claim 1, wherein the one or more further active ingredients comprise an anti-cancer agent.

\* \* \* \* \*